(12) United States Patent
Albino et al.

(10) Patent No.: US 10,709,164 B2
(45) Date of Patent: *Jul. 14, 2020

(54) REDUCED RISK TOBACCO PRODUCTS AND METHODS OF MAKING SAME

(71) Applicant: Vector Tobacco Inc., Morrisville, NC (US)

(72) Inventors: Anthony P. Albino, New York, NY (US); Wendy Jin, Chapel Hill, NC (US); Ellen Jorgensen, South Salem, NY (US)

(73) Assignee: Vector Tobacco Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,002

(22) Filed: May 25, 2018

(65) Prior Publication Data

US 2018/0332885 A1    Nov. 22, 2018

Related U.S. Application Data

(63) Continuation of application No. 15/243,675, filed on Aug. 22, 2016, now abandoned, which is a continuation of application No. 14/102,340, filed on Dec. 10, 2013, now Pat. No. 9,439,452, which is a continuation of application No. 11/913,870, filed as application No. PCT/US2006/018065 on May 10, 2006, now abandoned.

(60) Provisional application No. 60/680,283, filed on May 11, 2005.

(51) Int. Cl.
  *C12N 15/82* (2006.01)
  *A24B 13/00* (2006.01)

(52) U.S. Cl.
  CPC .......... *A24B 13/00* (2013.01); *C12N 15/8218* (2013.01); *C12N 15/8243* (2013.01)

(58) Field of Classification Search
  None
  See application file for complete search history.

(56) References Cited

U.S. PATENT DOCUMENTS

| | | |
|---|---|---|
| 3,499,454 A | 3/1970 | Preferably et al. |
| 3,586,005 A | 6/1971 | Lippman et al. |
| 3,644,355 A | 2/1972 | Ebner et al. |
| 3,687,808 A | 8/1972 | Merigan, Jr. et al. |
| 3,812,865 A | 5/1974 | Anderson |
| 3,840,025 A | 10/1974 | Fowler et al. |
| 3,905,123 A | 9/1975 | Fowler et al. |
| 3,991,772 A | 11/1976 | Smith, Jr. |
| 4,055,191 A | 10/1977 | Norman et al. |
| 4,177,822 A | 12/1979 | Bryant, Jr. et al. |
| 4,182,349 A | 1/1980 | Selke |
| 4,183,364 A | 1/1980 | Gumushan et al. |
| 4,192,323 A | 3/1980 | Horne |
| 4,215,706 A | 8/1980 | Larson et al. |
| 4,216,784 A | 8/1980 | Bryant, Jr. et al. |
| 4,235,251 A | 11/1980 | Bryant, Jr. et al. |
| 4,248,251 A | 2/1981 | Bryant, Jr. et al. |
| 4,257,430 A | 3/1981 | Collins et al. |
| 4,289,147 A | 9/1981 | Wildman et al. |
| 4,336,814 A | 6/1982 | Sykes et al. |
| 4,340,073 A | 7/1982 | Aument et al. |
| 4,347,324 A | 8/1982 | Wildman et al. |
| 4,350,073 A | 9/1982 | Peterson |
| 4,459,355 A | 7/1984 | Cello et al. |
| 4,499,911 A | 2/1985 | Johnson |
| 4,531,529 A | 7/1985 | White et al. |
| 4,557,280 A | 12/1985 | Gravely et al. |
| 4,561,452 A | 12/1985 | Gahrs |
| 4,795,855 A | 1/1989 | Fillatti et al. |
| 4,848,373 A | 7/1989 | Lenkey |
| 4,940,838 A | 7/1990 | Schilperoor et al. |
| 4,945,050 A | 7/1990 | Sanford et al. |
| 4,962,774 A | 10/1990 | Thomasson et al. |
| 4,987,071 A | 1/1991 | Cech et al. |
| 5,015,580 A | 5/1991 | Christou et al. |
| 5,260,205 A | 11/1993 | Nakatani et al. |
| 5,268,463 A | 12/1993 | Jefferson |
| 5,369,023 A | 11/1994 | Nakatani et al. |
| 5,432,081 A | 7/1995 | Jefferson |
| 5,459,252 A | 10/1995 | Conkling et al. |

(Continued)

FOREIGN PATENT DOCUMENTS

| | | |
|---|---|---|
| WO | WO 93/05646 | 4/1993 |
| WO | WO 94/28142 | 12/1994 |
| WO | WO 97/05261 | 2/1997 |
| WO | WO 98/56923 | 12/1998 |
| WO | WO 99/13085 | 3/1999 |
| WO | WO 99/14226 | 3/1999 |
| WO | WO 00/055333 | 9/2000 |
| WO | WO 00/67558 | 11/2000 |
| WO | WO 02/18607 | 3/2002 |
| WO | WO 03/086076 | 10/2003 |
| WO | WO 05/000352 | 1/2005 |
| WO | WO 05/018307 | 3/2005 |

OTHER PUBLICATIONS

Hibi et al, 1994, Plant Cell, 6:723-735.*

(Continued)

*Primary Examiner* — Jason Deveau Rosen
(74) *Attorney, Agent, or Firm* — Knobbe Martens Olson & Bear LLP

(57) ABSTRACT

Embodiments provided herein concern tobacco and tobacco products having a reduced amount of a harmful compound. More specifically, several embodiments concern approaches to modify the expression of a gene that is involved in the production of a harmful compound in tobacco, tobacco products made using these approaches and methods of determining whether the removal of said compounds using said approaches yields a tobacco and/or a tobacco product that has a reduced potential to contribute to a tobacco-related disease.

21 Claims, 53 Drawing Sheets

Specification includes a Sequence Listing.

(56) References Cited

U.S. PATENT DOCUMENTS

| | | | |
|---|---|---|---|
| 5,539,082 A | 7/1996 | Nielsen et al. | |
| 5,559,021 A | 9/1996 | Smith et al. | |
| 5,580,967 A | 12/1996 | Joyce | |
| 5,583,032 A | 12/1996 | Torrence et al. | |
| 5,589,367 A | 12/1996 | Donson et al. | |
| 5,591,601 A | 1/1997 | Wagner et al. | |
| 5,595,877 A | 1/1997 | Gold et al. | |
| 5,599,670 A | 2/1997 | Jefferson | |
| 5,622,854 A | 4/1997 | Draper | |
| 5,668,295 A | 9/1997 | Wahab et al. | |
| 5,685,710 A | 11/1997 | Martinez Sagrera et al. | |
| 5,714,331 A | 2/1998 | Buchardt et al. | |
| 5,719,262 A | 2/1998 | Buchardt et al. | |
| 5,767,247 A | 6/1998 | Kaneko et al. | |
| 5,837,876 A | 11/1998 | Conkling et al. | |
| 5,997,869 A | 12/1999 | Goletz et al. | |
| 6,362,317 B1 | 3/2002 | Bonner et al. | |
| 6,415,798 B1 | 7/2002 | Hersh et al. | |
| 6,416,948 B1 | 7/2002 | Pilarski et al. | |
| 6,423,520 B1 | 7/2002 | Conkling et al. | |
| 6,506,609 B1 | 1/2003 | Wada et al. | |
| 6,576,421 B1 | 6/2003 | Westbrook | |
| 6,586,661 B1 | 7/2003 | Conkling et al. | |
| 6,761,175 B2 | 7/2004 | Nakanishi et al. | |
| 6,789,548 B2 | 9/2004 | Bereman | |
| 6,832,612 B2 | 12/2004 | Zhao et al. | |
| 6,884,873 B2 | 4/2005 | Bonner et al. | |
| 6,907,887 B2 * | 6/2005 | Conkling | A24B 15/10 131/270 |
| 2002/0108151 A1 | 8/2002 | Conkling et al. | |
| 2002/0192692 A1 | 12/2002 | Palanisamy | |
| 2002/0197688 A1 | 12/2002 | Pandolfino | |
| 2003/0017462 A1 | 1/2003 | Hewitt | |
| 2003/0018997 A1 | 1/2003 | Conkling et al. | |
| 2003/0140366 A1 | 7/2003 | Conkling et al. | |
| 2004/0103454 A1 | 5/2004 | Conkling et al. | |
| 2004/0144397 A1 | 7/2004 | Conkling | |
| 2004/0235039 A1 | 11/2004 | Gray et al. | |
| 2005/0002552 A1 | 1/2005 | Dunn et al. | |
| 2005/0072047 A1 | 4/2005 | Conkling et al. | |
| 2007/0240728 A1 * | 10/2007 | Hashimoto | A24B 15/18 131/280 |

OTHER PUBLICATIONS

Shoji, et al., "Expression Patterns of Two Tobacco Isoflavone Reductase-Like Genes and Their Possible Roles in Secondary Metabolism in Tobacco," Plant Molecular Biology, vol. 50, pp. 427-440 (2002).
Hibi, et al., "Gene Expression in Tobacco Low-Nicotine Mutants," The Plant Cell, vol. 6, pp. 723-735 (1994).
Afshari et al., (Oct. 1999) "Application of complementary DNA microarray technology to carcinogen identification, toxicology, and drug safety evaluation." Cancer Research 59:4759-4760.
Allera et al., (Feb. 1997) "The Condensation in Apoptotic Thymocytes Shows a Specific Structural Change," J. Biol. Chem. 272:10817-10822.
Bhattachariee, et al. (Sep. 2001) "Classification of human lung carcinomas by mRNA expression profiling reveals distinct adenocarcinoma subclasses." Proc Natl Acad Sci USA 98:13790-13795.
Bombick, D.W. et al., (Jun. 1997) "Evaluation of the Genotoxic and Cytotoxic Potential of Mainstream Whole Smoke and Smoke Condensate from a Cigarette Containing a Novel Carbon Filter", Fundamental and Applied Toxicology, 39:11-17.
Broothaerts et al., (Feb. 2005) "Gene transfer to plants by diverse species of bacteria." Nature 433:629.
Brosius, (Nov. 1984) "Regulation of ribosomal RNA promoters with a synthetic lac operator", Proc. Natl. Acad. Sci. USA, 81:6929-6933.
Carmella et al., (Apr. 2000) "Enantiomeric composition of N?-nitrosonornicotine and N?-nitrosoanatabine in tobacco." Carcinogenesis, 21(4):839-843.

Cho et al., (Jun. 2002) "Optimal approach for classification of acute leukemia subtypes based on gene expression data." Biotechnol Prog 18: 847-854.
Chujo et al., (Apr. 2002) "Comparati ve genomic hybridization analysis detected frequent overrepresentation of chromosome 3q in squamous cell carcinoma of the lung." Lung Cancer 38: 23-29.
Clapp, W.L., et al., (Sep. 1999) "Reduction in Ames Salmonella mutagenicity of cigarette mainstream smoke condensate by tobacco protein removal", Mutation Research, 446:167-174.
Collins, (Mar. 2004) "The comet assay for DNA damage and repair." Mol. Biotechnology 26:249-261.
Communication pursuant to Rules 70(2) and 70a(2) EPS for 06770166. 4, dated Jul. 13, 2013.
Conkling et. al., (Jul. 1990) "Isolation of transcriptionally regulated root-specific genes from tobacco." Plant Physiol. 93:1203-1211.
Cornelissen et al., (Feb. 1989) "Both RNA Level and Translation Efficiency are Reduced by Anti-Sense RNA in Transgenic Tobacco", Nucleic Acids Res. 17:833-43.
Crooke et al., (May 1996) "Pharmacokinetic properties of several novel oligonucleotide analogs in mice." J. Pharmacol. Exp. Ther., 277:923-937.
Deen et al., (Apr. 1986) "Prediction of human tumor cell chemosensitivity using the sister chromatid exchange assay." Cancer Res. 46:1599-602.
Demarini, David M. (Nov. 2004), "Genotoxicity of tobacco smoke and tobacco smoke condensate: a review", Mutation Research 567:447-474.
Dillin, A. (May 2003) "The specifics of small interfering RNA specificity." Proc. Nat. Acad. Sci. USA, 100:6289-91.
Dobrucki et al., (Oct. 2001) "Chromatin condensation and sensitivity of DNA in situ to denaturation during cell cycle and apoptosis—a confocal microscopy study," Micron 32:645-52.
Doolin et al., (Oct. 1999) "The effect of Leukocyte infiltration of apoptosis in an in vitro thermal injury bioartificial living skin equivalent model." J. Burn Care Rehabil. 20: 374-376.
Dozmorov et al., (Jan. 2003) "An associative analysis of gene expression array data." Bioinformatics., 19(2): 204-211.
Dozmorov et al., (May 2004) "Statistical monitoring of weak spots for improvement of normalization and ratio estimates in microarrays." Bioinformatics 5:53 p. 1-9.
Driessens et al., (Dec. 2003) "Assessment of in vivo chemotherapy-induced DNA Damage in a p53-mutated rat tumor by micronuclei assay." Ann N Y Acad Sci. 1010:775-779.
Englisch et al., (Jun. 1991) "Chemically modified oligonucleotides as probes and inhibitors." Angewandte Chemie, International Edition, 30:613.
European Office Action dated Aug. 1, 2017 in European Patent Application No. 06770166.4, filed May 10, 2006.
Extended European Search Report for European Patent Application No. 06770166.4, dated Jun. 27, 2013.
Feth et al., (Apr. 1986) "Regulation in tobacco callus of enzyme activities of the nicotine pathway." Planta, 168:402-07.
Fielding, S. et al. (Feb. 1989) "Studies on the ability of smoke from different types of cigarettes to induce DNA single-strand breaks in cultured human cells", Mutation Research, 214:147-151.
Frankfurt et al., (Apr. 1996) "Monoclonal antibody to single-stranded DNA is a specific and sensitive cellular marker of apoptosis." Exp. Cell Res. 226:387-397.
Frankfurt et al., (Mar. 2001) "Enzyme-linked immunosorbent assay (ELISA) for the specific detection of apoptotic cells and its application to rapid drug screening." J. Immunol. Methods. 253: 133-144.
Frankfurt et al., (Mar. 2001) "Identification of apoptotic cells by formamide-induced DNA denaturation in condensed chromatin." J. Histochem. Cytochem. 49:369-378.
Garber et al., (Sep. 2001) "Diversity of gene expression in adenocarcinoma of the lung," Proc Natl Acad Sci USA 98: 13784-13789.
Gebel et al., (Oct. 2004) "Gene expression profiling in respiratory tissues from rats exposed to mainstream cigarette smoke." Carcinogenesis 25:169-178.

(56) References Cited

OTHER PUBLICATIONS

Gichner et al., (Apr. 2004) "Cadmium induces DNA damage in tobacco roots, but no DNA damage, somatic mutations or homologous recombination in tobacco leaves." *Mutation Res.* 559:49-57.
Gorczyca, (Mar. 1999) "Cytometric analyses to distinguish death processes." *Endocrine-Related Cancer* 6:17-19.
Gribskov et al., (1991) Sequence Analysis Primer. Stockton Press, New York.
Groos et al., (Apr. 2003) "General suitability of techniques for in situ detection of apoptosis in small intestinal epithelium." *Anat. Rec.* 272A:503-513.
Hanash et al., (Nov. 2001) "A proteomic approach to the identification of lung cancer markers." *Dis Markers* 17: 295-300.
Hibi et al., (May 1994) "Gene expression in tobacco low-niccotine mutants," *The Plant Cell*, 6:723-735.
Hsu, T.C. et al., (Jan. 1991) "Mitosis-arresting effects of cigarette smoke condensate on human lymphoid cell lines", *Mutation Research*, 259: 67-78.
Hughes et al., (Jan. 1993) "The salmonella typhimurium nadC gene: Sequence determination by use of Mud-P22 and purification of quinolinate phosphoribosyltransferase." J Bacteriol. 175:479-486.
International Search Report for PCT/US06/18065 dated Jul. 15, 2008.
ISO, (Aug. 1991) "Cigarettes—determination of total and nicotine-free dry particulate matter using a routine analytical smoking machine" ISO: 4387:1991.
Jarvis et al., (2004) "Novel approaches to gene expression analysis of active polyarticular juvenile rheumatoid arthritis." Arthritis Res Ther, 6: R15-R32.
Kabanov et al., (Jan. 1990) "A new class of antivirals: antisense oligonucleotides combines with a hydrophobic substituent effectively inhibit influenza virus reproduction and synthesis of virus-specific proteins in MDCK cells." FEBS Lett., 1990, 259, 327-330.
Kalyuzhny, (2002) "Simultaneous in situ detection of DNA fragmentation and RNA/DNA oxidative damage using TUNEL assay and immunohistochemical labeling for 8-hydroxy-2'-deoxyguanosine (8-OHdG)" Methods Mol. Biol. 203:219-34.
Klein-Szanto AJP et al., (1993) "A tobacco-specific N-nitrosamine or cigarette smoke condensate causes neoplastic transformation of xenotransplanted human bronchial epithelial cells", *Lung Cancer*, 10(1-2):124.Elsevier, Amsterdam, NL.
Knowlton, N. et al., (Jul. 2004) "Microarray Data Analysis Toolbox (MDAT): for normalization, adjustment and analysis of gene expression data," *Bioinformatics* 20: 3687-3690.
Lam et al., (Oct. 1989) "Site-Specific Mutations Alter In Vitro Factor Binding and Change Promoter Expression Pattern in Transgenic Plants", Proc. Nat. Acad Sci. USA 86:7890-94.
Lawry, (2004) "Detection of apoptosis by the TUNEL assay." *Methods Mol. Med.* 88:183-90.
Leanderson, Per et al., (Jan. 1992) "Cigarette smoke-induced DNA damage in cultured human lung cells: Role of hydroxyl radicals and endonuclease activation", *Chem. Biol. Interactions*, 81:197-208.
Legg et al., (1969) "Inheritance of percent total alkaloids in *Nicotiana tabacum* L." *J Hered*, 60:213-17.
Legg et al., (Jun. 1971) "Inheritance of per cent total alkaloids in *Nicotiana tabacum* L. II. Genetic effects of two loci in burley 21 x la burley 21 populations." *Can J Genet Cytol*, 13:287-91.
Letsinger et al., (Sep. 1989) "Cholesteryl-conjugated oligonucleotides: synthesis, properties, and activity as inhibitors of replication of human immunodeficiency virus in cell culture." Proc. Natl. Acad. Sci. USA, 86:6553-6556.
Luo, et al., Cigarette smoke induces anaphase bridges and genomic imbalances in normal cells, Mutation Research, 2004, pp. 375-385, vol. 554.
Manoharan et al., (1995) "Oligonucleotide conjugates: alteration of the pharmacokinetic properties of antisense agents" *Nucleosides & Nucleotides*, 14:969-973.
Manoharan et al., (Apr. 1994) "Cholic acid-oligonucleotide conjugates for antisense applications," *Bioorg. Med. Chem. Let.*, 4:1053-1060.
Manoharan et al., (Dec. 1993) "Introduction of a lipophilic thioether in the minor groove of nucleic acids for antisense applications" *Bioorg. Med. Chem. Let.*, 3:2765-2770.
Manoharan et al., (May 1995) "Lipidic nucleic acids," *Tetrahedron Lett.*, 36:3651-3654.
Manoharan et al., (Oct. 1992) "Chemical Modifications to Improve Uptake and Bioavailability of Antisense Oligonucleotides," *Ann. N.Y. Acad. Sci.*, 660:306-309.
Matsumoto, et al., (Jan. 1978) "Mutagenicities of the pyrolysis of peptides and proteins," *Mutation Research*, 56:281-288.
Mazur et al., (Jun. 2002) "Flow cytometric detection of apoptotic bone marrow cells with fractional DNA content after application of WR-2721, cyclophosphamide, cisplatin, and exposure of mice to gamma rays," Hum. Exp. Toxicol. 21:335-41.
Meyerowitz, (1987) "In situ hybridization to RNA in plant tissue," *Plant Mol. Biol. Rep.* 5(1):242-250.
Mishra et al., (Nov. 1995) "Improved leishmanicidal effect of phosphorotioate antisense oligonucleotides by LDL-mediated delivery" *Biochim. Biophys. Acta*, 1264(2):229-237.
Mullen, (2004) "PARP cleavage as a means of assessing apoptosis," *Methods Mol. Med.* 88:171-81.
Nadadur et al., (Mar. 2002) "Pulmonary gene expression profiles of spontaneously hypertensive rats exposed to environmental tobacco smoke," Chest 121: 83S-84S.
Neumann et al., (Dec. 2002) "DNA microarrays and toxicogenomics: applications for ecotoxicology?," *Biotechnol Adv* 20(5-6):391-419.
Nielsen et al., (Dec. 1991) "Sequence-selective recognition of DNA by strand displacement with a thymine-substituted polyamide," *Science*, 254:1497-1500.
Nordskog et al. (Jun. 2003) "Matrix-degrading and pro-inflammatory changes in human vascular endothelial cells exposed to cigarette smoke condensate," Cardiovasc Toxicol 3(2):101-117.
Oberhauser et al., (Feb. 1992) "Effective incorporation of 2'-O-methyl-oligoribonucleotides into liposomes and enhanced cell association through modification with thiocholesterol," *Nucl. Acids Res.* 20:533-538.
Offer et al., (Mar. 2005) "A simple assay for frequency of chromosome breaks and loss (micronuclei) by flow cytometry of human reticulocytes," *FASEB J.* 19:485-7.
Office Action for U.S. Appl. No. 11/285,537 dated Feb. 14, 2008.
Peng et al., (Mar. 2002) "Detection of B lymphoma cells undergoing apoptosis by Annexin-V assay," *Chin. Med. Sci. J.* 17:17-21.
Pilsbury, et al., (1969) "Tar and nicotine in cigarette smoke", *J. Assoc. Off. Analytical Chem.*, 52, 458-62.
Poulsen et al. (Sep. 1988) "Dissection of 5' Upstream Sequences for Selective Expression of the Nicotiana plumbaginifolia rbcS-8B Gene", *Mol. Gen. Genet.* 214:16-23.
Rezaian et al., (1988) "Anti-Sense RNAs of Cucumber Mosaic Virus in Transgenic Plants Assessed for Control of the Virus", *Plant Molecular Biology* 11:463-71.
Rodermel et al., (Nov. 1988) "Nuclear-Organelle Interactions: Nuclear Antisense Gene Inhibits Ribulose Bisphosphate Carboxylase Enzyme Levels in Transformed Tobacco Plants", *Cell* 55:673-81.
Saison-Behmoaras et al., (May 1991) "Short modified antisense oligonucleotides directed against Ha-ras point mutation induce selective cleavage of the mRNA and inhibit T24 cells proliferation," *EMBO J.*, 10:1111-1118.
Sambrook et al., (2d Ed. 1989) *Molecular Cloning, A Laboratory Manual* (Cold Spring Harbor Laboratory).
Sanghvi, Y. S., (1993) "Heterocyclic base modifications in nucleic acids and their applications in antisense nucleotides," Chapter 15:273-288, *Antisense Research and Applications, Crooke*, S. T. and Lebleu, B. ed., CRC Press.
Saunders and Bush (Aug. 1979) "Nicotine Biosynthetic Enzyme Activities in *Nicotiana tabacum* L. Genotypes with Different Alkaloid Levels," *Plant Physiol* 64:236.
Shea et al., (Jul. 1990) "Synthesis, hybridization properties and antiviral activity of lipid-oligodeoxynucleotide conjugates" *Nuc. Acids Res.*, 18:3777-3783.

(56) References Cited

OTHER PUBLICATIONS

Shillito et al., (1987) "Direct Gene Transfer to Protoplasts of Dicotyledonous and Monocotyledonous Plants by a Number of Methods, Including Electroporation", *Methods in Enzymology* 153, pp. 313-336.

Siminsky et al, (Aug. 2005) Conversion of nicotine to nornicotine in Nicotiana tabacum is mediated by CYP82E4, a Cytochrome P450 Monooxytenase, *Proc. Natl. Acad. Sci. USA*, 102:14919-14924.

Sinkó, Ildikó et al. (Jun. 2005), "Effect of cigarette smoking on DNA damage of human cumulus cells analyzed by comet assay", *Reproductive Toxicology*, 20:65-71.

Smith et al, (Sep. 2000) "Total silencing by intron-spliced hairpin RNAs", *Nature*, 407:319-320.

Smith et al., (1987) "Cell and tissue specific expression localized by in situ RNA hybridization in floral tissues," *Plant Mol. Biol. Rep.* 5:237-241.

Smith et al., (Aug. 1988) "Antisense RNA Inhibition of Polygalacturonase Gene Expression in Transgenic Tomatoes", Nature 334:724-26.

Smolewski et al., (Sep. 2001) "Micronuclei assay by laser scanning cytometry," *Cytometry* 45:19-26.

Soldani et al. (2001) "Two-color fluorescence detection of Poly (ADP-Ribose) Polymerase-1 (PARP-1) cleavage and DNA strand breaks in etoposide-induced apoptotic cells," *Eur. J. Histochem.* 45:389-92.

Spellman et al., (Dec. 1998) "Comprehensive identification of cell cycle-regulated genes of the yeast *Saccharomyces cerevisiae* by microarray hybridization.," *Mol Biol Cell* 9: 3273-3297.

Sun, Weimin et al., (Jun. 1995) "Effects of exposure to environmental tobacco smoke on a human tracheobronchial epithelial cell line", Toxicology, 100:163-174.

Svab, Z., et al., (1995) "Transgenic tobacco plants by cocultivation of leaf disks with pPZP Agrobacterium binary vectors," in *Methods in Plant Molecular Biology—A Laboratory Manual*, P. Maliga, D. Klessig, A.. Cashmore, W. Gruissem and J. Varner, eds. Cold Spring Harbor Press: 55-77.

Svinarchuk et al., (1993) "Inhibition of HIV proliferation in MT-4 cells by antisense oligonucleotide conjugated to lipophilic groups," Biochimie, 75:49-54.

The Concise Encyclopedia of Polymer Science and Engineering, pp. 858-859, Kroschwitz, J. I., ed. John Wiley & Sons, 1990.

Thomas, et al., (2001) "Size constraints for targeting post-transcriptional gene silencing and for RNA-directed methylation in *Nicotiana benthamiana* using a potato virus X vector," *The Plant Journal* 25(4):417-425.

Tice, et al. (2000) "Single cell gel/comet assay: guidelines for in vitro and in vivo genetic toxicology testing," *Environ. Mol. Mutagen.* 35(3):206-221.

Tounekti et al., (Apr. 1995) "Relationships between DNA fragmentation, chromatin condensation, and changes in flow cytometry profiles detected during apoptosis," Exp. Cell Res. 217:506-16.

Tso, (Sep. 1972) "The loci of alkaloid formation," in Physiology and Biochemistry of Tobacco Plants, pp. 233-234, Dowden, Hutchinson & Ross, Stroudsburg, Pa.

Van Der Krol et al., (Jun. 1988) "An Anti-Sense Chalcone Synthase Gene in Transgenic Plants Inhibits Flower Pigmentation", Nature 333:866-69.

Vermes et al., (Jul. 1995) "A novel assay for apoptosis. Flow cytometric detection of phosphatidylserine expression on early apoptotic cells using fluorescein labelled Annexin V," J. Immunol. Methods 184:39-51.

Wagner and Wagner, (Sep. 1985) "The pyridine-nucleotide cycle in tobacco Enzyme activities for the de-novo synthesis of NAD," *Planta* 165:532.

Wagner et al., (Dec. 1986)"The regulation of enzyme activities of the nicotine pathway in tobacco," *Physiol. Plantarum*, 68:667-72.

Wang, Hangun et al., (Dec. 2001) "Cigarette Smoke Inhibits Human Bronchial Epithelial Cell Repair Processes", Am. J. Respir. Cell Mol. Biol., 25:772-779.

Wilkins et al., (Apr. 2002) "Analysis of radiation-induced apoptosis in human lymphocytes: flow cytometry using Annexin V and propidium iodide versus the neutral comet assay," Cytometry 48:14-9.

Wistuba, et al. (Apr. 2001) "Molecular genetics of small cell lung carcinoma," *Semin Oncol* 28: 3-13, 2001.

Wolz, L. et al., (Jun. 2002) "In vitro genotoxicity assay of sidestream smoke using a human bronchial epithelial cell line", *Food and Chemical Toxicology*, 40:845-850.

Xu et al., (Feb. 2007) Biochemical and molecular characterizations of nicotine demethylase in tobacco, Physiologia Plantarum, 129:307-319.

Yamamoto et al., (Apr. 1991) "Characterization of cis-acting sequences regulating root-specific gene expression in tobacco," *The Plant Cell*3:371.

Yu et al., (Jul. 2002) "Mediation of poly(ADP-ribose) polymerase-1-dependent cell death by apoptosis-inducing factor," *Science* 297:259-63.

Zamzami et al., (Sep. 1999) "Condensed matter in cell death," *Nature* 401:127-128.

Zhang et al. (Jan. 2001) "Microarray analysis of nicotine-induced changes in gene expression in endothelial cells," *Physiol Genomics* 5: 187-192.

Zhou et al., (Apr. 2000) "Effects of soaking temperature and soaking time during preparation of water extract of tea on anticlastogenicity against environmental tobacco smoke in the sister-chromatid exchange assay," *Toxicology Letters* 115:23-32.

Hibi, et al., "Gene Expression in Tobacco Low-Nicotine Mutants," The Plant Cell, vol. 6, pp. 723-735 (May 1994)—1994 American Society of Plant Physiologists.

Shoji, et al., "Expression Patterns of Two Tobacco Isoflavone Reductase-Like Genes and Their Possible Roles in Secondary Metabolism in Tobacco," Plant Molecular Biology, vol. 50, pp. 427-440 (2002). 2002 Kluwer Academic Publishers. Printed in the Netherlands.

\* cited by examiner

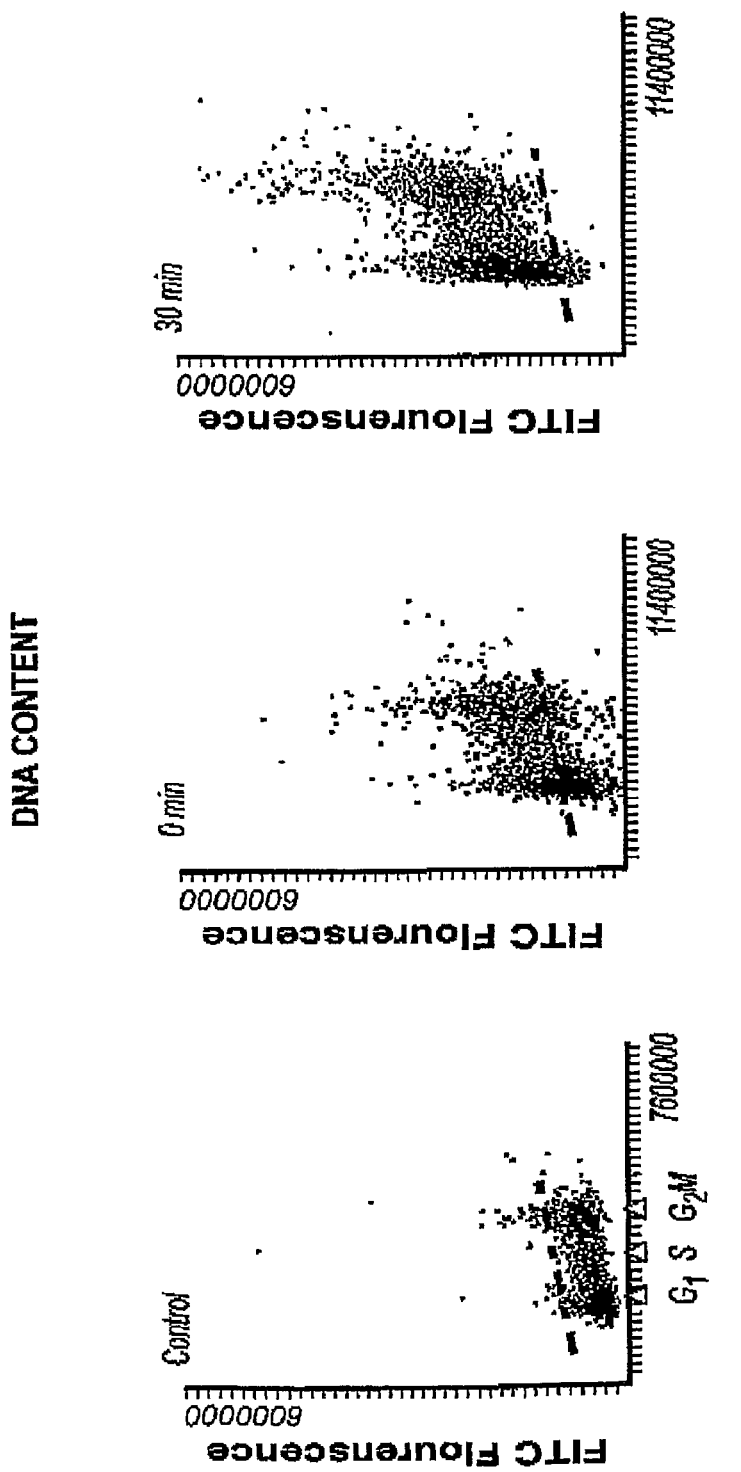

REDUCED RISK TOBACCO PRODUCTS AND METHODS OF MAKING SAME

CROSS-REFERENCE TO RELATED APPLICATIONS

The present application is a continuation of U.S. application Ser. No. 15/243,675, filed Aug. 22, 2016, which is a continuation of U.S. application Ser. No. 14/102,340, filed Dec. 10, 2013, now U.S. Pat. No. 9,439,452, which is a continuation of U.S. application Ser. No. 11/913,870, filed Mar. 25, 2011, now abandoned, which is a 371 entry into the U.S. of Paris Convention Application No. PCT/US2006/018065, filed May 10, 2006, which claims the benefit of priority to U.S. Provisional Application Ser. No. 60/680,283, filed May 11, 2005. Each of the above-mentioned priority documents is incorporated by reference in its entirety into the present application.

FIELD OF THE INVENTION

The invention relates to reduced risk tobacco and tobacco products and methods for detecting, identifying and evaluating such tobacco and tobacco products to determine the potential that these compositions have to contribute to a tobacco-related disease.

BACKGROUND

The leading preventable cause of death and disability in the United States is the chronic use of tobacco products, in particular, cigarettes. In addition to lung cancers, tobacco use plays important direct and indirect roles in the etiology of a wide range of other cancers, including those of the upper aerodigestive tract (i.e., oral cavity, pharynx, larynx, and esophagus), bladder, stomach, kidney, pancreas, uterine cervix, and blood (myeloid leukemia). Exposure to tobacco carcinogens and toxins is also a major cause of other diseases of the pulmonary system (e.g., bronchitis, emphysema, and chronic obstructive pulmonary disease), the cardiovascular system (e.g., stroke, atherosclerosis, and myocardial infarction), and the female reproductive system (e.g., increased risk of miscarriage, premature delivery, low birth weight, and stillbirth). While numerous studies have elucidated some of the biological effects of cigarette smoke that result in its ability to induce this range of pathologies in smokers, little is known about the nature and temporal association of molecular events that drive specific stages in the multi-step processes that result in clinically evident disease. This is due to the fact that cigarette smoke is a complex chemical mixture of gases and suspended particulate material that consists of a wide variety of condensed organic compounds (i.e., 'tar') that collectively contain a large number of toxins, carcinogens, co-carcinogens, mutagens, and reactive organic and inorganic molecules. Thus, there is a pressing need to decrease the health risk caused by tobacco products.

SUMMARY

Embodiments described herein generally relate to tobacco and/or tobacco products having a reduced amount of a harmful compound, and methods of developing, screening and using such tobacco and tobacco products. For example, several approaches are provided to reduce the amount of one or more harmful compounds in tobacco by, for example, modifying the expression of a gene that is involved in the production of a harmful compound in tobacco. Also provided are methods of determining whether the removal of a harmful compound yields a tobacco and/or a tobacco product that has a reduced potential to contribute to a tobacco-related disease. Also provided are reduced-risk tobacco and tobacco products made in accordance with the methods provided herein. Also provided are methods of using the reduced-risk tobacco and tobacco products made in accordance with the methods provided herein.

As described in more detail below, provided herein are nucleic acid molecules and nucleic acid constructs that contain sequences that can be used to inhibit expression of a gene involved in the biosynthesis of a compound associated with a tobacco-related disease. Also provided herein are modified tobaccos and modified tobacco products that have been modified by composition and/or configuration in order to deliver to the user a reduced amount of a compound associated with a tobacco-related disease. Exemplary modified tobaccos are tobaccos that have been genetically modified to contain a reduced amount of a compound associated with a tobacco-related disease. Exemplary genetically modified tobaccos are those containing the nucleic acid molecules or constructs provided herein. Exemplary modified tobacco products are those containing modified tobacco or, those containing a modified filter, where the modification results in delivery to the user of a reduced amount of a compound associated with a tobacco-related disease.

Also provided herein are methods of analyzing tobacco products such as the modified tobacco and modified tobacco products described herein, so as to determine whether the tobacco product is a reduced risk product (e.g., a product that has a reduced propensity to modulate cellular homeostasis, or a reduced level of induction of a cellular marker for a tobacco-related disease). Some of these methods can be practiced, for example, by identifying a compound that is related to a tobacco-related disease (e.g., nicotine or a sterol), removing the compound or a precursor for the compound by modification to the tobacco or tobacco product, and analyzing the ability of the modified tobacco or modified tobacco product to contribute to a tobacco related disease by monitoring the impact of the modified tobacco or modified tobacco product on a marker for cellular homeostasis. In one example, a cellular marker for a tobacco related disease is monitored. In another example, the transcriptome and/or proteome of the cell is monitored. These methods can be used for both in vitro and in vivo testing. That is, the same cellular markers that have been identified in the in vitro studies can be analyzed in smokers that consume reduced risk cigarettes developed according to the methods above and this data can be compared to the impact on the same cellular markers in smokers that consume conventional cigarettes. By these approaches, a cigarette that minimizes the disruptions of the cellular environment of a smoker can be obtained.

Further provided herein are kits that contain the modified tobacco or modified tobacco products provided herein, and smoking cessation programs, which utilize the modified tobacco or modified tobacco products provided herein.

Provided herein are methods of making a tobacco product with a reduced potential to contribute to a tobacco related disease by providing a genetically modified tobacco configured to deliver a reduced amount of a compound that contributes to a tobacco related disease, as compared to a reference tobacco or a conventional tobacco, contacting a mammalian cell with smoke, or a smoke condensate obtained from said genetically modified tobacco, identifying a modulation of homeostasis of said cell, as compared to a control cell, which has been contacted with smoke, or a smoke condensate obtained from said reference tobacco or said conventional tobacco, wherein a decreased modulation of homeostasis in said cell compared to modulation of homeostasis in said control cell indicates a reduction in the potential to contribute to a tobacco related disease, and incorporating said identified genetically modified tobacco into a tobacco product. In some such methods, modulation of homeostasis in the cell is identified by determining the presence, absence or level of a molecular marker in the cell. In some such methods, the mammalian cell is a lung cell or a cell of the oral cavity. In some such methods, the genetically modified tobacco is identified as producing a reduced amount of a compound that contributes to a tobacco related disease, as compared to a conventional tobacco product of the same class or a reference tobacco product of the same class. In some such methods, the genetically modified tobacco is incorporated into a tobacco product that contains a filter, which retains an increased amount of a compound that contributes to a tobacco related disease, as compared to a reference filter or a conventional filter. In some such methods, the genetically modified tobacco comprises a heterologous nucleic acid that inhibits expression of an enzyme in the nicotine biosynthetic pathway. In some such methods, the heterologous nucleic acid inhibits expression of at least two enzymes in the nicotine biosynthetic pathway. In some such methods, the genetically modified tobacco comprises a heterologous nucleic acid that inhibits expression of an enzyme in the sterol biosynthetic pathway. In some such methods, the heterologous nucleic acid inhibits expression of at least two enzymes in the sterol biosynthetic pathway. In some such methods, the genetically modified tobacco comprises a heterologous nucleic acid that inhibits expression of an enzyme in the nicotine biosynthetic pathway and an enzyme in the sterol biosynthetic pathway. In some such methods, the genetically modified tobacco has a reduced amount of nornicotine and a conventional amount of nicotine. In some such methods, genetically modified tobacco comprises a nucleic acid construct selected from the group consisting of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. Also provided herein are tobacco products made by the method provided herein.

Also provided herein are tobacco products comprising a genetically modified tobacco that comprises a reduced amount of nicotine as compared to a conventional tobacco product of the same class or a reference tobacco product of the same class and a heterologous nucleic acid that inhibits expression of at least two enzymes involved in nicotine biosynthesis. Also provided herein are tobacco products comprising a genetically modified tobacco that comprises a reduced amount of a sterol as compared to a conventional tobacco product of the same class or a reference tobacco product of the same class and a heterologous nucleic acid that inhibits expression of an enzyme involved in sterol biosynthesis. In some such tobacco products, the genetically modified tobacco comprises a nucleic acid construct as described herein. In some such tobacco products, the genetically modified tobacco comprises a nucleic acid construct selected from the group consisting of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

In the methods and tobacco products provided herein, the genetically modified tobacco comprises a reduced activity of a gene selected from the group consisting of arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), or A622 or comprises an inhibition of a gene that regulates the production of sterol biosynthesis include HMG-CoA reductase, 14alpha demethylase, squalene synthase, SMT2, SMT1, C14 sterol reductase, A8-A7-isomerase, and C4-demethylase. In the methods and tobacco products provided herein, the genetically modified tobacco has reduced production of a compound that contributes to a tobacco related disease which is stable over at least 2, 3, 4, 5, 6, 8, 10, 12, 15, 20, 25, 30, 40 or 50 generations. In the methods and tobacco products provided herein, the genetically modified tobacco has agronomic characteristics suitable for commercial production. In the methods and tobacco products provided herein, the agronomic characteristics are phenotypically different from conventional tobacco, and said agronomic characteristics can be compensated for by conventional agronomic methods. In the methods and tobacco products provided herein, the conventional agronomic methods are selected from the group consisting of irrigation, administration of fertilizer, and administration of nutrients.

Also provided herein are genetically modified tobaccos that produce a reduced amount of a compound that contributes to a tobacco related disease, as compared to a conventional tobacco product of the same class or a reference tobacco product of the same class, comprising a heterologous nucleic acid that inhibits expression of an enzyme in the biosynthetic pathway of a compound that contributes to a tobacco related disease. Also provided herein are reduced risk tobacco products comprising a genetically modified tobacco that produces a reduced amount of a compound that contributes to a tobacco related disease, as compared to a conventional tobacco product of the same class or a reference tobacco product of the same class. In some such tobaccos or tobacco products, the modified tobacco comprises a nucleic acid construct as described herein. In some such tobaccos or tobacco products, the modified tobacco comprises a heterologous nucleic acid that inhibits expression of at least two enzymes in the nicotine biosynthetic pathway. In some such tobaccos or tobacco products, the modified tobacco comprises a heterologous nucleic acid that inhibits expression of at least two enzymes in the sterol biosynthetic pathway.

Also provided herein are methods of making a reduced risk tobacco product by providing a modified tobacco or modified tobacco product configured to deliver to a user a reduced amount of a compound that contributes to a tobacco related disease, as compared to a reference tobacco or tobacco product or a conventional tobacco or tobacco product, contacting smoke or smoke condensate obtained from said modified tobacco or modified tobacco product with a cell, identifying a modulation of homeostasis of said cell, as compared to a control cell, which has been contacted with smoke or a smoke condensate obtained from said reference tobacco or tobacco product or said conventional tobacco or tobacco product, wherein a decreased modulation of homeostasis in said cell compared to modulation of homeostasis in said control cell indicates a reduction in the potential to contribute to a tobacco related disease, and incorporating said modified tobacco or modified tobacco product into said reduced risk tobacco product. In some such methods, modulation of homeostasis in the cell is identified by determining the presence, absence or level of a molecular marker in the cell. In some such methods, the modified tobacco is genetically modified tobacco. In some such methods, the genetically modified tobacco is modified according to the methods provided herein.

Also provided are reduced risk tobaccos as substantially described herein. Also provided are reduced risk tobacco products as substantially described herein. Also provided are uses of the tobaccos or tobacco products provided herein.

Also provided are isolated nucleic acids substantially as described herein. Also provided are isolated inhibition cassettes substantially as described herein.

Also provided is a genetically modified tobacco having a reduced amount of nicotine as compared to conventional tobacco, further comprising a heterologous nucleic acid that encodes a gene that produces a composition selected from the group consisting of a medicinal compound, industrial oil, or dietary supplement, wherein said composition is substantially not present in conventional or wild-type tobacco. In some such tobaccos, the medicinal compound is an antibody or fragment thereof or an immunogenic preparation. In some such tobaccos, the medicinal compound is a vaccine preparation. In some such tobaccos, the medicinal compound is a veterinary product.

Also provided are genetically modified tobaccos that produce a reduced amount of a compound that contributes to a tobacco related disease, as compared to a conventional tobacco product of the same class or a reference tobacco product of the same class, comprising a heterologous nucleic acid that inhibits expression of an enzyme in the biosynthetic pathway of a compound that contributes to a tobacco related disease. Also provided are reduced risk tobacco products comprising a genetically modified tobacco that produces a reduced amount of a compound that contributes to a tobacco related disease, as compared to a conventional tobacco product of the same class or a reference tobacco product of the same class. In some such tobaccos or tobacco products, the compound is nicotine. In some such tobaccos or tobacco products, the compound is a sterol. In some such tobaccos or tobacco products, the compound is a TSNA. In some such tobaccos or tobacco products, the compound is a PAH. In some such tobaccos or tobacco products, the compound is nornicotine. In some such tobaccos or tobacco products, the genetically modified tobacco has a reduced amount of nornicotine and a conventional amount of nicotine. In some such tobaccos or tobacco products, the genetically modified tobacco comprises a nucleic acid construct as described herein. In some such tobaccos or tobacco products, the genetically modified tobacco comprises a nucleic acid construct selected from the group consisting of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some such tobaccos or tobacco products, expression of two or more genes in the biosynthetic pathway of said compound is inhibited. In some such tobaccos or tobacco products, the genetically modified tobacco comprises two or more nucleic acid constructs as described herein. In some such tobaccos or tobacco products, the genetically modified tobacco comprises two or more nucleic acid constructs selected from the group consisting of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. Some such tobaccos or tobacco products comprise reduced activity of a gene selected from the group consisting of arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), or A622 or comprises an inhibition of a gene that regulates the production of sterol biosynthesis include HMG-CoA reductase, 14alpha demethylase, squalene synthase, SMT2, SMT1, C14 sterol reductase, A8-A7-isomerase, and C4-demethylase. Some such tobaccos or tobacco products comprise a genetically modified tobacco for which reduced production of a compound that contributes to a tobacco related disease is stable over at least 2, 3, 4, 5, 6, 8, 10, 12, 15, 20, 25, 30, 40 or 50 generations. Some such tobaccos or tobacco products comprise a genetically modified tobacco having agronomic characteristics suitable for commercial production.

Also provided herein are methods of making a reduced risk tobacco product by providing a modified tobacco or modified tobacco product configured to deliver to a user a reduced amount of a compound that contributes to a tobacco related disease, as compared to a reference tobacco or tobacco product or a conventional tobacco or tobacco product, contacting smoke or smoke condensate obtained from said modified tobacco or modified tobacco product with a cell identifying a modulation of homeostasis of said cell, as compared to a control cell, which has been contacted with smoke or a smoke condensate obtained from said reference tobacco or tobacco product or said conventional tobacco or tobacco product, wherein a decreased modulation of homeostasis in said cell compared to modulation of homeostasis in said control cell indicates a reduction in the potential to contribute to a tobacco related disease, and incorporating said modified tobacco or modified tobacco product into said reduced risk tobacco product. In some such methods, modulation of homeostasis in the cell is identified by determining the presence, absence or level of a molecular marker in the cell. In some such methods, the modified tobacco is genetically modified tobacco. In some such methods, the genetically modified tobacco is modified according to any of methods provided herein. In some such methods, the genetically modified tobacco is identified as producing a reduced amount of a compound that contributes to a tobacco related disease, as compared to a conventional tobacco product of the same class or a reference tobacco product of the same class. In some such methods, the modified tobacco product contains a filter that retains an increased amount of a compound that contributes to a tobacco related disease, as compared to a reference filter or a conventional filter. Also provided herein are reduced risk tobacco products made by any of the methods provided herein. Also provided herein are methods of using a reduced risk tobacco product of any of the methods provided herein to reduce the potential of an individual that smokes to acquire a tobacco related disease comprising identifying an individual in need of a reduced risk tobacco product and providing the individual the tobacco product of the methods provided herein.

Also provided herein are plant cells resistant to norflurazone comprising providing said cell the nucleic acid of SEQ ID No 10, 11, or 12; and also provided herein are method of making the same.

Also provided herein are crops of plants comprising the nucleic acid of SEQ ID No 10, 11, or 12. Also provided herein are methods of cultivation of a crop of plants comprising obtaining plants with the nucleic acid of SEQ ID No 10, 11, or 12, cultivating said plants, and contacting said plants with norflurazone.

Also provided herein are methods of selecting positively transformed plant cells comprising providing the nucleic acid of SEQ ID No 10, 11, or 12 to said plant cells and contacting said plant cells with norflurazone, whereby the cells that survive contact with norflurazone are positively transformed plant cells.

Also provided herein are isolated nucleic acids substantially as described herein. Also provided herein are isolated inhibition cassettes substantially as described herein. Also provided herein are isolated selection cassettes substantially described herein, wherein said selection cassette comprises the sequence of SEQ ID No 10, 11, or 12. Also provided herein are reduced risk tobaccos substantially described herein. Also provided herein are reduced risk tobacco products substantially described herein.

Also provided herein are reduced risk tobacco products comprising a transgenic tobacco that comprises a reduced expression of a plurality of genes that regulate the production of at least two different compounds in said tobacco that contribute to a tobacco related disease. In some such tobacco products, the two different compounds in said tobacco are nicotine and a sterol.

Also provided herein are kits comprising two or more different tobaccos or tobacco products in accordance with any of the methods provided herein. In some such kits, the different tobaccos or tobacco products are differently labeled.

Also provided herein are uses of a tobacco or tobacco product of any of the methods, tobaccos, tobacco products or kits provided herein. Some such uses are tobacco-use cessation methods.

BRIEF DESCRIPTION OF THE DRAWINGS

FIG. 13A-C. Bivariate (cellular DNA content vs cell immunofluorescence) distributions (scatterplots) of A549 cells, mock-treated (B) or exposed for 30 min to tobacco smoke (A, C), immuno-stained either with γH2AX Ab (B,C) or with an isotype control IgG (A). The dashed-line represents the maximal fluorescence level (for 99% cells) of the IgG control.

FIG. 35A shows Clusters that contain 50 or more genes in CSC-A-treated cells. FIG. 35B shows Clusters containing 50 or more genes in CSC-B-treated cells. FIG. 35C shows Clusters containing 50 or more genes in S9-treated cells.

FIG. 44A depicts γH2AX immunofluorescence for the unmodified cigarettes. FIG. 44B depicts γH2AX immunofluorescence for cigarettes containing IM16 tobacco and IM16, Omni® and Quest 3® filters. FIG. 44C depicts γH2AX immunofluorescence for cigarettes containing Omni® tobacco and either an IM16 or Omni® filter. FIG. 44D depicts γH2AX immunofluorescence for cigarettes containing Quest 3® tobacco and either an IM16 or Quest 3® filter.

DETAILED DESCRIPTION

I. Introduction

Figure 1:
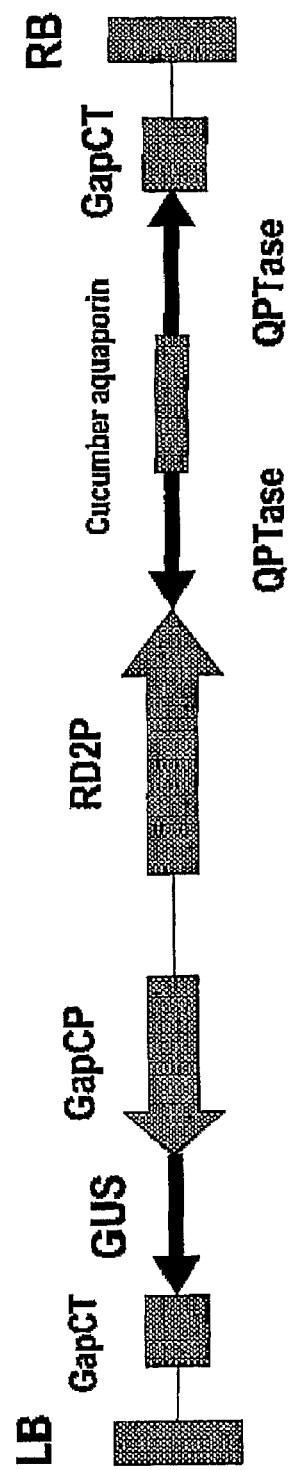
FIG. 1. An illustration of a QPTase inhibition construct comprising a QPTase inhibition cassette including full-length QPTase coding sequence and a GUS selection cassette.

The health consequences of tobacco consumption are known but many people continue to use tobacco products. The addictive properties of tobacco products are largely attributable to the presence of nicotine. In addition to being one of the most addictive substances known, nicotine is also a precursor for a large number of carcinogenic compounds present in tobacco and the body. Many other harmful compounds in addition to nicotine are present in conventional tobacco, however.

There is currently a great interest in developing approaches to decrease the levels of noxious, carcinogenic, or addictive substances including tar, TSNAs, and nicotine in tobacco. Although researchers have developed several approaches to reduce some of these harmful compounds, many conventional techniques result in a product that has poor taste, fragrance, or smoking properties. Some processes, for example, reduce the nicotine content of tobacco by microbial enzymatic degradation, chemical extraction, or high pressure extraction. (See e.g., U.S. Pat. Nos. 4,557,280; 4,561,452; 4,848,373; 4,183,364; and 4,215,706, all of which are hereby expressly incorporated by reference in their entireties). More recently, techniques in genetic engineering and chemically-induced gene suppression have been employed to make reduced nicotine and/or reduced tobacco specific nitrosamine (TSNA) tobacco. (See e.g., Conkling et al., WO98/56923; U.S. Pat. Nos. 6,586,661; 6,423,520; and U.S. patent application Ser. Nos. 09/963,340; 10/356,076; 09/941,042; 10/363,069; 10/729,121; 10/943,346; Timko et al., WO 00/67558, which designated the United States and was published in English, Nakatani et al., U.S. Pat. Nos. 5,684,241; 5,369,023; 5,260,205; and Roberts et al. U.S. Pat. No. 6,700,040, all of which are hereby expressly incorporated by reference in their entireties). In view of the foregoing, and notwithstanding the various efforts exemplified in the above reports, there remains a need for tobacco that has a reduced potential to contribute to a tobacco-related disease and methods of producing such tobacco.

Embodiments provided herein relate to tobacco and/or tobacco products having a reduced amount of a harmful compound, and methods of developing, screening and using such tobacco and tobacco products. Several approaches are provided to reduce the amount of one or more harmful compounds in tobacco by, for example, modifying the expression of a gene that is involved in the production of a harmful compound in tobacco. Also provided are methods of determining whether the removal of a harmful compound yields a tobacco and/or a tobacco product that has a reduced potential to contribute to a tobacco-related disease. Also provided are reduced-risk tobacco and tobacco products made in accordance with the methods provided herein. Also provided are methods of using the reduced-risk tobacco and tobacco products made in accordance with the methods provided herein.

II. Modified Tobacco

Several approaches to create a reduced risk tobacco product having a reduced amount of a harmful compound are described. At least some of the reduced risk tobacco products provided herein contain modified tobacco. As used herein, "modified tobacco" refers to a tobacco that has been subjected to one or more genetic, chemical or processing steps that is different than the conventional treatment or processing of traditional "wild-type" tobacco products. In one example, a tobacco product can be genetically modified, by, for example, administering to a tobacco plant a nucleic acid molecule that modulates expression of one or more genes in the tobacco plant that produce a compound. Genetically modified tobacco and methods of preparing same are provided elsewhere herein. In another example, a tobacco product can be chemically modified, by, for example, extracting or chemically altering one or more components of tobacco, according to methods known in the art as exemplified in U.S. Pat. Nos. 6,789,548, 4,557,280; 4,561,452; 4,848,373; 4,183,364; 4,215,706; 4,257,430; 4,248,251; 4,235,251; 4,216,784; 4,177,822; 4,055,191 (all of which are herein expressly incorporated by reference in their entireties) or by adding one or more compounds to a tobacco plant prior to harvesting the tobacco, as known in the art and exemplified in U.S. Pat. Pub. No. 20050072047, herein expressly incorporated by reference in its entirety. Additional modified tobaccos contemplated herein include reconstituted tobacco, extracted tobacco, and expanded or puffed tobacco. In some embodiments, the tobacco is modified to have a reduced amount of a compound that contributes to a tobacco-related disease, including, but not limited to, a compound associated with a tobacco-related disease or a metabolite thereof (e.g., tobacco sterols, nicotine, a TSNA, and a gene product that is involved in the production of a compound associated with a tobacco-related disease or a metabolite thereof).

The modified tobacco described herein is suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the modified tobacco (e.g., reduced nicotine/TSNA and/or sterol tobacco) described herein can be processed and blended with conventional tobacco so as to create a wide-range of tobacco products with varying amounts of nicotine, TSNAs, and/or sterols.

In some embodiments, the modified tobacco has reduced levels of nicotine, nornicotine, and/or sterols in tobacco. Alkaloids such as nicotine and nornicotine are precursors for a number of harmful compounds that contribute to tobacco-related disease (e.g., the tobacco specific nitrosamines (TSNAs): N'-nitrosonornicotine (NNN), N'-nitrosoanatabine (NAT), N'-nitrosoanabasine (NAB), 4-(N-nitrosomethylamino)-1-(3-pyridyl)-1-butanone (NNK), 4-(N-nitrosomethylamino)-4-(3-pyridyl)-1-butanal (NNA)-4-N-nitrosomethylamino)-1-(3-pyridyl)-1-butanol (NNAL), 4-N-nitrosomethylamino)-4-(3-pyridyl)-1-butanol (iso-NNAL) and/or 4-(N-nitrosomethylamino)-4-(3-pyridyl)-butanoic acid (iso-NNAC) and acrolein). Sterols are precursors for a number of harmful compounds, which are generated by pyrolysis of tobacco, that also contribute to tobacco-related disease (e.g., polycyclic aromatic hydrocarbons (PAHs), such as benz[a]pyrene (BAP), heterocyclic hydrocarbons, terpenes, paraffins, aromatic amines, and aldehydes). Because the presence of these harmful compounds in tobacco contributes to tobacco-related disease, a modified tobacco that comprises a reduced amount of any one of these compounds, as compared to a reference tobacco (e.g., the industry standard reference tobacco IM16 (Philip Morris® USA) or the low tar reference cigarette 2R4F or the ultra low tar cigarette 1R5F, which are Kentucky reference cigarettes that can be obtained from the Tobacco and Health Institute at the University of Kentucky), a conventional tobacco (e.g., a commercially available tobacco of the same class (e.g., "full-flavor" or "light" or "ultra-light")) or a non-transgenic tobacco (e.g., a tobacco of the same variety, such as Burley, Virginia Flue-cured, or Oriental, or strain, such as LA Burley 21, K326, Tn90, Djebe1174, as the transgenic tobacco prior to genetic modification) has a reduced potential to contribute to a tobacco-related disease. Tobacco products comprising the modified tobacco can also be analyzed by various approaches to confirm that the tobacco is "reduced risk," as compared to a parental strain or a reference tobacco using one or more of the assays described herein or otherwise known in the art. This "reduced risk" modified tobacco can then be processed, optionally, sterilized or otherwise made substantially-free of microbes, and said tobacco can be incorporated into tobacco products, preferably, cigarettes, optionally, by an aseptic approach so as to not introduce microbes (e.g., bacteria, mold, yeast, and fungi) into the products. Tobacco products comprising the modified tobacco can then be packaged, optionally, by an aseptic approach in air-tight or microbe-free packaging so as to not introduce microbes into the products.

In this manner, the conversion of alkaloid to TSNA, which results from microbial growth on the tobacco when microbes are introduced during processing, packaging, and storage, is significantly reduced. By using the embodied tobacco preparative methods, which may include several aseptic processing, manufacturing, and packaging procedures, one can maintain an amount of total TSNA (e.g., the collective content of NNN, NAT, NAB, and NNK) in or delivered by (e.g., as measured by FTC or ISO methodologies) a commercially available tobacco product of less than or equal to 0.5 μg/g (e.g., 0.05 μg/g, 0.1 μg, 0.2 μg/g, 0.3 μg/g, 0.4 μg/g, or 0.5 μg/g) for a period of at least 1 week, 1 month, or 1-5 years after packaging or incorporation of the tobacco into a tobacco product (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years).

In some embodiments, a modified tobacco comprising a reduced amount of alkaloid (e.g., a reduced amount of nicotine, nornicotine, and/or TSNAs) is contacted with an exogenous nicotine so as to raise the level of nicotine in the contacted transgenic tobacco in a controlled fashion. By this approach, nicotine levels in transgenic tobacco that comprises a reduced amount of endogenous nicotine (i.e., nicotine that is produced by the transgenic plant from which the transgenic tobacco is obtained) can be selectively raised to levels that are commensurate with conventional full-flavor cigarettes, light cigarettes, or ultra-light cigarettes. (See e.g., WO 2005/018307, which designates the United States and was published in English, herein expressly incorporated by reference in its entirety). For example, modified tobacco comprising a reduced amount of endogenous nicotine and/or TSNAs can be contacted with an amount of exogenous nicotine that is at least, equal to, or more than 0.3 mg/g-20.0 mg/g (nicotine/gram of tobacco). That is, modified tobacco comprising a reduced amount of endogenous nicotine and/or TSNAs can be contacted with an amount of exogenous nicotine that is or delivers (e.g., as measured by FTC or ISO methodologies) at least, equal to, or more than 0.3 mg/g, 0.4 mg/g, 0.5 mg/g, 0.6 mg/g, 0.7 mg/g, 0.8 mg/g, 0.9 mg/g, 1.0 mg/g, 1.1 mg/g, 1.2 mg/g, 1.3 mg/g, 1.4 mg/g, 1.5 mg/g, 1.6 mg/g, 1.7 mg/g, 1.8 mg/g, 1.9 mg/g, 2.0 mg/g, 2.1 mg/g, 2.2 mg/g, 2.3 mg/g, 2.4 mg/g, 2.5 mg/g, 2.6 mg/g, 2.7 mg/g, 2.8 mg/g, 2.9 mg/g, 3.0 mg/g, 3.1 mg/g, 3.2 mg/g, 3.3 mg/g, 3.4 mg/g, 3.5 mg/g, 3.6 mg/g, 3.7 mg/g, 3.8 mg/g, 3.9 mg/g, 4.0 mg/g, 4.1 mg/g, 4.2 mg/g, 4.3 mg/g, 4.4 mg/g, 4.5 mg/g, 4.6 mg/g, 4.7 mg/g, 4.8 mg/g, 4.9 mg/g, 5.0 mg/g, 5.1 mg/g, 5.2 mg/g, 5.3 mg/g, 5.4 mg/g, 5.5 mg/g, 5.6 mg/g, 5.7 mg/g, 5.8 mg/g, 5.9 mg/g, 6.0 mg/g, 6.1 mg/g, 6.2 mg/g, 6.3 mg/g, 6.4 mg/g, 6.5 mg/g, 6.6 mg/g, 6.7 mg/g, 6.8 mg/g, 6.9 mg/g, 7.0 mg/g, 7.1 mg/g, 7.2 mg/g, 7.3 mg/g, 7.4 mg/g, 7.5 mg/g, 7.6 mg/g, 7.7 mg/g, 7.8 mg/g, 7.9 mg/g, 8.0 mg/g, 8.1 mg/g, 8.2 mg/g, 8.3 mg/g, 8.4 mg/g, 8.5 mg/g, 8.6 mg/g, 8.7 mg/g, 8.8 mg/g, 8.9 mg/g, 9.0 mg/g, 9.1 mg/g, 9.2 mg/g, 9.3 mg/g, 9.4 mg/g, 9.5 mg/g, 9.6 mg/g, 9.7 mg/g, 9.8 mg/g, 9.9 mg/g, 10.0 mg/g, 10.1 mg/g, 10.2 mg/g, 10.3 mg/g, 10.4 mg/g, 10.5 mg/g, 10.6 mg/g, 10.7 mg/g, 10.8 mg/g, 10.9 mg/g, 11.0 mg/g, 11.1 mg/g, 11.2 mg/g, 11.3 mg/g, 11.4 mg/g, 11.5 mg/g, 11.6 mg/g, 11.7 mg/g, 11.8 mg/g, 11.9 mg/g, 12.0 mg/g, 12.1 mg/g, 12.2 mg/g, 12.3 mg/g, 12.4 mg/g, 12.5 mg/g, 12.6 mg/g, 12.7 mg/g, 12.8 mg/g, 12.9 mg/g, 13.0 mg/g, 13.1 mg/g, 13.2 mg/g, 13.3 mg/g, 13.4 mg/g, 13.5 mg/g, 13.6 mg/g, 13.7 mg/g, 13.8 mg/g, 13.9 mg/g, 14.0 mg/g, 14.1 mg/g, 14.2 mg/g, 14.3 mg/g, 14.4 mg/g, 14.5 mg/g, 14.6 mg/g, 14.7 mg/g, 14.8 mg/g, 14.9 mg/g, 15.0 mg/g, 15.1 mg/g, 15.2 mg/g, 15.3 mg/g, 15.4 mg/g, 15.5 mg/g, 15.6 mg/g, 15.7 mg/g, 15.8 mg/g, 15.9 mg/g, 16.0 mg/g, 16.1 mg/g, 16.2 mg/g, 16.3 mg/g, 16.4 mg/g, 16.5 mg/g, 16.6 mg/g, 16.7 mg/g, 16.8 mg/g, 16.9 mg/g, 17.0 mg/g, 17.1 mg/g, 17.2 mg/g, 17.3 mg/g, 17.4 mg/g, 17.5 mg/g, 17.6 mg/g, 17.7 mg/g, 17.8 mg/g, 17.9 mg/g, 18.0 mg/g, 18.1 mg/g, 18.2 mg/g, 18.3 mg/g, 18.4 mg/g, 18.5 mg/g, 18.6 mg/g, 18.7 mg/g, 18.8 mg/g, 18.9 mg/g, 19.0 mg/g, 19.1 mg/g, 19.2 mg/g, 19.3 mg/g, 19.4 mg/g, 19.5 mg/g, 19.6 mg/g, 19.7 mg/g, 19.8 mg/g, 19.9 mg/g, and 20.0 mg/g (nicotine/gram tobacco). In some of the aforementioned embodiments, the modified tobacco contacted with the exogenous nicotine is a transgenic tobacco comprising, for example, one or more of the isolated nucleic acids, isolated nucleic acid cassettes, or isolated nucleic acid constructs described herein.

Nicotine-containing fractions, nicotine, or nicotine salts of organic acids are added to the reduced-nicotine transgenic tobacco by contacting said tobacco (e.g., spraying or additive application), with or without propylene glycol, solvent, flavoring, or water at any stage of the harvesting, curing, fermenting, aging, reconstituting, expanding, or otherwise processing of the tobacco, preferably at a stage that is post-cure, when flavorings and additives are provided. By "exogenous nicotine" is meant nicotine, nicotine derivatives, nicotine analogs, nicotine-containing fractions (e.g., extracts of *Nicotiana*), and nicotine salts of organic acids obtained from a source outside of the transgenic tobacco to which the exogenous nicotine is applied. In this manner, a modified tobacco that provides virtually any amount of nicotine can be obtained.

In some embodiments, the exogenous nicotine (e.g., commercially available nicotine salts, liquid, or a nicotine-containing extract prepared from a *Nicotiana* plant or portion thereof) is contacted with a reduced-alkaloid modified tobacco (e.g., a transgenic tobacco comprising a reduced amount of nicotine and/or TSNA as prepared as described herein) after the modified tobacco has been made substantially free of microbes (e.g., bacteria, yeast, mold, or fungi). The reduced alkaloid modified tobacco can be made substantially-free of microbes (e.g., an aseptic preparation) by employing sterilization, heat treatment, pasteurization, steam treatment, gas treatment, and radiation (e.g., gamma, microwave, and ultraviolet). The term "substantially-free of microbes" in some contexts can mean an amount of bacteria, mold, fungi, or yeast that is reduced to the point that the conversion of nicotine or total alkaloid to TSNA is negligible (e.g., the resultant concentration of or the amount of delivered or provided total TSNA (e.g., NNN, NNK, NAT, and NAB) in or delivered by a tobacco or tobacco product is equal to or below 0.5 µg/g (e.g., 0.05 µg/g, 0.1 µg/g, 0.2 µg/g, 0.3 µg/g, 0.4 µg/g, or 0.5 µg/g) after prolonged storage (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years)). The term "substantially-free of microbes" also includes the term "substantially-free of bacteria," which means in some contexts that the tobacco or tobacco product is substantially-free of *Arthrobacter, Proteus*, nicotine oxidizing bacteria, such as P-34, *Pseudomonas, Xantomonas*, or *Zoogloea* strains of bacteria. For example, a tobacco or tobacco product is substantially-free of bacteria or a particular strain of bacteria when said tobacco or tobacco product has less than or equal to 20% of the bacteria or a specific strain of bacteria normally present on the tobacco or tobacco product in the absence of application of a technique to rid the tobacco or tobacco product of bacteria (e.g., less than or equal to 1%, 2%, 3%, 4% 5%, 6%, 7%, 8%, 9%, 10%, 11%, 12%, 13%, 14%, 15%, 16%, 17%, 18%, 19%, or 20%). With respect to modified tobacco described herein, the term "substantially-free of bacteria" can refer to tobacco or a tobacco product containing the modified tobacco that has less than or equal to 20% of the bacteria normally present on the strain of tobacco prior to modification and/or application of a technique to rid the tobacco or tobacco product of bacteria (e.g., less than or equal to 1%, 2%, 3%, 4% 5%, 6%, 7%, 8%, 9%, 10%, 11%, 12%, 13%, 14%, 15%, 16%, 17%, 18%, 19%, or 20%).

Once the exogenous nicotine has been contacted with the microbe-free modified tobacco, it is preferably processed and packaged aseptically and the tobacco product is maintained in an airtight container so as to not re-introduce microbes that convert the exogenous nicotine to TSNAs. By using the aseptic processing, manufacturing, and packaging procedures, described herein, one can maintain an amount of total TSNA (e.g., the collective content of NNN, NAT, NAB, and NNK) in a commercially available tobacco product or delivered by a commercially available tobacco product, which comprises exogenous nicotine, of less than or equal to 0.5 µg/g (e.g., 0.05 µg/g, 0.1 µg, 0.2 µg/g, 0.3 µg/g, 0.4 µg/g, or 0.5 µg/g) for at least 1 week, 1 month, or 1-5 years after packaging (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years). In some embodiments, the exogenous nicotine is contacted with a modified tobacco and a collective content of NNN, NAT, NAB, and NNN that is present or delivered by the tobacco is less than or equal to 0.5 µg/g (e.g., 0.05 µg/g, 0.1 µg, 0.2 µg/g, 0.3 µg/g, 0.4 µg/g, or 0.5 µg/g). In some embodiments, a collective content of NNN, NAT, NAB, and NNN of less than or equal to 0.5 µg/g (e.g., 0.05 µg/g, 0.1 µg, 0.2 µg/g, 0.3 µg/g, 0.4 µg/g, or 0.5 µg/g) in or delivered by a tobacco product containing said transgenic tobacco can be maintained for at least at least 1 week, 1 month, or 1-5 years after packaging (e.g., at least 1-30 days, 30-90 days, 90-180 days, 180-270 days, 270 days-365 days, 1 year-1.5 years, 1.5-2.0 years, 2.0 years-2.5 years, 2.5 years-3.0 years, 3.0 years-4 years, and 4.0 years-5.0 years). An exemplary modified tobacco is transgenic tobacco comprising, for example, one of the nucleic acid constructs described herein. Accordingly, several embodiments address the problem of gradually increasing TSNA levels in alkaloid-containing tobacco products by employing processing, storage, and packaging methods that reduce the amount of microbial flora on the tobacco, limit the re-introduction of microbes during processing and maintain a reduced amount of microbes (e.g., bacteria) once the product is packaged, stored, and sold. Tobacco and tobacco products comprising modified tobacco having a reduced amount of endogenous nicotine and an amount of exogenous nicotine can be analyzed by various methods to confirm that said tobacco and said tobacco products are "reduced risk" or have less of a potential to contribute to a tobacco-related disease, as compared to the parent strain of tobacco having conventional amounts of endogenous nicotine or a reference tobacco.

Tobacco products that comprise a modified tobacco described herein include "full-flavor," "lights," and "ultra light" cigarettes typically having both reduced levels of alkaloids and levels of alkaloids commensurate with a level of alkaloid common to the particular class of cigarette (i.e., a conventional amount of nicotine). The term "tobacco products" includes, but is not limited to, smoking materials (e.g., cigarettes, cigars, pipe tobacco), snuff, chewing tobacco, gum, and lozenges.

The term "reduced risk tobacco product" or "reduced risk tobacco" includes, but is not limited to, a tobacco product or tobacco comprising a modified tobacco that has a reduced amount of a compound that contributes to a tobacco-related disease, or increased amounts of a compound that reduces the harmful effects of a compound that contributes to a tobacco-related disease such as nicotine, nornicotine, a sterol, or the metabolites thereof including, but not limited to, a TSNA, an acrolein, an aldehyde, or harmful compounds generated upon pyrolysis of tobacco, including but not limited to, PAH, BAP, a heterocyclic hydrocarbon, or an aromatic amine, as compared to the amount of these compounds in or generated by a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue-cured, or Oriental) or strain (e.g., LA Burley 21, K326, Tn90, Djebe1174) as the transgenic tobacco prior to genetic modification). For example, a reduced risk tobacco or a reduced risk tobacco product can include a transgenic tobacco or a tobacco product comprising transgenic tobacco that up-regulates fewer genes associated with a tobacco-related disease as compared to a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue-cured, or Oriental) or strain (e.g., LA Burley 21, K326, Tn90, Djebe1174) as the transgenic tobacco prior to genetic modification).

Nitrosamines and Tobacco-Specific Nitrosamines

The term nitrosamine generally refers to any of a class of organic compounds with the general formula $R_2NNO$ or $RNHNO$ (where R denotes an amine-containing group). Nitrosamines are present in numerous foods and have been found to be carcinogenic in laboratory animals. These compounds are formed by nitrosation reactions of amines such as amino acids and alkaloids with nitrites and/or nitrous oxides. By themselves, nitrosamines are not carcinogenic substances, but in mammals nitrosamines undergo decomposition by enzymatic activation to form alkylating metabolites which appear to react with biopolymers to initiate their tumorgenic effect. Thus, by reducing the amount of nitrosamine intake, one has effectively reduced the carcinogenic potential in humans.

Nitrosamines have been identified in tobacco, tobacco products, and tobacco smoke by the use of techniques such as gas chromatography-thermal energy analysis (GC-TEA). Some of these nitrosamines have been identified as tobacco-specific nitrosamines (TSNAs). TSNAs are primarily formed by reactions between the two most abundant alkaloids, nicotine and nornicotine, with nitrous oxides (NOx), and they account proportionately for the highest concentration of nitrosamines in both tobacco products and in mainstream smoke. Of the TSNAs identified, and the subset that have been found to be present in cigarette smoke, the most characterized is N-nitrosamine, 4-(methylnitrosamino)-1-(3-pyridyl)-1-butanone (N-nitrosamine-ketone), or NNK. When injected at relatively high doses, NNK is carcinogenic in rodents. Minimal amounts of TSNAs are found in green tobacco, indicating that TSNA formation may occur during processing steps such as curing, drying, fermentation, burning or storage of tobacco.

TSNA formation is attributed to chemical, enzymatic and bacterial influences during tobacco processing, particularly during curing, fermentation and aging. Nitrosation of nornicotine, anatabine, and anabasine gives the corresponding nitrosamines: N'-nitrosonornicotine (NNN), N'-nitrosoanatabine (NAT) and N'-nitrosoanabasine (NAB). Nitrosation of nicotine in aqueous solution affords a mixture of 4-(N-nitrosomethylamino)-1-(3-pyridyl)-1-butanone (NNK), NNN, and 4-(N-nitrosomethylamino)-4-(3-pyridyl)-1-butanal (NNA). Less commonly encountered TSNAs include NNAL (4-N-nitrosomethylamino)-1-(3-pyridyl)-1-butanol), iso-NNAL (4-N-nitrosomethylamino)-4-(3-pyridyl)-1-butanol, 11) and iso-NNAC (4-(N-nitrosomethylamino)-4-(3-pyridyl)-butanoic acid, 12). See, U.S. Pat. No. 6,135,121, the entire disclosure of which is hereby expressly incorporated by reference in its entirety.

TSNA levels are particularly high in chewing tobaccos and snuff. The partially anaerobic processes that occur during fermentation promote the formation of TSNAs from tobacco alkaloids by promoting increased nitrite levels; in particular, over-fermentation can increase TSNA levels in snuff by its effects on nitrate levels and microbial enzymatic activity. The reduction of the TSNA level in snuff in recent years has been achieved by maintaining a better control over the bacterial content in these products.

Since the nitrate level of tobacco is important for TSNA formation in cigarette smoke, a significant reduction of TSNAs in smoke can be achieved by low-nitrate leaf and stem blends. However, these methods may negatively impact the smokability or the taste of the tobacco. The TSNA content of mainstream smoke can be reduced by as much as 80% by cellulose acetate filters, and it can be reduced still further by filter ventilation.

Air-cured tobaccos such as Burley and dark-fired may have higher levels of TSNAs than certain types of Flue-cured bright, Burley, or dark tobaccos apparently because the high temperatures associated with flue-curing can kill the micro-organisms that transform the alkaloids into TSNAs. In air-cured types, nitrate ($N-NO_3$) is more abundant in the leaf (particularly in the leaf and stems) than in Flue-cured tobacco and the alkaloid content is also much higher. This $N-NO_3$ is reduced to nitrite ($NO_2^-$) by microbes during curing and the $NO_2^-$ can be further reduced to NOx or react directly with alkaloids to form TSNAs.

It is contemplated that, in addition to the techniques described above, nitrate levels in tobacco (especially in the leaf) can be reduced by limiting exposure to nitrosating agents or conditions. Air-curing experiments at a higher temperature have shown that considerably higher levels of N-nitrosamines are formed at a curing temperature of 32° C. than at 16° C., which is associated with a rise of the nitrite level in the tobacco, and may also be associated with a rise in microbial enzymatic activity. Modified curing that involves faster drying from wider spacing or from more open curing structures has been shown to reduce TSNA levels in Burley tobacco. The climatic conditions prevailing during curing exert a major influence on N-nitrosamine formation, and the relative humidity during air-curing can be of importance. Stalk curing results in higher TSNA levels in the smoke than primed-leaf curing. Sun-cured Oriental tobaccos have lower TSNA levels than flue- and air-cured dark tobaccos. Accelerated curing of crude tobaccos such as homogenized leaf curing limits the ability of bacteria to carry out the nitrosation reactions. However, many of the methods described above for reducing TSNAs in Burley tobacco can have undesirable effects on tobacco taste.

TSNA formation in Flue-cured tobacco also results from exposure of the tobacco to combustion gases during curing, where nearly all of the TSNAs in Flue-cured tobacco (e.g., Virginia Flue-cured) result from a reaction involving NOx and nicotine. The predominant source of NOx is the mixture of combustion gases in direct-fired barns. At present, Flue-cured tobacco is predominantly cured in commercial bulk barns. As a result of energy pressures in the U.S. during the 1960's, farmer-built "stick barns" with heat-exchanged flue systems were gradually replaced with more energy efficient bulk barns using direct-fired liquid propane gas (LPG) burners. These LPG direct-fired burner systems exhaust combustion gases and combustion by-products directly into the barn where contact is made with the curing tobacco. Studies indicate that LPG combustion by-products react with naturally occurring tobacco alkaloids to form TSNA.

In contrast to direct-fired curing, heat-exchange burner configurations completely vent combustion gases and combustion by-products to the external atmosphere rather than into the barn. The heat-exchange process precludes exposure of the tobacco to LPG combustion by-products, thereby eliminating an important source of nitrosating agent for TSNA formation, without degrading leaf quality or smoking quality. The use of heat exchangers reduces TSNA levels by about 90%. Steps are being taken to reduce TSNA levels in US tobacco by converting barns to indirect heat through the use of a heat exchanger, but these methods are very expensive. Although many of the approaches described in this section have significant drawbacks, it should be understood that any or all of these techniques can be used with other techniques, as described herein, to make tobacco and tobacco products having reduced TSNAs. The section below provides more detail on nicotine and approaches to reduce nicotine in tobacco.

Nicotine

Nicotine is formed primarily in the roots of the tobacco plant and is subsequently transported to the leaves, where it is stored (Tso, Physiology and Biochemistry of Tobacco Plants, pp. 233-34, Dowden, Hutchinson & Ross, Stroudsburg, Pa. (1972)). Classical crop breeding techniques have produced tobacco with lower levels of nicotine, including varieties with as low as 8% of the amount of nicotine found in wild-type tobacco. The many methods described herein can be used with virtually any tobacco variety but are preferably used with Burley, Oriental or Flue-cured (e.g., Virginia Flue-cured) varieties.

Nicotine is produced in tobacco plants by the condensation of nicotinic acid and 4-methylaminobutanal. Two regulatory loci (Nic1 and Nic2) act as co-dominant regulators of nicotine production. Enzyme analyses of root tissue from single and double Nic mutants show that the activities of two enzymes, quinolate phosphoribosyl transferase ("QPTase") and putrescene methyl transferase (PMTase), are directly proportional to levels of nicotine biosynthesis. An obligatory step in nicotine biosynthesis is the formation of nicotinic acid from quinolinic acid, a step that is catalyzed by QPTase. QPTase appears to be a rate-limiting enzyme in the pathway supplying nicotinic acid for nicotine synthesis in tobacco. (See, eg., Feth et al., *Planta*, 168, pp. 402-07 (1986) and Wagner et al., *Physiol. Plant.*, 68, pp. 667-72 (1986), herein expressly incorporated by reference in its entirety). A comparison of enzyme activity in tobacco tissues (root and callus) with different capacities for nicotine synthesis shows that QPTase activity is strictly correlated with nicotine content (Wagner and Wagner, Planta 165:532 (1985), herein expressly incorporated by reference in its entirety). In fact, Saunders and Bush (Plant Physiol 64:236 (1979), herein expressly incorporated by reference in its entirety), showed that the level of QPTase in the roots of low nicotine mutants is proportional to the level of nicotine in the leaves.

The modification of nicotine levels in tobacco plants by antisense regulation of putrescene methyl transferase expression has been proposed in U.S. Pat. Nos. 5,369,023 and 5,260,205, to Nakatani and Malik, and in PCT application WO 94/28142 and U.S. Pat. No. 5,668,295 to Wahad and Malik, which describe DNA encoding PMT and the use of sense and antisense PMT constructs, the entire disclosures of each of which are hereby expressly incorporated by reference in their entireties. Other genetic modifications proposed to reduce nicotine levels are described in PCT application WO 00/67558, to Timko, and WO 93/05646, to Davis and Marcum; the entire contents of each are hereby expressly incorporated by reference in their entireties. Although these investigators made significant contributions, there were significant drawbacks to their experimental design.

Provided herein are tobacco and tobacco products in which a plurality of genes involved in nicotine biosynthesis are inhibited. Most notably, it is presently revealed that there are several different PMT genes and each may play a role in nicotine biosynthesis. Knocking-out only one PMT gene may create a leaky system allowing the other genes to compensate for the reduction in nicotine biosynthesis. Accordingly, the PMT constructs described herein were designed to inhibit a plurality of different PMT genes. That is, in some embodiments, the PMT constructs described herein are designed to complement common regions to all five of the PMT genes so that inhibition of each of the PMT genes can be accomplished with a single construct. Although many of the approaches described in this section have significant drawbacks, it should be understood that any or all of these techniques can be used with other techniques, as described herein, to make tobacco and tobacco products having reduced nicotine. The section below explains several approaches to reduce the amount of nicotine and sterols in tobacco and tobacco products.

Reducing the Amount of Nicotine and Sterols in Tobacco

As discussed above, TSNAs, nicotine, nornicotine, and sterols contribute significantly to tobacco-related disease, most notably the carcinogenic potential of tobacco and tobacco products. Thus, tobacco and tobacco products that have or produce reduced amounts of these compounds are reduced risk compositions (e.g., products that have a reduced potential to contribute to a tobacco-related disease). Without wishing to be bound by any particular theory, it is contemplated that the creation of tobacco plants, tobacco and tobacco products that have a reduced amount of nicotine will also have reduced amounts of TSNAs. That is, by removing nicotine from tobacco plants, tobacco and tobacco products, one effectively removes the most significant alkaloid substrate for TSNA formation. It was found that the reduction of nicotine in tobacco was directly related to the reduction of TSNAs. Similarly, it is contemplated that by removing sterols from tobacco, one can reduce the amount of PAHs generated from pyrolysis of the tobacco. Unexpectedly, the methods described herein not only produce tobacco with a reduced addictive potential but, concomitantly, produce a tobacco that has a reduced potential to contribute to a tobacco related disease.

It should be emphasized that the phrase "a reduced amount" as applied to nicotine and/or TSNAs is intended to refer to an amount of nicotine and/or TSNAs in a treated or transgenic tobacco plant, tobacco or a tobacco product that is less than what would be found in a tobacco plant, tobacco or a tobacco product from the same variety of tobacco, processed in the same manner, which has not been treated or was not made transgenic for reduced nicotine and/or TSNAs. Thus, in some contexts, wild-type tobacco of the same variety that has been processed in the same manner is used as a control by which to measure whether a reduction in nicotine, nornicotine, a sterol and/or TSNAs or PAHs has been obtained by the inventive methods described herein.

The amount of TSNAs (e.g., collective content of NNN, NAT, NAB, and NNK) and nicotine in wild-type tobacco varies significantly depending on the variety and the manner it is grown, harvested and cured. For example, a cured Burley tobacco leaf can have approximately 30,000 parts per million (ppm) nicotine and 8,000 parts per billion (ppb) TSNA (e.g., collective content of NNN, NAT, NAB, and NNK); a Flue-cured leaf can have approximately 20,000 ppm nicotine and 300 ppb TSNA (e.g., collective content of NNN, NAT, NAB, and NNK); and an Oriental cured leaf can have approximately 10,000 ppm nicotine and 100 ppb TSNA (e.g., collective content of NNN, NAT, NAB, and NNK). Tobacco having a reduced amount of nicotine and/or TSNA, can have no detectable nicotine and/or TSNA (e.g., collective content of NNN, NAT, NAB, and NNK), or may contain some detectable amounts of one or more of the TSNAs and/or nicotine, so long as the amount of nicotine and/or TSNA is less than that found in tobacco of the same variety, grown under similar conditions, and cured and/or processed in the same manner. That is, cured Burley tobacco, as described herein, having a reduced amount of nicotine can have between 0 and 30,000 ppm nicotine and 0 and 8,000 ppb TSNA, desirably between 0 and 20,000 ppm nicotine and 0 and 6,000 ppb TSNA, more desirably between 0 and 10,000 ppm nicotine and 0 and 5,000 ppb TSNA, preferably between 0 and 5,000 ppm nicotine and 0 and 4,000 ppb TSNA, more preferably between 0 and 2,500 ppm nicotine and 0 and 2,000 ppb TSNA and most preferably between 0 and 1,000 ppm nicotine and 0 and 1,000 ppb TSNA. Embodiments of cured Burley leaf prepared by the methods described herein can also have between 0 and 1000 ppm nicotine and 0 and 500 ppb TSNA, 0 and 500 ppm nicotine and 0 and 250 ppb TSNA, 0 and 250 ppm nicotine and 0 and 100 ppb TSNA, 0 and 100 ppm nicotine and 0 and 50 ppb TSNA, 0 and 50 ppm nicotine and 0 and 5 ppb TSNA and some embodiments of cured Burley leaf described herein have virtually no detectable amount of nicotine or TSNA. In some embodiments above, the amount of TSNA refers to the collective content of NNN, NAT, NAB, and NNK.

Similarly, a Flue-cured tobacco embodiment having a reduced amount of nicotine can have between 0 and 20,000 ppm nicotine and 0 and 300 ppb TSNA, desirably between 0 and 15,000 ppm nicotine and 0 and 250 ppb TSNA, more desirably between 0 and 10,000 ppm nicotine and 0 and 200 ppb TSNA, preferably between 0 and 5,000 ppm nicotine and 0 and 150 ppb TSNA, more preferably between 0 and 2,500 ppm nicotine and 0 and 100 ppb TSNA and most preferably between 0 and 1,000 ppm nicotine and 0 and 50 ppb TSNA. Embodiments of Flue-cured tobacco, as described herein, can also have between 0 and 500 ppm nicotine and 0 and 25 ppb TSNA, 0 and 200 ppm nicotine and 0 and 10 ppb TSNA, 0 and 100 ppm nicotine and 0 and 5 ppb TSNA and some embodiments of Flue-cured tobacco have virtually no detectable amount of nicotine or TSNA. In some embodiments above, the amount of TSNA refers to the collective content of NNN, NAT, NAB, and NNK.

Further, a cured Oriental tobacco embodiment having a reduced amount of nicotine can have between 0 and 10,000 ppm nicotine and 0 and 100 ppb TSNA, desirably between 0 and 7,000 ppm nicotine and 0 and 75 ppb TSNA, more desirably between 0 and 5,000 ppm nicotine and 0 and 50 ppb TSNA, preferably between 0 and 3,000 ppm nicotine and 0 and 25 ppb TSNA, more preferably between 0 and 1,500 ppm nicotine and 0 and 10 ppb TSNA and most preferably between 0 and 500 ppm nicotine and no detectable TSNA. Embodiments of cured Oriental tobacco can also have between 0 and 250 ppm nicotine and no detectable TSNA and some embodiments of cured Oriental tobacco have virtually no detectable amount of nicotine or TSNA. In some embodiments above, the amount of TSNA refers to the collective content of NNN, NAT, NAB, and NNK.

Some embodiments comprise cured tobaccos (e.g., Burley, Flue-cured, or Oriental) with reduced amounts of nicotine as compared to control varieties, wherein the amount of nicotine in or delivered by the product (e.g., as measured by FTC or ISO methodologies) is less than about 2 mg/g, 1 mg/g, 0.75 mg/g, 0.5 mg/g or desirably less than about 0.1 mg/g, and preferably less than 0.08 mg/g, 0.07 mg/g, 0.06 mg/g, 0.05 mg/g, 0.04 mg/g, 0.03 mg/g, 0.02 mg/g, 0.01 mg/g. Tobacco products made from these reduced nicotine and TSNA tobaccos are also embodiments. The term "tobacco products" include, but are not limited to, smoking materials (e.g., cigarettes, cigars, pipe tobacco), snuff, chewing tobacco, gum, and lozenges. As mentioned above, these reduced nicotine and TSNA tobaccos can be treated with exogenous nicotine so as to incrementally increase the amount of nicotine in the product and by employing aseptic processing and packaging techniques, the amounts of total TSNAs in the product can be kept at or below 0.5 µg/g for prolonged periods of time.

In some contexts, the phrase "reduced amount of nicotine and/or TSNAs" refers to the tobacco plants, cured tobacco, and tobacco products, as described herein, which have less nicotine and/or TSNAs (e.g., the collective content of NNN, NAT, NAB, and NNK) by weight than the same variety of tobacco grown, processed, and cured in the same way. For example, wild type cured tobacco can have has approximately 1-4% dry weight nicotine and approximately 0.2%-0.8% dry weight TSNA depending on the manner it was grown, harvested and cured. A typical cigarette has between 2-11 mg of nicotine and approximately 5.0 µg of TSNAs. Thus, the tobacco plants, tobacco and tobacco products provided herein can have or deliver, in dry weight for example, less than 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% nicotine and less than 0.01%, 0.015%, 0.02%, 0.025%, 0.03%, 0.035%, 0.04%, 0.045%, 0.05%, 0.055%, 0.06%, 0.065%, 0.07%, 0.075%, and 0.08% TSNA (e.g., collective content of NNN, NAT, NAB, and NNK).

Alternatively, a cigarette provided herein can have or deliver, for example, less than 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, 1.0 mg, 1.1 mg, 1.15 mg, 1.2 mg, 1.25 mg, 1.3 mg, 1.35 mg, 1.4 mg, 1.45 mg, 1.5 mg, 1.55 mg, 1.6 mg, 1.65 mg, 1.7 mg, 1.75 mg, 1.8 mg, 1.85 mg, 1.9 mg, 1.95 mg, 2.0 mg, 2.1 mg, 2.15 mg, 2.2 mg, 2.25 mg, 2.3 mg, 2.35 mg, 2.4 mg, 2.45 mg, 2.5 mg, 2.55 mg, 2.6 mg, 2.65 mg, 2.7 mg, 2.75 mg, 2.8 mg, 2.85 mg, 2.9 mg, 2.95 mg, 3.0 mg, 3.1 mg, 3.15 mg, 3.2 mg, 3.25 mg, 3.3 mg, 3.35 mg, 3.4 mg, 3.45 mg, 3.5 mg, 3.55 mg, 3.6 mg, 3.65 mg, 3.7 mg, 3.75 mg, 3.8 mg, 3.85 mg, 3.9 mg, 3.95 mg, 4.0 mg, 4.1 mg, 4.15 mg, 4.2 mg, 4.25 mg, 4.3 mg, 4.35 mg, 4.4 mg, 4.45 mg, 4.4 mg, 4.45 mg, 4.5 mg, 4.55 mg, 4.6 mg, 4.65 mg, 4.7 mg, 4.75 mg, 4.8 mg, 4.85 mg, 4.9 mg, 4.95 mg, 5.0 mg, 5.5 mg, 5.7 mg, 6.0 mg, 6.5 mgmg, 6.7 mg, 7.0 mg, 7.5 mg, 7.7 mg, 8.0 mg, 8.5 mg, 8.7 mg, 9.0 mg, 9.5 mg, 9.7 mg, 10.0 mg, 10.5 mg, 10.7 mg, and 11.0 mg nicotine and less than 0.001 µg, 0.002 µg, 0.003 µg, 0.004 µg, 0.005 µg, 0.006 µg, 0.007 µg, 0.008 µg, 0.009 µg, 0.01 µg, 0.02 µg, 0.03 µg, 0.04 µg, 0.05 µg, 0.06 µg, 0.07 µg, 0.08 µg, 0.09 µg, 0.1 µg, 0.15 µg, 0.2 µg, 0.25 µg, 0.3 µg, 0.336 µg, 0.339 µg, 0.345 µg, 0.35 µg, 0.375 µg, 0.4 µg, 0.414 µg, 0.45 µg, 0.5 µg, 0.515 µg, 0.55 µg, 0.555 µg, 0.56 µg, 0.578 µg, 0.58 µg, 0.6 µg, 0.611 µg, 0.624 µg, 0.65 µg, 0.7 µg, 0.75 µg, 0.8 µg, 0.85 µg, 0.9 µg, 0.95 µg, 1.0 µg, 1.1 µg, 1.114 µg, 1.15 µg, 1.2 µg, 1.25 µg, 1.3 µg, 1.35 µg, 1.4 µg, 1.45 µg, 1.5 µg, 1.55 µg, 1.6 µg, 1.65 µg, 1.7 µg, 1.75 µg, 1.8 µg, 1.85 µg, 1.9 µg, 1.95 µg, 2.0 µg, 2.1 µg, 2.15 µg, 2.2 µg TSNA (e.g., collective content of NNN, NAT, NAB, and NNK).

Unexpectedly, it was discovered that several methods for reducing endogenous levels of nicotine in a plant are suitable for producing tobacco that is substantially free of nitrosamines, especially TSNAs. Any method that reduces levels of other alkaloids, including norniticotine, is likewise suitable for producing tobacco substantially free of nitrosamines, especially TSNAs. As described, embodiments comprise methods of reducing the carcinogenic potential of a tobacco product comprising providing a cured tobacco as described herein and preparing a tobacco product from said cured tobacco, whereby the carcinogenic potential of said tobacco product is thereby reduced.

In some embodiments that employed the A622 inhibition construct, it was found that transgenic tobacco that had conventional levels of nicotine but significantly reduced levels of nornicotine were produced. This particular line of tobacco is particularly useful because nornicotine may be the most significant precursor for NNN in tobacco. Accordingly, reduced risk conventional cigarettes and other tobacco products (e.g., snuff) comprising the A622 inhibition construct are embodiments.

Other embodiments include the use of the cured tobacco described herein for the preparation of a tobacco product that contains reduced amounts of carcinogens as compared to control varieties and/or that reduces the amount of a TSNA or TSNA metabolite in a human that uses tobacco. In some embodiments, for example, the tobacco smoking products described herein reduce the carcinogenic potential of side stream or main stream tobacco smoke in humans exposed to said side stream or main stream tobacco smoke. By providing the modified cured tobacco described herein in a product that undergoes pyrolysis, for example, the side stream and/or main stream smoke produced by said product comprises a reduced amount of TSNAs and/or nicotine. Thus, the cured tobacco described herein can be used to prepare a tobacco smoking product that comprises a reduced amount of TSNAs in side stream and/or mainstream smoke.

In the United States, tar, nicotine, and carbon monoxide yields are obtained using the Federal Trade Commission (FTC) smoking-machine test method, which defines the measurement of tar as that material captured by a Cambridge pad when a cigarette is machine smoked, minus nicotine and water (Pillsbury, et al., 1969, "Tar and nicotine in cigarette smoke". *J. Assoc. Off. Analytical Chem.*, 52, 458-62). Specifically, the FTC cigarette-testing method collects smoke samples by simulating puffing volumes of 35 ml of cigarette smoke for two seconds every 58 seconds, with none of the filter ventilation holes blocked (if any), until the burn line reaches the tipping paper plus 2 mm, or a line drawn 23 mm from the end of a non-filter cigarette. This FTC smoking-machine test method has been used in the United States since 1967 to determine smoke cigarette yields for tar and nicotine. The determination of carbon monoxide yields in cigarette smoke was added to this method in 1980.

In 1967, when the FTC introduced its testing method, it issued a news release and explained that the purpose of the testing "is not to determine the amount of tar and nicotine inhaled by any human smoker, but rather to determine the amount of tar and nicotine generated when a cigarette is smoked by a machine in accordance with the prescribed method." Nevertheless, the method serves an important role in providing an accurate way to rank and compare cigarettes according to tar, nicotine and carbon monoxide yields.

The International Standards Organization (ISO) developed a very similar smoking-machine test method for tar, nicotine, and carbon monoxide yields of cigarettes (ISO, 1991 "Cigarettes—determination of total and nicotine-free dry particulate matter using a routine analytical smoking machine" ISO: 4387:1991).

The FTC and ISO smoking methods differ in the following eight areas.

The FTC method specifies laboratory environmental conditions of 75° F.±1° F. (23.8° C.±1° C.) and a relative humidity of 60%±2% for both the equilibration and testing. The time of equilibration is a minimum of 24 hours and a maximum of 14 days. This is compared to the ISO specifications of 22° C.±1° C. and 60%±2% relative humidity for equilibration, 22° C.±2° C. and 60% relative humidity±5% for testing. The equilibration time is a minimum of 48 hours and a maximum of 10 days.

The FTC defines the cigarette butt length as a minimum of 23 millimeters or the tipping paper plus three millimeters whichever is longer. ISO defines butt length as the longest of 23 millimeters or tipping paper plus three millimeters or the filter plus eight millimeters. Both methods specify a 23-millimeter butt length for non-filter cigarettes.

ISO defines the position of the ashtray at 20-60 millimeters below the cigarettes in the smoking machine. FTC does not specify a position.

ISO specifies a two-piece snap together reusable filter holder. This filter holder contains the Cambridge pad and uses a synthetic rubber perforated washer to partly obstruct the butt end of the cigarette. The FTC method defines the use of a Cambridge filter pad but does not specify a filter pad holder assembly.

The ISO method specifies airflow across the cigarettes at the cigarette level. FTC specifies the use of a monitor cigarette to adjust airflow.

The ISO procedure defines the process of wiping the excess total particulate matter (TPM) out of the used filter holder. The inner surfaces of the filter holder are wiped with two separate quarters of an unused conditioned filter pad. The FTC method uses the backside (the side opposite of the trapped TPM) to wipe the inner surface of the filter holder.

ISO specifies using 20 ml per Cambridge pad of extraction solution to analyze nicotine and water in TPM. The FTC procedure defines 10 ml per Cambridge pad.

ISO defines the internal standards for the gas chromatographic determination of nicotine and water. The FTC procedure does not specify the internal standards.

These differences typically result in slightly lower measured deliveries for the ISO Method versus the FTC Method. The measured values between FTC and ISO methods are within the detection limits of the test or about no greater than 0.4 mg tar and about 0.04 mg nicotine for cigarettes that yield over about 10 mg.

In some embodiments, for example, the collective content of NNN, NAT, NAB, and NNK in the mainstream or side stream smoke from a tobacco product comprising the modified tobacco, including genetically modified tobacco, described herein is between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g. That is, some embodiments are genetically modified Burley tobacco, wherein the side stream or mainstream smoke produced from a tobacco product comprising said Burley tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

Other embodiments concern modified Flue-cured tobacco, such as genetically modified Flue-cured tobacco, wherein the sidestream or mainstream smoke produced from a tobacco product comprising said Flue-cured tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

More embodiments concern modified Oriental tobacco, wherein the sidestream or mainstream smoke produced from a tobacco product comprising said Oriental tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

Additional Tobacco Modifications

Additional modified tobaccos that can be used in the methods and tobacco products provided herein include, but are not limited to, chemically modified tobacco, expanded, extracted, or puffed tobacco, and reconstituted tobacco.

Any of a variety of chemically modified tobaccos can be included in the methods and tobacco products provided herein. For example, the chemical modification can include palladium, or can include an auxin, auxin analog, or jasmonate antagonist (see e.g., U.S. Pat. No. 6,789,548 and U.S. Pat. App. Pub. No. 20050072047, both of which are hereby expressly incorporated by reference in their entirety).

By one approach, a chemically modified tobacco is made as follows. A tobacco is provided and a casing solution is applied thereto. Thereafter, a plurality of metallic or carbonaceous catalytic particles having a mean average or a mode average particle size of less than about 20 microns is applied to the tobacco in a form separate from the casing solution. Next, a nitrate or nitrite source in a form separate from the casing solution and in a form separate from the plurality of metallic or carbonaceous catalytic particles is applied to the tobacco, before, after or simultaneously with applying the plurality of particles but after applying the casing solution, whereby a smoking composition is obtained. In some embodiments of this modified tobacco, a polyaromatic hydrocarbon, azaarene, carbazole, or a phenolic compound is reduced. Using this approach, the Omni® tobacco product was developed.

By another approach, a chemically modified tobacco is made by identifying a tobacco plant in a field for nicotine reduction; and contacting said tobacco plant with a composition selected from the group consisting of an auxin, auxin analog, and jasmonate antagonist from between about 21 days before topping to about 21 days after topping said tobacco plant, whereby the amount of nicotine in said topped tobacco plant contacted with said composition is below that of a topped tobacco plant of the same variety, grown under the same conditions, which has not been contacted with said composition.

In another example, the chemically modified tobacco can be extracted tobacco. By some approaches the chemically modified tobacco is extracted with an organic solvent and other processes use super-critical fluid extraction or carbon dioxide. In another example, the chemical modification can be a biotic modification. Microbes that ingest nitrates and alkaloids can be applied to tobacco so as to obtain a reduced nicotine tobacco; for example such a biotic modification can include bacteria. In another example, the tobacco is processed to remove the presence of a microbe. In another example the chemically modified tobacco can be sterilized, pasteurized, or radiated.

In another example, the chemically modified tobacco can have added thereto an exogenous component of tobacco or analog thereof. Tobacco can be modified to increase or decrease one or more compounds such as proteins, metabolites, nicotine-related compounds and sterols. In some methods provided herein, a tobacco which has been modified to produce lower levels of one or more compounds such as nicotine or a nicotine metabolite, or a sterol, can have exogenously added thereto, one of these lower-level compounds, one or more but not all lower-level compounds, or all lower-level compounds or an analog of the compound(s).

Such tobaccos with one or more exogenously added compounds can be compared in accordance with the methods provided herein to the same tobacco to which no exogenous compound has been added, to which a different exogenous compound has been added, or to which a different level of the same exogenous compound has been added. For example, the methods provided herein can be used to compare a tobacco that has been genetically modified to produce reduced nicotine levels with the same tobacco to which exogenous nicotine or a nicotine analog has been added thereto. By performing such methods, the role of the exogenously added compound on cell damage or other response determined according to the methods provided herein (e.g., apoptosis or cell proliferation), can be determined.

In another example, the chemically modified tobacco has had added thereto a compound or composition containing antioxidants. Tobacco at any stage of its processing can have added thereto an antioxidant compound or a composition with antioxidant properties. Any of a variety of known antioxidant compounds can be added to the tobacco, including, but not limited to, lycopene, tocopherol, tocopherol metabolites, ascorbic acid, unsaturated fatty acids, N-acetyl cysteine, and other antioxidants known in the art. A composition with antioxidant properties can include a biological composition or extract that can neutralize oxidants, such as milk or milk proteins, tumeric or tumeric extracts, barley or barley extracts, alfalfa or alfalfa extracts. Other compounds that can be added to the tobacco include thiol-containing proteins, plant extracts, aromatic compounds (e.g., caffeine or pentoxyfyllen, which are contemplated to scavenge carcinogens).

Another form of modified tobacco is expanded or puffed tobacco. Included herein are methods to produce reduced-exposure tobacco products by utilizing the tobacco provided herein, deproteinized tobacco fiber, and freeze dried tobacco in any combination and in conjunction with expanded or puffed tobacco. More than 150 patents have been issued related to tobacco expansion (e.g., U.S. Pat. No. 3,991,772, herein expressly incorporated by reference in its entirety). "Expanded tobacco" is an important part of tobacco filler which is processed through expansion of suitable gases so that the tobacco is "puffed" resulting in reduced density and greater filling capacity. It reduces the weight of tobacco used in cigarettes. Advantageously, expanded tobacco reduces tar, nicotine and carbon monoxide deliveries and finds use, for example, in making low tar, low nicotine, and low carbon monoxide delivery cigarettes. Expanded tobacco is particularly useful in making low-tar delivery cigarettes. Carlton® cigarettes, which have had claims of being the lowest tar and nicotine delivery cigarette, are reportedly made with a very large percentage of expanded tobacco. However, use of expanded tobacco also results in reduced nicotine delivery, which can result in compensation.

Any method for expansion of tobacco known in the art can be used in the methods provided herein. The most common method used today incorporates liquid carbon dioxide (U.S. Pat. Nos. 4,340,073 and 4,336,814, herein expressly incorporated by reference in its entirety). Liquid propane has also been used for making commercial cigarettes, predominantly in Europe (U.S. Pat. No. 4,531,529, herein expressly incorporated by reference in its entirety). Liquid propane offers advantages over carbon dioxide since higher 3Q degrees of expansion are possible, in the range of 200%. Under pressure, the liquid carbon dioxide (or liquid propane) permeates the tobacco cell structure. When the tobacco is rapidly heated the carbon dioxide (or liquid propane) expands the cell back to its pre-cured size.

Another form of modified tobacco is reconstituted tobacco. Included herein are methods to produce reduced-exposure tobacco products by utilizing the tobacco provided herein, deproteinized tobacco fiber, and freeze dried tobacco in any combination and in conjunction with reconstituted tobacco. "Reconstituted tobacco" ("Recon") is an important part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

The process to produce sheets of Recon began during the 1950s. U.S. patents that describe such processes include: U.S. Pat. Nos. 3,499,454, 4,182,349 4,962,774, and 6,761,175, herein expressly incorporated by reference in their entirety. Recon is traditionally produced from tobacco stems and/or smaller leaf particles in a process that closely resembles a typical paper making process. The tar and nicotine yields of reconstituted tobacco are lower than those from equivalent quantities of whole tobacco leaf. This process entails processing the various tobacco portions that are to be made into Recon. After the Recon sheets are produced they are cut into a size and shape that resembles cut rag tobacco made from whole leaf tobacco. This cut Recon then gets mixed with cut-rag tobacco and is ready for cigarette making. Cigarettes can be manufactured with all Recon, no Recon, or any combination thereof. Most major brands have at least 10% of Recon in the Filler.

In another embodiment nicotine can be added, or nicotine salts, to produce Recon, which is made from reduced-nicotine transgenic tobacco or any non-tobacco plant material including but not limited to herbal blends so that when the Recon is burned it yields substantially less tobacco-specific nitrosamines and other carcinogens produced from conventional cigarettes, yet satisfactory amounts are nicotine are present.

Processes of removing proteins from tobacco, thereby creating "deproteinized tobacco fiber" are known in the art, as exemplified in U.S. Pat. Nos. 4,289,147 and 4,347,324, herein expressly incorporated by reference in its entirety. Tobacco fiber is a major byproduct after removing protein. The fibrous remains from deproteinized tobacco can be included in any percentage as an ingredient of Recon. Cigarettes made from deproteinized tobacco have a different taste than conventional cigarettes. However, appropriate amounts of additives, including flavorings and nicotine, can be added to help alleviate this taste deficiency.

Cigarettes containing deproteinized tobacco have a significant advantage over conventional cigarettes since they produce reduced levels of carcinogens and harmful combustion products. "A 71% reduction in protein content of a Flue-cured tobacco sheet resulted in an 81% reduction in the TA98 Ames mutagenicity" of the pyrolytic condensate (Clapp, W. L., et al., "Reduction in Ames *Salmonella* mutagenicity of cigarette mainstream smoke condensate by tobacco protein removal", Mutation Research, 446, pg 167-174, 1999). Previous research in this area had determined that tobacco leaf protein might be the principal precursor of mutagens in TSC (Matsumoto, et al., "Mutagenicities of the pyrolysis of peptides and proteins", Mutation Research, 56, pg 281-288, 1978).

Extracting tobacco fiber from genetically modified reduced-nicotine tobacco effectively eliminates virtually all carcinogenic TSNAs in such tobacco, since nitrosamines require relatively high concentrations of nicotine and other alkaloids to form at detectable levels. Therefore, it can be advantageous to utilize reduced-nicotine tobacco in reduced-exposure cigarettes or other tobacco products to further reduce TSNAs. Nicotine can be either left out or introduced later in the process, which can also be in the form of nicotine salts.

PAHs are formed from high temperature pyrolysis of amino acids, sugars, paraffins, terpenes, phytosterols, celluloses and other components of tobacco. Most of these components are greatly reduced in tobacco fiber, effectively reducing formation of PAHs. Catechols and phenols, recognized carcinogenic co-factors in CS, would also be reduced since low levels of soluble sugar are present in tobacco fiber.

Harmful gas phase compounds such as hydrogen cyanide, nitrogen oxides, and carbon monoxide are also reduced when cigarette containing only tobacco fiber is smoked compared to cigarettes made with whole-leaf tobacco. Hydrogen cyanide is formed from burning proteins and chlorophyll. Nitrogen oxides are formed from burning soluble protein, chlorophyll, nitrates, and alkaloids. These components would not be present in significant amounts in deproteinized tobacco. Tobacco fiber has approximately 85 percent less starches and cellulosic material thus reducing the major pyrolytic precursors of carbon monoxide.

In another embodiment, methods are provided to produce reconstituted tobacco that includes extracted tobacco fiber derived from conventional tobacco, reduced-nicotine transgenic tobacco, or increased-nicotine transgenic tobacco.

If the tobacco curing process is circumvented, virtually no TSNAs will be present in traditional tobacco products such as cigarettes, cigar filler or wrapper, roll-your-own tobacco for cigarettes, pipe tobacco, chewing tobacco, snuff, reconstituted tobacco and other preparations made with freeze-dried tobacco would contain virtually no TSNAs since traditional curing processes are eliminated.

In another embodiment TSNAs can be virtually eliminated through processing freshly harvested tobacco using lyophilization. This is accomplished by processing freshly harvested tobacco through freeze-drying units located near tobacco farms. Tobacco processed in this manner can be grown in a traditional fashion with spacing of plants or in a biomass setting. In addition to the economic advantages of eliminating the costs associated with the curing process, the tobacco can now be grown in a biomass fashion that can create hundreds of thousands of pounds of fresh tobacco per acre.

By growing tobacco in a biomass setting and immediately freeze drying the fresh tobacco for cigarettes, roll-your-own-tobacco, pipe tobacco, cigar filler or wrapper, chewing tobacco, snuff, and other versions of smokeless tobacco, labor is reduced not only by eliminating the transplant of each plant from greenhouse to the field but also by eliminating traditional harvesting and curing of the tobacco. Also, farmland needed for this purpose is greatly reduced. The yield of tobacco from one acre of tobacco grown in biomass is equivalent to approximately 100 acres of tobacco grown in a traditional manner.

"Tobacco biomass" is achieved by directly sowing an acre of land with copious quantities of tobacco seed within a few inches of each other in the field. Unlike tobacco planted with traditional spacing, individual plants can no longer be differentiated when tobacco is planted in a biomass fashion. An acre of tobacco biomass has the appearance of a continuous, dense, green carpet. U.S. Pub. Pat. App. No. 20020197688, herein expressly incorporated by reference in its entirety, describes such methods.

Lyophilization removes most of the water (~80%) from the weight of fresh harvested tobacco biomass. The result is Freeze Dried Tobacco ("FDT"). FDT is easily pulverized into fine particles suitable for processing into Recon. This Recon can be cut and made into any type of tobacco product such as filler for cigarettes, roll-your-own-tobacco, pipe tobacco, cigar filler or wrapper, chewing tobacco, snuff, and other forms of smokeless tobacco. Flavorings and additives, including sugars, can be incorporated into the recon process.

Such Recon can be made from 100 percent FDT or in any proportion that consumers prefer. The lyophilization process can have adverse affects on the taste of such tobacco products. Therefore, FDT can even be mixed in any percentage with traditional pulverized, cured tobacco so that the mixture can be made into Recon. Alternatively, FDT can be mixed in any percentages with any forms of traditional tobacco conducive to manufacturing cigarettes, roll-your-own tobacco, pipe tobacco, and cigar filler or wrapper, chewing tobacco, snuff and other versions of smokeless tobacco in order to satisfy the tastes of the mass market.

In another embodiment, genetically modified reduced-nicotine tobacco can be used for reducing TSNAs as described elsewhere herein, thereby creating an additional benefit of such cigarettes, roll-your-own-tobacco, pipe tobacco, cigar filler or wrapper, chewing tobacco, snuff and other versions of smokeless tobacco being non-addictive and without any TSNAs.

In another embodiment, nicotine can be added, in amounts that deliver the desired physiological response, back to the FDT for uses in cigarettes, cigar filler or wrapper, roll-your-own tobacco for cigarettes, pipe tobacco, chewing tobacco, snuff, and other versions of smokeless tobacco so that they will contain virtually no TSNAs. Cigarettes produced from tobacco fiber obtained from green leaf cured tobacco.

In another embodiment, *Nicotiana rustica* and/or increased-nicotine transgenic *Nicotiana tabacum* are freeze dried after harvest and are incorporated into recon. The benefits are that the high alkaloid content is preserved for low TNR cigarettes and that the tobacco curing step is saved. Also, the associated increase in TSNAs with high alkaloid tobaccos will not materialize. Preferred tobaccos for use with the methods described herein include genetically modified tobaccos as described in the following sections.

Curing

The curing process, which typically lasts about 1 week, brings out the flavor and aroma of tobacco. Several methods for curing tobacco may be used, and indeed many methods have been previously disclosed. For example, U.S. Pat. No. 4,499,911 to Johnson; U.S. Pat. No. 5,685,710 to Martinez Sagrera; U.S. Pat. No. 3,905,123 to Fowler; U.S. Pat. No. 3,840,025 to Fowler; and U.S. Pat. No. 4,192,323 to Home describe aspects of the tobacco curing process which may be used for some embodiments provided herein. Conventionally, "sticks" that are loaded with tobacco are placed into bulk containers and placed into closed buildings having a heat source known as a curing barn. A flue is often used to control the smoke (thus earning the term "Flue-cured"). The method of curing will depend, in some cases, on the type of tobacco-use cessation product desired, (i.e., snuff, cigarettes, or pipe tobacco may preferably utilize different curing methods) and preferred methods may vary from region to region and in different countries. In some approaches, the stems and midveins of the leaf are removed from the leaves prior to curing to yield a high quality, low TSNA tobacco product.

"Flue-curing" is a popular method for curing tobacco in Virginia, North Carolina, and the Coastal Plains regions of the United States. This method is used mainly in the manufacture of cigarettes. Flue-curing requires a closed building equipped with a system of ventilation and a source of heat. The heating can be direct or indirect (e.g., radiant heat). When heat and humidity are controlled, leaf color changes, moisture is quickly removed, and the leaf and stems dry. Careful monitoring of the heating and humidity can reduce the accumulation of TSNAs.

Another curing method is termed "air-curing". In this method, an open framework is prepared in which sticks of leaves (or whole plants) are hung so as to be protected from both wind and sun. Leaf color changes from green to yellow, as leaves and stems dry slowly.

"Fire-curing" employs an enclosed barn similar to that used for flue-curing. The tobacco is hung over low temperature fire so that the leaves cure in a smoke-laden atmosphere. This process uses lower temperatures, so the process may take up to a month, in contrast to flue-curing, which takes about 6 to 8 days.

A further curing method, termed "sun-curing" is the drying of uncovered sticks or strings of tobacco leaves in the sun. The best known sun-cured tobaccos are the so-called Oriental tobaccos of Turkey, Greece, Yugoslavia, and nearby countries.

The curing process, and most particularly the flue-curing process, is generally divided into the following four stages:

A) Firing Up: During this step, the tobacco leaves turn bright lemon-orange in color. This is achieved by a gradual increase in temperature.

B) Leaf Yellowing: In this step any moisture is removed. This creates the "yellowing" of the tobacco. It also prepares the tobacco for drying in the next step.

C) Leaf Drying: Leaf drying, an important step in the curing process, requires much time for the tobacco to dry properly. Additionally, air flow is increased in this step to facilitate the drying process.

D) Stem Drying: The drying process continues, as the stem of the tobacco leaf becomes dried.

The cured tobacco may then be blended with other tobaccos or other materials to create the product to be used for the tobacco-use cessation method. The section below describes typical methods of blending and preparing a tobacco product provided herein.

Tobacco Blending

It may be desirable to blend tobacco of varying nicotine levels to create the cessation product having the desired level of nicotine. This blending process is typically performed after the curing process, and may be performed by conventional methods. Preferred tobacco blending approaches are provided below. In some embodiments, blending of the transgenic tobacco is conducted to prepare the tobacco so that it will contain specific amounts of nicotine, nornicotine, sterol and/or TSNA in specific products. Preferably, the blending is conducted so that tobacco products of varying amounts of nicotine are made in specific products.

A mixture that contains different types of tobacco is desirably substantially homogeneous throughout in order to avoid undesirable fluctuations in taste or nicotine levels. Typically, tobacco to be blended may have a moisture content between 30 and 75%. As an example, the tobacco is first cut or shredded to a suitable size, then mixed in a mixing device, such as a rotating drum or a blending box. One such known mixing device is a tumbling apparatus that typically comprises a rotating housing enclosing mixing paddles which are attached to and, therefore, rotate with the housing to stir the tobacco components together in a tumbling action as the drum turns.

After the desired tobaccos are thoroughly mixed, the resulting tobacco blend is removed from the mixing apparatus and bulked to provide a continuous, generally uniform quantity of the tobacco blend. The tobacco is then allowed to remain relatively undisturbed (termed the "bulking step") for the required period of time before subsequent operations are performed. The bulking step typically takes 30 minutes or less, and may be carried out on a conveyor belt. The conveyor belt allows the blended tobacco to remain in bulk form in an undisturbed condition while it is continuously moving the tobacco blend through the process from the mixing stage to the expansion stage.

The tobacco blend is typically expanded by the application of steam. The tobacco mixture is typically subjected to at least 0.25 pounds of saturated steam at atmospheric conditions per pound of blended tobacco for at least 10 seconds to provide an increase in moisture of at least 2 weight percent to the tobacco blend. After the tobacco blend has been expanded, it is dried. A typical drying apparatus uses heated air or superheated steam to dry the tobacco as the tobacco is conveyed by the heated air or steam stream through a drying chamber or series of drying chambers. Generally, the wet bulb temperature of the drying air may be from about 150 degrees F. to about 211 degrees F. The tobacco blend is typically dried to a moisture content of from about 60% to about 5%. The dried, expanded tobacco blend is then in a suitable mode to be processed into the tobacco-use cessation product as described below.

Some blending approaches begin with tobacco prepared from varieties that have extremely low amounts of nicotine, nornicotine, sterols and/or TSNAs. By blending prepared tobacco from a low nicotine/TSNA variety (e.g., undetectable levels of nicotine and/or TSNAs) with a conventional tobacco (e.g., Burley, which has 30,000 parts per million (ppm) nicotine and 8,000 parts per billion (ppb) TSNA; Flue-cured, which has 20,000 ppm nicotine and 300 ppb TSNA; and Oriental, which has 10,000 ppm nicotine and 100 ppb TSNA), tobacco products having virtually any desired amount of nicotine and/or TSNAs can be manufactured. Other approaches blend only low nicotine/TSNA tobaccos (e.g., genetically modified Burley, genetically modified Virginia Flue-cured, and genetically modified Oriental tobaccos that contain reduced amounts of nicotine and/or TSNAs) and/or low sterol tobaccos (e.g., Burley, Flue-cured, and Oriental). Tobacco products having various amounts of nicotine and/or TSNAs can be incorporated into tobacco-use cessation kits and programs to help tobacco users reduce or eliminate their dependence on nicotine and reduce the carcinogenic potential.

By one approach, a step 1 tobacco product is comprised of approximately 25% low nicotine/TSNA tobacco and 75% conventional tobacco; a step 2 tobacco product can be comprised of approximately 50% low nicotine/TSNA tobacco and 50% conventional tobacco; a step 3 tobacco product can be comprised of approximately 75% low nicotine/TSNA tobacco and 25% conventional tobacco; and a step 4 tobacco product can be comprised of approximately 100% low nicotine/TSNA tobacco and 0% conventional tobacco. By another approach, a step 1 tobacco product is comprised of approximately 25% low sterol/PAH tobacco and 75% conventional tobacco; a step 2 tobacco product can be comprised of approximately 50% low sterol/PAH tobacco and 50% conventional tobacco; a step 3 tobacco product can be comprised of approximately 75% low sterol/PAH tobacco and 25% conventional tobacco; and a step 4 tobacco product can be comprised of approximately 100% low sterol/PAH tobacco and 0% conventional tobacco. By another approach, a step 1 tobacco product is comprised of approximately 25% low sterol/PAH and low nicotine/TSNA tobacco and 75% conventional tobacco; a step 2 tobacco product can be comprised of approximately 50% low sterol/PAH and low nicotine/TSNA tobacco and 50% conventional tobacco; a step 3 tobacco product can be comprised of approximately 75% low sterol/PAH and low nicotine/TSNA tobacco and 25% conventional tobacco; and a step 4 tobacco product can be comprised of approximately 100% low sterol/PAH and low nicotine/TSNA tobacco and 0% conventional tobacco. A tobacco-use cessation kit can comprise an amount of tobacco product from any combination of the aforementioned blends to satisfy a consumer for a single month program. That is, if the consumer is a one pack per day smoker, for example, a single month kit would provide 7 packs from each step, a total of 28 packs of cigarettes. Each tobacco-use cessation kit would include a set of instructions that specifically guide the consumer through the step-by-step process. Of course, tobacco products having specific amounts of nicotine, TSNA, sterol and/or PAH would be made available in conveniently sized amounts (e.g., boxes of cigars, packs of cigarettes, tins of snuff, and pouches or twists of chew) so that consumers could select the amount of nicotine, TSNA, sterol and/or PAH they individually desire. There are many ways to obtain various low nicotine/low TSNA and/or low sterol/low PAH tobacco blends using the tobaccos and teachings described herein and the following is intended merely to guide one of skill in the art to one possible approach.

To obtain a step 1 tobacco product, which is a 25% low nicotine/TSNA blend, prepared tobacco from an approximately 0 ppm nicotine/TSNA tobacco can be mixed with conventional Burley, Flue-cured, or Oriental in a 25%/75% ratio respectively to obtain a Burly tobacco product having 22,500 ppm nicotine and 6,000 ppb TSNA, a Flue-cured product having 15,000 ppm nicotine and 225 ppb TSNA, and an Oriental product having 7,500 ppm nicotine and 75 ppb TSNA. Similarly, to obtain a step 2 product, which is 50% low nicotine/TSNA blend, prepared tobacco from an approximately 0 ppm nicotine/TSNA tobacco can be mixed with conventional Burley, Flue-cured, or Oriental in a 50%/50% ratio respectively to obtain a Burly tobacco product having 15,000 ppm nicotine and 4,000 ppb TSNA, a Flue-cured product having 10,000 ppm nicotine and 150 ppb TSNA, and an Oriental product having 5000 ppm nicotine and 50 ppb TSNA. Further, a step 3 product, which is a 75%/25% low nicotine/TSNA blend, prepared tobacco from an approximately 0 ppm nicotine/TSNA tobacco can be mixed with conventional Burley, Flue-cured, or Oriental in a 75%/25% ratio respectively to obtain a Burly tobacco product having 7,500 ppm nicotine and 2,000 ppb TSNA, a Flue-cured product having 5,000 ppm nicotine and 75 ppb TSNA, and an Oriental product having 2,500 ppm nicotine and 25 ppb TSNA.

By a preferred method, conventional Virginia Flue-cured tobacco was blended with genetically modified Burley (i.e., Burley containing a significantly reduced amount of nicotine and TSNA) to yield a blended tobacco that was incorporated into three levels of reduced nicotine cigarettes: a step 1 cigarette containing 0.6 mg nicotine, a step 2 cigarette containing 0.3 mg nicotine, and a step 3 cigarette containing less than 0.05 mg nicotine. The amount of total TSNA was found to range between approximately 0.17 µg/g-0.6 µg/g.

In some cigarettes, approximately, 28% of the blend was Virginia Flue-cured tobacco, approximately 29% of the blend was genetically modified (i.e., reduced nicotine Burley), approximately 14% of the blend was Oriental, approximately 17% of the blend was expanded Flue-cured stem, and approximately 12% was standard commercial Recon. The amount of total TSNAs in cigarettes containing this blend was approximately 1.5 µg/g.

It should be appreciated that tobacco products are often a blend of many different types of tobaccos, which were grown in many different parts of the world under various growing conditions. As a result, the amount of nicotine, TSNAs, sterols and PAHs will differ from crop to crop. Nevertheless, by using conventional techniques one can easily determine an average amount of nicotine, TSNA, sterol and PAH per crop used to create a desired blend. It should also be appreciated that reconstituted, expanded, chemically treated, or microbial treated tobacco can be blended with the modified tobacco described herein, such as, for example the transgenic tobacco described herein. By adjusting the amount of each type of tobacco that makes up the blend one of skill can balance the amount of nicotine, TSNA, sterol and/or PAH with other considerations such as appearance, flavor, and smokability. In this manner, a variety of types of tobacco products having varying level of nicotine, TSNA, sterol and/or PAH, as well as, appearance, flavor and smokability can be created.

A. Genetically Modified Tobacco

In some embodiments, the modified tobacco is a genetically modified tobacco. Several approaches to create genetically modified tobacco having a reduced amount of a harmful compound are described. Many embodiments concern nucleic acid constructs that inhibit the expression of a gene, which regulates production of a compound that is associated with a tobacco-related disease. Since these nucleic acid constructs efficiently reduce the presence of a compound that contributes to a tobacco-related disease, the genetically modified tobacco, prepared as described herein, can be used to create a tobacco product, such as a cigarette, snuff or pipe tobacco, which has a reduced potential to contribute to a tobacco-related disease. That is, embodiments provided herein concern reduced risk tobacco products made from reduced risk transgenic tobacco created using the nucleic acid constructs described herein.

More specifically, embodiments provided herein concern nucleic acid constructs that inhibit the expression of a number of genes involved in the synthesis and regulation of the production of nicotine, nornicotine, and/or sterols in tobacco. Alkaloids such as nicotine and nornicotine are precursors for a number of harmful compounds that contribute to tobacco-related disease (e.g., the tobacco specific nitrosamines (TSNAs): N'-nitrosonornicotine (NNN), N'-nitrosoanatabine (NAT), N'-nitrosoanabasine (NAB), 4-(N-nitrosomethylamino)-1-(3-pyridyl)-1-butanone (NNK), 4-(N-nitrosomethylamino)-4-(3-pyridyl)-1-butanal (NNA)-4-N-nitrosomethylamino)-1-(3-pyridyl)-1-butanol (NNAL), 4-N-nitrosomethylamino)-4-(3-pyridyl)-1-butanol (iso-NNAL) and/or 4-(N-nitrosomethylamino)-4-(3-pyridyl)-butanoic acid (iso-NNAC) and acrolein). Sterols are precursors for a number of harmful compounds, which are generated by pyrolysis of tobacco, that also contribute to tobacco-related disease (e.g., polyaromatic hydrocarbons (PAHs), such as benz[a]pyrene (BAP), heterocyclic hydrocarbons, terpenes, paraffins and aromatic amines). Because the presence of these harmful compounds in tobacco contributes to tobacco-related disease, a transgenic or genetically modified tobacco that comprises a reduced amount of any one of these compounds, as compared to a reference tobacco has a reduced potential to contribute to a tobacco-related disease.

Other embodiments concern nucleic acid constructs for heterologous expression of a gene that reduces, or is related to production of a compound that reduces, the harmful effect of one or more compounds associated with a tobacco-related disease. Since these nucleic acid constructs introduce or increase the presence of a compound that results in reduction of the harmful effect of a compound associated with a tobacco-related disease, the genetically modified tobacco, prepared as described herein, can be used to create a tobacco product, such as a cigarette, snuff or pipe tobacco, which has a reduced potential to contribute to a tobacco-related disease. That is, embodiments provided herein concern reduced risk tobacco products made from reduced risk transgenic tobacco created using the nucleic acid constructs described herein.

Other embodiments are directed to genetically modified tobacco in which expression of two or more genes in the biosynthetic pathway of a compound associated with a tobacco-related disease is inhibited. Inhibition of two or more genes in the biosynthetic pathway of a compound associated with a tobacco-related disease can be attained by inhibition of two or more genes that act on a substrate at the same step in the biosynthetic pathway (e.g., inhibition of two or more isoforms of a biosynthetic gene) or inhibition of two or more genes that act on a substrate at different steps in the biosynthetic pathway. In such embodiments, the genetically modified tobacco can contain one or more heterologous nucleic acids such as the nucleic acids and constructs provided herein, where the heterologous nucleic acids can contain one or more sequences that can inhibit expression of two or more genes in the biosynthetic pathway of a compound associated with a tobacco-related disease.

Other embodiments are directed to genetically modified tobacco in which the active form of a gene in the biosynthetic pathway of a compound associated with a tobacco-related disease is inhibited. The active form of a gene in the biosynthetic pathway of a compound associated with a tobacco-related disease can be inhibited by any of a variety of methods for inhibiting protein activity, including, but not limited to: knocking out part or all of a gene encoding the endogenous protein using, for example, homologous recombination; and heterologous expression of a dominant negative protein that inhibits the activity of the endogenous protein.

By using the constructs described herein, the amount of harmful compounds in tobacco or the harmful effects thereof, such as alkaloids and sterols, can be reduced or removed and a tobacco product comprising this genetically modified tobacco, with or without exogenous nicotine, will have a reduced potential to contribute to a tobacco-related disease. That is, genetically modified tobacco comprising the constructs described herein can be used to manufacture "reduced risk" tobacco products (e.g., a tobacco product comprising a reduced endogenous nicotine, reduced endogenous nornicotine, and/or reduced sterol tobacco), such as a cigarette, snuff or pipe tobacco, which may have exogenous nicotine incorporated therein.

Accordingly, embodiments provided herein concern genetically modified tobacco and tobacco products containing a tobacco that comprises a genetic modification, which have a reduced amount or are substantially free of a harmful compound including, but not limited to, nicotine, nornicotine, a sterol, an acrolein, an aldehyde, a TSNA selected from the group consisting of N'-nitrosonornicotine (NNN), 4-(N-nitrosomethylamino)-1-(3-pyridyl)-1-butanone (NNK), N'-nitrosoanatabine (NAT), and/or N'-nitrosoanabasine (NAB) or generate a reduced amount of a PAH, a BAP, a heterocyclic hydrocarbon, an aromatic amine upon pyrolysis, wherein this reduced risk genetically modified tobacco is made by lowering the expression of a gene in said tobaccos with one of the constructs described herein. Preferred embodiments include a transgenic tobacco and a tobacco product (e.g., cigarette) that comprises a cured tobacco comprising a genetic modification and comprising or delivering by FTC method a reduced amount of nicotine or total alkaloid (e.g., below a conventional level of nicotine or total alkaloid typical for the strain of plant, preferably, less than or equal to 3,000 ppm, 2000 ppm, 1000 ppm, or 500 ppm), wherein said genetic modification comprises an inhibition of a gene that regulates the production of nicotine and/or nornicotine, such as arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), or A622 or comprises an inhibition of a gene that regulates the production of sterol biosynthesis include HMG-CoA reductase, 14alpha demethylase, squalene synthase, SMT2, SMT1, C14 sterol reductase, A8-A7-isomerase, or C4-demethylase, using one or more of the constructs described herein.

Preferred embodiments also include a transgenic tobacco and a tobacco product (e.g., cigarette, snuff or pipe tobacco) that comprises a cured tobacco comprising a genetic modification and a reduced amount of a sterol (e.g., comprises an amount of sterol or delivers and amount of sterol that is below a conventional level of said sterol typical for the strain of plant) wherein said genetic modification comprises an inhibition of a gene that regulates the production of a sterol in tobacco using one or more of the constructs described herein. Related embodiments include a transgenic tobacco and tobacco product made therefrom (e.g., a cigarette, snuff or pipe tobacco) that upon pyrolysis generates a reduced amount of a PAH, BAP, a heterocyclic hydrocarbon, or an aromatic amine, as compared to that generated by a reference tobacco or reference tobacco product (e.g., IM16, 2R4F or 1R5F), a commercially available tobacco product of the same class (e.g., full-flavor, lights, and ultra-lights), or, preferably, a tobacco of the same variety (e.g., Burley, Virginia Flue-cured, or Oriental) or strain (e.g., LA Burley 21, K326, Tn90, Djebe1174) as the transgenic tobacco prior to genetic modification).

Preferred embodiments also include a transgenic tobacco and a tobacco product (e.g., cigarette, snuff or pipe tobacco) that comprises a cured tobacco comprising a genetic modification and a reduced amount of nicotine or total alkaloid and a sterol (e.g., comprise or provides an amount of nicotine or total alkaloid an/or sterols that is below a conventional level of nicotine, total alkaloid, or sterol typical for the strain of plant) wherein said genetic modification comprises an inhibition of a gene that regulates the production of both nicotine and sterols in tobacco. That is, embodiments provided herein concern isolated nucleic acids, isolated nucleic acid cassettes, and isolated nucleic acid constructs that inhibit the expression of a plurality of genes that regulate the production of nicotine and TSNAs, isolated nucleic acids, isolated nucleic acid cassettes, and isolated nucleic acid constructs that inhibit the expression of a plurality of genes that regulate the production of sterols and, thus PAHs, and isolated nucleic acids, isolated nucleic acid cassettes, and isolated nucleic acid constructs that inhibit the expression of a plurality of genes that regulate the production of nicotine and TSNAs and sterols and, thus, PAHs (e.g., a double knock-out of at least two different genes that regulate the production of at least two different harmful compounds in tobacco).

In some embodiments, the tobacco that is substantially free or comprises a reduced amount of nicotine, nornicotine, TSNAs, sterols, and/or produces a reduced amount of PAHs upon pyrolysis is made by exposing at least one tobacco cell of a selected variety (e.g., Burley, Virginia Flue-cured, or Oriental) to an exogenous nucleic acid construct encoding an interfering RNA comprising an RNA duplex that comprises a first strand having a sequence that is substantially similar or identical to at least a portion of the coding sequence of a target gene and/or target gene product involved in nicotine biosynthesis or sterol biosynthesis, and a second strand that is complementary or substantially complementary to the first strand. In some embodiments, the nucleic acid construct further comprises a nucleotide sequence encoding the interfering RNA operably linked to a promoter operable in a plant cell. The tobacco cell is transformed with the nucleic acid construct, transformed cells are selected and at least one transgenic tobacco plant is regenerated from the transformed cells. The transgenic tobacco plants described herein can contain a reduced amount of anyone of nicotine, nornicotine, TSNAs and/or a sterol as compared to a control tobacco plant of the same variety. In some embodiments, nucleic acid constructs encoding interfering RNAs (RNAi) comprising a first strand having a sequence substantially similar or identical to the entire coding sequence of a target gene and/or target gene product involved in nicotine or sterol biosynthesis, and a second strand that is complementary or substantially complementary to the first strand, are contemplated.

In some embodiments, the genetically modified tobacco provided herein will be genetically stable for at least 2, 3, 4, 5, 6, 8, 10, 12, 15, 20, 25, 30, 40 or 50, or more, generations. For example, the genetically modified tobacco produces a reduced amount of a compound associated with a tobacco related disease for at least 2, 3, 4, 5, 6, 8, 10, 12, 15, 20, 25, 30, 40 or 50, or more, generations. It is contemplated, for example, that crossings of multiple tobaccos each having different genetic modifications that are stable over many generations can be performed so as to obtain a genetically modified tobacco having a reduced level of expression of a plurality of genes that encode precursors for various tobacco related diseases.

In some embodiments, the genetically modified tobacco provided herein will have agronomic characteristics suitable for commercial production. Although in some instances genetically modified tobacco can have agronomic characteristics that are different from conventional tobacco, such a tobacco can be suitable for commercial production because these different agronomic characteristics can be compensated for by employing techniques common to those of skill in the art. That is, although the agronomic characteristics for a genetically modified tobacco created as described herein may differ from those of conventional tobacco, such alterations may not necessarily yield a plant that is no longer suitable for commercial production. For example, a genetically modified tobacco may have a reduced root mass, but tobacco plants having reduced root mass can nevertheless be suitable for commercial production when such tobaccos are raised under conditions in which the plants are thoroughly irrigated and/or not subjected to drought conditions. Additional nutritional requirements (e.g., nitrogen) may be required. Any of a variety of conventional agronomic methods can be used to produce commercial quantities of a genetically modified tobacco, where such methods include, but are not limited to, irrigation, fertilization, providing nutrients for plant growth, and use of pesticides. As referred to herein, a genetically modified tobacco that is suitable for commercial production is a genetically modified tobacco that, under appropriate agronomic conditions will produce at least 25%, 30%, 40%, 50%, 60%, 70%, 75%, 80%, 85%, 90%, 95%, 100% or more, tobacco useful for creation of a tobacco product relative to an unmodified or conventional tobacco, grown under its standard growing conditions.

1. Genes to Modify

In some embodiments, the gene product is one that is involved in nicotine biosynthesis. Such enzymes include, but are not necessarily limited to, putrescene N-methyltransferase (PMTase), N-methylputrescene oxidase, ornithine decarboxylase, S-adenosylmethionine synthetase, NADH dehydrogenase, phosphoribosylanthranilate isomerase and quinolate phosphoribosyl transferase (QPTase). In preferred embodiments, the gene product that is inhibited using a construct described herein is QPTase, PMTase, and A622. In some embodiments, the tobacco that is made substantially free of nicotine and/or TSNAs (e.g., comprises or delivers less than or equal to 0.5 mg/g nicotine and/or less than or equal to 0.5 µg/g collective content of NNN, NAT, NAB, and NNK) is prepared from a variety of Burley tobacco (e.g., Burley 21 or Tn90), Oriental tobacco (Djebal 174), or Virginia Flue-cured (K326) tobacco. It should be understood, however, that most tobacco varieties can be made to have reduced amounts of nicotine and/or TSNAs or can be made substantially free of nicotine and/or TSNAs by using the embodiments described herein. For example, plant cells of the variety Burley 21 are used as the host for the genetic engineering that results in the reduction of nicotine and/or TSNAs so that the resultant transgenic plants are a Burley 21 variety that has a reduced amount of nicotine and/or TSNAs.

Accordingly, some embodiments concern a tobacco that comprises a genetic modification comprising a reduced amount or a reduced level of expression of QPTase, PMTase, or A622, comprising or delivering a reduced amount of nicotine or total alkaloid and/or a collective content of TSNA (e.g., NNN, NAT, NAB, or NNK) of less than or equal to 0.5 µg/g (e.g., 0.05 µg/g, 0.1 µg/g, 0.2 µg/g, 0.3 µg/g, 0.4 µg/g, or 0.5 µg/g). More embodiments concern a tobacco that comprises or delivers a reduced amount or a reduced level of expression of A622, a normal or conventional amount of nicotine (e.g., comprising or delivering by FTC methodology an amount of nicotine equal to, less than, or greater than 0.9 mg/g, 1.0 mg/g, 1.1 mg/g, 1.2 mg/g, 1.3 mg/g, 1.4 mg/g, 1.5 mg/g, 1.6 mg/g, 1.7 mg/g, 1.8 mg/g, 1.9 mg/g, and 2.0 mg/g), and a reduced amount of nornicotine (e.g., comprising or delivering by FTC methodology an amount of nornicotine less than or equal to 0.5 µg/g), and/or a reduced amount of NNN (e.g., comprising or delivering by FTC methodology an amount of total TSNAs equal to or less than 0.05 µg/g, 0.1 µg/g, 0.2 µg/g, 0.3 µg/g, 0.4 µg/g, or 0.5 µg/g). That is, particular lines of transgenic tobacco containing the A622 inhibition cassette described herein were unexpectedly found to have a reduced level of nornicotine but conventional levels of nicotine. This finding is particularly important since nornicotine may be a more important precursor for NNN than nicotine. (See Carmella et al., Carcinogenesis, Vol. 21, No. 4, 839-843, (April 2000), herein expressly incorporated by reference in its entirety). In other transgenic lines, wherein the A622 gene was inhibited using one of the constructs described herein, it was found that both nicotine and nornicotine were effectively reduced (e.g., total alkaloids were less than or equal to 7,000 ppm, 5000 ppm, 3000 ppm, 1000 ppm, or 500 ppm).

Some of the nucleic acid constructs provided herein employ interfering RNAs (e.g., siRNAs or dsRNAs) that comprise an RNA duplex wherein each RNA portion of the duplex is at least, greater than, or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 750, 1000, 1500, 2000, 2500, or 5000 consecutive nucleotides complementary or substantially complementary to an mRNA that encodes a gene product or the entire coding sequence of the enzyme or complement thereof of an enzyme that regulates nicotine or sterol biosynthesis. In some embodiments, the RNA duplex comprises a first RNA strand that is complementary to an mRNA that encodes a gene product involved in nicotine or sterol biosynthesis and a second RNA stand that is complementary to said first strand. Some interfering RNAs provided herein can comprise two separate RNA strands hybridized to each other by hydrogen bonding. Other interfering RNAs comprise a single RNA strand comprising a first and second regions of nucleotide sequence that are complementary to each other. In such embodiments, the first and second regions of nucleotide sequence are separated by a nucleotide sequence (e.g., a "linker") that permits or, in the case of the FAD2 intron described herein, facilitates formation of a hairpin structure upon hybridization of the first and second regions. This "linker" that permits formation of a hairpin structure is preferably at least, greater than, or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000 or more nucleotides in length.

A preferred method of producing tobacco having a reduced amount of nicotine and TSNAs, involves genetic engineering directed at reducing the levels of nicotine and/or nornicotine or other alkaloids. Any enzyme involved in the nicotine synthesis pathway can be a suitable target for genetic engineering to reduce levels of nicotine and, optionally, levels of other alkaloids including nornicotine. Suitable targets for genetic engineering to produce tobacco having a reduced amount of nicotine and/or nitrosamines, especially TSNAs, include but are not limited to putrescene N-methyltransferase, N-methylputrescene oxidase, ornithine decarboxylase, S-adenosylmethionine synthetase, NADH dehydrogenase, phosphoribosylanthranilate isomerase, quinolate phosphoribosyl transferase (QPTase) or a combination of any of the above targets. Additionally, enzymes that regulate the flow of precursors into the nicotine or sterol synthesis pathway are suitable targets for genetic engineering to produce tobacco with a reduced amount of nicotine and nitrosamines, especially TSNAs, and tobaccos with reduced amounts of sterols, which produce a reduced amount of PAHs upon pyrolysis. Suitable methods of genetic engineering are known in the art and include, for example, the use of antisense and sense suppression technology to reduce or eliminate the production of enzymes, the use of interfering RNA molecules (gene silencing) as described herein to reduce or eliminate the expression of gene products, and the use of random or targeted mutagenesis to disrupt gene function, for example, using T-DNA insertion or EMS mutagenesis. The next section provides more description of these techniques.

2. Modification Methods a) Knockouts

Inhibition of Gene Expression Using Nucleic Acids

Inhibition of gene expression refers to the absence or observable reduction in the level of polypeptide and/or mRNA gene product. Some embodiments provided herein relate to inhibiting the expression of one or more genes involved in the biosynthesis of nicotine, nornicotine, and/or sterols by genetically modifying a plant cell, such as a tobacco cell, by providing the cell with an inhibitory nucleic acid that reduces or eliminates the production of a gene product involved in nicotine or sterol biosynthesis. Inhibitory nucleic acids include, but are not limited to, interfering RNAs, antisense nucleic acids and catalytic RNAs. Some preferred embodiments provided herein relate to interfering RNAs (RNAi).

RNA interference and gene silencing are terms that are used to describe a phenomenon by which the expression of a gene product is inhibited by an interfering RNA molecule. Interfering RNA molecules are double-stranded RNAs (dsRNA) that are expressed in or otherwise introduced into a cell. The dsRNA molecules may be of any length, however, short dsRNA constructs are commonly used. Such constructs are known as small interfering RNAs (siRNA), and are typically 21-23 bp in length.

RNA interference is exhibited by nearly every eukaryote and is thought to function by a highly conserved mechanism (Dillin, A. *PNAS*, 100:6289-91). As with antisense inhibition of gene expression, inhibition mediated by RNA interference is gene specific. However, in contrast to antisense-mediated inhibition, inhibition mediated by interfering RNA appears to be inherited (Dillin, A. *PNAS*, 100:6289-91). Without being bound by theory, it is believed that specificity is achieved through nucleotide sequence interaction between complementary portions of a target mRNA and the interfering RNA. The target mRNA is selected based on the specific gene to be silenced. In particular, the target mRNA, corresponds to the sense strand of the gene to be silenced. An interfering RNA, such as a dsRNA or an siRNA, comprises an RNA duplex, which includes a first strand that is substantially similar or identical to at least a portion of the nucleotide sequence of the target mRNA, and a second strand having a nucleotide sequence that is complementary or substantially complementary to the first strand.

When used herein with reference to an RNA duplex of the interfering RNA, it will be appreciated that the terms "first strand" and "second strand" are used in a relative sense. For example, the first strand of an RNA duplex can be selected to comprise either a nucleotide sequence substantially similar or identical to at least a portion of the nucleotide sequence of the target mRNA or a nucleotide sequence that is complementary or substantially complementary to at least a portion of the nucleotide sequence of the target mRNA. If the first strand is selected to be substantially similar or identical to at least a portion of the nucleotide sequence of the target mRNA, then the second strand will be complementary to at least a portion of the target mRNA because it is complementary to the first strand. If the first strand is selected to be complementary or substantially complementary to at least a portion of the target mRNA, then the second strand will be substantially similar or identical to at least a portion of the nucleotide sequence of the target mRNA because it is complementary to the first strand.

As used herein with reference to nucleic acids, "portion" means at least 5 consecutive nucleotides, at least 6 consecutive nucleotides, at least 7 consecutive nucleotides, at least 8 consecutive nucleotides, at least 9 consecutive nucleotides, at least 10 consecutive nucleotides, at least 11 consecutive nucleotides, at least 12 consecutive nucleotides, at least 13 consecutive nucleotides, at least 14 consecutive nucleotides, at least 15 consecutive nucleotides, at least 16 consecutive nucleotides, at least 17 consecutive nucleotides, at least 18 consecutive nucleotides, at least 19 consecutive nucleotides, at least 20 consecutive nucleotides, at least 21 consecutive nucleotides, at least 22 consecutive nucleotides, at least 23 consecutive nucleotides, at least 24 consecutive nucleotides, at least 25 consecutive nucleotides, at least 30 consecutive nucleotides, at least 35 consecutive nucleotides, at least 40 consecutive nucleotides, at least 45 consecutive nucleotides, at least 50 consecutive nucleotides, at least 60 consecutive nucleotides, at least 70 consecutive nucleotides, at least 80 consecutive nucleotides, at least 90 consecutive nucleotides, at least 100 consecutive nucleotides, at least 125 consecutive nucleotides, at least 150 consecutive nucleotides, at least 175 consecutive nucleotides, at least 200 consecutive nucleotides, at least 250 consecutive nucleotides, at least 300 consecutive nucleotides, at least 350 consecutive nucleotides, at least 400 consecutive nucleotides, at least 450 consecutive nucleotides, at least 500 consecutive nucleotides, at least 600 consecutive nucleotides, at least 700 consecutive nucleotides, at least 800 consecutive nucleotides, at least 900 consecutive nucleotides, at least 1000 consecutive nucleotides, at least 1200 consecutive nucleotides, at least 1400 consecutive nucleotides, at least 1600 consecutive nucleotides, at least 1800 consecutive nucleotides, at least 2000 consecutive nucleotides, at least 2500 consecutive nucleotides, at least 3000 consecutive nucleotides, at least 4000 consecutive nucleotides, at least 5000 consecutive nucleotides or greater than at least 5000 consecutive nucleotides. In some preferred embodiments, a portion of a nucleotide sequence is between 20 and 25 consecutive nucleotides. In other preferred embodiments, a portion of a nucleotide sequence is between 21 and 23 consecutive nucleotides. In some embodiments provided herein, a portion of a nucleotide sequence includes the full-length coding sequence of the gene or the target mRNA.

Some preferred interfering RNAs that are described herein comprise an RNA duplex, which comprises a nucleotide sequence that is substantially similar or identical to at least a portion of the coding strand of a gene involved in nicotine or sterol biosynthesis. Although nucleic acid sequences that are substantially similar or identical to at least a portion of the coding strand of the target gene involved in nicotine biosynthesis are preferred, it will be appreciated that nucleotide sequences with insertions, deletions, and single point mutations relative to the target sequence are also effective for inhibition of gene expression. Sequence identity may be determined by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the interfering RNA and a portion of the target gene is preferred. In especially preferred embodiments, at least about 21 to about 23 contiguous nucleotides in the target gene are greater than 90% identical to a sequence present in the interfering RNA.

In other embodiments provided herein, the duplex region of the RNA may be defined functionally as including a nucleotide sequence that is capable of hybridizing with a portion of the target gene transcript. Exemplary hybridization conditions are 400 mM NaCl, 40 mM PIPES pH 6.4, 1 mM EDTA, 50° C. or 70° C. hybridization for 12-16 hours; followed by washing.

The modification of nicotine levels in tobacco plants by antisense regulation of putrescene methyl transferase (PMTase) expression has been proposed in U.S. Pat. Nos. 5,369,023 and 5,260,205, to Nakatani and Malik, and in PCT application WO 94/28142 and U.S. Pat. No. 5,668,295 to Wahad and Malik, which describe DNA encoding PMT and the use of sense and antisense PMT constructs, the entire disclosures of each of which are hereby expressly incorporated by reference in their entireties. Other genetic modifications proposed to reduce nicotine levels are described in PCT application WO 00/67558, to Timko, and WO 93/05646, to Davis and Marcum; the entire contents of each are hereby expressly incorporated by reference in their entireties. Although these investigators made significant contributions, there were significant drawbacks to their experimental design.

Provided herein are tobacco and tobacco products in which a plurality of genes involved in nicotine biosynthesis are inhibited. Most notably, it is presently revealed that there are several different PMT genes and each may play a role in nicotine biosynthesis. Knocking-out only one PMT gene can create a leaky system allowing the other PMT genes to compensate for the reduction. Accordingly, each of the PMT constructs described herein were designed to inhibit a plurality of different PMT genes with a single construct. That is, the PMT constructs described herein are designed to complement common regions to all five of the PMT genes so that inhibition of each of the PMT genes can be accomplished with one inhibitory fragment. Although many of the approaches described in this section have significant drawbacks, it should be understood that any or all of these techniques can be used with other techniques, as described herein, to make tobacco and tobacco products having reduced nicotine.

In some embodiments that employed the A622 inhibition construct, it was found that transgenic tobacco that had conventional levels of nicotine but significantly reduced levels of nornicotine were produced. This particular line of tobacco is particularly useful because nornicotine may be the most significant precursor for NNN in tobacco. Accordingly, reduced risk conventional cigarettes and other tobacco products (e.g., snuff) comprising the A622 inhibition construct are embodiments.

As described above, interfering RNAs disclosed herein comprise a sequence that is complementary to at least a portion of the sense strand of a gene encoding a target mRNA, which produces a polypeptide that is involved in nicotine biosynthesis. Preferred targets are the products of the quinolate phosphoribosyltransferase (QTPase) gene, the putrescene N-methyltransferase (PMTase) gene, and the A622 gene. However, it will be appreciated that interfering RNAs specific for other gene products or combinations of gene products involved in nicotine and nornicotine biosynthesis and/or sterol biosynthesis are contemplated. For example, additional gene products involved in nicotine biosynthesis include, but are not limited to, N-methylputrescene oxidase, ornithine decarboxylase, S-adenosylmethionine synthetase, NADH dehydrogenase, and phosphoribosylanthranilate isomerase. Additionally, it will be appreciated that interfering RNAs specific for other gene products or combinations of gene products involved in sterol biosynthesis include HMG-CoA reductase, 14alpha demethylase, squalene synthase, SMT2, SMT1, C14 sterol reductase, A8-A7-isomerase, and C4-demethylase.

Additionally, the interfering RNAs described herein can comprise a plurality nucleotide sequences that are each complementary to different portions of the sense strand of a gene involved in nicotine and/or sterol biosynthesis. Alternatively, the interfering RNAs described herein can comprise a plurality nucleotide sequences that are each complementary to at least a portion of the sense strands of different genes involved in nicotine and/or sterol biosynthesis. Still further, a single RNAi construct or inhibition cassette can be used to inhibit a plurality of genes involved in the regulation of the production of nicotine, nornicotine, or sterols. For example, as described below, it was found that the A622 inhibitory fragment and inhibition cassette (SEQ. ID. Nos. 5 and 26) efficiently reduced production of nicotine and nornicotine in some lines of tobacco and in other lines of tobacco conventional levels of nicotine were maintained but the amount of nornicotine in said tobacco was 0.00 mg/g. Still further, the PMTase inhibitory sequence and PMTase inhibition cassette (SEQ. ID. Nos. 4 and 25) were designed to complement common regions of a plurality of PMTase genes so that the production of multiple gene products can be inhibited or reduced with a single construct.

In still more embodiments, it is contemplated that a single T-DNA containing construct be used to overexpress one gene and, in the same construct, inhibiting expression of a second gene. That is, some embodiments concern constructs, tobacco containing said constructs, and tobacco products containing said tobacco, wherein said constructs comprise an overexpression cassette that comprises a gene that regulates the production of a compound that improves the composition of the tobacco (e.g, overexpression of a gene encoding an antioxidant) and, on the same construct, an inhibition cassette that comprises an inhibitory sequence that reduces the production of a compound that contributes to a tobacco related disease (e.g., nicotine, nornicotine, or a sterol).

In preferred embodiments, the interfering RNAs described herein comprise at least one region of double-stranded RNA (duplex RNA). This duplex RNA can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. Short regions of duplex RNA are often designated siRNA, whereas longer regions of RNA duplex are often termed dsRNA. In some embodiments provided herein, the interfering RNA duplex region is a dsRNA. In other embodiments, the interfering RNA duplex region is an siRNA. In a preferred embodiment, the duplex region about the length of the coding sequence of a target mRNA encoding a polypeptide involved in nicotine biosynthesis.

Interfering RNAs described herein can be generated using a variety of techniques. For example, an interfering RNA can be generated in a host cell in vivo by providing the cell with one or more a nucleic acid constructs that comprise the nucleic acids necessary to encode the strands of a double-stranded RNA. Such constructs can be included in various types of vectors. Exemplary vectors contemplated herein include, but are not limited to, plasmids, viral vectors, viroids, replicable and nonreplicable linear DNA molecules, replicable and nonreplicable linear RNA molecules, replicable and nonreplicable circular DNA molecules and replicable and nonreplicable circular RNA molecules. Preferred vectors include plasmid vectors, especially vector systems derived from the *Agrobacterium* Ti plasmid, such as pCambia vectors and derivatives thereof.

In some embodiments, both strands of the double-stranded region of the interfering RNA can be encoded by a single vector. In such cases, the vector comprises a first promoter operably linked to a first nucleic acid which is substantially similar or identical to at least a portion of the target mRNA. The vector also comprises a second promoter operably linked to a second nucleic acid, which is complementary or substantially to the first nucleic acid.

Another type of single vector construct, which can be used to generate interfering RNA, encodes a double-stranded RNA hairpin. In such embodiments, the vector comprises a promoter operably linked to a nucleic acid that encodes both strands of the duplex RNA. The first nucleotide sequence, which encodes the strand that is substantially similar or identical to at least a portion of the target mRNA, is separated from the second nucleotide sequence, which encodes a strand complementary or substantially complementary to the first strand, by a region of nucleotide sequence that does not substantially hybridize with either of the strands. This nonhybridizing region permits the RNA sequence transcribed from the vector promoter to fold back on itself, thereby permitting the complementary RNA sequences to hybridize so as to produce an RNA hairpin. Vectors comprising a plurality of nucleic acids, each of which encode both strands of the duplex RNA are also contemplated.

Other embodiments provided herein relate to multiple vector systems for the production of interfering RNA. In one example, a multiple vector system is used to produce a single interfering RNA that is specific for a single gene product involved in nicotine biosynthesis. In such embodiments, at least two vectors are used. The first vector comprises a promoter operably linked to a first nucleic acid that encodes a first strand of the RNA duplex that is present in the interfering RNA. The second vector comprises a promoter operably linked to a second nucleic acid that encodes the second strand of the RNA duplex, which is complementary to the first strand.

Other multiple vector systems are combinations of vectors, wherein each vector in the system encodes a different interfering RNA. Each of the interfering RNAs is specific for different gene products involved in nicotine biosynthesis. In some embodiments, the vectors in a multiple vector system can encode different interfering RNAs that are specific to different portions of a single gene product involved in nicotine biosynthesis.

It will be appreciated that the promoters used in the above-described vectors can either be constitutive or regulated. Constitutive promoters are promoters that are always expressed. The constitutive promoters selected for use in the above-described vectors can range from weak promoters to strong promoters depending on the desired amount of interfering RNA to be produced. Regulated promoters are promoters for which the desired level of expression can be controlled. An example of a regulated promoter is an inducible promoter. Using an inducible promoter in the above-described vector constructs permits expression of a wide range of concentrations of interfering RNA inside a cell.

It will also be appreciated that there is no requirement that the same or same types of promoters be used in vectors or multiple vector systems that comprise a plurality of promoters. For example, in some vectors or vector systems, a first promoter, which controls the expression of the first interfering RNA strand, can be an inducible promoter, whereas the second promoter, which controls the expression of the second RNA strand, can be a constitutive promoter. This same principal can also be illustrated in a multiple vector system. For example, a multiple vector system may have three vectors each of which includes one or more different types of promoters. Such a system can include, for example, a first vector having repressible promoter that controls the expression of an interfering RNA specific for a first gene product involved in nicotine biosynthesis, a second vector having a constitutive promoter that controls the expression of an interfering RNA specific for a second gene product involved in nicotine biosynthesis and a third vector having an inducible promoter that controls the expression of an interfering RNA specific for a third gene product involved in nicotine biosynthesis.

In other embodiments provided herein, interfering RNAs can be produced synthetically and introduced into a cell by methods known in the art. Synthetic interfering RNAs can include a variety of RNA molecules, which include, but are not limited to, nucleic acids having at least one region of duplex RNA. The duplex RNA in such molecules can comprise, for example, two antiparallel RNA strands that form a double-stranded RNA having flush ends, two antiparallel RNA strands that form a double-stranded RNA having at least one end that forms a hairpin structure, or two antiparallel RNA strands that form a double-stranded RNA, wherein both ends form a hairpin structure. In some embodiments, synthetic interfering RNAs comprise a plurality of RNA duplexes.

The regions of RNA duplex in synthetic interfering RNAs can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. In preferred embodiments, synthetic interfering RNAs are siRNAs. In another preferred embodiment, the synthetic interfering RNA is an siRNA specific for the coding sequence of a target mRNA encoding a polypeptide involved in nicotine biosynthesis. In another preferred embodiment, the synthetic interfering RNA is an siRNA specific for the coding sequence of a target mRNA encoding a polypeptide involved in sterol biosynthesis.

Some embodiments provided herein relate to interfering nucleic acids that are not comprised entirely of RNA. Still other aspects relate to interfering nucleic acids that do not comprise any RNA. Such interfering nucleic acids are synthetic interfering RNA analogs. These analogs substantially mimic the specificity and activity of interfering RNA from which they are modeled; however, they typically include additional properties which make their use desirable. For example, one or both strands of the interfering nucleic acid may contain one or more nonnatural nucleotide bases that improve the stability of the molecule, enhance that affinity of the molecule for the target mRNA and/or enhance cellular uptake of the molecule. Other modifications are also contemplated. For example, an interfering nucleic acid can include one or more nucleic acid strands composed of naturally-occurring nucleobases, sugars and covalent internucleoside (backbone) linkages as well as non-naturally-occurring nucleobases, sugars and covalent internucleoside linkages.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or the 5' hydroxyl moiety of the sugar. In forming nucleic acids, the phosphate groups covalently link adjacent nucleosides to one another to form a linear polymeric compound. In turn the respective ends of this linear polymeric structure can be further joined to form a circular structure. Within the nucleic acid structure, the phosphate groups are commonly referred to as forming the internucleoside backbone of the oligonucleotide. The normal linkage or backbone of RNA and DNA is a 3' to 5' phosphodiester linkage.

Specific examples of interfering nucleic acids useful in certain embodiments of provided herein include one or more nucleic acid strands containing modified backbones or non-natural internucleoside linkages. As used herein, nucleic acids having modified backbones include those that retain a phosphorus atom in the backbone and those that do not have a phosphorus atom in the backbone.

In some embodiments, modified nucleic acid backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain nucleic acids having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In some embodiments, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, the interfering nucleic acid can comprise one or more mimetic regions, wherein both the sugar and the internucleoside linkage, i.e., the backbone, of the nucleotide units are replaced with novel groups. In such embodiments, the base units are maintained for hybridization with an appropriate nucleic acid target compound. One such compound, a mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497-1500.

In still other embodiments provided herein, interfering nucleic acids may include nucleic acid strands having phosphorothioate backbones and/or heteroatom backbones. Modified interfering nucleic acids may also contain one or more substituted sugar moieties. In some embodiments, the interfering nucleic acids comprise one of the following at the 2' position: OH; F; O-, S-, or N-alkyl; S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2' $OCH_2CH_2OCH_3$, also known as 2'-O-(2-methoxyethyl) or 2'-MOE) (Martin et al., Helv. Chim. Acta, 1995, 78, 486-504).

An embodiment provided herein includes the use of Locked Nucleic Acids (LNAs) to generate interfering nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methylene ($—CH_2—$)n group bridging the 2' oxygen atom and the 4' carbon atom wherein n is 1 or 2. LNAs and preparation thereof are described in WO 98/39352 and WO 99/14226, the disclosures of which are incorporated herein by reference in their entireties.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Interfering nucleic acids may also have sugar mimetics such as cyclobutyl moieties in place of the pentofuranosyl sugar.

The interfering nucleic acids contemplated herein may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993, the disclosures of which are incorporated herein by reference in their entireties. Certain of these nucleobases are particularly useful for increasing the binding affinity of the interfering nucleic acids described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Another modification of the interfering nucleic acids described herein involves chemically linking to at least one of the nucleic acid strands one or more moieties or conjugates which enhance the activity, cellular distribution or cellular uptake of the of the interfering nucleic acid. The interfering nucleic acids can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of nucleic acids, and groups that enhance the pharmacokinetic properties of such molecules. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve interfering nucleic acid uptake, enhance its resistance to degradation, and/or strengthen sequence-specific hybridization with target molecules. Groups that enhance the pharmacokinetic properties, in the context of this invention, include groups that improve the uptake, distribution, metabolism or excretion of the interfering nucleic acid. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyloxycholesterol moiety (Crooke et al., J. Pharmacol. Exp. Ther., 1996, 277, 923-937).

As described above, it is not necessary for all positions in a given compound to be uniformly modified, and in fact, more than one of the aforementioned modifications may be incorporated in a single compound or even at a single nucleoside within a nucleic acid. The methods described herein also contemplate the use of interfering nucleic acids which are chimeric compounds. "Chimeric" interfering nucleic acid compounds or "chimeras," as used herein, are interfering nucleic acid compounds, which contain two or more chemically distinct regions, each made up of at least one monomer unit, i.e., a nucleotide in the case of a nucleic acid compound. These interfering nucleic acids typically contain at least one region wherein the nucleic acid is modified so as to confer upon the interfering nucleic acid increased resistance to nuclease degradation, increased cellular uptake, and/or increased binding affinity for the target nucleic acid. An additional region of the nucleic acid may serve as a substrate for enzymes capable of cleaving RNA: DNA or RNA:RNA hybrids. By way of example, RNase H is a cellular endonuclease which cleaves the RNA strand of an RNA:DNA duplex. Activation of RNase H, therefore, results in cleavage of the RNA target, thereby contributes further to the inhibition of gene expression by the interfering nucleic acid.

The above-described interfering nucleic acids may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The interfering nucleic acid compounds for use with the methods described herein encompass any pharmaceutically acceptable salts, esters, or salts of such esters, or any other compound.

Although terms, such as interfering RNA, dsRNA and siRNA, are used throughout the remainder of the specification, it will be appreciated that in the context of synthetically produced interfering nucleic acids, that such terms are meant to include interfering nucleic acids of all types, including those which incorporate modifications, such as those described above.

Some embodiments provided herein relate to methods of reducing or eliminating the expression of one or more target genes involved in nicotine, nornicotine, and/or sterol biosynthesis. Target genes that are involved in nicotine, nornicotine, and/or sterol biosynthesis are expressed through the transcription a first gene product, the target mRNA, which is then translated to produce a second gene product, the target polypeptide. Thus, reduction or elimination of the expression of one or more target genes results in the reduction or elimination of one or more target mRNAs and/or target polypeptides. Target polypeptides involved in nicotine and nornicotine biosynthesis include, for example, putrescene N-methyltransferase, N-methylputrescene oxidase, ornithine decarboxylase, S-adenosylmethionine synthetase, NADH dehydrogenase, phosphoribosylanthranilate isomerase, and quinolate phosphoribosyl transferase (QPTase). In a preferred embodiment, the expression of the QPTase, PMTase, and A622 product is inhibited. Target polypeptides involved in sterol biosynthesis include, for example, HMG-CoA reductase, 14alpha demethylase, squalene synthase, SMT2, SMT1, C14 sterol reductase, A8-A7-isomerase, and C4-demethylase.

Reduction of the expression of one or more target genes and/or target gene products that are involved in nicotine, nornicotine, and/or sterol biosynthesis leads to a reduction in the amount of nicotine, sterols, and TSNAs produced in tobacco and PAHs upon pyrolysis of the tobacco. In certain embodiments, the expression of one or more target gene products involved in nicotine, nornicotine, and/or sterol biosynthesis is eliminated. Elimination of such target gene products can result in the elimination of nicotine, nornicotine, and/or sterol biosynthesis, thereby reducing the amount of nicotine, nornicotine, and/or sterol present in tobacco to levels below the detection limit of methods commonly used. Reduction of the amount of nicotine and nornicotine present in tobacco can lead to a reduction in the amount of TSNAs produced in the tobacco. In some embodiments, the amount of TSNA present in tobacco is reduced to levels below the detection limit of methods commonly used to detect TSNAs. Similarly, the reduction in the amount of sterol present in tobacco can lead to a reduction in the amount of PAH generated from the tobacco upon pyrolysis. In some embodiments, the amount of PAH present in tobacco is reduced to levels below the detection limit of methods commonly used to detect PAH.

The reduction in or elimination of the expression of target genes or target gene products involved in nicotine, nornicotine, and/or sterol biosynthesis is achieved by providing an interfering RNA specific to one or more such target genes to a tobacco cell, thereby producing a genetically modified tobacco cell. The interfering RNA can be provided as a synthetic double-stranded RNA, or alternatively, as a nucleic acid construct capable of encoding the interfering RNA. Synthetic double-stranded interfering RNAs are taken up by the cell directly whereas interfering RNAs encoded by a nucleic acid construct are expressed from the construct subsequent to the entry of the construct inside the cell. The reduction in or elimination of the expression of the target genes and/or the target gene products is mediated by the presence of the interfering RNA inside the cell.

In general, the interfering RNAs that are produced inside the cell, whether expressed from a nucleic acid construct or provided as synthetic double-stranded RNA molecules, include an RNA duplex having a first and second strand. At least a portion the first strand of the duplex is substantially similar or identical to at least a portion of a target mRNA or a target gene involved in nicotine biosynthesis. Correspondingly, at least a portion of the second strand of the duplex is complementary or substantially complementary to the first strand, and thus, at least a portion of the second strand is complementary or substantially complementary to at least a portion of the mRNA encoded by the target gene. In some embodiments provided herein, the interfering RNA can comprise a first strand that is substantially similar or identical to the entire coding sequence of the target gene or target mRNA involved in nicotine biosynthesis and a second strand complementary or substantially complementary to the first strand. In some embodiments provided herein, the interfering RNA can comprise a first strand that is substantially similar or identical to the entire coding sequence of the target gene or target mRNA involved in sterol biosynthesis and a second strand complementary or substantially complementary to the first strand.

The reduction in or elimination of the expression of genes and/or gene products involved in nicotine, nornicotine, and/or sterol biosynthesis can be characterized by comparing the amount of nicotine, nornicotine, and/or sterol produced in genetically modified cells, with the amount of nicotine, nornicotine, and/or sterol produced in cells that have not been genetically modified. Alternatively, such reduction in or elimination of gene expression can be characterized by genetically analyzing plant cells so as to determine the level of mRNA present in the genetically modified plant cell as compared to a non-modified plant cell. Depending on the assay, quantitation of the amount of gene expression allows one to determine a degree of reduction in gene expression, which can be greater than 10%, 33%, 50%, 90%, 95% or 99% as compared to an untreated cell. As with nicotine and nornicotine, the reduction in or elimination of TSNA production in tobacco can be characterized by comparing the amount of TSNAs produced in genetically modified cells, with the amount of TSNAs produced in cells that have not been genetically modified. The section below provides more description of the transgenic plants and cells provided herein.

b) Transgenics

Transgenic Plant Cells and Plants

Embodiments provided herein concern transgenic plant cells comprising one or more interfering RNAs that are capable of reducing or eliminating the expression of one or more target genes and/or target gene products involved in nicotine, nornicotine, and/or sterol biosynthesis. As described above, an appropriate interfering RNA comprises a duplex RNA that comprises a first strand that is substantially similar or identical to at least a portion of a target gene or target mRNA, which encodes a gene product involved in nicotine, nornicotine, and/or sterol biosynthesis. The RNA duplex also comprises a second strand that is complementary or substantially complementary to the first strand.

The interfering RNA or nucleic acid construct comprising the interfering RNA can be introduced into the plant cell in any suitable manner. Plant cells possessing stable interfering RNA activity, for example, by having a nucleic acid construct stably integrated into a chromosome, can be used to regenerate whole plants using methods known in the art. As such, some embodiments provided herein relate to plants, such as tobacco plants, transformed with one or more nucleic acid constructs and/or vectors which encode at least one interfering RNA that is capable of reducing or eliminating the expression of a gene product involved in nicotine biosynthesis. Transgenic tobacco cells and the plants described herein are characterized in that they have a reduced amount of nicotine, nornicotine, sterol and/or TSNA and/or generate a reduced amount of PAHs upon pyrolysis, as compared to unmodified or control tobacco cells and plants.

The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the low nicotine and/or TSNA tobacco described herein can be processed and blended with conventional tobacco so as to create a wide-range of tobacco products with varying amounts of nicotine and/or TSNAs. These blended tobacco products can be used in tobacco product cessation programs so as to slowly move a consumer from a high nicotine and/or sterol product to a low nicotine and/or sterol product. Some embodiments provided herein comprise a tobacco use cessation kit, comprising two or more tobacco products with different levels of nicotine. For example, a smoker can begin the program smoking blended cigarettes having or delivering 0.6 mg of nicotine, gradually move to smoking cigarettes having or delivering 0.3 mg of nicotine, followed by cigarettes having or delivering less than 0.1 mg nicotine until the consumer decides to quit smoking altogether. Accordingly, the blended cigarettes described herein provide the basis for an approach to reduce the exposure of a tobacco consumer to a tobacco related disease in a step-wise fashion. The components of the tobacco use cessation kit described herein may include other tobacco products, including but not limited to, smoking materials (e.g., cigarettes, cigars, pipe tobacco), snuff, chewing tobacco, gum, and lozenges.

Gene silencing has been employed in several laboratories to create transgenic plants characterized by lower than normal amounts of specific gene products. As used herein, "exogenous" or "heterologous" nucleic acids, including DNAs and/or RNAs, refer to nucleic acids that have been introduced into a cell (or the cell's ancestor) through the efforts of humans. The nucleic acid constructs that are used with the transgenic plants and the methods for producing the transgenic plants described herein encode one or more interfering RNA constructs comprising regulatory sequences, which include, but are not limited to, a transcription initiation sequence ("promoter") operable in the plant being transformed, and a polyadenylation/transcription termination sequence. Typically, the promoter is located upstream of the 5'-end of the nucleotide sequence to be expressed. The transcription termination sequence is generally located just downstream of the 3'-end of the nucleotide sequence to be transcribed.

In some preferred embodiments, the nucleic acid encoding the exogenous interfering RNA, which is transformed into a tobacco cell, comprises a first RNA strand that is identical to the an endogenous coding sequence of a gene encoding a gene product involved in nicotine biosynthesis. However, minor variations between the exogenous and endogenous sequences can be tolerated. It is preferred, but not necessarily required, that the exogenously-produced interfering RNA sequence, which is substantially similar to the endogenous gene coding sequence, be of sufficient similarity to the endogenous gene coding sequence, such that the complementary interfering RNA strand is capable of binding to the endogenous sequence in the cell to be regulated under stringent conditions as described below.

In some embodiments, the heterologous sequence utilized in the methods provided herein may be selected so as to produce an interfering RNA product comprising a first strand that is substantially similar or identical to the entire QTPase mRNA sequence, or to a portion thereof, and a second strand that is complementary to the entire QPTase mRNA sequence, or to a portion thereof. The interfering RNA may be complementary to any contiguous sequence of the natural messenger RNA. For example, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the C-terminus of the coding region, or complementary to the 3'-untranslated region of the mRNA.

As used herein, the term "gene" refers to a DNA sequence that incorporates (1) upstream (5') regulatory signals including the promoter, (2) a coding region specifying the product, protein or RNA of the gene, (3) downstream regions including transcription termination and polyadenylation signals and (4) associated sequences required for efficient and specific expression. The DNA sequence provided herein may consist essentially of the sequence provided herein, or equivalent nucleotide sequences representing alleles or polymorphic variants of these genes, or coding regions thereof. Use of the phrase "substantial sequence similarity" or "substantially similar" in the present specification and claims means that DNA, RNA or amino acid sequences which have slight and non-consequential sequence variations from the actual sequences disclosed and claimed herein are considered to be equivalent to the sequences provided herein. In this regard, "slight and non-consequential sequence variations" mean that "similar" sequences (i.e., the sequences that have substantial sequence similarity with the DNA, RNA or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

As used herein, a "native nucleotide sequence" or "natural nucleotide sequence" means a nucleotide sequence that can be isolated from non-transgenic cells or tissue. Native nucleotide sequences are those which have not been artificially altered, such as by site-directed mutagenesis. Once native nucleotide sequences are identified, nucleic acid molecules having native nucleotide sequences may be chemically synthesized or produced using recombinant nucleic acid procedures as are known in the art. As used herein, a "native plant nucleotide sequence" is that which can be isolated from non-transgenic plant cells or tissue. As used herein, a "native tobacco nucleotide sequence" is that which can be isolated from non-transgenic tobacco cells or tissue. Use of the phrase "isolated" or "substantially pure" in the present specification and claims as a modifier of nucleic acids, polypeptides or proteins means that the nucleic acids, polypeptides or proteins so designated have been separated from their in vivo cellular environments through the efforts of human beings.

The nucleotide sequences provided herein, such as interfering RNAs or nucleic acids encoding interfering RNAs, can be transformed into a variety of host cells. As used herein, "transformation" refers to the introduction of exogenous nucleic acid into cells so as to produce transgenic cells stably transformed with the exogenous nucleic acid. A variety of suitable host cells, having desirable growth and handling properties, are readily available in the art.

Standard techniques, such as restriction mapping, Southern blot hybridization, polymerase chain reaction (PCR) and/or nucleotide sequence analysis can be employed to identify clones expressing the desired interfering RNA construct. Following the introduction and verification of the desired interfering RNA or nucleic acid construct encoding the desired interfering RNA, whole plants can be regenerated from successfully transformed cells using conventional techniques.

Nucleic acid constructs, or "transcription cassettes," encoding the interfering RNAs that are used to produce the transgenic cells and plants provided herein include, 5' to 3' in the direction of transcription, a promoter as described herein, a nucleotide sequence as described herein operatively associated with the promoter, and, optionally, a termination sequence including stop signal for RNA polymerase and a polyadenylation signal. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator or native termination signals, derived from the same gene as the transcriptional initiation region or derived from a different gene. (See, e.g., Rezian et al. (1988) supra, and Rodermel et al. (1988), supra).

The term "operatively associated," as used herein, refers to nucleotide sequences on a single nucleic acid molecule that are associated so that the function of one sequence is affected by the other. Thus, a promoter is operatively associated with a nucleotide sequence when it is capable of affecting the transcription of that sequence (i.e., the nucleic acid is under the transcriptional control of the promoter). The promoter is said to be "upstream" from the transcribed nucleotide sequence, which is in turn said to be "downstream" from the promoter.

In some embodiments, the transcription cassette may be provided in a DNA construct that also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide (such as antibiotics, toxins, heavy metals or the like), provide complementation by imparting prototrophy to an auxotrophic host and/or provide a visible phenotype through the production of a novel compound in the plant.

The various fragments comprising the various constructs, transcription cassettes, markers and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature as demonstrated by J. Sambrook et al., Molecular Cloning, A Laboratory Manual (2d Ed. 1989) (Cold Spring Harbor Laboratory).

Vectors that may be used to transform plant tissue with nucleic acid constructs provided herein include *Agrobacterium* and Transbacter vectors and ballistic vectors, as well as vectors suitable for DNA-mediated transformation. In this particular embodiment, the promoter is a region of a DNA sequence that incorporates the necessary signals for the efficient expression of the coding sequence. This region may include sequences to which an RNA polymerase binds, but is not limited to such sequences, and may include sequences to which other regulatory proteins bind along with sequences involved in the control of protein translation. Such regions may also include coding sequences.

Promoters employed in carrying out the invention may be constitutively active promoters. Numerous constitutively active promoters that are operable in plants are available. A preferred example is the Cauliflower Mosaic Virus (CaMV) 35S promoter, which is expressed constitutively in most plant tissues. As an alternative, the promoter may be a root-specific promoter or root cortex specific promoter, as explained in greater detail below.

Nucleic acid sequences have been expressed in transgenic tobacco plants utilizing the Cauliflower Mosaic Virus (CaMV) 35S promoter. (See, e.g., Cornelissen et al., "Both RNA Level and Translation Efficiency are Reduced by Anti-Sense RNA in Transgenic Tobacco", Nucleic Acids Res. 17, pp. 833-43 (1989); Rezaian et al., "Anti-Sense RNAs of Cucumber Mosaic Virus in Transgenic Plants Assessed for Control of the Virus", Plant Molecular Biology 11, pp. 463-71 (1988); Rodermel et al., "Nuclear-Organelle Interactions: Nuclear Antisense Gene Inhibits Ribulose Bisphosphate Carboxylase Enzyme Levels in Transformed Tobacco Plants", Cell 55, pp. 673-81 (1988); Smith et al., "Antisense RNA Inhibition of Polygalacturonase Gene Expression in Transgenic Tomatoes", Nature 334, pp. 724-26 (1988); Van der Krol et al., "An Anti-Sense Chalcone Synthase Gene in Transgenic Plants Inhibits Flower Pigmentation", Nature 333, pp. 866-69 (1988)).

Use of the CaMV 35S promoter for expression of interfering RNAs in the transformed tobacco cells and plants provided herein is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", Proc. Nat. Acad Sci. USA 86, pp. 7890-94 (1989); Poulsen et al. "Dissection of 5' Upstream Sequences for Selective Expression of the *Nicotiana plumbaginifolia* rbcS-8B Gene", Mol. Gen. Genet. 214, pp. 16-23 (1988)). Other promoters that are active only in root tissues (root specific promoters) are also particularly suited to the methods provided herein. See, e.g., U.S. Pat. No. 5,459,252 to Conkling et al.; Yamamoto et al., The Plant Cell, 3:371 (1991). The TobRD2 root-cortex specific promoter may also be utilized. All patents cited herein are intended to be incorporated herein by reference in their entirety.

The recombinant interfering nucleic acid molecules and vectors used to produce the transformed tobacco cells and plants provided herein may further comprise a dominant selectable marker gene. Suitable dominant selectable markers for use in tobacco include, inter alia, antibiotic resistance genes encoding neomycin phosphotransferase (NPTII) and hygromycin phosphotransferase (HPT). Preferred selectable markers include the norflurazone resistance genes described in this disclosure. Other well-known selectable markers that are suitable for use in tobacco include a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply. Additionally, the positive selection techniques described by Jefferson (e.g., WO 00055333; WO 09913085; U.S. Pat. Nos. 5,599,670; 5,432,081; and 5,268,463, hereby expressly incorporated by reference in their entireties) can be used.

Methods of making recombinant plants provided herein, in general, involve first providing a plant cell capable of regeneration (the plant cell typically residing in a tissue capable of regeneration). The plant cell is then transformed with an interfering RNA or a nucleic acid construct encoding an interfering RNA comprising a transcription cassette provided herein (as described above) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the transcription cassette or any other technique suitable for the production of a transgenic plant.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention, all references are hereby expressly incorporated by reference in their entireties.

Microparticles suitable for the ballistic transformation of a plant cell, carrying a nucleic acid construct provided herein, are also useful for making the transformed plants described herein. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 µm gold spheres. The nucleic acid construct may be deposited on the microparticle by any suitable technique, such as by precipitation.

Plant species may be transformed with the interfering RNA or nucleic acid construct encoding an interfering RNA provided herein by the nucleic acid-mediated transformation of plant cell protoplasts. Plants may be subsequently regenerated from the transformed protoplasts in accordance with procedures well known in the art. Fusion of tobacco protoplasts with nucleic acid-containing liposomes or with nucleic acid constructs via electroporation is known in the art. (Shillito et al., "Direct Gene Transfer to Protoplasts of Dicotyledonous and Monocotyledonous Plants by a Number of Methods, Including Electroporation", Methods in Enzymology 153, pp. 313-36 (1987)).

These inhibition constructs or RNAi constructs can be transferred to plant cells by any known method in the art. Preferably, *Agrobacterium*-mediated or Biolistic-mediated transformation are used, according to well-established protocols. It is also contemplated that Transbacter-mediated transformation can be used, as described below. (See Broothaerts et al., Nature 433, 629 (2005), herein expressly incorporated by reference in its entirety).

By this approach, first bacteria are prepared as follows. YM plus antibiotic plates (see below) are streaked with bacteria and the plates are incubated for 2-3 days at 28° C. Transformation is accomplished by measuring about 20 mL Minimal A medium for each bacterial strain. Scrapping or washing the Scrape or wash bacteria from plate with sterile loop and then suspending said bacteria in 20 mL of Minimal A medium. The cell density is adjusted to an OD600 0.9-1.0.

Next, the first healthy fully expanded leaves from 4-5 week old tissue culture grown tobacco plants are cut into 0.5 cm squares (or can use a cork borer, which is about 1.0 cm diameter) in deep petri dish, under sterile RMOP liquid medium. The tissue pieces are stored in RMOP in a deep petri dish. The leaf pieces (about 20 per transformation) are then transferred to a deep petri dish containing bacterial suspension. To ensure that the bacteria have contacted a cut edge of the leaf, the suspension with leaf cutting is swirled and is left standing for 5 minutes. The leaf pieces are then removed from the suspension and blotted dry on filter paper or on the edge of the container. The leaf pieces are then placed with adaxial side (upper leaf surface) on solid RMOP at about 10 pieces per plate.

The plates are then incubated in the dark at 28° C. for: 2-3 days, if *A. tumefaciens* is used, 5 days if *S. mehlotiis* used, 5 days *M. loti* is used, and 5-11 days if *Rhizobium* sp. NGR234 is used. Over the next week, selection is performed. For the purposes of this example, hygromycin selection is performed. Accordingly, the leaf pieces are transferred onto solid RMOP-TCH, with abaxial surface (lower surface of leaf) in contact with media.

The plates are incubated for 2-3 weeks in the light at 28° C., with 16 hours daylight per day. Subculture occurs every 2 weeks.

Plantlet formation is accomplished as follows. Once shoots appear, the plantlet is transferred to MST-TCH pots. The plantlets are grown with 16 hours daylight for 1-2 weeks. Once roots form the plants appear, the plants can be transferred to soil in the greenhouse.

Media and Solutions for Tobacco Transformation:

YM Media (1 L)

| Mannitol | 10 g |
|---|---|
| Yeast extract | 0.4 g |
| K2HPO4 (10% w/v stock) | 1 ml |
| KH2PO4 (10% w/v stock) | 4 ml |
| NaCl (10% w/v stock) | 1 ml |
| MgSO4•7H2O (10% w/v stock) | 2 ml |
| pH 6.8 | |
| Agar 15 g/L | |
| Autoclave | |

*When ready to pour add antibiotic selection if required

Keep poured plates for 2 days at room temperature to visualize any contamination, then store at 4° C.

RMOP+RMOP-TCH Media (Svab, Z., et al., 1975. Transgenic tobacco plants by cocultivation of leaf disks with pPZP *Agrobacterium* binary vectors. In "Methods in Plant Molecular Biology-A Laboratory Manual", P. Maliga, D. Klessig, A. Cashmore, W. Gruissem and J. Varner, eds. Cold Spring Harbor Press: 55-77), herein expressly incorporated by reference in its entirety).

1 L Final Conc.

| Sucrose 30 g | (3%) |
|---|---|
| Myo-inositol 100 mg | (0.1%) |
| MS Macro 10x 100 mL | (1x) |
| MS Micro 1000x 1 mL | (1x) |
| Fe2EDTA Iron 100x 10 mL | (1x) |
| Thiamine-HCl (10 mg/mL stock) | 100 µL (1 mg) |
| NAA (1 mg/mL stock) 100 µL | 0.1 mg) |
| BAP (1 mg/mL stock) 1 mL | (1 mg) |
| pH 5.8 | |
| Phytagel 2.5 g/L for solid autoclave | |

*for RMOP-TCH, when ready to pour add: Timentin (200 mg/mL stock) 1 mL, Claforan (250 mg/mL stock) 1 mL, and Hygromycin (50 mg/mL stock) 1 mL BAP (1 mg/ml) (6-Benzylaminopurine)

Add 1N KOH drop wise to 100 mg BAP until dissolved. Make up to 100 Ml with Milli-Q H2O and store at 4° C.

NAA (1 mg/ml) (Naphthalene Acetic Acid)

Dissolve 100 mg NAA in 1 mL absolute ethanol. Add 3 mL 1N KOH. Make up to 80 mL with Milli-Q H2O. Adjust pH to 6.0 with 1N HCl, make up to 100 mL with Milli-Q H2O, and store at 4° C.

Cefotaxamine (250 mg/ml)

Add 8 ml sterile Milli-Q H2O to 2 g Claforan and store at 4° C. in dark

Timentin (200 mg/ml)

Add 15 ml sterile Milli-Q H2O to 3 g Timentin and store at 4° C.

MST+MST-TCH Media (Svab, Z., et al., 1975. Transgenic tobacco plants by cocultivation of leaf disks with pPZP *Agrobacterium* binary vectors. In "Methods in Plant Molecular Biology-A Laboratory Manual", P. Maliga, D. Klessig, A., Cashmore, W. Gruissem and J. Varner, eds. Cold Spring Harbor Press: 55-77), herein expressly incorporated by reference in its entirety).

1 L Final Concentration

| Sucrose 30 g | (3%) |
|---|---|
| MS Macro 10x 100 mL | (1x) |
| MS Micro 1000x 1 mL | (1x) |
| Fe2EDTA Iron 100x 10 mL | (1x) |
| pH 5.8 | |
| Phytagel 2.5 g/L | |
| Autoclave | |
| For MST-TCH, when ready to pour add: | |
| Timentin (200 mg/mL stock) | (1 mL) |
| Cefotaxamine (250 mg/mL stock) | (1 mL) |
| Hygromycin (50 mg/mL stock) | (1 mL) |

MS Macro 10× ((Murashige and Skoog., *Phys. Plant.* 15: 473-497 (1962), herein expressly incorporated by reference in its entirety)).

Final Concentration

| 10x | (g/L) |
|---|---|
| KNO3 | 19.0 |
| NH4 N03 | 16.5 |
| CaCl2•2H2O | 4.4 |
| MgS04•7H2O | 3.7 |
| KH2PO4 | 1.7 |

Store 4° C.
Substituting chemicals:

CaCl2 3.3 g/L
MgS04 1.8 g/L

MS Micro 1000× (Murashige and Skoog., *Phys. Plant.* 15: 473-497 (1962), herein expressly incorporated by reference in its entirety).
Final Concentration

| 1000x | (g/L) |
|---|---|
| MnS04•4H20 | 22.3 |
| ZnS04•7H20 | 8.6 |
| H3BO3 | 6.2 |
| KI | 0.83 |
| Na2MoO4•2H2O | 0.25 |
| CuSO4•5H2O | 25 mg |
| CoCl2•6H2O | 25 mg |

Store 4° C.
Substituting chemicals:

MnS04•H20 16.9/L

FeSO4EDTA Iron 100×

| | (g/1 L) |
|---|---|
| FeS04•7H20 | 2.78 |
| Na2EDTA | 3.72 |

Store 4° C. in dark bottle

Once the transformed cells are selected, by any of the approaches described above, they are induced to regenerate intact tobacco plants through application of tobacco cell and tissue culture techniques that are well known in the art. The method of plant regeneration is chosen so as to be compatible with the method of transformation. The stable presence of an interfering RNA or a nucleic acid encoding an interfering RNA in transgenic tobacco plants can be verified by Mendelian inheritance of the interfering RNA or a nucleic acid encoding an interfering RNA sequence, as revealed by standard methods of nucleic acid analysis applied to progeny resulting from controlled crosses. After regeneration of transgenic tobacco plants from transformed cells, the introduced nucleic acid sequence can be readily transferred to other tobacco varieties through conventional plant breeding practices and without undue experimentation.

For example, to analyze the segregation of the transgene, regenerated transformed plants (TO) may be grown to maturity, tested for nicotine and/or TSNA levels, and selfed to produce $T_1$ plants. A percentage of $T_1$ plants carrying the transgene are homozygous for the transgene. To identify homozygous $T_1$ plants, transgenic $T_1$ plants are grown to maturity and selfed. Homozygous $T_1$ plants will produce $T_2$ progeny where each progeny plant carries the transgene; progeny of heterozygous $T_1$, plants will segregate 3:1.

Any plant tissue capable of subsequent clonal propagation, whether by organogenesis or embryogenesis, may be transformed with a nucleic acid embodiment provided herein. Preferred plants for introduction of a nucleic acid embodiment, described herein, include *Nicotiana*. Preferred varieties of *Nicotiana* for introduction of a nucleic acid embodiment as described herein include the *Nicotiana tabacum* varieties provided in Table 1.

TABLE 1

| Burley Varieties | Dark Varieties | Flu Cured | Other | Virginia | Hybrid | One Sucker | Newest Varieties | Oriental |
|---|---|---|---|---|---|---|---|---|
| KT 200 LC | BLACK MAMMOTH | K 149 | CU 748 | BROWN LEAF LIZARD TAIL | NBH 98 MS 21 × KY | OS400 KY | GL 350 | D174 |
| KT 204 LC | DF 485 | K 326 | GL 737 | ORNOCO LIZARD TAIL | 10 MS | 160 | | Izmir |
| KY | DF 911 | K 346 | OX 207 PVH | TURTLE FOOT | 14 × KY L8 | | | |
| KY 10 | DT 508 | K 394 | 03 PVH | M and N | TN 97 | | | |
| KY 14 | DT 518 | K 730 Coker | 09 PVH | SHIREY WALKER | KT 200 | | | |
| KY 17 | DT 592 GREEN | 371 Gold | 2040 | BROADLEAF | | | | |
| KY 907 KY 907 LC | WOOD IMPROVED MADOLE | CU 748 GL 737 | RG 17 RG 81 | | | | | |
| KY 908 | KT-D4 LC | GL 939 | RGH 4 RGH | | | | | |
| KY 908 | KY 160 | GL 973 | 51 RS | | | | | |
| KY 910 MS Burley 21 × KY | KY 171 | K 358 | 1410 | | | | | |
| 10 MS | KY 171 | K 399 | Speight 168 | | | | | |

TABLE 1-continued

| Burley Varieties | Dark Varieties | Flu Cured | Other | Virginia | Hybrid | One Sucker | Newest Varieties | Oriental |
|---|---|---|---|---|---|---|---|---|
| KY14 × L8 | LITTLE CRITTENDEN | NC 102 | Speight 179 | | | | | |
| N 126 | LITTLE WOOD NARROW LEAF | NC 291 | Speight 190 | | | | | |
| N 777 | MADOLE | NC 297 | Speight 196 | | | | | |
| N 88 | NEWTON'S VH MADOLE | NC 55 | Speight 200A Speight | | | | | |
| NBH 98 | NL MADOLE | NC 606 | 210 Speight | | | | | |
| TN 86 | TN D94 | NC 71 | 218 Speight | | | | | |
| TN 86 LC | TN D950 | NC 72 | 220 Speight | | | | | |
| TN 90 | TR MADOLE | NC 810 | H-20 Speight | | | | | |
| TN 90 LC | VA 309 | RGH 4 | H-6 Speight | | | | | |
| TN 97 LC | VA 312 | RGH 51 | NF-3 VA | | | | | |
| VA 509 | VA 355 | | 119 NC 37 | | | | | |
| LA21 | VA 359 | | NF OX 414 NF Sp. G-172 | | | | | |

The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems) and induced meristem tissue (e.g., cotyledon meristem and hypocotyl meristem).

Plants provided herein may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in *citrus* species). The transformed plants may be propagated by a variety of means, such as by clonal propagation or classical breeding techniques. For example, first generation (or $T_1$) transformed plants may be selfed to give homozygous second generation (or $T_2$) transformed plants and the $T_2$ plants further propagated through classical breeding techniques. A dominant selectable marker (such as nptII) can be associated with the transcription cassette to assist in breeding.

As used herein, a crop comprises a plurality of plants provided herein, and of the same genus, planted together in an agricultural field. By "agricultural field" is meant a common plot of soil or a greenhouse. Thus, the present invention provides a method of producing a crop of plants having reduced amounts of nicotine, nornicotine, and/or sterol, as compared to a similar crop of non-transformed plants of the same species and variety.

The modified tobacco plants described herein are suitable for conventional growing and harvesting techniques (e.g. topping or no topping, bagging the flowers or not bagging the flowers, cultivation in manure rich soil or without manure). The harvested tobacco leaves and stems are suitable for conventional methods of processing such as curing and blending. The modified tobacco is suitable for use in any traditional tobacco product including, but not limited to, pipe, cigar and cigarette tobacco, and chewing tobacco in any form including leaf tobacco, shredded tobacco, or cut tobacco.

Some embodiments concern the production and identification of particular lines of a transgenic Burley variety (Vector 21-41), which have very low levels of nicotine and TSNAs. The constructs used to create these particular lines of transgenic Burley tobacco are provided in Conkling et al., WO98/56923; U.S. Pat. Nos. 6,586,661; 6,423,520; and U.S. patent application Ser. Nos. 09/963,340; 10/356,076; 09/941,042; 10/363,069; 10/729,121; 10/943,346, all of which are hereby expressly incorporated by reference in their entireties. After the creation and analysis of nearly 2,000 lines of transgenic Burley tobacco, these particular lines of reduced nicotine and TSNA transgenic tobacco were identified. Tobacco harvested from these lines were incorporated into tobacco products (Quest 1®, Quest 2®, and Quest 3®) and were analyzed for their ability to reduce the potential to contribute to a tobacco-related disease, as described in the sections above. It was found that tobacco products comprising these lines of transgenic Burley tobacco, had a reduced potential to contribute to a tobacco-related disease (i.e., that these tobacco products are reduced risk tobacco products).

3. Exemplary Constructs

Several embodiments concern isolated nucleic acids that comprise, consist, or consist essentially of the nucleic acids described in the sequence listing (SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50) and fragments thereof at least 30 consecutive nucleotides in length. That is, embodiments provided herein include an isolated nucleic acid comprising, consisting of, consisting essentially of, any one or more of the sequences of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50, or a fragment thereof (e.g., a fragment that is at least, less than or equal to or greater than 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, or 9000 consecutive nucleotides of SEQ. ID. NOs.: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In preferred embodiments, the target gene or target mRNA encodes QTPase, PMTase, or the A622 gene product. In preferred embodiments, an interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NOS: 2, 3, 4, 5, 39 or 40, and inhibits the production of QTPase, PMTase, A622, nicotine, nornicotine, NNN, NNK, NAT, or NAB in a tobacco. In related embodiments, the interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NO: 5, and inhibits production of nornicotine but not nicotine in a tobacco. In still more embodiments, the interfering RNA comprises, consists, or consists essentially of an RNA strand that is complementary to each least a portion (e.g., less than, greater than or equal to 30, 35, 40, 45, 50, 60, 75, 100, 150, 250, 500, 750, or 1000 consecutive nucleotides) of SEQ ID NO: 6, 7, 8, or 9, and inhibits production of at least one sterol (e.g., squalene synthase, HMG-CoA reductase, SMT2, or 14alpha demethylase) in a tobacco and at least one PAH upon pyrolysis of said tobacco.

Some of these nucleic acid embodiments comprise, consist, or consist essentially of fragments of the QPTase, PMTase, and A622 genes that were found to inhibit gene expression unexpectedly well in the RNAi constructs described herein, producing reduced alkaloid tobacco (below 7,000 ppm, 1,000 ppm, or 500 ppm). Some of these nucleic acids concern fragments of genes involved in sterol biosynthesis (e.g., squalene synthase, HMG-CoA reductase, SMT2, or 14alpha demethylase) and these fragments are particularly useful for inhibiting production of sterols in tobacco and PAHs when said tobacco undergoes pyrolysis.

Still more of the nucleic acid embodiments concern several phytoene desaturase (PDS) mutants (e.g., PDSM-1, PDSM-2, and PDSM-3, SEQ. ID. NOs.: 10, 11, or 12) that were developed to confer resistance to norflurazone, which allows both tissue-culture selection of cells transformed with the construct, as well as, field-based selection, wherein weeds and tobacco, which do not contain an herbicide resistance gene, are removed from the field or crop by spraying the herbicide norflurazone or an herbicide of the same class or activity (e.g., herbicides that contain $C_{12}H_9ClF_3N_3O$ (see U.S. Pat. No. 3,644,355, herein expressly incorporated by reference in its entirety), but plants expressing PDSM-1, PDSM-2, or PDSM-3 survive the herbicide contact). That is, some embodiments include isolated nucleic acids that comprise, consist, or consist essentially of the PDS mutant sequences provided by SEQ. ID. NOs.:10, 11, or 12 and fragments thereof at least 30 nucleotides in length (e.g., less than, greater than or equal to 30, 35, 40, 45, 50, 60, 75, 100, 150, 250, 500, 750, 1000, 1100, 1200, 1300, 1400, 1500, 1600, 1700, or 1729 consecutive nucleotides) that include a mutation (e.g., T1478G, which encodes Val493Gly; G863C, which encodes Arg288Pro; and T1226C, which encodes Leu409Pro) that confers resistance to norflurazone). Preferably, the fragments of the PDS mutants described herein confer resistance to norflurazone, although fragments that do not confer resistance to the herbicide are also useful in the field in assays designed to follow the retention of constructs described herein in successive generations of transgenic plants. Approaches to develop more norflurazone-resistance genes are also provided herein.

Additional embodiments include isolated nucleic acids that comprise, consist, or consist essentially of root-specific promoters, constitutive promoters, and developmentally regulated promoters, which can be used interchangeably with the nucleic acid sequences described herein. Some embodiments, for example, include a root-specific promoter such as the RD2 promotor (SEQ. ID NO. 37 or SEQ. ID NO. 50), truncated RD2 promoter (SEQ. ID NO. 13) or the Putrescene methyl transferase promoter (PMT-1) (SEQ. ID NO. 14). Constitutive promoters that can be used with embodiments described herein include the GapC promoter (SEQ. ID. NO.: 15), Actin 2 promoter (Act2P) (SEQ. ID NO. 16), the tobacco alcohol dehydrogenase promoter (ADP) (SEQ. ID NO. 17), the *Arabidopsis* ribosomal protein L2 promoter (RPL2P) (SEQ. ID NO. 18), and the nopaline synthase promoter (NOS P) (SEQ ID NO. 46). Developmentally regulated promoters that can be used with the nucleic acid sequences described herein include the cinnamyl alcohol dehydrogenase promoter (SEQ. ID NO. 19) and the metallothionein I promoter (SEQ. ID NO. 20). Additional embodiments also include isolated nucleic acids that comprise, consist, or consist essentially of the GAD2 terminator (SEQ. ID NO. 21), nopaline synthase terminator (NOS T) (SEQ ID NO 38), a FAD2 intron (provided by (SEQ. ID NO. 22), ACT11 intron 3 (SEQ ID NO 41), which was used as a spacer in several of the RNAi constructs, and the PAP1 intron (provided by nucleotides 6446-7625 of (SEQ. ID NO. 33). Because of the unique properties of the FAD2 intron, in particular the hair-pin secondary structure afforded by the interaction of splice sites in the sequence, it was found, unexpectedly, that transgenic tobacco could be made with various inhibitory sequences with nearly equivalent success (e.g., approximately 50% of the reduced nicotine lines created by multiple constructs were found to have less than 1,000 ppm total alkaloid). Accordingly, significantly improved RNAi constructs were generated using this spacer. That is, embodiments provided herein concern the use of an intronic sequence comprising splicing recognition sequences (preferably FAD2 or PAP1 intron) to link or join a first RNA sequence to a second RNA sequence that is complementary to said first RNA sequence, wherein said first or second RNA sequence is complementary to a target RNA, which, preferably, regulates the production of a harmful compound in tobacco (e.g., nicotine, nornicotine, or a sterol).

Embodiments provided herein also concern isolated nucleic acids that comprise, consist, or consist essentially of the inhibition and selection cassettes identified as SEQ. ID. Nos. 23, 24, 25, 26, 27, 28, 29, 30, 31, 32, 33, 34, 35, 36, 37, 38, 39, 40, 41, 42, 43, 44, 45, 46, 47, 48, 49 or 50 and fragments thereof (e.g., a fragment that is at least, less than or equal to or greater than 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, or 9000 consecutive nucleotides) of SEQ. ID. Nos. 23, 24, 25, 26, 27, 28, 29, 30, 31, 32, 33, 34, 35, 36, 37, 38, 39, 40, 41, 42, 43, 44, 45, 46, 47, 48, 49 or 50).

Embodiments provided herein also concern isolated nucleic acids that comprise, consist, or consist essentially of a plurality of the nucleic acid sequences described herein. For example, a double knock-out construct comprising a portion of the A622 gene and a portion of the QPTase gene has been made and it is expected that this construct will efficiently reduce expression of at least two genes involved in the synthesis or regulation of the production of nicotine (SEQ. ID. No. 27). Another double knock-out construct comprises, consists of or consists essentially of a first isolated nucleic acid that inhibits nicotine biosynthesis (e.g., A622) and a second isolated nucleic acid that inhibits synthesis of at least one sterol (e.g., SMT2). (See (SEQ. ID. No. 33)). Accordingly, embodiments provided herein concern an isolated nucleic acid construct that inhibits the expression of a plurality of genes that regulate the production of more than one harmful compound in tobacco. In some aspects of these embodiments, said isolated nucleic acid construct inhibits the expression of at least two nicotine biosynthesis genes, a nicotine biosynthesis gene and a sterol biosynthesis gene, or two sterol biosynthesis genes. It should also be understood that embodiments provided herein concern tobacco generated by crossing the transgenic tobaccos described herein. For example, some embodiments concern progeny of a cross between a transgenic tobacco having a reduced amount of nicotine and a transgenic tobacco having a reduced amount of a sterol. Crossings of the transgenic tobacco described herein and wild-type tobacco are also embodiments provided herein.

The interfering RNAs used with the embodied nucleic acids can be expressed from nucleic acid construct that encodes one or more strands of the RNA duplex of the interfering RNA. In some embodiments, the nucleic acid construct is present on a vector. The vectors may be viral vectors, plasmids, or any other vehicles for nucleic acid delivery. In other embodiments, the interfering RNAs described herein can be generated synthetically by methods, such as direct synthesis or in vitro transcription. In some embodiments, synthetic interfering nucleic acids comprising modified nucleic acids are contemplated. Other embodiments provided herein include multiple vector systems for producing an interfering RNA wherein a first vector encodes the first strand of the interfering RNA and a second vector encodes the second strand of the interfering RNA.

Still other embodiments provided herein relate to tobacco cells comprising one or more of the nucleic acid constructs described herein, which encode an interfering RNA that is specific for a gene product involved in nicotine or sterol biosynthesis. In such embodiments, the interfering RNA reduces or eliminates the expression of such gene product. Additional embodiments relate to tobacco cells comprising one or more interfering RNAs that are specific for a gene product involved in nicotine biosynthesis. In certain embodiments, the interfering RNAs are synthetic interfering RNAs.

Certain embodiments provided herein relate to tobacco plants and cured tobacco products having a reduced amount or nicotine, nornicotine, TSNAs, and/or sterols. In such embodiments, reduction in nicotine, nornicotine, TSNAs, and/or sterol amounts in the tobacco plants and cured tobacco products is mediated by an interfering RNA comprising an RNA duplex wherein at least 30 consecutive nucleotides (e.g., at least or equal to 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 800, 900, 1000 consecutive nucleotides) of the RNA duplex are complementary or substantially complementary to a target mRNA that encodes a gene product involved in nicotine biosynthesis. Further aspects relate to a field or crop of tobacco plants comprising one or more of the constructs described herein. Still other aspects relate to a tobacco seed produced from one or more of the tobacco plants provided herein.

Transgenic tobacco plants produced by the methods described herein can be cured by any of the tobacco curing techniques that are known in the art. As such, some embodiments provided herein relate to cured tobacco and cure tobacco products made from the transgenic plants described herein. In some embodiments, the cured tobacco product is a blended tobacco product. In some embodiments, the cured tobacco product is processed in a microbe-free environment. In other embodiments, the cured tobacco is contacted with sterilizing vapor, heat, or radiation so as to prevent the conversion of alkaloid to TSNAs.

Some embodiments provided herein relate to methods of preparing a tobacco cell having a reduced nicotine and/or sterol content, wherein the method comprises providing a tobacco cell with one or more interfering RNAs or one or more nucleic acid constructs encoding an interfering RNA comprising an RNA duplex, which comprises a first strand having a sequence substantially similar or identical to at least a portion of the coding sequence of a target gene and/or target gene product involved in nicotine and/or sterol biosynthesis, and a second strand that is complementary or substantially complementary to the first strand. In a preferred embodiment, the target gene product involved in nicotine biosynthesis is QTPase, PMTase, or A622 and the target gene product involved in sterol biosynthesis is squalene synthase, HMG-CoA reductase, SMT2, or 14alpha demethylase.

Other embodiments provided herein relate to methods of preparing a tobacco plant having a reduced nicotine and/or sterol content comprising obtaining a tobacco cell in culture; providing to the tobacco cell one or more interfering RNAs or one or more nucleic acid constructs encoding an interfering RNA comprising an RNA duplex, which comprises a first strand having a sequence substantially similar or identical to at least a portion of the coding sequence of a target gene and/or target gene product involved in nicotine and/or sterol biosynthesis, and a second strand that is complementary or substantially complementary to the first strand; allowing expression of the interfering RNA, thereby reducing cellular nicotine and/or sterol content; and regenerating a tobacco plant from the tobacco cell. In some embodiments, the tobacco plants prepared by such method also have a reduced TSNA content and/or produce a reduced amount of PAHs upon pyrolysis, as compared to a conventional tobacco product of the same class, a reference tobacco product (e.g., IM16), or the same strain of tobacco prior to genetic modification.

As mentioned above, additional embodiments include tobacco products that have been carefully blended so that desired levels of nicotine, TSNAs, and/or sterols are obtained. For example, tobacco having a reduced level of nicotine and/or TSNAs, prepared as described above, can be blended with conventional tobacco so as to obtain virtually any amount of nicotine and/or sterols. Additionally, as mentioned above, exogenous nicotine can be added to the tobacco or tobacco product. Further, two or more varieties of tobacco (e.g., transgenic reduced alkaloid Burley, transgenic reduced alkaloid Flue-cured, and/or transgenic reduced alkaloid Oriental) can be blended so as to achieve a desired taste while maintaining nicotine levels in or delivered by the product (e.g., as measured by FTC methodology) at less than 7,000 ppm, 5,000 ppm, 3000 ppm, 2000 ppm, 1000 ppm, or 500 ppm and TSNA levels at 0.5 µg/g or less. Similarly, two or more varieties of transgenic tobacco having a reduced amount of sterols can be blended, as above, or varieties of sterol-reduced transgenic tobacco can be blended with varieties of nicotine reduced transgenic tobacco. In this manner, differences in variety, flavor, as well as amounts of nicotine and/or sterols can be incrementally adjusted. These blended tobaccos can be processed into tobacco products, which can be incorporated into tobacco use cessation kits (e.g., a multiple step nicotine reduction program, whereby a consumer's exposure to nicotine, TSNA, or PAH is gradually reduced over time by consumption of tobacco products that have increasingly smaller quantities of these compounds). Such kits and programs, are designed to reduce or eliminate nicotine dependence and reduce the potential to contribute to a tobacco related disease.

More embodiments concern methods to reduce the carcinogenic potential of tobacco products, including cigarettes, cigars, chewing tobacco, snuff and tobacco-containing gum and lozenges. Some methods, for example involve the use of the constructs described herein to obtain transgenic tobacco that comprises a reduced amount of nicotine, TSNAs, and/or sterols and the manufacture of tobacco products containing said tobacco. Accordingly, the transgenic tobacco plants, described above, are harvested, cured, and processed into tobacco products. These tobacco products have a reduced carcinogenic potential because they are prepared from tobacco that has a reduced amount of nicotine, TSNAs, and sterols. Smoke or smoke condensate generated from these tobaccos and tobacco products can also be evaluated using the assays provided herein so as to confirm that said tobaccos and tobacco products have a reduced potential to contribute to a tobacco-related disease and that said tobaccos and tobacco products are reduced risk compositions.

Yet another aspect provided herein concerns the reduction of the amount of TSNAs, preferably NNN and NNK, and polyaromatic hydrocarbons (PAHs), preferably, benz[a]pyrene and metabolites thereof in humans who smoke, consume or otherwise ingest tobacco. This method is practiced by providing a tobacco product comprising a transgenic tobacco that comprises a reduced amount of nicotine and/or a sterol to said humans, thereby lowering the amount of TSNAs and/or PAHs in said humans exposed to said tobacco product. By one approach, for example, the carcinogenic potential of side stream or main stream tobacco smoke in a human exposed to said side stream or main stream tobacco smoke is reduced by providing the cured tobacco as described above in a product that undergoes pyrolysis, wherein pyrolysis of said product results in side stream or main stream smoke comprising a reduced amount of TSNAs and/or PAHs. The section below describes several preferred approaches to develop genetically modified tobaccos and tobacco products containing genetically modified tobacco that have a reduced amount of a compound that contributes to a tobacco related disease.

Preparation of Preferred Transgenic Tobaccos

A first generation of transgenic Burley tobacco was created using a full-length antisense QPTase construct. Tobacco of the variety Burley 21 LA was transformed with the binary *Agrobacterium* vector pYTY32 to produce a low nicotine tobacco variety, Vector 21-41. The binary vector pYTY32 carried the 2.0 kb NtQPT1 root-cortex-specific promoter driving antisense expression of the NtQPT1 cDNA (SEQ. ID. NO. 2) and the nopaline synthase (nos) 3' termination sequences from *Agrobacterium tumefaciens* T-DNA. The selectable marker for this construct was neomycin phosphotransferase (nptII) from *E. coli* Tn5 which confers resistance to kanamycin, and the expression nptII was directed by the nos promoter from *Agrobacterium tumefaciens* T-DNA. Transformed cells, tissues, and seedlings were selected by their ability to grow on Murashige-Skoog (MS) medium containing 300 µg/ml kanamycin. Burley 21 LA is a variety of Burley 21 with substantially reduced levels of nicotine as compared with Burley 21 (i.e., Burley 21 LA has 8% the nicotine levels of Burley 21, see Legg et al., *Can J Genet Cytol*, 13:287-91 (1971); Legg et al., *J Hered*, 60:213-17 (1969)).

One-hundred independent pYTY32 transformants of Burley 21 LA (T0) were allowed to self. Progeny of the selfed plants ($T_1$) were germinated on medium containing kanamycin and the segregation of kanamycin resistance scored. $T_1$ progeny segregating 3:1 resulted from transformation at a single locus and were subjected to further analysis.

Nicotine levels of $T_1$ progeny segregating 3:1 were measured qualitatively using a micro-assay technique. Approximately ~200 mg fresh tobacco leaves were collected and ground in 1 ml extraction solution (Extraction solution: 1 ml Acetic acid in 100 ml $H_2O$). Homogenate was centrifuged for 5 min at 14,000×g and supernatant removed to a clean tube, to which the following reagents were added: 100 µL $NH_4OAC$ (5 g/100 ml $H_2O$+50 µL Brij 35); 500 µL Cyanogen Bromide (Sigma C-6388, 0.5 g/100 ml $H_2O$+50 µL Brij 35); 400 µL Aniline (0.3 ml buffered Aniline in 100 ml $NH_4OAC$+50 µL Brij 35). A nicotine standard stock solution of 10 mg/ml in extraction solution was prepared and diluted to create a standard series for calibration. Absorbance at 460 nm was read and nicotine content of test samples were determined using the standard calibration curve.

$T_1$ progeny that had less than 10% of the nicotine levels of the Burley 21 LA parent were allowed to self to produce $T_2$ progeny. Homozygous $T_2$ progeny were identified by germinating seeds on medium containing kanamycin and selecting clones in which 100% of the progeny were resistant to kanamycin (i.e., segregated 4:0; heterozygous progeny would segregate 3:1). Nicotine levels in homozygous and heterozygous T$_2$ progeny were qualitatively determined using the micro-assay and again showed levels less than 10% of the Burley 21 LA parent. Leaf samples of homozygous T$_2$ progeny were sent to the Southern Research and Testing Laboratory in Wilson, N.C. for quantitative analysis of nicotine levels using Gas Chromatography/Flame Ionization Detection (GC/FID). Homozygous T$_2$ progeny of transformant #41 gave the lowest nicotine levels (~70 ppm), and this transformant was designated as "Vector 21-41."

Vector 21-41 plants were allowed to self-cross, producing T$_3$ progeny. T$_3$ progeny were grown and nicotine levels assayed qualitatively and quantitatively. T$_3$ progeny were allowed to self-cross, producing T$_4$ progeny. Samples of the bulked seeds of the T$_4$ progeny were grown and nicotine levels tested.

In general, Vector 21-41 is similar to Burley 21 LA in all assessed characteristics, with the exception of alkaloid content and total reducing sugars (e.g., nicotine and nor-nicotine). Vector 21-41 may be distinguished from the parent Burley 21 LA by its substantially reduced content of nicotine, nor-nicotine and total alkaloids. As shown below, total alkaloid concentrations in Vector 21-41 are significantly reduced to approximately relative to the levels in the parent Burley 21 LA, and nicotine and nor-nicotine concentrations show dramatic reductions in Vector 21-41 as compared with Burley 21 LA. Vector 21-41 also has significantly higher levels of reducing sugars as compared with Burley 21 LA.

Field trials of Vector 21-41 T$_4$ progeny were performed at the Central Crops Research Station (Clayton, N.C.) and compared to the Burley 21 LA parent. The design was three treatments (Vector 21-41, a Burley 21 LA transformed line carrying only the NtQPT1 promoter [Promoter-Control], and untransformed Burley 21 LA [Wild-type]), 15 replicates, 10 plants per replicate. The following agronomic traits were measured and compared: days from transplant to flowering; height at flowering; leaf number at flowering; yield; percent nicotine; percent nor-nicotine; percent total nitrogen; and percent reducing sugars.

Vector 21-41 was also grown on approximately 5000 acres by greater than 600 farmers in five states (Pennsylvania, Mississippi, Louisiana, Iowa, and Illinois). The US Department of Agriculture, Agriculture Marketing Service (USDA-AMS) quantified nicotine levels (expressed as percent nicotine per dry weight) using the FTC method of 2,701 samples taken from these farms. Nicotine levels ranged from 0.01% to 0.57%. The average percent nicotine level for all these samples was 0.09%, with the median of 0.07%. Burley tobacco cultivars typically have nicotine levels between 2% and 4% dry weight (Tso, T. C., 1972, *Physiology and Biochemistry of Tobacco Plants*. Dowden, Hutchinson, and Ross, Inc. Stroudsbury).

A transgenic Flue-cured tobacco with a reduced amount of nicotine and TSNAs was created using an RNAi approach. FIG. 1 illustrates an RNAi construct that was used to create a reduced nicotine tobacco, wherein the root-specific promoter RD2 (Bp 1-2010) was used to drive expression of an RNAi cassette comprising an antisense full-length QPTase cDNA (Bp 2011-3409) linked to a 382 bp fragment of the cucumber aquaporin gene (Bp 3410-3792), which is linked to a sense full-length QPTase cDNA (Bp 3793-5191) and the GapC terminator (Bp5192-5688) (see SEQ. ID. No. 23). This first RNAi construct also comprises a GUS-selection cassette comprising the GapC promoter (Bp 1-1291), which drives expression of the GUS gene (Bp 1292-3103), linked to the GapC terminator (Bp 3104-3600) (see SEQ. ID. No. 34). This first RNAi construct was ligated into a binary vector, pBin19 which was then introduced into *Agrobacterium tumefaciens*. Leaf disks from Flue-cured variety K326 were then transformed with *Agrobacterium* that contained the RNAi construct comprising the RNAi cassette and the GUS selection cassette. GUS-based selection was then employed to select positively transformed plantlets (buds), which were then regenerated to plants. Leaf samples were then harvested and the alkaloid content was then determined. The alkaloid content of samples obtained from some of the transgenic lines created with this first RNAi construct was 6000 ppm. Since the total alkaloid content in tobacco is about 90% nicotine, it is understood by those skilled in the art that the transgenic Flue-cured tobacco created using the construct shown in FIG. 1 has significantly reduced levels of nicotine and TSNA, as compared to a conventional tobacco, a reference tobacco, or the parental strain of tobacco prior to genetic modification. Accordingly, tobacco products (e.g., cigarettes), tobacco, tobacco plants, tobacco cells, tobacco seeds, in Burley, Flue-cured or Oriental comprising this RNAi construct are embodiments provided herein.

Figure 2:
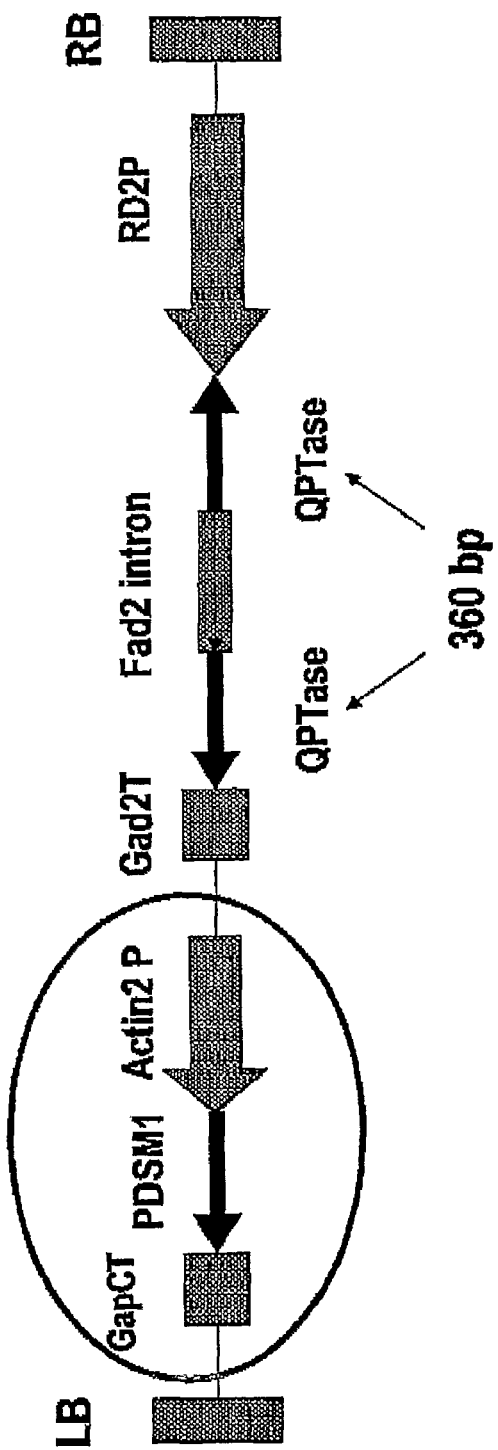
FIG. 2. An illustration of a QPTase inhibition construct comprising a QPTase inhibition cassette including a 360 bp fragment of the QPTase gene and a norflurazone resistance selection cassette including a mutant phytoene desaturase gene (PDSM-1).

FIG. 2 shows another RNAi construct that was used to generate several lines of reduced nicotine and TSNA tobacco. This RNAi construct has a QTPase inhibition cassette (SEQ. ID. No. 24) and a norflurazone selection cassette (SEQ. ID. No. 35). Starting from the right border (RB), the QPTase inhibition cassette comprises an RD2 promoter (Bp 1-2010) operably linked to an antisense fragment (360 bp) (Bp 2011-2370) of the QTPase gene, joined to a FAD2 intron (Bp 2371-3501), which is joined to a sense fragment of the QTPase gene (360 bp) (Bp 3502-3861), which is joined to the GAD2 terminator (Bp 3862-4134). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 2 using *Agrobacterium*-mediated transformation and 1,140 independent lines were selected, regenerated, and transplanted in the greenhouse. Of the 1, 140 independent lines, 1,097 plants were harvested and tested for alkaloid content. A total of 608 lines were identified as having less than 1,000 ppm total alkaloid and 139 lines were identified as having less than 500 ppm total alkaloid. Accordingly, the transgenic Flue-cured tobacco created using the construct shown in FIG. 2 has significantly reduced levels of nicotine and TSNA, as compared to a conventional tobacco, a reference tobacco, or the parental strain of tobacco prior to genetic modification.

Burley tobacco was also transformed with the construct shown in FIG. 2 using *Agrobacterium*-mediated transformation and 385 independent lines were selected, regenerated, and transplanted in the greenhouse. Of the 385 independent lines, 350 lines of plants were harvested and tested for alkaloid content. A total of 142 lines were identified as having less than 1,000 ppm total alkaloid and 10 lines were identified as having less than 500 ppm total alkaloid. Accordingly, it is understood by those skilled in the art that the transgenic Burley tobacco created using the construct shown in FIG. 2 also has significantly reduced levels of nicotine and TSNA, as compared to a conventional tobacco, a reference tobacco, or the parental strain of tobacco prior to genetic modification.

Oriental tobacco will be transformed with the construct shown in FIG. 2 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 2 will have significantly reduced levels of nicotine and TSNA, as compared to a conventional tobacco, a reference tobacco, or the parental strain of tobacco prior to genetic modification.

Figure 3:
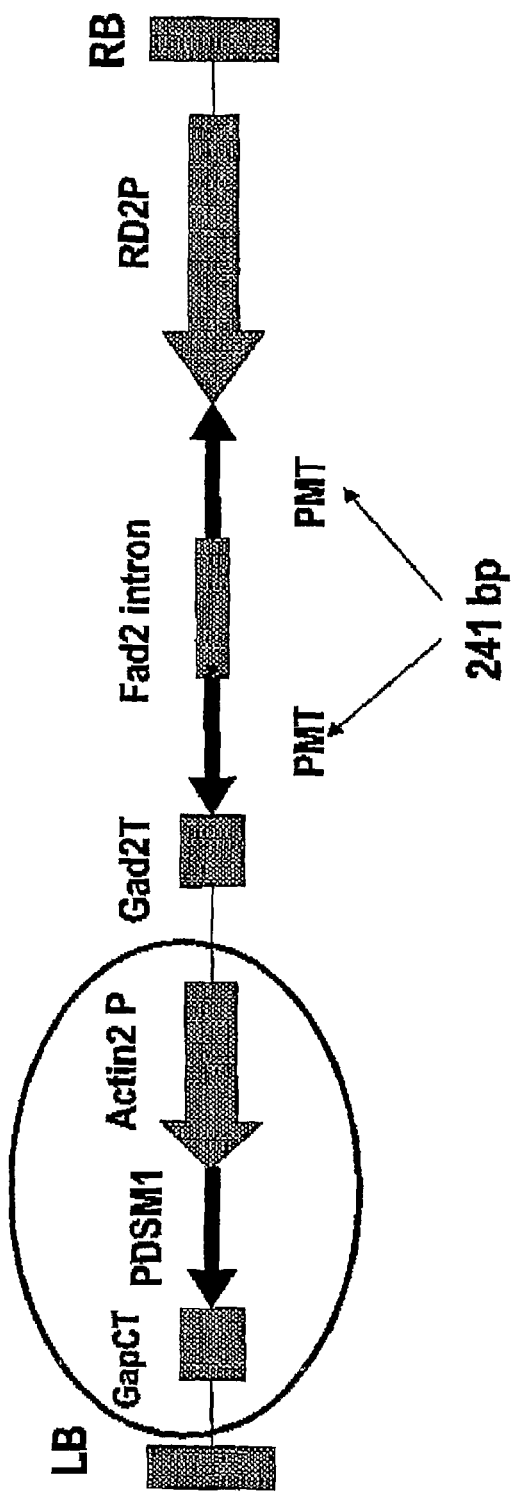
FIG. 3. An illustration of a PMTase inhibition construct comprising a PMTase inhibition cassette including a 241 bp fragment of the PMTase gene and a norflurazone resistance selection cassette including a mutant phytoene desaturase gene (PDSM-1).

FIG. 3 illustrates another RNAi construct that can be used to create a reduced nicotine and TSNA transgenic tobacco. This RNAi construct has a PMTase inhibition cassette (SEQ. ID. No. 25) and a norflurazone selection cassette (SEQ. ID. No. 35). Starting from the right border (RB), the PMTase inhibition cassette comprises an RD2 promoter (Bp 1-2010) operably linked to an antisense nucleic acid (241 bp) (Bp 2011-2251) of a PMTase gene, joined to a FAD2 intron (Bp 2252-3382), which is joined to a sense nucleic acid of the PMTase gene (241 bp) (Bp 3383-3623), which is joined to the GAD2 terminator (Bp 3624-3896). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the construct shown in FIG. 3 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Flue-cured tobacco that will be created using the construct shown in FIG. 3 will have significantly reduced levels of nicotine and TSNA, as compared to a conventional tobacco, a reference tobacco, or the parental strain of tobacco prior to genetic modification.

Burley tobacco will be transformed with the construct shown in FIG. 3 using *Agrobacterium*-mediated, Transbacter-mediated (see e.g., Broothaerts et al., *Nature* 433:629 (2005), herein expressly incorporated by reference in its entirety) or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 3 will have significantly reduced levels of nicotine and TSNA, as compared to a conventional tobacco, a reference tobacco, or the parental strain of tobacco prior to genetic modification.

Oriental tobacco will also be transformed with the construct shown in FIG. 3 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 3 will have significantly reduced levels of nicotine and TSNA, as compared to a conventional tobacco, a reference tobacco, or the parental strain of tobacco prior to genetic modification.

Figure 4:
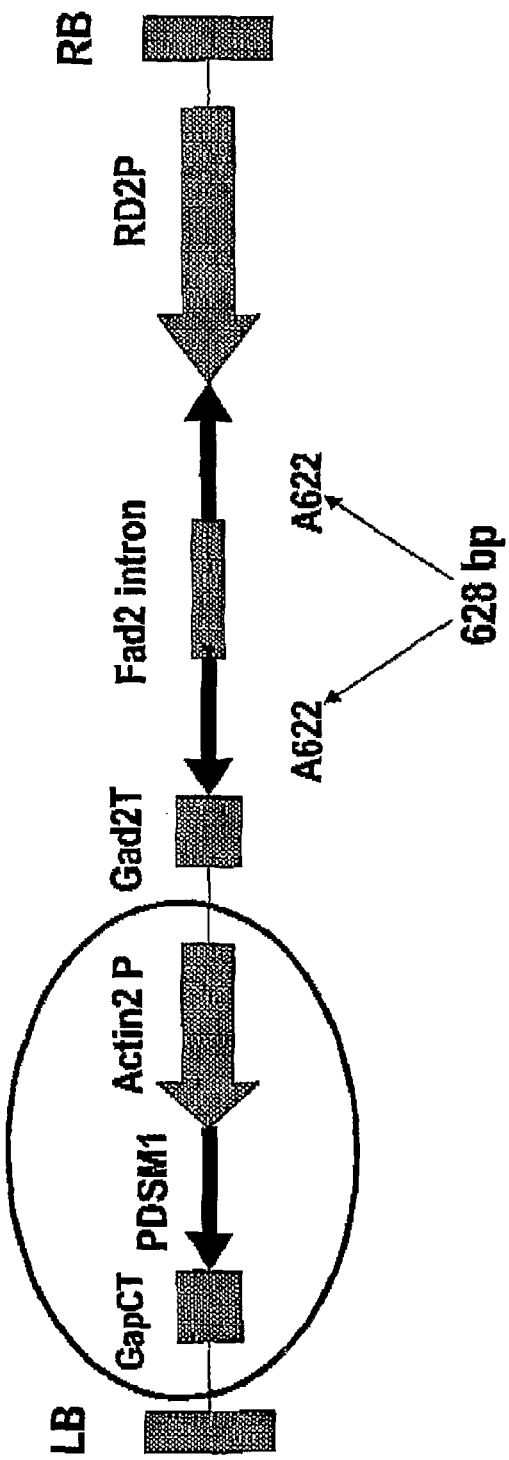
FIG. 4. An illustration of a A622 inhibition construct comprising a A622 inhibition cassette including a 628 bp fragment of the A622 gene and a norflurazone resistance selection cassette including a mutant phytoene desaturase gene (PDSM-1).

FIG. 4 illustrates another RNAi construct that was used to create a reduced nicotine and TSNA transgenic tobacco. This RNAi construct has a A622 inhibition cassette (SEQ. ID. No. 26) and a norflurazone selection cassette (SEQ. ID. No. 35). Starting from the right border (RB), the A622 inhibition cassette comprises an RD2 promoter (Bp 1-2010) operably linked to an antisense nucleic acid (628 bp) (Bp 2011-2638) of the A622 gene, joined to a FAD2 intron (Bp 2639-3769), which is joined to a sense nucleic acid of the A622 gene (628 bp) (Bp 3770-4397), which is joined to the GAD2 terminator (Bp 4398-4670). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 4 using *Agrobacterium*-mediated transformation and 270 independent lines were selected, regenerated, and transplanted in the greenhouse. Of the 270 independent lines, 259 plants were harvested and tested for alkaloid content. A total of 131 lines were identified as having less than 1,000 ppm total alkaloid and 45 lines were identified as having less than 500 ppm total alkaloid. Accordingly, it is understood by those skilled in the art that the transgenic Flue-cured tobacco created using the construct shown in FIG. 4 also has significantly reduced levels of nicotine and TSNA, as compared to a conventional tobacco, a reference tobacco, or the parental strain of tobacco prior to genetic modification.

Several lines that were transformed with this construct were unexpectedly found to have conventional levels of nicotine but a significantly reduced amount of nornicotine. That is, 9 lines were found to have nicotine levels ranging from 2.17 mg/g to 3.99 mg/g and nornicotine levels less than or equal to 0.00 to 0.06 mg/g (see Table 2).

TABLE 2

Transgenic tobacco having reduced nornicotine and conventional amounts of nicotine

| new I.D | Alkaloid (ppm) | Nornicotine (mg/g) | Nicotine (mg/g) |
| --- | --- | --- | --- |
| VDG 020 | 2486.53 | 0.00 | 2.30 |
| VDG 032 | 4683.01 | 0.00 | 3.48 |
| VDG 045 | 4490.79 | 0.00 | 3.94 |
| VDG 052 | 2855.58 | 0.00 | 2.61 |
| VDG 054 | 2291.89 | 0.00 | 2.17 |
| VDG 077 | 4857.86 | 0.06 | 3.99 |
| VDG 097 | 3072.40 | 0.00 | 2.58 |
| VDG 107 | 4921.31 | 0.03 | 3.59 |
| VDG 116 | 4960.64 | 0.00 | 3.56 |

TABLE 2-continued

Transgenic tobacco having reduced nornicotine and conventional amounts of nicotine

| new I.D | Alkaloid (ppm) | Nornicotine (mg/g) | Nicotine (mg/g) |
|---|---|---|---|
| Control-8 | 5005.22 | 0.28 | 4.02 |
| Control-20 | 5711.97 | 0.34 | 5.35 |
| Control-28 | 5196.25 | 0.24 | 4.52 |

*Highlighted entries show transgenic tobacco lines having a reduced amount of nornicotine and conventional amounts of nicotine.

Tobacco products containing the selectively reduced nornicotine transgenic tobacco described above are also embodiments provided herein. That is, tobacco products comprising a transgenic tobacco that comprises a conventional amount of nicotine (e.g., comprise or delivers according to FTC methodology at least, less than, greater than, or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/g nicotine) and a reduced amount of nornicotine (e.g., 0.00, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 mg/g), as compared to a conventional tobacco, a reference tobacco, or the parental strain of tobacco prior to genetic modification, are embodiments provided herein. Particularly preferred are transgenic tobacco and tobacco products made therefrom, which comprise a conventional amount of nicotine (e.g., comprises or delivers by FTC methodology at least, less than, greater than, or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/g nicotine) and a reduced amount of nornicotine (e.g., 0.00, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 mg/g), as compared to a conventional tobacco, a reference tobacco, or the parental strain of tobacco prior to genetic modification, and an isolated fragment of the A622 gene, in particular, comprising, consisting of, or consisting essentially of an isolated nucleic acid of SEQ. ID. No. 5, or the cassette of SEQ. ID. No. 26.

Burley tobacco will be transformed with the construct shown in FIG. 4 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 4 will have significantly reduced levels of nicotine and TSNA, as compared to a conventional tobacco, a reference tobacco, or the parental strain of tobacco prior to genetic modification. It is also expected that some lines of tobacco created with the afore-mentioned nucleic acid construct will retain conventional amounts of nicotine but will comprise a reduced amount of nornicotine, as compared to a conventional tobacco, a reference tobacco, or the parental strain of tobacco prior to genetic modification.

Oriental tobacco will also be transformed with the construct shown in FIG. 4 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 4 will have significantly reduced levels of nicotine and TSNA, as compared to a conventional tobacco, a reference tobacco, or the parental strain of tobacco prior to genetic modification. It is also expected that some lines of tobacco created with the afore-mentioned nucleic acid construct will retain conventional amounts of nicotine but will comprise a reduced amount of nornicotine, as compared to a conventional tobacco, a reference tobacco, or the parental strain of tobacco prior to genetic modification.

Figure 5:
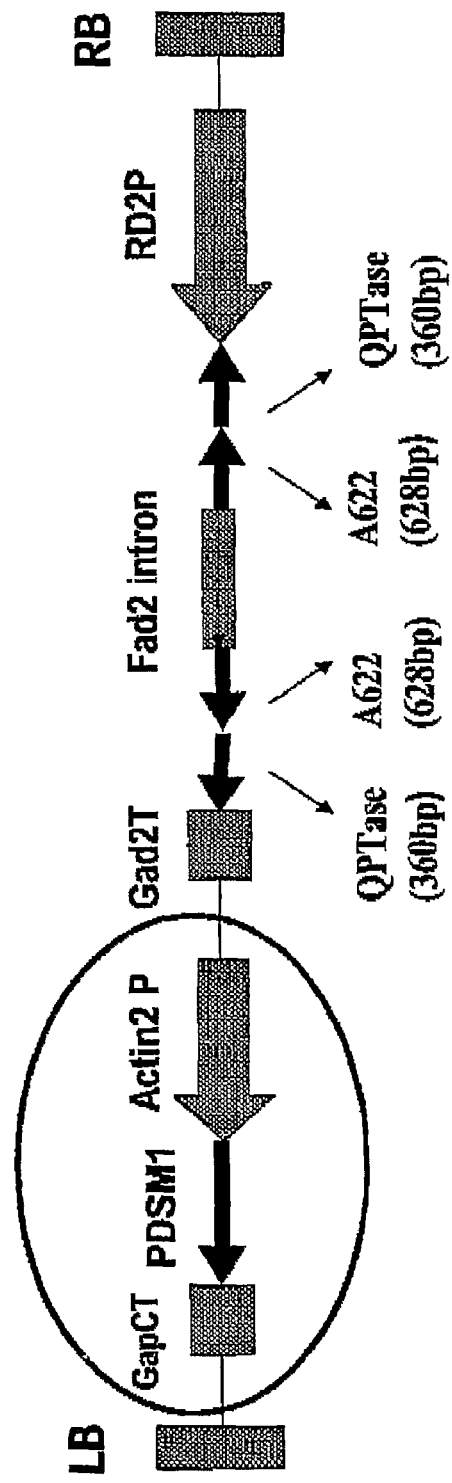
FIG. 5. An illustration of a QPTase/A622 double inhibition construct comprising a QPTase/A622 inhibition cassette including a 360 bp fragment of the QPTase gene and a 628 bp fragment of the A622 gene and a norflurazone resistance selection cassette including a mutant phytoene desaturase gene (PDSM-1).

FIG. 5 illustrates a double-knock-out RNAi construct, which has been created to develop a reduced nicotine and TSNA transgenic tobacco. This double-knock-out RNAi construct has a QPTase/A622 inhibition cassette (SEQ. ID. No. 27) and a norflurazone selection cassette (SEQ. ID. No. 35). Starting from the right border (RB), the QPTase/A622 inhibition cassette comprises an RD2 promoter (Bp 1-2010) operably linked to a QPTase antisense nucleic acid (360 bp) (Bp 2011-2370) of a QPTase gene, which is joined to a A622 antisense nucleic acid (628 bp) (Bp 2371-2998) of a A622 gene, which is joined to a FAD2 intron (Bp 2999-4129), which is joined to a sense nucleic acid of the A622 gene (628 bp) (Bp 4130-4757), which is joined to a sense nucleic acid of the QPTase gene (360 bp) (Bp 4758-5117), which is joined to the GAD2 terminator (Bp 5118-5390). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the construct shown in FIG. 5 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Flue-cured tobacco that will be created using the construct shown in FIG. 5 will have significantly reduced levels of nicotine and TSNA, as compared to a conventional tobacco, a reference tobacco, or the parental strain of tobacco prior to genetic modification.

Burley tobacco will be transformed with the construct shown in FIG. 5 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Burley tobacco that will be created using the construct shown in FIG. 5 will have significantly reduced levels of nicotine and TSNA, as compared to a conventional tobacco, a reference tobacco, or the parental strain of tobacco prior to genetic modification.

Oriental tobacco will also be transformed with the construct shown in FIG. 5 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 5 will have significantly reduced levels of nicotine and TSNA, as compared to a conventional tobacco, a reference tobacco, or the parental strain of tobacco prior to genetic modification.

More embodiments concern an RNAi construct designed to reduce the amount of sterols in tobacco and thereby reduce production of a PAH upon pyrolysis of said transgenic tobacco. A first sterol-reducing RNAi construct has a 14alpha demethylase inhibition cassette (SEQ. ID. No. 28). The 14alpha demethylase inhibition cassette comprises a double (two promoters in tandem) 35S promoter (Bp 1-618) operably linked to an antisense 14alpha demethylase nucleic acid (Bp 619-1503), which is joined to a FAD2 intron (Bp 1504-2634), which is joined to a sense nucleic acid of the 14alpha demethylase gene (Bp 2635-3519), which is joined to the Nos terminator (Bp 3520-3773). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the 14alpha demethylase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern another RNAi construct designed to reduce the amount of a sterol in tobacco and thereby reduce production of a PAH upon pyrolysis of said transgenic tobacco. A second sterol-reducing RNAi construct has a SMT2 inhibition cassette (SEQ. ID. No. 29). The SMT2 inhibition cassette comprises a double (two promoters in tandem) 35S promoter (Bp 1-618) operably linked to an antisense SMT2 nucleic acid (Bp 619-1398), which is joined to a FAD2 intron (Bp 1399-2529), which is joined to a sense nucleic acid of the SMT2 gene (Bp 2530-3309), which is joined to the Nos terminator (Bp 3310-3563). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterols and will generate significantly less PAHs upon pyrolysis, as compared to a conventional tobacco, a reference tobacco, or the parental strain of tobacco prior to genetic modification.

More embodiments concern another RNAi construct designed to reduce the amount of a sterol in tobacco and thereby reduce production of a PAH upon pyrolysis of said transgenic tobacco. A third sterol-reducing RNAi construct has a squalene synthase inhibition cassette (SEQ. ID. No. 30). The squalene synthase inhibition cassette comprises a double (two promoters in tandem) 35S promoter (Bp 1-618) operably linked to an antisense squalene synthase nucleic acid (Bp 619-1057), which is joined to a FAD2 intron (Bp 1058-2188), which is joined to a sense nucleic acid of the squalene synthase gene (Bp 2189-2627), which is joined to the Nos terminator (Bp 2628-2881). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the squalene synthase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern yet another RNAi construct designed to reduce the amount of a sterol in tobacco and thereby reduce production of a PAH upon pyrolysis of said transgenic tobacco. A fourth sterol-reducing RNAi construct has a HMG-CoA reductase inhibition cassette (SEQ. ID. No. 31). The HMG-CoA reductase inhibition cassette comprises a double (two promoters in tandem) 35S promoter (Bp 1-618) operably linked to an antisense HMG-CoA reductase nucleic acid (Bp 619-1468), which is joined to a FAD2 intron (Bp 1469-2599), which is joined to a sense nucleic acid of the HMG-CoA reductase gene (Bp 2600-3449), which is joined to the Nos terminator (Bp 3450-3703). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco (K326) was transformed with the HMG-CoA reductase inhibition cassette using *Agrobacterium*-mediated transformation and independent lines were selected, regenerated, and transplanted in the greenhouse. Several independent lines grown in the greenhouse were harvested and tested for the presence of various sterols (see Table 3). As shown in the table, several lines (e.g., HMGIR 1, HMGIR 2, HMGIR 3-2, HMGIR 4, HMGIR 7, HMGIR 11, HMGIR 13, HMGIR 16, HMGIR 18, HMGIR 19) were found to have significantly reduced levels of sterols, as compared to the parental strain of tobacco (i.e., tobacco of the same variety prior to genetic modification). Accordingly, embodiments include transgenic tobacco and tobacco products made therefrom comprising a reduced amount of sterols, as compared to a tobacco of the same variety, parental strain or a tobacco that has not been genetically modified. It is expected that the transgenic Flue-cured tobacco that was created using the construct above will generate significantly less PAHs upon pyrolysis, as compared to a conventional tobacco, a reference tobacco, or the parental strain of tobacco prior to genetic modification.

TABLE 3

| | K 326 cont | HMGIR 1 | HMGIR 2 | HMGIR 3-2 | HMGIR 4 | HMGIR 7 | HMGIR 11 | HMGIR 13 | HMGIR 16 | HMGIR 18 | HMGIR 19 |
|---|---|---|---|---|---|---|---|---|---|---|---|
| Squalene | 1 | 1.47 | 0.90 | 1.96 | 2.64 | 1.00 | 1.25 | 1.21 | 0.72 | 0.90 | 0.75 |
| Squalene | 1 | 1.48 | 0.88 | 2.13 | 2.78 | 0.94 | 1.14 | 1.12 | 0.97 | 0.73 | 0.96 |
| Tocopherol | 1 | 1.67 | 2.02 | 1.15 | 1.40 | 1.13 | 1.69 | 1.15 | 1.36 | 1.48 | 1.13 |
| Tocopherol | 1 | 1.73 | 2.08 | 1.33 | 1.34 | 0.84 | 1.54 | 0.88 | 1.05 | 1.11 | 0.87 |
| Campesterol | 1 | 0.74 | 1.13 | 0.47 | 0.60 | 0.76 | 0.75 | 0.83 | 0.90 | 1.20 | 1.21 |
| Stigmasterol | 1 | 0.45 | 1.00 | 0.34 | 0.30 | 0.50 | 0.55 | 0.65 | 0.85 | 1.42 | 1.27 |
| Sitosterol | 1 | 0.84 | 0.59 | 0.69 | 0.92 | 0.86 | 0.93 | 1.01 | 0.76 | 0.83 | 0.84 |

*Highlighted entries indicate transgenic tobacco lines having a reduction in sterols Burley tobacco will be transformed with the HMG-CoA reductase cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the HMG-CoA reductase inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

More embodiments concern still another RNAi construct designed to reduce the amount of a sterol in tobacco and thereby reduce production of a PAH upon pyrolysis of said transgenic tobacco. A fifth sterol-reducing RNAi construct has a developmentally regulated SMT2 inhibition cassette (SEQ. ID. No. 32). The developmentally regulated SMT2 inhibition cassette comprises a cinnamyl alcohol dehydrogenase promoter (Bp 1-995) operably linked to an antisense SMT2 nucleic acid (Bp 996-1775), which is joined to a PAP 1 intron (Bp 1776-2955), which is joined to a sense nucleic acid of the SMT2 gene (Bp 2956-3735), which is joined to the RuBisCo small subunit terminator (Bp 3736-4286). Accordingly, tobacco products (e.g., cigarettes), tobacco, tobacco plants, tobacco cells, tobacco seeds, in barley, Flue-cured or Oriental comprising this RNAi construct are embodiments provided herein.

Flue-cured tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Flue-cured tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Burley tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Burley tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Oriental tobacco will be transformed with the developmentally regulated SMT2 inhibition cassette using *Agrobacterium*-mediated, Transbacter-mediated, or biolistic transformation and independent lines will be selected, regenerated, and transplanted in the greenhouse. Most of the independent lines grown in the greenhouse will be harvested and tested for sterol content. It is expected that approximately 50% of the lines tested will have significantly less sterol than the parent strain of tobacco. Accordingly, it is expected that the transgenic Oriental tobacco that will be created using the construct above will have significantly reduced levels of sterol and will generate significantly less PAHs upon pyrolysis, as compared to a conventional tobacco, a reference tobacco, or the parental strain of tobacco prior to genetic modification.

Figure 6:
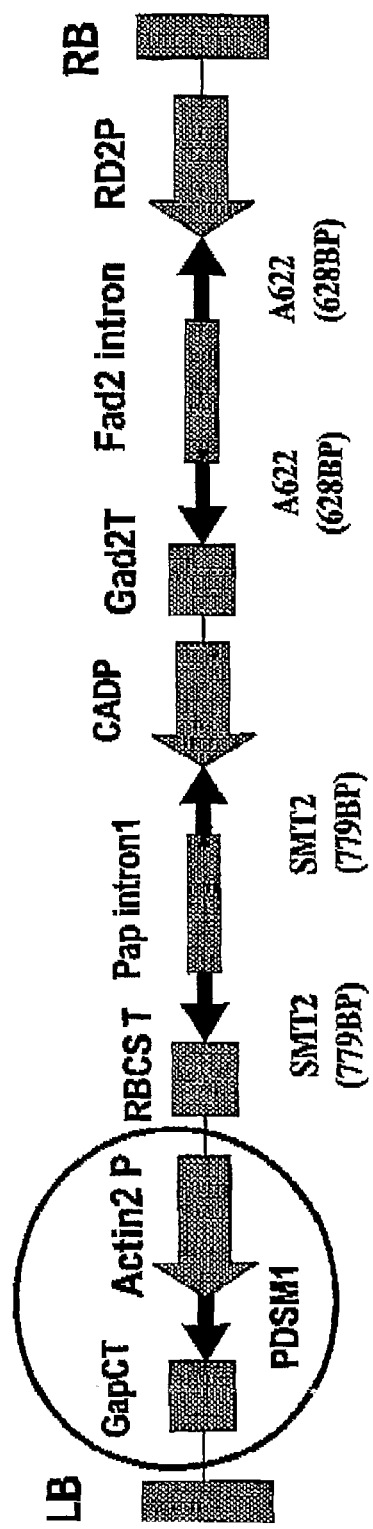
FIG. 6. An illustration of a SMT2/A622 double inhibition construct comprising a A622 inhibition cassette including a 628 bp fragment of the A622 gene, an SMT2 inhibition cassette including a 779 bp fragment of the SMT2 gene and a norflurazone resistance selection cassette including a mutant phytoene desaturase gene (PDSM-1).

FIG. 6 illustrates a double-knock-out RNAi construct that can be used to create a reduced nicotine, TSNA, sterol transgenic tobacco that generates a reduced amount of PAH upon pyrolysis. This double-knock-out RNAi construct has a A622/SMT2 inhibition cassette (SEQ. ID. No. 33) and a norflurazone selection cassette (SEQ. ID. No. 35). Starting from the right border (RB), the A622/SMT2 inhibition cassette comprises an RD2 promoter (Bp 1-2010) operably linked to a A622 antisense nucleic acid (628 bp) (Bp 2011-2638) of a A622 gene, which is joined to a FAD2 intron (Bp 2639-3769), which is joined to a sense nucleic acid of the A622 gene (628 bp) (Bp3770-4397), which is joined to the GAD2 terminator (Bp 4398-4670); which is joined to a cinnamyl alcohol dehydrogenase promoter (Bp 4671-5665) operably linked to an antisense SMT2 nucleic acid (Bp 5666-6445), which is joined to a PAP 1 intron (Bp 6446-7625), which is joined to a sense nucleic acid of the SMT2 gene (Bp 7626-8405), which is joined to the RuBisCo small subunit terminator (Bp 8406-8956). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the construct shown in FIG. 6 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Flue-cured tobacco that will be created using the construct shown in FIG. 6 will have significantly reduced levels of nicotine, TSNA, sterol, and will generate significantly less PAHs upon pyrolysis, as compared to a conventional tobacco, a reference tobacco, or the parental strain of tobacco prior to genetic modification.

Burley tobacco will be transformed with the construct shown in FIG. 6 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Burley tobacco that will be created using the construct shown in FIG. 6 will have significantly reduced levels of nicotine, TSNA, sterol, and will generate significantly less PAHs upon pyrolysis, as compared to a conventional tobacco, a reference tobacco, or the parental strain of tobacco prior to genetic modification.

Oriental tobacco will be transformed with the construct shown in FIG. 6 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid and sterol content. It is expected that approximately 50% of the lines tested will have less than 1,000 ppm total alkaloid and a reduced amount of sterols, as compared to the parental strain of tobacco, and approximately 10% of the lines tested will have less than 500 ppm total alkaloid and a reduced amount of sterols, as compared to the parental strain of tobacco. Accordingly, it is expected that the transgenic Oriental tobacco that will be created using the construct shown in FIG. 6 will have significantly reduced levels of nicotine, TSNA, sterol, and will generate significantly less PAHs upon pyrolysis, as compared to a conventional tobacco, a reference tobacco, or the parental strain of tobacco prior to genetic modification.

Figure 7:
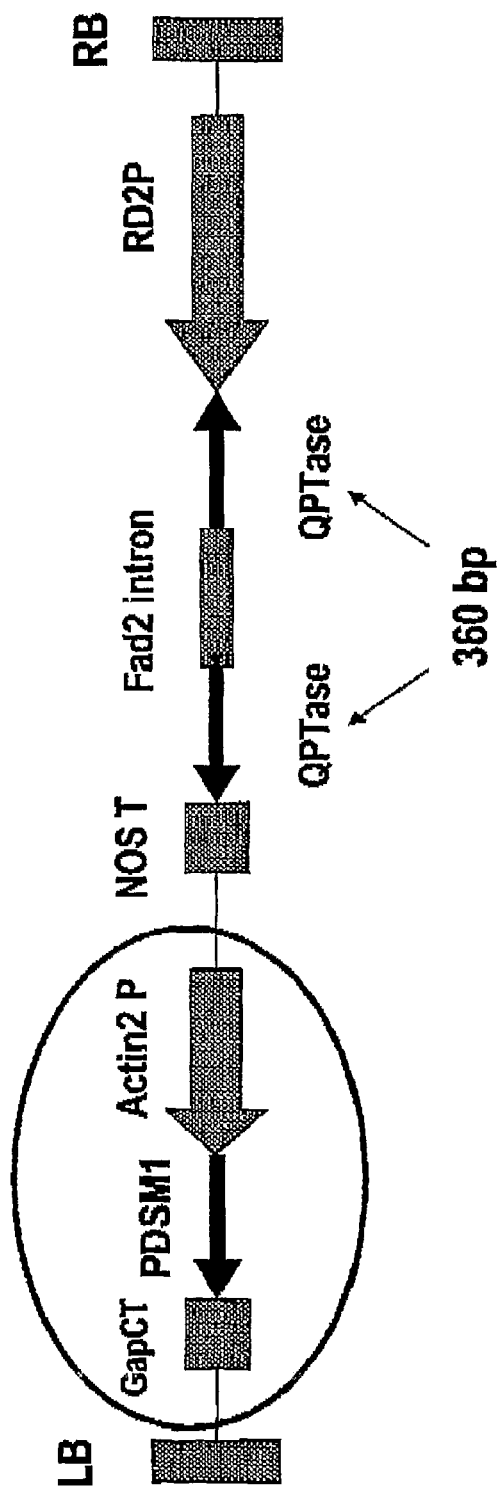
FIG. 7. An illustration of a QPTase inhibition construct comprising a QPTase inhibition cassette including a 360 bp fragment of the QPTase gene and a norflurazone resistance selection cassette including a mutant phytoene desaturase gene (PDSM-1).

FIG. 7 shows another RNAi construct that was used to generate several lines of reduced nicotine and TSNA tobacco. This RNAi construct has a QTPase inhibition cassette (SEQ. ID. No. 42) and a norflurazone selection cassette (SEQ. ID. No. 35). Starting from the right border (RB), the QPTase inhibition cassette comprises an RD2 promoter (Bp 1-2010) operably linked to an antisense fragment (360 bp) (Bp 2011-2370) of the QTPase gene, joined to a FAD2 intron (Bp 2371-3501), which is joined to a sense fragment of the QTPase gene (360 bp) (Bp 3502-3861), which is joined to the nopaline synthase (NOS) terminator (Bp 3862-4115). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco will be transformed with the construct shown in FIG. 7 using *Agrobacterium*-mediated, Transbacter-mediated, or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid, as compared to the parental strain of tobacco, and approximately 10% of the lines tested will have less than 500 ppm total alkaloid, as compared to the parental strain of tobacco. Accordingly, it is expected that the transgenic Flue-cured tobacco that will be created using the construct shown in FIG. 7 will have significantly reduced levels of nicotine and TSNA, as compared to a conventional tobacco, a reference tobacco, or the parental strain of tobacco prior to genetic modification.

Burley tobacco will be transformed with the construct shown in FIG. 7 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid, as compared to the parental strain of tobacco, and approximately 10% of the lines tested will have less than 500 ppm total alkaloid, as compared to the parental strain of tobacco. Accordingly, it is expected that the transgenic Burley tobacco that will be created using the construct shown in FIG. 7 will have significantly reduced levels of nicotine and TSNA, as compared to a conventional tobacco, a reference tobacco, or the parental strain of tobacco prior to genetic modification.

Oriental tobacco will be transformed with the construct shown in FIG. 7 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 7 will have significantly reduced levels of nicotine and TSNA, as compared to a conventional tobacco, a reference tobacco, or the parental strain of tobacco prior to genetic modification.

Figure 8:
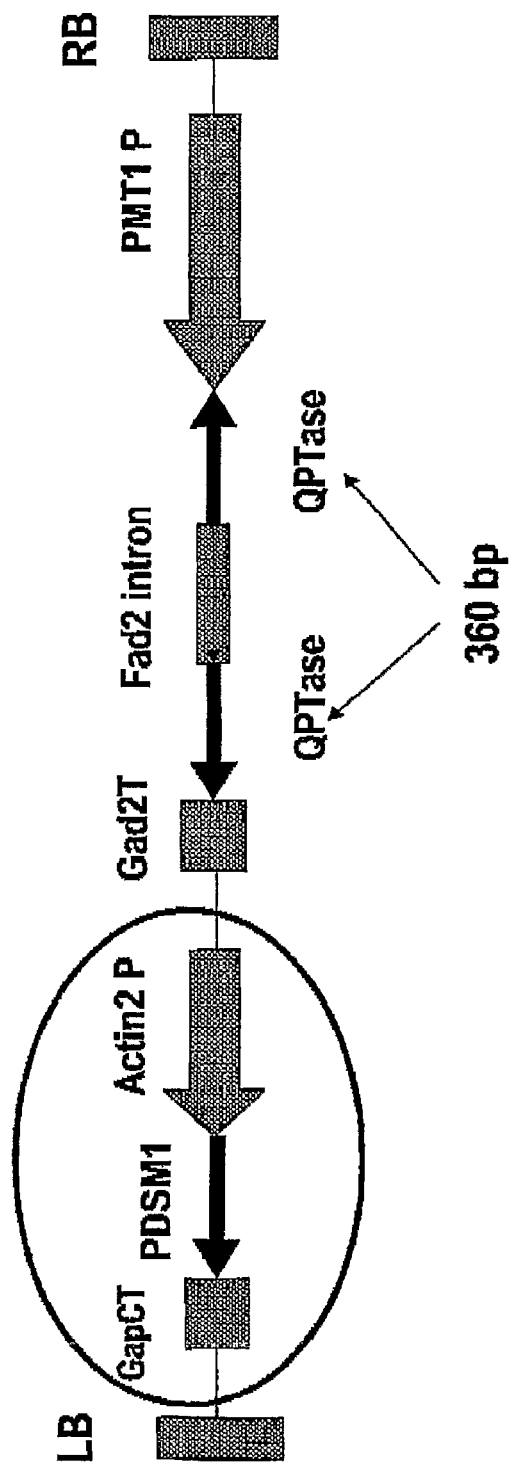
FIG. 8. An illustration of a QPTase inhibition construct comprising a QPTase inhibition cassette including a 360 bp fragment of the QPTase gene and a norflurazone resistance selection cassette including a mutant phytoene desaturase gene (PDSM-1).

FIG. 8 shows another RNAi construct that was used to generate several lines of reduced nicotine and TSNA tobacco. This RNAi construct has a QTPase inhibition cassette (SEQ. ID. No. 43) and a norflurazone selection cassette (SEQ. ID. No. 35). Starting from the right border (RB), the QPTase inhibition cassette comprises a PMTase1 promoter (Bp 1-711) operably linked to an antisense fragment (360 bp) (Bp 712-1071) of the QTPase gene, joined to a FAD2 intron (Bp 1072-2202), which is joined to a sense fragment of the QTPase gene (360 bp) (Bp 2203-2562), which is joined to the Gad2 terminator (Bp 2563-2835). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 8 using *Agrobacterium*-mediated transformation and more than about 98% of putative transformants were successfully transformed. Of the independent lines, 200 plants were regenerated, transplanted in the greenhouse, harvested and tested for alkaloid content. A total of 75 lines were identified as having less than 1,000 ppm total alkaloid and no lines were identified as having less than 500 ppm total alkaloid. Accordingly, the transgenic Flue-cured tobacco created using the construct shown in FIG. 8 has significantly reduced levels of nicotine and TSNA, as compared to a conventional tobacco, a reference tobacco, or the parental strain of tobacco prior to genetic modification.

Burley tobacco was also transformed with the construct shown in FIG. 8 using *Agrobacterium*-mediated transformation and more than about 98% of putative transformants were successfully transformed. Of the independent lines, 201 plants were regenerated, transplanted in the greenhouse, harvested and tested for alkaloid content. A total of 86 lines were identified as having less than 3,000 ppm total alkaloid and 12 lines were identified as having less than 1,000 ppm total alkaloid. Accordingly, it is understood by those skilled in the art that the transgenic Burley tobacco created using the construct shown in FIG. 8 also has significantly reduced levels of nicotine and TSNA, as compared to a conventional tobacco, a reference tobacco, or the parental strain of tobacco prior to genetic modification.

Oriental tobacco will be transformed with the construct shown in FIG. 8 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 8 will have significantly reduced levels of nicotine and TSNA, as compared to a conventional tobacco, a reference tobacco, or the parental strain of tobacco prior to genetic modification.

Figure 9:
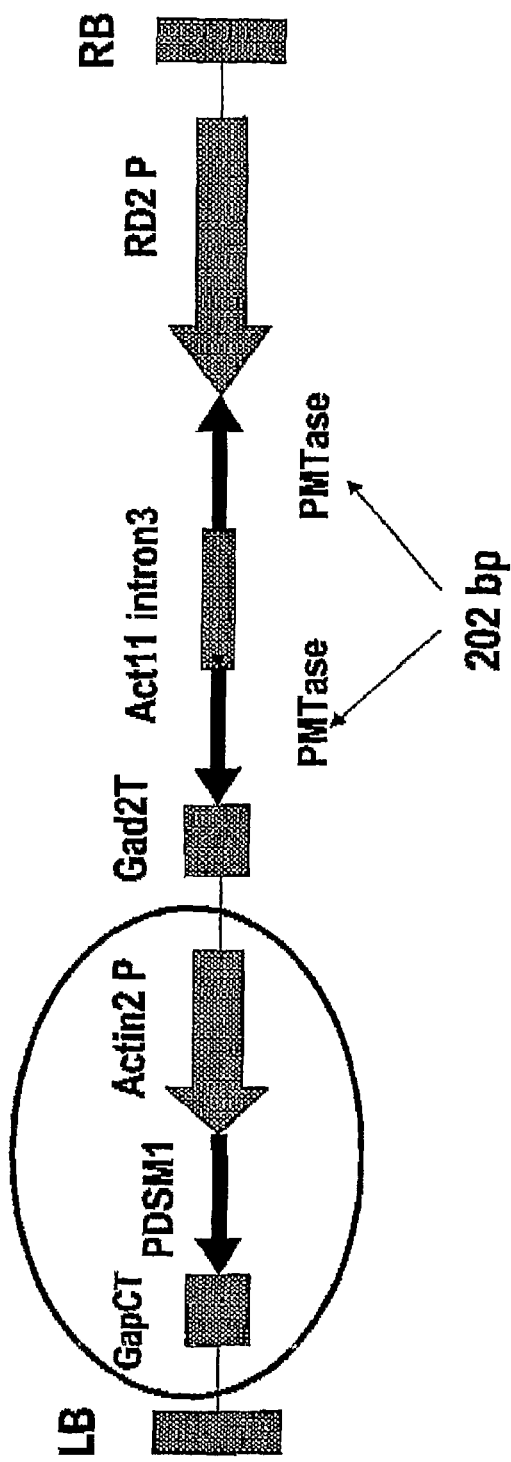
FIG. 9. An illustration of a PMTase inhibition construct comprising a PMTase inhibition cassette including a 202 bp fragment of the PMTase gene and a norflurazone resistance selection cassette including a mutant phytoene desaturase gene (PDSM-1).

FIG. 9 shows another RNAi construct that was used to generate several lines of reduced nicotine and TSNA tobacco. This RNAi construct has a PMTase inhibition cassette (SEQ. ID. No. 44) and a norflurazone selection cassette (SEQ. ID. No. 35). Starting from the right border (RB), the PMTase inhibition cassette comprises a truncated RD2 promoter (Bp 1-1061) operably linked to an antisense fragment (202 bp) (Bp 1062-1263) of the PMTase gene, joined to an Act11 intron (Bp 1264-1418), which is joined to a sense fragment of the PMTase gene (262 bp) (Bp 1419-1620), which is joined to the Gad2 terminator (Bp 1621-1893). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 9 using *Agrobacterium*-mediated transformation and more than about 98% of putative transformants were successfully transformed. Of the independent lines, 100 plants were regenerated, transplanted in the greenhouse, harvested and tested for alkaloid content. A total of 86 lines were identified as having less than 1,000 ppm total alkaloid and 12 lines were identified as having less than 500 ppm total alkaloid. Accordingly, the transgenic Flue-cured tobacco created using the construct shown in FIG. 9 has significantly reduced levels of nicotine and TSNA, as compared to a conventional tobacco, a reference tobacco, or the parental strain of tobacco prior to genetic modification.

Burley tobacco was also transformed with the construct shown in FIG. 9 using *Agrobacterium*-mediated transformation and more than about 98% of putative transformants were successfully transformed. Of the independent lines, 99 plants were regenerated, transplanted in the greenhouse, harvested and tested for alkaloid content. A total of 29 lines were identified as having less than 3,000 ppm total alkaloid and no lines were identified as having less than 1,000 ppm total alkaloid. Accordingly, it is understood by those skilled in the art that the transgenic Burley tobacco created using the construct shown in FIG. 9 also has significantly reduced levels of nicotine and TSNA, as compared to a conventional tobacco, a reference tobacco, or the parental strain of tobacco prior to genetic modification.

Oriental tobacco will be transformed with the construct shown in FIG. 9 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 9 will have significantly reduced levels of nicotine and TSNA, as compared to a conventional tobacco, a reference tobacco, or the parental strain of tobacco prior to genetic modification.

Figure 10:
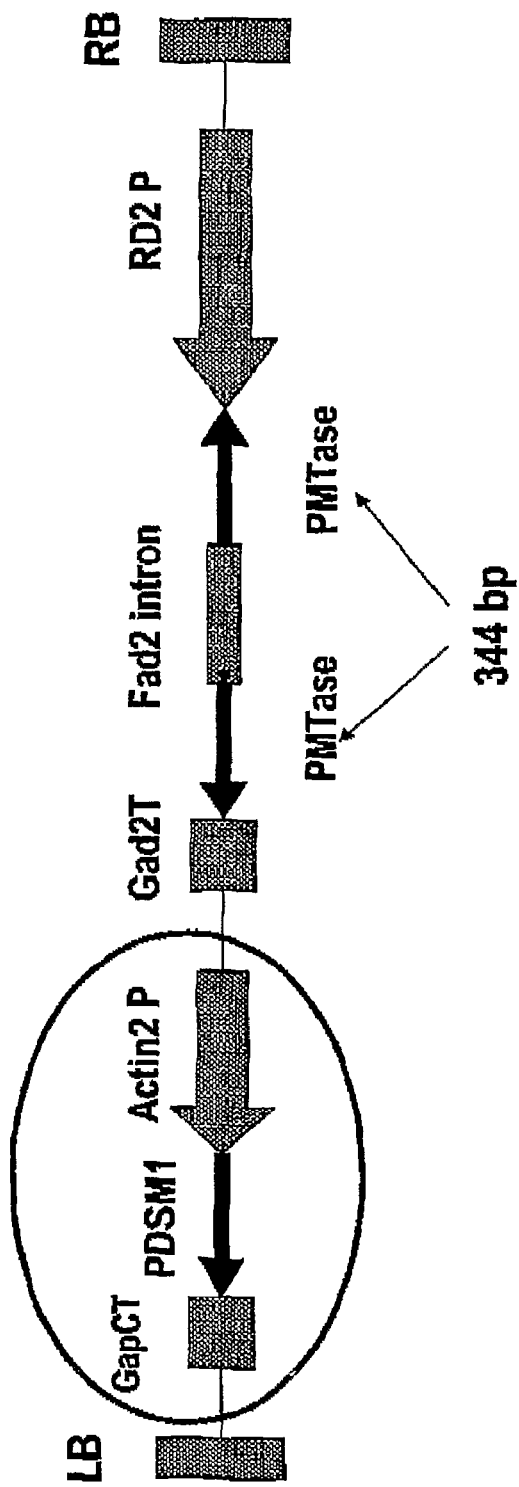
FIG. 10. An illustration of a PMTase inhibition construct comprising a PMTase inhibition cassette including a 344 bp fragment of the PMTase gene and a norflurazone resistance selection cassette including a mutant phytoene desaturase gene (PDSM-1).

FIG. 10 shows another RNAi construct that was used to generate several lines of reduced nicotine and TSNA tobacco. This RNAi construct has a PMTase inhibition cassette (SEQ. ID. No. 45) and a norflurazone selection cassette (SEQ. ID. No. 35). Starting from the right border (RB), the PMTase inhibition cassette comprises a RD2 promoter (Bp 1-2006) operably linked to an antisense fragment (344 bp) (Bp 2007-2350) of the PMTase gene, joined to an Fad2 intron (Bp 2351-3481), which is joined to a sense fragment of the PMTase gene (344 bp) (Bp 3482-3825), which is joined to the Gad2 terminator (Bp 3826-4098) at the left border (LB). The selection cassette comprises the Actin 2 promoter (Bp 1-1161) operably linked to a mutant phytoene desaturase gene (PDSM1) (Bp 1162-2890) joined to the GapC terminator (Bp 2891-3387) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 10 using *Agrobacterium*-mediated transformation and more than about 98% of putative transformants were successfully transformed. Of the independent lines, 66 plants were regenerated, transplanted in the greenhouse, harvested and tested for alkaloid content. A total of 44 lines were identified as having less than 1,000 ppm total alkaloid and 17 lines were identified as having less than 500 ppm total alkaloid. Accordingly, the transgenic Flue-cured tobacco created using the construct shown in FIG. 10 has significantly reduced levels of nicotine and TSNA, as compared to a conventional tobacco, a reference tobacco, or the parental strain of tobacco prior to genetic modification.

Burley tobacco will be transformed with the construct shown in FIG. 10 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid, as compared to the parental strain of tobacco, and approximately 10% of the lines tested will have less than 500 ppm total alkaloid, as compared to the parental strain of tobacco. Accordingly, it is expected that the transgenic Burley tobacco that will be created using the construct shown in FIG. 10 will have significantly reduced levels of nicotine and TSNA, as compared to a conventional tobacco, a reference tobacco, or the parental strain of tobacco prior to genetic modification.

Oriental tobacco will be transformed with the construct shown in FIG. 10 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid and approximately 10% of the lines tested will have less than 500 ppm total alkaloid. Accordingly, it is expected that the transgenic Oriental tobacco that will be created using the construct shown in FIG. 10 will have significantly reduced levels of nicotine and TSNA, as compared to a conventional tobacco, a reference tobacco, or the parental strain of tobacco prior to genetic modification.

Figure 11:
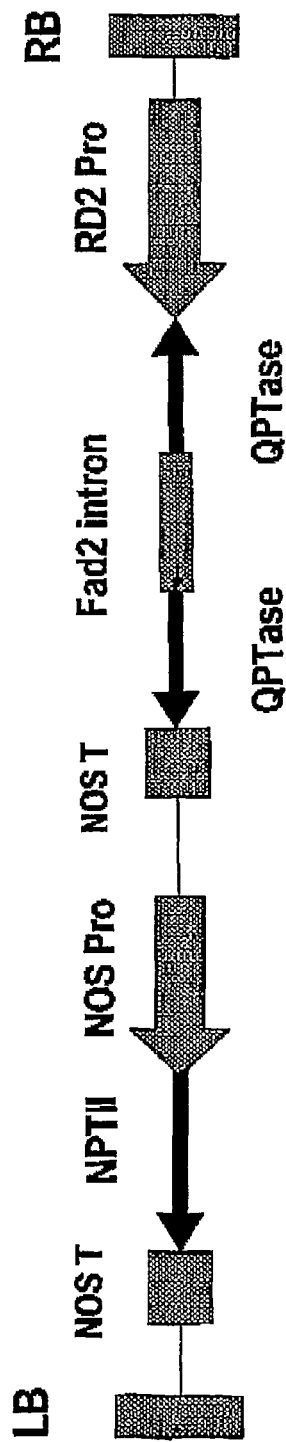
FIG. 11. An illustration of a QPTase inhibition construct comprising a QPTase inhibition cassette including a 360 bp fragment of the QPTase gene and a kanamycin resistance selection cassette including a neomycin phosphotransferase gene (NPTII).

FIG. 11 shows another RNAi construct that was used to generate several lines of reduced nicotine and TSNA tobacco. This RNAi construct (SEQ ID No 49) has a QTPase inhibition cassette (SEQ. ID. No. 42) and a kanamycin selection cassette (SEQ. ID. No. 48). Starting from the right border (RB), The QPTase inhibition cassette comprises an RD2 promoter (Bp 1-2010) operably linked to an antisense fragment (360 bp) (Bp 2011-2370) of the QTPase gene, joined to a FAD2 intron (Bp 2371-3501), which is joined to a sense fragment of the QPTase gene (360 bp) (Bp 3502-3861), which is joined to the NOS terminator (Bp 3862-4115). The selection cassette comprises the nopaline synthase (NOS) promoter (Bp 4116-4422) operably linked to a neomycin phosphotransferase (NPTII) gene (Bp 4435-5229) joined to the NOS terminator (Bp 5619-5872) at the left border (LB). Accordingly, tobacco products (e.g., cigarettes), tobacco, tobacco plants, tobacco cells, tobacco seeds, in Burley, Flue-cured or Oriental comprising this RNAi construct are embodiments provided herein.

Flue-cured tobacco was transformed with the construct shown in FIG. 11 using *Agrobacterium*-mediated transformation and more than about 98% of putative transformants were successfully transformed. Of the independent lines, 99 plants were regenerated, transplanted in the greenhouse, harvested and tested for alkaloid content. A total of 43 lines were identified as having less than 1,000 ppm total alkaloid and 15 lines were identified as having less than 500 ppm total alkaloid. Accordingly, the transgenic Flue-cured tobacco created using the construct shown in FIG. 11 has significantly reduced levels of nicotine and TSNA, as compared to a conventional tobacco, a reference tobacco, or the parental strain of tobacco prior to genetic modification.

Burley tobacco will be transformed with the construct shown in FIG. 11 using *Agrobacterium*-mediated, Transbacter-mediated or biolistic transformation and independent lines will be selected, regenerated, and transplanted in the greenhouse. Most of the independent lines grown in the greenhouse will be harvested and tested for alkaloid content. It is expected that approximately 50% of the lines tested will have less than 1,000 ppm total alkaloid, as compared to the parental strain of tobacco, and approximately 10% of the lines tested will have less than 500 ppm total alkaloid, as compared to the parental strain of tobacco. Accordingly, it is expected that the transgenic Burley tobacco that will be created using the construct shown in FIG. 11 will have significantly reduced levels of nicotine and TSNA, as compared to a conventional tobacco, a reference tobacco, or the parental strain of tobacco prior to genetic modification.

Oriental tobacco was transformed with the construct shown in FIG. 11 using *Agrobacterium*-mediated transformation and more than about 98% of putative transformants were successfully transformed. Of the independent lines, 122 plants were regenerated, transplanted in the greenhouse, harvested and tested for alkaloid content. A total of 22 lines were identified as having less than 1,000 ppm total alkaloid and 6 lines were identified as having less than 500 ppm total alkaloid. Accordingly, the transgenic Flue-cured tobacco created using the construct shown in FIG. 11 has significantly reduced levels of nicotine and TSNA, as compared to a conventional tobacco, a reference tobacco, or the parental strain of tobacco prior to genetic modification.

It should be emphasized that other promoters and terminators can be used with the nucleic acids provided herein interchangeably. Although RD2 (SEQ. ID. No. 13, 37, or 50) is a preferred root-specific promoter, there are other root-specific promoters that can be used, as well. For example, the putrescene methyl transferase 1 promoter (PMT-1) (SEQ. ID. No. 14) is a root-specific promoter that can be used in place of the RD2 promoter in any of the constructs described above. Similarly, although the actin2 promoter (SEQ. ID. No. 16) is preferred for driving expression of a norflurazone resistance gene, other constitutive promoters such as the GapC promoter (SEQ. ID. No. 15), the tobacco alcohol dehydrogenase (ADP) (SEQ. ID. No. 17) and the *Arabidopsis* ribosomal protein L2 (RPL2P) (SEQ. ID. No. 18) can be used to drive expression of the norflurazone resistance gene. Additionally, developmentally regulated promoters such as, cinnamyl alcohol dehydrogenase (SEQ. ID. No. 19) and metallothionein I promoter (SEQ. ID. No. 20) can be used interchangeable with the cassettes described herein.

Further, in some embodiments, a plurality of constitutive promoters, in tandem, can be used to drive expression of the norflurazone resistance gene. Additionally, a plurality of root-specific promoters can be used to drive expression one or more of the inhibition cassettes described above (e.g., the QTPase inhibition cassette, the PMTase inhibition cassette, the A622 inhibition cassette, a sterol inhibition cassette, or a double-knockout inhibition cassette). Developmentally regulated promoters, a plurality of developmentally regulated promoters, constitutive promoters, or a plurality of constitutive promoters can also be used to drive expression of one or more of the inhibition or selection cassettes described above. Accordingly, any promoter operable in tobacco can be used to drive expression of any of the inhibition cassettes or the selection cassette described herein (e.g., nos, 35S, or CAMV). Terminators, such as GAD2 terminator (SEQ. ID. No. 21), NOS terminator (SEQ ID No 38) and the FAD 2 (SEQ. ID. No. 22) or PAP1 introns can be used interchangeably, as well.

Other embodiments provided herein concern the discovery of several mutants of the phytoene desaturase gene that confer resistance to the herbicide norflurazone (e.g., SEQ. ID. Nos. 10, 11, and 12). These herbicide resistance genes were used as selectable markers in the transformations above. Typically, the selection was accomplished by introducing the transformed plant tissue to the norflurazone (e.g., 0.005 uM-0.1 uM conc.). That is, the concentration of norflurazone that can be used to select positive transformants containing a norflurazone resistance gene, as described herein can be at least, less than, greater than, or equal to 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 uM. Preferably, less than or equal to 0.05 uM concentration of norflurazone is used when selecting transformants with Flue-cured tobacco and less than or equal to 0.0125 uM concentration norflurazone is used when selecting transformants with Burley tobacco. As the plantlet develops, selection was accomplished by differentiating the green shoots (positive transformants) from the yellow or white shoots (negative transformants). Once selection was made, the herbicide was removed and the plantlet was allowed to develop in the greenhouse.

The norflurazone resistant phytoene desaturase mutants (PDSM-1, PDSM-2, and PDSM-3) were generated by site-directed mutagenesis of particular regions of the gene believed to be involved in binding of the herbicide. Constructs carrying the various PDSM genes were then transferred to tobacco leaf disks by conventional *Agrobacterium* transformation and the resistance to norflurazone was analyzed at various concentrations. After several iterations, the mutants described as SEQ. ID. Nos. 10, 11, and 12, were identified as sequences that confer resistance to norflurazone. Accordingly, embodiments provided herein concern the PDSM genes described herein, their use in plants as selectable markers to identify plant cells that contain a transformed gene, whether in tissue culture or in the field, and methods of identifying new PDSM genes that confer norflurazone resistance.

In a first selection construct, the *Arabidopsis* phytoene desaturase gene (PDS) (SEQ. ID. No. 36) was mutated using site-directed mutagenesis, such that a T to G mutation at position 1478, resulting in a Valine to *Glycine* change at amino acid residue 493 was created. To generate the norflurazone resistance gene, the open reading frame of the *Arabidopsis* phytoene desaturase gene was amplified and cloned into the TOPO vector (Invitrogen). A single base pair change from T-G at nucleotide position 1478, leading to a Valine to *Glycine* change at amino acid residue 493, was introduced using QuickChange Site-directed Mutagenisis Kit (Stratgene). The point mutation was verified by sequencing and the resultant mutant was named PDSM-1 (SEQ. ID. No. 10). The 1.729 Kb PDSM1 sequence was then amplified and ligated into the binary vector pWJ001, a pCambia derivative that contained the RNAi cassettes above, which was then introduced into *Agrobacterium tumefaciens*. A similar approach was used to generate the PDSM-2 and PDSM-3 mutants described in the sequence listing as SEQ. ID. NOs. 11 and 12.

That is, in a second selection construct, the *Arabidopsis* phytoene desaturase gene (PDS) (SEQ. ID. No. 36) was mutated using site-directed mutagenesis, such that a G to C mutation at position 863, resulting in a Arginine to Proline change at amino acid residue 288 was created. To generate the norflurazone resistance gene, the open reading frame of the *Arabidopsis* phytoene desaturase gene was amplified and cloned into the TOPO vector (Invitrogen). A single base pair change was introduced using QuickChange Site-directed Mutagenisis Kit (Stratgene). The point mutation was verified by sequencing and the resultant mutant was named PDSM-2. The 1.729 Kb PDSM-2 sequence was then amplified and ligated into the binary vector pWJ001, a pCambia derivative that contained the RNAi cassettes above, which was then introduced into *Agrobacterium tumefaciens*

Further, in a third selection construct, the *Arabidopsis* phytoene desaturase gene (PDS) (SEQ. ID. No. 36) was mutated using site-directed mutagenesis, such that a T to C mutation at position 1226, resulting in a Leucine to Proline change at amino acid residue 409 was created. To generate the norflurazone resistance gene, the open reading frame of the *Arabidopsis* phytoene desaturase gene was amplified and cloned into the TOPO vector (Invitrogen). A single base pair change was introduced using QuickChange Site-directed Mutagenisis Kit (Stratgene). The point mutation was verified by sequencing and the resultant mutant was named PDSM-3. The 1.729 Kb PDSM-2 sequence was then amplified and ligated into the binary vector pWJ001, a pCambia derivative that contained the RNAi cassettes above, which was then introduced into *Agrobacterium tumefaciens*

Accordingly, embodiments provided herein concern methods of identifying a mutation on a phytoene desaturase gene that confers resistance to an herbicide, preferably norflurazone. By one approach, a phytoene desaturase gene is provided, preferably SEQ. ID. No. 36, a nucleotide in said gene is mutated so as to generate a mutant phytoene desaturase gene, said mutant phytoene desaturase gene is transformed to a plant cell so as to generate a plant cell comprising said mutant phytoene desaturase gene, said plant cell comprising said mutant phytoene desaturase gene is then contacted with an herbicide, preferably norflurazone, and the presence or absence of a resistance to said herbicide is identified, whereby the presence of a resistance to said herbicide identifies said mutation as one that confers resistance to said herbicide. By one approach, the entire sequence of a phytoene desaturase gene (e.g., SEQ. ID. NO. 36) is mutated one residue at a time and each mutant is screened for resistance to the herbicide. Accordingly, embodiments provided herein include compositions (e.g., nucleic acid constructs or cassettes, plant cells, plants, tobacco, or tobacco products) that comprise, consist, consist essentially of a mutant phytoene desaturase nucleic acid of SEQ. ID. NO. 10, 11, or 12 or fragment thereof at least or equal to 30, 50, 100, 200, 400, 500, 700, 900, 1000, 1200, 1400, 1600, or 1700 consecutive nucleotides of in length that confers resistance to an herbicide, in particular norflurazone. Embodiments provided herein also include compositions (e.g., nucleic acid constructs or cassettes, plant cells, plants, tobacco, or tobacco products) comprising the mutant phytoene desaturase protein or fragments thereof (e.g., at least 15, 25, 50, 100, 200, 300, 400, 500 consecutive amino acids of a protein encoded by SEQ. ID. Nos. 10, 11, or 12) that confer resistance to an herbicide, in particular norflurazone.

The nucleic acid sequences, cassettes, and constructs described herein can also be altered by mutation such as substitutions, additions, or deletions that provide for sequences encoding functionally equivalent molecules. Due to the degeneracy of nucleotide coding sequences, other DNA sequences that encode substantially the same amino acid sequence can be used in some embodiments provided herein. These include, but are not limited to, nucleic acid sequences comprising all or portions of the nucleic acid embodiments described herein that complement said sequences and have been altered by the substitution of different codons that encode a functionally equivalent amino acid residue within the sequence, thus producing a silent change. In some contexts, the phrase "substantial sequence similarity" in the present specification and claims means that DNA, RNA or amino acid sequences which have slight and non-consequential sequence variations from the actual sequences disclosed and claimed herein are considered to be equivalent to the sequences provided herein. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Additional nucleic acid embodiments include sequences that are at least 80%, 81%, 82%, 83%, 84%, 85%, 86%, 87%, 88%, 89%, 90%, 91%, 92%, 93%, 94%, 95%, 96%, 97%, 98%, 99%, and 100% identical to the nucleic acids, nucleic acid constructs, and nucleic acid cassettes provided herein. Preferably these sequences also perform the functions of the particular nucleic acid embodiment (e.g., inhibition of nicotine, nornicotine, or sterol production or confer resistance to norflurazone). Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.

Additional nucleic acid embodiments also include nucleic acids that hybridize to the nucleic acid sequences disclosed herein under low, medium, and high stringency, wherein said additional nucleic acid embodiments also perform the function of the particular embodiment (e.g., inhibit nicotine, nornicotine, or sterol production or confer resistance to norflurazone). Identification of nucleic acids that hybridize to the embodiments described herein can be determined in a routine manner. (See J. Sambrook et al., Molecular Cloning, A Laboratory Manual (2d Ed. 1989) (Cold Spring Harbor Laboratory)). For example, hybridization of such sequences may be carried out under conditions of reduced stringency or even stringent conditions (e.g., conditions represented by a wash stringency of 0.3 M NaCl, 0.03 M sodium citrate, 0.1% SDS at 60 degrees C., or even 70 degrees C.). Preferably these sequences also perform the functions of the particular nucleic acid embodiment (e.g., inhibition of nicotine, nornicotine, or sterol production or confer resistance to norflurazone).

Accordingly embodiments provided herein also include compositions comprising, consisting of, or consisting essentially of: (a) the nucleic acid sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50); (b) nucleotide sequences encoding the amino acid sequences encoded by the nucleic acids of the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50); (c) any nucleotide sequences that hybridizes to the complement of the sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50) under stringent conditions, e.g., hybridization to filter-bound DNA in 0.5 M NaHPO$_4$, 7.0% sodium dodecyl sulfate (SDS), 1 mM EDTA at 50 degrees C. and washing in 0.2.times.SSC/0.2% SDS at 50 degrees C.; and (d) any nucleotide sequence that hybridizes to the complement of the sequences shown in the sequence listing (SEQ. ID. NOS. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50) under less stringent conditions (e.g., hybridization in 0.5 M NaHPO$_4$, 7.0% sodium dodecyl sulfate (SDS), 1 mM EDTA at 37 degrees C. and washing in 0.2.times.SSC/0.2% SDS at 37 degrees C. Preferably these sequences also perform the functions of the particular nucleic acid embodiment (e.g., inhibition of nicotine, nornicotine, or sterol production or confer resistance to norflurazone). Embodiments provided herein also include peptides encoded by the nucleic acid sequences of (a), (b), (c), or (d), above.

The examples described herein demonstrate that several different RNAi constructs can be used to effectively reduce the levels of nicotine, nornicotine, and sterols in tobacco. Additionally, these examples demonstrate that several mutant phytoene desaturase genes, which confer resistance to the herbicide norflurazone, have been created and that selection cassettes comprising these herbicide resistant nucleic acids can be used to determine the presence of a linked gene in transformed tobacco cells. Additionally, the norflurazone resistance nucleic acids described herein can be used in a general sense (e.g., in plants other than tobacco) to efficiently select positively transformed plant cells from plant cells that do not contain a construct comprising the norflurazone resistance gene. Thus, the norflurazone selection cassette or the norflurazone resistance gene described herein can be used to confer resistance to norflurazone in plants including, but not limited to, corn (*Zea mays*), canola (*Brassica napus, Brassica rapa* ssp.), alfalfa (*Medicago saliva*), rice (*Orya sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats, barley, vegetables, ornamentals, conifers, and turfgrasses (e.g., for ornamental, recreational or forage purposes). Vegetables include *Solanaceous* species (e.g., tomatoes; *Lycopersicon esculentum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschtata*), Zucchini (*C. pepo*), Crookneck squash (*C. crookneck*), *C. argyrosperma, C. argyrosperma* ssp, *C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*). Ornamental plants include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and *chrysanthemum*. Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Turf grass include but are not limited to zoysia grasses, bentgrasses, fescue grasses, bluegrasses, St.

Augustine grasses, Bermuda grasses, buffalo grasses, ryegrasses, and orchard grasses. Also included are plants that serve primarily as laboratory models, e.g., *Arabidopsis*. Preferred plants for use in the present methods include (but are not limited to) legumes, *solanaceous* species (e.g., tomatoes), leafy vegetables such as lettuce and cabbage, turf grasses, and crop plants (e.g., tobacco, wheat, *sorghum*, barley, rye, rice, corn, soybean, cotton, cassava, and the like), and laboratory plants (e.g., *Arabidopsis*). While any plant may be used to carry out this aspect provided herein, tobacco plants are particularly preferred.

Further, embodiments provided herein concern the production of norflurazone-resistant or tolerant plants, which can be sprayed with the herbicide in the field. In this manner, weeds and non-transformed plants will die after contact with the herbicide but plants containing the construct harboring the norflurazone resistance gene will survive. In one embodiment, for example, a norflurazone-containing herbicide is applied to the plant comprising the DNA constructs provided herein, and the plants are evaluated for tolerance to the herbicide. Any formulation of norflurazone can be used for testing plants comprising the DNA constructs provided herein. The testing parameters for an evaluation of the norflurazone tolerance of the plant will vary depending on a number of factors. Factors would include, but are not limited to the type of norflurazone formulation, the concentration and amount of norflurazone used in the formulation, the type of plant, the plant developmental stage during the time of the application, environmental conditions, the application method, and the number of times a particular formulation is applied. For example, plants can be tested in a greenhouse environment using a spray application method. The testing range using norflurazone can include, but is not limited to 0.5 oz/acre to 500 oz/acre. That is, the amount of herbicide that can be applied to transgenic plants containing a norflurazone-resistance gene in a field can be less than, equal to, or more than 0.5, 0.6, 0.7, 0.8, 0.9. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, or 500 oz/acre. In some embodiments, the norflurazone application rate is 2.24 kg to 4.48 kg ai/hectare (2 to 4 lbs ai/acre) or 2.8 to 5.6 kg granules/hectare (2.5 to 5 lb/acre) or 234 L/hectare (25 gal/acre) in solution. Higher amounts are preferred for finer textured soils or when longer residual activity is desired.

The preferred commercially effective range can be from 25 oz/acre to 100 oz/acre of norflurazone, depending on the crop and stage of plant development. A crop can be sprayed with at least one application of a norflurazone. For testing in cotton an application of 32 oz/acre at the 3-leaf stage may be followed by additional applications at later stages in development. For wheat, corn, soybean, and tobacco an application of 32 oz/acre of norflurazone at the 3-5 leaf stage can be used. The test parameters can be optimized for each crop in order to find the particular plant comprising the constructs provided herein that confers the desired commercially effective norflurazone tolerance level. The section below describes typical curing methods which may be used to prepare the tobacco once it is harvested.

a) Heterologous Expression

Tobacco has well-established transformation procedures and well-characterized regulatory elements for the control of transgene expression. Tobacco also has a high biomass yields and rapid scalability, which makes it a very suitable platform for commercial molecular farming. Since tobacco is a non-food and non-feed crop it also carries a reduced risk that the transgenic material or recombinant proteins would contaminate animal feed and would enter the human food chain. Because conventional or wild-type tobacco has a high content of nicotine and other toxic alkaloids, however, investigators have not explored the ability to use tobacco as a bioreactor. Further, the high cost of nicotine removal has steered investigators away from this technology.

The present disclosure, however, provides several types of genetically modified tobacco that can be used as a platform into which genes encoding commercially valuable compounds can be introduced. That is, by using genetically modified tobaccos having reduced levels of nicotine, sterols, and/or TSNAs, as bioreactors, it is contemplated that many commercially valuable industrial oils, pharmaceuticals, dietary supplements can be obtained with fewer processing steps (e.g., the removal of nicotine is no longer required). Accordingly, some embodiments concern tobaccos that are genetically modified to have a reduced level of nicotine, sterols, and/or TSNAs, further comprising a heterologous gene that produces a medicinal compound, industrial oil, or dietary supplement, which can be harvested and/or isolated or purified from said tobacco. Compounds generated in this manner can be used for a variety of applications such as the preparation of immunogens, vaccines, cooking oils, pharmaceuticals and dietary supplements. Techniques for the production of medicinal compounds in low-nicotine tobacco, such as a protein, for industrial or pharmaceutical application has been described in the art. It is contemplated, that these techniques can be readily used with the tobaccos and techniques that are described herein.

As an exemplary, non-liming example, the N-terminal fragment of SARS-CoV S protein (S1) can be expressed in low-nicotine tobacco plants, as is known in the art and exemplified in Pogrebnyak et al., Proc. Natl. Acad. Sci. USA (2005) 102:9062-9067. Incorporation of the S1 fragment into plant genomes as well as its transcription can be confirmed by PCR and RT-PCR analyses. High levels of expression of recombinant S1 protein can be observed in several transgenic lines by Western blot analysis using specific antibodies. Mammals parenterally primed with tobacco-derived S1 protein can have sera containing SARS-CoV-specific IgG as detected by Western blot and ELISA analysis.

The original gene encoding the human SARS-CoV spike glycoprotein (strain TOR2, National Center for Biotechnology Information no. NC 004718) is known in the art. DNA encoding a 79-kDa S protein fragment, corresponding to amino acids 14-714, can be amplified by two consecutive rounds of PCR to generate XbaI and SacI sites at the 5' and 3' ends, respectively, by using the following primers: SP-F1-CCT TGC GCT TCT CAG CCA CGC AAA CTC AAG AGG ATC GCA TCA CCA TCA CCA TCA CAG TGA CCT TGA CCG GTG CAC (SEQ ID NO 51), XbaI-F2-ATA ATC TAG ATG ATC ATG GCT TCC TCC AAG TTA CTC TCC CTA GCC CTC TTC CTT GCG CTT CTC AGC CAC G (SEQ ID NO 52), and SacI-HDELR-ATT CGA GCT CTT AAA GTT CAT CAT GAG CCA TAG AAA CAG GCA TTA CT (SEQ ID NO 53). The expression cassette of SARS-CoV 51 protein can contain the plant-derived 23-aa {MIMASSKLLSLALFLALLSHANS (SEQ. ID. No. 54}, signal peptide (SP), and a histidine tag {RGSHHHHHH (SEQ. ID. NO. 55} at the N-terminal portion of the resulting 79-kDa polypeptide. After addition of the plant-specific endoplasmic reticulum retention signal {HDEL (SEQ. ID. NO. 56}, the cassette can be subcloned into the XbaI/SacI site of the plant binary vector pE1801, which is known as a super promoter, followed by a tomato etch virus translation enhancer. The vector also can contain the npt II gene for kanamycin selection of transgenic plants. Plasmid pE1801-79SHDEL can be electroporated into *Agrobacterium tumefaciens* strain LBA4404 and used for plant transformations.

A genetically modified reduced nicotine and reduced TSNA tobacco, made as described herein, can be used as the platform. The low-nicotine/TSNA tobacco can be transformed by *Agrobacterium*-mediated transformation as is known in the art. Independent kanamycin-resistant (KmR) tobacco lines can be used for molecular analyses. The presence of the spike gene in transgenic plants can be confirmed by PCR using genomic DNA. KmR transgenic plants with PCR-confirmed presence of the S transgene can be further analyzed for gene-specific mRNA expression by quantitative RT-PCR as is known in the art. Western blot analysis of transgenic lines with polyclonal SARS-specific antibodies Sm and Sn can confirm the presence of SARS-CoV S-specific 79-kDa protein and its derivatives. KmR T1 tobacco lines (cv. LAMD-609) can be grown hydroponically to obtain large amounts of root tissue for immunological experiments. Western blot analysis of T1 lines can reveal high levels of S protein expression comparable with the original T0 transgenic lines.

Immunological assessment of the plant-expressed S protein can be performed in 6- to 8-week-old female BALB/c mice. For parenteral immunization, mice can be injected three times at 2-week intervals with an equivalent of 50 mg of dry tobacco root material per mouse. Powdered plant material can be reconstituted with saline (1/1 by weight) just before immunization. First and second immunizations can be given s.c. with complete and incomplete Freund's adjuvant, respectively; the third dose can be administered i.p. in saline. Sera can be collected retroorbitally from each mouse before and 10 days after each immunization. Four weeks after the last immunization, mice can receive an i.p. booster dose of 1 μg of commercially obtained S peptide (Cell Sciences, Canton, Mass.) without adjuvant. After 10 days, mice can be killed and exanguinated by heart puncture, and sera can be assayed by ELISA and Western blot analysis. Solid-phase ELISA can be carried out as known in the art MaxiSorp 96-well plates (Nalge Nunc) coated overnight at 4° C. with the same S peptides obtained from Cell Sciences at a concentration of 1 μg/ml in PBS. Antigen-specific antibodies can be detected by using the following antibodies: rabbit anti-mouse IgG (total) and anti-mouse IgG1 (both from BD Biosciences Pharmingen), anti-mouse IgG2a, IgG2b, IgG3, IgM, and IgA (all from Organon Teknika), and anti-mouse IgE (eBioscience, San Diego). A serum dilution with an OD450 of 0.15 units above background can be considered the ELISA titer.

III. Tobacco Products

Although the modified tobaccos described herein are preferably used to create tobacco products for human consumption (e.g., cigarettes, chew, snuff, plug, etc.) it should be realized that the tobacco described herein can be used for other applications such as animal feed, pharmaceutical production, and, in particular, the gernation of proteins (e.g., antiviral or anti-oncogenic peptides or antibodies or fragments thereof). Preferably, however, the tobacco and methods provided herein can be applied to any tobacco product, including, but not limited to pipe, cigar and cigarette tobacco and chewing tobacco in any form including leaf tobacco, shredded tobacco or cut tobacco. The term "tobacco product" includes, but is not limited to, smoking materials (e.g., cigarettes, cigars, pipe tobacco), snuff, chewing tobacco, gum, and lozenges. In numerous embodiments, the methods provided herein are applied to tobacco used to create the tobacco product.

A. Reduced Risk Tobacco Products

Provided herein are reduced risk tobacco products. A reduced risk tobacco product provided herein can be a traditionally configured tobacco product containing a reduced risk tobacco, such as a modified tobacco as provided herein. A reduced risk tobacco product provided herein also can contain conventional tobacco and be configured to reduce the risk of using the tobacco product. An example of such a reduced risk tobacco product is a cigarette containing a filter designed to reduce the risk associated with cigarette smoke. A reduced risk tobacco product also can contain a reduced risk tobacco and be configured to reduce the risk of using the tobacco product. An example of such a reduced risk tobacco product is a cigarette containing a reduced risk tobacco and a filter designed to reduce the risk associated with cigarette smoke. In some such embodiments, the reduced risk tobacco and reduced risk configuration act synergistically to reduce the overall risk of using the tobacco product.

Typical configurations of a tobacco product that reduces the risk of the tobacco product will include a filter that reduces the risk of exposure to tobacco smoke. A filter can be configured to be used with any smoking tobacco product, including cigars, pipes and cigarettes, as is known in the art. In one embodiment, the reduced risk tobacco product is a cigarette containing a filter that reduces the risk of exposure to tobacco smoke. Any of a variety of known filters that reduce the risk of exposure to tobacco smoke can be used in the reduced risk tobacco products provided herein, including, but not limited to, commercially available filters provided in cigarette products, and other filters known in the art, such as filters containing antioxidants, copper, carbon or activated charcoal, and/or paper-containing filters. One exemplary filter can be a filter containing an antioxidant or a radical scavenger. Filters containing antioxidants or radical scavengers can be prepared according to known methods, as exemplified in U.S. Pat. Nos. 6,832,612 and 6,415,798, herein expressly incorporated by reference in their entireties. Another exemplary filter is a filter that can reduce tobacco smoke-induced modulation of cell homeostasis, as can be assessed by determining, for example, modulation of the transcriptome or proteome, cell viability, or integrity of genetic material. Such filters can include a compound that sequesters or intercepts harmful components that generate DNA breaks, or enhance DNA breakage, thereby yielding a filter that removes harmful smoke components. For example, a filter can contain flat aromatic compounds that can scavenge potential carcinogens (e.g., components of tar), where exemplary flat aromatic compounds include caffeine and pontoxyfyllen. In some of the methods provided herein the filter comprises an interceptor of the carcinogen that has aromatic chemical structure: the carcinogen associates then with interceptor forming a complex that is retained in the filter.

The methods provided herein can be used for evaluating modifications to tobacco product configurations. For example, the methods provided herein can be used as assays for evaluating the effectiveness of a cigarette filler or filter. These methods also can be used to test any effect that can be resultant from a particular tobacco product configuration in combination with a modified tobacco. For example, the methods provided herein can be used to test a selected filter in combination with a modified tobacco. Accordingly, the methods provided herein provide a basis for evaluating and developing a reduced risk tobacco product. The methods provided herein further provide a basis for evaluating any further reduction in risk that can result from specific combinations of modified tobaccos and filters.

As provided herein, methods can be used for testing modulation of cell homeostasis by, for example, monitoring a molecular marker of modulation of cell homeostasis, when the cells are exposed to a tobacco composition from a modified tobacco configured in a tobacco product with a filter, or configured in a plurality of tobacco products with a plurality of different filters. Similarly, methods can be used for testing modulation of cell homeostasis when the cells are exposed to a tobacco composition from a plurality of modified tobaccos configured in a tobacco product with a filter, or configured in a plurality of tobacco products with a plurality of different filters. Accordingly, a variety of combinations of modified tobaccos and tobacco configurations can be tested for their properties of modulating cell homeostasis. The examples provided herein demonstrate that the risk-reducing properties of a tobacco and the risk-reducing properties of a filter can be interrelated such that the risk-reducing properties of a particular filter can vary depending on the type of tobacco used. The methods provided herein can be used to evaluate the degree to which a particular filter reduces the risk of one or more tobacco products, and also can be used to evaluate the ability of one or more filters to reduce the risk of a particular tobacco product. The methods provided herein also can be used to evaluate the ability of one or more filters in combination with one or more tobaccos to have additive risk-reducing properties, thereby forming an even further reduced-risk tobacco product.

B. Methods for Evaluating Tobacco and/or Tobacco Product

Methods for Determining the Risk Potential of Tobacco and Tobacco Products

Provided herein are several methods for identifying the propensity of a tobacco or tobacco product to contribute to a tobacco related disease. Generally, these approaches are practiced by providing a tobacco, obtaining smoke or a smoke condensate from the tobacco, contacting a cell with the smoke or smoke condensate, and identifying one or more attributes of the contacted cell. Tobacco products contain a number of compounds that induce various types of changes to a cell, including cell damage, change in gene expression including mRNA and/or protein expression, mutations, chromosomal aberrations, aberrant sister chromatid exchanges and micronuclei. Attributes of contacted cells indicative of such tobacco-induced cell changes can be identified in the methods provided herein, which address changes in cell homeostasis, as indicated by changes in gene expression, genetic mutations or aberrations, and modulation of cell viability and/or apoptosis. The methods provided herein can be used to determine affect of a tobacco or a tobacco product on a cell by determination of the presence, absence, or change in a molecular marker. For example, a molecular marker can be monitored, which is indicative of an affect on mRNA, protein, DNA damage, cell viability or apoptosis can be determined according to the methods provided herein or other methods generally known in the art, where monitoring of the molecular marker can be used to determine the affect of a tobacco or tobacco product on cell homeostasis. Exemplary affects of a tobacco or tobacco product on a cell include, but are not limited to, induction of a double-strand DNA break, inhibition of apoptosis, inhibition of cell proliferation, and modulation of gene expression, including modulation of the transcriptome and/or modulation of the proteome. Accordingly, the methods provided herein can be used to establish a profile for a particular tobacco by employing assay methods, including assays that identify tobacco products that modulate cell homeostasis from tobacco products that do not. For example, assays for induction of damage of cellular genetic material or assays for modulation of gene expression can be used to differentiate reduced risk tobacco products from conventional tobacco products. For example, the methods provided herein can be used to characterize a tobacco by assay methods including an assay for the induction of a double-strand DNA break, inhibition of apoptosis, inhibition of cell proliferation, modulation of transcription, or modulation of translation.

Several other assays have classically been used to analyze tobacco for the risk of adverse health effects. Traditionally, the first manner of testing consists of analysis of cigarette smoke for various components that can relate to health effects associated with smoking. A second manner of testing includes testing cigarette smoke tar on living cells. One of these tests detects changes in the genetic material of bacteria. Another test uses mouse cells grown in Petri dishes to detect potential cancer-causing activity. A third manner of testing seeks to determine if people smoke the tested tobacco cigarettes differently than the comparable brand or type currently on the market. If the way the cigarettes are smoked is different, then the other manners of testing can be repeated with the smoking machines set to reflect the change in smoking behavior. A fourth manner of testing examines the response of animals to cigarette smoke or tar. One such type of test looks for inflammation in the lungs of mice in response to cigarette smoke. A second test looks for tumor formation in the upper respiratory tract of hamsters exposed to smoke. A third test looks for the cancer producing ability of cigarette smoke tar by applying the tar to the skin of mice. Each manner of testing can include comparing tobacco cigarettes and both the effects of mainstream and sidestream smoke can be tested.

During smoking, both mainstream smoke (inhaled by the smoker) and sidestream smoke (mainly from the burning end of the cigarette) are generated. While mainstream and sidestream smoke are qualitatively similar the quantity of specific components differs between the two. Additionally, modifications to the cigarette can independently affect the composition of sidestream and mainstream smoke. It is concluded, therefore, that testing of tobacco or cigarettes can be assayed for both mainstream and sidestream smoke.

Epidemiology is not a practical approach for addressing the issue of the health effects of changes in a cigarette composition. Because people can smoke cigarettes differently (ex. longer or faster puffs) it can be important to consider whether these changes affect smoke chemistry and therefore toxicity. For example, a new, cigarette type can result in a smoker taking longer puffs, which can then change the smoke chemistry and toxicity.

Testing, however, can examine the effects on toxicity of a single design change in a cigarette or can examine the effects of a set of design changes compared to an unchanged control. Testing protocols can follow either a screening or a tradeoff approach. In the screening approach new designs can be subjected to a series of tests each with criteria for passing or failing. Designs that fail are eliminated from further testing, while those passing are subjected to additional scrutiny. In the tradeoff approach the relative changes in each test would be assessed in light of other information about the particular design.

The FTC method describes: how cigarettes are to be prepared for smoking, the type of smoking machine to use, the way the smoking machine should be operated, the method for collecting smoke products, and ways to measure moisture content, nicotine, carbon monoxide and tar. Typically in the methods provided herein, the FTC protocol for studies of cigarette smoke chemistry and toxicity are used.

Toxicity of cigarette smoke is directly related to the composition of the smoke and the composition of smoke can be changed if the way the cigarettes are smoked is changed.

There are a variety of chemical analyses that can be done to aid in the determination of the change in toxicity of a tobacco. These relate to the chemical composition of tobacco smoke. The following lists the chemical composition analysis and the health effect associated with the component or property measured: Total Particulate Matter (TPM; carcinogen), pH (effect on nicotine toxicity), Redox Potential (influence toxicity of whole smoke), Carbon Monoxide (reduces ability of blood to carry oxygen), Nitrogen Oxides (NOx; increases nitrosamine formation, inhibits enzyme function), Hydrogen Cyanide (inhibits lung clearance, lowers ability of body to use oxygen), Hydrocarbons (benzene, butadiene; suspected or known carcinogens), Aldehydes (ex. formaldehyde, acrolein; inhibit lung clearance, animal carcinogens), Volatile nitrosamines (strong animal carcinogens), Tobacco-specific nitrosamines (strong animal carcinogens), Nicotine (associated with cardiovascular disease), Phenols (enhance carcinogen action) Catechol (major carcinogen), and Polynuclear Aromatic Hydrocarbons (PNAs; major tumor initiators).

There are also a variety of known cell toxicity tests that can be performed in a relatively short time scale: bacterial mutagenicity test, animal cell test to detect potential carcinogens, and lung inflammation test in animals. One test, the Ames test, uses certain types of *Salmonella* bacteria to quantitatively assess the ability of a material to cause mutations, such as mutations involved in the process of carcinogenesis. In this test a solution of collected smoke particulates is mixed with the bacteria. Bacteria with the ability to grow in the absence of a particular nutrient are scored as mutants.

The potential cancer-causing ability of chemicals can also be evaluated using a cell transformation assay. In this assay, solutions of smoke particulates are given to animal cells grown in Petri dishes in the laboratory. After several weeks the cells are examined under the microscope. At this time the cells are scored for abnormal growth patterns. The number of clusters of abnormally growing cells is then compared among cigarette types.

In animal studies, inflammation of the lungs can be assessed. The changes measured in this test can be related to the development of chronic obstructive pulmonary disease. In these tests mice can be exposed to whole smoke two times per day, for any number of days according to the experimental design. At the end of the exposure period the animals would be killed and their lungs washed out to collect inflammatory cells. The numbers and kinds of the cells would be measured.

Two long-term animal tests for cancer causing ability of tobacco can be performed. In the first, test cigarette tar is applied to the back skin of mice. Skin tumors are then scored over the life of the animals. The use of this test is based on two observations: (1) in studies of tumor formation by smoke in hamsters whole smoke is active but smoke free of particulates is not and (2) a large number of known carcinogens are contained in the particulate portion of cigarette smoke.

The second test examines the tumor forming ability, of whole smoke in hamsters. A positive response can be observed in the larynx of hamsters exposed over their lifetime to whole cigarette smoke. In this test the animals are exposed twice daily to the diluted smoke of one cigarette every day for their entire lives. Tumor formation is the endpoint measured in this assay. Because the test is so labor intensive it is recommended only as a last step in a series of tests.

These known methods for assaying tobacco toxicity have limitations in terms of time length and/or expense relative to the assay methods provided herein. Accordingly, there is a long felt need for more rapid and less costly methods of analysis of tobacco products of different compositions. Despite the inefficiencies of the approaches above, it is contemplated herein that these methods for assaying tobacco toxicity can be used alone or in conjunction with the methods provided herein so as to provide additional information regarding the properties of the tobacco being characterized.

In the methods provided herein, one or more cells can be contacted with a tobacco composition such as tobacco smoke (TS), a tobacco smoke condensate (TSC), or total particulate matter (TPM), where exemplary TS and TSC are cigarette smoke (CS) and cigarette smoke condensate (CSC). Preparation of the tobacco composition used in the methods provided herein can be performed in accordance with the teachings herein and the knowledge and skill in the art. For example, TS can be collected using a smoking machine such as an INBIFO-Condor smoking machine, and TSC can be collected using cold traps, and TPM can be collected using a filter, as is known in the art. For example, CSC for testing can be prepared by passing smoke through a series of cold traps containing glass beads upon which CSC condenses; the CSC can then be collected by washing the beads with acetone as described in Mathewson, H. D. Beitrage zur Tabforschung. 3(6):430-7. September 1966. In addition, cells can be contacted with smoke provided in diluted form, where diluted smoke can be produced in a dilution chamber, as known in the art. For example, a smoking setup can contain a dilution chamber where the concentration of the smoke being applied to the cells can be varied by dilution with air in order to produce different dosages and intensities of smoke. The dilution chamber can be located between the burning cigarette and the cell exposure chamber. In addition, cigarette particulate matter for testing can be prepared by passing smoke through a glass fiber filter which is subsequently washed with solvent to collect the sample as described in Coresta Recommended Method No. 23 (August 1991). Although the description herein provides several methods in the context of characterizing tobacco and tobacco products that undergo pyrolysis (e.g., cigarettes, pipe tobacco, and cigars), similar approaches can be applied to the evaluate snuff, chew, and other tobacco products that do not undergo pyrolysis. Accordingly, the methods provided herein are not limited to smoke or smoke condensate, but can be applied to any tobacco composition known in the art. The preparation and analysis of compositions from such non-pyrolysis tobacco products is straightforward given the teachings provided herein or otherwise known in the art. Methods for contacting cells with compositions from such non-pyrolysis tobacco products also is straightforward given the teachings provided herein or otherwise known in the art.

The tobacco derived composition (i) can originate in a tobacco product, which can be either pure tobacco or a tobacco formulation (such as a cigarette, cigar, pipe or chewing tobacco) having multiple compositional elements, for example but not limited to structural elements, flavor chemicals and/or other additives, and (ii) can have multiple components (e.g., smoke or a smoke condensate, also referred to collectively as "smoke products") or can be a single known or unidentified component (e.g., a single chemical compound). The composition can be "derived" from tobacco or a tobacco formulation (i) by simple physical separation; (ii) as a product of combustion or heating, (iii) by solvent extraction, (iv) by chemical reaction(s) or (v) by enzyme activity (e.g., smoke concentrate treated with a microsomal cellular fraction or purified cytochrome P450).

In some methods provided herein, cells are contacted with TS, such as CS. The contacting of the cells with the CS, CSC, TS, TSC or TPM can be accomplished using any method known to one of skill in the art, including but not limited to, placing said cells into a smoking machine or smoke chamber (e.g., CULTEX®) for a period of time to allow the cells to be contacted with smoke, and/or providing a CSC or TSC to the media for a designated period of time (e.g., in 0.5% dimethylsulfoxide or other formulation). The contacting can be for any amount of time, however, preferably the cells are contacted for an amount of time that does not result in nonviability of more than 50% of the cells. In some embodiments, the amount of time can be varied and the results are compared. In a further embodiment, the cells are treated for an amount of time in which the gene expression is modulated, but the majority of cells are still viable. That is, in some embodiments, the cells are treated to a point in which the cells are at least, equal to, or more than 1% viable, including but not limited to 1%, 5%, 10%, 15%, 20%, 25%, 30%, 35%, 40%, 45%, 50%, 55%, 60%, 65%, 70%, 75%, 80%, 85%, 90%, 95%, 99%, and 100% viable.

In a another embodiment, the amount of time for contacting a cell with the CS, CSC, TS, TSC or TPM is any amount selected from the group consisting of about at least, equal to, or more than 1 seconds to about 24 hours, including but not limited to at least, equal to, or more than 1 second, 15 seconds, 30 seconds, 45 seconds, 1 minute, 3 minutes, 5 minutes, 10 minutes, 15 minutes, 20 minutes, 25 minutes, 30 minutes, 35 minutes, 40 minutes, 45 minutes, 60 minutes, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 22 hours 23 hours and 24 hours. In a further embodiment, the cells are contacted for less than and including about 20 minutes. In yet another embodiment, the cells are contacted for about 2 to about 20 minutes.

The amount of smoke with which the cells are contacted can be any of a variety of amounts according to the desired level of exposure. For example, smoke exposure can be performed in accordance with FTC parameters: 2.0 second puff duration, 35 mL puff every 60 seconds. Puff duration, volume and frequency can be increased or decreased to achieve different levels of smoke exposure, as desired. Similarly, smoke condensate or other tobacco compositions can be contacted with cells at a variety of different concentrations and for a variety of different durations, as desired. For example, smoke condensate at 20 mg/mL can be contacted with cells for any of the above-provided amounts of time, as desired.

Tobacco smoke or smoke products can be treated prior to contacting the cells with the smoke or smoke product. For example, the smoke or smoke concentrate can be contacted with a filter, such as a filter provided herein, for example by obtaining smoke or smoke condensate from a cigarette after passing through a filter attached to the tobacco product, such as a cigarette.

The cells suitable for use in the methods provided herein include human as well as non-human cells, but are preferably human pulmonary cells (e.g., lung or bronchial cell), although cells of other systems impacted by smoking, including but not limited to cells of the upper aerodigestive tract (e.g., oral cavity including cheek, pharynx, larynx, and esophagus), bladder, stomach, kidney, pancreas, and blood (e.g., lymphocytes, monocytes, neutrophils, esoinophils or basophils, or neoplastic blood cells such as myeloid leukemia cells); cells of the cardiovascular system (including endothelial cells, smooth muscle cells (e.g. from vessel walls, myocardial cells, etc.) and cells of the female reproductive system (e.g. cells of the uterus, cervix, fallopian tubes, ovary, and placenta), can also be used. The cells can be normal or can be neoplastic, metaplastic, dysplastic or malignant. The cells can be collected from a living organism (e.g., a pulmonary lavage specimen, tissue section such as a lung or bronchial section, oral mucosa sample, cheek swab, or sputum sample), can be primary cell cultures, or can be established cell cultures. In some embodiments, the cells can be obtained from a living organism, including a human, after the organism is contacted with a tobacco composition, for example, after a human consumes a cigarette. Cells collected from a living organism can be collected using any of a variety of known methods known in the art, according to the cell type to be collected (e.g., a cheek scrape or lung lavage). In specific, non-limiting embodiments, the cells can be NHBE cells, or can be human epithelian pulmonary type II cells, such as A549 cells, or can be cells obtained from a human primary culture.

Many embodiments described herein employ NHBE cells that are maintained in culture, and other embodiments employ human lung carcinoma cells (A549 cells). Although NHBE and A549 cells are preferred for the methods described herein, it should be understood that many other cells that are typically contacted with tobacco or TS during the process of smoking (e.g., lung cells, bronchial cells, cells of the oral mucosa, pharynx, larynx, and tongue) can also be used. Additionally, many immortal cell lines can be used with the methods described herein. Preferred cells for use with the embodied approaches include, but are not limited to, human bronchial cells (e.g., BEP2D or 16HBE140 cells), human bronchial epithelial cells (e.g., HBEC cells, 1198, or 1170-I cells), NHBE cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226), tongue cells (e.g., CAL 27), and mouth cells (e.g., Ueda-1)). Many of such cultures are available commercially or through a public repository (e.g., ATCC). Further, several techniques exist that allow for one to generate primary cultures of said cells and these primary cultures can be used with the methods described herein.

Conventional approaches in tissue culture can be used to establish and maintain said cells in preparation for the methods described herein. That is, the cells may be grown in culture by any method known to one of skill in the art and with the appropriate media and conditions. The cells grown in culture may require feeder layers, for example. The cells may be grown to confluence or may be grown to less than confluence before, during, or after treatment. In some embodiments the cells are grown to between about 10% and about 90% confluence, including but not limited to, at least, equal to, or more than 15%, 20%, 25%, 30%, 35%, 40%, 45%, 50%, 55%, 60%, 65%, 70%, 75%, 80%, 85%, 90%, 95%, and 99% confluence before contact with CS, CSC, TS, or TSC.

In some embodiments, the cells contacted and assayed in accordance with the methods provided herein are manipulated to control and/or modify the percentage of cells that are in one or more phases of the cell cycle. For example, the cells can be manipulated such that at least 50% of the cells of the population of cells are in the S phase. The cells used herein can be manipulated to control the population of cells in one or more of G0, G1, S, G2, or M phases of the cell cycle. For example, cells can be manipulated such that at least 50%, 60%, 70%, 75%, 80%, 85%, 90%, 95%, or 100%, of the population of cells are in G0, G1, S, G2, or M phase. In another example, cells can be manipulated such that greater than 50%, 60%, 70%, 75%, 80%, 85%, 90%, 95%, or 100%, of the population of cells are in G0, G1, S, G2, or M phase. In another example, cells can be manipulated such that 50%, 60%, 70%, 75%, 80%, 85%, 90%, 95%, or 100%, of the population of cells are in G0, G1, S, G2, or M phase. The section below describes several preferred methods for characterizing tobacco and tobacco products in greater detail.

Exemplary Assays

The methods provided herein for characterizing tobacco or a tobacco product can be used in a variety of applications, including, but not limited to, the comparison of two or more tobaccos or two or more tobacco products, identifying a modulation of cell homeostasis, identifying an induction of damage of cellular genetic material, or identifying a modulation of gene expression including mRNA and/or protein expression. The methods provided herein for characterizing tobacco also can be used for identifying a tobacco product that has a reduced potential to contribute to a tobacco-related disease, and making a tobacco product that has a reduced potential to contribute to a tobacco-related disease. In addition to methods provided herein for characterizing tobacco or a tobacco product, additional methods known in the art for characterizing tobacco or a tobacco product can be used in the place of, or in conjunction with, the methods provided herein.

The methods of identifying a tobacco, identifying a compound in tobacco, identifying a tobacco product, and making a tobacco product provided herein, can in addition be utilized in methods of identifying two or more tobaccos, identifying a compound in two or more tobaccos, identifying a tobacco product by comparing two or more tobacco products, and making a tobacco product by comparing two or more tobacco products. In some embodiments, the two or more tobaccos or tobacco products can be compared for their effect on cell homeostasis, gene expression including mRNA and/or protein expression, or damage to genetic material of cells. In some embodiments, at least one tobacco or tobacco product can be a reduced risk tobacco or tobacco product, respectively. In some embodiments, at least one tobacco can be a modified tobacco, such as a chemically modified tobacco or a genetically modified tobacco. In some embodiments, at least one tobacco can be a reduced risk tobacco product, such as a tobacco product configured to contain a filter that reduces the risk of tobacco exposure such as a filter provided herein. In one example, two or more tobaccos can be compared to identify a compound in tobacco that modulates gene expression including mRNA and/or protein expression. In one example, two or more tobacco products can be compared to identify a compound in tobacco that modulates gene expression including mRNA and/or protein expression.

In some embodiments, a second tobacco product (e.g., a cigarette) is compared to a first tobacco product (e.g., a cigarette) using the methods above so as to identify which of the two tobacco products is less likely to contribute to a tobacco-related disease. For example, a first population of isolated human cells of the mouth, tongue, oral cavity, or lungs (e.g., NHBE cells), is contacted with a CS from a first tobacco product (e.g., a "reduced risk full flavor" cigarette) in an amount and for a time sufficient to modulate cell homeostasis, such as inducing damage of cellular genetic material or modulating gene expression including mRNA and/or protein expression. A second population of isolated human cells of the mouth, tongue, oral cavity, or lungs (e.g., NHBE cells), preferably the same type of cell as used in the analysis of the first tobacco product, is also contacted with a CS from a second tobacco product (e.g., a cigarette) in an amount and for the same amount of time as used with the first product or for a time sufficient to modulate cell homeostasis by, for example, inducing damage of cellular genetic material or modulating gene expression including mRNA and/or protein expression.

The data obtained from the analysis of the first tobacco product can be compared to the data obtained from the analysis of the second tobacco product so as to identify, for example, an increased risk tobacco or a compound in tobacco. The data also can be used to identify a reduced risk tobacco. The data further can be used to identify a tobacco product configuration, such as a filter, with increased risk or with reduced risk. Thus, by analyzing the differences between the tobacco products, one can identify a tobacco product that has less potential to contribute to a tobacco related disease or to identify, for example, a first tobacco product that has a reduced risk to contribute to a tobacco-related disease, as compared to a second tobacco product or vice versa. By one technique, a tobacco product that is less likely to contribute to a tobacco-related disease is identified because it causes less modulation of cell homeostasis. By another technique, a tobacco product that is less likely to contribute to a tobacco-related disease is identified because it causes less modulation of cell homeostasis under the same level of damage induced to cellular genetic material. In another technique, a tobacco product that is less likely to contribute to a tobacco-related disease is identified because it induces less damage to cellular genetic material. In another technique, a tobacco product that is less likely to contribute to a tobacco-related disease is identified because it induces fewer or smaller in degree changes in gene expression such as changes in the transcriptome or changes in the proteome.

The methods provided herein can be used not only to identify a tobacco product that has a reduced potential to contribute to a tobacco-related disease, as compared to a second tobacco product, but also to develop tobacco products that have a reduced potential to contribute to a tobacco-related disease, as compared to a second tobacco product. For example, by screening modified tobacco (e.g., chemically or genetically modified tobacco) or a tobacco product with a modified configuration in accordance with the methods disclosed herein, one can rapidly determine whether the modified tobacco or modified tobacco product has an increased or decreased potential to contribute to a tobacco-related disease, as compared to the tobacco or tobacco product that is not modified.

More embodiments concern methods to identify components of a tobacco product that contribute to a tobacco-related disease, the selective removal or inhibition of production of these components, and the determination that the removal of the component(s) results in a reduced risk tobacco product. Such a determination that the removal of the component(s) results in a reduced risk tobacco product can be indicated by, for example, a molecular marker that is associated with a tobacco-related disease. Exemplary molecular markers of a tobacco-related disease include, but are not limited to a molecular marker indicative of apoptosis, a molecular marker indicative of double-stranded DNA breaks, an overexpressed or underexpressed mRNA, an overexpressed or underexpressed polypeptide. In one example methods are provided to identify components of a tobacco product that contribute to a tobacco-related disease, the selective removal or inhibition of production of these components, and the determination that the removal of the component(s) modulates expression of a gene that is associated with a tobacco-related disease in a manner that reduces the potential for the tobacco product to contribute to a tobacco related disease. It is contemplated that particular components of tobacco products are the factors that modulate responses in human cells that contribute to tobacco-related disease. It is further contemplated that modification of the tobacco product will, concomitantly, result in a modulation of the response in human cells contacted with the smoke from said modified tobacco product, which modulates the likelihood to contribute to a tobacco-related disease relative to an unmodified tobacco product. For example, modification of genes that contribute to the production of these toxic components in tobacco (e.g., genetic engineering or chemical treatment) will, concomitantly, result in a modulation of the response in human cells contacted with the smoke from said modified tobacco, which modulates the likelihood to contribute to a tobacco-related disease relative to tobacco prior to modification of the component-producing gene. Accordingly, by selectively removing the components from a tobacco product (e.g., by modifying a tobacco or a tobacco product configuration) that induce the events that contribute to tobacco-related disease in a human, one can develop tobacco products that are less likely to contribute to a tobacco-related disease.

Methods for Identifying a Tobacco or Tobacco Product that Modulates Cell Homeostasis Provided herein are methods for identifying a tobacco that modulates cell homeostasis by providing a tobacco, obtaining a tobacco composition from the tobacco, contacting a cell with the tobacco composition, and identifying the presence or absence of a modulation of cell homeostasis after contact with the tobacco composition. In some embodiments, the methods provided herein can be used to identify a tobacco that affects cell homeostasis as can be monitored by, for example, determining that the tobacco induces double strand DNA breaks, modulates apoptosis, modulates cell proliferation, or induces expression of a gene that is silent during homeostasis or repress a gene that is active during homeostasis. In some embodiments, the tobacco composition can be smoke or smoke condensate. By modulation of homeostasis of a cell is meant the change in the state of a cell upon contact of the cell by a tobacco or tobacco composition (e.g., tobacco smoke or tobacco smoke condensate), where the state of the cell can be the cell cycle, the apoptotic state, the expression levels of one or more genes as represented by mRNA levels and/or protein levels or post-translational modifications to proteins. Typically modulation of cell homeostasis can be monitored by measurement of one or more molecular markers of the state of a cell. It is contemplated herein that any tobacco-induced change in cell homeostasis can serve as an indicator that said tobacco or tobacco composition may contribute to a tobacco-related disease. Because it is known that tobacco or tobacco compositions can have a plurality of adverse affects on cells, it is contemplated that typically a less pronounced modulation of cell homeostasis after the cell is contacted with a tobacco or tobacco composition (e.g., tobacco smoke or tobacco smoke condensate), the greater propensity that the tobacco or tobacco composition will present a reduced level of risk for developing a tobacco related disease relative to a conventional or reference tobacco. Accordingly, it is contemplated herein that a tobacco or tobacco composition characterized as reduced risk tobacco or tobacco composition is one that, upon contact with a cell, does not modulate cell homeostasis or modulates cell homeostasis to a lesser degree than the cell homeostasis modulation induced by a conventional or reference tobacco.

Also provided herein are methods of identifying a compound in tobacco that modulates cell homeostasis by providing a first tobacco, obtaining a tobacco composition from the first tobacco, contacting a first population of cells with the tobacco composition from the first tobacco, identifying the degree of modulation of cell homeostasis in the first population of cells after contact with the tobacco composition from the first tobacco, providing a second tobacco that has been modified to reduce a compound in the second tobacco, obtaining a tobacco composition from the second tobacco, contacting a second population of cells with the tobacco composition from the second tobacco, and identifying the degree of modulation of cell homeostasis after contact with the tobacco composition from the second tobacco, where an identification of a reduction in the degree of modulation of cell homeostasis after contact with the tobacco composition from the second tobacco identifies the compound as one that modulates cell homeostasis. In some embodiments, the methods provided herein can be used to identify a compound in tobacco that modulates apoptosis. In some embodiments, the methods provided herein can be used to identify a compound in tobacco that modulates cell proliferation. In some embodiments, the tobacco composition can be smoke or smoke condensate.

Also provided herein are methods of identifying a tobacco product that has a reduced potential to contribute to a tobacco-related disease by providing a first tobacco product, obtaining a tobacco composition from the first tobacco product, contacting a first population of cells with the tobacco composition from the first tobacco product, identifying the degree of modulation of cell homeostasis in the first population of cells after contact with the tobacco composition from the first tobacco product, providing a second tobacco product, obtaining a tobacco composition from the second tobacco product, contacting a second population of cells with the tobacco composition from the second tobacco product, and identifying the degree of modulation of cell homeostasis after contact with the tobacco composition from the second tobacco product, where an identification of a reduction in the degree of modulation of cell homeostasis after contact with the tobacco composition from the second tobacco product as compared to the degree of modulation of cell homeostasis after contact with the tobacco composition from the first tobacco product identifies the second tobacco product as one that has a reduced potential to contribute to a tobacco-related disease. In some embodiments, the second tobacco product has been modified to reduce a compound in the second tobacco. In some embodiments, the second tobacco product can be genetically modified to reduce the expression of at least one gene that regulates production of the compound. In some embodiments of the methods provided herein, the degree of modulation of cell homeostasis can be determined by identifying the degree of modulation of apoptosis. In some embodiments of the methods provided herein, the degree of modulation of cell homeostasis can be determined by identifying the degree of modulation of cell proliferation. In some embodiments, the tobacco composition can be smoke or smoke condensate.

Also provided herein are methods of making a tobacco product that has a reduced potential to contribute to a tobacco-related disease by providing a first tobacco, obtaining a tobacco composition from the first tobacco, contacting a first population of cells with the tobacco composition from the first tobacco, identifying the degree of modulation of cell homeostasis in the first population of cells after contact with the tobacco composition from the first tobacco, providing a second tobacco, obtaining a tobacco composition from the second tobacco, contacting a second population of cells with the tobacco composition from the second tobacco, identifying the degree of modulation of cell homeostasis after contact with the tobacco composition from the second tobacco product, where an identification of a reduction in the degree of modulation of cell homeostasis after contact with the tobacco composition from the second tobacco as compared to the degree of modulation of cell homeostasis after contact with the tobacco composition from the first tobacco identifies the second tobacco as one that has a reduced potential to contribute to a tobacco-related disease, and incorporating the second tobacco, which has a reduced potential to contribute to a tobacco-related disease, into a tobacco product. In some embodiments, the second tobacco has been modified to reduce a compound in the second tobacco. In some embodiments, the second tobacco can be genetically modified to reduce the expression of at least one gene that regulates production of the compound. In some embodiments of the methods provided herein, the degree of modulation of cell homeostasis can be determined by identifying the degree of modulation of apoptosis. In some embodiments of the methods provided herein, the degree of modulation of cell homeostasis can be determined by identifying the degree of modulation of cell proliferation. In some embodiments, the tobacco composition can be smoke or smoke condensate.

The methods provided herein can be used to determine the effect of a tobacco product or a compound from a tobacco product, on cell homeostasis. Cells of an organism contacted with a tobacco composition, e.g., mammalian epithelial cells, can undergo apoptosis and can proliferate at particular levels under "normal" conditions, where "normal" as used in this context refers to conditions in which cells are not contacted with tobacco or a tobacco composition and are not otherwise placed under atypical (e.g., stressful) environmental conditions. Environmental conditions, for example, contacting the cells with a tobacco composition, can modulate apoptosis of the contacted cells and also can modulate the proliferation of the contacted cells. Such modulation can result in processes that can directly lead to cellular events in tobacco-related disease (e.g., apoptosis can be decreased, which can lead to neoplastic cell growth) or can indirectly lead to cellular events in tobacco-related disease (e.g., apoptosis can be increased, which can trigger a cell growth response in an organism, which can lead to neoplastic cell growth). The methods provided herein can be used to examine the affect of a tobacco product or a compound from a tobacco product, on cell homeostasis by, for example, determining the affect of a tobacco or tobacco compound on apoptosis in a cell or a cell population, or, for example, determining the affect of a tobacco or tobacco compound on cell proliferation of a cell or a cell population. In some embodiments, a first tobacco that causes a lesser degree of modulation of cell homeostasis relative to a second tobacco can be characterized as a reduced risk tobacco. In some embodiments, a first tobacco that causes a lesser degree of inhibition of apoptosis relative to a second tobacco can be characterized as a reduced risk tobacco. In some embodiments, a first tobacco that causes a lesser degree of inhibition of cell proliferation relative to a second tobacco can be characterized as a reduced risk tobacco. Any of a variety of known methods for determining modulation of cell homeostasis by, for example, modulating apoptosis, modulating cell proliferation, modulating gene expression (e.g., mRNA or protein levels) as exemplified herein, can be used in the methods provided herein.

Also provided herein are methods for determining cell response to cell damage. Cells can be exposed to environmental input, such as a tobacco composition, that causes cell damage. The response of these cells to the environmental input-mediated damage can be indicative of the likelihood of the environmental input leading to an environmental input-related disease. In one embodiment, cells can be contacted with a tobacco composition, and the response of the cells to the contact by the tobacco composition can indicate the likelihood of the tobacco composition leading to a tobacco-related disease.

As provided herein, cells contacted by different environmental inputs, for example, different tobacco compositions, can respond differently to cell damage caused by the environmental input, where some cell responses are more indicative of leading to a disease state compared to other cell responses. Thus, contemplated herein, two or more tobacco compositions can be compared and characterized according to the cell responses in reaction to damage induced by exposure to the tobacco compositions. In such methods, exposure conditions can be manipulated such that the amount of damage to the cells is equivalent for each different tobacco composition, resulting in a determination of different characteristic cell responses to the same amount of cell damage.

Accordingly, methods are provided herein for comparing two or more tobacco compositions by contacting a first tobacco composition with a first population of cells, and contacting a second composition with a second population of cells, where the two different contacting steps are performed in such a manner that the first and second population of cells undergo equivalent amount of cell damage, and then determining the degree of modulation of cell homeostasis in the first and second populations of cells, where the tobacco composition that is characterized by the lowest degree of cell modulation can be identified as a tobacco with reduced likelihood of causing a tobacco-related disease. In such methods, damage to the cells caused by the tobacco compositions can be measured by, for example, measuring the degree of damage to the genetic material of the cells, in accordance with the methods provided herein or otherwise known in the art. Also in such methods, the degree of modulation of cell homeostasis can be determined by the degree of modulation of apoptosis or cell proliferation relative to cells not contacted by a tobacco composition or relative to cells contacted by a tobacco composition from a tobacco, such as a reduced risk tobacco with a known degree of modulation of cell homeostasis. The following section describes several methods for differentiating tobaccos and tobacco products that induce genetic damage from those that do not.

Analysis of Changes to Cell Homeostasis: Identifying a Tobacco that Induces Genetic Damage Provided herein are methods of identifying a tobacco that induces genetic damage by providing a tobacco, obtaining a tobacco composition from the tobacco, contacting a cell with the tobacco composition, and identifying the presence or absence of damage of cellular genetic material in the cell after contact with the tobacco composition. In some embodiments, the methods provided herein can be used to identify a tobacco that induces a double-strand DNA break. In some embodiments, the tobacco composition can be smoke or smoke condensate.

Also provided herein are methods of identifying a compound in tobacco that induces damage of cellular genetic material by providing a first tobacco, obtaining a tobacco composition from the first tobacco, contacting a first population of cells with the tobacco composition from the first tobacco, identifying the amount of damage of cellular genetic material in the first population of cells after contact with the tobacco composition from the first tobacco, providing a second tobacco that has been modified to reduce a compound in the second tobacco, obtaining a tobacco composition from the second tobacco, contacting a second population of cells with the tobacco composition from the second tobacco, and identifying the amount of damage of cellular genetic material after contact with the tobacco composition from the second tobacco, where an identification of a reduction in the amount of damage of cellular genetic material after contact with the tobacco composition from the second tobacco identifies the compound as one that induces the damage of cellular genetic material. In some embodiments, the methods provided herein can be used to identify a compound in tobacco that induces a double-strand DNA break. In some embodiments, the tobacco composition can be smoke or smoke condensate.

Also provided herein are methods of identifying a tobacco product that has a reduced potential to contribute to a tobacco-related disease by providing a first tobacco product, obtaining a tobacco composition from the first tobacco product, contacting a first population of cells with the tobacco composition from the first tobacco product, identifying the amount of damage of cellular genetic material in the first population of cells after contact with the tobacco composition from the first tobacco product, providing a second tobacco product, obtaining a tobacco composition from the second tobacco product, contacting a second population of cells with the tobacco composition from the second tobacco product, and identifying the amount of damage of cellular genetic material after contact with the tobacco composition from the second tobacco product, where an identification of a reduction in the amount of damage of cellular genetic material after contact with the tobacco composition from the second tobacco product as compared to the amount of damage of cellular genetic material after contact with the tobacco composition from the first tobacco product identifies the second tobacco product as one that has a reduced potential to contribute to a tobacco-related disease. In some embodiments, the second tobacco product has been modified to reduce a compound in the second tobacco. In some embodiments, the second tobacco product can be genetically modified to reduce the expression of at least one gene that regulates production of the compound. In some embodiments of the methods provided herein, the amount of damage of cellular genetic material can be determined by identifying the induction of double-strand DNA breaks. In some embodiments, the tobacco composition can be smoke or smoke condensate.

Also provided herein are methods of making a tobacco product that has a reduced potential to contribute to a tobacco-related disease by providing a first tobacco, obtaining a tobacco composition from the first tobacco, contacting a first population of cells with the tobacco composition from the first tobacco, identifying the amount of damage of cellular genetic material in the first population of cells after contact with the tobacco composition from the first tobacco, providing a second tobacco, obtaining a tobacco composition from the second tobacco, contacting a second population of cells with the tobacco composition from the second tobacco, identifying the amount of damage of cellular genetic material after contact with the tobacco composition from the second tobacco product, where an identification of a reduction in the amount of damage of cellular genetic material after contact with the tobacco composition from the second tobacco as compared to the amount of damage of cellular genetic material after contact with the tobacco composition from the first tobacco identifies the second tobacco as one that has a reduced potential to contribute to a tobacco-related disease, and incorporating the second tobacco, which has a reduced potential to contribute to a tobacco-related disease, into a tobacco product. In some embodiments, the second tobacco has been modified to reduce a compound in the second tobacco. In some embodiments, the second tobacco can be genetically modified to reduce the expression of at least one gene that regulates production of the compound. In some embodiments of the methods provided herein, the amount of damage of cellular genetic material can be determined by identifying the induction of double-strand DNA breaks. In some embodiments, the tobacco composition can be smoke or smoke condensate.

Also provided herein are methods, compositions and kits for evaluating the ability of a tobacco-derived substance to produce DSBs in chromosomal DNA. The presence of DSBs is detected using an appropriate marker, which, in preferred embodiments provided herein, is phosphorylated histone H2AX (also referred to herein as "γH2AX"). The presence of DSBs also can be detected by detecting (i) activation of one or more of the protein kinases that are responsible for H2AX phosphorylation (e.g., ATM, ATR and/or DNA-PK); (ii) appearance of nuclear foci that are induced by histone H2AX phosphorylation; or (iii) activation of one or more protein components of nuclear foci induced by H2AX phosphorylation that are associated with DNA repair. The term "activation" in regard to proteins activated by DSBs refers to a chemical modification such as phosphorylation, acetylation, ubiquitinylation or poly(ADP)ribosylation, and/or a change in protein conformation, occurring in response to formation of DSBs. Activated proteins can be detected, for example, immunocytochemically.

Some of the assays provided concern methods of detecting, quantifying, identifying and/or evaluating (e.g., for harmfulness) a tobacco-derived substance in the course of research or in the environment via its promotion of DSBs in the chromosomal DNA of a test cell. A correlation with harmful potential is drawn based upon the known relationship between DSBs and genetic mutations (including cancer-causing and teratogenic mutations) as well as cell damage and death.

Accordingly, one set of preferred embodiments provided herein are methods of detecting a harmful tobacco-derived substance comprising the steps of (a) exposing a test cell (or test cell population) to a tobacco test composition; (b)

measuring the degree of H2AX phosphorylation in the test cell or cell population; and (c) comparing the degree of H2AX phosphorylation determined in the test cell or cell population to the degree of H2AX phosphorylation in a control cell or control cell population; wherein a higher degree of H2AX phosphorylation in the test cell compared to the control cell indicates the presence of a harmful tobacco derived substance in the tobacco test composition. The presence of DSBs also can be detected by detecting (i) activation of one or more of the protein kinases that are responsible for H2AX phosphorylation (e.g., ATM, ATR and/or DNA-PK); (ii) appearance of nuclear foci that are induced by histone H2AX phosphorylation; or (iii) activation of one or more protein components of nuclear foci induced by H2AX phosphorylation that are associated with DNA repair.

Another set of non-limiting embodiments, provided herein include methods for identifying one or more harmful components of TS comprising the steps of: (a) exposing a first test cell population to a first smoke product generated from a first tobacco composition; (b) exposing a second test cell population to a second smoke product generated from a second tobacco composition, wherein the first and second smoke products are prepared using essentially equivalent protocols; (c) measuring the degree of H2AX phosphorylation in the first and second test cell populations; and (d) comparing the degree of H2AX phosphorylation in the first and second test cell populations; (e) identifying the tobacco composition associated with a greater degree of H2AX phosphorylation in steps (a)-(d); and (f) comparing the components of the first and second tobacco composition to identify one or more component present in the tobacco composition of step (e) but absent in the other tobacco composition. Methods for detecting activation of protein kinases such as ATM, ATR and/or DNA-PK as well as formation of nuclear foci and protein components of the nuclear foci can be performed according to the same steps. According to such embodiments, the first tobacco composition can differ from the second tobacco composition in its ingredients and/or in the way it was processed. The information obtained by this method can be used to develop a tobacco product that lacks or has lower levels of the identified harmful component(s), which can render the product lower-risk. Alternatively, the information can be used in an environmental context: for example, air purifiers can be modified to extract the harmful component from smoke-contaminated air.

Another set of non-limiting embodiments provided herein concern methods for identifying one or more harmful components of TS comprising the steps of: (a) exposing a first test cell population to a first smoke product generated from a tobacco composition; (b) exposing a second test cell population to a second smoke product generated from the tobacco composition, wherein the first and second smoke products are prepared differently; (c) measuring the degree of H2AX phosphorylation in the first and second test cell populations; (d) comparing the degree of H2AX phosphorylation in the first and second test cell populations; and (e) identifying the method of smoke product preparation associated with a greater degree of H2AX phosphorylation in steps (a)-(d); wherein the method of smoke product preparation identified in step (e) has greater harmful potential. Methods for detecting activation of protein kinases such as ATM, ATR and/or DNA-PK as well as formation of nuclear foci and protein components of the nuclear foci can be performed according to the same steps. In such embodiments, the methods of smoke product preparation can differ in the rate of combustion of the tobacco composition (including whether the tobacco composition is burned or heated), or can differ in the filtering of the smoke product (e.g., unfiltered, filtered with a traditional filter, or filtered with a filter containing an antioxidant), or can differ by other known methods of altering tobacco smoke products. The components of the different smoke products can be compared to identify one or more harmful components. As above, the identification of a harmful component can facilitate the development of lower-risk tobacco products and/or environmental safeguards.

Also provided herein are methods for comparing the harmful potentials of a first and a second tobacco composition comprising the steps of: (a) exposing a first test cell population to a first smoke product generated from the first tobacco composition; (b) exposing a second test cell population to a second smoke product generated from the second tobacco composition, wherein the first and second smoke products are prepared using essentially equivalent protocols; (c) measuring the degree of H2AX phosphorylation in the first and second test cell populations; and (d) comparing the degree of H2AX phosphorylation in the first and second test cell populations; wherein the tobacco composition which generated the smoke product that produced a higher degree of H2AX phosphorylation has greater harmful potential. Methods for detecting activation of protein kinases such as ATM, ATR and/or DNA-PK as well as formation of nuclear foci and protein components of the nuclear foci can be performed according to the same steps.

Accordingly, the methods provided herein include one or more steps of determining whether damage of cellular genetic material has occurred. Typically, such methods include assays for damage to the genomic DNA of the cell. Any of a variety of methods known in the art for assaying damage of cellular genetic material, such as genomic DNA, can be used in the methods provided herein. Exemplary known assays include assays for double-strand DNA breaks, assays for single-strand DNA breaks, and assays for modulated properties of DNA resultant from damage, such as assays for micronuclei and assays for chromosome exchange. Assays for DNA breaks are known in the art, as exemplified in U.S. Pat. Pub. No. 20040132004 and U.S. Pat. No. 6,309,838, all of which are hereby expressly incorporated by reference in their entireties.

In one example, the methods provided herein can include detection of double-strand DNA breaks by detection of phosphorylation of histone H2AX. Mammalian cells respond to agents that introduce DNA double-stranded breaks with the immediate and substantial phosphorylation of histone H2AX. While not wishing to be bound to the following theory, which is only offered to explain one possible mechanism, H2AX is thought to be involved in the recognition of regions of chromatin containing a DNA double-stranded break. Formation of the phosphorylated H2AX protein, termed gamma-H2AX, can be detected as an indicator of DNA double-stranded breaks. Known antibodies or antigenically-reactive fragments thereof that specifically bind to a C-terminal phosphorylated serine in an H2AX histone protein can be used for the detection of gamma-H2AX, and, thus can be used to indicate the presence of double stranded breaks in a cell. Thus, in the methods provided herein, the presence or absence of DNA damage can be detected by detecting the presence or absence of phosphorylation of histone H2AX. For example, the presence or absence of phosphorylation of histone H2AX can be identified with an antibody or fragment thereof, which binds to phosphorylated H2AX but not unphosphorylated H2AX. Antibodies and fragments thereof, and related methods for selectively detecting gamma-H2AX, are known in the art, as exemplified in U.S. Pat. Nos. 6,362,317 and 6,884,873, all of which hereby expressly incorporated by reference in their entireties.

In some embodiments provided herein, the methods include assaying a cell for double-strand DNA breaks (DSBs). DSBs are generated by a variety of genotoxic agents, and are among the most critical lesions that lead either to apoptosis, mutations or the loss of significant sections of chromosomal material. Detection of DSBs upon cell exposure to a potential carcinogen, therefore, provides the means to assess the potential hazard of the exposure in terms of cancer induction. In one embodiment, a sensitive assay of DSBs detection based on analysis of histone H2AX phosphorylation can be used. Histone H2AX, a variant of a family of at least eight protein species of the nucleosome core histone H2A, becomes phosphorylated in live cells upon induction of DNA double strand breaks (DSBs). The phosphorylation of H2AX on Ser 139 at sites flanking the DSBs is carried out by ATM-, ATR-, and/or DNA-dependent protein kinases (DNA-PKs). The phosphorylated form of H2AX is denoted γH2AX.

The availability of antibodies to γH2AX allow for immunocytochemical detection of DSBs. After induction of DSBs, the appearance of γH2AX in chromatin manifests in the form of discrete foci, each focus considered to represent a single DSB. Checkpoint and DNA repair proteins such as Rad50, Rad51 and Brca1 co-localize with γH2AX. The intensity of γH2AX immunofluorescence (IF) measured by cytometry was reported to strongly correlate with the dose of ionizing radiation and thus with the number of the induced DSBs. However, because untreated cells, particularly cells replicating DNA, express γH2AX, to obtain a stoichiometric relationship between DSBs and the intensity of γH2AX IF, it is necessary to compensate for the extent of this "programmed" H2AX phosphorylation. Following compensation, the γH2AX IF measured by cytometry offers a sensitive and convenient means to detect and measure DSBs in individual cells following radiation. In fact, γH2AX IF can be a surrogate for cell killing in viability assays of radiated cells.

γH2AX antibody ("Ab") in conjunction with multiparameter flow- and laser scanning cytometry can be used in assays of DSBs, to detect and measure their induction in individual, live cancer cells exposed to antitumor drugs in vitro. The intensity of γH2AX IF correlates well with the drug concentration and duration of cell exposure to the drug, indicating a relationship between the incidence of DSBs induced by these drugs and γH2AX IF intensity. Multiparameter analysis of γH2AX IF and cellular DNA content made it possible to relate the abundance of DSBs (extent of DNA damage) to the position of the cell in the cycle.

The ability of the tobacco-derived substance to promote the formation of DSBs is measured using an appropriate DSB marker, which is preferably γH2AX (phosphorylated histone H2AX), but which can be another associated molecule, such as, but not limited to, Rad50, Rad51 and Brca1, and other proteins that are characteristic of nuclear foci formation. Formation of DSBs also can be detected by detecting activate protein kinases associated with DSBs such as ATM, ATR or DNA-PK. The presence of such markers can be determined using a marker-specific antibody (or derivative or fragment thereof), preferably an antibody (or fragment or derivative thereof) specific for γH2AX, or an antibody (or derivative or fragment thereof) specific for Rad50, Rad51 or Brca1, or ATM, ATR or DNA-PK. The presence of such markers can be determined using a marker-specific antibody (or derivative or fragment thereof), preferably an antibody (or fragment or derivative thereof) specific for a polypeptide encoded by a gene provided in Tables 1 and 2. The genes provided in Table 4 encode polypeptides that are involved in homologous recombination processes in the cell, and these genes can be activated in response to cellular damage of genetic material. Accordingly, detection of one or more products of the genes of Table 4 can be indicative of cellular damage of genetic material, for example, double-strand DNA breaks. The genes provided in Table 5 encode polypeptides that are involved in non-homologous nucleic acid end-joining processes in the cell, and these genes can be activated in response to cellular damage of genetic material. Accordingly, detection of one or more products of the genes of Table 5 can be indicative of cellular damage of genetic material, for example, double-strand DNA breaks. Provided herein is an exemplary use of antibody directed to γH2AX; analogous methods can be applied using antibodies directed to Rad50, Rad51, Brca1, ATM, ATR or DNA-PK, or the products of the genes listed in Tables 1 and 2. In preferred non-limiting embodiments provided herein, antibody binding can be detected by immunofluorescence-based techniques. Various antibodies for Rad50, Rad51, Brca1, ATM, ATR, DNA-PK, and the products of the genes listed in Tables 1 and 2 are known in the art and can be readily obtained for use in accordance with the methods provided herein; for example, Anti-phospho-ATM (Ser1981), is available from Upstate USA as clone 10H11.E12. Such techniques can optionally be used in conjunction with automated cytometry, such as, for example, flow and/or laser scanning cytometry.

TABLE 4

| Homologous recombination | | | Top of Page |
|---|---|---|---|
| RAD51 | Homologous pairing | 15q15.1 | NM_002875 |
| RAD51L1 (RAD51B) | Rad51 homolog | 14q24.1 | NM_002877 |
| RAD51C | Rad51 homolog | 17q23.2 | NM_002876 |
| RAD51L3 (RAD51D) | Rad51 homolog | 17q12 | NM_002878 |
| DMC1 | Rad51 homolog, meiosis | 22q13.1 | NM_007068 |
| XRCC2 | DNA break and crosslink repair XRCC2, XRCC3 | 7q36.1 | NM_005431 |
| XRCC3 | | 14q32.33 | NM_005432 |
| RAD52 | Accessory factors for recombination | 12p13.33 | NM_002879 |
| RAD54L | | 1p34.1 | NM_003579 |
| RAD54B | RAD52, RAD54L, RAD54B | 8q22.1 | NM_012415 |
| BRCA1 | Accessory factor for transcription and recombination, E3 Ubiquitin ligase | 17q21.31 | NM_007295 |
| BRCA2 | Cooperation with RAD51, essential function | 13q13.1 | NM_000059 |
| SHFM1 (DSS1) | BRCA2 associated | 7q21.3 | NM_006304 |
| RAD50 | ATPase in complex with MRE11A, NBS1 | 5q23.3 | NM_005732 |
| MRE11A | 3' exonuclease | 11q21 | NM_005590 |
| NBS1 | Mutated in Nijmegen breakage syndrome | 8q21.3 | NM_002485 |
| MUS81 | A structure-specific DNA nuclease MUS81, MMS4 | 11q13.1 | NM_025128 |
| EME1 (MMS4L) | | 17q21.33 | NM_152463 |

TABLE 5

| Non-homologous end-joining | | |
|---|---|---|
| G22P1 (Ku70) | 22q13.2 | NM_001469 |
| XRCC5 (Ku80) | 2q35 | NM_021141 |

TABLE 5-continued

| Non-homologous end-joining | | |
|---|---|---|
| PRKDC | 8q11.21 | NM_006904 |
| LIG4 | 13q33.3 | NM_002312 |
| XRCC4 | 5q14.2 | NM_003401 |
| DCLRE1C (Artemis) | 10p13 | NM_022487 |

The term "immunofluorescence-based techniques" or "immunocytochemical-based techniques" encompasses various forms of such assays, as are known in the art. For example, and not by way of limitation, an immunofluorescence-based technique can use an unlabelled primary antibody and a fluorescently labeled secondary antibody (as illustrated, for example, in Example 1); or can use a primary antibody that carries a fluorescent tag to detect the phosphorylated H2AX molecule directly; or the primary antibody can carry a biotin molecule while the secondary antibody can carry both an avidin molecule (which binds specifically to biotin) and a fluorescence molecule. In the biotin/avidin approach, the binding of the secondary antibody is based on binding of biotin by avidin rather than the binding of an antibody of one species directed against a protein of another species. Other variations of such techniques that would be known to the skilled artisan as "immunofluorescence-based techniques" or "immunocytochemical-based techniques" can be used according to the invention. Likewise, detection can be made using analogous methods that utilize a modality other than fluorescence, such as chromogenic or colorimetric assays, radiologic assays, and so forth.

Techniques such as immunocytochemical-based techniques can be used in conjunction with methods for counting cells, sorting cells, or other method for further characterizing cells. Exemplary methods include, but are not limited to, flow cytometry, laser scanning cytometry, fluorescence image analysis, chromogenic product imaging, fluorescence microscopy or transmission microscopy.

The "degree of phosphorylation of H2AX" as used herein refers to the relative, rather than absolute, amount of γH2AX. This is because γH2AX is produced during normal progression of the cell cycle. As discussed in Example 1, allowance can be made for normally occurring phosphorylation of H2AX. For example, the data can preferably be subjected to two normalization processes. First, allowance can be made for the normally occurring "programmed" phosphorylation of H2AX. Second, correction can be made for the fact that histone content is exactly doubled over the course of a cell cycle, doubling the size of the target (histone). In a specific non-limiting embodiment, a data value from cells with twice the DNA content (e.g., G2 and mitotic cells) with twice the histone target can be divided by 2 while a data value from cells in S phase having an intermediate in histone content can be divided by 1.5. In this manner, the amount of γH2AX detected beyond what occurs in an untreated control cell or cell population is normalized to a unit of histone so that one can refer to the "degree of histone H2AX phosphorylation" on a per unit of histone basis.

In another example, the methods provided herein can include detection of DNA breaks and other forms of genomic damage by Comet assay. Comet assay can be used to detect damaged DNA pulled from the nucleus of cells exposed to an electric field. Comet assay is a fluorescent microscopic method to examine DNA damage and repair at individual cell level. For example, cells can be embedded in agarose on a microscope slide and lysed with detergent and high salt to form nucleoids containing supercoiled loops of DNA linked to the nuclear matrix, and electrophoresis at high pH can result in structures resembling comets, observed by fluorescence microscopy. The intensity of the comet tail relative to the head reflects the number of DNA breaks. This assay can be used for detecting various forms of DNA damage (e.g., single- and double-strand breaks, oxidative DNA base damage, and DNA-DNA/DNA-protein/DNA-Drug cross-linking) and DNA repair in many eukaryotic cell types. Comet assay not only provides an estimate of how much damage is present in cells, but what form it takes. Although it is primarily a method for measuring DNA breaks, modifications of the methods, for example, by introducing lesion-specific endonucleases, allows detection of, for example, pyrimidine dimers, oxidized bases, and alkylation damage. Thus, in the methods provided herein, the presence or absence of DNA damage can be identified by, for example, the presence or absence of comet tails when cells are analyzed using the Comet assay. Various methods for performing Comet assays are known in the art, as exemplified in Collins, (2004) Mol. Biotechnology 26:249-261, Tice, et al. (2000) Environ. Mol. Mutagen. 35:206-221 and Gichner et al. (2004) Mutation Res. 559:49-57, all of which are hereby expressly incorporated by reference in their entireties.

In another example, the methods provided herein can include detection of double-strand DNA breaks by TUNEL assay. TUNEL assay can be used to measure double-strand breaks by incorporation of labeled nucleotides at the site of double-strand breaks using terminal transferase. The labeled nucleotides can then be detected with antibodies. TUNEL assay is frequently used to detect apoptosis-induced DNA fragmentation through a quantitative fluorescence assay. In one exemplary protocol, terminal deoxynucleotidyl transferase (TdT) catalyzes the incorporation of bromo-deoxyuridine (BrdU) residues into the fragmenting nuclear DNA at the 3'-hydroxyl ends by nicked end labeling. A TRITC-conjugated anti-BrdU antibody can then label the 3'-hydroxyl ends for detection. The TUNEL assay distinguishes two populations of cells: non-apoptotic cells (TUNEL-negative) and apoptotic cells (TUNEL-positive). Thus, in the methods provided herein, the presence or absence of DNA damage can identified by, for example, detecting the presence or absence of labeled nucleotides at the site of double-strand breaks, incorporated by, for example, terminal transferase. A variety of methods of performing TUNEL assays is known in the art, as exemplified in Doolin et al., J. Burn Care Rehabil. 20: 374-376, 1999; Kalyuzhny (2002) Methods Mol. Biol. 203:219-34; Lawry, Methods Mol. Med. (2004) 88:183-90; U.S. Pat. No. 6,506,609 and U.S. Pat. Pub. No. 20030017462, all of which are hereby expressly incorporated by reference in their entireties.

In another example, the methods provided herein can include detection of double-strand DNA breaks by sister chromatid exchange assay. Sister chromatid exchange assays detect late damage when genetic material is exchanged between sister chromatids. Sister chromatid exchange refers to a reciprocal interchange of the two chromatid arms within a single chromosome. This exchange can be visualized during the metaphase portion of the cell cycle and can be mediated by the enzymatic incision, translocation and ligation of at least two DNA helices. Thus, in the methods provided herein, the presence or absence of DNA damage can identified by, for example, detecting the presence or absence of interchange of chromatid arms within a single chromosome by, for example, sister chromatid exchange assay. A variety of methods for performing sister chromatid exchange assays are known in the art, as exemplified in 40 C.F.R. § 79.65, 40 C.F.R. § 798.5915, Renqing et al., (2000) Toxicology Letters 115:23-32, Deen et al. and Cancer Res. (1986) 46:1599-602, all of which are hereby expressly incorporated by reference in their entireties.

In another example, the methods provided herein can include detection of double-strand DNA breaks by micronuclei assays. Micronuclei assays can be used to detect late damage occurring after cells attempt to divide so that non-centromeric DNA forms as micronuclei in daughter cells. The test is based on the observation that a secondary nucleus (micronucleus) is formed around a chromosomal fragment, outside the main nucleus of a dividing cell. A micronucleus may also be produced due to a lagging whole chromosome formed as a result of a chromosome loss at anaphase. Thus, in the methods provided herein, the presence or absence of micronuclei can be identified. Micronuclei can be detected by microscopic methods, flow cytometric methods and automated image recognition methods, as known in the art and exemplified in Offer et al., FASEB J. (2005) 19:485-7; Smolewski et al., Cytometry (2001) 45:19-26; Driessens et al., Ann N Y Acad Sci. (2003) 1010:775-9; and U.S. Pat. Pub. No. 20050002552, all of which are hereby expressly incorporated by reference in their entireties.

In another example, the methods provided herein can include detection of chromosomal translocations. Chromosomal translocations can occur as a result of DNA damage. Methods for detecting chromosomal translocations can include fluorescence in situ hybridization methods (FISH), in which probe hybridization patterns in cells containing chromosomal translocation are altered relative to wild type. Thus, in the methods provided herein, the presence or absence of DNA damage can identified by, for example, detecting the presence or absence of chromosomal translocations by, for example, FISH. Methods for detecting chromosomal translocations are known in the art, as exemplified by U.S. Pat. Nos. 5,997,869, 6,576,421, and 6,416,948, and U.S. Pat. Pub. Nos. 20040235039 and 20020192692, all of which are hereby expressly incorporated by reference in their entireties.

The example below provides one non-limiting specific example of the DSB detection methods and materials. Variations of the assay method used in terms of materials, assay times, instrumentation and protocols would be apparent to the skilled artisan for detecting and/or quantifying DSBs, for example via γH2AX.

Example 1

Preparation of Cigarette Smoke Condensates

Smoke was generated from a commercially available nationally sold brand of American cigarettes (non-menthol, full-flavor type with averaged FTC measured values of 14.5 mg tar/1.04 mg nicotine) using an INBIFO-Condor smoking machine under Federal Trade Commission (FTC) smoking parameters (2.0 second puff duration 35 milliliter puff every 60 seconds). The cigarettes had been equilibrated at 23.9° C.±1.1° C. and 60%±2% relative humidity for a minimum of 24 hours and a maximum of 14 days. CSC was collected from the smoke via a series of three cold traps (−10° C., −40° C., and −70° C.) onto impingers filled with glass beads. The smoke condensate was dissolved in acetone, which was then removed by rotary evaporation at 35° C. The resulting smoke condensate was weighed and dissolved in dimethyl-sulfoxide (DMSO) to make a stock solution at a concentration of 20 mg/mL, which was stored at −20° C. prior to use.

NHBE Cell Culture and Smoke Condensate Treatment

NHBE cells were purchased from Cambrex Corporation, East Rutherford, N.J. The cells were cultured in complete Bronchial Epithelial Cell Growth Medium (BEGM), prepared by supplementing Bronchial Epithelial Basal Medium with retinoic acid, human epidermal growth factor, epinephrine, transferrin, triiodothyronine, insulin, hydrocortisone, bovine pituitary extract and gentamicin by addition of SingleQuots™ (both medium and the supplements were purchased from Cambrex Corporation, East Rutherford, N.J.). Dual-chambered slides (Nunc Lab-Tek II, Fisher Scientific, Pittsburgh, Pa.) were seeded with 1 ml of 8×10$^4$ cells/ml cell suspension per chamber. All incubations were at 37° C. in a humidified atmosphere of 5% CO2 in air. Cells were grown to 50% confluency, at which time they were treated with medium containing smoke condensate. Appropriate dilutions of the 20 mg/ml smoke condensate in DMSO stock solution were used to prepare culture medium containing 10, 25, or 50 µg/mL smoke condensate. The final DMSO concentration was 0.5%. Cells were treated by carefully aspirating the culture medium from each chamber and replacing it with 1 ml per chamber of smoke condensate-containing medium at 37° C. For control slides, the medium was replaced with 1 mL of either fresh medium (mock-treated control) or medium containing 0.5% DMSO (vehicle control). Slides were immediately returned to the incubator for up to 24 hours. At the end of the treatment, medium from each chamber was carefully aspirated and 1 ml of 1% fresh paraformaldehyde in 1× Dulbecco's PBS was added to each chamber and the cells fixed by gently rocking the slides at room temperature for 15 minutes. Following aspiration of the fixative, the chamber slides were disassembled and the slides submerged in 50 ml conical tubes filled with 70% ethanol. The fixed slides were stored at 4° C. prior to analysis.

A549 Cell Culture and Smoke Treatment

A549 cells were purchased from American Type Culture Collection (ATCC #CCL-185, Manassas, Va.). The cells were cultured in Ham's F12K medium with 2 mM L-glutamine adjusted to contain 1.5 g/L sodium bicarbonate (ATCC, Manassas, Va.) and supplemented with 10% fetal bovine serum (ATCC, Manassas, Va.). Dual-chambered slides (Nunc Lab-Tek II) were seeded with 1 ml of 10$^5$ cells/ml cell suspension per chamber 48 hours before exposure. All incubations were at 37° C. in a humidified atmosphere of 5% CO2 in air. Cells were grown to 70% confluency, at which time they were treated with smoke. The cell culture medium was replaced with 37° C. Dulbecco's PBS (D-PBS) containing calcium and magnesium (Sigma, St. Louis, Mo.) for the smoke exposure. Slide chamber covers were removed and the slides were placed in a smoke exposure chamber (20.6 cm×6.7 cm×6.3 cm—L×W×H). Smoke was generated from IM16 (Industry Monitor #16, Philip-Morris, Richmond Va.) cigarettes under FTC smoking conditions using a KC 5 Port Smoker (KC Automation, Richmond, Va.). The smoke was diluted by drawing it through a 250 mL round-bottom flask prior to its reaching the exposure chamber. The time and distance that the smoke traveled from the end of the cigarette to the exposure chamber was minimized by using the shortest lengths of tubing possible between the parts of the apparatus. Cigarettes were smoked to within 3 mm of the filter tip. Cells were exposed to smoke for up to 40 minutes. Mock-exposed (control) cells were treated under identical conditions as the exposed cells except for the absence of a cigarette in the smoking port. They were mock-exposed for 10 minutes. Following treatment or mock treatment, the D-PBS was aspirated and replaced with 1 ml per chamber of fresh culture medium at 37° C. The slides were placed in the 37° C., 5% CO2 incubator and incubated for 15 minutes. Following incubation, the medium was aspirated and the cells fixed as described above for the NHBE experiment.

Immunocytochemical Detection of Phosphorylated Histone H2AX and Caspase-3 Activation Cells were treated with smoke (i.e., A549) or smoke condensate (i.e., NHBE) and fixed as described above, then rinsed twice in PBS and immersed in 0.2% Triton X-100 (Sigma) in a solution of 1% (w/v) bovine serum albumin (BSA; Sigma) in PBS for 30 min to suppress non-specific antibody binding. The cells were then incubated in 100 µl volume of 1% BSA containing 1:200 dilution of anti-phosphorylated histone H2AX (γ-H2AX) rabbit polyclonal Ab (Trevigen, Gaithersburg, Md.). After overnight incubation at 4° C., the slides were washed twice with PBS and then incubated in 100 µl of 1:200 dilution of Alexa Fluor 488 goat anti-rabbit IgG (H+L) (Molecular Probes, Eugene, Oreg.) for 45 min at room temperature in the dark. Parallel samples were incubated with 1:100 diluted anti-cleaved (activated) caspase-3 rabbit polyclonal Ab (Cell Signaling Technology, Beverly, Mass.) overnight at 4° C., washed twice with PBS and incubated with 1:30 diluted FITC-conjugated F(ab')2 fragment of swine anti-rabbit immunoglobulin (DAKO, Carpinteria, Calif.) for 30 min in room temperature in the dark. The cells were then counterstained with 1 µg/ml 4,6-diamidino-2-phenylindole (DAPI, Molecular Probes, Eugene, Oreg.) in PBS for 5 min. Each experiment was performed with an IgG control in which cells were labeled only with secondary antibody, Alexa Fluor 488 goat anti-rabbit IgG (H+L) or FITC-conjugated F(ab')2 fragment of goat anti-mouse immunoglobulins, without primary antibody incubation to estimate the extent of nonspecific binding of the secondary antibody to the cells.

Measurement of Cell Fluorescence by Laser Scanning Cytometry

Cellular green (phosphorylated histone H2AX and cleaved caspase 3), and blue (DNA-bound DAPI) fluorescence emission was measured using a Laser Scanning Cytometer (LSC; CompuCyte, Cambridge, Mass.), utilizing standard filter settings; fluorescence was excited with 488-nm argon ion and violet diode lasers, respectively. The intensities of maximal pixel and integrated fluorescence were measured and recorded for each cell. At least 3,000 cells were measured per sample.

Statistical Analysis

To compare the changes in immunofluorescence intensity, the mean fluorescence intensity (integral values of individual cells) was calculated for cells in each phase of the cycle by gating G1, S and G2/M cells based on differences in DNA content. The means of the fluorescence value for G1, S and G2/M populations of cells in the IgG control groups were then subtracted from the respective means of the smoke condensate or smoke-treated cells. All experiments were run under identical instrument settings. Data is presented as mean γH2AX fluorescence of each cell cycle compartment or where not indicated, of the entire population (G1, S and G2M). Each experiment was run in duplicate or triplicate. All experiments were repeated at least three times.

Filter Comparison

Tests for phosphorylated histone H2AX also were applied to tests of several filters attached to different tobaccos. Filters and tobacco were obtained from: (1) the industry standard reference tobacco IM16 (Philip Morris® USA); (2) reduced risk cigarette Omni® (Vector Tobacco Ltd.); and (3) reduced risk cigarette Quest 3® (Vector Tobacco Ltd.). A549 cells were exposed to mock treatment (control) and cigarette smoke substantially as provided in the above smoke treatment description.

Figure 44:
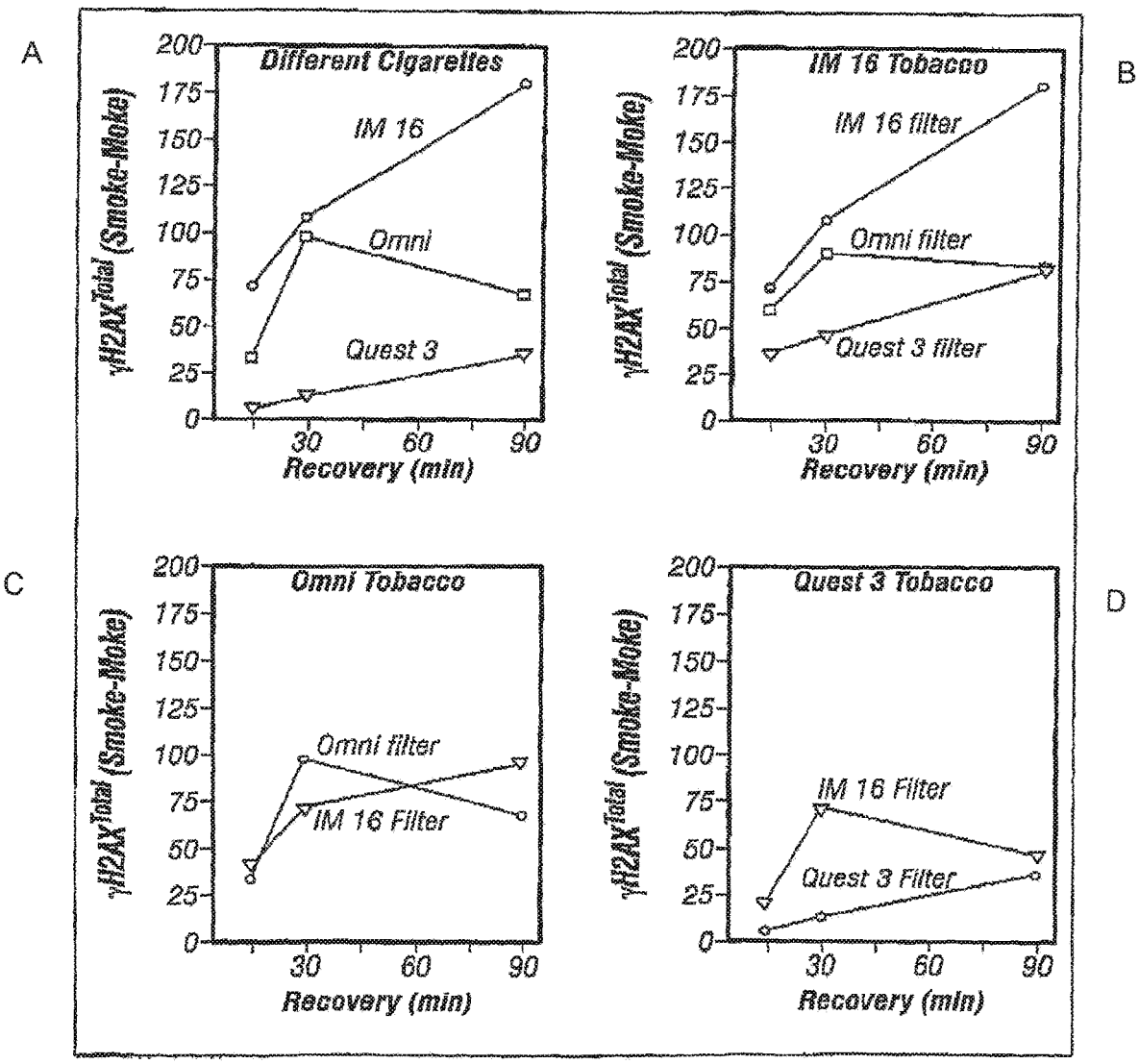
FIG. 44 shows a plot of γH2AX immunofluorescence in A549 cells exposed to smoke of different combinations of tobaccos and filters from IM16, Omni® and Quest 3® cigarettes, corrected according to the γH2AX immunofluorescence for mock-exposed cells.

Each of IM16, Omni® and Quest 3® were tested, and the γH2AX (smoke-mock) time course for each is presented in FIG. 44A. FIG. 44A demonstrates that each of IM16, Omni® and Quest 3® have clearly different influences on γH2AX levels, where the γH2AX levels parallel the expected level of risk attributed to the tobacco product (IM16 is highest expected risk and has the highest γH2AX levels, while Quest 3® is lowest expected risk and has the lowest γH2AX levels).

Next, the influence of IM16, Omni® and Quest 3® filters were compared by configuring a cigarette with IM16 tobacco, and each of the IM16, Omni® and Quest 3® filters. FIG. 44B demonstrates that the cigarette configured with the IM16 filter resulted in the highest γH2AX levels, while the cigarette configured with the Quest 3® filter resulted in the lowest γH2AX levels. Thus, when the same tobacco (IM16) is used, the γH2AX levels reflect the influence of the filter on the number of double stranded DNA breaks caused by tobacco smoke. In the instant example, when IM16 tobacco is used, the γH2AX levels parallel the expected level of risk attributed to the tobacco filter (IM16 is highest risk filter and has the highest γH2AX levels, while Quest 3® is lowest risk filter and has the lowest γH2AX levels).

Next, the filters were tested using Omni® and Quest 3® tobaccos. FIG. 44C demonstrates that when Omni® tobacco is used, a cigarette containing the IM16 filter results in comparable γH2AX levels as compared to a cigarette containing the Omni® filter. Thus, FIG. 44C demonstrates that the risk-reducing properties of the tobacco and the risk-reducing properties of the filter can be interrelated such that the risk-reducing properties of a particular filter can vary depending on the type of tobacco used. FIG. 44D demonstrates that when Quest 3® tobacco is used, a cigarette containing the IM16 filter results in higher γH2AX levels as compared to a cigarette containing the Quest 3® filter.

Figure 12A:
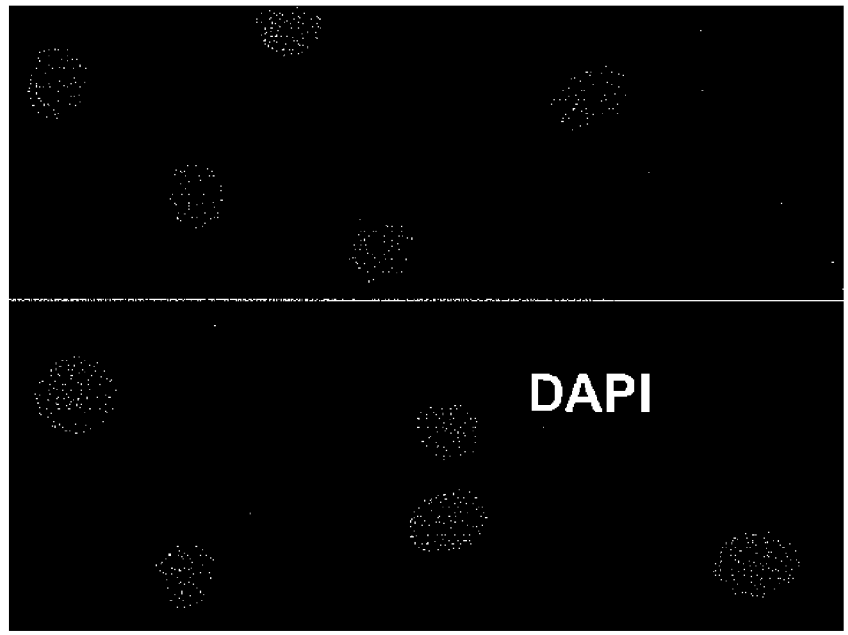
FIG. 12A-B. Fluorescence photomicrographs of NHBE cells exposed to 25 µg/ml of tobacco smoke condensate for 24 h. The cells stained with DAPI and immuno-stained with γH2AX Ab were examined under UV light—(A) or blue light—(B) fluorescence excitation (Nikon Microphot FXA, 60× Objective.).
Figure 12B:

Exposure of A549 cells to TS induces H2AX phosphorylation, which can be detected immunocytochemically (FIG. 12). Though the intensity of green γH2AX IF varies from cell to cell, its distribution is nuclear and punctuate. Mock-treated cells have minimal, but still detectable levels of γH2AX IF.

FIG. 13 illustrates the raw data in the form of scattergrams of the A549 cells untreated (0 time) and exposed to TS for 30 min. A scattergram representing cells immunostained with an irrelevant isotype control IgG is also included in the figure. The intensity of fluorescence of the mock-exposed cells is distinctly higher than that of the isotype control. This is a reflection of the "programmed" phosphorylation of H2AX, known to occur during normal progression through the cell cycle. Exposure of A549 cells to smoke, in this instance, markedly increased cellular γH2AX IF. The increase, however, was proportional for the cells in each phase of the cell cycle.

Figure 14:
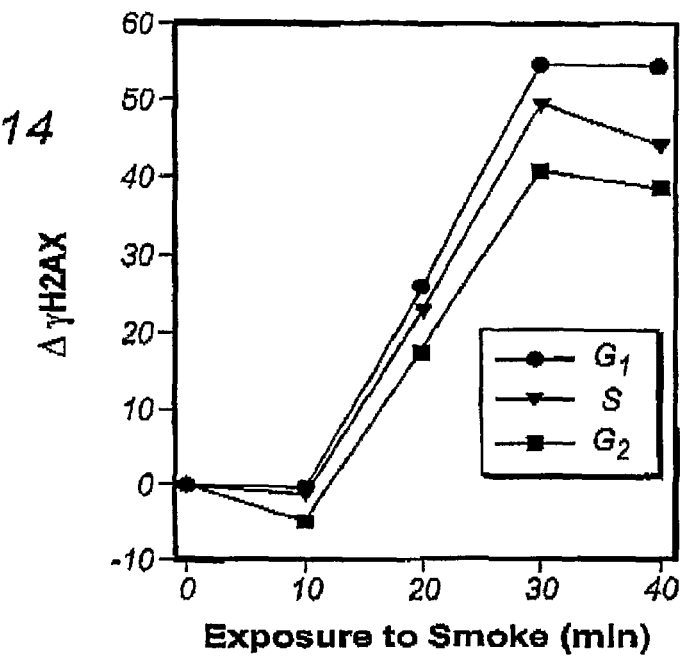
FIG. 14. Plots showing the percent increase (Δ) in mean γH2AX immunofluorescence of A549 cells (per unit of DNA) exposed to smoke for different time intervals, calculated for cells in particular phases of the cell cycle, as described in Example 1. The value for mock-exposed cells was subtracted from those exposed to smoke.
Figure 15:
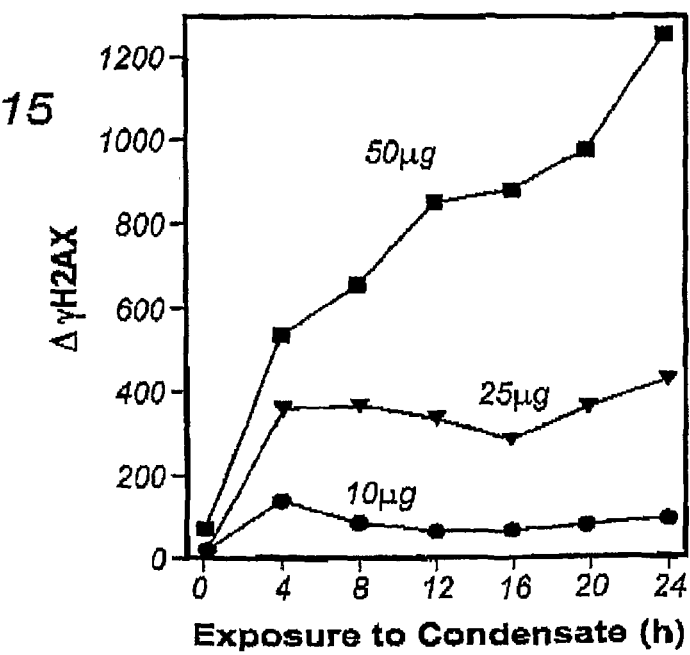
FIG. 15. Plots showing percent increase (Δ) in mean γH2AX immunofluorescence of NHBE cells treated with 10, 25 or 50 µg/ml concentrations of smoke condensate for different periods of time. As in FIG. 14, the γH2AX value for the mock-exposed cells was subtracted from the values of the cells exposed to different concentrations of condensate.

As noted above, the mean "programmed" H2AX IF was subtracted from the mean γH2AX IF of the cells exposed to either smoke or smoke condensate, separately for cells in each phase of the cell cycle, for each data-point shown in the FIGS. 14 and 15. In addition, since the amount of histone doubles as cells proceed from $G_1$ to $G_2$ phase, γH2AX IF was normalized to DNA/histone content by dividing the mean γH2AX IF of the S and $G_2M$ phase cells by 1.5 and 2, respectively. The normalized data, therefore, does not represent the total amount of phosphorylated H2AX per cells but rather the degree of H2AX phosphorylation, independent of the increase in total H2AX IF that occurs during progression through S.

During the initial 10 min exposure of A549 cells to smoke, no change in γH2AX IF was apparent (FIG. 14). However, between 10 and 20 min exposure to smoke, γH2AX IF increased by 71%, 67.5% and 45.7% for $G_1$, S and $G_2M$ phase cells, respectively. An additional 10 min of exposure to smoke (30 min in total) resulted in an additional increase in γH2AX IF compared to mock-exposed cells: 151.2%, 132.2% and 109.3% for $G_1$, S or $G_2M$ phase cells.

Figure 16:
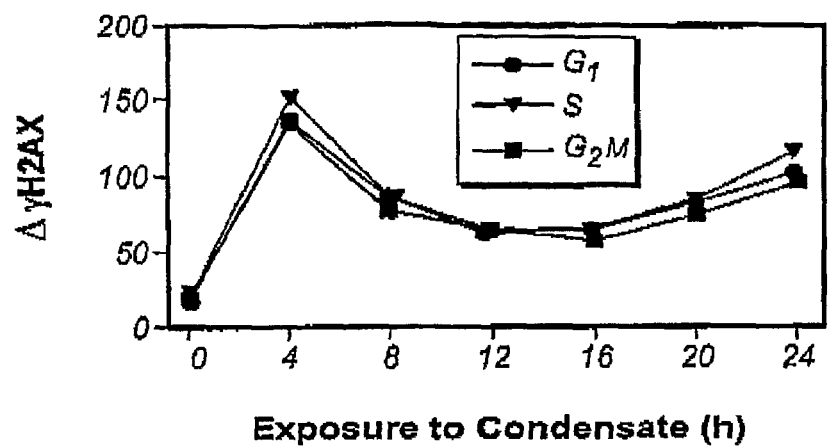
FIG. 16. Percent increase (Δ) in mean γH2AX immunofluorescence of NHBE cells treated with 10 µg/ml of smoke condensate for different intervals of time, in relation to cell cycle phase. As in FIG. 14, the γH2AX value for the mock-exposed cells was subtracted from the values of the cells exposed to condensate.

The plots shown in FIG. 15 display the increase in the level of H2AX phosphorylation as a function of length of exposure of NHBE cells to 10, 25 or 50 µg/ml concentrations of smoke condensate. At each concentration, the maximal rate of increase in H2AX IF was seen during the initial 4 h of cell treatment. However, whereas at 10 and 25 µg/ml of smoke condensate the peak of H2AX phosphorylation occurred at 4 h, followed by a plateau up to 24 h, at a smoke condensate concentration of 50 µg/ml, H2AX phosphorylation increased during the entire 24 h time course of the experiment. No cell cycle phase specificity was apparent in H2AX phosphorylation when cells were exposed to 10 µg/ml smoke condensate (FIG. 16). The same was true for these cells exposed to 25 or 50 µg/ml.

Activation of caspase-3 was measured in samples parallel to those that were subjected to analysis of H2AX phosphorylation, by detecting the presence of activated caspase-3 immunocytochemically. Exposure of A549 cells to smoke for up to 40 min followed by their fixation at 15 minutes had no effect on caspase-3 activation: less than 0.5% of the cells demonstrated the presence of activated caspase-3 in either mock-exposed or smoke treated cultures (Table 6). Caspase-3 activation could be shown, however, if A549 cells exposed to smoke for 20 min were allowed to grow in culture for an extended period of time (24 h) at which point virtually half the cells were positive for activated caspase-3 (Table 6).

TABLE 6

Effect of Smoke on Caspase-3 Activation

| Exposure to smoke (min) | Time in culture following exposure (h) | % Caspase-3 positive cells (%)* |
|---|---|---|
| 0 | 0.25 | 0.1 |
| 10 | 0.25 | 0.4 |
| 20 | 0.25 | 0.1 |
| 30 | 0.25 | 0.4 |
| 40 | 0.25 | 0.1 |
| 0 | 24 | 0.2 |
| 20 | 24 | 49.9 |

*Caspase-3 positive cells were detected immunocytochemically, as described elsewhere.

The present results demonstrate that exposure of A549 cells to TS or NHBE cells to TSC induces phosphorylation of H2AX. The extent of H2AX phosphorylation is concentration-dependent. It also correlated with the duration of exposure. In the case of NHBE cells, while at lower smoke condensate concentrations (10 and 25 µg/ml), a plateau is achieved after 4 h, at 50 µg/ml concentration, progressive phosphorylation continues for up to 24 h. H2AX phosphorylation in the A549 cells exposed to smoke also progresses with time of exposure, although it appears to plateau after 30 min. Phosphorylation of H2AX is a specific marker of induction of DSBs; the present data indicate that TS and TSC both induce such breaks in A549 cells and NHBE cells in a dose and time dependent manner.

It should be noted that H2AX is intensely phosphorylated in response to DNA fragmentation that occurs upon induction of apoptosis. Caspase activation, however, is required to trigger apoptosis-related DNA fragmentation. In fact, inhibition of caspase-3 activity (e.g. by z-VAD-FMK) can prevent the apoptosis-associated H2AX phosphorylation. In the present study, no caspase-3 activation was detected in the cells exposed for up to 40 min to smoke (Table 6). Thus, apoptosis-associated phosphorylation of H2AX did not contribute to the γH2AX IF measured in A549 cells exposed to smoke for up to 40 min, when the cells were collected within 15 min of exposure.

The present assay provides quantitative results. Specifically, the number of H2AX phosphorylation foci is considered to correspond to the number of DSBs. Assuming that the individual foci have comparable intensity of IF, the integrated value H2AX IF, as presently measured, would be expected to correspond to the number of foci, hence, to the number of DSBs. Furthermore, the mean γH2AX IF of the mock-exposed cells was subtracted from each mean of cells exposed to smoke or smoke condensate, to ensure that the measurement was not affected by the level of "programmed" H2AX phosphorylation in these cells (see FIG. 13). Though not applicable in the present instance in which the time between exposure to smoke or smoke condensate and harvesting of the cells was relatively short (55 min or less), a phosphatase inhibitor such as calyculin A or okadaic acid can be included in the culture to prevent possible dephosphorylation of H2AX molecules. The data presented in the plots, therefore, represent the smoke-induced differential γH2AX IF. Furthermore, since the H2AX content increases as cells traverse through S phase, the mean values γH2AX IF for S and $G_2$/M cells were compensated for the H2AX increase. The intensity of γH2AX IF so compensated, thus, reflects the degree of H2AX phosphorylation in the cell, i.e. is unrelated to H2AX content.

There is little evidence that CS and specific smoke constituents can cause single strand breaks (SSBs) in the normal human genome, but no evidence for the induction of DSBs. DSBs are among the most deleterious types of DNA damage in mammalian cells. A cell that incurs DSBs is at major risk for developing genomic instability, which can result in an array of specific defects such as chromosome fragmentation, translocation, rearrangement and loss. More importantly, each of these chromosomal abnormalities can play a pivotal role in the etiology or progression of a wide range of human cancers. Consequently, in order to ensure the faithful repair of DSBs and maintain genomic integrity, the cell has evolved sensitive DNA damage-activated checkpoint control pathways that are coupled to an interconnected web of efficient repair mechanisms, the most prominent of which are homologous recombination and non-homologous end joining. Individuals who either have debilitating alterations or deletions of the genes involved in detecting and repairing DSBs tend to manifest the dual syndromes of chromosome instability and higher incidence of various cancers. Clearly, therefore, the induction of DSBs by an exogenous agent like TS can be a potentially hazardous genetic event in the long-term smoker. In particular, if overall repair efficiencies of DSBs are not as efficient as for other types of DNA damage, e.g., single strand breaks (SSBs), and/or if an individual smoker has specific polymorphisms in the relevant genes that reduce their effectiveness, then cells chronically exposed to TS can manifest the genetically dangerous combination of increased levels of DSBs and compromised repair capacities. Furthermore, in addition to DSB level and repair capacity, the genomic positioning of DSBs can be another factor that determines how successfully a cell responds to this type of damage. For example, the probability that a DSB break is inaccurately rejoined is relatively low when DSBs are spatially separated but increases considerably when multiple breaks coincide.

The successful repair of DSBs appears also to depend on cell cycle position. The data, however, show no obvious cell cycle specificity in terms of accumulation of DSBs. Thus, if proliferating cells exposed to TS experience similar levels of DSBs during each phase of the cell cycle but dissimilar repair rates, they can be particularly susceptible to accumulating deleterious DNA defects during that specific phase. It is relevant to point out that although the rates of DSB induction and repair in noncycling cells, which are one of the initial primary target cells in lungs exposed to CS, can be different than in cycling cells, the lungs of persistent smokers undergo a significant increase in the number of proliferating cells due to smoke-induced damage. Moreover, cells actively dividing at the time of carcinogen exposure are at particular risk for transformation-related events.

The methods of identifying a tobacco, identifying a compound in tobacco, identifying a tobacco product, and making a tobacco product provided herein, can additionally be used to compare two or more tobaccos so as to identify a toxic compound, evaluate the potential risk posed by the tobacco products, or to develop reduced risk tobacco products. In some embodiments, the two or more tobaccos are compared for their ability to induce damage to the genetic material of cells. In some embodiments, at least one tobacco is a reduced risk tobacco or identified as a reduced risk tobacco. In some embodiments, at least one tobacco is a modified tobacco, such as a chemically modified tobacco or a genetically modified tobacco.

Example 2 below provides one non-limiting specific example of methods for comparing tobaccos in accordance with the methods provided herein. Variations of the assay method used in terms of assay methodologies (e.g., assay for apoptosis or for cell proliferation) would be apparent to the skilled artisan for comparing tobaccos.

Example 2

A549 cells were exposed to whole smoke from IM16 cigarettes for various lengths of time, washed and allowed to grow for an additional hour before being harvested for analysis. DNA damage was identified as an increase in phosphorylation of histone H2AX denoted as γH2AX.

In order to compare DNA damage as a function of the cell's position in the cell cycle, γH2AX values were normalized to DNA content since histone content doubles as cells proceed from G1 to G2 phase. Thus, in order to determine any change in histone H2AX phosphorylation independent of changes in histone/DNA content or DNA ploidy, the values for S and G2M phase populations, gated according to DNA content, were multiplied by 0.75 and 0.5, respectively. In instances where "normalized" values of γH2AX are presented, these values were obtained by subtracting the mean values of each cell cycle population (or the total population) from the mean of the mock-treated population whose γH2AX values represent "scheduled" γH2AX expression. In all instances, the values presented represent the mean γH2AX fluorescence of the population; typically 3-5×10³ cells were analyzed for each condition.

Figure 17:
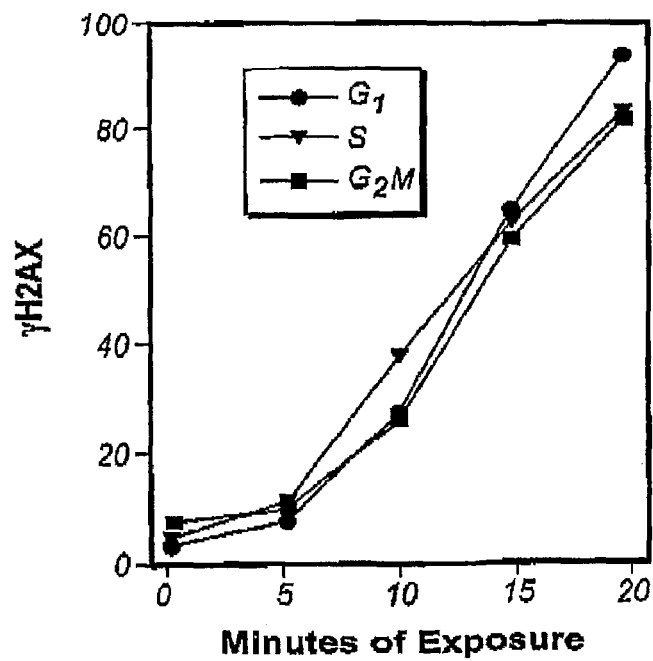
FIG. 17. Plots showing the percent increase (Δ) in mean γH2AX immunofluorescence of A549 cells (per unit of DNA) exposed to smoke of IM16 cigarettes for different time intervals, calculated for cells in particular phases of the cell cycle, as described in Example 2.

As illustrated in FIG. 17, there was little or no change in γH2AX when exposure of A549 cells to whole smoke was limited to 5 min. However, as the time of exposure exceeded 5 min there was a more or less linear increase in γH2AX. Initially, S phase cells appeared most sensitive to DNA damage expressing approximately 37% higher levels of γH2AX than G1 phase cells following 10 min of exposure to smoke. When the length of exposure was increased to 20 min, G1 phase cells invariably expressed 10-20% higher levels of γH2AX-associated fluorescence.

In another set of experiments it was determined that the extent of DNA damage varied with the length of time of recovery following exposure to whole smoke. Previous studies have shown that following exposure to whole smoke for times in excess of 20 min leads to a significant increase in apoptotic cells in the population depending upon when the assay is performed. Apoptotic cells contained significantly increased levels γH2AX compared to what one sees when assessing the primary breaks due to DNA damaging agents. Based on the absence of activation of caspase 3, there is little or no induction of apoptosis in A549 cells within the first 3 h following 20 min exposure to whole smoke from IM16.

Figure 18A:
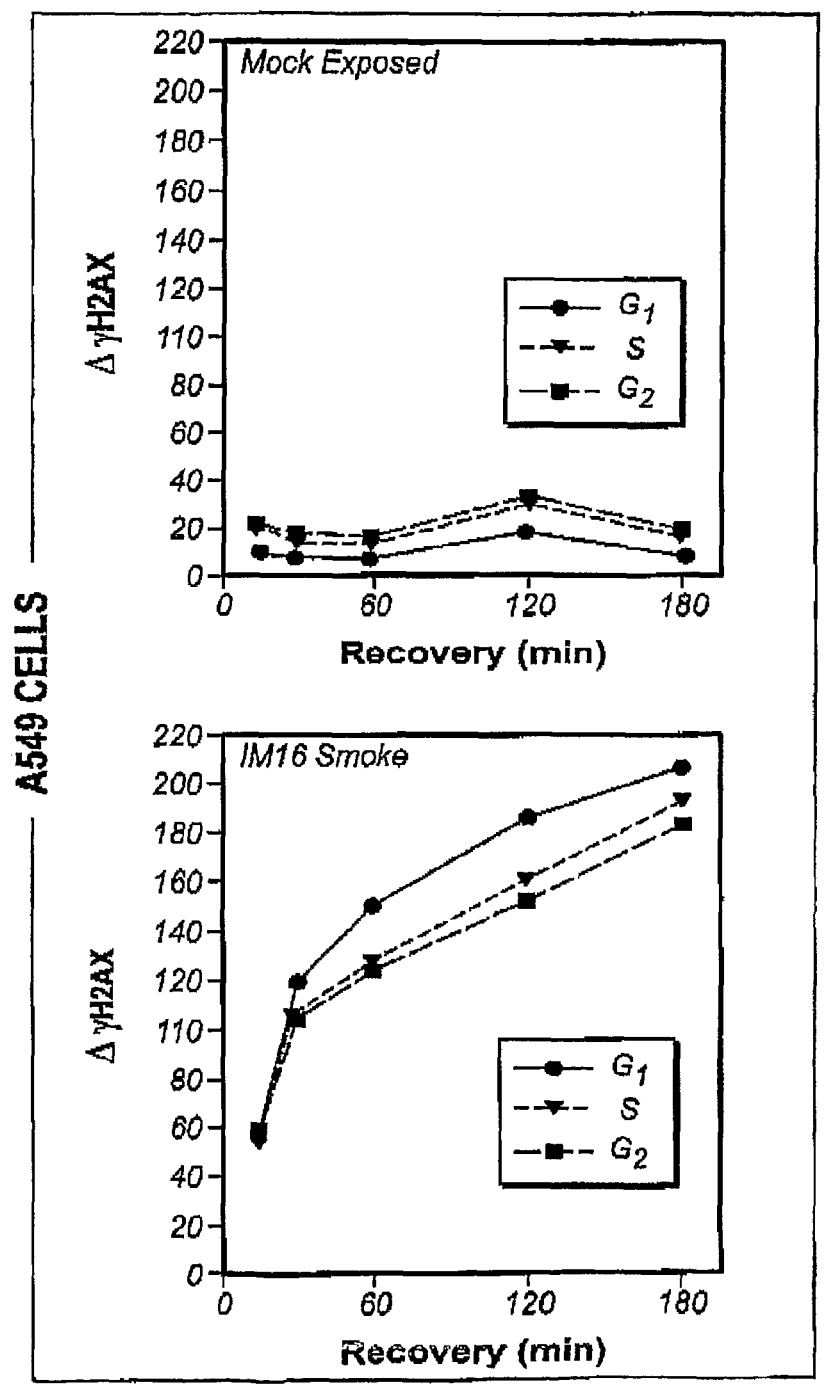
FIG. 18A-D. (A) Plots showing increase (Δ) in mean γH2AX immunofluorescence of A549 cells exposed to smoke of IM16 cigarettes for 15 minutes, relative to mock exposed cells. (B) Scatter plots showing the increase in γH2AX following 60 min of recovery of the A549 cells in particular phases of the cell cycle for mock exposed (upper plot) and for IM16 smoke exposed (lower plot) cells. (C) Plots showing increase (Δ) in mean γH2AX immunofluorescence of NHBE cells exposed to smoke of IM16 cigarettes for 20 minutes, relative to mock exposed cells. (D) Scatter plot relative increase in γH2AX following 60 min of recovery of the NHBE cells in particular phases of the cell cycle for mock exposed (upper plot) and for IM16 smoke exposed (lower plot) cells.
Figure 18B:
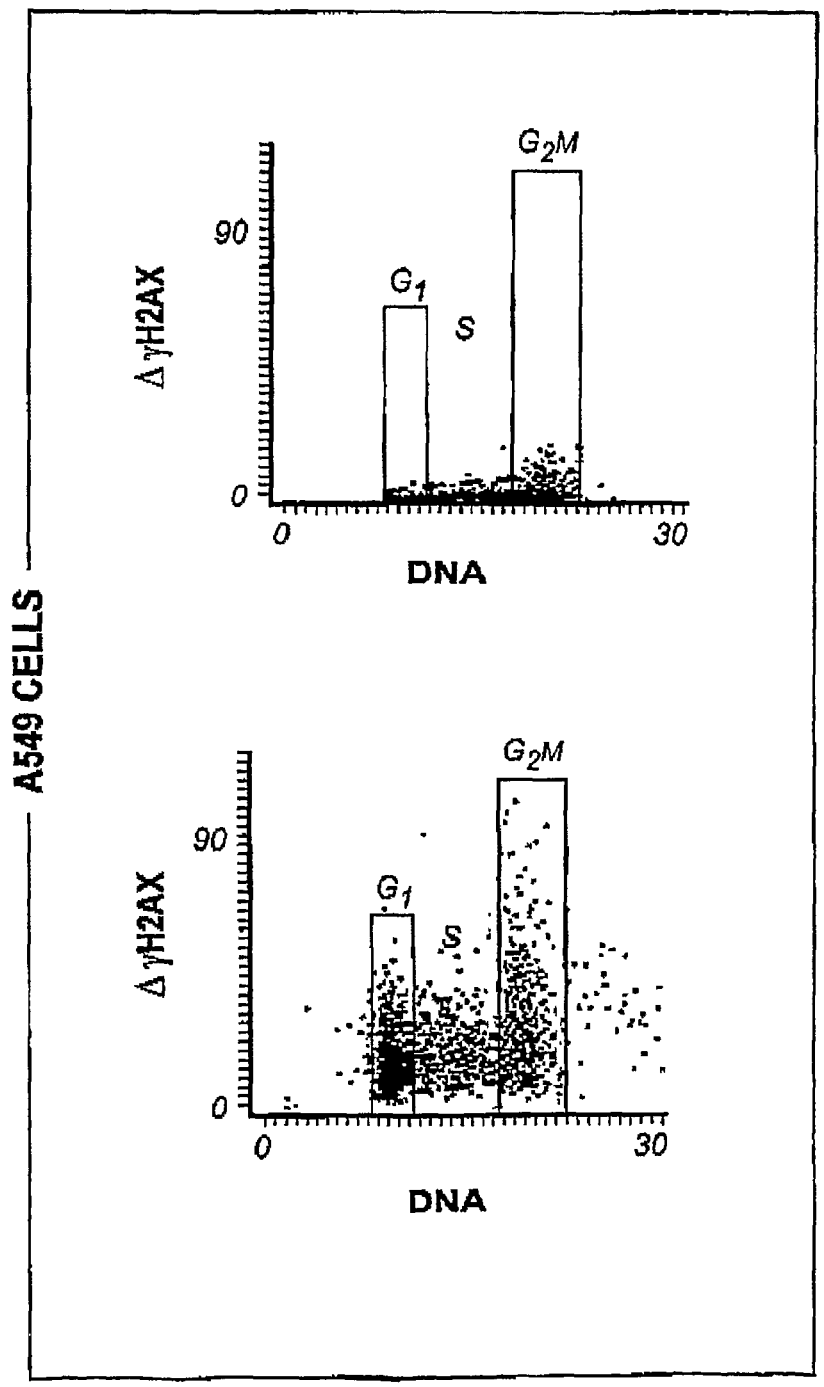

Within 15 min of exposure to whole smoke, A549 cells already displayed a dramatic increase in γH2AX relative to mock exposed cells (FIG. 18A). Increasing the recovery time following exposure led to continued increase in DNA damage. As noted above, $G_1$ cells appear to be the most sensitive to smoke especially when the cells are harvested 30 min or longer after exposure to whole smoke. The relative increase in γH2AX following 60 min of recovery is illustrated in FIG. 18B where it can be observed that virtually all smoke-exposed cells (right) express levels of γH2AX in excess of the expression observed in the mock-treated cells (left).

Figure 18C:
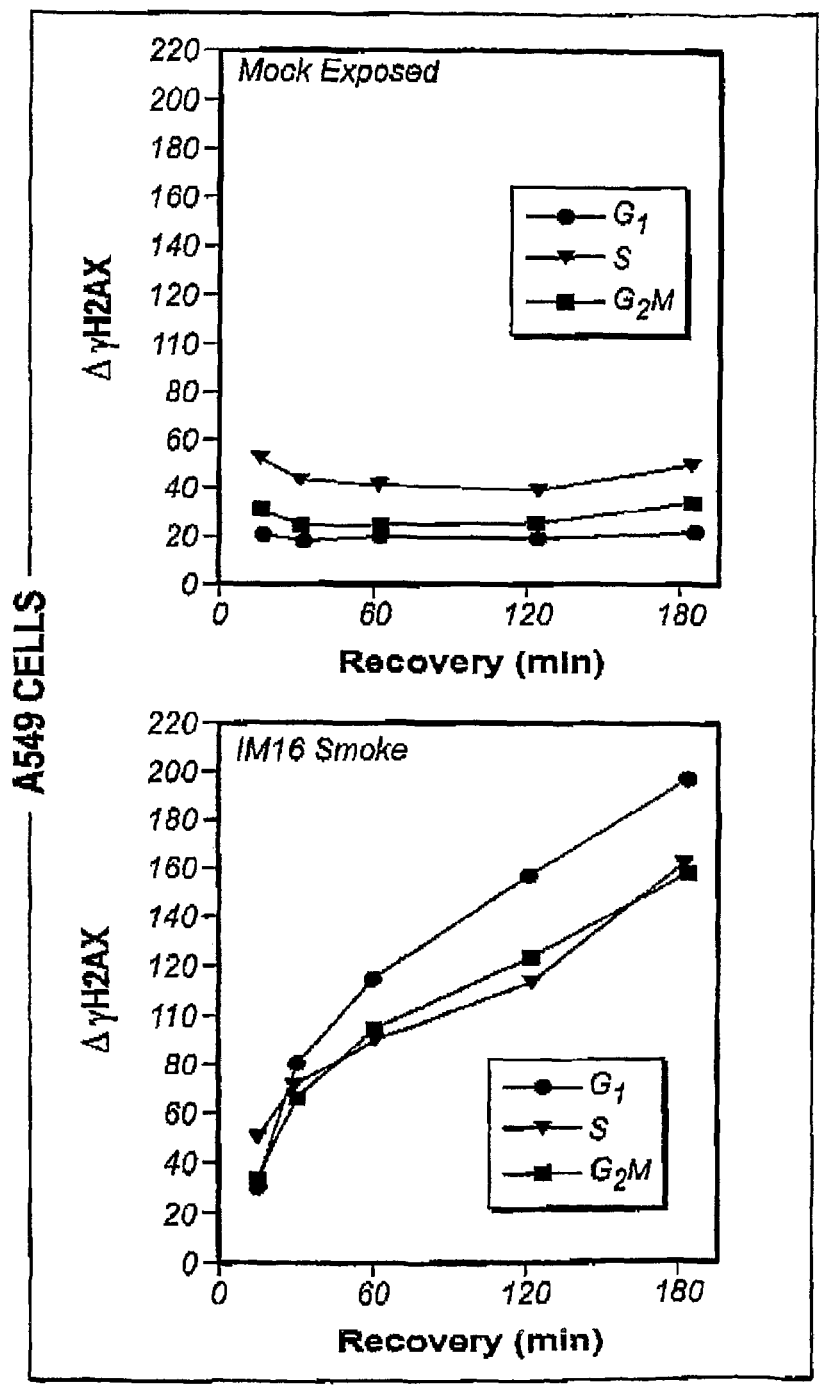
Figure 18D:
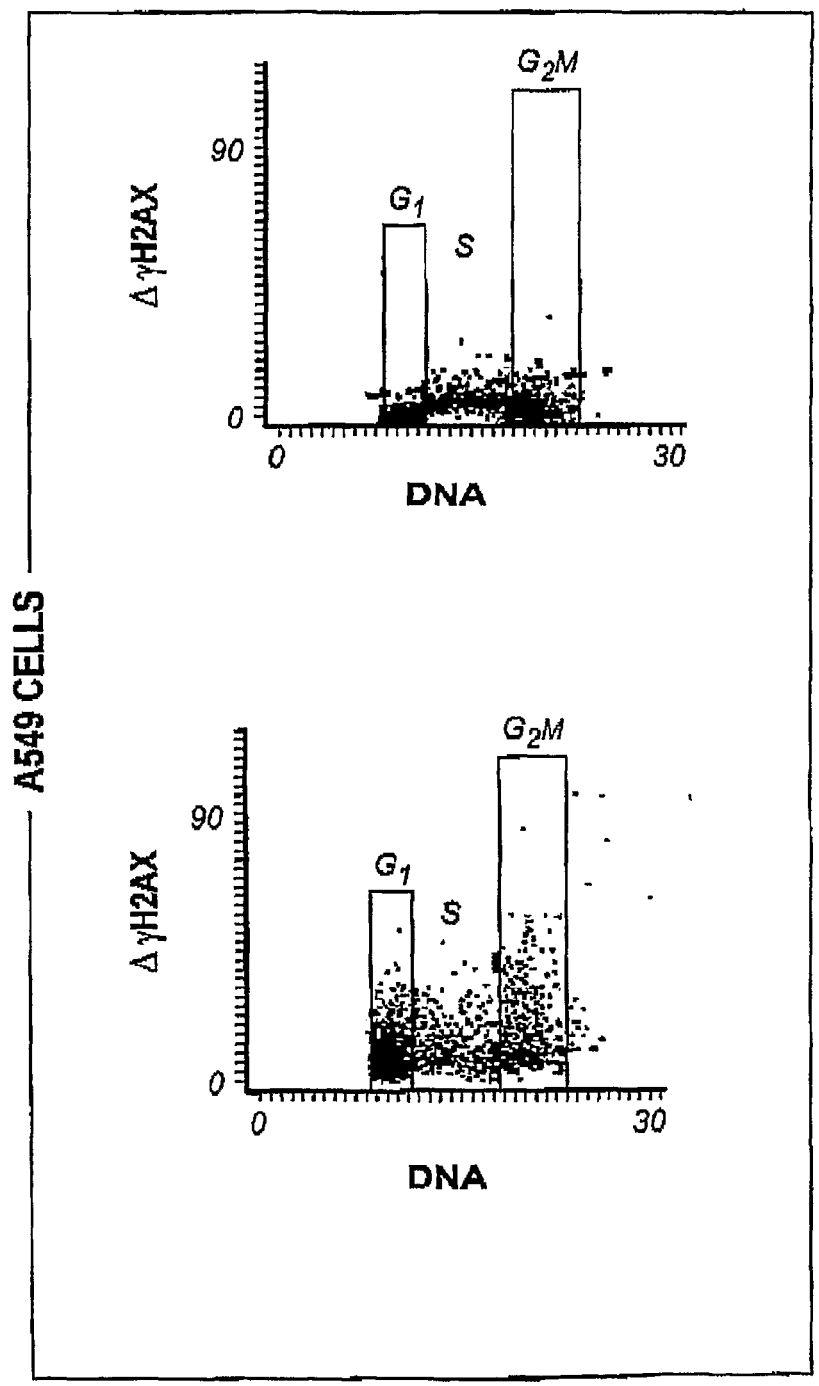

The response of NHBE cells to whole smoke from IM16 cigarettes was more or less identical to that observed for A549 cells (FIG. 18C). The one difference between the two cell lines was that S phase cells in NHBE cultures always expressed higher "scheduled" amounts of γH2AX. Nevertheless, as with A549 cells, $G_1$ cells are the most sensitive to smoke-induced DNA damage in these cultures. FIG. 18D demonstrates both the increased basal level of γH2AX in mock-treated cultures (left) and the extensive increase in γH2AX expression observed 60 min following a 20 min exposure of cells to whole smoke (right).

Figure 19:
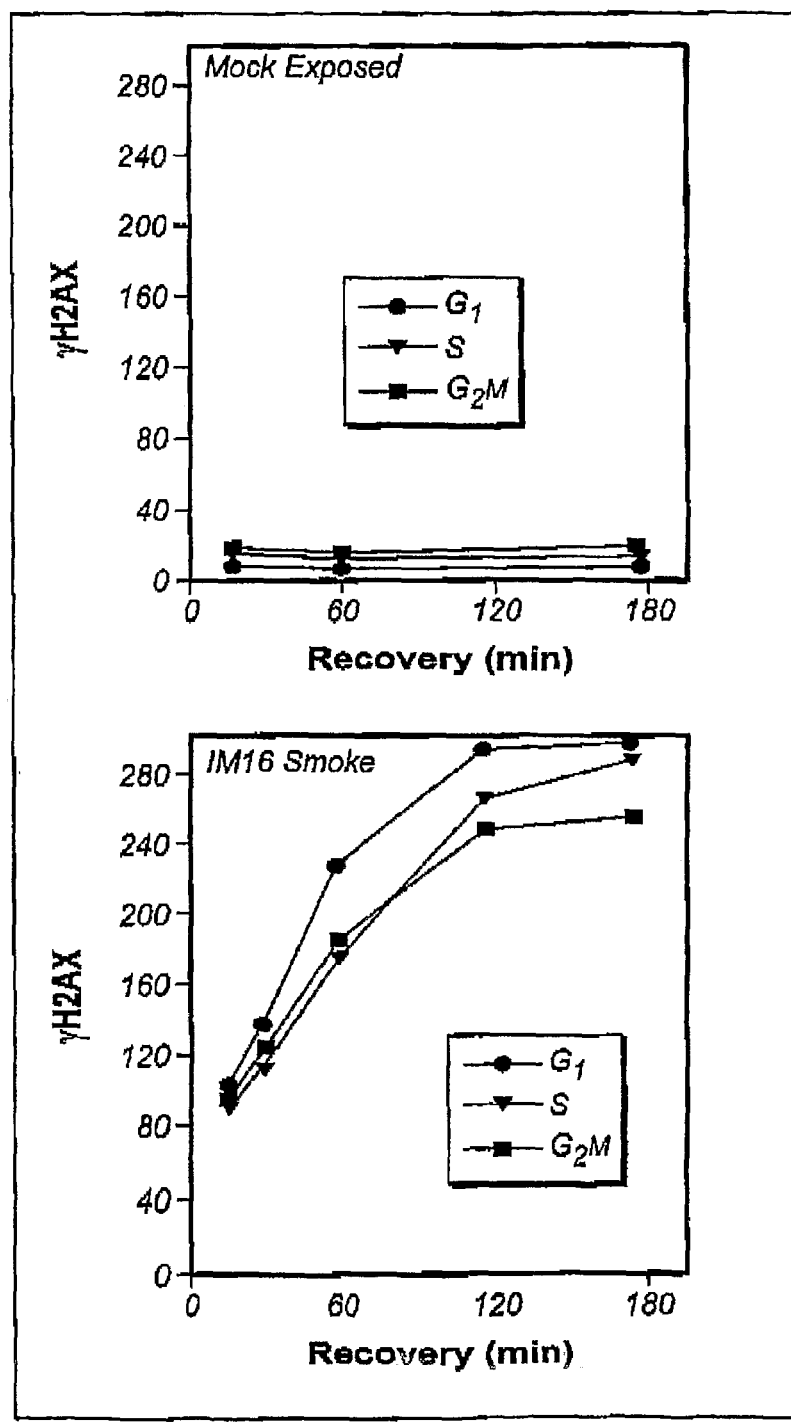
FIG. 19. Plots showing the increase (Δ) in mean γH2AX immunofluorescence during different time points of the recovery of A549 cells (per unit of DNA) after exposure to smoke of IM16, Quest 3®, and Omni® cigarettes for 20 minutes, calculated for cells in particular phases of the cell cycle.
Figure 19:
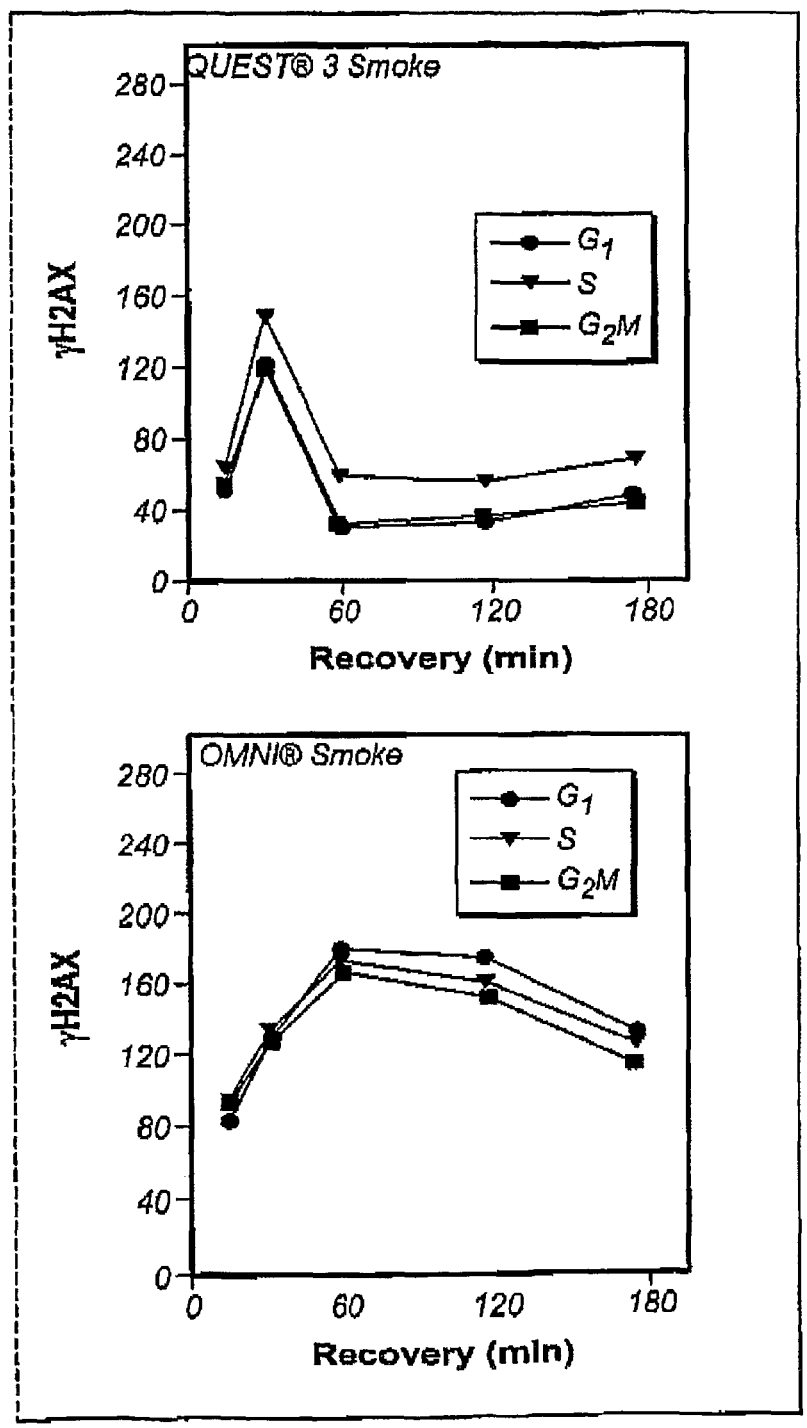

In the next series of experiments, the DNA damage caused by whole smoke from different sources was compared. Using an exposure time of 20 min, damage due to whole smoke from two other cigarettes could be compared to that caused by IM16 following various recovery times. The curves of γH2AX following exposure of A549 cells to IM16 (FIG. 19, top right) were comparable to that displayed in FIG. 18A. Exposure of the same cells to whole smoke from Quest 3® on the other hand resulted in an initial increase in γH2AX at 30 min that returned to near background levels when assayed after longer recovery times (FIG. 19, bottom left). Whole smoke from Omni® cigarettes caused damage intermediate between that of Quest 3® and IM16 (FIG. 19, bottom right). The DNA damage caused by Omni® increased until 60 min after which it more or less plateaued. Smoke from Quest 3® cigarettes affects S phase cells to a greater extent than any other phase while G1 cells are invariably most sensitive to smoke from IM16 and Omni®. Importantly, these data demonstrate that tobacco products containing modified tobacco (i.e., Omni® and Quest 3®) induced less DNA damage than a reference tobacco product (i.e., IM16). Accordingly, the modified tobacco products Omni®, and Quest 3® have a reduced potential to contribute to a tobacco related disease (i.e., Omni®, and Quest 3® are reduced risk tobacco products) according to the double strand break assay.

In the next series of experiments, it was determined that DNA damage caused by whole smoke can be mitigated by the presence of NAC. Using a standardized set of conditions (20 min of exposure followed by a 1 h recovery), DNA damage caused by whole smoke from IM16 cigarettes was assayed in both A549 and NHBE cells. NAC at a concentration of 25 mM was either absent or present during exposure and absent or present during the 1 h recovery time. In this instance, the background or "scheduled" γH2AX expression observed in Mock-treated cells was subtracted from each measurement. The remaining fluorescence should be indicative of the level of DNA DSBs under each set of conditions.

In A549 cells (FIG. 20, top), IM16 caused a dramatic increase in H2AX phosphorylation in the absence of NAC (PBS, PBS). Applying NAC to the media following exposure to smoke did nothing to mitigate the DNA damage caused by whole smoke. However, if NAC was present during exposure to smoke, DNA damage was suppressed by greater than 80% for the entire population; the suppression was greatest for G1 cells (91%), intermediate for G2M (88%) and least for S (82%) phase cells. The presence of NAC both during exposure to smoke and during the 1 h recovery period provided slightly more protection increasing suppression of γH2AX to 90% for the entire population.

Figure 20:
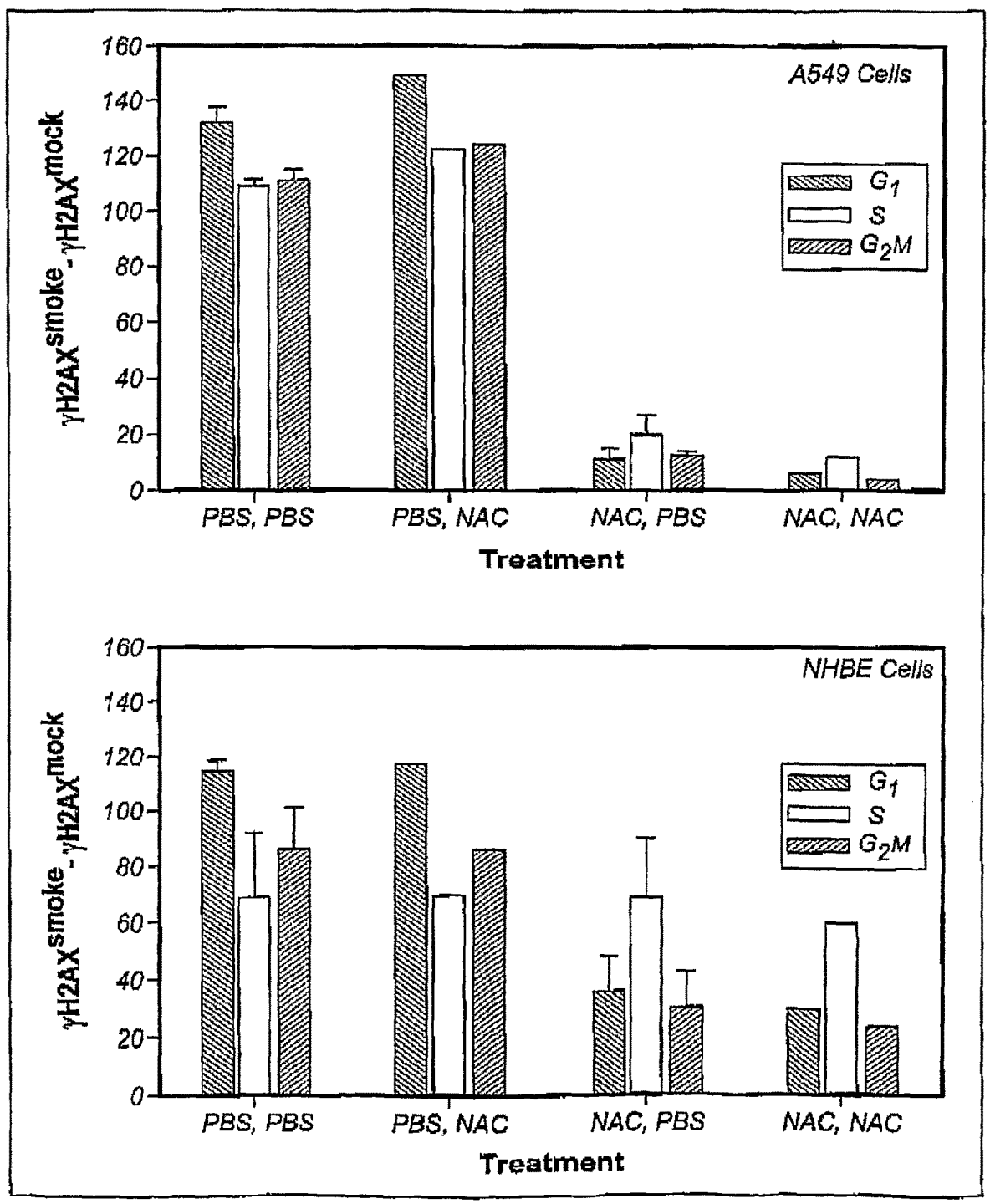
FIG. 20. Bar plots showing the increase (Δ) in mean γH2AX immunofluorescence of A549 cells (top) and NHBE cells (bottom) exposed to smoke of IM16 cigarettes for 20 minutes, followed by a 1 hour recovery, for cells treated with phosphate-buffered saline (PBS) or N-acetyl-L-cysteine (NAC) during exposure (first value) and during recovery (second value).

As with A549 cells, when NHBE cells were exposed to whole smoke from IM16 cigarettes, the cells in G1 phase were the most sensitive. However, since the S phase cells express somewhat higher levels of "scheduled" γH2AX and are not as sensitive as G1 cells to smoke (FIG. 18C), the value for S phase cell DNA damage was considerably less than for cells in G1 or G2M phase (FIG. 20, bottom). Addition of NAC only during recovery had little effect on the level of DNA damage induced by whole smoke. NAC present during exposure diminished the damage observed in G1 cells by nearly 69%; the decrease was about 65% for G2M cells but S phase cells were afforded no protection. NAC present both during exposure and recovery provided a small degree of additional protection.

Figure 21:
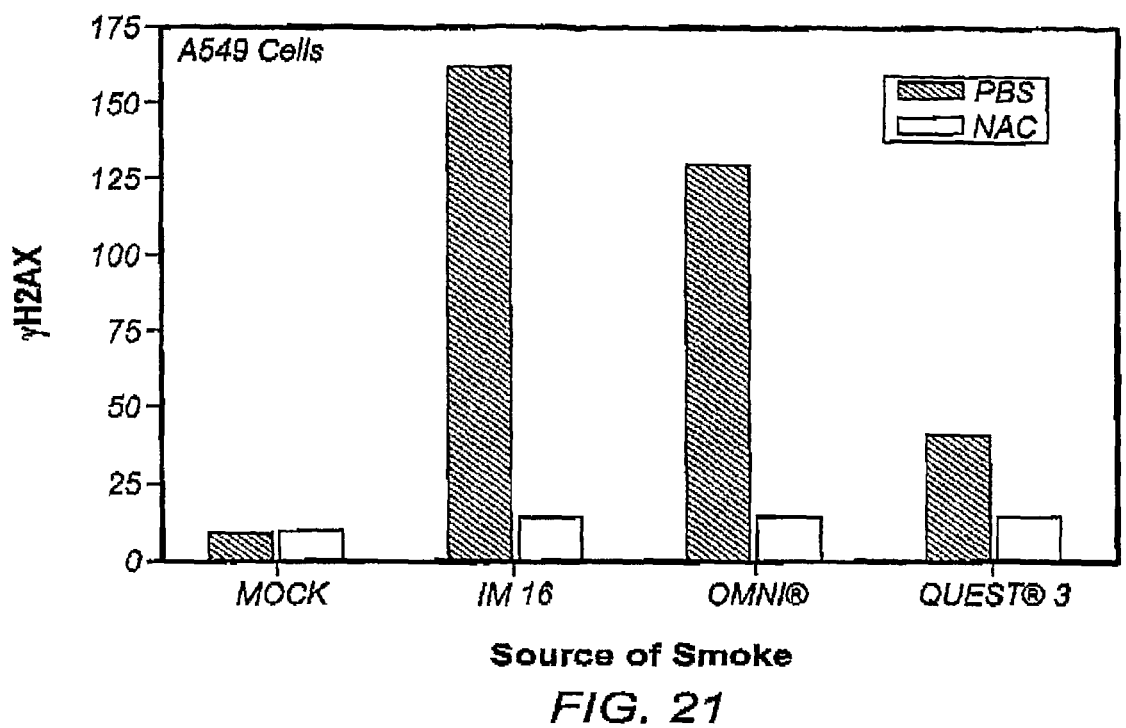
FIG. 21. Bar plot showing the increase (Δ) in mean γH2AX immunofluorescence of A549 cells exposed to smoke from IM16, Omni® and Quest 3® in the presence of PBS or NAC.

Next, the effect of NAC on DNA damage caused by whole smoke from various sources was evaluated. A549 cells were exposed to smoke from IM16, Omni® and Quest 3® cigarettes in the presence and absence of NAC during exposure. As illustrated in FIG. 21, NAC dramatically reduced the effects of smoke from IM16 cells. Omni® produced less damage than IM16 but NAC reduced the damage to near background levels. Quest 3® smoke caused the least amount of damage which could also be reduced to background levels by the presence of 25 mM NAC during exposure. In all instances, the level of damage following exposure to smoke in the presence of NAC was approximately the same, just slightly more than the background or scheduled level of γH2AX expression. As above, the data from this assay demonstrates that tobacco products containing modified tobacco (i.e., Omni® and Quest 3®) induced less DNA damage than a reference tobacco product (i.e., IM16). Again, the double strand break assay has shown that the modified tobacco products Omni®, and Quest 3® have a reduced potential to contribute to a tobacco related disease (i.e., Omni®, and Quest 3® are reduced risk tobacco products).

In more experiments, the cell cycle specific inhibition of whole smoke-induced DNA damage by NAC was analyzed. A549 cells were exposed to whole smoke in the presence and absence of various concentrations of NAC. Exposure was always for 20 min and recovery was 1 h. In each instance, the background or "scheduled" expression of γH2AX was subtracted from the value obtained for each population in each cell cycle phase. Since G1 phase cells were the most sensitive and had the highest value, all other measurements were normalized to that of G1 phase cells exposed to IM16 smoke in the absence of NAC (plotted as 0.1 mM NAC on the log plot).

Figure 22:
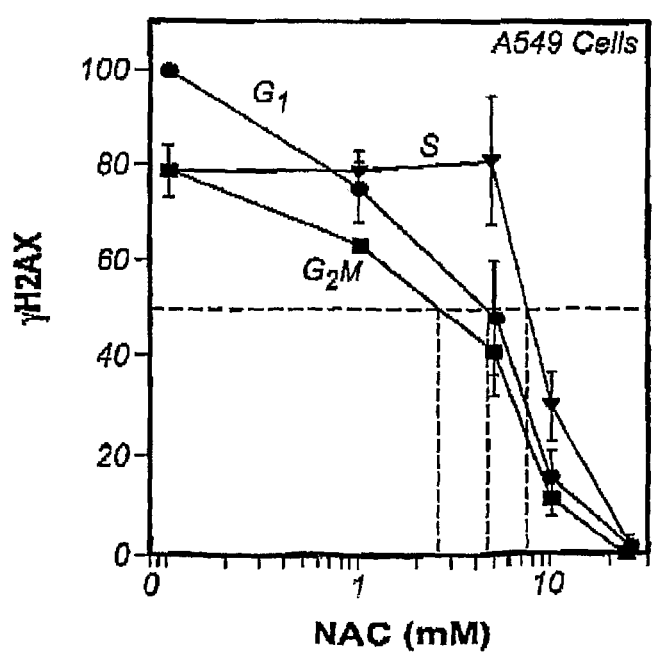
FIG. 22. Plot of the relative amount of mean γH2AX immunofluorescence of A549 cells exposed to smoke from IM16 as a function of different concentrations of NAC, calculated for cells in particular phases of the cell cycle. Horizontal dashed line indicates 50% reduction in γH2AX immunofluorescence. Vertical dashed lines indicate the estimated NAC concentration for each cell type at 50% reduction.

As can be seen in FIG. 22, damage by whole smoke from IM16 to S phase A549 cells was unaffected by the presence of NAC up to a concentration of 5 mM. In contrast, damage caused to both G1 and G2M cells began to decrease when as little as 1 mM NAC was present during exposure. The damage caused to S phase cells decreased sharply as the NAC concentration was increased to 10 mM and, by 25 mM, there was little difference in residual γH2AX expression between cells in any phase of the cycle.

The concentration of NAC that reduced DNA damage by 50% for each cell cycle phase can be determined from the graph in FIG. 22. For G1, S and G2M phase cells the values were approximately 4.5, 2.6 and 7.5 mM NAC.

Figure 23:
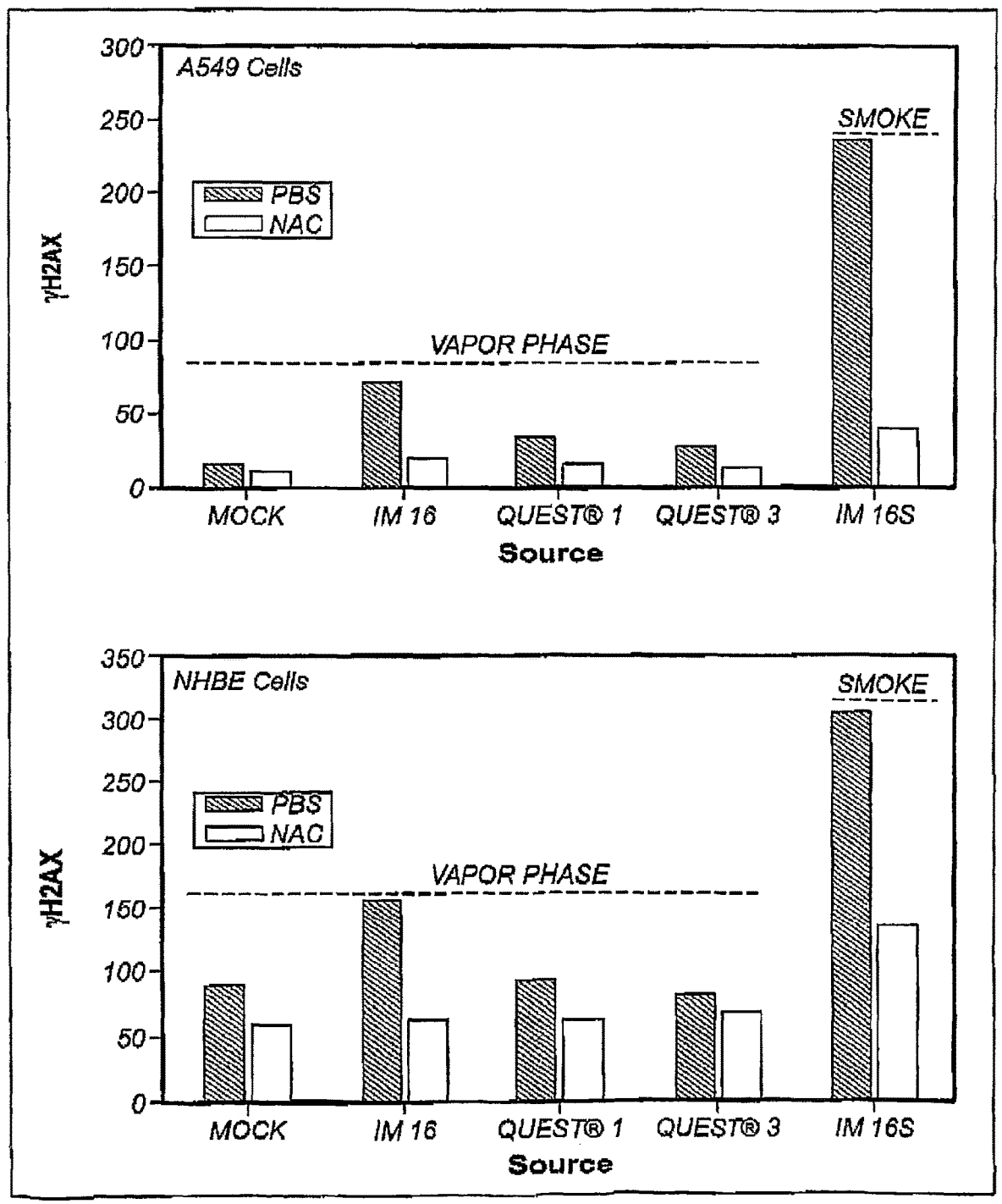
FIG. 23. Bar plots showing the increase (Δ) in mean γH2AX immunofluorescence of A549 cells (upper plot) and NHBE cells (lower plot) exposed to the vapor phase of smoke from IM16, Quest 1® and Quest 3®, and smoke from IM16 in the presence of PBS or NAC.

In more experiments, it was determined that the vapor phase of smoke induces damage that is abrogated by the presence of NAC. FIG. 23 (top) illustrates the ability of the vapor phase of smoke from various tobacco sources to cause DNA damage to A549 cells in comparison to whole smoke from IM16 cigarettes. Thus, the vapor phase from IM16 cigarettes using standard conditions of exposure and recovery caused only about 26% of the DNA damage (γH2AX) as whole smoke from the same source. In the same comparison, the vapor phase from Quest 1® and Quest 3® caused only 8.1% and 5.6% of the damage caused by whole smoke from IM16. As a direct comparison, the vapor phase of smoke from Quest 1® and Quest® caused 68.8% and 78.5%, respectively, less damage than the vapor phase of smoke from IM16.

The presence of 25 mM NAC during exposure of A549 cells to whole smoke form IM16 cigarettes reduced γH2AX by nearly 90% (89.1%) compared to cells exposed to whole smoke in the absence of NAC. NAC present during cell exposure to the vapor phase of smoke from IM16, Quest 1® and Quest 3®, reduced γH2AX by 93.2%, 98.9% and 100%, respectively compared to the damage caused by the vapor phase of smoke in the absence of NAC.

The same experiment performed on NHBE cells resulted in more or less comparable results (FIG. 23, bottom). Whole smoke from IM16 cells produced less damage in NHBE cells under standard conditions compared to A549 cells (note the greater background observed in NHBE cells). The vapor phase from IM16 CS caused only about 30% (29.7%) of the damage caused by whole smoke whereas the vapor phase of smoke from Quest 1® caused 97% less damage than whole smoke from IM16 cigarettes. The vapor phase of smoke from Quest 3® produced no increase in γH2AX over background in NHBE cells.

The presence of NAC during exposure of NHBE cells to whole smoke from IM16 cigarettes reduced γH2AX by about 78% (77.9%). The presence of NAC during exposure of cells the vapor phase of IM16, Quest 1® or Quest 3® abolished virtually all DNA damage relative to mock-treated cells; i.e., γH2AX was reduced to background levels or below.

Figure 24:
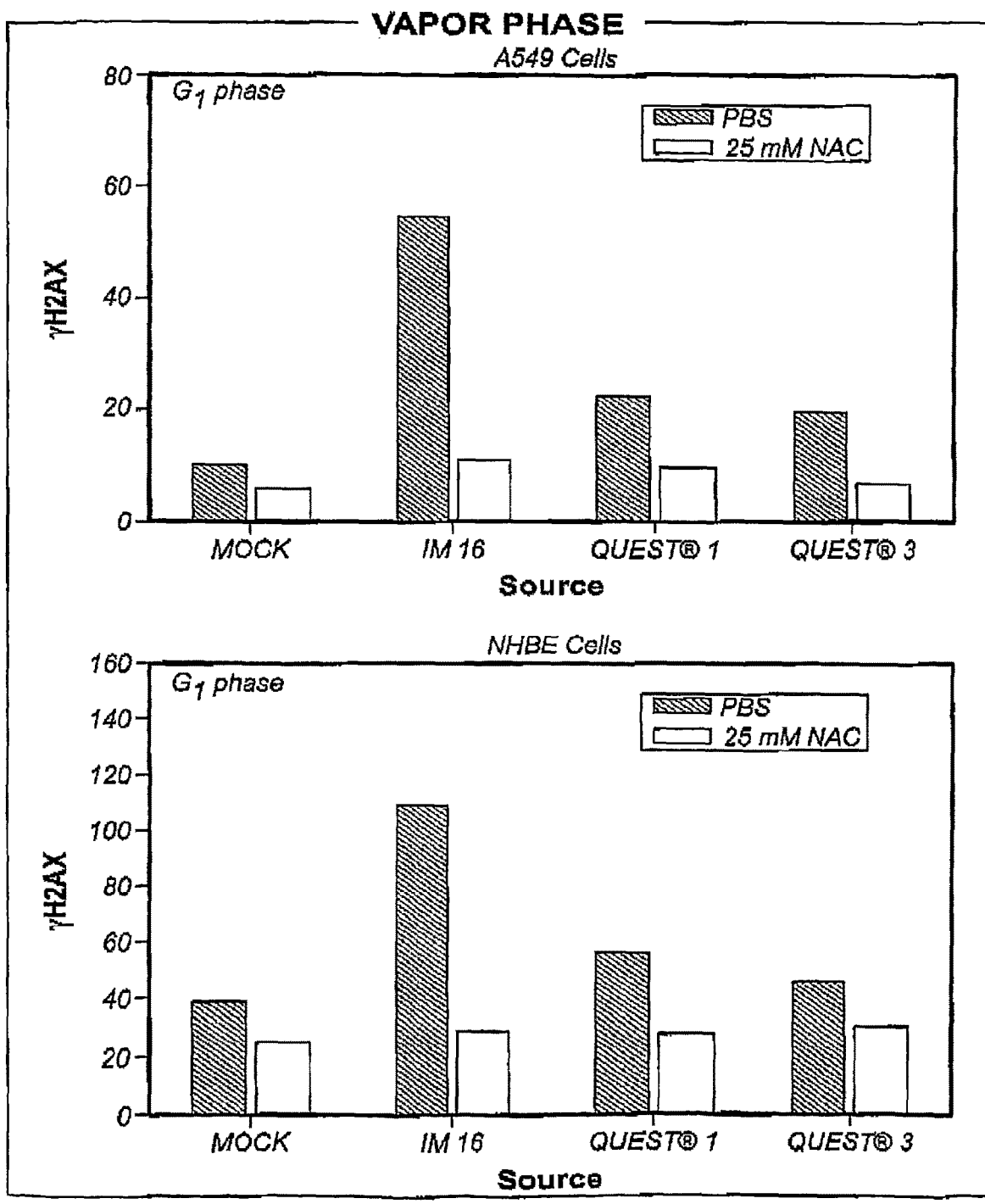
FIG. 24. Bar plots showing the increase (Δ) in mean γH2AX immunofluorescence of $G_1$, S and $G_2M$ phase A549 cells (left plots) and $G_1$, S and $G_2M$ phase NHBE cells (right plots) exposed to the vapor phase of smoke from IM16, Quest 1® and Quest 3® in the presence of PBS or NAC.
Figure 24:
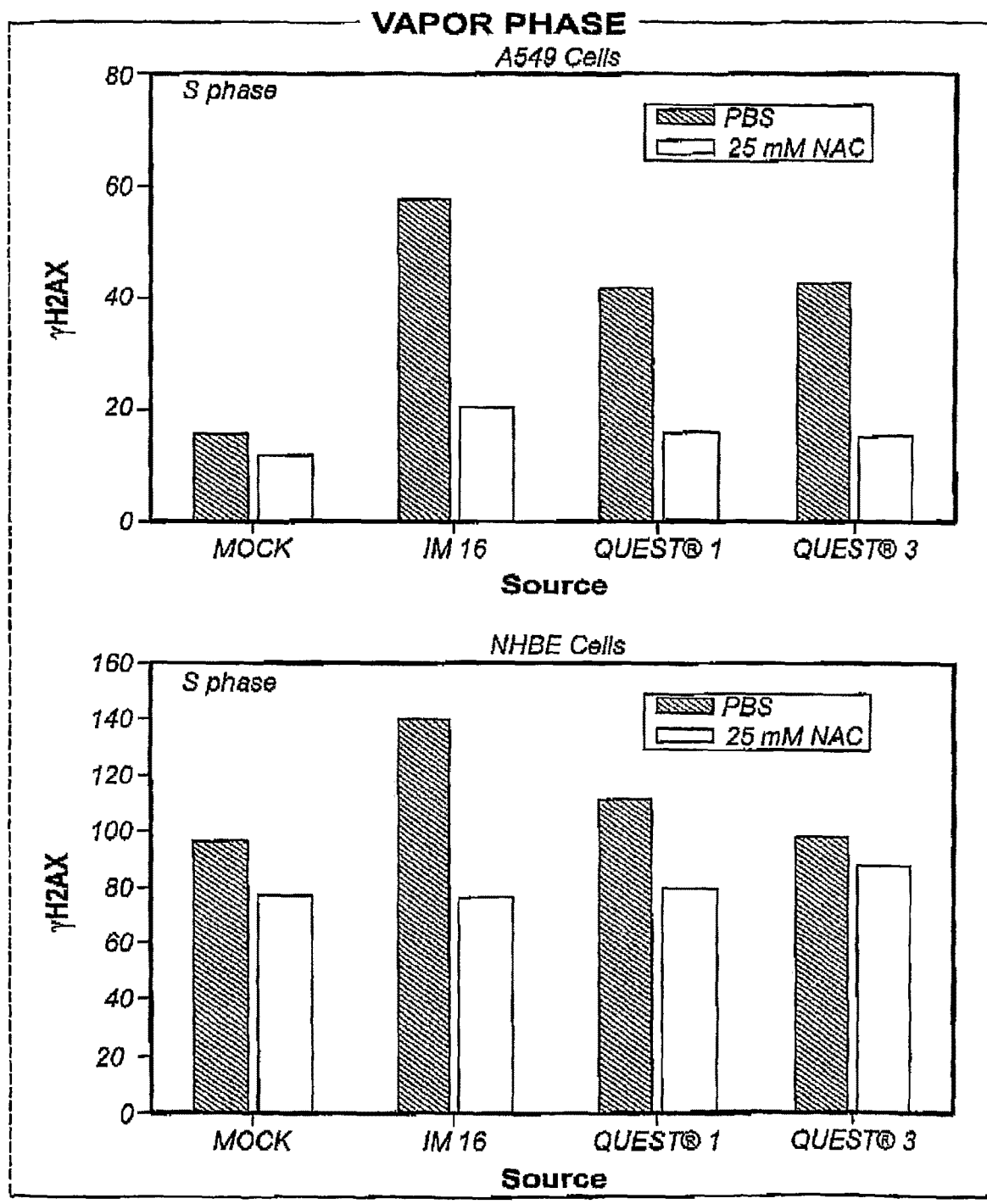
Figure 24:
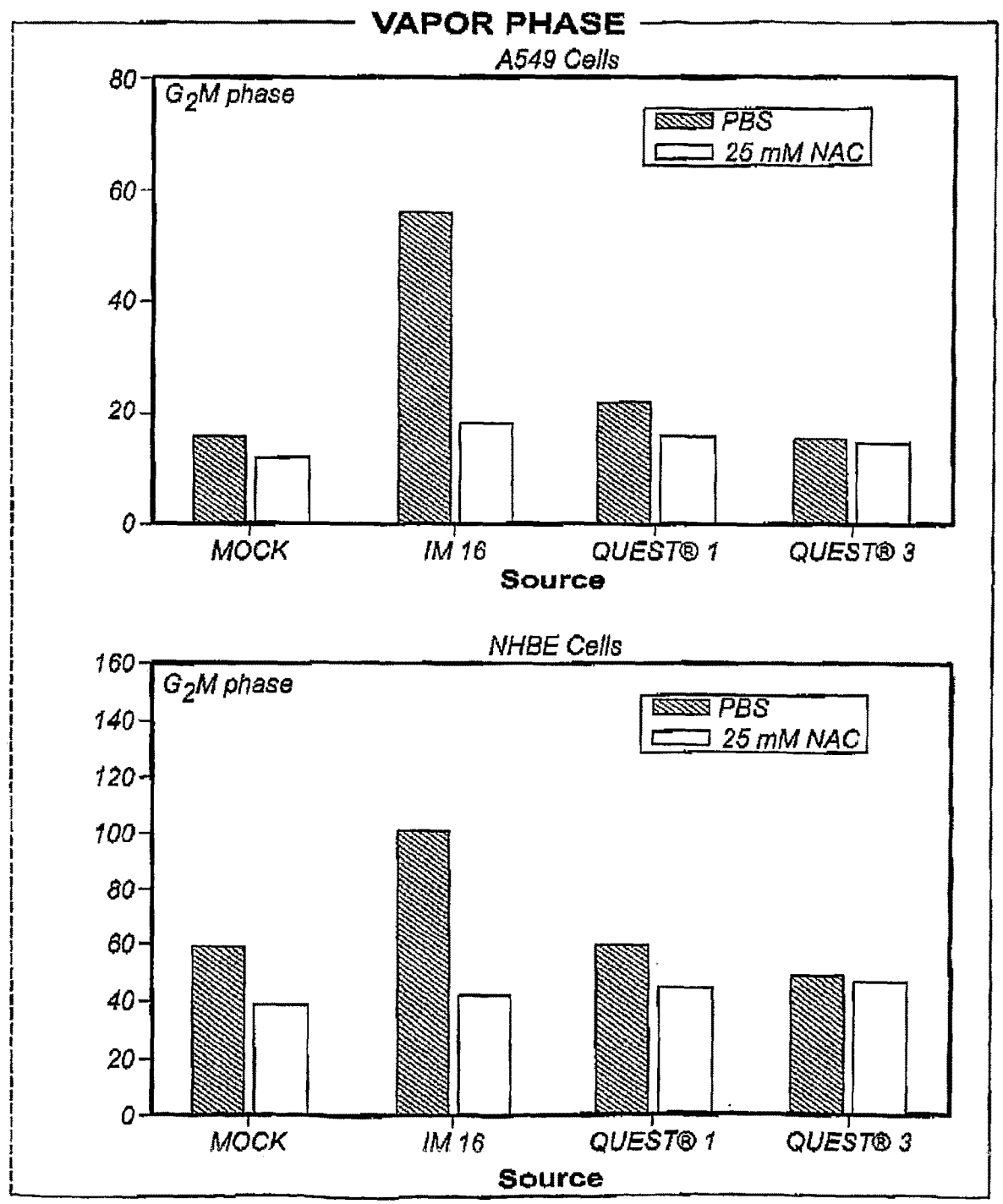

The cell cycle phase specific results are comparable to that for the whole populations (FIG. 24). The vapor phase of smoke from IM16 caused comparable amounts of damage in each cell cycle phase in A549 cells though the reduction of damage in G1 phase by NAC was somewhat higher than it was for S and G2M phase; 98.5% versus 89.0% and 92.2%, respectively. The vapor phase from both Quest 1® and Quest 3® caused more damage to S phase cells though in each instance, the presence of NAC reduced damage to background levels for each cell cycle phase.

NHBE cells as noted earlier have higher γH2AX levels in S phase of mock-treated cells as can be seen in FIG. 24. The largest increase in damage caused by the vapor phase of smoke from IM16 occurred in G1 phase cells (54.4% and 66.9% greater than for cells in S or G2M, respectively). The presence of NAC reduced the damage caused by the vapor phase of smoke from IM16 to background levels or below. The vapor phase of smoke from Quest 1® and Quest 3® cigarettes had only a small effect on DNA damage in cells in G1 or S but not G2M phase. All damage caused by the vapor phase of smoke from Quest® cigarettes in NHBE cells was inhibited in the presence of NAC. Importantly, this data provide more evidence that the tobacco products containing modified tobacco (i.e., Quest 1® and Quest 3®) induced significantly less DNA damage (i.e., double strand DNA breaks) than that of a reference tobacco product (i.e., IM16). Accordingly, the modified tobacco products Quest 1®, and Quest 3® have a reduced potential to contribute to a tobacco related disease (i.e., Quest 1® and Quest 3® are reduced risk tobacco products, according to the double strand DNA break assay.

Figure 30:
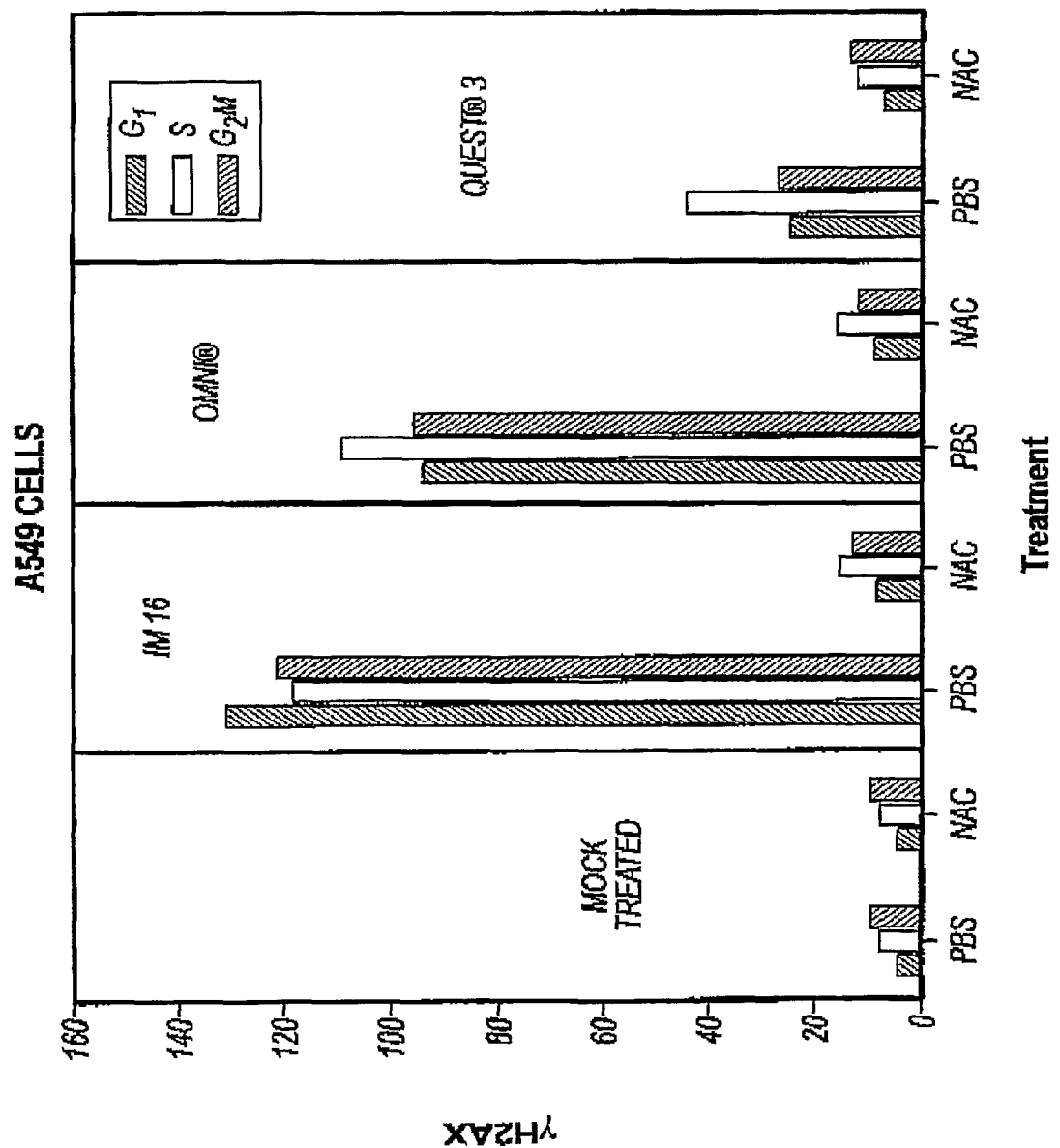
FIG. 30. Bar plot of results from Example 2 showing the increase (Δ) in mean γH2AX immunofluorescence of A549 cells exposed to smoke from IM16, Omni® and Quest 3® in the presence of PBS or NAC, calculated for cells in particular phases of the cell cycle.
Figure 32:
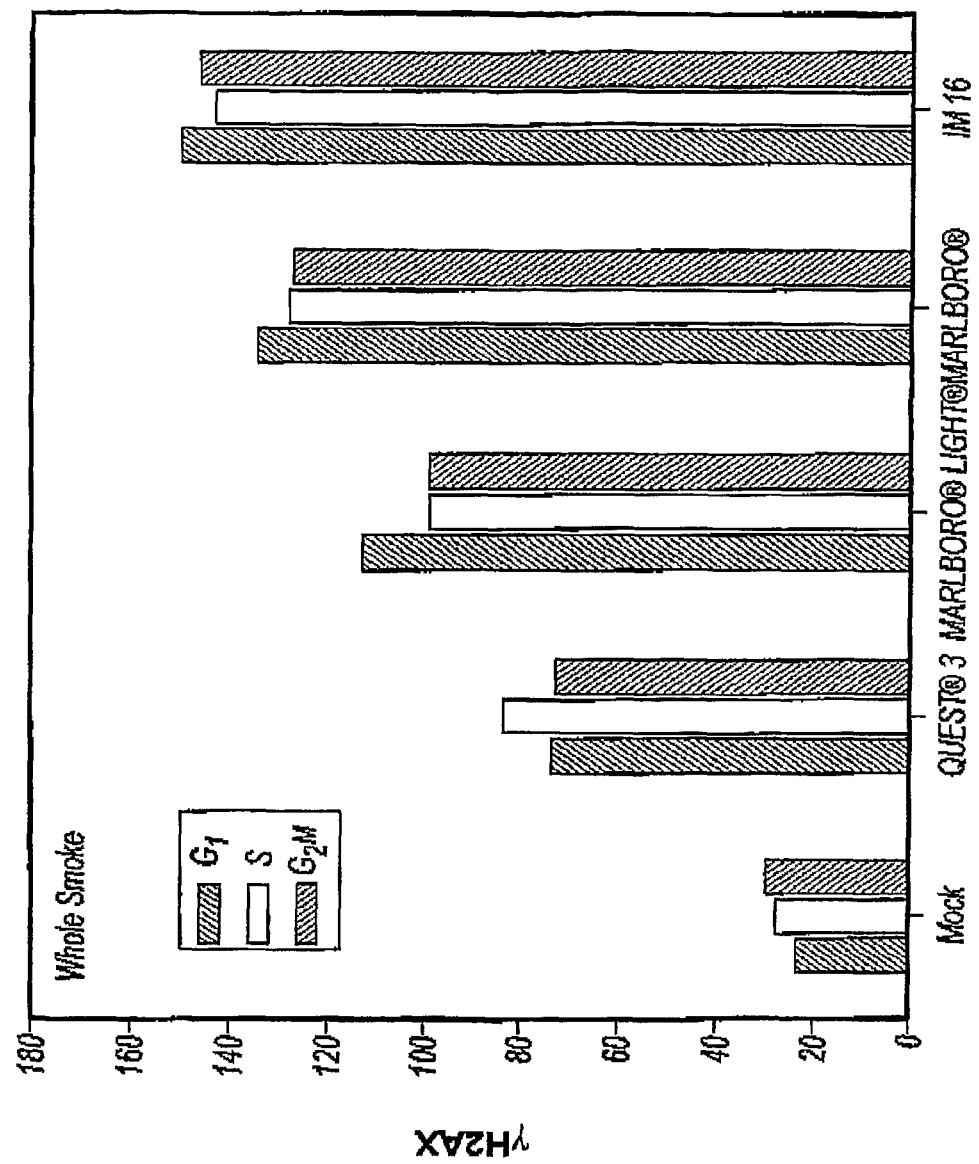
FIG. 32. Bar plot of results from Example 2 showing the increase (Δ) in mean γH2AX immunofluorescence of A549 cells exposed to smoke from IM16, Marlboro®, Marlboro Light®, and Quest 3®, calculated for cells in particular phases of the cell cycle.
Figure 33:
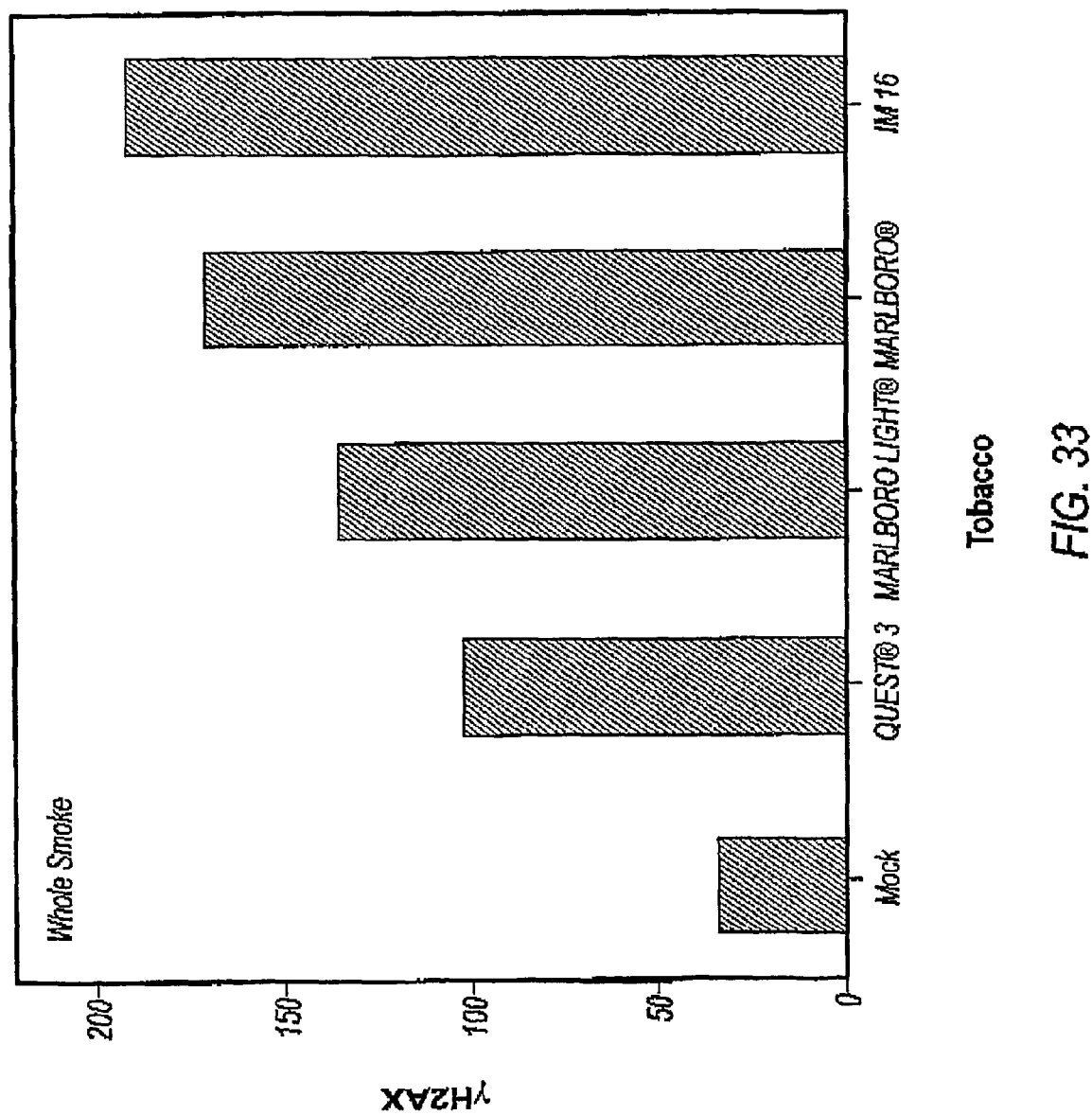
FIG. 33. Bar plot of results from FIG. 32 showing the increase (Δ) in mean γH2AX immunofluorescence of A549 cells exposed to smoke from IM16, Marlboro®, Marlboro Light®, and Quest 3®, averaged for all cell cycles.

FIGS. 30, 32 and 33 show additional comparisons of reactions of A549 cells to smoke from various cigarettes, where the affect can vary for different cigarettes, and can vary according to the cell cycle of the cells, and can vary according to the presence of antioxidant.

Figure 31:
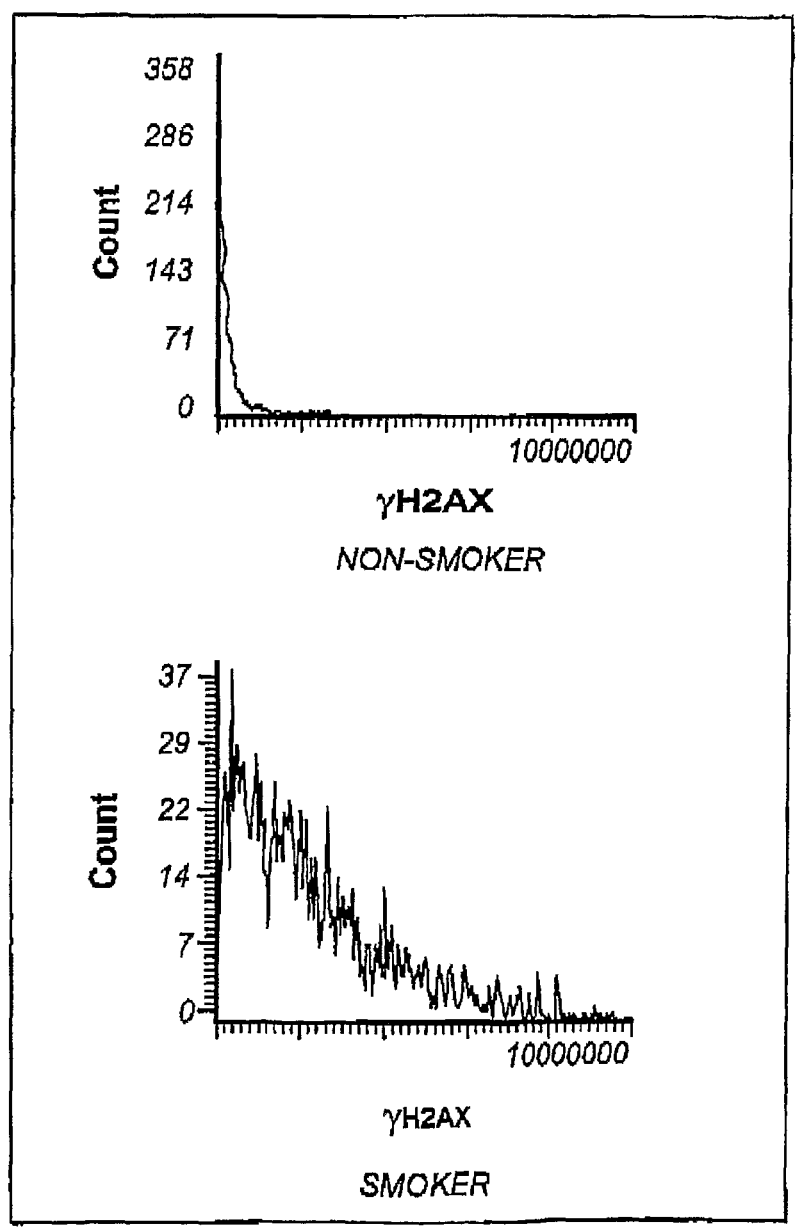
FIG. 31. Plot depicting γH2AX associated fluorescence (γH2AX; X-axis) and the number of cells having the corresponding γH2AX fluorescence level (Y axis), for buccal cells of a subject subsequent to smoking a cigarette (smoker) or a subject who did not smoke a cigarette (non-smoker).

Further performed was a test of double-strand DNA breaks in the cells of a human subject exposed to tobacco smoke. The level of γH2AX expression in the buccal mucosa of a smoker was compared to the level of γH2AX expression in the buccal mucosa of a nonsmoker. A cheek swab was collected from a subject (smoker) within 5 min completion of smoking a Marlboro Light® cigarette, and a second check swab was collected from a subject that did not smoke a cigarette (non-smoker). Levels of γH2AX were then measured for both cell samples. As seen in FIG. 31 the X axis depicts γH2AX associated fluorescence (γH2AX), and the Y axis depicts the number of cells having the corresponding γH2AX fluorescence level. There were 358 cells with a very low value of γH2AX in the non-smoker sample, whereas the smoker sample had cells with γH2AX values spread over a wide range. Each histogram represents 3×103 cells. The buccal cells from the smoker showed a low number of cells having little or no γH2AX fluorescence signal, and showed a large number of cells with higher γH2AX fluorescence levels. In contrast, almost all cells of the non-smoker had little or no γH2AX fluorescence. Thus, human buccal cells exposed to tobacco smoke have an increased level of double strand DNA breaks relative to human buccal cells not exposed to tobacco smoke. These results parallel the in vitro results observed for A549 cells and for NHBE cells. Thus, the in vitro approaches described herein are predictive of in vivo responses.

Accordingly, the methods that were applied to A549 cells and NHBE cells for comparing different tobacco products, analyzing cells at different stages in cell cycle, and determining protection provided by the presence of an antioxidant, will be performed on human samples of buccal cells and it is expected, as shown in the in vitro experiments, that modified tobaccos, in particular genetically modified tobaccos that have a reduced amount of one or more compounds that contribute to a tobacco related disease (e.g., genetically modified tobacco having a reduced nicotine, TSNA, and/or sterol content) will induce fewer or a reduced amount of double strand DNA breaks in humans that are contacted with smoke from said modified tobaccos than will be observed in humans that are contacted with smoke from conventional tobacco products, reference tobacco products, or non-transgenic (wild-type tobacco of the same variety as the parental strain prior to genetic modification). The following section describes several methods to evaluate the ability of a tobacco or a tobacco product to modulate apoptosis in greater detail.

Analysis of Changes in Cell Homeostasis: Changes in the Fidelity of the DNA, Double Strand Breaks By one approach, for example, CS is generated using a smoking machine from a first tobacco modified product, e.g., a product containing tobacco that has been genetically modified to have a reduced amount of a compound. A first population of NHBE cells is contacted with said CS obtained from the modified tobacco product, and the cells contacted with CS are assayed for double-strand DNA breaks. A second population of NHBE cells is then contacted with CS generated from an unmodified tobacco product, wherein the unmodified tobacco product retains the component that was removed or inhibited in the modified tobacco product. An unmodified tobacco product can be, for example a product containing the parental variety of tobacco, where the parental variety of tobacco is the unmodified tobacco variety used to generate the modified tobacco variety. The second population of cells contacted with CS is then assayed for double-strand DNA breaks. A comparison of the data obtained from the analysis of the first and second tobacco products will reveal that the difference in double-strand DNA breaks caused by the modified tobacco product relative to the unmodified tobacco product. By this approach, one can effectively identify the contribution of individual components of a tobacco product to double-strand DNA breaks, or other assay conditions provided herein. These methods can thereby be used to identify the contribution of individual components of a tobacco product to a tobacco-related disease. This approach can be used to develop tobacco products that are less likely to contribute to a tobacco-related disease and reduced risk tobacco products identified by these methods are embodiments provided herein. Further, tobacco products prepared by these approaches can be prepared according to good manufacturing processes (GMP) (e.g., suitable for or accepted by a governmental regulatory body, such as the Federal Drug Administration (FDA), and containers that house said tobacco products can comprise a label or other indicia, with or without structure-function indicia, which reflects approval of said tobacco product from said regulatory body.

Thus, the methods provided herein can be used to characterize a first and a second tobacco product by providing the first and second tobacco products, obtaining a first and second tobacco composition from the first and second tobacco products, respectively, contacting a first cell with the first tobacco composition and contacting the second cell with the second tobacco composition, and identifying one or more attributes of the contacted cells. Different tobacco products can contain different levels of carcinogens that can induce various types of cell damage including mutations, chromosomal aberrations, aberrant sister chromatid exchanges and micronuclei. Comparison of attributes of cells contacted with different tobacco compositions can be performed in the methods provided herein, and such attributes include, but are not limited to, differential levels of mRNA, differential levels of protein, induction of damage of cellular genetic material or modulation of cell homeostasis. Accordingly, the methods provided herein can be used to compare two or more tobacco products by assay methods including assay for differential levels of mRNA, differential levels of protein, induction of damage of cellular genetic material or modulation of cell homeostasis. Exemplary assay methods include microarray assays, ELISA assays, Western blot assays, assays of a double-strand DNA break, inhibition of apoptosis, or inhibition of cell proliferation.

In some embodiments, the first and second smoke products are prepared using essentially equivalent protocols. The phrase, "wherein the first and second smoke products are prepared using essentially equivalent protocols," as used herein, means that the two smoke products can be validly compared. For example, both products can be smoke or both products can be smoke concentrates.

The methods provided herein include methods of identifying a compound in tobacco that induces damage of cellular genetic material or modulates cell homeostasis by providing a first tobacco, obtaining smoke or a smoke condensate from the first tobacco, contacting a first population of cells with the smoke or smoke condensate from the first tobacco, identifying induction of damage of cellular genetic material or modulation of cell homeostasis in the first population of cells after contact with the smoke or smoke condensate from the first tobacco, providing a second tobacco that has been modified to reduce a compound in the second tobacco, obtaining smoke or a smoke condensate from the second tobacco, contacting a second population of cells with the smoke or smoke condensate from the second tobacco, and identifying an induction of damage of cellular genetic material or modulation of cell homeostasis in the second population of cells after contact with the smoke or smoke condensate from the second tobacco, where an identification of a reduction in the induction of damage of cellular genetic material or modulation of cell homeostasis in the second population of cells after contact with the smoke or smoke condensate from the second tobacco identifies the compound as one that induces damage of cellular genetic material or modulates cell homeostasis. Compounds identified in accordance with the methods provided herein can be, for example, compounds that induce the double strand DNA breaks, inhibit apoptosis, or inhibit cell proliferation. In some embodiments, the second tobacco can be genetically modified to reduce the expression of at least one gene that regulates production of the compound.

The compound in tobacco that induces damage of cellular genetic material or modulates cell homeostasis identified by the methods provided herein can be a tobacco-derived substance associated with double-strand DNA breaks (DSBs). The tobacco-derived substance associated with DSBs can be detected in the context of comparing the harmful potential of two different tobacco or smoke products (as provided herein elsewhere) or can be detected in an environmental context, such as TS in a business office, train car, or restaurant. The ability to detect the tobacco derived substance can depend on not only its presence, but also its concentration in the "tobacco test composition" (which can be smoke, a smoke concentrate, or, for example, an air sample containing or potentially containing TS). To that end, useful parameters for assessing the degree of harmfulness can include, for example, not only the degree of phosphorylation of H2AX (or accumulation of another DSB marker), but also the initial rate of DSB accumulation, the period of time required to reach a plateau and the degree of phosphorylated DSB at the plateau level where a rapid rise in the degree of H2AX phosphorylation, a protracted period of time to reach a plateau, and a high plateau level can be correlated with increased harmful potential (for example, see FIGS. 14 and 15 and accompanying text). Note that where assay conditions are relatively prolonged (for example, longer than 55 minutes) it can be desirable to include, in the assay, a phosphatase inhibitor such as calyculin A or okadaic acid to inhibit and/or prevent possible dephosphorylation of H2AX molecules.

Also provided herein are methods of identifying a tobacco product that has a reduced potential to contribute to a tobacco-related disease by providing a first tobacco product, obtaining smoke or a smoke condensate from the first tobacco product, contacting a first population of cells with the smoke or smoke condensate from the first tobacco product, identifying the presence or absence of an induction of damage of cellular genetic material or modulation of cell homeostasis in the first population of cells after contact with the smoke or smoke condensate from the first tobacco product, providing a second tobacco product, obtaining smoke or a smoke condensate from the second tobacco product, contacting a second population of cells with the smoke or smoke condensate from the second tobacco product, and identifying the presence or absence of an induction of damage of cellular genetic material or modulation of cell homeostasis in the second population of cells after contact with the smoke or smoke condensate from the second tobacco product, where an identification of a reduction in the amount or the absence of an induction of damage of cellular genetic material or modulation of cell homeostasis in the second population of cells after contact with the smoke or smoke condensate from the second tobacco product, as compared to the amount or presence of an induction of damage of cellular genetic material or modulation of cell homeostasis identified in the first population of cells identifies the second tobacco product as one that has a reduced potential to contribute to a tobacco-related disease. Tobacco products identified as having a reduced potential to contribute to a tobacco-related disease in accordance with the methods provided herein can be, for example, tobacco products that are characterized by a reduced induction of double strand DNA breaks, a lower level of inhibition of apoptosis, or a lower level of inhibition of cell proliferation.

Also provided herein are methods of making a tobacco product that has a reduced potential to contribute to a tobacco-related disease by providing a first tobacco, obtaining smoke or a smoke condensate from the first tobacco, contacting a first population of cells with the smoke or smoke condensate from the first tobacco, identifying the presence or absence or amount of induction of damage of cellular genetic material or modulation of cell homeostasis in the first population of cells after contact with the smoke or smoke condensate from the first tobacco, providing a second tobacco that is genetically modified to reduce the expression of at least one gene that regulates production of a compound in the second tobacco, obtaining smoke or a smoke condensate from the second tobacco, contacting a second population of cells with the smoke or smoke condensate from the second tobacco, identifying the presence or absence or amount of induction of damage of cellular genetic material or modulation of cell homeostasis in the second population of cells after contact with the smoke or smoke condensate from the second tobacco, where an identification of a reduction in the presence or amount of induction of damage of cellular genetic material or modulation of cell homeostasis in the second population of cells after contact with the smoke or smoke condensate from the second tobacco, as compared to the presence or amount of induction of damage of cellular genetic material or modulation of cell homeostasis identified in the first cell population identifies the second tobacco as one that has a reduced potential to contribute to a tobacco-related disease, and incorporation of the second tobacco, which has a reduced potential to contribute to a tobacco-related disease, into a tobacco product. Tobacco products identified as having a reduced potential to contribute to a tobacco-related disease in accordance with the methods provided herein, which are incorporated into a tobacco product, can be, for example, tobacco products that are characterized by a lower induction of double strand DNA breaks, lower level of inhibition of apoptosis, lower level of inhibition of cell proliferation, or reduced level of modulation of cell homeostasis (e.g., a reduced amount of perturbation of gene expression; such as reduced amount of expression of genes involved in oncogenesis or a reduced inhibition of genes involved in oxidative repair as compared to a conventional tobacco product). The section that follows describes several methods for identifying a tobacco or tobacco products that modulate cell homeostasis.

Analysis of Changes to Cell Homeostasis: Modulation of Apoptosis

In some embodiments, modulation of cell homeostasis can be identified by determining a modulation of apoptosis. Thus, provided herein are methods of identifying a tobacco that modulates apoptosis by providing a tobacco, obtaining a tobacco composition from the tobacco, contacting a cell with the tobacco composition, and identifying a modulation of apoptosis in the cell after contact with the tobacco composition. Also provided herein are methods of identifying a compound in tobacco that modulates apoptosis, methods of identifying a tobacco product that has a reduced potential to contribute to a tobacco-related disease, and methods of making a tobacco product that has a reduced potential to contribute to a tobacco-related disease, in accordance with the methods of identifying a tobacco or tobacco compound that modulates cell homeostasis provided herein elsewhere. Also provided herein are methods of identifying a compound in tobacco that modulates apoptosis, methods of identifying a tobacco product that has a reduced potential to contribute to a tobacco-related disease, and methods of making a tobacco product that has a reduced potential to contribute to a tobacco-related disease, in conjunction with the methods of identifying a tobacco or tobacco compound that modulates cell proliferation provided herein.

Also provided herein are methods of comparing two or more tobacco products. In some embodiments, a tobacco or tobacco compound that induces a lower degree of apoptosis can be characterized as a tobacco that has a potential to contribute to a tobacco-related disease. In some embodiments, a first tobacco that induces a lower degree of apoptosis than a second tobacco can be characterized as a tobacco that has an increased potential to contribute to a tobacco-related disease. In some embodiments, a first tobacco that induces a higher degree of apoptosis than a second tobacco can be characterized as a tobacco that has a reduced potential to contribute to a tobacco-related disease. In some embodiments, a tobacco or tobacco compound that induces a higher degree of apoptosis can be characterized as a tobacco that has a potential to contribute to a tobacco-related disease. In some embodiments, a first tobacco that induces a higher degree of apoptosis than a second tobacco can be characterized as a tobacco that has an increased potential to contribute to a tobacco-related disease. In some embodiments, a first tobacco that induces a lesser degree of apoptosis than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

Also provided herein are methods of comparing two or more tobacco products. In some embodiments, a tobacco or tobacco compound that inhibits apoptosis can be characterized as a tobacco that has a potential to contribute to a tobacco-related disease. In some embodiments, upon inducing the same degree of DNA damage (DSBs) a first tobacco that induces lesser degree of apoptosis than a second tobacco can be characterized as a tobacco that has an increased potential to contribute to a tobacco-related disease. In some embodiments, upon inducing the same degree of DNA damage (DSBs) a first tobacco that induces lesser degree of apoptosis than a second tobacco can be characterized as a tobacco that has a reduced potential to contribute to a tobacco-related disease. In some embodiments, a tobacco or tobacco compound that increases apoptosis can be characterized as a tobacco that has a potential to contribute to a tobacco-related disease. In some embodiments, a first tobacco that increases apoptosis to a greater degree than a second tobacco can be characterized as a tobacco that has an increased potential to contribute to a tobacco-related disease. In some embodiments, a first tobacco that increases apoptosis to a lesser degree than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

As used herein, a tobacco or tobacco compound that induces a lower or higher degree of apoptosis refers to a tobacco or tobacco compound that causes a cell or cell population to decrease or increase, respectively, apoptosis in that cell or cell population relative to a cell or cell population that is not contacted by the tobacco or tobacco compound. Any of a variety of methods can be used to determine apoptosis in a cell or cell population, including those provided herein, and other methods known in the art.

While not intending to be limited by the following explanation, a decreased degree of apoptosis in cells may result in cells with damaged DNA that can survive and be tumorigenic rather than die and be eliminated. In other cellular functions, extensive apoptosis may induce compensatory stem cell proliferation and result in tumorigenesis. Accordingly, as contemplated herein an increase or decrease in apoptosis can lead to a tobacco-related disease.

Also provided herein are methods of comparing two or more tobacco products when the two or more tobacco products induce the same level of damage to cells. In some embodiments, a tobacco or tobacco compound that inhibits apoptosis can be characterized as a tobacco that has a potential to contribute to a tobacco-related disease. In some embodiments, upon inducing the same degree of DNA damage (DSBs) a first tobacco that induces lesser degree of apoptosis than a second tobacco can be characterized as a tobacco that has an increased potential to contribute to a tobacco-related disease. In some embodiments, upon inducing the same degree of DNA damage, a first tobacco that induces lesser degree of apoptosis than a second tobacco can be characterized as a tobacco that has a reduced potential to contribute to a tobacco-related disease. In some embodiments, upon inducing the same degree of DNA damage, a tobacco or tobacco compound that increases apoptosis can be characterized as a tobacco that has a potential to contribute to a tobacco-related disease. In some embodiments, upon inducing the same degree of DNA damage, a first tobacco that increases apoptosis to a greater degree than a second tobacco can be characterized as a tobacco that has an increased potential to contribute to a tobacco-related disease. In some embodiments, upon inducing the same degree of DNA damage, a first tobacco that increases apoptosis to a lesser degree than a second tobacco can be characterized as a tobacco that has a reduced potential to contribute to a tobacco-related disease. In some embodiments, the methods of identifying a tobacco that modulates apoptosis can be used to identify modified tobacco that modulates apoptosis as provided herein or otherwise known in the art.

The methods provided herein can include one or more steps of determining modulation of apoptosis. Typically, such methods include assays for modulation of apoptosis in a population of cells. Any of a variety of methods known in the art for assaying apoptosis can be used in the methods provided herein. Exemplary known assays include assays for activation of apoptosis-related proteins, assays for double-strand DNA breaks, and assays for membrane permeability.

In one exemplary method, modulation of apoptosis can be identified by determining caspase activation. Caspases are proteases involved in apoptosis. Activation of caspases can lead to apoptosis in the cell. Accordingly, measurement of activated caspases can be used to identify apoptosis in cells. Typically, caspases are activated by a cleavage reaction. Thus, activated caspase can be determined by detecting activated cleaved caspases. For example, caspase activation can be identified using an antibody or fragment thereof, which binds to activated caspase but not inactive caspase. There are a number of caspases that can be screened in accordance with the methods provided herein, including but not limited to, caspase 1, 3 and 9. In another example, activation of caspase by its catalytic activity can be determined. For example, caspase-3 has substrate selectivity for the amino acid sequence Asp-Glu-Val-Asp (DEVD) (SEQ. ID. NO. 1). A fluorogenic indicator such as Ac-DEVD-AMC can be used for fluorometric assay of caspase-3 activity. A variety of caspase activation assays are known in the art, as exemplified in Gown et al., J. Histochem. Cytochem. (2002) 50:449-54; Iordanov et al., Apoptosis (2005) 10:153-66; and Kahlenberg et al., J. Leukoc. Biol. (2004) 76:676-84, all of which are hereby expressly incorporated by reference in their entireties.

In another exemplary method, modulation of apoptosis can be identified by determining cleavage of the protein poly(ADP-ribose) polymerase (PARP). Enzymatic cleavage of the PARP occurs uniquely during apoptosis. Activation of caspases results in cleavage of PARP, which produces inactive PARP fragments. One inactive PARP fragment binds DNA and inhibits DNA repair. Thus, cleavage of PARP can be determined using an antibody specific to cleaved PARP fragments. Cleavage of PARP also can be determined by measuring decrease in PARP activity. PARP catalyzes the NAD-dependent addition of poly(ADP-ribose) to nuclear proteins such as histone. Thus, in one exemplary assay, incorporation of biotinylated poly(ADP-ribose) onto histone proteins can be measured as an indicator of PARP activity. Methods for determining PARP cleavage are known in the art, as exemplified in Mullen, Methods Mol. Med. (2004) 88:171-81; Yu et al., Science (2002) 297:259-63; and Saldani et al. Eur. J. Histochem. (2001) 45:389-92, all of which are hereby expressly incorporated by reference in their entireties.

In another exemplary method, modulation of apoptosis can be identified by determining annexin V binding. Annexin V binds to phosphotidylserine on the cell membrane, a phenomenon that occurs only in cells undergoing apoptosis. In one exemplary assay, fluorescently labeled annexin V can be added to cells, and presence of the fluorescent marker on the cells is indicative of annexin binding. In another example, antibodies specific for annexin V can be used to detect the presence of annexin V on the cell membrane. This technique is often combined with the use of fluorescent dyes that are normally not able to penetrate the cell membrane unless it is damaged these include dyes such as propidium iodide and acridine orange. Methods for determining annexin V binding are known in the art, as exemplified in U.S. Pat. No. 5,767,247, Vermes et al., J. Immunol. Methods (1995) 184:39-51; Wilkins et al., Cytometry (2002) 48:14-9; and Peng et al., Chin. Med. Sci. J. (2002) 17:17-21, all of which are hereby expressly incorporated by reference in their entireties.

In another exemplary method, modulation of apoptosis can be identified by determining chromatin condensation. Chromatin condensation is a well-established indicator of apoptosis. Chromatin condensation can be detected by a variety of methods, for example, detection by decreased forward angle light scatter or decreased right angle light scatter, and detection by presence of a specific dye such as Hoechst 33342. Methods for determining chromatin condensation are known in the art, as exemplified in Tounekti et al., Exp. Cell Res. (1995) 217:506-16 and Dobrucki et al., Micron (2001) 32:645-52, all of which are hereby expressly incorporated by reference in their entireties.

In another exemplary method, modulation of apoptosis can be identified by determining an increase sensitivity of chromatin in cells to acid or heat-induced denaturation. Sensitivity of chromatin in cells can be a marker of apoptosis. Chromatin sensitivity to acid or heat-induced denaturation can be detected by a variety of methods known in the art, such as detecting the altered binding of the metachromatic dye acridine orange. Methods for assaying chromatin sensitivity to denaturation are known in the art, as exemplified in Frankfurt et al., (1996) Exp. Cell Res. 226: 387-397, Frankfurt et al., (2001) J. Histochem. Cytochem. 49:369-378, Frankfurt et al., (2001) J. Immunol. Methods. 253: 133-144, Groos et al., (2003) Anat. Rec. 272A:503-513, Zamzani et al., (1999) Nature 401:127-128, and Allera et al., (1997) J. Biol. Chem. 272:10817-10822, all of which are hereby expressly incorporated by reference in their entireties.

In another exemplary method, modulation of apoptosis can be identified by determining fractional DNA content. Under appropriate conditions, small molecular weight DNA fragments occurring as the result of the apoptotic process can be removed from cells, resulting in cells with decreased DNA content. Assays can be used to detect cells with decreased (fractional) DNA content by using, for example, DNA dyes in flow cytometry according to known methods. Methods for assaying fractional DNA content are known in the art, as exemplified in Mazur et al., Hum. Exp. Toxicol. (2002) 21:335-41 and Gorczyca, Endocrine-Related Cancer (1999) 6:17-19, all of which are hereby expressly incorporated by reference in their entireties.

In another exemplary method, modulation of apoptosis can be identified by determining TUNEL assay, as discussed herein elsewhere. TUNEL assay can detect DNA strand breaks occurring following activation of an apoptosis-specific nuclease. Incorporation of labeled nucleotides at the site of the double-strand breaks can be detected by, for example, binding of antibodies or other molecules (biotin-avidin) carrying a fluorescent tag.

An exemplary assay for cell apoptosis determination is provided in Example 1 for caspase-3 activation measurement. Briefly, cells were treated with smoke (i.e., A549) or smoke condensate (i.e., NHBE) and fixed as described above, then rinsed twice in PBS and immersed in 0.2% Triton X-100 (Sigma) in a solution of 1% (w/v) bovine serum albumin (BSA; Sigma) in PBS for 30 min to suppress non specific antibody binding. The cells were then incubated in 100 µl volume of 1% BSA containing 1:100 dilution of anti-cleaved (activated) caspase-3 rabbit polyclonal Ab (Cell Signaling Technology, Beverly, Mass.) overnight at 4° C., washed twice with PBS and incubated with 1:30 diluted FITC-conjugated F(ab')2 fragment of swine anti-rabbit immunoglobulin (DAKO, Carpinteria, Calif.) for 30 min in room temperature in the dark. The cells were then counterstained with 1 µg/ml 4,6-diamidino-2-phenylindole (DAPI, Molecular Probes, Eugene, Oreg.) in PBS for 5 min. Each experiment was performed with an IgG control in which cells were labeled only with secondary antibody, FITC-conjugated F(ab')2 fragment of goat anti-mouse immunoglobulins, without primary antibody incubation to estimate the extent of nonspecific binding of the secondary antibody to the cells. The following section describes several assays that can be used to evaluate the ability of a tobacco or a tobacco product to modulate cell proliferation.

Analysis of Changes to Cell Homeostasis: Modulation of Cell Proliferation

In some embodiments, modulation of cell homeostasis can be identified by determining modulation of cell proliferation. Thus, provided herein are methods of identifying a tobacco that modulates cell proliferation by providing a tobacco, obtaining a tobacco composition from the tobacco, contacting a cell with the tobacco composition, and identifying a modulation of cell proliferation in the cell after contact with the tobacco composition. Also provided herein are methods of identifying a compound in tobacco that modulates cell proliferation, methods of identifying a tobacco product that has a reduced potential to contribute to a tobacco-related disease, and methods of making a tobacco product that has a reduced potential to contribute to a tobacco-related disease, in accordance with the methods of identifying a tobacco or tobacco compound that modulates cell homeostasis provided herein elsewhere. Also provided herein are methods of identifying a compound in tobacco that modulates cell proliferation, methods of identifying a tobacco product that has a reduced potential to contribute to a tobacco-related disease, and methods of making a tobacco product that has a reduced potential to contribute to a tobacco-related disease, in conjunction with the methods of identifying a tobacco or tobacco compound that modulates cell proliferation provided herein.

Also provided herein are methods of comparing two or more tobacco products. In some embodiments, a tobacco or tobacco compound that inhibits cell proliferation can be characterized as a tobacco that has a potential to contribute to a tobacco-related disease. In some embodiments, a first tobacco that inhibits cell proliferation to a greater degree than a second tobacco can be characterized as a tobacco that has an increased potential to contribute to a tobacco-related disease. In some embodiments, a first tobacco that inhibits cell proliferation to a lesser degree than a second tobacco can be characterized as a tobacco that has a reduced potential to contribute to a tobacco-related disease. In some embodiments, a tobacco or tobacco compound that increases cell proliferation can be characterized as a tobacco that has a potential to contribute to a tobacco-related disease. In some embodiments, a first tobacco that increases cell proliferation to a greater degree than a second tobacco can be characterized as a tobacco that has an increased potential to contribute to a tobacco-related disease. In some embodiments, a first tobacco that increases cell proliferation to a lesser degree than a second tobacco can be characterized as a tobacco that has a reduced potential to contribute to a tobacco-related disease. In some embodiments, the methods of identifying a tobacco that modulates cell proliferation can be used to identify modified tobacco that modulates cell proliferation as provided herein or otherwise known in the art.

As used herein, a tobacco or tobacco compound that inhibits or increases cell proliferation refers to a tobacco or tobacco compound that causes a cell or cell population to proliferate at a decreased or increased rate, respectively, relative to a cell or cell population that is not contacted by the tobacco or tobacco compound. Any of a variety of methods can be used to determine cell proliferation in a cell or cell population, including those provided herein, and other methods known in the art.

Any of a variety of assays can be used that monitor alterations to the viability and growth potential of cells in vitro when challenged by exposure to a vast array of insults (e.g., ionizing radiation, ultraviolet radiation, drugs, toxins, carcinogens, CS, CSC, TPM, viruses, chemicals, free radicals, pollution, and the like). Assays that can be used in the methods provided herein can include assays that monitor proliferative rates (cell proliferation assays) and assays that monitor survivability and proliferation with time (e.g., clonogenic survival assay).

In one example, clonogenic survival can be monitored. The clonogenic survival assay can be used to study the ability of specific agents to impact the proliferation of cells. This assay is frequently employed in cancer research laboratories to determine the effect, if any, of a range of substances (e.g., drugs, radiation, chemicals, organic mixtures, etc), on the proliferation of tumor cells. The term "clonogenic" refers to the fact that these cells are clones of one another. Any of a variety of cell types can be used in such experiments. The cells used typically come from established cell lines, which have been well-studied and whose general characteristics are known. Typically, a clonogenic survival assay has four major steps: (1) inoculating cells into culture dishes and incubate the cells (e.g., 24-48 hours); (2) upon the cells reaching the logarithmic phase of growth, the treating the cells with a tobacco composition (e.g., contacting the cells with freshly prepared and diluted CS for different periods of time); (3) allowing the cells to recover for a set number of hours (e.g., up to 24 hours), then treating the cells and allowing the cells to grow further (e.g., trypsinizing the cells, replating the cells at specific dilutions, and allowing the cells to grow for 5-7 days); and (4) fixing, staining and counting the cells. Experimental specifics such as time of incubation and growth, number of cells to use for plating, and the like, can be readily determined by one skilled in the art according to the type of cell used. Typically, the number of surviving colonies of 25-50 cells is representative of the percentage of cells that survived the treatment. A graphical representation of survival versus exposure time to a tobacco composition can then be generated. The surviving fraction can be determined by dividing the number of colonies in the dish by the number of the colonies in the control (non-treated) dish.

In addition to clonogenic assays, any of a variety of cell proliferation assays can be used to monitor an increase or decrease in proliferative capacity and which can be used in context with exposure to a tobacco composition such as CS, CSC and/or TPMs.

In one example of cell proliferation assays, intake and conversion of a dye can be an indicator of cell proliferation. One example of such an assay is a resazurin-based assay. Resazurin is a redox dye which is not fluorescent, but upon reduction by metabolically active cells, is converted into a highly fluorescent product (resorufin). Living cells can readily reduce this non-toxic reagent and the resulting increase in fluorescence intensity is monitored using a fluorescence spectrophotometer or plate reader. Exemplary commercially available assays include alamarBlue™ reagent from BioSource International, Camarillo Calif.

Another example of dye intake and conversion-based cell proliferation assays is a tetrazolium salt-based assay. The tetrazolium salt assay is a colorimetric assay is based on the conversion of a tetrazolium salt (MTT, WST, or other) to formazan, a purple dye. This cellular reduction reaction involves the pyridine nucleotide cofactors NADH/NADPH and is only catalyzed by living cells. The formazan product has a low aqueous solubility and is present as purple crystals. Dissolving the resulting formazan with a solubilization buffer permits the convenient quantification of product formation. The intensity of the product color is directly proportional to the number of living cells in the culture. Exemplary commercially available assays include Quick Cell Proliferation Assay Kit from BioVision Inc., Mountain View, Calif.

In another example of cell proliferation assays, cells can be monitored for plasma membrane damage. Plasma membrane damage-based assays can be used to monitor cell death or cytotoxicity. Typical assays quantitate molecules released from damaged cells such as adenylate kinase and lactate dehydrogenase. Exemplary commercially available assays include LDH-Cytotoxicity Assay Kit from BioVision Inc., Mountain View, Calif.

In another example of cell proliferation assays, cells can be monitored for dye exclusion/dye uptake assays. Dye exclusion/uptake assays distinguish live from dead cells based on dyes which specifically stain either live or dead cells. Exemplary commercially available assays include trypan blue dye exclusion, Live-Dye™ (a cell-permeable green fluorescent dye that stains live cells) from BioVision Inc., Mountain View, Calif.

In another example of cell proliferation assays, cells can be monitored for ATP and ADP levels. ATP and ADP level-based assays utilize the phenomenon that increased levels of ATP and decreased levels of ADP have been recognized in proliferating cells. Exemplary commercially available assays include ApoSENSOR™ Cell Viability Assay Kit from MBL International, Woburn Mass.

In another example of cell proliferation assays, cells can be monitored for protein or DNA levels in the cells. Cell proliferation is associated with increased protein and DNA synthesis. DNA quantitation-based assays can use, for example, [3H]-thymidine incorporation, the fluorescence of a DNA-dye complex from lysed cells, or other known markers of DNA synthesis. Similarly, protein synthesis can be monitored for incorporation of labeled amino acids into the proteins. Exemplary commercially available assays include Quantos™ Cell Proliferation Assay Kit from Stratagene, La Jolla, Calif.

Example 3 below provides one non-limiting specific example of the clonogenic survival assay methods provided herein. Variations of the assay method used in terms of materials, assay times, instrumentation and protocols would be apparent to the skilled artisan.

Example 3

A clonogenic survival assay was used to study the ability of tobaccos and tobacco products to impact the proliferation of cells. The experiment involves four major steps: (1) inoculate cells into culture dishes and incubate for 24-48 hours; (2) upon reaching the logarithmic phase of growth, the treatment is applied; the treatment in this case is freshly prepared and diluted CS for increasing periods of time; (3) the cells are then allowed to recover for a set number of hours (up to 24), then the cells are trypsinized, replated at specific dilutions, and allowed to continue growing for 5-7 days; the number of cells used depends largely on the plating efficiency of the cell line and must be determined empirically prior to the experiment; and (4) at the conclusion of the experiment, the cells are fixed, stained, and counted. The primary measure is to count surviving colonies of 25-50 cells which is presented as the percentage of cells which survived the treatment. A graphical representation of survival versus exposure time to CS is then generated. The surviving fraction is determined by dividing the number of colonies in the dish by the number of the colonies in the control (non-treated) dish.

A549 cells were exposed to smoke as described above. Following smoke exposure the medium is aspirated and the cells rinsed refed with 37° C. BEGM and placed in a 37° C., 5% CO2 humidified incubator for two to three hours. The cells are harvested by trypsinization with trypsin-EDTA (0.25% trypsin-0.38 mg/ml EDTA, Invitrogen). Cells are centrifuged at 260×g for 8 min. Cell pellets are resuspended in 1 ml of Ham's F-12K medium, 10% FBS (complete medium) per pellet and counted. Cells are serially diluted so that the mock treated have ~65 cells per well and smoke treated have ~300 cells per well when seeded onto 96-well flat bottom tissue culture plates; one plate per condition. The plates are incubated for five days in a 37° C., 5% CO2 humidified incubator. The colonies of cells are fixed with 5% formaldehyde/PBS and colored with 0.8% crystal violet solution for visualization. The colonies are counted with the aid of a macroscopic dissecting microscope. The cloning efficiency results are expressed in relation to the mock exposed cells. Unless otherwise indicated, each bar in the graphs represents three replicate data points per experiment.

Figure 25:
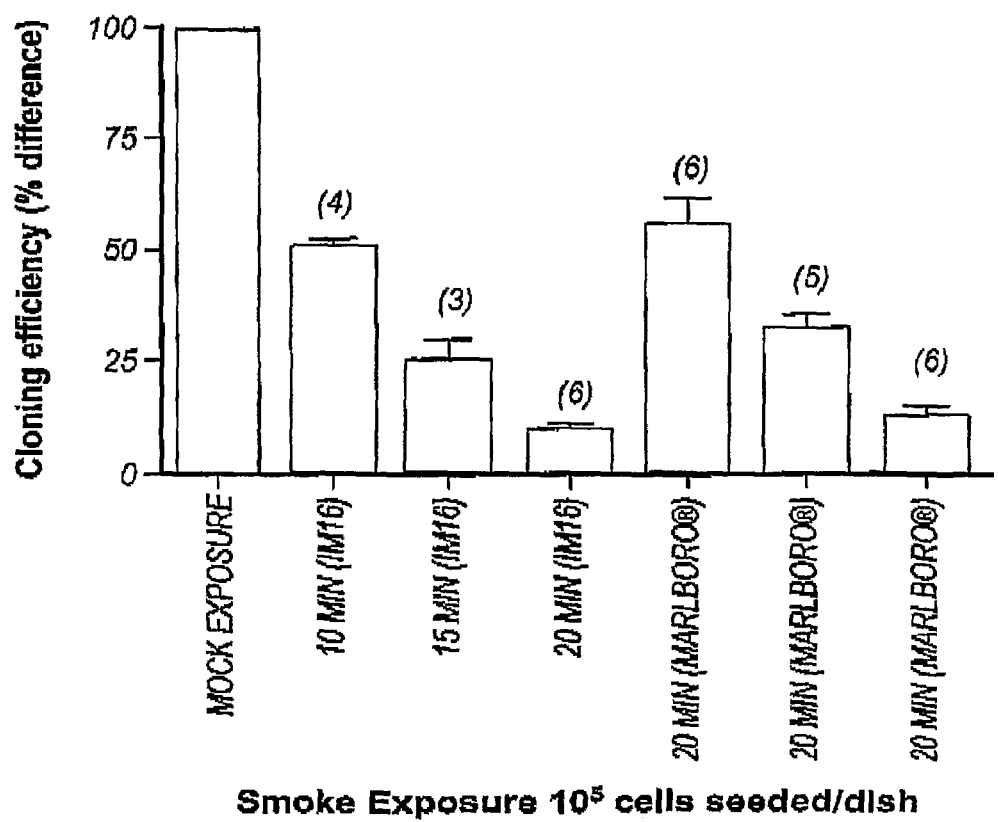
FIG. 25. Bar plot showing the relative percent cloning efficiency of A549 cells 5 days after exposure to smoke from IM16 or Marlboro® for 10, 15 or 20 minutes.

A549 cells were exposed to whole smoke from IM16 or Marlboro® cigarettes for various lengths of time after which clonogenic assays were performed. FIG. 25 is a summary of multiple experiments. The numbers in parentheses indicate the number of experiments represented by each bar. The industry monitor reference cigarette IM16 shows an effect on viability essentially identical to that of the Marlboro® cigarettes. In both cases there was a linear decrease in cell viability with increasing smoke exposure.

Figure 26:
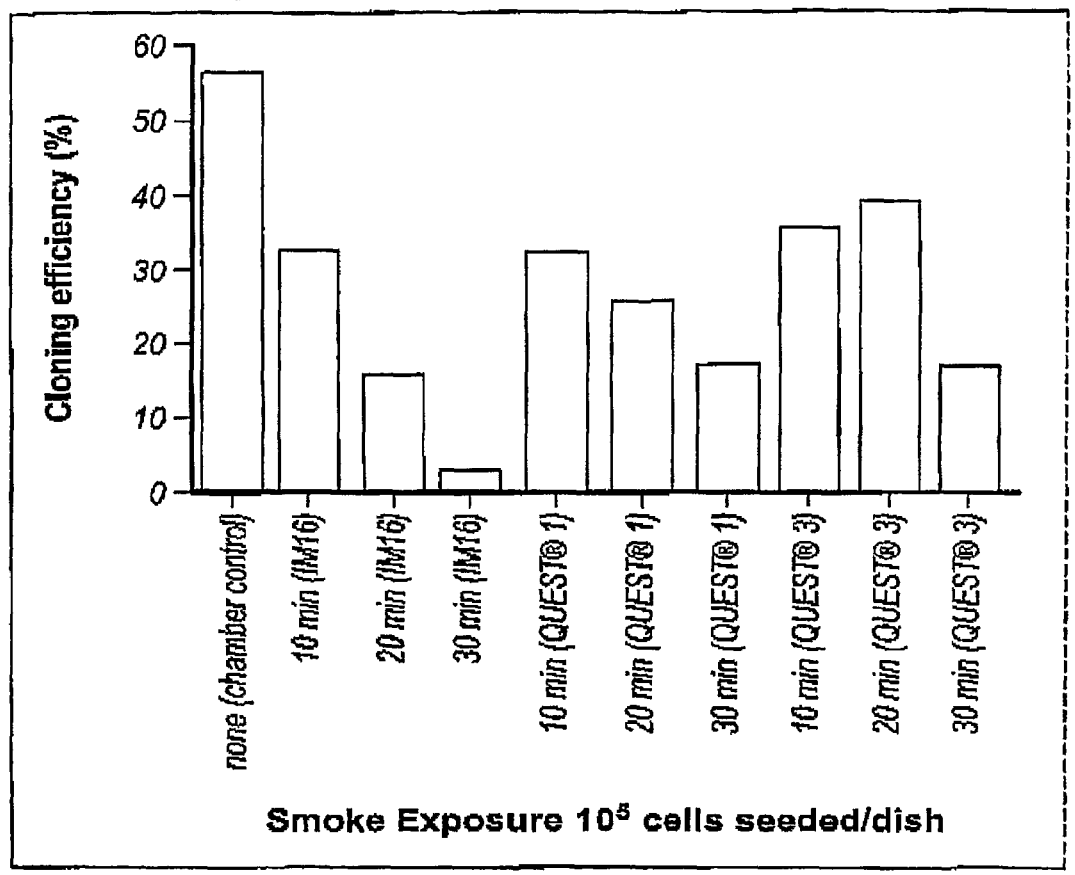
FIG. 26. Bar plots showing the relative percent cloning efficiency of A549 cells 5 days after exposure to smoke from IM16, Quest 1® or Quest 3® for 10, 20 or 30 minutes (top two plots), or 6 days after (bottom plot) exposure to smoke from IM16, Marlboro® or Omni®, for 10, 15 or 20 minutes.
Figure 26:
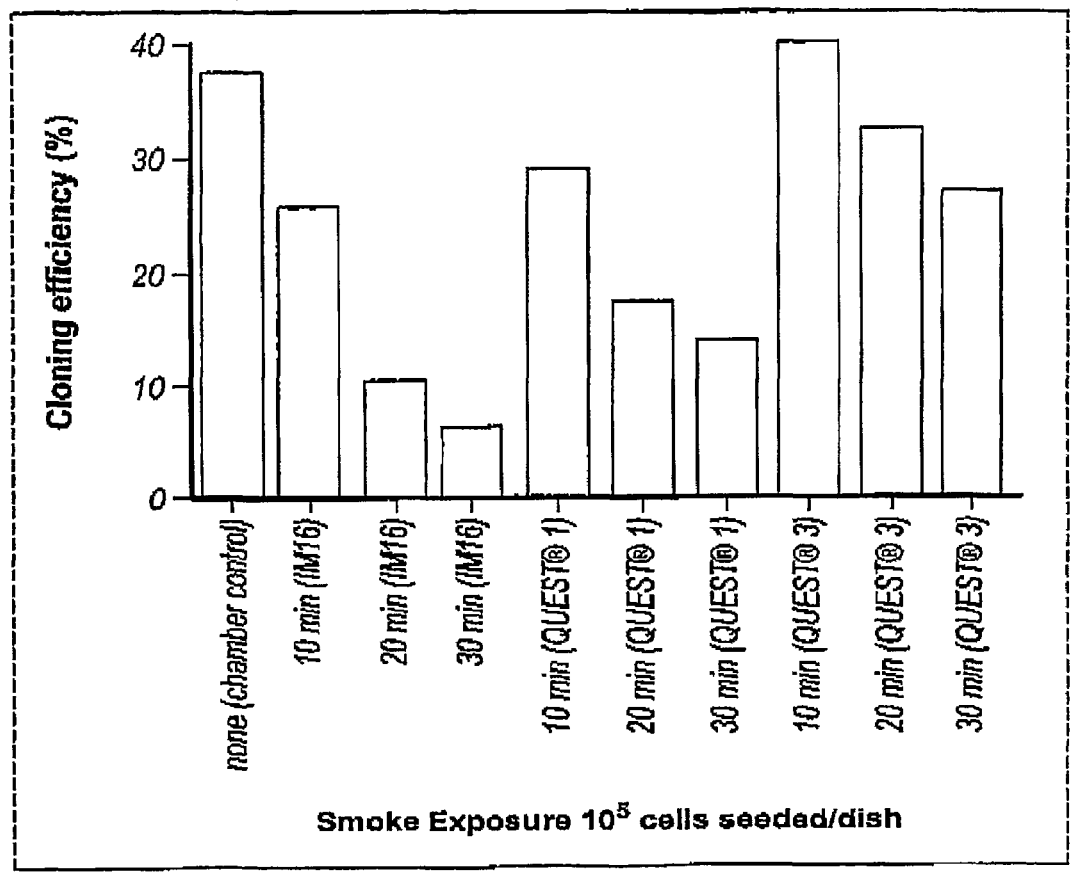
Figure 26:
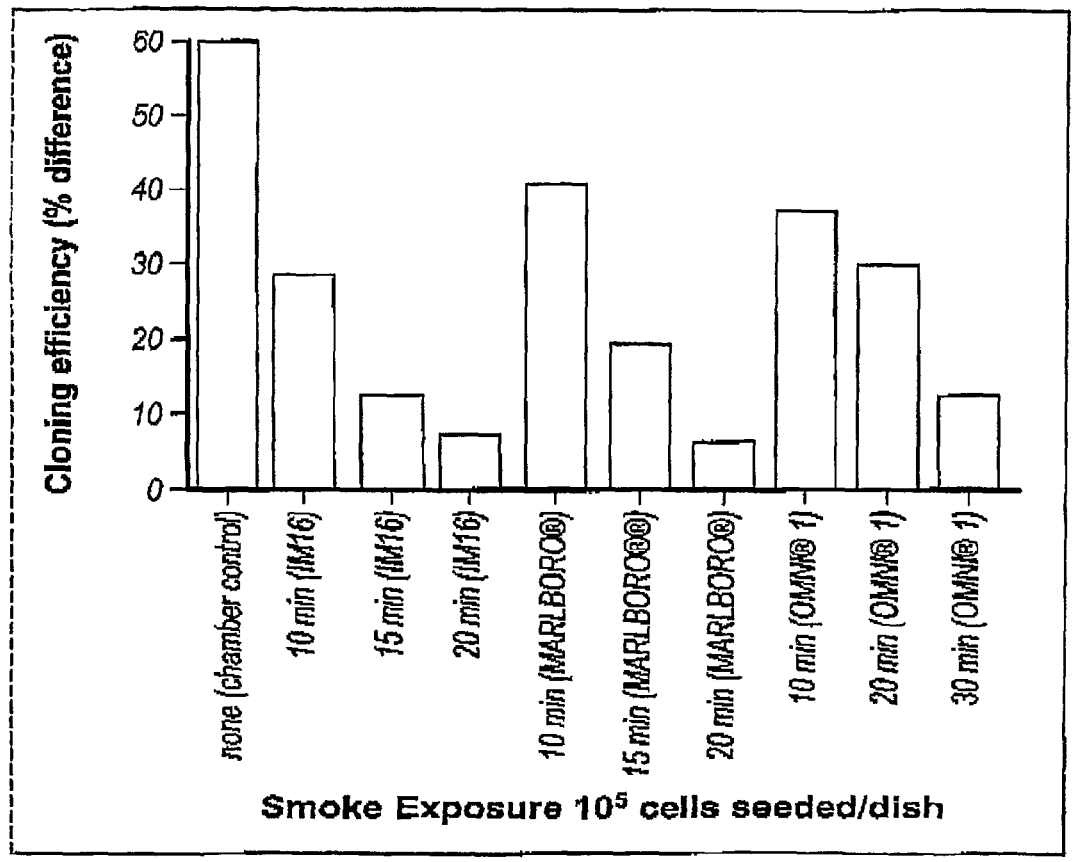

In one set of experiments, A549 cells were exposed to smoke from various cigarettes for 20 min and clonogenic assays were performed. IM16, Omni®, Marlboro®, Quest 1 ®, or Quest 3® brand cigarettes were compared. Each graph of FIG. 26 represents a separate experiment. The assay distinguishes between the cigarettes, with Quest 3® treatment having the least impact on cell viability and IM16 having the greatest. An overall ranking of the cigarettes in terms of impact on viability can be seen: Quest 3®<Quest 1® and Omni®<Marlboro®<IM16. Thus, the tobacco products containing modified tobacco (i.e., Omni®, Quest 1®, and Quest 3® had the an impact on cell viability that was significantly less than a reference tobacco product (i.e., IM16) and a conventional, commercially available, traditional tobacco product (i.e., Marlboro®). Accordingly, the modified tobacco products Omni®, Quest 1®, and Quest 3® have a reduced potential to contribute to a tobacco related disease (i.e., Omni®, Quest 1®, and Quest 3® are reduced risk tobacco products) according to the clonogenic assay.

Figure 27:
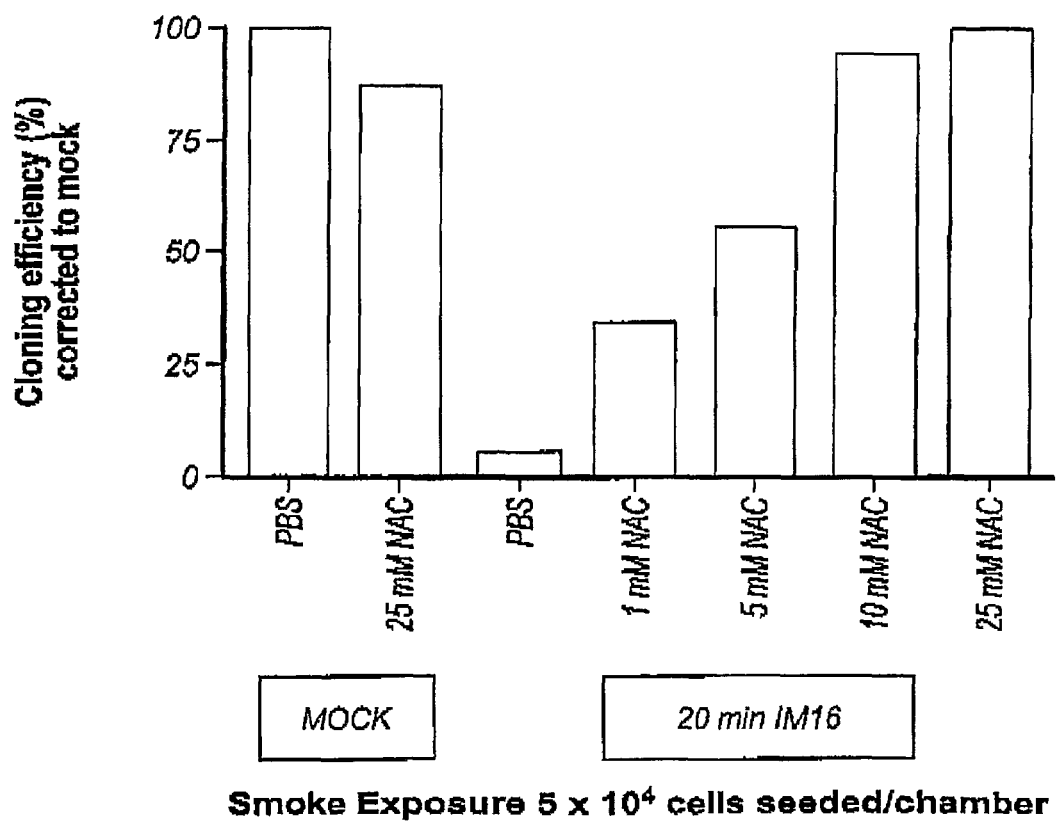
FIG. 27. Bar plot showing the relative percent cloning efficiency of A549 cells 5 days after exposure to smoke from IM16 for 20 minutes in the presence of PBS or 1 mM, 5 mM, 10 mM or 25 mM NAC.

In a next set of experiments, the mitigation of the effect of whole smoke on cell viability by the presence of NAC was evaluated. A549 cells were exposed to 20 min IM16 smoke in the presence of various concentrations of the free radical scavenger N-acetylcysteine (NAC) and the clonogenic assay performed. NAC protected the viability of the cells in a dose-dependent manner. FIG. 27 shows the increasing degree of proliferation resulting from increasing concentrations of NAC.

Figure 28:
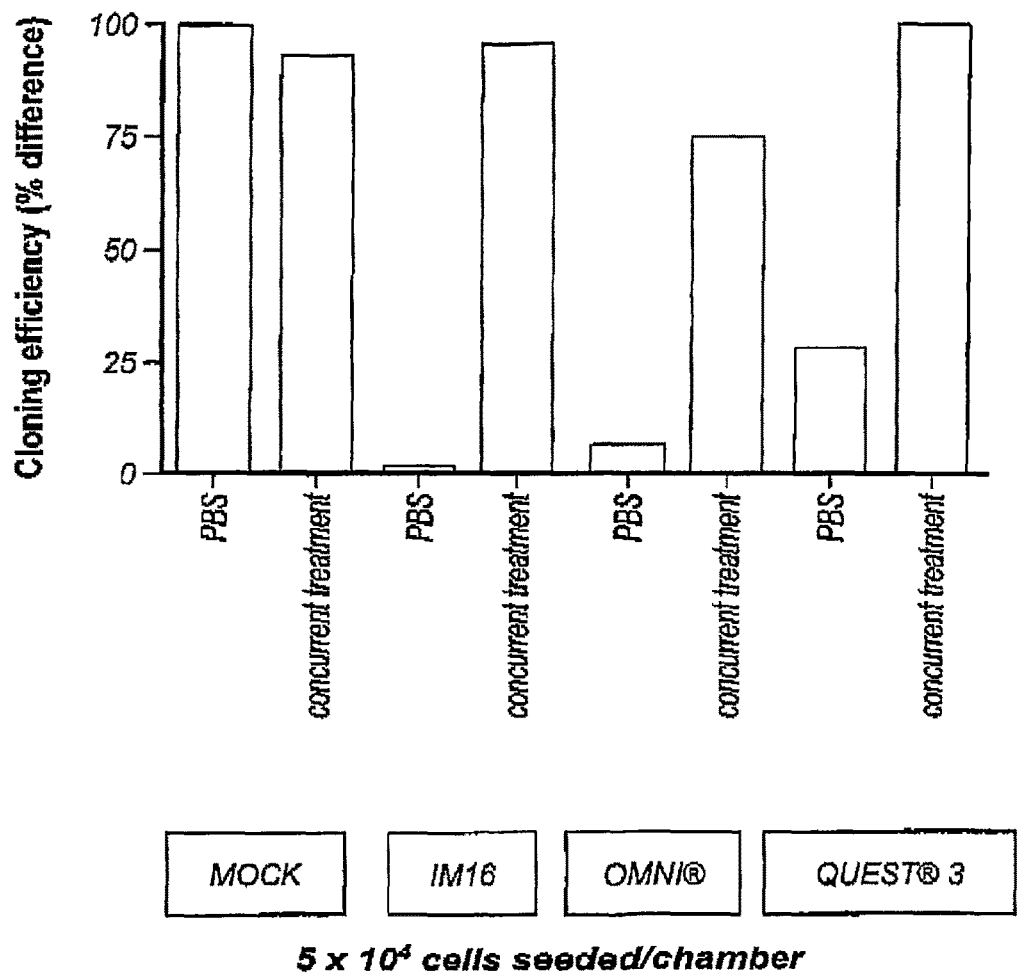
FIG. 28. Bar plot showing the relative percent cloning efficiency of A549 cells 5 days after exposure to smoke from IM16, Omni® or Quest 3® for 20 minutes in the presence of PBS or 25 mM NAC.

In another series of experiments, the effect of NAC on the viability of cells contacted with whole smoke from different cigarettes was evaluated. A549 cells were exposed to smoke from various cigarettes for 20 min in the presence or absence of 25 mM NAC and the clonogenic assay performed. IM16, Omni®, and Quest 3® cigarettes were compared. NAC completely protected the cells exposed to Quest 3® smoke, and partially protected cells exposed to Omni® or IM16 (FIG. 28). Again, these data show that tobacco products containing modified tobacco (i.e., Omni® and Quest 3®) had the an impact on cell viability that was significantly less than a reference tobacco product (i.e., IM16). Accordingly, the modified tobacco products Omni® and Quest 3® have a reduced potential to contribute to a tobacco related disease (i.e., Omni® and Quest 3® are reduced risk tobacco products).

In yet another series of experiments, the effect of NAC on cell death caused by the VAPOR phase of smoke from different cigarettes was evaluated. A549 cells were exposed to the vapor phase of smoke for 20 min by inserting a Cambridge filter pad immediately after the cigarette in the smoking apparatus so as to filter out the particulate matter ("tar") and leave only the vapor phase. Three different cigarettes were used: IM16, Quest 1® and Quest 3®. Cells were exposed in the presence or absence of 25 mM NAC. The clonogenic assay was subsequently performed.

Figure 29:
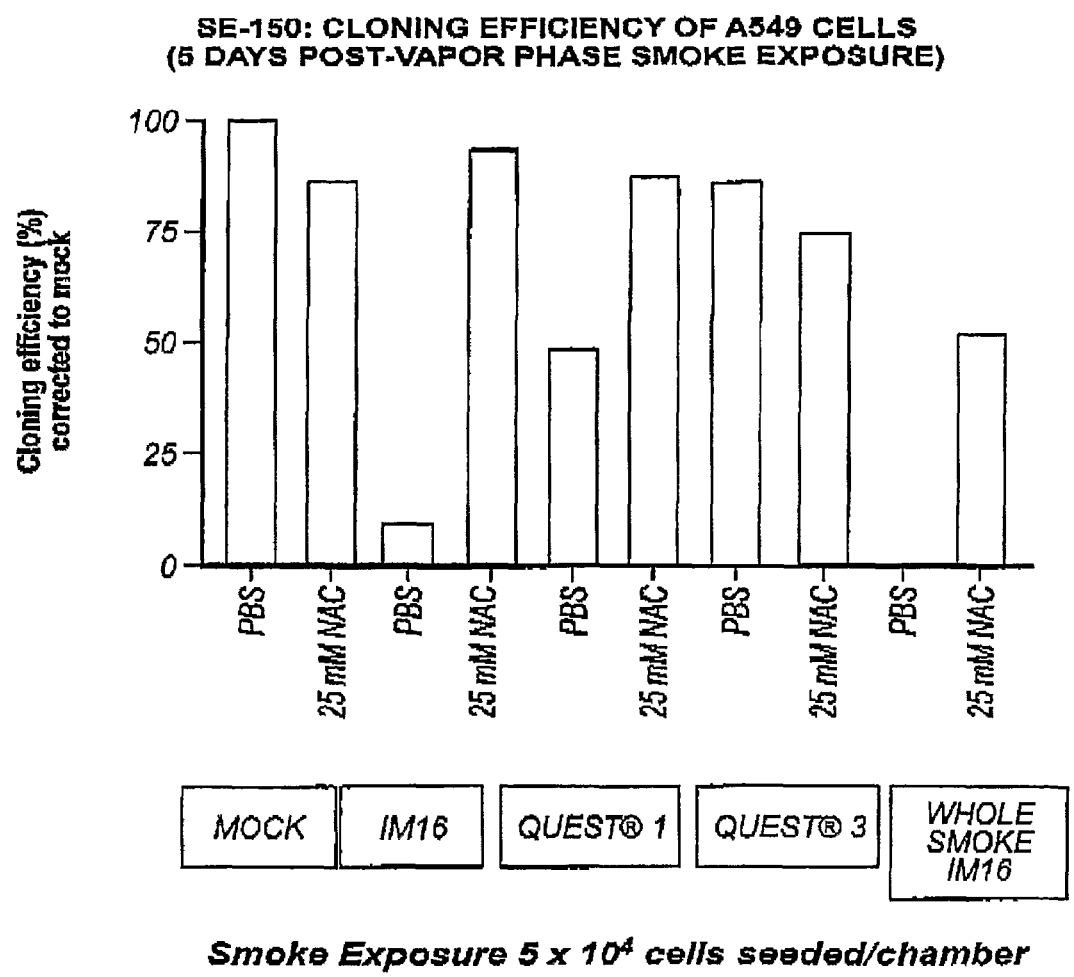
FIG. 29. Bar plot showing the relative percent cloning efficiency of A549 cells 5 days after exposure to vapor phase of smoke from IM16, Quest 1® or Quest 3®, or smoke of IM16 for 20 minutes in the presence of PBS or 25 mM NAC.

The vapor phase of all cigarettes showed less effect on cell viability than the corresponding whole smoke exposure, with Quest 3® exhibiting almost no effect (FIG. 29). The effect of various cigarette modifications on vapor phase toxicity can thus be selectively monitored. In all vapor phase exposures, the presence of the free radical scavenger NAC protected the cells against viability loss. These experiments provide more evidence that the tobacco products containing modified tobacco (i.e., Quest 1®, and Quest 3® had an impact on cell viability that was significantly less than a reference tobacco product (i.e., IM16) and, thus, Quest 1®, and Quest 3® have a reduced potential to contribute to a tobacco related disease (i.e., Quest 1® and Quest 3® are reduced risk tobacco products).

Filter Comparison

Clongenic assays also were applied to tests of several filters attached to different tobaccos. Filters and tobacco were obtained from: (1) the industry standard reference tobacco IM16 (Philip Morris® USA); (2) reduced risk cigarette Omni® (Vector Tobacco Ltd.); (3) reduced risk cigarette Quest 1® (Vector Tobacco Ltd.), and (4) reduced risk cigarette Quest 3® (Vector Tobacco Ltd.). A549 cells were exposed to mock treatment (control) and cigarette smoke substantially as provided in the above smoke treatment description.

Figure 45:
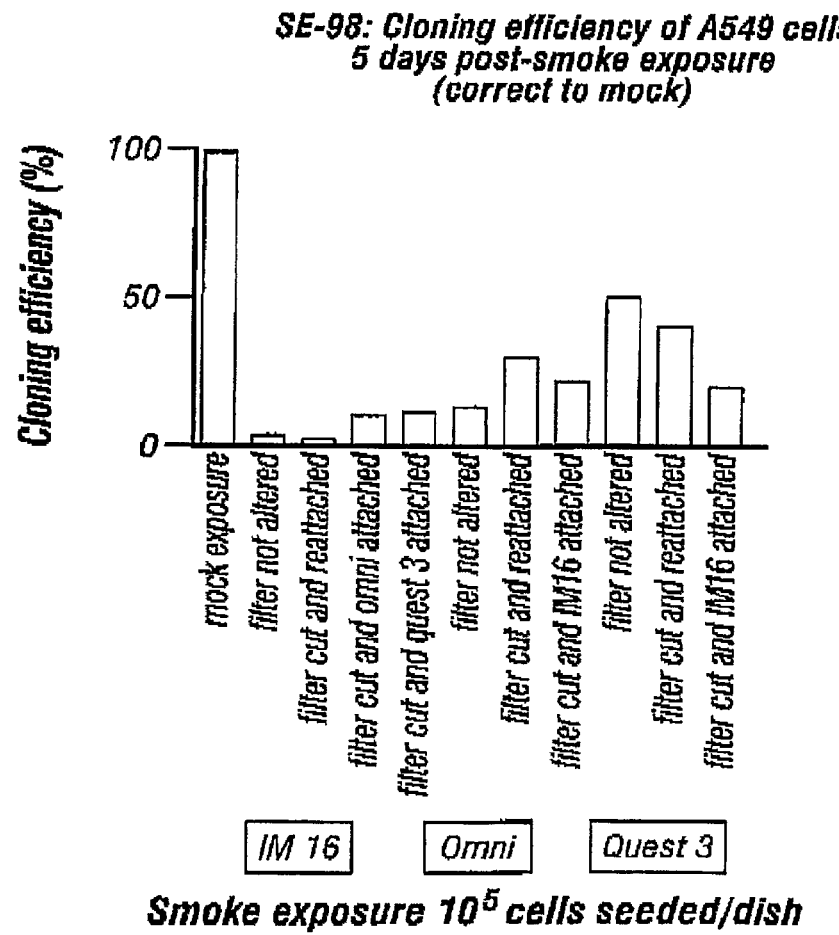
FIG. 45 shows bar plots showing the relative percent cloning efficiency of A549 cells 5 days after exposure to smoke of different combinations of tobaccos and filters from IM16, Omni® or Quest 3® cigarettes, relative to mock cloning efficiency.
Figure 46:
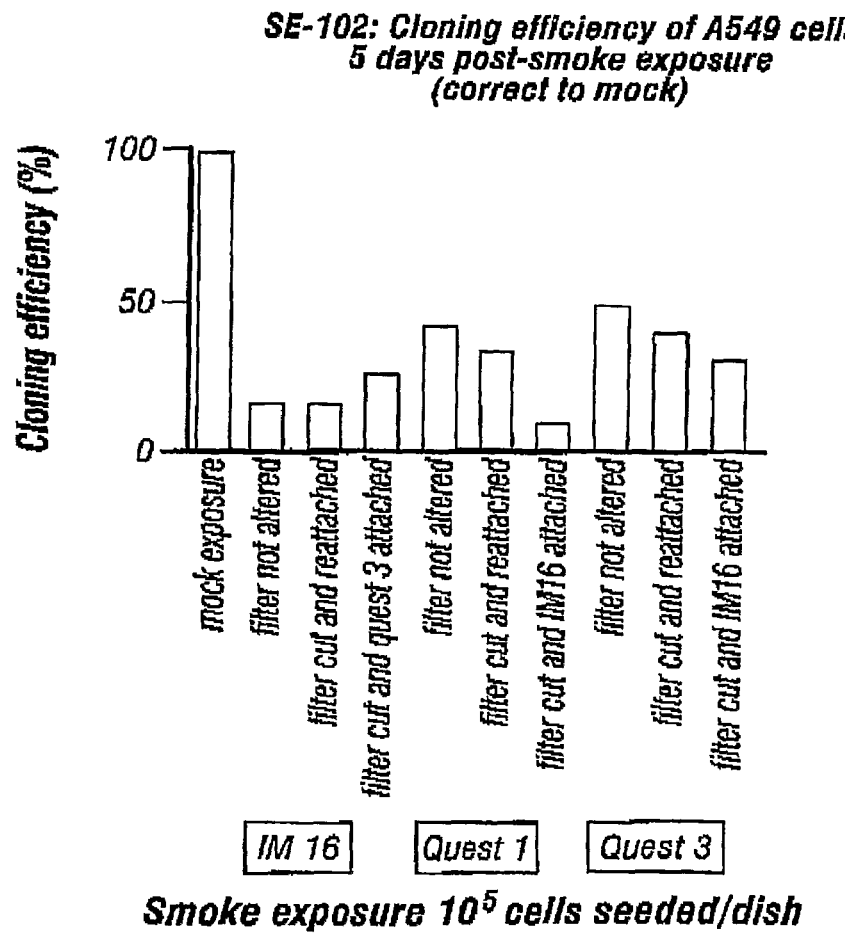
FIG. 46 shows bar plots showing the relative percent cloning efficiency of A549 cells 5 days after exposure to smoke of different combinations of tobaccos and filters from IM16, Quest 1® or Quest 3®, relative to mock cloning efficiency.
Figure 47:
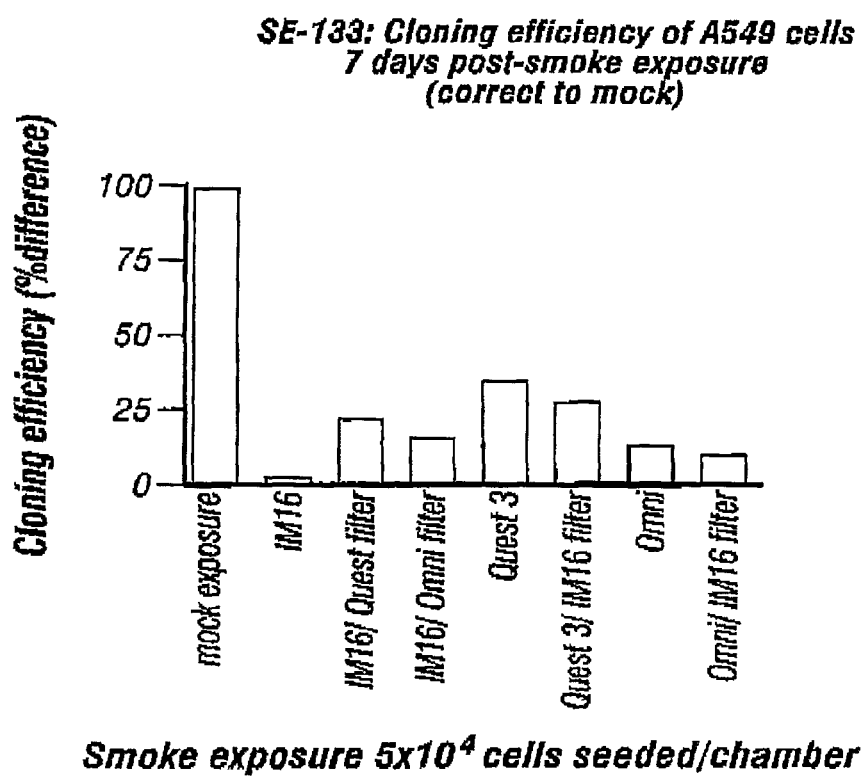
FIG. 47 shows bar plots showing the relative percent cloning efficiency of A549 cells 5 days after exposure to smoke of different combinations of tobaccos and filters from IM16, Omni® or Quest 3® cigarettes, relative to mock cloning efficiency.

Numerous combinations of tobacco and filters from IM16, Omni®, Quest 1® and Quest 3® were tested, and the cloning efficiency relative to mock is presented in FIGS. 45-47. FIG. 45 shows clonogenic results for each of IM16, Omni®, and Quest 3® with the cigarette in tact, and the filter cut and then reattached to the same tobacco rod. FIG. 45 further shows clonogenic results for Omni® and Quest 3® filters attached to IM16 tobacco rods, and IM16 filters attached to Omni® and Quest 3® tobacco rods. The results show that while there was some variation in cloning efficiency when filters were cut and reattached to the same tobacco rod, Omni® and Quest 3® filters attached to IM16 tobacco rods provided increased cloning efficiency, while the IM16 filter attached to the Quest 3® tobacco rod provided decreased cloning efficiency. These results show that different filters attached to the same tobacco rod have different influences on cloning efficiency, where the cloning efficiencies are inversely related to the expected levels of risk attributed to the tobacco product (IM16 is highest expected risk and has the lowest cloning efficiencies, while Quest 3® is lowest expected risk and has the highest cloning efficiencies). Similar experiments were repeated: (1) where IM16, Quest 1® and Quest 3® tobaccos and filters were exchanged and compared (FIG. 46) and (2) where cloning efficiency was tested at 7 days (FIG. 47). The results in FIGS. 46 and 47 are comparable to those of FIG. 45 and again reflect inverse relationship between the expected levels of risk attributed to the tobacco product and cloning efficiency. The following section describes several epidemiological approaches to determine the potential of a tobacco or a tobacco product to contribute to a tobacco related disease.

Analysis of Changes in Cell Homeostasis: Modulation of the Transcriptome or Proteome Provided herein are methods for identifying a tobacco that modulates cell homeostasis by providing a tobacco, obtaining a tobacco composition from the tobacco, contacting a cell with the tobacco composition, and identifying any modulation of the cell transcriptome or proteome after contact with the tobacco composition. In some embodiments, the methods provided herein can monitor induction of expression of a gene that is silent during homeostasis or repression a gene that is active during homeostasis. In some embodiments, the tobacco composition can be smoke or smoke condensate.

The methods provided herein can be used to characterize a first and a second tobacco product by providing the first and second tobacco products, obtaining a first and second tobacco composition from the first and second tobacco products, respectively, contacting a first cell with the first tobacco composition and contacting the second cell with the second tobacco composition, and identifying one or more attributes of the transcriptome or proteome of the contacted cells. Different tobacco products can contain different levels of carcinogens that can induce various types of changes to mRNA or protein levels, or modifications of mRNA or protein molecules. Comparison of attributes of cells contacted with different tobacco compositions can be performed in the methods provided herein, and such attributes include, but are not limited to, differential levels of mRNA, differential levels of protein and changes to the post-tranlsational protein modifications. Accordingly, the methods provided herein can be used to compare two or more tobacco products by assay methods including assay for differential levels of mRNA, differential levels of protein, and changes to post-tranlsational protein modification. Exemplary assay methods include microarray assays, qRT-PCR assays, Western blota assays, and ELISA assays.

By one approach, for example, CS is generated using a smoking machine from a first tobacco modified product, e.g., a product containing tobacco that has been genetically modified to have a reduced amount of a compound. A first population of NHBE cells is contacted with said CS obtained from the modified tobacco product, and the cells contacted with CS are assayed for mRNA or protein levels. A second population of NHBE cells is then contacted with CS generated from an unmodified or reference tobacco product. The second population of cells contacted with CS is then assayed for mRNA or protein levels. A comparison of the data obtained from the analysis of the first and second tobacco products will reveal that the difference in mRNA or protein levels caused by the modified tobacco product relative to the unmodified tobacco product. By this approach, one can effectively identify the contribution of individual components of a tobacco product to mRNA or protein levels, or other assay conditions provided herein or otherwise known in the art. These methods can thereby be used to identify the contribution of individual components of a tobacco product to a tobacco-related disease. This approach can be used to develop tobacco products that are less likely to contribute to a tobacco-related disease and reduced risk tobacco products identified by these methods are embodiments provided herein. Further, tobacco products prepared by these approaches can be prepared according to good manufacturing processes (GMP) (e.g., suitable for or accepted by a governmental regulatory body, such as the Federal Drug Administration (FDA), and containers that house said tobacco products can comprise a label or other indicia, with or without structure-function indicia, which reflects approval of said tobacco product from said regulatory body.

In a first series of experiments, the influence of cigarette smoke condensates (CSC) from two different tobacco products (cigarettes) on the gene expression of NHBE cells was examined. In a second set of experiments, the influence of cigarette smoke (CS) generated from one tobacco product (a cigarette) on the gene expression of NHBE cells was examined. Although NHBE cells are preferred for the methods described herein, other cells of the mouth, oral cavity, trachea, and lungs, either normal or immortalized cell lines (e.g., human bronchial cells (e.g., BEP2D or 16HBE140 cells), human bronchial epithelial cells (e.g., HBEC cells, 1198, or 1170-I cells), normal human bronchial epithelial cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)) can be used. Accordingly, several embodiments concern methods of identifying one or more genes present in human cells of the mouth, tongue, oral cavity, trachea, or lungs (e.g., NHBE cells) that are modulated by exposure to CS, CSC, TS, TSC or TPM.

In some embodiments, the methods include providing a first population of isolated human cells of the mouth, tongue, oral cavity, or lungs (e.g., NHBE cells), contacting the cells with a CS, CSC, TS, TSC or TPM from a first tobacco product (e.g., a cigarette) in an amount and for a time sufficient to modulate expression or modification of one or more genes or gene products, and identifying the gene that is modulated or the modified gene product (e.g., phosphorylated) or the level or amount of gene expression or modification. The identification of a gene that is modulated or modified gene product or the level or amount of gene expression or presence or absence of a modification on a gene product can be accomplished using any technique available that analyzes transcription (e.g., microarray, genechip, oligonucleotide array, an amplification technique, qRT-PCR, or hybridization), protein production (e.g., ELISA, Western blot, or other antibody detection techniques), or modifications of proteins (e.g., oxidation or phosphorylation, such as detection methods that employ anti-phospho-tyrosine antibodies). Additionally, the appearance or disappearance of metabolites associated with genes that are modulated in response to exposure to CS, CSC, TS, TSC or TPM can also be monitored (e.g., cysteine, glutathione, fragments of proteins or lipids or fatty acids) using techniques that are available.

In some embodiments, the pattern and/or level of gene expression or gene product modification of a control population (e.g., a second population of isolated human cells of the mouth, tongue, oral cavity, or lungs (e.g., NHBE cells)), is compared to the level of expression or gene product modification in the first population of isolated cells. By this approach, preferably using the same type of cells for each of the two populations, a first population is contacted with a CS, CSC, TS, TSC or TPM and the second population of isolated cells is not. In this manner, the second population of isolated cells is a control population, which will exhibit the baseline pattern or level or amount of gene expression or gene product modification (homeostasis). Data generated from the first or second population of isolated cells before or after exposure to CS, CSC, TS, TSC, TPM or air (control) can be recorded on a computer readable media and databases containing this information can be used to identify a gene that is modulated in response to contact with a CS, CSC, TS, TSC or TPM or to investigate the gene expression pathways that lead to a particular tobacco-related disease.

In some embodiments, a second tobacco product (e.g., a cigarette) is compared to a first tobacco product (e.g., a cigarette) using the analysis above. That is, for example, a first population of isolated human cells of the mouth, tongue, oral cavity, or lungs (e.g., NHBE cells), is contacted with a CS, CSC, TS, TSC or TPM from a first tobacco product (e.g., a cigarette) in an amount and for a time sufficient to modulate expression of one or more genes or to modify a gene product, and identification of a gene that is modulated or modified gene product (e.g., phosphorylated) or the level or amount of gene expression or modification can be determined using any technique available that analyzes transcription (e.g., qRT-PCR or hybridization), protein production (e.g., ELISA, Western blot, or other antibody detection techniques), modifications of proteins (e.g., oxidation or phosphorylation), or the appearance or disappearance of metabolites associated with genes that are modulated in response to exposure to CS, CSC, TS, TSC or TPM (e.g., cysteine, glutathione, fragments of proteins or lipids or fatty acids). A second population of isolated human cells of the mouth, tongue, oral cavity, or lungs (e.g., NHBE cells), preferably the same type of cell as used in the analysis of the first tobacco product, is also contacted with a CS, CSC, TS, TSC or TPM from a second tobacco product (e.g., a cigarette) in an amount and for a time sufficient to modulate expression of one or more genes or to modify a gene product. Identification of a gene that is modulated or modified gene product (e.g., phosphorylated) or the level or amount of gene expression or modification can also be accomplished using any technique available that analyzes transcription (e.g., qRT-PCR or hybridization), protein production (e.g., ELISA, Western blot, or other antibody detection techniques), modifications of proteins (e.g., oxidation or phosphorylation), or the appearance or disappearance of metabolites associated with genes that are modulated in response to exposure to CS, CSC, TS, TSC or TPM (e.g., cysteine, glutathione, fragments of proteins or lipids or fatty acids).

The data obtained from the analysis of the first tobacco product can be compared to the data obtained from the analysis of the second tobacco product so as to identify, for example, a gene(s) that is induced in response to exposure to the first tobacco product but not the second tobacco product or vice versa. Additionally, the comparison will reveal that the level of expression of one or more genes induced by both tobacco products differs with respect to the two tobacco products or that the first product has more, less, or no modification of a particular gene product (e.g., phosphorylation), as compared to the second tobacco product or vice versa. These data (e.g., the types of genes expressed, the amount of expression, and modification) allow one to develop a profile for each tobacco product analyzed (in this example only two products are being compared but a plurality of products can be compared using the same approach). These tobacco product profiles can be recorded on a computer readable media and databases containing this information can be created. Many of the genes that are expressed, the amount of expression, and/or modification can be associated with molecular events that contribute to a tobacco related disease. By analyzing the differences between the tobacco products analyzed, (e.g., the types of genes expressed, the amount of expression, and modification), one can identify a tobacco product that has less potential to contribute to a tobacco related disease or that, for example, a first tobacco product has a reduced risk to contribute to a tobacco-related disease, as compared to a second tobacco product or vice versa. Thus, reduced risk tobacco products identified by the approaches described herein are embodiments of the invention.

More embodiments concern methods to identify components of CS, CSC, TS, TSC or TPM that modulate the expression of a gene that contributes to a tobacco-related disease. In one embodiment, the pattern or level of gene expression or modification of a gene product in cells of the mouth, oral cavity, trachea, or lung (e.g., NHBE cells) that are exposed to a first tobacco product that lacks a component associated with a tobacco-related disease (e.g., nicotine) is compared to a second tobacco product (preferably of the same type of tobacco as the first tobacco product) that contains the component (e.g., nicotine) and the impact on the types of genes expressed, the amount of expression, and modification of gene products is analyzed (e.g., microarray analysis, Western blot, ELISA, and/or qRT-PCR). By this approach, the genes or modifications of a gene product, which are modulated as a result of the presence or absence of the component (e.g., nicotine), can be identified. Because many of these modulated genes or modifications of gene products will be associated with molecular events that contribute to a tobacco-related disease, one can rapidly identify whether the presence or absence of a particular component in a tobacco product elevate the risk of acquiring a particular tobacco-related disease. Once a component that contributes to a tobacco-related disease has been identified using the approaches described herein, one can use various techniques to remove this component from tobacco (e.g., genetic modification, chemical treatment, or adjustments in the harvesting, curing, or processing of the tobacco) and thereby develop reduced risk tobacco products (e.g., cigarettes). Thus, reduced risk tobacco products identified by these approaches are embodiments of the invention.

Many embodiments described herein employ normal human bronchial cells (NHBE cells) that are maintained in culture. Although NHBE cells are preferred for the methods described herein, it should be understood that many other cells that are typically contacted with tobacco or tobacco smoke during the process of smoking (e.g., lung cells, bronchial cells, cells of the mouth, pharynx, larynx, and tongue) can also be used. Additionally, many immortal cell lines can be used with the methods described herein. Preferred cells for use with the embodied approaches include, but are not limited to, human bronchial cells (e.g., BEP2D or 16HBE140 cells), human bronchial epithelial cells (e.g., HBEC cells, 1198, or 1170-I cells), normal human bronchial epithelial cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226), tongue cells (e.g., CAL 27), and mouth cells (e.g., Ueda-1)). Many of such cultures are available commercially or through a public repository (e.g., ATCC). Further, several techniques exist that allow for one to generate primary cultures of said cells and these primary cultures can be used with the methods described herein.

Example 4

Treatment of NHBE Cells with CSCs

The tobacco smoke condensates were prepared as follows. Smoke was generated from two commercially available nationally sold brands of American cigarettes (Brand A and Brand B) using an INBIFO-Condor smoking machine under Federal Trade Commission (FTC) smoking parameters (2.0 second puff duration, 35 milliliter puff every 60 seconds). Both brands of cigarettes were non-menthol, full-flavor types of American-blended cigarettes with averaged FTC measured values of 13.2 mg tar/0.88 mg nicotine (Brand A), and 14.5 mg tar/1.04 mg nicotine (Brand B). Brand A contains tobacco that has been chemically modified to reduce carcinogens (see U.S. Pat. No. 6,789,548, herein expressly incorporated by reference in its entirety), whereas Brand B contains conventional tobacco. Smoke condensates extracted from these two cigarette brands and designated CSC-A and CSC-B, respectively, were collected from the smoke via a series of three cold traps (−10° C., −40° C., and −70° C.) onto impingers filled with glass beads. The condensates were dissolved in acetone, which was then removed by rotary evaporation at 35° C. The resulting cigarette smoke condensates (CSCs) were weighed and dissolved in dimethylsulfoxide (DMSO) to make stock solutions of each condensate at a concentration of 40 mg/mL, which were stored at −20° C. prior to use.

NHBE (Normal Human Bronchial Epithelial) cells were purchased from Cambrex Corporation, East Rutherford, N.J. The cells were cultured in complete Bronchial Epithelial Cell Growth Medium (BEGM), prepared by supplementing Bronchial Epithelial Basal Medium with retinoic acid, epidermal growth factor, epinephrine, transferrin, T3, insulin, hydrocortisone, antimicrobial agents and bovine pituitary extract by addition of SingleQuots,™ (both purchased from Cambrex Corporation, East Rutherford, N.J.). S9 metabolic fraction from Aroclor 1254-treated rats was obtained from BioReliance Corporation, Rockville, Md. A 5× concentration of S9 microsomal fraction with cofactors was prepared immediately before treating the cells, and contained 10% S9 microsomal fraction, 4 mM NADP, 5 mM glucose-6-phosphate, 50 mM phosphate buffer pH 8.0, 30 mM KCl, and 10 mM $CaCl_2$).

Twenty-eight flasks were seeded with 14.6 ml of a 2.52×$10^4$ cells/ml cell suspension and an additional 15.4 ml pre-warmed BEGM were added to each flask for a final volume of 30 mL/flask. All incubations were at 37° C. in a humidified atmosphere of 5% $CO_2$ in air. Cells were grown to 40% confluence, at which time the cultures were treated. Four flasks were used as untreated control cultures. Following medium removal in these four control flasks, the cells were re-fed with 30 ml pre-warmed BEGM and their RNA harvested at 0 h (2 flasks) and 20 hr (2 flasks). The remaining 24 experimental flasks were treated with either CSC-A in the presence of 2% S9 microsomal fraction, CSC-B in the presence of 2% S9 fraction, or 2% S9 microsomal fraction alone. Following medium removal, each flask received 9.0 ml of fresh BEGM, 15.0 mL BEGM containing CSC or vehicle (400 µg/ml of CSC-A or CSC-B and 1% DMSO for the CSC-treated groups, 15.0 mL containing 1% DMSO for the S9-only group), and 6 ml of 5× S9 fraction for a final concentration of 2% S9 and a final media volume of 30 mL. Incubation was carried out under the incubation conditions described above. Duplicate flasks were used for each treatment/time point of the experiment (i.e., 2, 4, 8, and 12 h).

The monolayer cultures of NHBE cells were treated in logarithmic phase of growth for up to 12 hours with CSC-A or CSC-B in the presence of 2% S9 microsomal fraction, or with 2% S9 fraction alone. Cell viability after 12 hours exposure was 84% and 73% for CSC-A and CSC-B treatments, respectively, when compared to untreated cells. RNA was then extracted from cells at 2, 4, 8, and 12 hours post-treatment, fluorescently labeled and hybridized to genome-scale microarrays, as described in the examples that follow.

Treatment of NHBE Cells with CS

Two identical and independent smoke exposure experiments using NHBE cells were performed. In both experiments, the cells were exposed to cigarette smoke (CS) or air ("mock-exposed") for 15 min, after which the cells were re-fed with fresh media and allowed to incubate for either 4 h or 24 h (the "washout" period). In preparation for exposure, cells were seeded into 35 mm Petri dishes (Fisher Scientific, Falcon #35-3001, Pittsburgh, Pa.) at a density of 105 cells/dish. This resulted in no more than 70% confluence at the time of smoke treatment 48 hours later.

Experiment 1 used cells from a 23-year-old nonsmoking, non-diabetic male donor purchased from Cambrex Corporation (Walkersville, Md.). A total of ten Petri dishes were treated: two dishes were mock-exposed with a 4 h washout, two dishes were CS-exposed with a 4 h washout, three dishes were mock-exposed with a 24 h washout, and three dishes were CS-exposed with a 24 h washout.

Experiment 2 was performed in an essentially identical manner as Experiment 1, except for the cell donor (a 13-year-old nonsmoking, non-diabetic male, purchased from Cambrex Corporation, Walkersville, Md.), and the number of Petri dishes used for the mock- and CS-exposed samples with a 24 h washout (two instead of three). This resulted in a total of eight Petri dishes treated for Experiment 2.

Smoke was generated from a commercially available, nationally sold, non-menthol, full-flavor brand of American filter cigarettes (averaged FTC measured values of 14.5 mg tar/1.04 mg nicotine) using a KC 5 Port Smoker (KC Automation, Richmond, Va.) smoking machine under Federal Trade Commission (FTC) smoking parameters (35±0.3 cc puff volume, one puff every 60 seconds, 2-second puff duration with none of the ventilation holes blocked, using cigarettes which have been equilibrated at 23.9° C.±1.1° C. and 60%±2% relative humidity for a minimum of 24 hours and a maximum of 14 days).

Immediately prior to smoke exposure the culture medium was removed from each dish and replaced with pre-warmed Dulbecco's Phosphate Buffered Saline (PBS) containing calcium and magnesium (BioSource, Rockville, Md.). The Petri dishes were placed in a smoke exposure chamber (20.6 cm×6.7 cm×6.3 cm). Each 35 cc puff was diluted to 500 cc using compressed air containing 5% CO2 and then was drawn over the cells with the aid of a vacuum pump in order to keep a constant flow of smoke over the cells with minimal accumulation in the exposure chamber. Cigarettes were smoked to a maximum of seven puffs per cigarette, within 3 mm of the filter tip. Mock exposure conditions were identical to smoke conditions without a cigarette placed in the smoking port. Immediately after exposure, the PBS was removed from each dish and replaced with fresh pre-warmed cell culture medium. The Petri dishes were transferred to a 37° C. 5% CO2 incubator and incubated for 4 or 24 hours post-exposure.

Cells were cultured in complete Bronchial Epithelial Cell Growth Medium, prepared by supplementing Bronchial Epithelial Basal Medium with retinoic acid, epidermal growth factor, epinephrine, transferrin, T3, insulin, hydrocortisone, antimicrobial agents and bovine pituitary extract by addition of SingleQuots,™ (Cambrex Corporation, Walkersville, Md.). All incubations were at 37° C. in a humidified atmosphere of 5% CO2 in air. All cells were used before their fifth passage, although NHBE cells can be used up to 10 passages or more in the methods described herein.

Once the cells are contacted with a CS, CSC, TS, TSC or TPM, an approach to analyze the genes that are modulated in response to the exposure is employed. In some embodiments, the identification of at least one gene that is modulated by exposure to CS, CSC, TS, TSC or TPM is accomplished using an array technology, an oligonucleotide array technology, a genechip technology, any type of hybridization or blot, PCR, QRT-PCR, another amplification technology or protein detection methodologies, such as antibody detection methods, ELISA and Western blot. In some embodiments, the identification is made by observing a modulation (up-regulation or down-regulation) in the level or activity of an mRNA and/or a protein. In some embodiments, the modulation is seen as an increase in mRNA or protein production. In other embodiments, the modulation is seen as a decrease in mRNA or protein production. In some embodiments, the modulation is identified as being statistically relevant. In some embodiments, the presence or absence of a modification of a gene product (e.g., phosphorylation, acylation, or cleavage of a peptide) or the presence or absence of a metabolite (e.g., cysteine or glutathione) is analyzed. In still more embodiments the modulation, modification, metabolite or amounts thereof are recorded on a computer readable medium (e.g., disc drive, floppy, CD-ROM, DVD-ROM, zip disc, memory cache, and the like). Accordingly, specific genes or patterns of genes and modified gene products that appear in response to exposure to CS, CSC, TS, TSC or TPM can be identified, recorded on a computer readable medium and this data can be used to generate a profile for each product tested.

In the example that follows, approaches that were used to analyze the pattern and level of expression of genes from NHBE cells exposed to a tobacco smoke condensate (CSC) from two different tobacco products are described.

Example 5

Isolation of RNA from CSC-Treated Cells and Production of cDNA

After NHBE cells were exposed to the cigarette smoke condensates (CSC-A and CSC-B), as explained in Example 4, RNA was prepared by harvesting cells for total RNA extraction after 0 (untreated), 2, 4, 8, and 12 hours of treatment. The medium was aspirated and the flasks were rinsed twice with pre-warmed 15 mL Dulbecco's Phosphate Buffered Saline. After the second rinse, 5.0 mL of cold TRIzol® (Invitrogen Corp., Carlsbad, Calif.) were added to cover the cells in each flask. Each flask was vigorously vortexed for approximately one minute. The TRIzol® was pipetted up and down over the surface of the flask at least five times to suspend the cell lysate. The resulting TRIzol®/cell lysate was allowed to remain in the flask for at least 10 minutes at room temperature after which it was transferred to microfuge tubes and extracted with 0.2 ml chloroform per 1.0 ml TRIzol/cell lysate. The tubes were capped and shaken vigorously to initiate the RNA extraction, and centrifuged at >15,000×g for two 5-minute spins. Following the second 5-minute centrifugation, the aqueous layer was collected (~500 µl) and transferred to a second set of microfuge tubes containing an equal volume of isopropyl alcohol. The samples were centrifuged for 30 minutes at >15,000×g. Following centrifugation, most (~90%) of the liquid was removed from the microfuge tube. The remaining RNA pellet was frozen and stored at <−60° C. RNA was resuspended in diethylpyrocarbonate-treated water. RNA integrity was assessed using capillary gel electrophoresis (Agilent Technologies, Palo Alto, Calif.) to determine the ratio of 28s:18s rRNA in each sample. cDNA was synthesized with a direct incorporation of Cy3-dUTP from 2 µg total RNA using Clontech Powerscript (Clontech, Palo Alto, Calif.) reverse transcriptase. Labeled cDNA was then purified using a Montage 96-well vacuum system.

Microarray Printing and Processing in CSC Experiments

The microarrays used in experiments involving CSC-treated cells were purchased from the Oklahoma Medical Research Foundation Microarray Research Facility. Slides were produced using commercially available libraries of 70 nucleotide long DNA molecules whose length and sequence specificity were optimized to reduce the cross-hybridization problems encountered with cDNA-based microarrays (Human Genome Oligo Set Version 2.0, Qiagen, Valencia, Calif.). The microarrays had 21,329 human genes represented. The oligonucleotides were derived from the Uni-Gene and RefSeq databases. The RefSeq database is an effort by the NCBI to create a true reference database of genomic information for all genes of known function. For the genes present in this database, information on gene function, chromosomal location, and reference naming are available. All 11,000 human genes of known or suspected function are represented on these arrays. In addition, most undefined open reading frames were represented (approximately 10,000 additional genes). Oligonucleotides were resuspended at 4004 concentrations in 3×SSC and spotted onto Corning® UltraGAPS™ amino-silane coated slides, rehydrated with water vapor, snap dried at 90° C., and then covalently fixed to the surface of the glass using 300 mJ, 254 nm wavelength ultraviolet radiation. Unbound free amines on the glass surface were blocked for 15 min with moderate agitation in a 143 mM solution of succinic anhydride dissolved in 1-methyl-2-pyrrolidinone, 20 mM sodium borate, pH 8.0. Slides were rinsed for 2 min in distilled water, immersed for 1 min in 95% ethanol, and dried with a stream of nitrogen gas.

The cDNA generated above was added to hybridization buffer containing Cot-1 DNA (0.5 mg/ml final concentration), yeast tRNA (0.2 mg/ml), and poly(dA)$_{40-60}$ (0.4 mg/ml). Hybridization was performed on a Ventana Discovery system for 6 hr at 42° C. (Ventana Medical Systems, Tucson, Ariz.). Microarrays were washed to a final stringency of 0.1×SSC. Microarrays were scanned on a dual-channel, dynamic auto focus, fluorescent scanner at 10 um resolution (Agilent Technologies, Palo Alto, Calif.). Fluorescent intensity was determined using Imagene™ software (BioDiscovery, Marina del Rey, Calif.).

Genechip Analysis in CSC Experiments

CSC-induced changes in gene expression were then determined in a comprehensive manner using hypervariable analysis, which is based on the observation that gene expression for a majority of genes is relatively stable among replicates in untreated cells. Any measurable variation in this large set of genes by micro array analysis reflects the combined effects of intrinsic normal biologic variation and extrinsic technological variation in an unmanipulated cell. Genes that were impacted by exposure to CSCs, and whose mRNA expression varied over time in a statistically significant manner, which was greater than this normal biologic and technical variation, are termed "hypervariable" (HV).

Signals from independent samples can vary on a global-basis and, preferably, are adjusted to a common standard. Adjustment of expression levels in compared samples was performed as described. (See Dozmorov, et al. Bioinformatics 19:204-211, 2003, expressly incorporated by reference in its entirety). Briefly, compared samples were first normalized using low level noise signals (commonly referred to as additive noise (AN). The parameters of the AN were calculated from non-expressed genes whose signal values exhibited a normal distribution. The mean and standard deviation (SD) of the AN signals was obtained by nonlinear curve fitting after exclusion of expressed genes from the distribution. Expression values from a given chip were then normalized such that the AN distribution had a mean of 0 and a SD of 1. Genes expressed 3 SD above the mean of AN are defined as expressed genes and used for further analysis. A second scaling step was then performed on expressed genes that were scaled to a common standard through a robust linear regression analysis.

Genes responsive to CSCs were also identified using an analysis of temporally induced gene expression changes. This procedure utilized an internal standard, denoted "the reference group" to define the levels of technologic and normal biologic variance in the experiment so that these values can be used to define stimuli-induced variation in a statistically robust manner. The majority of genes in the control group were not sensitive to temporal changes. The reference group was therefore composed of a group of genes that were statistically expressed significantly above the mean of AN in control samples, whose residuals approximate a normal distribution based on the Kolmogorov-Smirnov criterion, and that have low variability of expression over time as determined by an F-test. Variance in the reference group is due only to technical variation and normal biologic variation and therefore the distribution of expression of the reference group can be used to identify genes that vary due to experimental conditions in a manner that is statistically significantly higher than the technologic and normal biologic variance of the system using an F-test.

Genes identified using these procedures are denoted "hypervariable genes" or "HV-genes".

F-means cluster analysis of HV-genes co-expression involved groupings of genes that varied in expression over time in a similar manner, based on the technologic and normal biologic variation in the system, in a given cluster. The reference group defined above is once again used as a reference to define statistically significant thresholds for clustering parameters used in an F-test. In this manner, the variance of the system is used to define the number of clusters thus removing the subjective nature of most clustering methods. The method is not without some subjective criterion as genes can belong to multiple clusters. In this method, a given gene is placed into the largest cluster such that the broadest biologic phenomena of the system, that is those involving the largest number of genes, can be distinguished. To do this, clustering is begun by defining a simple parameter for each HV-gene. This parameter, denoted connectivity, is equal to the number of genes that vary in expression in a similar manner as a given gene. Clusters are nucleated starting with genes of highest connectivity. Genes of lower connectivity will be included in a given cluster if their expression varies over time in a manner similar to the gene used to nucleate the cluster, i.e. if their deviations of expression over time do not exceed the variation of the residuals in the reference group based on an F test.

F-clustering was used to identify the kinetic behavior of genes for each stimulus. Correlation coefficient analysis was used to identify genes that behave in a similar manner among groups. In this type of analysis, a Pearson correlation coefficient is used for clustering of genes with similar time-dependent behavior among groups. A correlation threshold was established using a Monte-Carlo simulation experiment such that the chances of identifying a false positive or false negative selection is <1. Matrices of correlation coefficients are calculated for these clusters and are represented in a graphical output termed a connectivity mosaic such that patterns of correlated and non-correlated behavior of genes can be identified by visual inspection.

Discriminant function analysis (DFA) is a method that identifies a subset of genes whose expression values can be linearly combined in an equation, denoted a root, whose overall value is distinct for a given characterized group. DFA therefore, allows the genes that maximally discriminate among the distinct groups analyzed to be identified. (See Moore et al. Genet Epidemiol 23: 57-69, (2002), expressly incorporated by reference in its entirety). In the experiments described herein, a variant of the classical DFA, named the Forward Stepwise Analysis, was used for selection of the set of genes whose expression maximally discriminates among experimentally distinct groups. The Forward Stepwise Analysis was built systematically. Specifically, at each step all variables were reviewed to identify the one that most contributes to the discrimination between groups. This variable was included in the model, and the process proceeds to the next step. The statistical significance of discriminative power of each gene was also characterized by partial Wilk's Lambda coefficients (see Cho et al., Optimal approach for classification of acute leukemia subtypes based on gene expression data. Biotechnol Prog 18: 847-854, 2002), expressly incorporated by reference in its entirety, which are equivalent to the partial correlation coefficients generated by multiple regression analyses. The Wilk's Lambda coefficient used a ratio of within group differences and the sum of within plus between group differences. Its value ranged from 1.0 (no discriminatory power) to 0.0 (perfect discriminatory power).

Figure 34A:
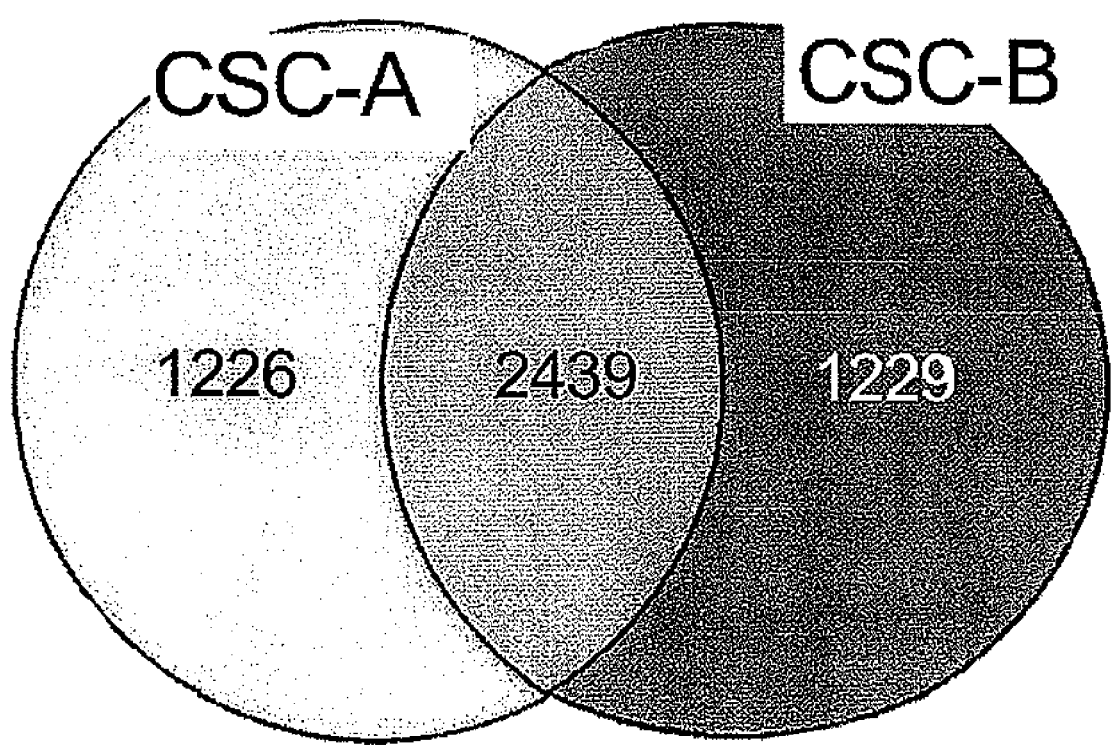
FIG. 34A is a Venn diagram comparing gene expression modulations induced by cigarette smoke condensates of two different tobacco products (e.g., cigarettes) CSC-A (3665) and CSC-B (3668). The number of genes uniquely affected by exposure to each product CSC-A (1226) and CSC-B (1229) is given in each sector. The intersections between sectors reflect the number of genes that are affected by both CSCs (2439).

Of the 21,349 genes and open reading frames (ORFs) on the high-density array used in these experiments, a combined total of 4,894 (22.9%) were classified as HV after CSC treatment (see FIG. 34A). Individually, the expression of 3,665 genes/ORFs was modulated by CSC-A contact (i.e., 17.2% of all the genes/ORFs on the array), and the expression of 3,668 genes/ORFs was modulated by CSC-B contact (17.2%). These genes were hypervariable in at least one time point during the 12-hour exposure period to CSC-A and CSC-B respectively (see FIG. 36, Table 7). The observation that the expression of a large number of genes was altered in a significant manner during the 12 h treatment demonstrated a significant impact by CSCs on steady-state levels of mRNAs in NHBE cells. A majority of the HV genes (i.e., 2,439) were common to both CSC-treated groups, providing evidence that the two CSCs affected cells largely in a similar manner. However, unique non-overlapping sets of HV genes were also identified after treatment with CSC-A (i.e., 1226 genes) and CSC-B (i.e., 1229 genes), which demonstrate that each tobacco product has a specific quantitative and/or qualitative difference in the chemical constituents comprising the two CSCs and the cellular responses thereto.

TABLE 7

Genes Common to CSC-A and CSC-B exposed cells, which are associated with a tobacco-related disease

| GenBank accession no. | Gene Abbreviation | Gene description | Disease |
|---|---|---|---|
| NM_001610 | ACTA2 | Actin, alpha 2, smooth muscle, aorta | Lung Cancer |
| NM_005181 | CA3 | Carbonic anhydrase III, muscle specific | Lung Cancer |
| NM_005199 | CHRNG | Cholinergic receptor, nicotinic, gamma polypeptide | Lung Cancer |
| NM_002594 | PCSK2 | Proprotein convertase subtilisin/kexin type 2 (PC2) | Lung Cancer |
| NM_004624 | VIPR1 | Vasoactive intestinal peptide receptor 1 (VPAC1) | Lung Cancer |
| NM_004448 | ERBB2 (HER2/NEU) | V-erb-b2 erythroblastic leukemia viral oncogene homolog 2 | Lung Cancer |
| NM_024083 | ASPSCR1 | Alveolar soft part sarcoma chromosome region, candidate 1 | Lung Cancer |
| NM_003872 | NRP2 | Neuropilin 2 | Lung Cancer |

TABLE 7-continued

Genes Common to CSC-A and CSC-B exposed cells, which are associated with a tobacco-related disease

| GenBank accession no. | Gene Abbreviation | Gene description | Disease |
|---|---|---|---|
| U33749 | TITF1 | Thyroid transcription factor 1 | Lung Cancer |
| NM_002639 | SERPINB5 | Serine (or cysteine) proteinase inhibitor, clade B (ovalbumin), member 5, (maspin) | Lung Cancer |
| AF135794 | AKT3 | V-akt murine thymoma viral oncogene homolog 3 (protein kinase B, gamma) | Lung Cancer |
| NM_001618 | ADPRT | ADP-ribosyltransferase (NAD+; poly (ADP-ribose) polymerase) PARP1 | Lung Cancer |
| NM_016434 | TNFRSF6B | Tumor necrosis factor receptor superfamily, member 6b, decoy | Lung Cancer |
| NM_003072 | SMARCA4 (BRG1) | SWI/SNF related, matrix associated, actin dependent regulator of chromatin, subfamily a, member 4 | Lung Cancer |
| NM_004061 | CDH12 | Cadherin 12, type 2 (N-cadherin 2) | Lung Cancer |
| U28749 | HMGIC | High-mobility group (nonhistone chromosomal) protein isoform I-C | Lung Cancer |
| NM_002592 | PCNA | Proliferating cell nuclear antigen | Lung Cancer |
| NM_033215 | PPP1R3F | Protein phosphatase 1, regulatory (inhibitor) subunit 3F (PPP1R3F), mRNA | Lung Cancer |
| NM_006218 | PIK3CA | Phosphoinositide 3-kinase, catalytic, alpha polypeptide | Lung Cancer |
| NM_005506 | CD36L2 | CD36 antigen (collagen type I receptor, thrombospondin receptor)-like 2 (lysosomal integral membrane | Lung Cancer |
| NM_004994 | MMP9 | Matrix metalloproteinase 9 | Lung Cancer |
| NM_003810 | TNFSF10 | Tumor necrosis factor (ligand) superfamily, member 10 (TRAIL) | Lung Cancer |
| NM_002961 | S100A4 | S100 calcium binding protein A4 (calcium protein, calvasculin, metastasin, murine placental homolog) | Lung Cancer |
| NM_007084 | SOX21 | SRY (sex determining region Y)-box 21 | Lung Cancer |
| NM_003682 | MADD | MAP-kinase activating death domain (DENN) | Lung Cancer |
| BC002712 | MYCN | V-myc myelocytomatosis viral related oncogene, neuroblastoma derived (avian) | Lung Cancer |
| NM_004353 | SERPINH1 | Serine (or cysteine) proteinase inhibitor, clade H), member 1, HSP47 | Oral Cancer |
| NM_000640 | IL13RA2 | Interleukin 13 receptor, alpha 2 | Asthma |
| NM_002046 | GAPD | Glyceraldehyde-3-phosphate dehydrogenase | Asthma |
| NM_021804 | ACE2 | Angiotensin I converting enzyme (peptidyl-dipeptidase A) 2 | Coronary Heart Disease |
| NM_017614 | BHMT2 | Betaine-homocysteine methyltransferase 2 | Coronary Heart Disease |
| NM_020974 | CEGP1 | CEGP1 protein | Coronary Heart Disease |
| NM_018641 | C4S0 | Chondroitin 4-O-sulfotransferase 2 | Coronary Heart Disease |
| NM_006874 | ELF2 | E74-like factor 2 (ets domain transcription factor), NERF | Coronary Heart Disease |

*The sequences of the genes above are available from GenBank using the referenced Gene ID No. and said sequences are hereby expressly incorporated by reference in their entireties.

The 1229 genes that were induced by exposure to CSC-B but not CSC-A were also analyzed with the commercially-available microarray data analysis software Genespring (version 7.2, Agilent Technologies), which identifies genes that are associated with a tobacco-related disease. Of the 1229 unique genes that were induced by exposure to CSC-B but not CSC-A, a total of 33 genes were identified as being associated with cancer (see Table 8).

TABLE 8

Genes modulated by contact with CSC-B but not CSC-A, which are associated with a tobacco-related disease

| GeneBank # | Name | Description |
|---|---|---|
| NM_00359 | CUL4A | Cullin 4A |
| NM_00405 | CDR1 | Cerebellar degeneration-related protein (34 kD) |
| NM_00521 | CSF1R | Colony stimulating factor 1 receptor, formerly McDonough feline sarcoma viral (v-fms) oncogene homol |

TABLE 8-continued

Genes modulated by contact with CSC-B but not CSC-A, which are associated with a tobacco-related disease

| GeneBank # | Name | Description |
| --- | --- | --- |
| NM_00626 | TFDP2 | Transcription factor Dp-2 (E2F dimerization partner 2) |
| NM_01225 | SNW1 | SKI-interacting protein |
| NM_00482 | NTN1 | Netrin 1 |
| NM_00284 | RAP1A | RAP1A, member of RAS oncogene family |
| AF308602 | NOTCH1 | Notch homolog 1, translocation-associated (*Drosophila*) |
| NM_01438 | LAMP3 | Lysosomal-associated membrane protein 3 |
| NM_00371 | PPAP2A | Phosphatidic acid phosphatase type 2A |
| NM_00164 | ARHA | Ras homolog gene family, member A |
| NM_01633 | LOC51191 | Cyclin-E binding protein 1 |
| NM_01865 | ERBB2IP | Erbb2 interacting protein |
| NM_01242 | SETDB1 | SET domain, bifurcated 1 |
| AF156165 | DCTN4 | Dynactin 4 (p62) |
| NM_00205 | FOXO1A | Forkhead box O1A (rhabdomyosarcoma) |
| AF163473 | PPP2R1B | Protein phosphatase 2 (formerly 2A), regulatory subunit A (PR 65), beta isoform |
| NM_03328 | PML | Promyelocytic leukemia |
| AK024486 | GLTSCR2 | Glioma tumor suppressor candidate region gene 2 |
| NM_00343 | ZNF151 | Zinc finger protein 151 (pHZ-67) |
| U18018 | ETV4 | Ets variant gene 4 (E1A enhancer binding protein, E1AF) |
| NM_00523 | EWSR1 | Ewing sarcoma breakpoint region 1 |
| BC013971 | HOXA10 | Homeo box A10 |
| AJ420488 | EEF1A1 | Eukaryotic translation elongation factor 1 alpha 1 |
| NM_00548 | ST5 | Suppression of tumorigenicity 5 |
| NM_00578 | HNRPA3 | Heterogeneous nuclear ribonucleoprotein A3 |
| NM_00094 | RARA | Retinoic acid receptor, alpha |
| NM_00675 | N33 | Putative prostate cancer tumor suppressor |
| NM_00228 | JUN | V-jun sarcoma virus 17 oncogene homolog (avian) |
| AL110274 | ALDH1A2 | Aldehyde dehydrogenase 1 family, member A2 |
| NM_01428 | RBX1 | Ring-box 1 |
| NM_01787 | FLJ20429 | Hypothetical protein FLJ20429 |
| NM_00437 | BCR | Breakpoint cluster region |

*The sequences of the genes above are available from GenBank using the referenced Gene ID No. and these sequences are hereby expressly incorporated by reference in their entireties.

Notably, it was discovered that CSC-B induced expression of the proto/oncogenes Cullin 4A, C-jun, Hoxa10, and PPP2R1B, whereas CSC-A did not. Cullin 4A has been described in non-small cell lung cancer (see Singhal et al., Cancer Biol. Ther. 2(3):291-298 (2003)); C-jun has been found to be amplified or over expressed in small cell lung cancer (see Cook et al., Curr. Probl. Cancer 17(2):69-141 (1993)); Hoxa10 has been found to be amplified or over expressed in leukemia (see Calvo et al., Proc. Natl. Acad. Sci. USA 97(23):12776-12781 (2000)); and altered expression of PPP2R1B is involved in lung and colorectal carcinomas (see Calin et al., Oncogene 19(9):1191-1195 (2000); all of these references are expressly incorporated by reference in their entireties). Accordingly, these results demonstrate that the tobacco product comprising chemically modified tobacco (Brand A cigarette), which was used to generate CSC-A, has a reduced potential to contribute to a tobacco-related disease as compared to the tobacco product (Brand B cigarette) used to generate CSC-B because CSC-A induces expression of fewer genes associated with a tobacco-related disease (e.g., 33 fewer genes associated with cancer). Notably, the tobacco product used to generate CSC-A (Brand A) does not induce key genes that have been associated with cancer in humans (e.g., the proto/oncogenes Cullin 4A, C-jun, Hoxa10, and PPP2R1B); whereas the tobacco product used to generate CSC-B (Brand B) induces expression of these proto/oncogenes. Further, these results demonstrate that the methods described herein can be used to effectively identify a tobacco product that is less likely or more likely to contribute to a tobacco related disease (e.g., cancer). That is, this example demonstrates that the approaches described herein can be used to identify a reduced risk tobacco product, which can be a tobacco product that is less likely to contribute to a tobacco-related disease because it modulates fewer genes associated with a tobacco-related disease (e.g., cancer) or induces fewer modifications to a gene product, which are associated with a tobacco-related disease, as compared to a second tobacco product. To confirm these data, more experiments were conducted on the tobacco product used to generate CSC-A (Brand A) to determine whether it was in fact less likely to contribute to a tobacco-related disease (e.g., cancer), as compared to the tobacco product used to generate CSC-B (Brand B). These experiments are discussed in the following example.

Example 6

This example describes experiments that were conducted on mice to demonstrate that the tobacco product used to generate CSC-A (Brand A) is a reduced risk tobacco product in that it was less likely to contribute to a tobacco-related disease, as compared to a conventional tobacco product of the same class (e.g., "full flavor" cigarette), Brand B, which was used to generate CSC-B in the previous examples. In summary, the response of previously initiated SENCAR mice to repeated topical applications of Brand-A or Brand-B Cigarette Smoke Condensates (CSC-A or CSC-B), was tested over a period of 24 consecutive weeks. One week after a single initiating dose of 50 µg 7,12-dimethylbenzanthracene (7,12-DMBA), female SENCAR mice were exposed to the following three-times-per-week treatment regimen: Negative-Initiation Control (0.1 ml acetone promotion); Positive Control (1 µg TPA promotion); Test (Brand-A CSC promotion, low-dose [10 mg] and high-dose [20 mg]); or Test (Brand-B CSC promotion, low-dose [10 mg] and high-dose [20 mg]). The condensates and positive control articles were dissolved in acetone and applied three times a week to the shaved dorsal skin of female SENCAR mice. In addition, a vehicle control group was initiated and promoted with acetone only. The effects of treatment with the various articles on survival and group mean body weights did not appear to be significantly affected by the Test CSC's during the duration of the study phase.

The extent of tumor promotion by the cigarette smoke condensates was quantitated by the incidence of tumor-bearing animals per group, the multiplicity of tumors per animal, and the latency period until the appearance of tumors. All quantitative scoring was based on gross tumor detection, gross tumor numbers, and gross characterization of tumors which was shown to be accurate by histopathologic examination. The response to the Test CSCs was evident in 13-87% incidence of DMBA-initiated animals exhibiting actual tumors in the effective animals of those groups after 25 weeks compared to a 3% incidence (a single animal) exhibiting actual tumors in the Negative Control (DMBA-Initiated) group. There were no incidences of animals exhibiting actual tumors in the acetone-initiated group.

The SENCAR mouse is an acceptable short-term in vivo model for evaluating the promoting potential of a cigarette on multi-stage epidermal carcinogenesis. This assay system takes advantage of a mouse strain that is extremely sensitive to the two-stage induction of skin tumors. SENCAR mice were bred for increased sensitivity to skin tumor initiation and promotion. The strain originated from Rockland all-purpose mice which were inbred for sensitivity to skin tumor initiation by DMBA and promotion by 12-0-tetradecanoyl-phorbol-13-acetate (TPA) in 1959. In 1971, these susceptible mice were outbred with Charles River CD-1 mice to produce hybrid vigor. These mice have been bred for use in skin carcinogenesis studies of up to 12 months duration.

Accordingly, the SENCAR mouse skin painting bioassay was utilized to determine the relative promoting potential of various cigarette smoke condensate (CSC) preparations applied topically for 24 consecutive weeks. The mice in Groups, as described below, were initiated with a single application of 50 µg 7,12-dimethylbenzanthracene (DMBA). One week after initiation, the animals of each group received three topical applications per week of either acetone (Negative Controls), TPA (Positive Control), or one of two dose levels of cigarette smoke condensates (CSC) from the Test cigarettes. The mice in Group 1 were initiated with acetone vehicle rather than DMBA and received acetone promotion thereafter.

Late in the quarantine period, the animals were weighed and randomly distributed into nine study groups using a computerized randomization program. This program insured that no statistically significant differences in the group mean body weights existed between the study groups at study start. Animals with body weights that were ±20% of the mean body weight of the animal pool were assigned to the study. Following assignment to a group (as listed in TABLE 9), each animal was identified by a uniquely numbered tail tattoo. A color-coded card which listed the study number, animal number, group designation and treatment was displayed on each cage.

TABLE 9

| Group No. | Animal No. | Test Group | No. of Animals | Test Article No. |
|---|---|---|---|---|
| 1 | 1-30 | Negative-Vehicle Control, Acetone Initiation and Acetone Promotion (0.1 ml each) | 30 | Not Applicable |
| 2 | 31-60 | Negative-Initiation Control, DMBA Initiation (50 µg) Acetone Promotion (0.1 ml) | 30 | Not Applicable |
| 3 | 61-80 | Positive Control, DMBA Initiation (50 µg) TPA promotion (1 µg) | 20 | Not Applicable |
| 4 | 81-120 | Low Dose Brand A, DMBA Initiation (50 µg) Brand A CSC Promotion (10 mg) | 40 | AA49LY |
| 5 | 121-160 | High Dose Brand A, DMBA Initiation (50 µg) Brand A CSC Promotion (20 mg) | 40 | AA49LY |
| 8 | 241-280 | Low Dose Brand B, DMBA Initiation (50 µg) Brand B CSC Promotion (10 mg) | 40 | AA52CE |
| 9 | 281-320 | High Dose Brand B, DMBA Initiation (50 µg) Brand B CSC Promotion (20 mg) | 40 | AA52CE |

The Test cigarette smoke condensates at 100 and 200 mg total tar content/ml were collected and prepared by Arista Laboratories at a frequency of approximately every 8 weeks. Upon receipt, the CSC samples were stored at ≤−20° C. until further sub-aliquoted by BioReliance (5.0 ml per vial for both the low and high doses) and stored at ≤−20° C. The dose preparations, as received from Arista Laboratories, were divided into 26 tightly sealed amber vials, with an expiration date of approximately 13 weeks and stored at ≤−20° C. This allowed the use of one vial per dosing day and two backups which could be used in case of spillage. All dosing solutions were used within eight weeks of preparation. The Positive Control article (TPA) was diluted with acetone to produce the desired concentration of 10.0 µg/ml once (prior to initiation of dosing) and delivered to the animal laboratory and stored at room temperature (an extra vial was stored at ≤−20° C.).

The mice from Groups 2-9 received a single topical application of DMBA (50 µg/0.1 ml acetone/animal) as an initiator on Day 1 of the study. The mice from Group 1 received a single topical application of acetone vehicle (0.1 ml) as an initiator. After one week, the animals were dosed topically three times a week (Monday, Wednesday and Friday except for Holidays) for 24 consecutive weeks with the appropriate Vehicle Control, Positive Control or Test article.

The dorsal application site (approximately 2×3 cm) was shaved 3 days prior to the single application of the initiator, and at least once a week thereafter, at least one day prior to application of the appropriate dosing solution or vehicle. Shaving was performed on all animals with an Oster Model 76059 small animal electric clippers (Oster Co., Racine, Wis.) using a narrow blade.

The animals were weighed at study initiation and at weekly intervals for the next 11 weeks (12 total data collection points), and once every four weeks thereafter and at terminal sacrifice. The animals were observed twice daily (including weekends and holidays) for mortality and moribundity, once in the morning before 10:00 a.m. and once in the afternoon after 2:00 p.m. (at least six hours apart). Clinical observations performed cage-side to detect abnormalities other than skin tumor responses were made once daily for the first 5 weeks of the study (Days 1-35) and hands on once every two weeks thereafter (beginning on Day 36). Clinical signs noted at times other than the scheduled observation timepoints were recorded on the Unscheduled Observations Sheet.

On Day 1 and at weekly intervals thereafter, the mice were examined grossly for the presence of skin tumors. Pertinent information such as date of observation, lesion location, morphology, and type were recorded for each lesion at each observation time. At necropsy, all representative skin from the application site, skin from an untreated area, and other lesions taken for histopathologic evaluation were indicated on the necropsy data sheet. Lesions were identified in a manner which allowed correlation of the individual lesion-specific histopathologic findings with data collected during the in-life phase of the study.

A tissue mass (in vivo) was considered to be a tumor (papilloma) when that mass attained a 2 mm diameter and protruded from the surface of the skin. The date at which a 2 mm diameter was attained was recorded and represented the end of the "tumor latency period" for that animal and the tumor was scored as a latent papilloma. If a latent tumor remained countable for three (3) consecutive weeks, it was considered an actual tumor. Such a tumor remained in the total count of actual tumors for that animal even if it subsequently decreased in size, disappeared, or the animal died or was sacrificed early. The record of skin lesion data served to differentiate papillomas from carcinomas and latent tumors from actual tumors. In vivo differentiation of papillomas and carcinomas was made on the basis of palpation, evidence of subcutaneous invasion, and ulceration.

Group 3 (the positive control) served as a qualitative indicator of the test system's response to a known and chemically defined initiator (DMBA) and promotor (TPA). Considering the time course and magnitude of the response in SENCAR mice, treated as described above, collection of skin lesion data in the positive control was discontinued after 90-100% of the animals in the group exhibited tumors and the mean number of tumors per animal was at least 8. Since this group was not counted through the entire study, it was not included in any group comparisons noted below.

The number and location of skin papillomas (benign tissue masses having attained a diameter >2 mm and protruding from the surface) and carcinomas (malignant tissue masses with gross evidence of invasive growth and tissue necrosis due to growth outstripping vascular supply) were documented weekly. The reliability of gross diagnoses of tumors was confirmed by representative histopathologic examination of individually identified and historically tracked skin lesions. Tumor data for specific groups were calculated based on the appearance of tumors of either type. The following parameters were recorded or calculated for all groups (with the exception of Group 3, Positive Control):
1. Date of tumor appearance for all tumors on all mice.
2. Date of appearance of latent and actual tumors.
3. Date of death or sacrifice for each mouse.
4. Time interval from Day 1 of the study until the date of the appearance of; (1) latent papillomas and carcinomas and, (2) actual papillomas or carcinomas on each mouse.
5. Latency for all latent or actual tumors (i.e., this was defined as the time from Day 1 to the time a mass qualified as a latent tumor and subsequently as an actual tumor). Three methods for numerically scoring latency were used:
   a. The time elapsed until the appearance of the first tumor of a specific type in a group.
   b. The mean time elapsed until the appearance of all first tumors of a specific type from all animals in a group developing one or more such tumors.
   c. Time elapsed to attain 50% of the maximum incidence of animals in a group with one or more tumors of a specific type.
6. Percent of mice developing one or more latent and/or actual tumors (Incidence) equals:
   Number of mice with at least one latent and/or actual tumor×100
   Number of mice surviving at the time the first non-positive control group shows a tumor
7. Tumors per tumor-bearing animal=Number of total or specific-type tumors Number of animals bearing that type of tumor Group means and standard deviations were calculated for body weights and skin tumor data. A Fisher's Exact test was performed to analyze the percent of surviving animals in each group which developed latent and/or actual tumors and percent of animals started on study which developed actual tumors. Analysis of Variance tests (ANOVA) were performed in order to determine if differences in group means existed for the selected parameters. If a significant F ratio was obtained (p<0.05), a Dunnett's t-test was used for pair-wise comparisons of treatment test CSC groups to the Negative Control (non-Initiated DMBA) and test CSC groups with each other.

Incidence of Tumor-Bearing Animals

Statistical analysis of the incidence of animals bearing actual tumors (Fisher's Exact Test, p<0.05) indicated a significant increase in both the low- and high-dose groups receiving CSC-B when compared to the negative vehicle control group. Of the groups receiving the CSC-A, only the high-dose exhibited a significantly increased number of animals bearing actual tumors when compared to the negative vehicle control group. When comparing the incidence of animals bearing actual tumors in the low-dose CSC treatment groups to each other, a significant increase was noted in the groups that received CSC-B when compared to the group that received CSC-A. The same results were obtained when making the same comparisons in the groups receiving the high-dose CSC treatment. These findings are presented in TABLE 10.

TABLE 10

Statistical Results of Analysis of Percent of Animals Bearing Actual Tumors

| Group | Treatment | Percent of Animals Bearing Actual Tumors[a, b] |
| --- | --- | --- |
| 1 | Negative Vehicle Control | 0% |
| 4 | Low-Dose Brand A | 13% |
| 5 | High-Dose Brand A | 40% |
| 8 | Low-Dose Brand B | 53% |
| 9 | High-Dose Brand B | 78% |

[a]Represents the percent of animals started on study that developed at least one actual tumor.
[b]Significantly increased when compared to the group indicated in the superscript (Fisher's exact test, p < 0.05).

Statistical analysis of the incidence of animals bearing actual and/or latent tumors (Fisher's Exact Test, p<0.05) comparing the CSC treatment groups to the negative vehicle control indicated the same results as the analyses of animals bearing actual tumors discussed above.

Tumor Multiplicity

Statistical analysis of the number of actual tumors (papillomas and carcinomas combined) per animal, after 24 weeks, revealed significant increases (ANOVA, p≤0.05) in the groups treated with the high-dose CSC-B when compared to the negative control group (acetone-initiated Group 1). The number of actual tumors per animal in the group treated with the high-dose CSC-A group was statistically comparable to the negative vehicle control group. Analysis of the number of actual tumors per animal in the low-dose CSC treatment groups indicated the group treated with the low-dose Brand B CSC exhibited a statistically significantly increased number of actual tumors when compared to the negative control group. Group means, standard deviations, and statistical results are presented in TABLE 11.

TABLE 11

Statistical Results of Analysis Number of Actual Tumors per Animal

| Group | Treatment | Mean Number of Actual Tumors per Animal [a] |
| --- | --- | --- |
| 1 | Negative Vehicle Control | 0.00 ± 0.00 |
| 4 | Low-Dose Brand A | 1.03 ± 3.90 |
| 5 | High-Dose Brand A | 2.58 ± 8.05 |
| 8 | Low-Dose Brand B | 3.80 ± 7.22 |
| 9 | High-Dose Brand B | 7.46 ± 7.86 |

[a] Significantly increased when compared to the group indicated in the superscript.

When comparing the high-dose CSC treatment groups against each other, a statistically significantly increased number of actual tumors per animal was noted in the high-dose groups treated with the Brand B CSC when compared to the high-dose Brand A group. No statistically significant differences in the numbers of actual tumors were noted in the low dose CSC treatment groups when compared to each other. Statistical analysis of the number of actual and/or latent tumors (ANOVA, p≤0.05) indicated the same results as the analyses of the number of actual tumors per animal, as discussed above. Results are presented in the following Table.

TABLE 12

Statistical Results of Analysis Number of Latent and Actual Tumors per Animal

| Group | Treatment | Mean Number of Actual Tumors per Animal [a] |
|---|---|---|
| 1 | Negative Vehicle Control | 0.00 ± 0.00 |
| 4 | Low-Dose Brand A | 1.20 ± 4.33 |
| 5 | High-Dose Brand A | 2.75 ± 8.13 |
| 8 | Low-Dose Brand B | 4.73 ± 8.35 [1] |
| 9 | High-Dose Brand B | 8.49 ± 8.70 [1, 5] |

[a] Significantly increased when compared to the group indicated in the superscript.

Latency Period Until Appearance of Tumors

Mean latency per group when defined as the time elapsed until the appearance of the first actual tumor per animal was 18 weeks in the low-dose of both CSC-A and CSC-B treatment groups. In the high-dose CSC treatment groups, mean actual tumor latency was 19 and 15 weeks in the groups treated with CSCs obtained from Brands A and B, respectively.

Thus, the promotional capacity of the Brand A CSC was statistically comparable to the negative vehicle control group in terms of the incidences of tumor-bearing animals (at the low-dose level) and the number of tumors per animal (both dose levels). Statistical analysis comparing the groups that received the CSCs to each other revealed significant increases in the high-dose Brand B group when compared to the high-dose Brand A group in terms of percent of animals bearing designated tumor types and the number of those tumors per animal. Also, at the high-dose level, the Brand A CSC mean latency period (until the appearance of the first tumor per animal) was longer than the latency period of the Brand B CSC treatment groups. The data provided in this example confirm that the in vitro methods described herein, which utilize cell cultures that are contacted with CS, CSC, TS, TSC or TPM (see Examples 4, 5, and 8-13), accurately identify a tobacco product that has less potential to contribute to a tobacco-related disease than another tobacco product. The data provided in this example also confirm that the in vitro methods described herein (see Examples 4, 5, and 8-13), can be used to develop tobacco products that have a reduced potential to contribute to a tobacco-related disease and provide further evidence, in particular, that Brand A is a reduced risk tobacco product, as compared to Brand B.

Subsequent to exposure in vivo, the human body attempts to detoxify, neutralize, and eliminate cigarette smoke toxins through the action of Phase I and Phase II enzymes functioning in various metabolic pathways. During this detoxification process, however, a number of pro-carcinogenic compounds in tobacco smoke are bioactivated into reactive electrophiles that have potent carcinogenic potential in exposed cells. Thus, in order to dissect the full biological potential of complex chemical mixtures, such as a cigarette smoke condensate, it is desirable to evaluate the pattern of gene expression after tobacco smoke condensate exposure in an environment that contains a mixture of enzymes that mimic the detoxification process in mammalian cells. The S9 microsomal fraction from Aroclor 1254-treated rats, provides a set of enzymes that mimic the detoxification process in mammalian cells. Accordingly, experiments were conducted in the presence of the S9 microsomal fraction, as described in the following example, to elucidate how the genetic fingerprint of particular tobacco products shift in the presence of a mixture of enzymes that mimic the detoxification process in mammals.

Example 7

S9 Microsomal Fraction Experiments

NHBE cells were exposed to cigarette smoke condensate (CSC) in conjunction with an S9 microsomal fraction so as to identify the effect detoxification enzymes have on the pattern or level of gene expression. As a control to discriminate the effects of the S9 microsomal fraction on gene expression, alone, some experiments were conducted on NHBE cells in the presence of the S9 microsomal fraction in the absence of contact with a tobacco condensate. As described above, an HV analysis was performed on microarray results obtained from cells treated only with the S9 microsomal fraction for 2, 4, 8, and 12 hours.

Figure 34B:
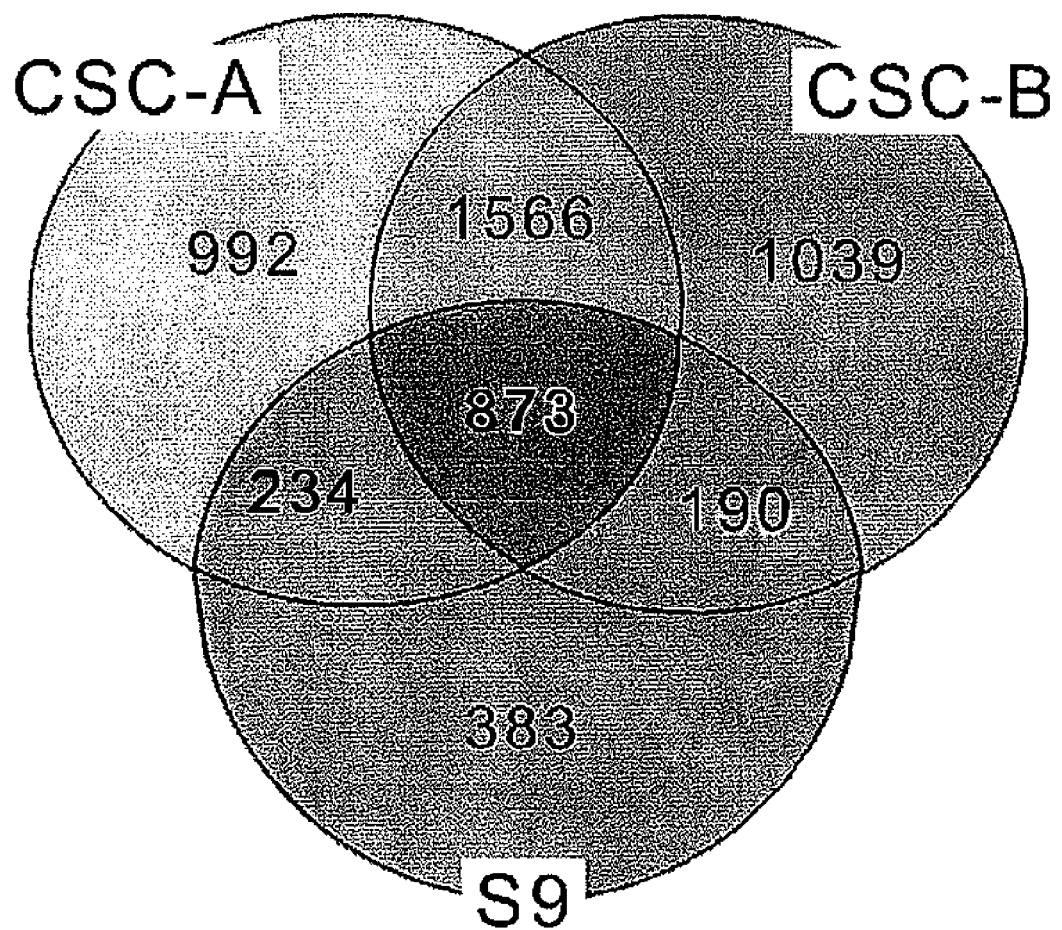
FIG. 34B is a Venn diagram comparing gene expression modulations induced by CSC-A (3665), CSC-B (3668), and S9 metabolic fraction (1680). The number of unique genes affected by each treatment is given, CSC-A (992), CSC-B (1039), and S9 (383) and the intersections between sectors reflect the number of genes that are affected by more than one treatment (e.g., a common set of 873 genes is affected by CSC-A, CSC-B and S9).

Several interesting observations emerged from this analysis. First, the expression of 1680 (7.9%) genes became HV sometime during the 12-hour exposure period with the S9 microsomal fraction (see FIG. 34B). Second, FIG. 34B also shows that 1297 of these 1680 genes were also HV in one or both CSC treatments, which is not surprising since all three treatment conditions (i.e., CSC-A, CSC-B, and S9) had the same concentration of S9 microsomal fraction. Third, even though the CSCs and the S9 microsomal fraction induce a HV state in a large common set of genes, CSCs and the S9 microsomal fraction did not affect these genes in similar ways indicating differential kinetic effects between the S9 microsomal fraction alone and the S9 microsomal fraction in conjunction with CSCs.

Subsequent to determining that the complex mixture of toxins and carcinogens in CSCs had a broad impact on the transcriptome of NHBE cells, it was contemplated that a sustained treatment to CSCs (e.g., over a 12-hour period) would also allow detection, not only of alterations such as induction and suppression, but of gene induction/suppression with transient, sustained, or periodic characteristics. Accordingly, the kinetic effects of gene expression profiles generated from cells treated with CSC-A, CSC-B, or S9 microsomal fraction from 0-12 hours using F-cluster analysis were defined, which is a statistically robust method for defining clusters of genes with similar expression patterns over time. These experiments are described in the following example.

Example 8

Gene Expression Kinetics in CSC-Treated Cells

In this analysis, the normal variance of the system was calculated and used to identify a statistical threshold for cluster selection at which groups of genes were likely to cluster by chance. This threshold was then used for further analysis to ensure the statistical robustness of the clustering process. The biologic significance of the cluster is related to cluster size, as the largest clusters identified represent synchronous changes in the greatest number of cellular processes. (See Spellman et al., Mol Biol Cell 9: 3273-3297, 1998). Specifically, larger clusters represent, in a statistically robust manner, the most significant experimentally induced processes in these cells. When F-cluster analysis was applied to the total HV set of 4894 genes/ORFs, 306 clusters were defined by statistical analysis, the majority of which contained less than 50 member genes. Cluster numbers were arbitrarily assigned from −150 to 150, with the corresponding positive and negative numbers representing complementary gene expression patterns (e.g., steady increase in expression over time compared to a steady decrease in expression).

Figure 35A:
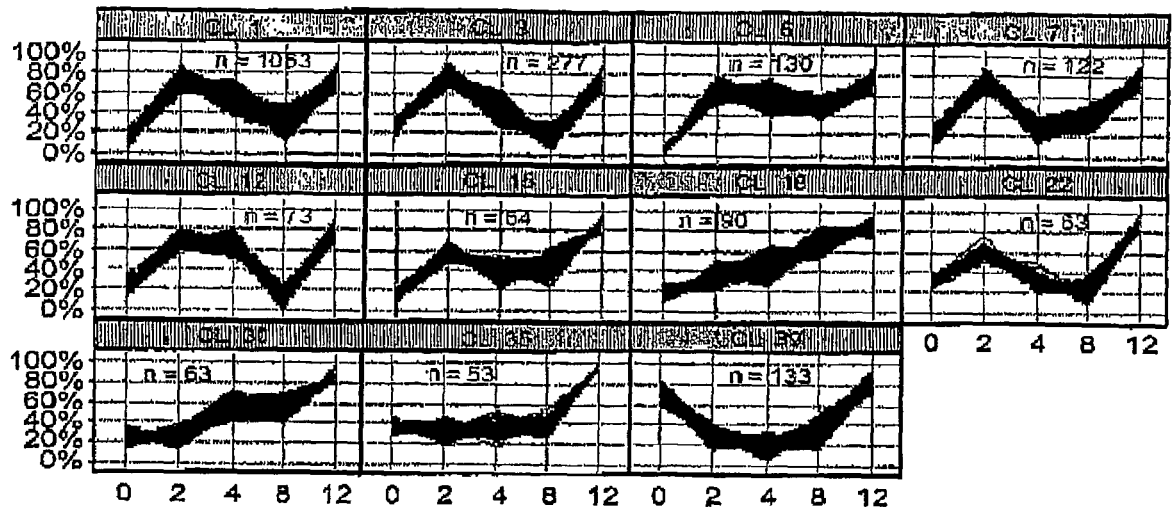
FIG. 35A-C illustrate gene expression profiles between 0 and 12 hours, which are expressed a percent of highest expression value for each gene. F-cluster numbers are given at the top of each cluster of profiles. The number of member genes in each cluster (n) is shown for each cluster.
Figure 35B:
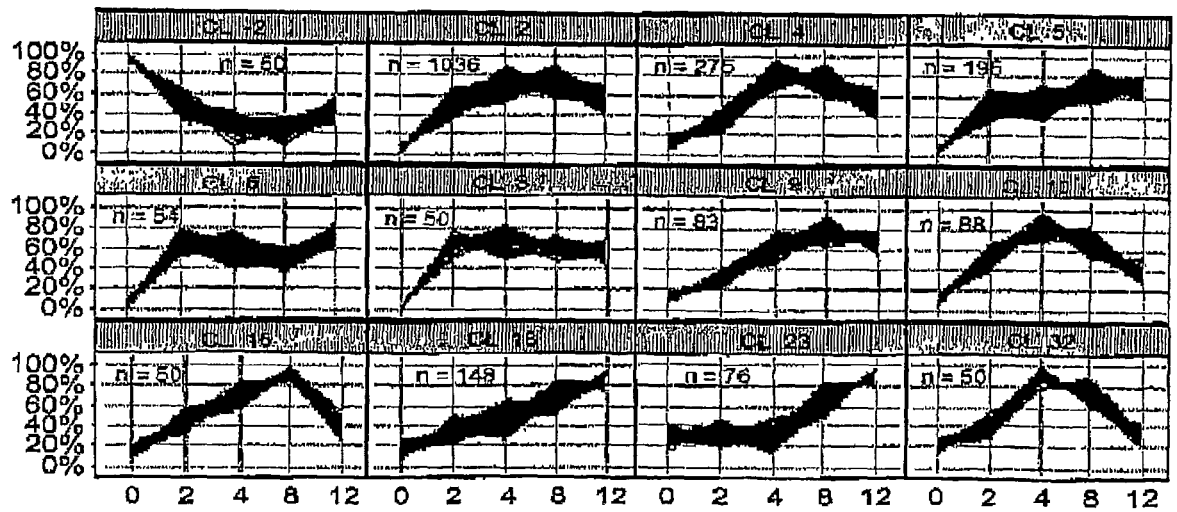
Figure 35C:
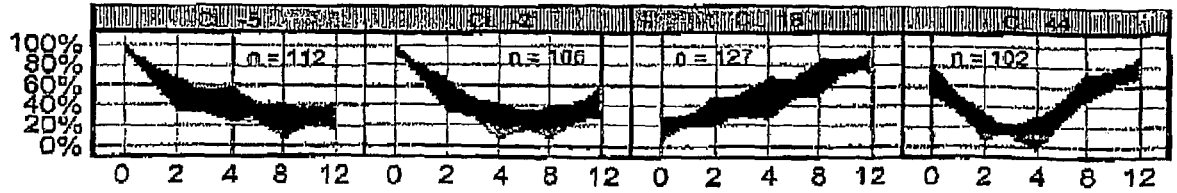

In each of the three treatment conditions, clusters containing 50 or more genes were chosen for further characterization because this cutoff generated a sufficient number of large clusters that adequately represented the major kinetic changes caused by each treatment (see FIGS. 2 A-C and TABLE 13). As predicted, gene expression changes induced by CSCs were complex, with the majority of clusters in CSC-treated cells being multi-modal (see FIGS. 2A and B). For example, in CSC-A-treated cells, genes in clusters 1, 3, 7, 12, 15, and 22 were up-regulated within the first two hours, began to return to baseline, then were once again induced late in the experiment, indicating that initial treatment effected gene expression and some secondary effect (e.g., a CSC metabolite or the action of early gene expression changes, reinitiated a cellular response). (See FIG. 35A). While genes within each of these clusters showed early increases in expression (within the first 2 h of treatment), indicating that CSC-A treatment had immediate effects on cells, Clusters 18, 30, 35, and 39 showed a later increase in gene expression (i.e., ≥4 h). FIG. 35B shows that in CSC-B treated cells, cluster analysis revealed that gene expression peaks primarily between 4-8 hours, as opposed to a 2 hour peak in CSC-A treated cells, providing evidence that some of the effects of CSC-B treatment were delayed with respect to those of CSC-A (e.g., see clusters 4, 5, 9, 10, 16, and 32). These data are in distinct contrast to the major clusters of genes in S9-only treated cells, which displayed simple kinetics, i.e., expression decreasing or increasing continuously over time (see FIG. 35C). Although 66% of HV genes affected by CSC-A and CSC-B were identical (see FIG. 34), it is clear from FIG. 35 that the expression kinetics for these genes were nevertheless distinct for the two different CSCs. This is evidenced by the fact that the predominant coordinated behavior in CSC-A-treated cells is represented by the largest cluster (i.e., cluster 1), that contains 1063 HV genes and whose expression peaked at 2 hours post-treatment. This is in contrast to CSC-B-treated cells in which case the predominant behavior of genes is represented by cluster 2, which contains 1,036 genes and whose expression peaked at 4-8 hours, indicating that some of the effects of CSC-B treatment are delayed with respect to those of CSC-A.

TABLE 13

HV Genes Specific for CSC-A and CSC-B Treatment

| GenBank accession no. | Gene abbreviation | Gene description |
|---|---|---|
| AB032985 | NXPH3 | Neurexophilin 3 |
| AB046848 | KIAA1628 | KIAA1628 protein |
| AB058772 | SEMA6C | Sema domain, transmembrane domain (TM), and cytoplasmic domain, (semaphorin) 6C |
| AF178532 | BACE2 | Beta-site APP-cleaving enzyme 2 |
| BC015737 | | Homo sapiens, ninjurin 2, clone MGC: 22993 IMAGE: 4907813 |
| BC015929 | NR1D2 | Nuclear receptor subfamily 1, group D, member 2 |
| BC017732 | STRBP | Spermatid perinuclear RNA binding protein |
| M23326 | TRDV3 | T cell receptor delta variable 3 |
| NM_000341 | SLC3A1 | Solute carrier family 3 (cystine, dibasic and neutral amino acid transporters, activator of cystine), member 1 |
| NM_000663 | ABAT | 4-aminobutyrate aminotransferase |
| NM_000922 | PDE3B | Phosphodiesterase 3B, cGMP-inhibited |
| NM_000981 | RPL19 | Ribosomal protein L19 |
| NM_001383 | DPH2L1 | Diptheria toxin resistance protein required for diphthamide biosynthesis-like 1 (S. cerevisiae) |
| NM_002046 | GAPD | Glyceraldehyde-3-phosphate dehydrogenase |
| NM_002757 | MAP2K5 | Mitogen-activated protein kinase kinase 5 |
| NM_002890 | RASA1 | RAS p21 protein activator (GTPase activating protein) 1 |
| NM_003286 | TOP1 | Topoisomerase (DNA) I |
| NM_003408 | ZFP37 | Zinc finger protein 37 homolog (mouse) |
| NM_004057 | CALB3 | Calbindin 3, (vitamin D-dependent calcium binding protein) |
| NM_004066 | CETN1 | Centrin, EF-hand protein, 1 |
| NM_004083 | DDIT3 | DNA-damage-inducible transcript 3 |
| NM_004282 | BAG2 | BCL2-associated athanogene 2 |
| NM_004846 | EIF4EL3 | Eukaryotic translation initiation factor 4E-like 3 |
| NM_004939 | DDX1 | DEAD/H (Asp-Glu-Ala-Asp/His) box polypeptide 1 |
| NM_005476 | GNE | UDP-N-acetylglucosamine-2-epimerase/N-acetylmannosamine kinase |
| NM_005619 | RTN2 | Reticulon 2 |
| NM_007217 | PDCD10 | Programmed cell death 10 |
| NM_007275 | FUS1 | Lung cancer candidate |
| NM_012192 | FXC1 | Fracture callus 1 homolog (rat) |
| NM_012288 | KIAA0057 | TRAM-like protein |
| NM_013366 | APC2 | Anaphase-promoting complex subunit 2 |
| NM_013401 | RAB3IL1 | RAB3A interacting protein (rabin3)-like 1 |
| NM_014395 | DAPP1 | Dual adaptor of phosphotyrosine and 3-phosphoinositides |
| NM_015057 | KIAA0916 | KIAA0916 protein |
| NM_017491 | WDR1 | WD repeat domain 1 |
| NM_017581 | CHRNA9 | Cholinergic receptor, nicotinic, alpha polypeptide 9 |
| NM_020122 | PCMF | Potassium channel modulatory factor |
| NM_020685 | HT021 | HT021 |
| NM_021120 | DLG3 | Discs, large (Drosophila) homolog 3 (neuroendocrine-dlg) |
| NM_031310 | PLVAP | Plasmalemma vesicle associated protein |

Accordingly, these experiments demonstrated that not only do different tobacco products induce different genes, gene expression patterns, and kinetics of gene expression but different tobacco products have a different impact on a cell or a tobacco consumer. That is, the procedures described above can be used to obtain a genetic signature, pattern, or profile for a plurality of tobacco products and, because some of the modulated genes are associated with the induction or repression of a tobacco-related disease, this data can be compared and/or analyzed to identify a tobacco product with a reduced potential to contribute to a tobacco-related disease.

Since clusters with a large number of member genes reflect predominant biological behavior patterns that are likely to be functionally interrelated, it was contemplated that the cluster 1 set of 1063 genes from CSC-A-treated cells and the cluster 2 set of 1036 genes from CSC-B-treated cells corresponded to important biological phenomena common to the two CSCs. If this were correct, then despite the fact that CSC-A and CSC-B treatments modulate genes in a temporally distinct manner, the two clusters should contain many of the same genes. To demonstrate this point, the experiments in the following example were conducted.

Example 9

Analysis of Cluster 1 and Cluster 2 in CSC-Treated Cells

Upon analysis of cluster 1 and cluster 2 in CSC-treated cells, it was found that a set of 554 genes (approximately 50% of the genes in each cluster) were present in both cluster 1 (from CSC-A) and cluster 2 (from CSC-B). A total of 330 genes from this set of 554 genes (59.5%) have known functions while the remaining 224 are ORFs.

Functional classification of these 330 genes common to cluster 1 and cluster 2 indicates that 10% have functional roles in proliferation, 12.4% in transcription, 4.5% in apoptosis, and 5.1% in damage/repair responses. In addition, as shown in TABLE 7, 34 (10%) of the identified genes are documented as having roles in diseases that are associated with/long-term tobacco exposure (e.g., lung cancer, coronary heart disease, and asthma).

Figure 36:
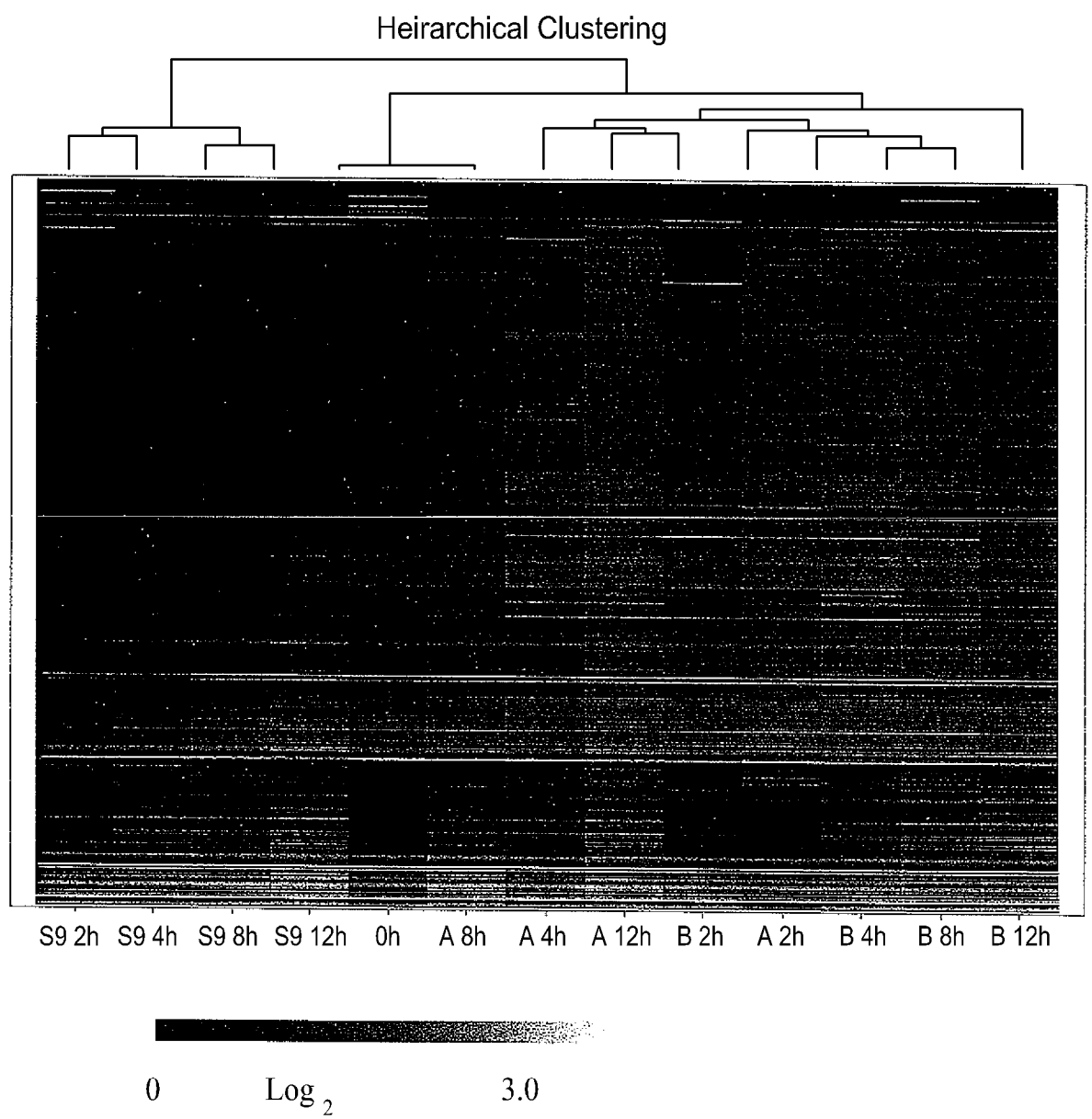
FIG. 36 illustrates a cluster analysis of genes that were hypervariable (HV) in all three treatment groups (A: CSC-A, B: CSC-B, and S9) in the form of a Dendrogram that depicts the hierarchical relationship between the three treatments based on their gene expression patterns at all time points from 0-12 hours.

In clear contrast to both CSC-A and CSC-B treated cells, the S9 microsomal fraction-treated cells show a pronounced tendency towards suppression of gene expression. An F-clustering analysis of the S9 microsomal fraction data (shown in FIG. 35C) resulted in only four clusters that contained 50 or more genes. Clusters 2, 5, and 44 all show decreases in gene expression level with a nadir at 4-8 h. Cluster 18 contains genes that show an increase in gene expression levels, but whose expression peaks at 12 h, which is notably different from the robust early gene responses elicited by treatment with both CSCs. Additional evidence that the overall effects of S9 microsomal fraction and CSC exposure on gene expression levels are quite distinct was obtained when traditional hierarchical clustering algorithms were used to compare the overall differences in HV gene expression in each treatment group over the entire 12-hour time course. FIG. 36 shows the results of this analysis for the common subset of genes that were HV in all three treatment groups (i.e., the 873 genes denoted in FIG. 34). Notably, the expression data for these 873 genes partition into two separate groups with S9-treated cells being clearly distinguishable from CSC-A and CSC-B treated cells, which are similar to each other. The data further indicate that the S9 microsomal fraction exerts a largely suppressive effect on the transcriptome of NHBE cells in contrast to a predominant inductive effect of CSC-A and CSC-B.

As discussed above, tobacco smoke condensates induce a range of temporally distinct alterations to the homeostatic transcriptome of the NHBE cells, which were unique in that they were qualitatively and quantitatively dissimilar from the effects of exposure to a S9 microsomal fraction. In an attempt to define a biological context for these data, correlation analyses was used to identify genes whose expression changes were highly correlated in CSC-A and CSC-B treated cells but not in S9-treated cells. This was achieved using a Monte Carlo analysis to establish a statistical threshold above which correlated behavior was unlikely to have occurred by chance. By this approach, gene expression levels were randomized maintaining the same mean and standard deviation. A correlation coefficient was then identified above which no genes were correlated in the randomized data sets. The probability that genes that correlate in experimental data sets above this threshold would occur by chance is <1/total number of genes analyzed. The following example describes these experiments in greater detail.

Example 10

Defining CSC-Specific Toxicological Effects

The evidence provided in FIGS. 2 and 3 indicated that the effect of exposure to CSC was significantly different than exposure to an S9 microsomal fraction. Using the Monte Carlo analysis, as shown in TABLE 13, forty HV genes were identified as having a modulation of gene expression that was correlated in CSC-A and CSC-B treated cells but not in S9-treated cells. The similarities between the two tobacco-treated sample groups can be visualized by applying a correlation coefficient analysis to the genes within a given treatment, representing this visually in a correlation mosaic, and comparing the visual pattern of the mosaic to other such mosaics generated using data from different treatments. The correlation coefficients of these genes were presented in a correlation mosaic map (see FIG. 37) in which genes with a highly correlated behavior were denoted by a grey pixel, and genes with highly negatively correlated behavior by a black pixel. This mosaic provided a way to assess the similarities of expression behavior of the correlated genes in CSC-A, CSC-B, and S9-treated cells by visual inspection.

The highly correlated expression characteristics of the CSC-impacted genes identified by this analysis indicated that these genes were likely to participate in pathways relevant to the effects specific to CSC exposure and not to exposure to the S9 microsomal fraction. These pathways were more clearly defined using PathwayAssist™ software (Stratagene, La Jolla, Calif.), a commercially available visualization engine that scans and assesses documented literature and available standardized databases in order to filter, classify, and prioritize proteins in terms of their functional relationships to known biological pathways. The results, provided in FIG. 38, highlight the fact that this set of genes encodes proteins that play key roles in pathways that are relevant to the documented pathological effects of cigarette smoke. For example, several of the genes listed in TABLE 13 are implicated in lung oncogenesis (e.g., FUS1, GAPD, & semaphorin), in various types of dysfunctions in lung cells involving apoptosis (e.g., PDE3B, PDCD10), in cell cycle control (e.g., MAP2K5, RASA1, APC2, RASA1), in DNA topology and DNA repair (e.g., TOP1, DDIT3), and in cellular stress (e.g., BAG2). In addition, several genes are involved in neurosignaling (e.g., neurexophilin, KIAA1628), neuroregeneration (e.g., semaphorin), neuropathology (e.g., BACE2, ABAT, DLG3), and inflammation (e.g., NINJ2, TRDV3, SLC3A1).

The induction of a range of neuroendocrine-related genes is interesting in light of the fact that many small cell lung cancers and some non-small cell lung cancers exhibit a variety of pathological and molecular features of pulmonary endocrine cells, and can be stimulated by an autocrine/paracrine array of neuroendocrine peptides. Accordingly, expression of neuroendocrine markers has been shown to be useful in the differential diagnosis of lung cancers. The gene set shown in TABLE 13 also includes CHRNA9, a human nicotinic acetylcholine receptor expressed in several tissues including inner ear hair cells, brain, and in activated fibrosarcoma cells and whose relevance to nicotine signaling in primary lung cells is as yet uncharacterized.

Figure 37:
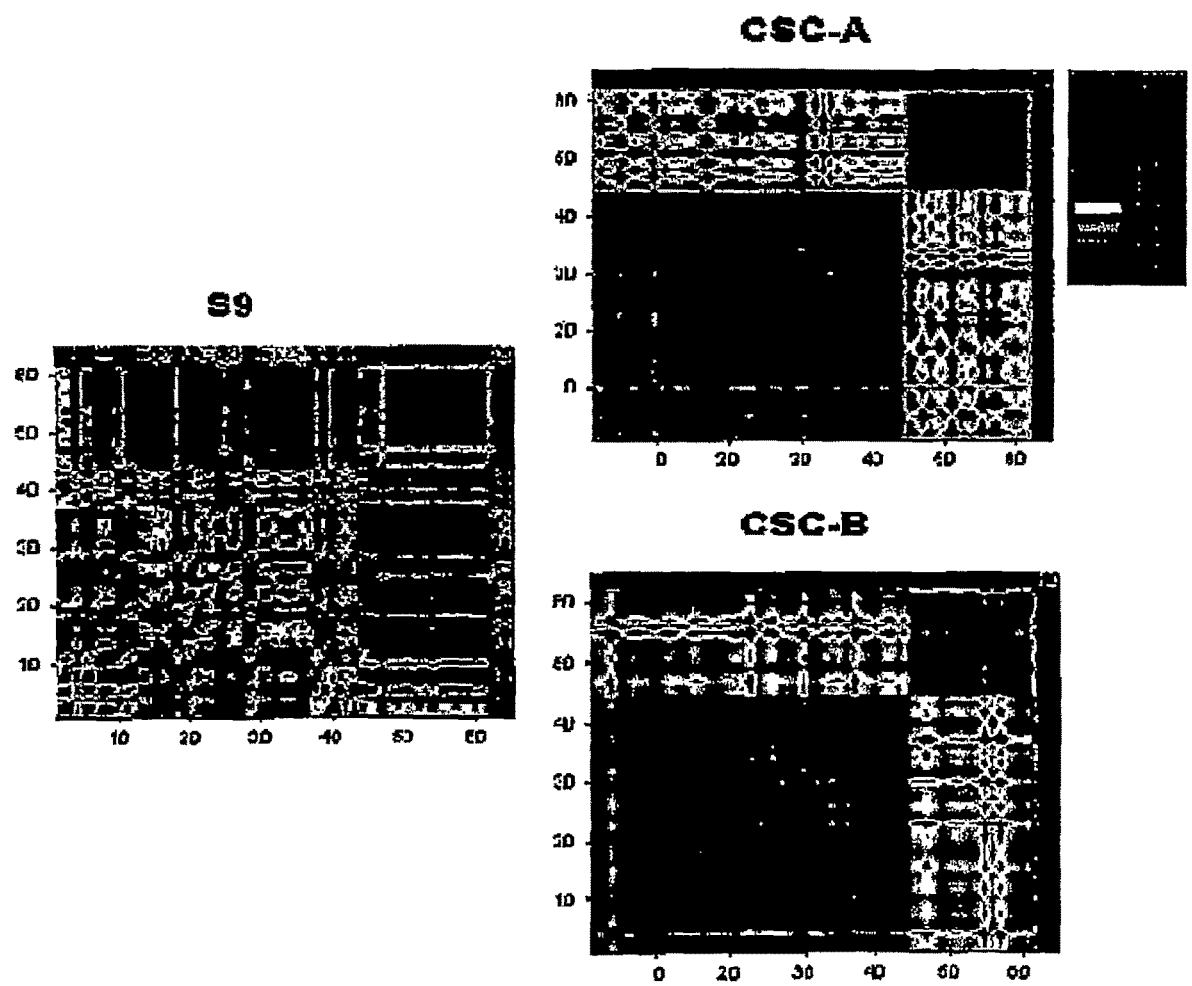
FIG. 37 shows correlation mosaics of the genes listed in Table 2. Correlation coefficients were generated for each of the 40 genes in Table 2, comparing the set to itself in each of the three conditions. The same gene order runs across the x and y axes of the mosaics. Correlation mosaics for HV genes highly correlated in response to CSC-A and CSC-B, and not correlated with responses to S9. Each pixel in the plot represents a correlation coefficient of gene expression. Genes highly positively correlated are denoted in gray and those highly negatively correlated are in black. The same order of the genes along axis is used for all three mosaics. Genes highly correlated in CSC-A and CSC-B, but not in S9-treated cells are denoted as a gray cluster in the lower left hand corner of CSC-A and the CSC-B mosaic. This cluster is disrupted in the S9 mosaic demonstrating the variance in gene regulation that occurred in S9-treated cells.

Using a similar approach, as described for the analysis of CSC exposure in TABLE 13 and FIG. 37, the global effects of the exposure to the S9 microsomal fraction were assessed by first identifying the subset of HV genes that were correlated among all three treatment groups and then assuming that the effect on these genes was due to the S9 microsomal fraction solely, since their expression characteristics did not change when the S9 microsomal fraction was combined with contact to a CSC. As described above, a Monte Carlo analysis was performed to define a statistically robust correlation coefficient unlikely to occur by chance. Using this threshold, the probability of identifying a gene correlated in all three groups by chance was <1/total number of genes analyzed, thereby confirming the high statistical specificity of this method.

Figure 39:
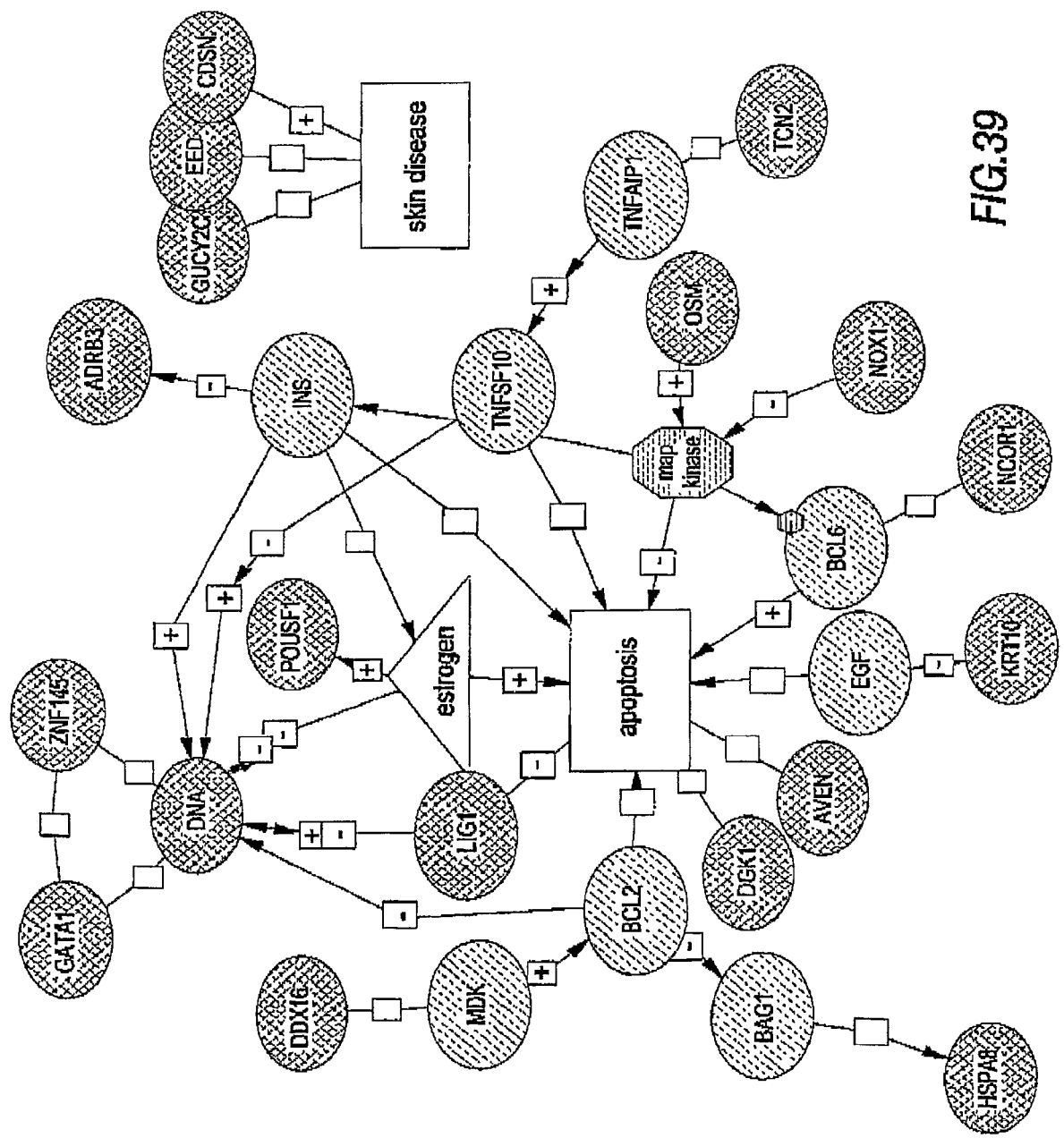
FIG. 39 shows the functional associations of genes, which are highly correlated in all three treatment groups (CSC-A, CSC-B, and S9). The genes, pathways, and functional interconnections among these elements for genes correlated in all three treatment groups are represented. Gene and pathway symbols are described in FIG. 38. Cross-hatched ovals indicate genes from Table 3 (i.e., genes specific for S9 treatment). Ovals with slanted lines (indicate additional proteins not in Table 3), cross-hatched oval (cell object—DNA) and white triangle (indicating small molecule—estrogen) were added to better define the regulatory networks of the genes identified in this analysis. Ovals with dashed lines indicate classes of functional peptides. White rectangles indicate cellular processes in which these genes participate. Each line indicates a regulatory relationship (binding, regulation, etc.) based upon a literature reference. Regulatory relationships are denoted in a box on the line with positive regulation represented as a plus sign, negative regulation as a minus sign, and unknown relationships by no sign.

As shown in TABLE 14, a set of 52 genes was identified and the probable function of these genes was assessed using PathwayAssist™ software (see FIG. 39). Many of the genes appeared to have roles in modulating apoptosis (e.g., AVEN, LIG1, PTEN, etc.) indicating that the predominant cellular response to chronic S9 microsomal fraction exposure is to activate apoptotic programs. A second group of S9-modulated genes modulates cellular surface chemistry, adhesion, and cellular differentiation (e.g., SIAT4B, KRT10, CDSN and EXT2). These results indicate that the inclusion of S9 microsomal fractions in toxicogenetic experiments significantly modulates cellular physiology, which may complicate and bias the results assessing the effects of CSCs or any other type of complex hydrocarbon mix requiring metabolic activation.

TABLE 14

Genes Specific for S9 Treatment

| GenBank accession no. | Gene abbreviation | Gene description |
| --- | --- | --- |
| NM_001303 | COX10 | COX10 homolog, cytochrome c oxidase assembly protein |
| AK056540 | | *Homo sapiens* cDNA FLJ31978, weakly similar to Probable hexosyltransferase |
| NM_016013 | LOC51103 | CGI-65 protein |
| NM_031916 | ASP | AKAP-associated sperm protein |
| NM_000947 | PRIM2A | Primase, polypeptide 2A (58 kD) |
| NM_006927 | SIAT4B | Sialyltransferase 4B |
| NM_006441 | MTHFS | 5,10-methenyltetrahydrofolate synthetase |
| NM_002699 | POU3F1 | POU domain, class 3, transcription factor 1 |
| NM_002954 | RPS27A | Ribosomal protein S27a |
| AK055508 | FLJ11785 | Rad50-interacting protein 1 |
| NM_024636 | FLJ23153 | Likely ortholog of mouse tumor necrosis-alpha-induced adipose-related protein |
| BC011231 | | *Homo sapiens*, Similar to angiotensinogen |
| NM_007052 | NOX1 | NADPH oxidase 1 |
| NM_000234 | LIG1 | Ligase I, DNA, ATP-dependent |
| NM_032553 | FKSG79 | Putative purinergic receptor |
| NM_000025 | ADRB3 | Adrenergic, beta-3-, receptor |
| AF023203 | | *Homo sapiens* homeobox protein Og12 |
| U50536 | | Human BRCA2 region, mRNA sequence CG011 |
| NM_000421 | KRT10 | Keratin 10 (epidermolytic hyperkeratosis; keratosis palmariset plantaris) |
| NM_001264 | CDSN | Corneodesmosin |
| NM_000355 | TCN2 | Transcobalamin II; macrocytic anemia |
| NM_000401 | EXT2 | Exostoses (multiple) 2 |
| NM_014214 | IMPA2 | Inositol(myo)-1(or 4)-monophosphatase 2 |
| NM_003797 | EED | Embryonic ectoderm development |
| AF319523 | | *Homo sapiens* RT-LI mRNA, complete sequence |
| AF074331 | PAPSS2 | 3'-phosphoadenosine 5'-phosphosulfate synthase 2 |
| AF189011 | RNASE3L | Putative ribonuclease III |
| BC009752 | | *Homo sapiens*, Similar to sex comb on midleg-like 1 (*Drosophila*) |
| NM_000691 | ALDH3A1 | Aldehyde dehydrogenase 3 family, memberA1 |
| NM_006006 | ZNF145 | Zinc finger protein 145 (expressed in promyelocytic leukemia) |
| NM_005831 | NDP52 | Nuclear domain 10 protein |
| L26584 | RASGRF1 | Ras protein-specific guanine nucleotide-releasing factor 1 |
| NM_014182 | HSPC160 | HSPC160 protein |
| NM_004963 | GUCY2C | Guanylate cyclase 2C (heat stable enterotoxin receptor) |
| AB023223 | STXBP-TOM | Tomosyn |
| NM_018919 | PCDHGA6 | Protocadherin gamma subfamily A, 6 |
| NM_002968 | SALL1 | Sal-like 1 (*Drosophila*) |
| NM_003587 | DDX16 | DEAD/H (Asp-Glu-Ala-Asp/His) box polypeptide 16 |
| AK024449 | PP2135 | PP2135 protein |
| AB034205 | LUC7A | Cisplatin resistance-associated overexpressed protein |
| BC011589 | OSM | Oncostatin M |
| NM_006597 | HSPA8 | Heat shock 70 kD protein 8 |
| NM_004384 | CSNK1G3 | Casein kinase 1, gamma 3 |
| AK057672 | | *Homo sapiens* cDNA FLJ33110 fis |
| NM_016344 | PRO1900 | PRO1900 protein |
| NM_018651 | ZFP | Zinc finger protein |
| NM_004717 | DGKI | Diacylglycerol kinase, iota |
| NM_006479 | PIR51 | RAD51-interacting protein |
| AK024250 | | *Homo sapiens* cDNA FLJ14188 fis |

TABLE 14-continued

Genes Specific for S9 Treatment

| GenBank accession no. | Gene abbreviation | Gene description |
|---|---|---|
| NM_001382 | DPAGT1 | Dolichyl-phosphate N-acetylglucosaminephosphotransferase 1 |
| NM_020371 | AVEN | Cell death regulator aven |
| NM_006311 | NCOR1 | Nuclear receptor co-repressor 1 |

Discriminant Function Analysis (DFA) is a form of multivariate analysis that identifies subsets of dependent variables that characterize a system made up of related groups. In this kind of gene expression analysis, a linear equation is calculated, denoted a root, whose overall value is distinct for a given characterized group. Accordingly, DFA identifies genes most characteristic of a given state. DFA analysis was conducted on the genes that were correlated after CSC treatment but not correlated after S9 treatment, as described in the following example.

Example 11

Refined Analysis of CSC-Correlated Genes Using Discriminant Function Analysis (DFA)

The set of 40 genes that were correlated after CSC treatments (see Table 13 and FIG. 37) but not correlated after S9 microsomal fraction treatment were further analyzed using DFA. Of the 40 CSC-correlated genes, 11 were identified by DFA as being most highly distinct among CSC and S9 treated cells (Table 15). Interestingly, a significant number of these genes were associated with oncogenesis. For example, this gene set included 3 putative proto-oncogenes including (1) MAP2K5, the over-expression of which is associated with increased proliferative and invasive potential of metastatic prostate cancer and is reported to be a potent survival molecule in APO-MCF-7 breast carcinoma cells; (2) DDIT3, a C/EBP transcriptional regulator involved in growth arrest induced by DNA damage that is a common breakpoint in human myxoid liposarcomas; and (3) BAG2, a BCL-2-binding apoptosis suppressor that is over-expressed in human cervical, breast and lung cancer cell lines. In addition, three putative tumor suppressor genes were also identified in this gene set. These were FUS1, RASA1, and FPH2L1. FUS1 can inhibit tumor cell growth by inducing apoptosis, and was first identified in a search for potential tumor suppressors within a critical homozygous deletion region at 3p21.3 common in lung cancers. RASA1 as a key member of the GAP1 family of GTPase-activating proteins plays a key role in the Ras signaling pathway. DPH2L1 is a BRCA1-induced gene that maps within a region of 17p13.3, which is deleted in 80% of all ovarian epithelial malignancies. DPH2L1 was identified by exon trapping in this region and was implicated as a tumor suppressor as its expression is reduced or undetectable in ovarian tumors and tumor cell lines. In addition, a nicotinic cholinergic receptor, CHRNA9, and two putative neural growth factors, NxpH3, a neuropeptide-like neural signaling molecule, and NINJ2, a gene up-regulated in damaged nerve cells that upregulates neurite outgrowth, were also identified in this gene set. The impact on neural growth factors is not surprising in light of the fact that many lung cancers express neuroendocrine features and are also stimulated by an autocrine/paracrine system of neuroendocrine peptide hormones.

Figure 40:
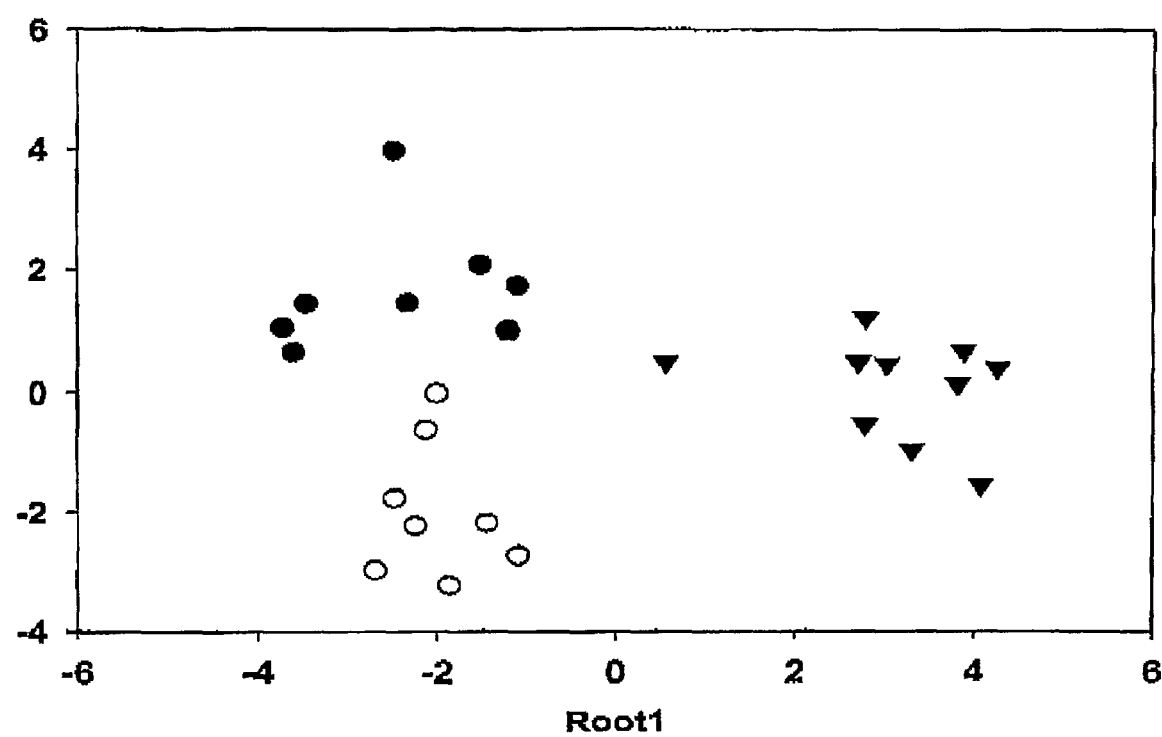
FIG. 40 shows the results of a discriminant function analysis (DFA), which identified genes having high discriminatory capabilities. Values of the roots obtained by DFA analysis were used to graphically depict the differences of the gene expression values obtained for the three treatments (CSC-A, CSC-B, and S9). Root values for the 2-12 h time points for each treatment are represented by filled circles (CSC-A), open circles (CSC-B), and filled triangles (S9).

A graphical representation of the DFA results for the three treatment conditions at all time points was generated. The spatial organization of the elements in this representation provided a measure of the overall variance among groups (see FIG. 40). The genes used for this analysis were correlated in CSC exposed cells and not correlated in S9-treated cells. A correlation coefficient of 0.8 was used as a threshold for defining similarity. The expression of these genes should therefore be similar in CSC-treated cells. Indeed the two CSC groups were more closely associated than either CSC group was to the S9 microsomal fraction-treated group. Of note, the samples from the CSC groups did not overlap, indicating that the two CSC treatments elicit somewhat distinct responses even in genes highly correlated in their behavior in each CSC group.

TABLE 15

Discriminant Function Analysis of CSC-Correlated Genes

| GenBank accession no. | Gene abbreviation | Gene description |
|---|---|---|
| M23326 | TRDV3 | T cell receptor delta variable 3 |
| NM_002757 | MAP2K5 | Mitogen-activated protein kinase kinase 5 |
| NM_004083 | DDIT3 | DNA-damage-inducible transcript 3 |
| NM_004282 | BAG2 | BCL2-associated athanogene 2 |
| NM_007275 | FUS1 | Lung cancer candidate |
| NM_003408 | ZFP37 | Zinc finger protein 37 homolog (mouse) |
| NM_002046 | GAPD | Glyceraldehyde-3-phosphate dehydrogenase |
| NM_017581 | CHRNA9 | Cholinergic receptor, nicotinic |
| BC015737 | NINJ2 | Ninjurin 2 |
| AB032985 | NXPH3 | Neurexophilin 3 |
| NM_002890 | RASA1 | RAS p21 protein activator |
| NM_001383 | DPH2L1 | Diptheria toxin resistance protein |

Figure 38:
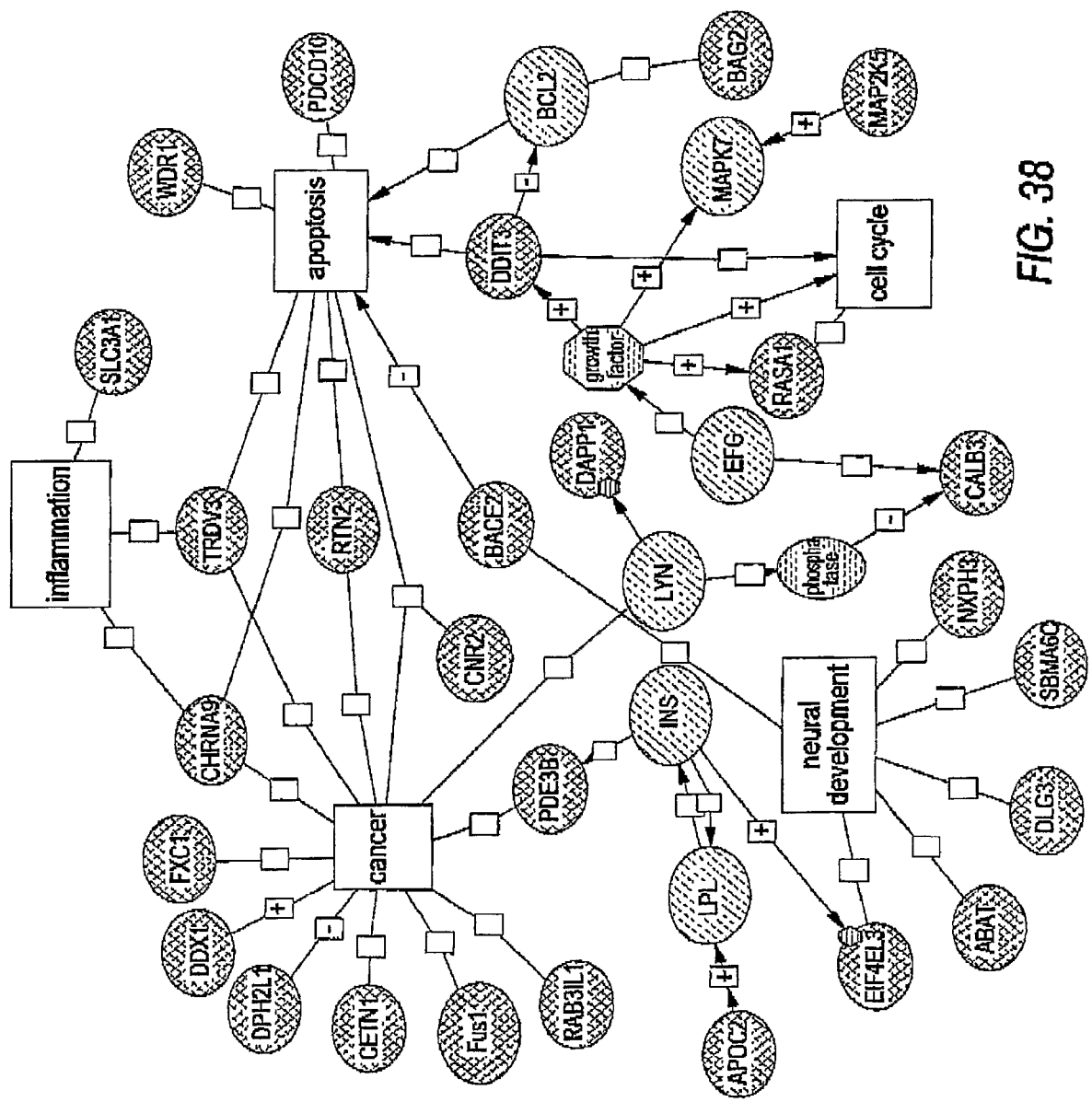
FIG. 38 shows the functional associations of HV genes specific for CSC-A and CSC-B treatment. The expression patterns of this set of genes are highly correlated in CSC-treated NHBE cells and not correlated with those seen in cells treated with S9 alone. Cross-hatched ovals indicate genes from Table 2 (i.e., HV genes specific for CSC-A and CSC-B treatment). Ovals with slanted lines (indicating additional proteins not in Table 2) were added to better define the regulatory networks of the genes identified in this analysis. Ovals with dashed lines indicate classes of functional peptides. Rectangles indicate cellular processes in which these genes participate. Each line indicates a regulatory relationship (binding, regulation, etc.) based upon a literature reference. Regulatory relationships are denoted in a box on the line with positive regulation represented as a plus sign, negative regulation as a minus sign, and unknown relationships by no sign.
Figure 41:
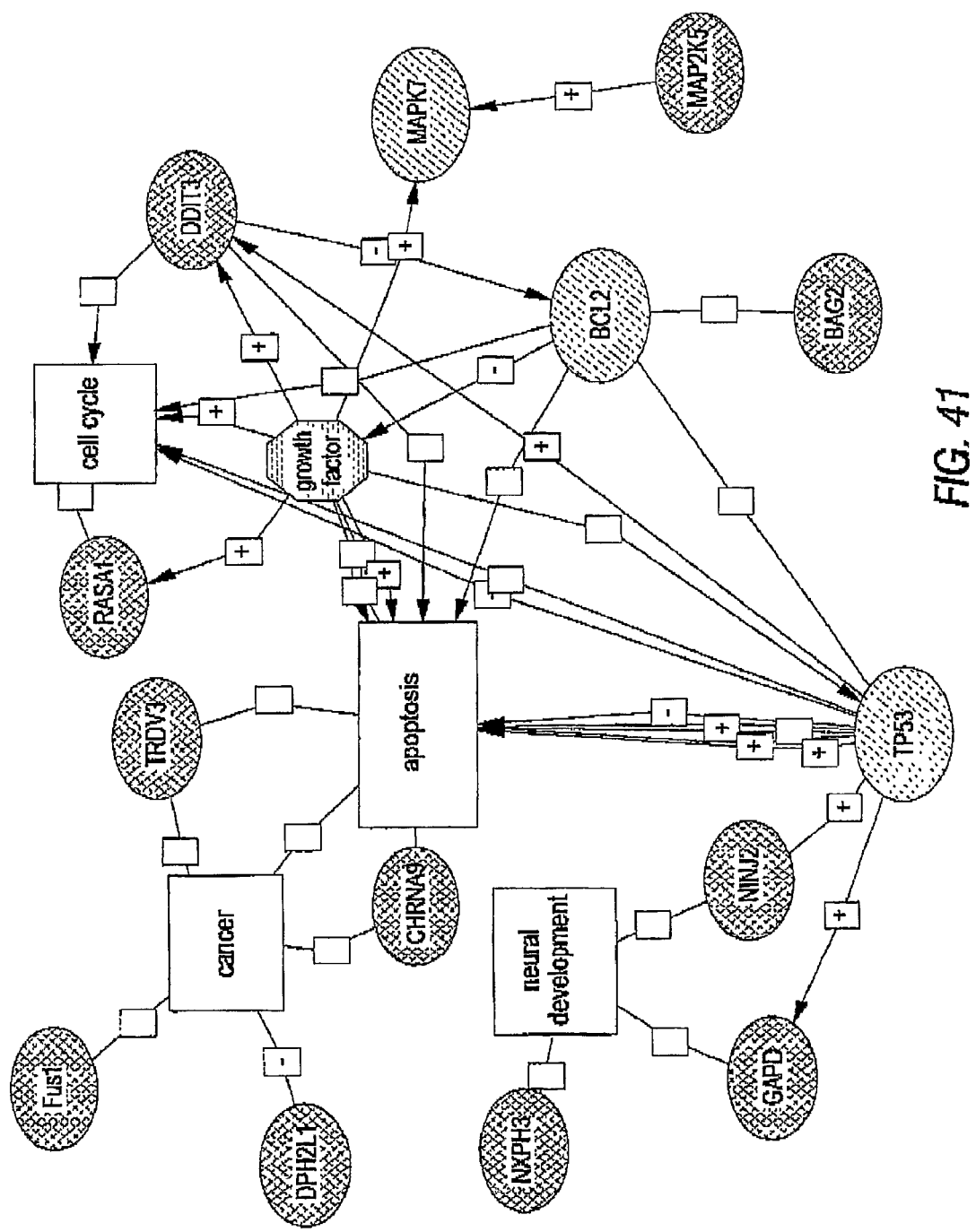
FIG. 41 shows the functional associations of genes, which are provided in Table 3. The genes, pathways, and functional interconnections among these elements for genes having the highest discriminatory potential among all three treatment groups are represented. Gene and pathway symbols are described in previous figures.

FIG. 41 shows the result of a functional analysis of the gene set in TABLE 14 using Pathway Assist. Not surprisingly, the major cellular processes affected by these genes were subset of the processes affected by the parent gene set, as illustrated in FIG. 38.

Four post-treatment expression characteristics were established for each gene on the array: (1) whether or not the gene was expressed above background at each time-point; (2) whether or not the gene showed hypervariability (i.e. change greater than normal) of expression in one, two, or all three treatment conditions over the 12 h treatment period; (3) what was the specific pattern of gene expression over the 12 h treatment period; and (4) whether or not the gene expression pattern in each condition correlated with its behavior under the two other conditions from 0-12 h. Several interesting observations emerged from this analysis. Significantly, treatment of NHBE cells with CSCs from two American brands of cigarettes altered the expression of approximately 3600 genes and ORFs (or 17% of the array) sometime during the 12-hour exposure (see FIGS. 1 and 2). These data provide evidence that due to their chemical complexity and temporal requirement for metabolic activation, CSCs should have a broad and dynamic effect on the homeostatic transcriptome of the NHBE cell. In addition to the quantitative similarities in gene alterations induced by the different CSCs, there were also qualitative similarities in that both CSCs affected a large common block of genes, which is not surprising given the relatively comparable types of blended tobaccos used in most American cigarette brands.

Several approaches were employed to discriminate and cluster genes that became hypervariable after CSC treatment so as to develop a robust and accurate statistical estimate of functional significance for these perturbations. For example, as shown in FIG. 38, CSCs affected networks of genes that intersect critical signaling pathways such as apoptosis, transcription, and cell cycle regulation, which are known to play key roles in specific diseases such as cancer, chronic inflammation, and impaired neural development, and which both epidemiological and functional studies conclude can be caused by chronic cigarette smoking. The relevance of these pathways to smoking-related diseases is further supported by a limited body of published data in which other cell types or tissues exposed to either smoke, CSC, or a specific substance in CSC (e.g., benzo[a]pyrene, nicotine, etc.) were assessed using low-density arrays (see Nadadur et al., *Chest* 121: 83S-84S, 2002; Nordskog et al. *Cardiovasc Toxicol* 3: 101-117, 2003; Zhang et al. *Physiol Genomics* 5: 187-192, 2001; Gebel et al. *Carcinogenesis* 25:169-178, 2003).

The sensitivity and accuracy of the methodologies used herein to identify genes impacted by CSCs was further shown by the fact that the set of HV genes in CSC-treated cells included many of the genes and/or gene families that have been identified using various global expression analyses (e.g., Serial Analysis of Gene Expression, Differential Display, and microarrays) and concluded to be of importance in the development and/or maintenance of lung cancers. These include erb-B2, matrix metalloproteinase 9 (MMP9), the heterogeneous nuclear ribonucleoprotein (hnRNP) family, the Fus1 lung cancer candidate, glutathione S-transferase pi, the β-retinoic acid receptor, chromogranin B, RAB5, death-associated protein kinase 1 (DAPK), various cancer/testis antigens [MAGE genes], and others. For the first time, however, the present disclosure demonstrates that expression of these genes is altered in normal bronchial epithelial cells exposed to CSCs for only a short period of time, which provides evidence that one or more of these genes are an early indicator of tobacco-related cellular damage. In addition, the data herein identify a large number of genes and gene families that had not yet been associated with the induction or maintenance of pulmonary neoplasms or to other tobacco-related diseases involving the cardiovascular and immune systems. Accordingly, many of the genes identified using the approaches described herein are particularly useful biomarkers of the pathogenesis of these diseases.

The highly correlated expression characteristics of the CSC-impacted genes shown in TABLE 7 and FIG. 38, for example, highlight several genes that appear to play prominent roles in tobacco-related diseases. Both DPH2L1 and Fus1 are putative tumor suppressor genes associated with ovarian and lung cancer, respectively. Fus1 is found at a homozygous deleted region of chromosome 3p21 in lung tumors, and its forced expression in lung carcinoma cells suppresses cell growth in vitro and growth and metastases of tumors in vivo by mechanisms involving G1-arrest and induction of apoptosis. The RASA1 is a component of the GAP1 family of GTPase-activating proteins, which can suppress proliferation signals by enhancing the weak intrinsic GTPase activity of normal RAS p21 protein and maintaining it in its inactive GDP-bound form. It is contemplated that Ras acts as a major nexus for multiple signaling pathways that control a diverse range of functions, but many of the subtleties of Ras functioning in individual cell types remain unclear. It is also though that Ras plays an important role in tumor cell survival. The MAP2K5 is a novel mitogen activated protein kinase implicated in the regulation of cell proliferation. Over-expression of MAP2K5 can, in cooperation with other effectors, transform rodent cells, and function as a potent survival molecule in breast cancer cells. MAP2K5 represents a potential therapeutic target in prostate cancer as over-expression of MAP2K5 can induce proliferation, motility, and invasion. Interestingly, MAP2K5 also dramatically up-regulates the expression of matrix metalloproteinase-9 (MMP9) in prostate cancers. As shown in TABLE 7, MMP9 was hypervariable in both CSC-treatment groups. The matrix metalloproteinases (MMPs) are a large family of extracellular matrix degrading enzymes believed to play central roles in degradation, remodeling, and repair of basement membranes. Inappropriate or over-expression of these proteins appear to a critical determinant in tumor invasion and metastasis of a number of neoplasms including those of the lung. For example, MMP9 potentiates pulmonary metastasis formation, and high serum levels of MMP9 in patients with non-small-cell lung cancer (NSCLC) correlated with significantly shorter survival than patients with low serum levels of this protein.

In addition to a common set of affected genes, each individual CSC also altered the expression of a relatively large gene set that was unique to each CSC. That is, it was discovered that each tobacco smoke condensate was associated with a unique genetic fingerprint. The impact on these unique gene sets may be due to qualitative and/or quantitative differences in the constellation of chemical constituents in the two CSCs. It is interesting to note that despite the fact that both Brand A and Brand B are similar types of cigarettes (i.e., 'full-flavor') as determined by FTC criteria, there are measurable differences in the quantities of nicotine, tar, as well as, toxins and carcinogens between Brand-A and Brand-B cigarettes. It is contemplated that the differences in one or more of these substances directly correlates with the observed differences in gene induction and level of expression. Moreover, it is contemplated that each unique gene set affected by CSC-A and CSC-B ultimately influences different cellular pathways and results in different biological consequences.

Several basic assumptions of the emerging field of toxicogenomics are that there are reasonable similarities in gene expression patterns induced by multiple members of one specific class of toxicants, and subtle differences in these gene expression patterns may distinguish distinct chemical-specific 'gene signatures' of exposure (Afshari et al., *Cancer Res* 59: 4759-4760, 1999; Neumann et al. *Biotechnol Adv* 20: 391-419, 2002). For the first time, the approaches described herein provide one with the ability to identify a unique genetic fingerprint or signature for a plurality of tobacco products by contacting NHBE cells or another cell type of the lung, mouth or oral cavity with a tobacco smoke condensate or tobacco smoke from said plurality of tobacco products, identifying the genes expressed as a result of the contact in each individual tobacco product, as well as the level of expression of each, comparing the fingerprint or component thereof (e.g., a specific gene or set of genes or level of expression of a specific gene or set of genes) of the plurality of tobacco products that are being analyzed (or to a database containing genetic fingerprints of tobacco products), identifying differences in the fingerprint or component thereof between the products that are being analyzed, and associating the difference in the fingerprint or component thereof to an increased or decreased risk, proclivity, or potential to acquire a tobacco-related disease (e.g., lung cancer).

Another significant discovery made in the experiments described above, as shown in FIG. 35, is that the majority of CSC-affected genes do not return to baseline within the 12-hour treatment period, especially for CSC-B-affected genes. This observation is not simply due to the fact that the cells were chronically exposed to the CSCs for the entire 12-hours, as is discussed-infra. It is contemplated that many of the affected genes require a significant amount of time to return to baseline even after exposure is terminated. Accordingly, a current pack-a-day smoker who averages >150 cigarette puffs/day may alter the homeostatic expression of a large number of genes that cannot return to a baseline state during a typical day. This chronically perturbed state (either increased or decreased compared to baseline) of one or more of these genes may ultimately be etiologically involved in various pathological states caused by exposure to cigarette smoke. Evidence of this is provided by the fact that in subjects who quit smoking there is both short-term improvement in the functioning of a number of affected organ systems (e.g., lung, cardiovascular structures, kidneys, etc.) and a long-term decline in incidence and mortality from various diseases affecting these systems. Presumably, this reversal of smoking-related damage at the tissue and population levels reflects a corresponding reversal at a molecular and cellular level.

For example, chronic inflammatory processes in smokers play fundamental roles in the pathogenesis of atherosclerosis, and increased plasma and tissue levels of several biomarkers associated with inflammation such as various cytokines (e.g., IL-1β, TNF-α), pro-atherogenic enzymes (e.g., lipoprotein lipase) and cell adhesion molecules (e.g., VCAM-1) are associated with future cardiovascular risk, while smoking cessation leads to decreased expression of many pro-inflammatory biomolecules and a concomitant reduction in cardiovascular risk. It is also possible that the altered expression of one or more genes in the habitual smoker becomes attenuated with time as an adaptive response to the stress of chronic activation, and this phenomenon may have unanticipated long-term biological consequences for the smoker.

Another unexpected finding of this study was that the S9 metabolic enzyme fraction significantly influenced gene expression in NHBE cells. S9-exposed cells are traditionally considered a negative control for toxicogenetic experiments performed to establish environmental and occupational exposure guidelines. The fact that gene alterations were observed as early as 2 hours post-S9 exposure has interpretive implications for standard toxicological assays that routinely measure biological and genetic effects of control and test substances after 4 hours of exposure. This observation is particularly relevant as the global shift towards advanced genomic and proteomic technologies transforms the field of toxicology from one relying on the induction of gross genetic abnormalities such as mutations and structural/numerical chromosomal abnormalities to one where altered expression of panels of genes and proteins are used to determine risk to the human population. In order to clearly establish the potential toxicity or efficacy of an environmental substance, drug, or chemopreventive agent, it is important to show that control substances or vehicles used in the methodology cause minimal disruption of the physiologically normal transcriptome. Furthermore, since S9 can induce a range of alterations in gene expression levels independent of any test substance, it is possible that one or more S9-induced effects can be synergistic or antagonistic with the test substances. For example, FIG. 36 shows that many of the same genes that are down-regulated in S9-treated cells are up-regulated in CSC-treated cells despite the fact that CSCs contain the same concentration of S9 enzymes. Alternatively, the effects of S9 can be mitigated by the test substance. Evidence for this is strongly supported by the data, which shows that a number of genes whose steady-state mRNA level were found to be altered only by S9 were not found to be altered when cells were exposed to S9 in context with either CSC-A or CSC-B. In this scenario, the direct effects of S9, which can be directly cytotoxic to cells in cultures, may be attenuated when sequestered and modified through contact with substances in CSCs.

Although the analysis of normal human bronchial epithelial cells (NHBE cells) contacted with tobacco smoke condensates, described above, provide several ways to identify the genes that are modulated in response to human exposure to tobacco smoke, another approach involves analysis of cells of the mouth, oral cavity, trachea, and lungs, either normal or immortalized cell lines (e.g., human bronchial cells (e.g., BEP2D or 16HBE140 cells), human bronchial epithelial cells (e.g., HBEC cells, 1198, or 1170-I cells), normal human bronchial epithelial cells (NHBE cells), BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)), which are contacted with cigarette smoke. Accordingly, as described in the following example, several experiments were conducted to evaluate the genes that were expressed, as well as the expression levels, when NHBE cells were exposed to tobacco smoke.

Example 12

Microarray Analysis in CS Experiments

Once the NHBE cells were contacted with tobacco smoke or with air ("mock exposure"), as described in Example 4, the cDNA of NHBE cells that were either mock exposed or tobacco smoke exposed was prepared for microarray analysis as follows. Cells were harvested for total RNA extraction after either mock or smoke treatment. The RNA from each Petri dish was used for a separate microarray chip, which resulted in a total of 18 microarrays (ten from Experiment 1 and eight from Experiment 2). The medium was aspirated and the dishes were rinsed twice with 1 mL prewarmed PBS per dish. After the second rinse, 1 mL of cold TRIzol® (Invitrogen Corp., Carlsbad, Calif.) was added to each dish. NHBE cell lysates were prepared and the RNA was extracted according to the manufacturer's protocol. The RNA pellet was frozen and stored at −80° C.

Prior to cDNA synthesis, the RNA was resuspended in diethylpyrocarbonate-treated water. RNA integrity was assessed using capillary gel electrophoresis (Agilent Bio-Analyzer, Agilent Technologies, Palo Alto, Calif.) to determine the ratio of 28s:18s rRNA in each sample. A threshold of 1.0 was used to define samples of sufficient quality and only these samples were used for microarray studies. The RNA quality of all samples was extremely high with no ratios less than 1.8. Fluorescently labeled cDNA was synthesized and purified as previously described. (See Jarvis et al. Arthritis Res Ther, 6: R15-R32, 2004, expressly incorporated by reference in its entirety).

A commercially available, genome-scale oligonucleotide library containing gene-specific 70-mer oligonucleotides representing 21,329 human genes was used for microarray production (QIAGEN Inc., Valencia, Calif.). Oligonucleotides were spotted onto Corning® UltraGAPS™ aminosilane coated slides, which were then rehydrated with water vapor, snap dried at 90° C. Oligonucleotide DNAs were covalently fixed to the surface of the glass using 300 mJ of ultraviolet radiation at a 254 nm wavelength. Unbound free amines on the glass surface were blocked for 15 min with moderate agitation in a solution of 143 mM succinic anhydride dissolved in 1-methyl-2-pyrrolidinone, 20 mM sodium borate, pH 8.0. Slides were rinsed for 2 min in distilled water, immersed for 1 min in 95% ethanol, and dried with a stream of nitrogen gas.

Hybridization was performed in an automated liquid delivery, air-vortexed, hybridization station for 9 hr at 58° C. under an oil-based cover slip (Ventana Medical Systems, Inc. Tucson, Ariz.). Microarrays were washed at a final stringency of 0.1×SSC. Microarrays were scanned using a simultaneous dual color, 48-slide scanner (Agilent Technologies). Fluorescent intensity was quantified using Imagene™ software (BioDiscovery, Marina del Rey, Calif.).

Adjustment of expression levels in compared samples was performed as previously described. (See Dozmorov, et al. Bioinformatics., 19: 2004-211, 2003; Knowlton, N., et al. Bioinformatics., 20: 3687-3690, 2004; and Dozmorov, et al. Bioinformatics., 5:53, 2004, each of which is incorporated by reference in its entirety). To determine differentially expressed genes, the analysis was confined to the set of genes that were expressed above background in at least one condition (i.e., 4 and/or 24 hours post-exposure, CS-treated or mock-treated). For each experiment, replicates from each condition were averaged and genes that were under- or over-expressed ("modulated") in response to tobacco smoke treatment (e.g., cigarette smoke (CS)) by 1.5-fold or more at either or both time points were identified. Genes exhibiting similar expression behavior in both experiments were determined.

Quantitative Reverse Transcriptase PCR (qRT-PCR)

To determine the level of expression, RNA was reverse-transcribed using an Omniscript RT™ kit according to manufacturer's instructions (Qiagen, Valencia, Calif.) and the resultant cDNA subsequently purified using the Montage PCR 96-well cleanup plate (Millipore, Billerica, Mass., USA). The qRT-PCR amplifications were performed on an ABI®PRISM 7700 sequence detection system using SYBR®Green I dye assay chemistry. A 15 uL PCR reaction for each gene of interest was prepared consisting of 7.5 uL of 2× SYBR®Green PCR mix (Applied Biosystems Inc., Foster City, Calif.), 4.9 µl of H2O, 0.6 µl (30 pmoles) of gene-specific forward and reverse primers, and 2 µl (1 ng) of cDNA template. All samples were run in triplicate with the appropriate single qRT-PCR controls (no reverse transcriptase and no template). Cycling conditions used for all amplifications were one cycle of 95° C. for 10 minutes and 40 cycles of 95° C. for 15 seconds and 60° C. for 1 minute. Following the qRT-PCR, dissociation curve analysis was performed to determine if the desired single gene product was produced.

Gene Expression Alterations Induced by CS Exposure

In order to determine the broad impact of a brief transient exposure to cigarette smoke (CS) on the transcriptome of NHBE cells, monolayer cultures of NHBE cells were treated in logarithmic phase of growth for 15 minutes with whole smoke from a leading representative brand of American cigarettes, and then assessed for global alterations in their transcriptome at 4 h and 24 h post-exposure. Furthermore, in an attempt to unambiguously define a set of genes consistently impacted by CS, this experiment was performed twice and then the focus was restricted to only those individual genes whose RNA levels similarly deviated by 1.5 fold or greater in the two experiments (either overexpressed or underexpressed in response to CS treatment). By assessing global RNA changes at 4 and 24 h post-exposure, the temporal relationships of those genes whose RNA levels were altered a) by 4 hours and that returned to baseline by 24 hours; b) by 4 hours and did not return to baseline by 24 hours; and c) only by 24 hours could be observed.

Approximately 10% of the 21,329 human genes represented on the array were expressed above background in mock-treated cells. This amount of expression presumably represents the typical transcriptome of unstressed NHBE cells in vitro, and agrees well with published data on the human airway transcriptome of healthy nonsmokers. Interestingly, CS-treated NHBE cells also expressed approximately 10% of the total gene complement, suggesting that brief CS-exposure does not induce a major quantitative reorganization of the normal transcriptome of lung cells.

Of the 21,329 genes on the array, a set of 364 genes exhibited similar changes in expression level in both experiments (See TABLE 16). A subset of 298 genes that were overexpressed 1.5-fold or more in both experiments was compared to mock-treated cells. Of this set of 298 up-regulated genes, 184 were up-regulated exclusively at 4 h post cigarette smoke exposure, while 69 were up-regulated exclusively at 24 h post-exposure, and 45 were up-regulated at both time points. The number of genes that were under-expressed at least 1.5-fold in cells exposed to cigarette smoke was 66, with 35 down-regulated exclusively at 4 h post CS-exposure, 30 down-regulated exclusively at 24 h post-exposure, and one down-regulated at both time points. Further confirmation that the entire set of 364 up and down-regulated genes accurately reflect a reliable genetic response to cigarette smoke exposure is evidenced by the fact that a majority of the genes exhibited remarkably consistent expression behaviors in both experiments.

TABLE 16

Genes Upregulated by Cigarette Smoke

| Gene ID | Gene Name | Description | Fold Increase at 4 h | Fold Increase at 24 h |
| --- | --- | --- | --- | --- |
| NM_004261 | SEP 15 | 15 kDa selenoprotein | 1.71 | 1.29 |
| NM_000859 | HMGCR | 3-hydroxy-3-methylglutaryl-Coenzyme A reductase | 2.25 | 1.33 |
| AK025736 | HMGCS1 | 3-hydroxy-3-methylglutaryl-Coenzyme A synthase 1 (soluble) | 1.02 | 1.63 |
| NM_002526 | NT5 | 5' nucleotidase (CD73) | 1.45 | 1.69 |

TABLE 16-continued

| | | | | |
|---|---|---|---|---|
| NM_001109 | ADAM8 | A disintegrin and metalloproteinase domain 8 | 1.17 | 2.72 |
| NM_005891 | ACAT2 | Acetyl-Coenzyme A acetyltransferase 2 (acetoacetyl Coenzyme A thiolase) | 1.44 | 1.77 |
| NM_006409 | ARPC1A | Actin related protein 2/3 complex, subunit 1A (41 kD) | 2.01 | 1.79 |
| NM_018445 | LOC55829 | AD-015 protein | 1.64 | 2.02 |
| NM_001284 | AP3S1 | Adaptor-related protein complex 3, sigma 1 subunit | 2.18 | 1.27 |
| NM_000485 | APRT | Adenine phosphoribosyltransferase | 1.56 | 1.63 |
| NM_007002 | ADRM1 | Adhesion regulating molecule 1 | 1.68 | 1.61 |
| NM_006829 | APM2 | Adipose specific 2 | 1.96 | 2.34 |
| NM_001667 | ARL2 | ADP-ribosylation factor-like 2 | 2.06 | 0.80 |
| NM_000693 | ALDH1A3 | Aldehyde dehydrogenase 1 family, member A3 | 0.82 | 2.88 |
| NM_001635 | AMPH | Amphiphysin (Stiff-Mann syndrome with breast cancer 128 kD autoantigen) | 1.78 | 2.16 |
| NM_001657 | AREG | Amphiregulin (schwannoma-derived growth factor) | 1.96 | 0.33 |
| NM_001145 | ANG | Angiogenin, ribonuclease, RNase A family, 5 | 1.61 | 1.10 |
| NM_000700 | ANXA1 | Annexin A1 | 1.39 | 1.82 |
| NM_005139 | ANXA3 | Annexin A3 | 1.34 | 1.71 |
| NM_001154 | ANXA5 | Annexin A5 | 2.40 | 2.43 |
| NM_004034 | ANXA7 | Annexin A7 | 2.10 | 1.64 |
| NM_016476 | ANAPC11 | APC11 anaphase promoting complex subunit 11 homolog (yeast) | 1.68 | 1.30 |
| NM_016085 | APR-3 | Apoptosis related protein APR-3 | 1.44 | 0.84 |
| NM_005721 | ACTR3 | ARP3 actin-related protein 3 homolog (yeast) | 1.63 | 1.72 |
| NM_017900 | AKIP | aurora-A kinase interacting protein | 2.07 | 5.18 |
| M90355 | BTF3L2 | Basic transcription factor 3, like 2 | 1.87 | 1.47 |
| NM_004281 | BAG3 | BCL2-associated athanogene 3 | 3.85 | 1.58 |
| NM_001196 | BID | BH3 interacting domain death agonist | 1.54 | 1.05 |
| NM_003860 | BCRP1 | Breakpoint cluster region protein, uterine leiomyoma, 1-barrier to autointegration factor | 1.99 | 1.52 |
| NM_014567 | BCAR1 | Breast cancer anti-estrogen resistance 1 | 1.00 | 1.88 |
| NM_021096 | CACNA1I | Calcium channel, voltage-dependent, alpha 1I subunit | 1.68 | 2.75 |
| NM_005186 | CAPN1 | Calpain 1, (mu/I) large subunit | 1.62 | 1.11 |
| NM_001750 | CAST | Calpastatin | 1.47 | 1.76 |
| NM_013376 | SEI1 | CDK4-binding protein p34SEI1 | 2.46 | 1.87 |
| NM_015965 | GRIM19 | Cell death-regulatory protein GRIM19 | 2.16 | 2.23 |
| NM_016041 | F-LAN-1 | CGI-101 protein | 1.51 | 1.58 |
| NM_016038 | LOC51119 | CGI-97 protein | 1.78 | 2.34 |
| BC002971 | CCT5 | Chaperonin containing TCP1, subunit 5 (epsilon) | 1.81 | 1.74 |
| NM_006429 | CCT7 | Chaperonin containing TCP1, subunit 7 (eta) | 2.85 | 3.21 |
| NM_000647 | CCR2 | Chemokine (C-C motif) receptor 2 | 0.69 | 3.35 |
| NM_012111 | C14orf3 | Chromosome 14 open reading frame 3 | 1.88 | 1.15 |
| AK026450 | C20orf162 | Chromosome 20 open reading frame 162 | 1.16 | 1.49 |
| NM_007096 | CLTA | Clathrin, light polypeptide (Lca) | 1.96 | 2.01 |
| BC010039 | CLP | Coactosin-like protein | 1.54 | 1.24 |
| NM_016451 | COPB | Coatomer protein complex, subunit beta | 1.82 | 1.79 |
| NM_007263 | COPE | Coatomer protein complex, subunit epsilon | 2.58 | 2.98 |
| NM_004645 | COIL | Coilin | 1.21 | 1.79 |
| AL162070 | CORO1C | Coronin, actin binding protein, 1C | 2.00 | 1.59 |
| NM_000389 | CDKN1A | Cyclin-dependent kinase inhibitor 1A (p21, Cip1) | 4.69 | 1.38 |
| NM_000099 | CST3 | Cystatin C (amyloid angiopathy and cerebral hemorrhage) | 2.11 | 1.54 |
| NM_001554 | CYR61 | Cysteine-rich, angiogenic inducer, 61 | 2.44 | 0.67 |
| NM_007274 | HBACH | Cytosolic acyl coenzyme A thioester hydrolase | 1.61 | 2.28 |
| NM_020189 | DC6 | DC6 protein | 1.64 | 1.73 |

TABLE 16-continued

| | | | | |
|---|---|---|---|---|
| NM_004396 | DDX5 | DEAD/H (Asp-Glu-Ala-Asp/His) box polypeptide 5 (RNA helicase, 68 kD) | 2.01 | 4.10 |
| NM_001357 | DDX9 | DEAD/H (Asp-Glu-Ala-Asp/His) box polypeptide 9 (RNA helicase A, nuclear DNA helicase II-leukophysin | 1.44 | 1.53 |
| AB040961 | DTX2 | Deltex homolog 2 (*Drosophila*) | 1.76 | 1.62 |
| NM_007326 | DIA1 | Diaphorase (NADH) (cytochrome b-5 reductase) | 1.84 | 2.06 |
| NM_020548 | DBI | Diazepam binding inhibitor (GABA receptor modulator, acyl-Coenzyme A binding protein) | 1.69 | 1.84 |
| NM_013253 | DKK3 | Dickkopf homolog 3 (*Xenopus laevis*) | 1.64 | 0.84 |
| NM_004405 | DLX2 | Distal-less homeo box 2 | 29.27 | 2.13 |
| AL080156 | DKFZP434J214 | DKFZP434J214 protein | 2.97 | 1.43 |
| NM_014045 | DKFZP564C1940 | DKFZP564C1940 protein | 1.79 | 1.73 |
| NM_001539 | DNAJA1 | DnaJ (Hsp40) homolog, subfamily A, member 1 | 2.11 | 1.85 |
| NM_006145 | DNAJB1 | DnaJ (Hsp40) homolog, subfmaily B, member 1 | 4.99 | 1.57 |
| NM_004419 | DUSP5 | Dual specificity phosphatase 5 | 1.97 | 0.47 |
| NM_001946 | DUSP6 | Dual specificity phosphatase 6 | 2.08 | 2.29 |
| NM_014390 | p100 | EBNA-2 co-activator (100 kD) | 2.00 | 1.02 |
| NM_005451 | ENIGMA | Enigma (LIM domain protein) | 1.21 | 2.34 |
| NM_004092 | ECHS1 | Enoyl Coenzyme A hydratase, short chain, 1, mitochondrial | 1.60 | 1.23 |
| NM_004431 | EPHA2 | EphA2 | 2.37 | 1.93 |
| NM_016357 | EPLIN | Epithelial protein lost in neoplasm beta | 1.74 | 1.63 |
| BF541376 | | ESTs, Weakly similar to FRHUL ferritin light chain [*H. sapiens*] | 2.71 | 4.50 |
| NM_003757 | EIF3S2 | Eukaryotic translation initiation factor 3, subunit 2 (beta, 36 kD) | 1.83 | 1.47 |
| NM_003755 | EIF3S4 | Eukaryotic translation initiation factor 3, subunit 4 (delta, 44 kD) | 2.12 | 2.40 |
| NM_001417 | EIF4B | Eukaryotic translation initiation factor 4B | 2.33 | 2.41 |
| NM_004095 | EIF4EBP1 | Eukaryotic translation initiation factor 4E binding protein 1 | 1.69 | 1.26 |
| NM_005243 | EWSR1 | Ewing sarcoma breakpoint region 1 | 2.02 | 1.33 |
| NM_005245 | FAT | FAT tumor suppressor homolog 1 (*Drosophila*) | 1.87 | 0.77 |
| NM_004104 | FASN | Fatty acid synthase | 1.24 | 1.60 |
| AK054816 | FTH1 | Ferritin, heavy polypeptide 1 | 2.07 | 3.32 |
| NM_001457 | FLNB | Filamin B, beta (actin binding protein 278) | 1.05 | 1.90 |
| NM_014164 | FXYD5 | FXYD domain-containing ion transport regulator 5 | 1.24 | 1.67 |
| AL365404 | GPR108 | G protein-coupled receptor 108 | 2.00 | 1.17 |
| NM_007278 | GABARAP | GABA(A) receptor-associated protein | 1.55 | 1.75 |
| NM_001520 | GTF3C1 | General transcription factor IIIC, polypeptide 1 (alpha subunit, 220 kD) | 8.72 | 0.41 |
| AK024486 | GLTSCR2 | Glioma tumor suppressor candidate region gene 2 | 2.63 | 1.85 |
| NM_001498 | GCLC | Glutamate-cysteine ligase, catalytic subunit | 8.96 | 1.40 |
| NM_002061 | GCLM | Glutamate-cysteine ligase, modifier subunit | 2.85 | 1.56 |
| NM_004446 | EPRS | Glutamyl-prolyl-tRNA synthetase | 1.76 | 0.73 |
| NM_002064 | GLRX | Glutaredoxin (thioltransferase) | 3.12 | 2.31 |
| NM_002083 | GPX2 | Glutathione peroxidase 2 (gastrointestinal) | 3.71 | 9.99 |
| NM_000637 | GSR | Glutathione reductase | 1.57 | 1.54 |
| NM_002087 | GRN | Granulin | 1.36 | 1.58 |
| L24498 | GADD45A | Growth arrest and DNA-damage-inducible, alpha | 2.81 | 0.61 |
| NM_006644 | HSP105B | Heat shock 105 kD | 2.83 | 1.02 |
| NM_002157 | HSPE1 | Heat shock 10 kD protein 1 (chaperonin 10) | 1.92 | 1.34 |
| NM_005345 | HSPA1A | Heat shock 70 kD protein 1A | 5.77 | 1.30 |
| NM_006597 | HSPA8 | Heat shock 70 kD protein 8 | 1.48 | 4.56 |
| NM_004134 | HSPA9B | Heat shock 70 kD protein 9B (mortalin-2) | 2.23 | 1.39 |
| NM_016292 | TRAP1 | Heat shock protein 75 | 1.57 | 1.05 |
| NM_002133 | HMOX1 | Heme oxygenase (decycling) 1 | 55.83 | 2.81 |

TABLE 16-continued

| | | | | |
|---|---|---|---|---|
| NM_004712 | HGS | Hepatocyte growth factor-regulated tyrosine kinase substrate | 1.21 | 1.64 |
| NM_001533 | HNRPL | Heterogeneous nuclear ribonucleoprotein L | 1.50 | 0.89 |
| AK057120 | HMG1 | High-mobility group (nonhistone chromosomal) protein 1 | 1.72 | 0.79 |
| AF130111 | HDAC3 | Histone deacetylase 3 | 1.92 | 1.38 |
| NM_001536 | HRMT1L2 | HMT1 hnRNP methyltransferase-like 2 (*S. cerevisiae*) | 1.83 | 1.16 |
| AK023395 | | *Homo sapiens* cDNA FLJ13333 fis, clone OVARC1001828 | 1.82 | 1.39 |
| AK054711 | | *Homo sapiens* cDNA FLJ30149 fis, clone BRACE2000280, weakly similar to MNN4 PROTEIN | 1.57 | 0.76 |
| AK055071 | | *Homo sapiens* cDNA FLJ30509 fis, clone BRAWH2000595 | 1.36 | 1.64 |
| AK056736 | | *Homo sapiens* cDNA FLJ32174 fis, clone PLACE6001064 | 1.18 | 4.26 |
| AK024927 | | *Homo sapiens* cDNA: FLJ21274 fis, clone COL01781 | 1.83 | 0.89 |
| AK055564 | | *Homo sapiens* cDNA: FLJ22182 fis, clone HRC00953 | 1.00 | 1.50 |
| AK026181 | | *Homo sapiens* cDNA: FLJ22528 fis, clone HRC12825 | 4.30 | 1.72 |
| AK026902 | | *Homo sapiens* cDNA: FLJ23249 fis, clone COL04196 | 1.76 | 1.09 |
| AL512727 | | *Homo sapiens* mRNA-cDNA DKFZp547P042 (from clone DKFZp547P042) | 2.01 | 2.48 |
| AL117595 | | *Homo sapiens* mRNA-cDNA DKFZp564C2063 (from clone DKFZp564C2063) | 2.71 | 1.30 |
| AL050378 | | *Homo sapiens* mRNA-cDNA DKFZp586I1420 (from clone DKFZp586I1420)-partial cds | 1.37 | 1.70 |
| AF041429 | | *Homo sapiens* pRGR1 mRNA, partial cds | 1.37 | 1.86 |
| AF118072 | | *Homo sapiens* PRO1716 mRNA, complete cds | 5.32 | 19.31 |
| AF065241 | | *Homo sapiens* thioredoxin delta 3 (TXN delta 3) mRNA, partial cds | 1.20 | 1.80 |
| BC010009 | | *Homo sapiens*, clone IMAGE: 3355383, mRNA, partial cds | 1.49 | 1.93 |
| BC011880 | | *Homo sapiens*, Similar to hypothetical protein, MGC: 7764, clone MGC: 20548 IMAGE: 3607345, mRNA, comple | 1.07 | 1.65 |
| BC017001 | | *Homo sapiens*, Similar to RIKEN cDNA 1700127B04 gene, clone IMAGE: 4425440, mRNA, partial cds | 26.36 | 5.69 |
| BC007307 | | *Homo sapiens*, Similar to zinc finger protein 268, clone IMAGE: 3352268, mRNA, partial cds | 1.89 | 1.59 |
| NM_014029 | HSPC022 | HSPC022 protein | 1.33 | 3.77 |
| NM_014047 | HSPC023 | HSPC023 protein | 1.64 | 1.98 |
| AF161415 | HSPC030 | HSPC030 protein | 4.27 | 1.52 |
| NM_016099 | LOC51125 | HSPC041 protein | 1.46 | 1.08 |
| NM_014168 | HSPC133 | HSPC133 protein | 1.58 | 1.41 |
| NM_014182 | HSPC160 | HSPC160 protein | 1.28 | 2.58 |
| AL139112 | | Human DNA sequence from clone GS1-103B18 on chromosome Xq27.1-27.3 Contains ESTs, STSs and GSSs. Con | 1.88 | 2.68 |
| AL354915 | | Human DNA sequence from clone RP11-392A19 on chromosome 13. Contains ESTs, STSs and GSSs. Contains a | 1.38 | 2.01 |
| NM_000182 | HADHA | Hydroxyacyl-Coenzyme A dehydrogenase/3-ketoacyl-Coenzyme A thiolase/enoyl-Coenzyme A hydratase (trif | 2.39 | 1.22 |
| NM_016404 | HSPC152 | Hypothetical protein | 1.59 | 1.30 |
| NM_016623 | BM-009 | Hypothetical protein | 1.53 | 1.08 |
| NM_015932 | HSPC014 | Hypothetical protein | 1.31 | 1.56 |
| NM_015343 | HSA011916 | Hypothetical protein | 1.79 | 1.22 |
| AF103803 | H41 | Hypothetical protein | 1.63 | 2.00 |

TABLE 16-continued

| | | | | |
|---|---|---|---|---|
| NM_014886 | YR-29 | Hypothetical protein | 1.53 | 1.44 |
| NM_018437 | EDAG-1 | Hypothetical protein EDAG-1 | 1.46 | 1.94 |
| NM_018306 | FLJ11036 | Hypothetical protein FLJ11036 | 2.07 | 2.12 |
| NM_032813 | FLJ14624 | Hypothetical protein FLJ14624 | 1.80 | 2.88 |
| NM_022842 | FLJ22969 | Hypothetical protein FLJ22969 | 3.39 | 31.88 |
| NM_031207 | HT036 | Hypothetical protein HT036 | 1.26 | 2.55 |
| NM_024508 | MGC10796 | Hypothetical protein MGC10796 | 1.46 | 1.84 |
| AK027859 | MGC11266 | Hypothetical protein MGC11266 | 2.46 | 2.14 |
| NM_032771 | MGC12217 | Hypothetical protein MGC12217 | 1.56 | 1.02 |
| BC014850 | MGC13071 | Hypothetical protein MGC13071 | 1.74 | 1.98 |
| NM_032899 | MGC14128 | Hypothetical protein MGC14128 | 1.15 | 6.78 |
| NM_024040 | MGC2491 | Hypothetical protein MGC2491 | 2.69 | 2.86 |
| NM_024038 | MGC2803 | Hypothetical protein MGC2803 | 1.59 | 1.48 |
| NM_031943 | IFP38 | IFP38 | 2.11 | 1.95 |
| NM_052815 | IER3 | Immediate early response 3 | 2.94 | 1.54 |
| NM_016545 | IER5 | Immediate early response 5 | 9.20 | 1.18 |
| NM_005542 | INSIG1 | Insulin induced gene 1 | 2.02 | 2.62 |
| NM_021999 | ITM2B | Integral membrane protein 2B | 1.84 | 1.06 |
| NM_006147 | IRF6 | Interferon regulatory factor 6 | 2.30 | 1.09 |
| NM_000576 | IL1B | Interleukin 1, beta | 0.98 | 3.03 |
| Z17227 | IL10RB | Interleukin 10 receptor, beta | 1.74 | 1.68 |
| NM_004508 | IDI1 | Isopentenyl-diphosphate delta isomerase | 1.89 | 2.68 |
| NM_005354 | JUND | Jun D proto-oncogene | 1.67 | 1.25 |
| NM_006854 | KDELR2 | KDEL (Lys-Asp-Glu-Leu) endoplasmic reticulum protein retention receptor 2 | 2.03 | 1.42 |
| NM_000421 | KRT10 | Keratin 10 (epidermolytic hyperkeratosis-keratosis palmaris et plantaris) | 1.87 | 1.68 |
| NM_000224 | KRT18 | Keratin 18 | 1.22 | 1.81 |
| NM_005555 | KRT6B | Keratin 6B | 1.44 | 2.26 |
| NM_014815 | KIAA0130 | KIAA0130 gene product | 1.31 | 4.73 |
| NM_000899 | KITLG | KIT ligand | 1.35 | 2.21 |
| NM_001730 | KLF5 | Kruppel-like factor 5 (intestinal) | 2.34 | 1.01 |
| NM_003937 | KYNU | Kynureninase (L-kynurenine hydrolase) | 3.31 | 3.29 |
| NM_005558 | LAD1 | Ladinin 1 | 1.44 | 2.29 |
| NM_016201 | LCCP | Leman coiled-coil protein | 1.89 | 1.09 |
| NM_015925 | LISCH7 | Liver-specific bHLH-Zip transcription factor | 1.29 | 1.64 |
| NM_014463 | LSM3 | Lsm3 protein | 1.85 | 1.98 |
| NM_004995 | MMP14 | Matrix metalloproteinase 14 (membrane-inserted) | 2.20 | 2.57 |
| NM_005916 | MCM7 | MCM7 minichromosome maintenance deficient 7 (S. cerevisiae) | 1.60 | 1.07 |
| NM_006428 | MAAT1 | Melanoma-associated antigen recognised by cytotoxic T lymphocytes | 1.99 | 1.43 |
| NM_006636 | MTHFD2 | Methylene tetrahydrofolate dehydrogenase (NAD+ dependent), methenyltetrahydrofolate cyclohydrolase | 1.81 | 0.68 |
| NM_004528 | MGST3 | Microsomal glutathione S-transferase 3 | 1.73 | 1.76 |
| NM_022818 | MAP1A/1BLC3 | Microtubule-associated proteins 1A/1B light chain 3 | 2.18 | 0.95 |
| NM_014341 | MTCH1 | Mitochondrial carrier homolog 1 | 1.81 | 1.69 |
| NM_014161 | MRPL18 | Mitochondrial ribosomal protein L18 | 3.58 | 1.63 |
| NM_021134 | MRPL23 | Mitochondrial ribosomal protein L23 | 1.58 | 1.23 |
| NM_017446 | MRPL39 | Mitochondrial ribosomal protein L39 | 1.74 | 1.13 |
| NM_021210 | MUM2 | MUM2 protein | 1.20 | 1.61 |
| NM_004529 | MLLT3 | Myeloid/lymphoid or mixed-lineage leukemia (trithorax homolog, Drosophila)-translocated to, 3 | 1.15 | 2.41 |
| NM_033546 | MLC-B | Myosin regulatory light chain | 1.95 | 1.89 |
| AB032945 | MYO5B | Myosin VB | 1.50 | 1.74 |
| NM_017534 | MYH2 | Myosin, heavy polypeptide 2, skeletal muscle, adult | 1.66 | 0.90 |
| NM_002473 | MYH9 | Myosin, heavy polypeptide 9, non-muscle | 1.82 | 2.60 |
| NM_002356 | MARCKS | Myristoylated alanine-rich protein kinase C substrate | 0.22 | 2.70 |
| NM_000903 | NQO1 | NAD(P)H dehydrogenase, quinone 1 | 2.64 | 2.77 |

TABLE 16-continued

| | | | | |
|---|---|---|---|---|
| NM_004541 | NDUFA1 | NADH dehydrogenase (ubiquinone) 1 alpha subcomplex, 1 (7.5 kD, MWFE) | 1.27 | 1.88 |
| NM_004548 | NDUFB10 | NADH dehydrogenase (ubiquinone) 1 beta subcomplex, 10 (22 kD, PDSW) | 1.63 | 1.29 |
| NM_004547 | NDUFB4 | NADH dehydrogenase (ubiquinone) 1 beta subcomplex, 4 (15 kD, B15) | 1.63 | 2.11 |
| NM_002494 | NDUFC1 | NADH dehydrogenase (ubiquinone) 1, subcomplex unknown, 1 (6 kD, KFYI) | 1.70 | 1.17 |
| NM_014328 | NESCA | Nesca protein | 1.52 | 1.23 |
| BC010285 | NET1 | Neuroepithelial cell transforming gene 1 | 0.78 | 2.28 |
| NM_000271 | NPC1 | Niemann-Pick disease, type C1 | 2.31 | 1.39 |
| NM_006096 | NDRG1 | N-myc downstream regulated gene 1 | 1.50 | 1.95 |
| NM_006164 | NFE2L2 | Nuclear factor (erythroid-derived 2)-like 2 | 3.80 | 1.23 |
| NM_003489 | NRIP1 | Nuclear receptor interacting protein 1 | 0.94 | 1.63 |
| NM_017838 | NOLA2 | Nucleolar protein family A, member 2 (H/ACA small nucleolar RNPs) | 1.83 | 1.94 |
| NM_002820 | PTHLH | Parathyroid hormone-like hormone | 1.66 | 2.59 |
| NM_020992 | PDLIM1 | PDZ and LIM domain 1 (elfin) | 1.56 | 1.60 |
| NM_002574 | PRDX1 | Peroxiredoxin 1 | 1.68 | 1.80 |
| NM_003713 | PPAP2B | Phosphatidic acid phosphatase type 2B | 1.22 | 1.84 |
| NM_002631 | PGD | Phosphogluconate dehydrogenase | 4.37 | 23.25 |
| NM_002632 | PGF | Placental growth factor, vascular endothelial growth factor-related protein | 3.61 | 1.79 |
| NM_002658 | PLAU | Plasminogen activator, urokinase | 1.69 | 1.78 |
| NM_014287 | PM5 | PM5 protein | 1.55 | 1.54 |
| NM_003819 | PABPC4 | Poly(A) binding protein, cytoplasmic 4 (inducible form) | 1.62 | 1.25 |
| NM_000937 | POLR2A | Polymerase (RNA) II (DNA directed) polypeptide A (220 kD) | 1.23 | 1.65 |
| NM_001198 | PRDM1 | PR domain containing 1, with ZNF domain | 7.04 | 3.20 |
| NM_002583 | PAWR | PRKC, apoptosis, WT1, regulator | 1.96 | 1.50 |
| NM_000917 | P4HA1 | Procollagen-proline, 2-oxoglutarate 4-dioxygenase (proline 4-hydroxylase), alpha polypeptide I | 1.08 | 1.51 |
| NM_053024 | PFN2 | Profilin 2 | 1.73 | 1.17 |
| AB051437 | ProSAP2 | Proline rich synapse associated protein 2 (rat) | 2.30 | 1.25 |
| NM_002778 | PSAP | Prosaposin (variant Gaucher disease and variant metachromatic leukodystrophy) | 1.70 | 2.72 |
| NM_000963 | PTGS2 | Prostaglandin-endoperoxide synthase 2 (prostaglandin G/H synthase and cyclooxygenase) | 6.51 | 0.98 |
| BC013908 | PSMC1 | Proteasome (prosome, macropain) 26S subunit, ATPase, 1 | 1.68 | 1.13 |
| NM_002806 | PSMC6 | Proteasome (prosome, macropain) 26S subunit, ATPase, 6 | 1.64 | 1.25 |
| NM_002815 | PSMD11 | Proteasome (prosome, macropain) 26S subunit, non-ATPase, 11 | 1.77 | 1.35 |
| NM_002812 | PSMD8 | Proteasome (prosome, macropain) 26S subunit, non-ATPase, 8 | 2.17 | 3.03 |
| NM_002797 | PSMB5 | Proteasome (prosome, macropain) subunit, beta type, 5 | 2.82 | 3.28 |
| NM_002799 | PSMB7 | Proteasome (prosome, macropain) subunit, beta type, 7 | 1.36 | 1.74 |
| NM_014330 | PPP1R15A | Protein phosphatase 1, regulatory (inhibitor) subunit 15A | 7.10 | 0.88 |
| NM_004156 | PPP2CB | Protein phosphatase 2 (formerly 2A), catalytic subunit, beta isoform | 1.67 | 1.11 |
| NM_006808 | SEC61B | Protein translocation complex beta | 1.44 | 1.57 |
| NM_015714 | G0S2 | Putative lymphocyte G0/G1 switch gene | 0.90 | 6.31 |
| BC012513 | ARHE | Ras homolog gene family, member E | 2.39 | 0.99 |
| NM_003979 | RAI3 | Retinoic acid induced 3 | 1.05 | 3.46 |
| NM_001666 | ARHGAP4 | Rho GTPase activating protein 4 | 2.49 | 1.96 |

TABLE 16-continued

| | | | | |
|---|---|---|---|---|
| NM_001033 | RRM1 | Ribonucleotide reductase M1 polypeptide | 1.54 | 0.87 |
| NM_002950 | RPN1 | Ribophorin I | 2.08 | 1.10 |
| NM_001029 | RPS26 | Ribosomal protein S26 | 1.31 | 1.70 |
| NM_002953 | RPS6KA1 | Ribosomal protein S6 kinase, 90 kD, polypeptide 1 | 1.65 | 2.00 |
| AB037819 | RRBP1 | Ribosome binding protein 1 homolog 180 kD (dog) | 3.68 | 2.68 |
| NM_014248 | RBX1 | Ring-box 1 | 1.30 | 2.13 |
| NM_006743 | RBM3 | RNA binding motif protein 3 | 2.01 | 1.74 |
| NM_004902 | RNPC2 | RNA-binding region (RNP1, RRM) containing 2 | 1.61 | 0.75 |
| NM_000687 | AHCY | S-adenosylhomocysteine hydrolase | 1.74 | 1.82 |
| AB051532 | SEMA4B | Sema domain, immunoglobulin domain (Ig), transmembrane domain (TM) and short cytoplasmic domain, (se | 1.11 | 1.77 |
| NM_003900 | SQSTM1 | Sequestosome 1 | 3.34 | 2.82 |
| NM_001085 | SERPINA3 | Serine (or cysteine) proteinase inhibitor, clade A (alpha-1 antiproteinase, antitrypsin), member 3 | 2.74 | #DIV/0! |
| NM_030666 | SERPINB1 | Serine (or cysteine) proteinase inhibitor, clade B (ovalbumin), member 1 | 3.11 | 2.58 |
| NM_000602 | SERPINE1 | Serine (or cysteine) proteinase inhibitor, clade E (nexin, plasminogen activator inhibitor type 1), | 2.32 | 2.38 |
| NM_015966 | SDBCAG84 | Serologically defined breast cancer antigen 84 | 1.86 | 1.45 |
| NM_006622 | SNK | Serum-inducible kinase | 3.02 | 1.13 |
| AB000462 | SH3BP2 | SH3-domain binding protein 2 | 4.63 | 2.02 |
| NM_003134 | SRP14 | Signal recognition particle 14 kD (homologous Alu RNA binding protein) | 1.58 | 1.45 |
| NM_003145 | SSR2 | Signal sequence receptor, beta (translocon-associated protein beta) | 1.64 | 1.79 |
| NM_007107 | SSR3 | Signal sequence receptor, gamma (translocon-associated protein gamma) | 1.74 | 1.26 |
| AF395440 | HEJ1 | Similar to DNAJ | 2.50 | 1.94 |
| NM_005870 | SAP18 | Sin3-associated polypeptide, 18 kD | 1.50 | 1.21 |
| NM_006109 | SKB1 | SKB1 homolog (S. pombe) | 1.55 | 2.52 |
| NM_015523 | DKFZP566E144 | Small fragment nuclease | 2.04 | 1.55 |
| NM_030981 | RAB1B | Small GTP-binding protein | 1.53 | 1.16 |
| NM_006518 | SPRR2C | Small proline-rich protein 2C | 1.41 | 4.09 |
| NM_005628 | SLC1A5 | Solute carrier family 1 (neutral amino acid transporter), member 5 | 1.87 | 0.82 |
| NM_004207 | SLC16A3 | Solute carrier family 16 (monocarboxylic acid transporters), member 3 | 1.56 | 2.65 |
| NM_018976 | SLC38A2 | Solute carrier family 38, member 2 | 2.48 | 0.85 |
| NM_014331 | SLC7A11 | Solute carrier family 7, (cationic amino acid transporter, y+ system) member 11 | 2.40 | 0.73 |
| NM_003130 | SRI | Sorcin | 0.92 | 1.80 |
| NM_004599 | SREBF2 | Sterol regulatory element binding transcription factor 2 | 1.47 | 1.03 |
| NM_006745 | SC4MOL | Sterol-C4-methyl oxidase-like | 1.68 | 1.82 |
| NM_006918 | SC5DL | Sterol-C5-desaturase (ERG3 delta-5-desaturase homolog, fungal)-like | 1.59 | 1.11 |
| NM_006819 | STIP1 | Stress-induced-phosphoprotein 1 (Hsp70/Hsp90-organizing protein) | 2.88 | 2.34 |
| NM_006704 | SGT1 | Suppressor of G2 allele of SKP1, S. cerevisiae, homolog of | 1.81 | 1.32 |
| NM_002999 | SDC4 | Syndecan 4 (amphiglycan, ryudocan) | 1.21 | 1.71 |
| NM_006289 | TLN1 | Talin 1 | 1.53 | 1.59 |
| NM_015641 | TES | Testis derived transcript (3 LIM domains) | 2.10 | 0.95 |
| NM_003217 | TEGT | Testis enhanced gene transcript (BAX inhibitor 1) | 1.71 | 1.28 |
| NM_003314 | TTC1 | Tetratricopeptide repeat domain 1 | 1.68 | 2.06 |
| NM_003329 | TXN | Thioredoxin | 1.39 | 2.24 |
| NM_003330 | TXNRD1 | Thioredoxin reductase 1 | 7.66 | 2.72 |

TABLE 16-continued

| Gene ID | Gene Name | Description | | |
|---|---|---|---|---|
| NM_004238 | TRIP12 | Thyroid hormone receptor interactor 12 | 1.73 | 1.43 |
| NM_006755 | TALDO1 | Transaldolase 1 | 1.96 | 1.72 |
| NM_003234 | TFRC | Transferrin receptor (p90, CD71) | 1.51 | 3.15 |
| NM_001064 | TKT | Transketolase (Wernicke-Korsakoff syndrome) | 1.60 | 1.44 |
| NM_012459 | TIMM8B | Translocase of inner mitochondrial membrane 8 homolog B (yeast) | 1.32 | 1.57 |
| NM_006470 | TRIM16 | Tripartite motif-containing 16 | 1.57 | 1.53 |
| NM_003449 | TRIM26 | Tripartite motif-containing 26 | 1.39 | 2.55 |
| NM_003289 | TPM2 | Tropomyosin 2 (beta) | 2.13 | 1.79 |
| NM_003404 | YWHAB | Tyrosine 3-monooxygenase/tryptophan 5-monooxygenase activation protein, beta polypeptide | 2.06 | 3.12 |
| NM_012321 | LSM4 | U6 snRNA-associated Sm-like protein | 1.61 | 0.95 |
| M26880 | UBC | Ubiquitin C | 1.73 | 1.07 |
| NM_014501 | E2-EPF | Ubiquitin carrier protein | 1.83 | 1.41 |
| NM_003334 | UBE1 | Ubiquitin-activating enzyme E1 (A1S9T and BN75 temperature sensitivity complementing) | 1.91 | 1.67 |
| AL110132 | UBE2V1 | Ubiquitin-conjugating enzyme E2 variant 1 | 1.80 | 1.66 |
| BC007657 | UBE2M | Ubiquitin-conjugating enzyme E2M (UBC12 homolog, yeast) | 1.58 | 1.80 |
| NM_003364 | UP | Uridine phosphorylase | 2.48 | 1.13 |
| NM_003574 | VAPA | VAMP (vesicle-associated membrane protein)-associated protein A (33 kD) | 1.85 | 1.71 |
| NM_012323 | MAFF | V-maf musculoaponeurotic fibrosarcoma oncogene homolog F (avian) | 1.71 | 0.72 |
| NM_002359 | MAFG | V-maf musculoaponeurotic fibrosarcoma oncogene homolog G (avian) | 1.85 | 1.41 |
| NM_002467 | MYC | V-myc myelocytomatosis viral oncogene homolog (avian) | 2.75 | 1.98 |
| NM_006007 | ZNF216 | Zinc finger protein 216 | 2.01 | 1.29 |
| NM_013360 | ZNF222 | Zinc finger protein 222 | 2.26 | 1.86 |
| NM_004234 | ZFP93 | Zinc finger protein 93 homolog (mouse) | 0.75 | 1.64 |

| Genes Downregulated by Cigarette Smoke | | | | |
|---|---|---|---|---|
| Gene ID | Gene Name | Description | M4/S4 | M24/S24 |
| NM_006856 | ATF7 | activating transcription factor 7 | 0.81 | 2.32 |
| NM_001143 | AMELY | amelogenin, Y-linked | 1.61 | 1.03 |
| NM_001657 | AREG | amphiregulin (schwannoma-derived growth factor) | 0.50 | 2.95 |
| AB053314 | ALS2CR12 | amyotrophic lateral sclerosis 2 (juvenile) chromosome region, candidate 12 | 2.01 | 1.12 |
| AK023086 | | CDNA FLJ13024 fis, clone NT2RP3000865 | 1.56 | 1.05 |
| BI820294 | | CDNA FLJ26296 fis, clone DMC07192, highly similar to Ig kappa chain V-III region HAH precursor | 1.69 | 0.89 |
| AK025253 | | CDNA FLJ42432 fis, clone BLADE2006412 | 2.15 | 1.70 |
| NM_001271 | CHD2 | chromodomain helicase DNA binding protein 2 | 1.10 | 1.62 |
| NM_006589 | C1orf2 | chromosome 1 open reading frame 2 | 1.56 | 0.87 |
| AK000796 | C14orf129 | chromosome 14 open reading frame 129 | 0.79 | 1.80 |
| NM_001934 | DLX4 | distal-less homeobox 4 | 1.29 | 2.08 |
| NM_005509 | DMXL1 | Dmx-like 1 | 2.05 | 1.22 |
| NM_004419 | DUSP5 | Dual specificity phosphatase 5 | 0.45 | 2.37 |
| NM_003494 | DYSF | dysferlin, limb girdle muscular dystrophy 2B (autosomal recessive) | 1.19 | 2.31 |
| NM_000145 | FSHR | follicle stimulating hormone receptor | 1.58 | 1.29 |
| NM_005708 | GPC6 | glypican 6 | 1.78 | 1.51 |
| NM_002053 | GBP1 | guanylate binding protein 1, interferon-inducible, 67 kDa | 1.31 | 1.58 |

TABLE 16-continued

| | | | | |
|---|---|---|---|---|
| AB033063 | HEG | HEG homolog | 0.88 | 1.97 |
| NM_002129 | HMGB2 | High-mobility group box 2 | 0.69 | 2.78 |
| NM_003542 | HIST1H4F | histone 1, H4f | 1.57 | 1.92 |
| NM_024598 | FLJ13154 | hypothetical protein FLJ13154 | 0.81 | 1.67 |
| NM_017933 | FLJ20701 | hypothetical protein FLJ20701 | 1.37 | 2.03 |
| NM_024037 | MGC2603 | hypothetical protein MGC2603 | 1.59 | 0.74 |
| BC016840 | MGC34695 | hypothetical protein MGC34695 | 0.99 | 2.33 |
| AK027858 | MGC4248 | hypothetical protein MGC4248 | 1.53 | 0.92 |
| NM_006903 | PPA2 | inorganic pyrophosphatase 2 | 0.63 | 1.64 |
| NM_000526 | KRT14 | keratin 14 (epidermolysis bullosa simplex, Dowling-Meara, Koebner) | 1.09 | 2.13 |
| NM_000424 | KRT5 | keratin 5 (epidermolysis bullosa simplex, Dowling-Meara/Kobner/Weber-Cockayne types) | 1.48 | 1.86 |
| NM_005554 | KRT6A | keratin 6A | 1.53 | 1.17 |
| NM_005556 | KRT7 | keratin 7 | 1.54 | 1.06 |
| AK024583 | | LOC400078 (LOC387888), mRNA | 1.60 | 1.19 |
| NM_005583 | LYL1 | lymphoblastic leukemia derived sequence 1 | 1.73 | 1.17 |
| AL137524 | | MRNA* cDNA DKFZp434H2218 (from clone DKFZp434H2218) | 1.03 | 1.67 |
| AL117623 | | MRNA* cDNA DKFZp564O2364 (from clone DKFZp564O2364) | 1.72 | 1.02 |
| NM_012334 | MYO10 | myosin X | 2.08 | 1.13 |
| AB007959 | NHLH2 | nescient helix loop helix 2 | 1.08 | 1.53 |
| NM_002520 | NPM1 | nucleophosmin (nucleolar phosphoprotein B23, numatrin) | 1.62 | 1.67 |
| NM_033014 | OGN | osteoglycin (osteoinductive factor, mimecan) | 1.21 | 1.62 |
| NM_024594 | PANK3 | pantothenate kinase 3 | 1.88 | 1.42 |
| AB029015 | PLCL2 | Phospholipase C-like 2 | 5.45 | 2.99 |
| NM_018049 | PLEKHJ1 | pleckstrin homology domain containing, family J member 1 | 2.48 | 1.68 |
| BC015542 | PVR | poliovirus receptor | 1.54 | 0.98 |
| NM_018936 | PCDHB2 | protocadherin beta 2 | 1.64 | 1.02 |
| NM_000320 | QDPR | quinoid dihydropteridine reductase | 1.24 | 1.81 |
| NM_000456 | RAB5B | RAB5B, member RAS oncogene family | 2.56 | 2.22 |
| NM_007273 | REA | repressor of estrogen receptor activity | 0.83 | 1.51 |
| NM_005978 | S100A2 | S100 calcium binding protein A2 | 1.89 | 1.55 |
| NM_016372 | TPRA40 | seven transmembrane domain orphan receptor | 1.57 | 0.84 |
| NM_006456 | SIAT7B | sialyltransferase 7 ((alpha-N-acetylneuraminyl-2,3-beta-galactosyl-1,3)-N-acetyl galactosaminide alpha-2,6-sialyltransferase) B | 0.77 | 2.21 |
| NM_024624 | SMC6L1 | SMC6 structural maintenance of chromosomes 6-like 1 (yeast) | 1.74 | 1.71 |
| AL353933 | SLC22A15 | solute carrier family 22 (organic cation transporter), member 15 | 1.85 | 1.07 |
| AK027663 | STC2 | stanniocalcin 2 | 0.77 | 1.74 |
| AK024451 | DKFZp762C186 | Tangerine | 1.56 | 1.30 |
| NM_005480 | TROAP | trophinin associated protein (tastin) | 1.77 | 1.12 |
| NM_002466 | MYBL2 | v-myb myeloblastosis viral oncogene homolog (avian)-like 2 | 1.01 | 1.63 |
| NM_006385 | ZNF211 | Zinc finger protein 211 | 1.96 | 1.22 |
| NM_005096 | ZNF261 | Zinc finger protein 261 | 1.68 | 1.53 |
| NM_003430 | ZNF91 | Zinc finger protein 91 (HPF7, HTF10) | 1.47 | 1.53 |
| AC006033 | | | 1.52 | 1.21 |
| AF111848 | | | 1.68 | 1.27 |
| AK025272 | | | 8.36 | 4.55 |
| AL137077 | | | 2.59 | 1.28 |
| L24498 | | | 0.31 | 1.58 |
| NM_003590 | | | 2.06 | 1.03 |
| NM_005774 | | | 1.72 | 1.29 |
| NM_014111 | | | 1.53 | 2.49 |

Figure 42A:
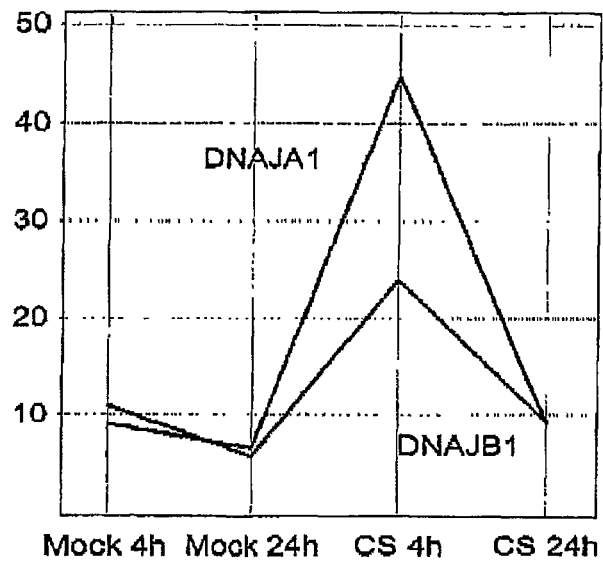
FIGS. 42A and B show a comparison of expression behavior of heat shock protein family members DNAJA1 and DNAJB1 in Experiment 1 (FIG. 42A) and 2 (FIG. 42B). Each time point represents the average of 2 or 3 replicates per condition.
Figure 42B:
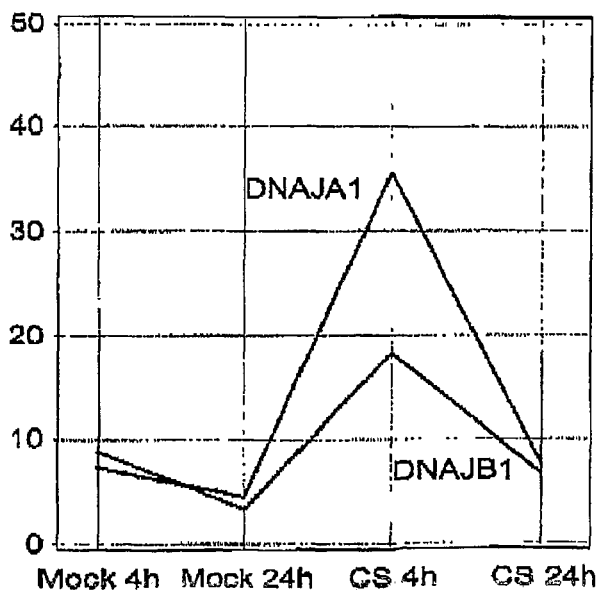

A typical example is shown in FIG. 42, which compares the expression of the heat shock genes DnaJ (HSP40) A1/B1 at 4 and 24 h in mock-treated and CS-treated cells in both experiments. The figure shows not only a consistent temporal relationship in the two experiments with both genes being up-regulated by 4 hrs and then returning to baseline by 24 hrs, but also that there is a consistent relative level of expression between the two genes (i.e., 4 hr expression levels of B1 exceed that of A1 in both experiments).

Confirmation of Differential Expression by qRT-PCR

The relative expression levels of 6 genes that were determined by microarray analysis to be up-regulated in CS-treated NHBE cells were reassessed by quantitative PCR using RNA from samples taken at both 4 and 24 hr. This gene set included: ferritin heavy polypeptide, nuclear factor (erythroid-derived 2)-like 2, heat shock protein 70, heme oxygenase, thioredoxin reductase, cyclooxygenase 2, and sequestosome 1. It was determined that beta-actin expression levels in the normalized microarray data were nearly identical among all the CS and mock-treated samples, so this gene was used as an internal normalization standard in these experiments. Quantitative PCR results were in strong qualitative agreement with the microarray results, as all 6 genes were also up-regulated by CS when assessed by qRT-PCR. Moreover, the qRT-PCR results recapitulated the general trends of expression at both 4 and 24 hr that were observed by microarray (Table 17).

TABLE 17

Microarray data

| Gene 1 | microarray 4 hr/fold change | Qpcr 4 hr/fold change | microarray 24 hr/fold change | qRT-PCR 24 hr/fold change |
|---|---|---|---|---|
| FTH1 | 2.3 | 2.6 | 3.4 | 3.5 |
| HSPA1A | 16.1 | 25.1 | 2.4 | 5.0 |
| NFE2L2 | 3.8 | 3.47 | 1.23 | 1.21 |
| TXNRD1 | 11.4 | 16.0 | 3.2 | 2.0 |
| HMOX1 | 42.5 | 77.6 | 1.7 | 4.7 |
| PTGS2 | 5.4 | 17.0 | 0 | 0 |
| SQSTM1 | 3.9 | 7.7 | 2.6 | 3.3 |

Since the wide range of gases, toxins, free radicals, and carcinogens present in tobacco smoke are believed to cause multiple types of structural and chemical damage, the NHBE cells that are exposed to tobacco smoke would presumably have to mount an integrated biological and genetic response in an attempt to prioritize and attenuate this damage. In an effort to understand the type of response mounted by the NHBE cells after cigarette smoke exposure, several databases were analyzed and genes that were identified as being over-expressed or under-expressed in response to exposure to cigarette smoke were grouped according to functional similarities. The following example describes this effort in greater detail.

Example 13

Functional Grouping of Genes Modulated in Response to CS Exposure

Information from the Gene Ontology (GO) Consortium and from the scientific literature was used to categorize the genes identified as being modulated (i.e., over-expressed or under-expressed) in response to cigarette smoke exposure. Of the genes up-regulated by CS exposure that have known functions (235 out of 298 genes), four major groups of functionally related genes were identified (Table 11). These four groups collectively represent a large proportion (45%; 105 out of 235 genes) of the differentially expressed genes with known function, indicating that these genes are involved in biological pathways that are highly responsive to CS-induced damage. In contrast, although 42 of the 66 genes that were under-expressed in response to CS have known functions, they reflected multiple biological processes without a clear dominance of specific function. As can be seen in Table 11, the predominant pathways highlighted by the over-expressed gene set indicate that the cell is responding to a sudden increase in oxidative stress and the concentration of misfolded or damaged proteins, while simultaneously attempting to modulate its cell cycle and apoptotic controls. Unexpectedly, it was also observed that a proportionally large group of CS-responsive genes are related to the metabolism and cellular trafficking of cholesterol.

TABLE 18

| Gene ID | Symbol | Description | Fold Increase at 4 h | Fold Increase at 24 h |
|---|---|---|---|---|
| | | RESPONSE TO OXIDATIVE STRESS | | |
| BF541376 | FTL | ESTs, Weakly similar to FRHUL ferritin light chain [*H. sapiens*] | 2.71 | 4.50 |
| AK054816 | FTH1 | Ferritin, heavy polypeptide 1 | 2.07 | 3.32 |
| NM_001498 | GCLC | Glutamate-cysteine ligase, catalytic subunit | 8.96 | 1.40 |
| NM_002061 | GCLM | Glutamate-cysteine ligase, modifier subunit | 2.85 | 1.56 |
| NM_002064 | GLRX | Glutaredoxin (thioltransferase) | 3.12 | 2.31 |
| NM_002083 | GPX2 | Glutathione peroxidase 2 (gastrointestinal) | 3.71 | 9.99 |
| NM_000637 | GSR | Glutathione reductase | 1.57 | 1.54 |
| NM_002133 | HMOX1 | Heme oxygenase (decycling) 1 | 55.83 | 2.81 |
| NM_005354 | JUND | Jun D proto-oncogene | 1.67 | 1.25 |
| NM_004528 | MGST3 | Microsomal glutathione S-transferase 3 | 1.73 | 1.76 |
| NM_000903 | NQO1 | NAD(P)H dehydrogenase, quinone 1 | 2.64 | 2.77 |
| NM_006096 | NDRG1 | N-myc downstream regulated gene 1 | 1.50 | 1.95 |
| NM_006164 | NFE2L2 | Nuclear factor (erythroid-derived 2)-like 2 | 3.80 | 1.23 |
| NM_020992 | PDLIM1 | PDZ and LIM domain 1 (elfin) | 1.56 | 1.60 |
| NM_002574 | PRDX1 | Peroxiredoxin 1 | 1.68 | 1.80 |
| NM_000687 | AHCY | S-adenosylhomocysteine hydrolase | 1.74 | 1.82 |
| NM_003329 | TXN | Thioredoxin | 1.39 | 2.24 |

TABLE 18-continued

| Gene ID | Symbol | Description | Fold Increase at 4 h | Fold Increase at 24 h |
|---|---|---|---|---|
| NM_003330 | TXNRD1 | Thioredoxin reductase 1 | 7.66 | 2.72 |
| NM_012323 | MAFF | V-maf musculoaponeurotic fibrosarcoma oncogene homolog F (avian) | 1.71 | 0.72 |
| NM_002359 | MAFG | V-maf musculoaponeurotic fibrosarcoma oncogene homolog G (avian) | 1.85 | 1.41 |
| CELL GROWTH/PROLIFERATION/APOPTOSIS | | | | |
| NM_001657 | AREG | Amphiregulin (schwannoma-derived growth factor) | 1.96 | 0.33 |
| NM_016085 | APR-3 | Apoptosis related protein APR-3 | 1.44 | 0.84 |
| NM_017900 | AKIP | aurora-A kinase interacting protein | 2.07 | 5.18 |
| NM_001196 | BID | BH3 interacting domain death agonist | 1.54 | 1.05 |
| NM_005186 | CAPN1 | Calpain 1, (mu/I) large subunit | 1.62 | 1.11 |
| NM_013376 | SEI1 | CDK4-binding protein p34SEI1 | 2.46 | 1.87 |
| NM_015965 | GRIM19 | Cell death-regulatory protein GRIM19 | 2.16 | 2.23 |
| NM_001554 | CYR61 | Cysteine-rich, angiogenic inducer, 61 | 2.44 | 0.67 |
| NM_004396 | DDX5 | DEAD/H (Asp-Glu-Ala-Asp/His) box polypeptide 5 (RNA helicase, 68 kD) | 2.01 | 4.10 |
| NM_013253 | DKK3 | Dickkopf homolog 3 (*Xenopus laevis*) | 1.64 | 0.84 |
| NM_004419 | DUSP5 | Dual specificity phosphatase 5 | 1.97 | 0.47 |
| NM_001946 | DUSP6 | Dual specificity phosphatase 6 | 2.08 | 2.29 |
| NM_004431 | EPHA2 | EphA2 | 2.37 | 1.93 |
| NM_005245 | FAT | FAT tumor suppressor homolog 1 (*Drosophila*) | 1.87 | 0.77 |
| NM_002087 | GRN | Granulin | 1.36 | 1.58 |
| L24498 | GADD45A | Growth arrest and DNA-damage-inducible, alpha | 2.81 | 0.61 |
| AF130111 | HDAC3 | Histone deacetylase 3 | 1.92 | 1.38 |
| AF103803 | H41 | Hypothetical protein | 1.63 | 2.00 |
| NM_052815 | IER3 | Immediate early response 3 | 2.94 | 1.54 |
| NM_016545 | IER5 | Immediate early response 5 | 9.20 | 1.18 |
| NM_000576 | IL1B | Interleukin 1, beta | 0.98 | 3.03 |
| NM_001730 | KLF5 | Kruppel-like factor 5 (intestinal) | 2.34 | 1.01 |
| NM_004529 | MLLT3 | Myeloid/lymphoid or mixed-lineage leukemia (trithorax homolog, *Drosophila*)-translocated to, 3 | 1.15 | 2.41 |
| NM_002632 | PGF | Placental growth factor, vascular endothelial growth factor-related protein | 3.61 | 1.79 |
| NM_002658 | PLAU | Plasminogen activator, urokinase | 1.69 | 1.78 |
| NM_001198 | PRDM1 | PR domain containing 1, with ZNF domain | 7.04 | 3.20 |
| NM_002583 | PAWR | PRKC, apoptosis, WT1, regulator | 1.96 | 1.50 |
| NM_014330 | PPP1R15A | Protein phosphatase 1, regulatory (inhibitor) subunit 15A | 7.10 | 0.88 |
| NM_015714 | G0S2 | Putative lymphocyte G0/G1 switch gene | 0.90 | 6.31 |
| NM_001666 | ARHGAP4 | Rho GTPase activating protein 4 | 2.49 | 1.96 |
| NM_006622 | SNK | Serum-inducible kinase | 3.02 | 1.13 |
| NM_006109 | SKB1 | SKB1 homolog (*S. pombe*) | 1.55 | 2.52 |
| NM_006704 | SGT1 | Suppressor of G2 allele of SKP1, *S. cerevisiae*, homolog | 1.81 | 1.32 |
| NM_003217 | TEGT | Testis enhanced gene transcript (BAX inhibitor 1) | 1.71 | 1.28 |
| NM_002467 | MYC | V-myc myelocytomatosis viral oncogene homolog (avian) | 2.75 | 1.98 |
| UBIQUITINATION/PROTEIN TURNOVER/HEAT SHOCK | | | | |
| NM_001109 | ADAM8 | A disintegrin and metalloproteinase domain 8 | 1.17 | 2.72 |
| NM_004281 | BAG3 | BCL2-associated athanogene 3 | 3.85 | 1.58 |
| BC002971 | CCT5 | Chaperonin containing TCP1, subunit 5 (epsilon) | 1.81 | 1.74 |
| NM_006429 | CCT7 | Chaperonin containing TCP1, subunit 7 (eta) | 2.85 | 3.21 |
| NM_007278 | GABARAP | GABA(A) receptor-associated protein | 1.55 | 1.75 |
| NM_001539 | DNAJA1 | DnaJ (Hsp40) homolog, subfamily A, member 1 | 2.11 | 1.85 |

TABLE 18-continued

| Gene ID | Symbol | Description | Fold Increase at 4 h | Fold Increase at 24 h |
| --- | --- | --- | --- | --- |
| NM_006145 | DNAJB1 | DnaJ (Hsp40) homolog, subfmaily B, member 1 | 4.99 | 1.57 |
| AF395440 | HEJ1 | Similar to DNAJ | 2.50 | 1.94 |
| NM_006644 | HSP105B | Heat shock 105 kD | 2.83 | 1.02 |
| NM_002157 | HSPE1 | Heat shock 10 kD protein 1 (chaperonin 10) | 1.92 | 1.34 |
| NM_005345 | HSPA1A | Heat shock 70 kD protein 1A | 5.77 | 1.30 |
| NM_006597 | HSPA8 | Heat shock 70 kD protein 8 | 1.48 | 4.56 |
| NM_004134 | HSPA9B | Heat shock 70 kD protein 9B (mortalin-2) | 2.23 | 1.39 |
| NM_016292 | TRAP1 | Heat shock protein 75 | 1.57 | 1.05 |
| NM_006819 | STIP1 | Stress-induced-phosphoprotein 1 (Hsp70/Hsp90-organizing protein) | 2.88 | 2.34 |
| NM_004995 | MMP14 | Matrix metalloproteinase 14 (membrane-inserted) | 2.20 | 2.57 |
| BC013908 | PSMC1 | Proteasome (prosome, macropain) 26S subunit, ATPase, 1 | 1.68 | 1.13 |
| NM_002806 | PSMC6 | Proteasome (prosome, macropain) 26S subunit, ATPase, 6 | 1.64 | 1.25 |
| NM_002815 | PSMD11 | Proteasome (prosome, macropain) 26S subunit, non-ATPase, 11 | 1.77 | 1.35 |
| NM_002812 | PSMD8 | Proteasome (prosome, macropain) 26S subunit, non-ATPase, 8 | 2.17 | 3.03 |
| NM_002797 | PSMB5 | Proteasome (prosome, macropain) subunit, beta type, 5 | 2.82 | 3.28 |
| NM_002799 | PSMB7 | Proteasome (prosome, macropain) subunit, beta type, 7 | 1.36 | 1.74 |
| NM_006808 | SEC61B | Protein translocation complex beta | 1.44 | 1.57 |
| NM_014248 | RBX1 | Ring-box 1 | 1.30 | 2.13 |
| NM_003900 | SQSTM1 | Sequestosome 1 | 3.34 | 2.82 |
| NM_003134 | SRP14 | Signal recognition particle 14 kD (homologous Alu RNA binding protein) | 1.58 | 1.45 |
| NM_003314 | TTC1 | Tetratricopeptide repeat domain 1 | 1.68 | 2.06 |
| NM_004238 | TRIP12 | Thyroid hormone receptor interactor 12 | 1.73 | 1.43 |
| M26880 | UBC | Ubiquitin C | 1.73 | 1.07 |
| NM_014501 | E2-EPF | Ubiquitin carrier protein | 1.83 | 1.41 |
| NM_003334 | UBE1 | Ubiquitin-activating enzyme E1 (A1S9T and BN75 temperature sensitivity complementing) | 1.91 | 1.67 |
| AL110132 | UBE2V1 | Ubiquitin-conjugating enzyme E2 variant 1 | 1.80 | 1.66 |
| BC007657 | UBE2M | Ubiquitin-conjugating enzyme E2M (UBC12 homolog, yeast) | 1.58 | 1.80 |
| NM_000859 | HMGCR | 3-hydroxy-3-methylglutaryl-Coenzyme A reductase | 2.25 | 1.33 |
| AK025736 | HMGCS1 | 3-hydroxy-3-methylglutaryl-Coenzyme A synthase 1 (soluble) | 1.02 | 1.63 |
| CHOLESTEROL/LIPID METABOLISM | | | | |
| NM_005891 | ACAT2 | Acetyl-Coenzyme A acetyltransferase 2 (acetoacetyl Coenzyme A thiolase) | 1.44 | 1.77 |
| NM_000700 | ANXA1 | Annexin A1 | 1.39 | 1.82 |
| NM_007274 | HBACH | Cytosolic acyl coenzyme A thioester hydrolase | 1.61 | 2.28 |
| NM_020548 | DBI | Diazepam binding inhibitor (GABA receptor modulator, acyl-Coenzyme A binding protein) | 1.69 | 1.84 |
| NM_004092 | ECHS1 | Enoyl Coenzyme A hydratase, short chain, 1, mitochondrial | 1.60 | 1.23 |
| NM_004104 | FASN | Fatty acid synthase | 1.24 | 1.60 |
| NM_000182 | HADHA | Hydroxyacyl-Coenzyme A dehydrogenase/3-ketoacyl-Coenzyme A thiolase/enoyl-Coenzyme A hydratase | 2.39 | 1.22 |
| NM_005542 | INSIG1 | Insulin induced gene 1 | 2.02 | 2.62 |
| NM_004508 | IDI1 | Isopentenyl-diphosphate delta isomerase | 1.89 | 2.68 |
| NM_000271 | NPC1 | Niemann-Pick disease, type C1 | 2.31 | 1.39 |
| NM_003713 | PPAP2B | Phosphatidic acid phosphatase type 2B | 1.22 | 1.84 |
| NM_002778 | PSAP | Prosaposin (variant Gaucher disease and variant metachromatic leukodystrophy) | 1.70 | 2.72 |

TABLE 18-continued

| Gene ID | Symbol | Description | Fold Increase at 4 h | Fold Increase at 24 h |
|---|---|---|---|---|
| NM_004599 | SREBF2 | Sterol regulatory element binding transcription factor 2 | 1.47 | 1.03 |
| NM_006745 | SC4MOL | Sterol-C4-methyl oxidase-like | 1.68 | 1.82 |
| NM_006918 | SC5DL | Sterol-C5-desaturase (ERG3 delta-5-desaturase homolog, fungal)-like | 1.59 | 1.11 |

Figure 43:
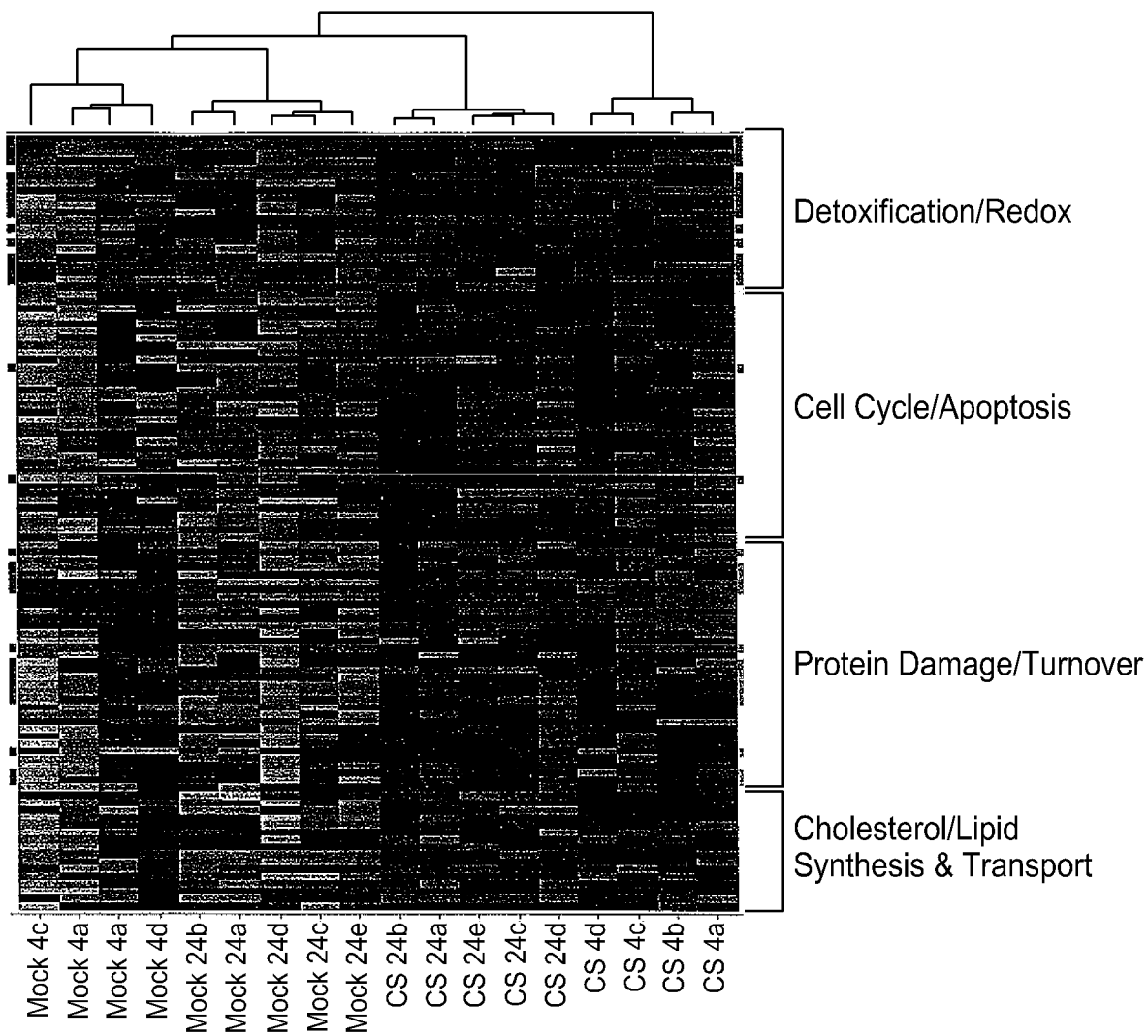
FIG. 43 is a hierarchical clustering of samples using 105 genes that were both over-expressed upon treatment of NHBE cells with CS in two separate experiments, and encoded protein products that modulate one of the 4 major CS-affected GO-defined cellular functions identified. Samples a-b are from Experiment 1, samples c-e are from Experiment 2. A bar indicates heat shock and heat shock-associated genes showing greatly increased expression exclusively at 4 h. Markings indicate genes whose expression is known to be regulated by transcription factor NRF2.

In order to visualize any underlying temporal expression patterns among these four functional classes a hierarchical clustering of the genes was made (see FIG. 43). This cluster analysis of the expression data shows two important points: 1) that the four conditions (4 & 24 h mock-treated and 4 & 24 h CS-treated) are clearly distinguishable by these functional groups of genes; and 2) that the expression of the specific genes in the four functional groups do not have strong temporal relationships (i.e. they do not overwhelmingly cluster within either the 0-4 hours or 4-24 hour time frame). However, it is clear from FIG. 43 that the majority of the CS-responsive genes in these functional groups exhibit a higher expression at 4 h post-exposure than at 24 h. Since the cells were treated for only 15 minutes and then analyzed for a change in gene expression after 4 and 24 hrs, the decrease in expression for many of these genes by 24 hrs indicates that the cell is attempting to "reset" its transcriptome to pre-exposure levels, which would not be an unexpected response to a transient insult. However, the fact that the expression of many of these genes remains increased over pre-exposure levels for up to 24 hrs also indicates that the biological ramifications of CS-exposure can affect the cell for a long period of time after exposure to tobacco smoke is terminated. Accordingly, it is plausible that many of these genes may not return to homeostatic baseline in a habitual smoker, which may have unforeseen pathological consequences.

A notable exception to most of the genes shown in FIG. 43 and TABLE 18, whose expression remain elevated up to 24 hrs post-exposure, is a large block of genes in the protein damage/turnover group, and which encode primarily heat shock and heat shock-associated proteins. The expression of these heat shock related genes is dramatically elevated at 4 hrs but returns to baseline by 24 hrs, indicating that the processes that engage and clear a buildup of CS-induced damaged and dysfunctional proteins are rapid. Finally, there are a small subset of genes whose expression levels are higher at 24 h than at 4 h, including ferritin, NADH dehydrogenase, peroxiredoxin 1, and glutathione peroxidase. Since each of these genes is involved in redox reactions, it could signify that oxidative stress caused by CS induces long-lived perturbations to redox homeostasis.

The four major functional groups of genes listed in Table 18 and shown in FIG. 43 show a well-organized attempt by the NHBE cell to attenuate the damage caused by exposure to tobacco smoke. This type of coordinated response provides evidence that functionally related blocks of genes are transcriptionally regulated by the same or similar transcriptional activators. In the full set of 298 genes up-regulated by CS (see TABLE 16), there are 21 genes with gene products that function as transcriptional regulators, including v-myc, interferon regulatory factor 6, eukaryotic translation initiation factor 4B, Kruppel-like factor 5, sterol regulatory element binding transcription factor 2 (SREB2), and Nuclear factor (erythroid-derived 2)-like 2 (NRF2). NRF2 is of particular interest in this regard since studies of NRF2-knockout mice show that this transcription factor activates over 200 genes in several functional classes with the two most predominant being oxidative stress response and protein turnover (Kwak et al., J. Biol. Chem. (2003) 278:8135-8145). As shown in Table 18, both of these classes of genes are disproportionately activated by exposure of NHBE cells to tobacco smoke. Specifically, of the 105 genes presented in Table 18, 33 are known to be under transcriptional control of NRF2, or to act as cofactors for NRF2-regulated transcription (see FIG. 43).

In addition, it has been shown that the short-term exposure of mice to cigarette smoke results in the induction of a set of 46 protective genes, all of which are under the control of NRF2 (Rangasamy et al., J. Clin. Invest. (2004) 114:1248-1259). In concordance with this observation, the data show that despite only brief exposure cells to CS in vitro, the RNA levels of 19 human homologues of these 46 mouse genes (41%) are similarly induced, indicating that the CS-related molecular events occurring in vitro are very similar to those observed in vivo. This set of CS-induced genes in both the mouse and NHBE cells includes those responsive to oxidative stress (heme oxygenase, phosphogluconate dehydrogenase, thioredoxin reductase, glutathione pathway genes, NADPH:quinone reductase), protein damage (HSP40, mortalin, GADD45), and protein turnover (ubiquitin C, proteasome subunits, sequestosome).

The fact that cigarette smoke, as well as various constituents of cigarette smoke, can cause disruptions to the genome, transcriptome, and proteome, allows one to develop a set of relevant biomarkers that are useful for monitoring exposure to tobacco toxins, detecting pre-malignant disease, improving diagnosis and prognosis of current disease, developing new treatment options, and testing risk reduction strategies for current and former smokers. A number of studies assessing the clinical usefulness of alterations in global gene and protein expression patterns in malignant and normal human lung tissues have recently shown that quantitative and/or qualitative changes in a small number of expressed genes and proteins, in combination with standard clinicopathological variables, may have prognostic and/or diagnostic potential in patients with tobacco-related diseases. Thus, elucidating the various molecular, genetic, and cellular dysfunctions induced by tobacco smoke may not only reveal a useful set of tobacco-specific biomarkers, but also result in a detailed mechanistic understanding of how chronic tobacco exposure causes disease.

In more embodiments, a second tobacco product (e.g., a cigarette) is compared to a first tobacco product (e.g., a cigarette) using the methods above so as to identify which of the two tobacco products is less likely to contribute to a tobacco-related disease. For example, a first population of isolated human cells of the mouth, tongue, oral cavity, or lungs (e.g., NHBE cells), is contacted with a CS from a first tobacco product (e.g., a "reduced risk full flavor" cigarette)

in an amount and for a time sufficient to modulate expression of one or more genes or to modify a gene product, and identification of the genes that are modulated or modified gene product (e.g., phosphorylated) or the level or amount of gene expression or modification can be determined using any technique available that analyzes transcription (e.g., microarray, genechip, qRT-PCR or hybridization), protein production (e.g., ELISA, Western blot, or other antibody detection techniques), modifications of proteins (e.g., oxidation or phosphorylation), or the appearance or disappearance of metabolites associated with genes that are modulated in response to exposure to CS (e.g., cysteine, glutathione, fragments of proteins or lipids or fatty acids). A second population of isolated human cells of the mouth, tongue, oral cavity, or lungs (e.g., NHBE cells), preferably the same type of cell as used in the analysis of the first tobacco product, is also contacted with a CS from a second tobacco product (e.g., a cigarette) in an amount and for a time sufficient to modulate expression of one or more genes or to modify a gene product. Identification of a gene that is modulated or modified gene product (e.g., phosphorylated) or the level or amount of gene expression or modification can be accomplished using any technique available that analyzes transcription (e.g., microarray, genechip, qRT-PCR or hybridization), protein production (e.g., ELISA, Western blot, or other antibody detection techniques), modifications of proteins (e.g., oxidation or phosphorylation), or the appearance or disappearance of metabolites associated with genes that are modulated in response to exposure to CS (e.g., cysteine, glutathione, fragments of proteins or lipids or fatty acids).

The data obtained from the analysis of the first tobacco product can be compared to the data obtained from the analysis of the second tobacco product so as to identify, for example, a gene(s) that are induced in response to exposure to the first tobacco product but not the second tobacco product or vice versa. Additionally, the comparison will reveal that the level of expression of one or more genes induced by both tobacco products differs with respect to the two tobacco products or that the first product has more, less, or no modification of a particular gene product (e.g., phosphorylation), as compared to the second tobacco product or vice versa. These data (e.g., the types of genes expressed, the amount of expression, and modification) allow one to develop a profile for each tobacco product analyzed (in this example only two products are being compared but a plurality of products can be compared using the same approach). These tobacco product profiles can be recorded on a computer readable media and databases containing this information can be created. Once a gene is identified, it can be analyzed using PathwayAssist™ software (Stratagene, La Jolla, Calif.), Genespring (version 7.2, Agilent Technologies), or other similar software so as to determine whether the gene contributes to a tobacco-related disease.

By analyzing the differences between the tobacco products analyzed, (e.g., the types of genes expressed, the amount of expression, and modifications), one can identify a tobacco product that has less potential to contribute to a tobacco related disease or that, for example, a first tobacco product has a reduced risk to contribute to a tobacco-related disease, as compared to a second tobacco product or vice versa. By one technique, for example, a tobacco product that is less likely to contribute to a tobacco-related disease is identified because it induces fewer genes associated with a tobacco-related disease. A related approach (using CSC) was employed to identify a tobacco product as having a reduced potential to contribute to a tobacco-related disease, as compared to a second tobacco product. (See Examples 4-6).

The methods provided herein can be used not only to identify a tobacco product that has a reduced potential to contribute to a tobacco-related disease, as compared to a second tobacco product, but also to develop tobacco products that have a reduced potential to contribute to a tobacco-related disease, as compared to a second tobacco product. That is, by coordinating techniques (e.g., chemical or genetic modification) to modulate expression of genes that produce various components in tobacco with the analytical methods disclosed herein, one can rapidly determine whether the modulation of a particular gene that produces a particular component in tobacco results in a modulation of a gene in human cells (e.g., NHBE cells) that results in a reduced potential to contribute to a tobacco-related disease, as compared to the tobacco prior to modulation of component-producing gene. The section below describes these embodiments in greater detail.

Epidemiological Determinations

In still more embodiments, cells of the mouth, oral cavity, trachea, or lung (e.g., NHBE cells) from a plurality of individuals, preferably the same cell type, are independently contacted with a tobacco composition (e.g., CS) in an amount and for a time sufficient to induce damage of cellular genetic material or modulate cell homeostasis. The fact that CS, as well as various constituents of CS, can cause disruptions to the cell allows one to develop a set of relevant biomarkers that are useful for monitoring exposure to tobacco toxins, detecting pre-malignant disease, improving diagnosis and prognosis of current disease, developing new treatment options, testing chemopreventive compounds, and testing risk reduction strategies for current and former smokers. Accordingly, also provided herein are methods of detecting pre-malignant disease, improving diagnosis and prognosis of current disease, developing new treatment options, testing chemopreventive compounds, and testing risk reduction strategies for current and former smokers by determining the amount of induction of damage of cellular genetic material or modulation of cell homeostasis to the cells of a smoker or other tobacco consumer or a subject exposed to a tobacco composition. The cells of different individuals can respond differently to tobacco compositions and thereby have different levels of risk of developing a tobacco-related disease. The methods provided herein for determining a modulation of cell homeostasis, or determining a marker indicative of modulation of cell homeostatis, such as the methods of determining a modulation of gene expression (e.g., transcriptome or proteome modulation), or determining the amount of induction of damage of cellular genetic material in cells contacted with a tobacco composition can be used to assess a subject's level of risk of developing a tobacco-related disease. Such methods can be generally performed in accordance with the methods provided herein, where the cells of the subject can be first contacted with smoke from the tobacco product in vivo (e.g., by the subject smoking a cigarette or side-stream smoke exposure), and then the cells can be harvested using known methods (e.g., lung lavage or cheek swab); alternatively, the cells of a subject can be first harvested and optionally cultured, and then contacted with smoke from the tobacco product in accordance with the methods provided herein. Provided below are non-limiting exemplary methods for testing tobaccos, tobacco products, compounds and the like; it is understood that any of the methods provided herein for monitoring a modulation of cell homeostasis can be used in the examples provided below.

In one example, primary cultures of lung cells, bronchial cells, cells of the mouth, pharynx, larynx, and tongue can be generated from an individual to be tested and these cells are be contacted with a tobacco composition (e.g., CS from a tobacco product) so as to elucidate the individuals proclivity to acquire a tobacco related disease. Certain patterns of amount of induction of damage of cellular genetic material or modulation of cell homeostasis to tobacco compositions can be associated with individuals that do not develop a tobacco related disease and a different pattern of amount of induction of damage of cellular genetic material or modulation of cell homeostasis can be associated with individuals that have developed a tobacco-related disease. Analysis of the amount of induction of damage of cellular genetic material or modulation of cell homeostasis of many of such individuals allows the development of databases that provide an expected type and amount of induction of damage of cellular genetic material or modulation of cell homeostasis that is associated or not associated with a tobacco-related disease. That is, this information can be used to provide a baseline for an individual that is not likely to acquire a tobacco-related disease (e.g., a control level exemplified by non-tobacco users that do not develop a tobacco-related disease) and a baseline for an individual that is likely to acquire a tobacco related disease (e.g., a control level exemplified by tobacco users that have developed a tobacco-related disease). Accordingly, when a subject is analyzed for the predilection to develop a tobacco-related disease, the amount of induction of damage of cellular genetic material or modulation of cell homeostasis can be evaluated and, by comparing the determined values to that in one or both of the databases described above, the analyzed subject can be identified as having a predilection for developing a tobacco-related disease.

Additionally, a comparison of the induction of DNA damage induced by conventional tobacco products and a tobacco product containing a modified tobacco (e.g., a genetically modified tobacco) is contemplated. By one approach, a first set of biological samples (e.g., cells of the oral cavity (cheek or gum swab) or lung cells (lung lavage)) are obtained from individuals that are consumers of conventional tobacco products. These cells are analyzed for double strand DNA breaks using one of the assays described herein. Next, the individuals are provided a tobacco product comprising a modified tobacco to consume exclusively (i.e., in replacement for the conventional product). After a period of time has passed (e.g., 1, 2, 3, or 4 weeks or 1, 2, 3, 4, 5, 6, 7, 8, 9, 10, 11, or 12 months since the conversion from the conventional tobacco product to the tobacco product containing the modified tobacco), a second set of biological samples are taken from the individual and are analyzed for the presence of double strand DNA breaks. It will be determined that fewer double strand breaks will be observed in the second set of biological samples than the first set, which will provide evidence that the tobacco product comprising the modified tobacco has a reduced potential to contribute to a tobacco related disease (i.e., that said tobacco product comprising the modified tobacco is a reduced risk tobacco product).

Additionally, a reduction by a chemopreventive compound of the induction of DNA damage induced by a tobacco product can also be measured by the methods provided herein. By one approach, a first set of biological samples (e.g., cells of the oral cavity (cheek or gum swab) or lung cells (lung lavage)) are obtained from individuals that are consumers of tobacco products. These cells are analyzed for double strand DNA breaks using one of the assays described herein. Next, the individuals are provided a candidate chemoprotective compound to consume or use before, during, or after use of the tobacco product. After a period of time has passed (e.g., 1, 2, 3, or 4 weeks or 1, 2, 3, 4, 5, 6, 7, 8, 9, 10, 11, or 12 months) since the commencement of using the test chemoprotective compound, a second set of biological samples are taken from the individual and are analyzed for the presence of double strand DNA breaks. It will be determined that fewer double strand breaks will be observed in the second set of biological samples than the first set, which will provide evidence that the test chemoprotective compound can reduce the potential of tobacco to contribute to a tobacco related disease.

Further provided herein are kits to be used in practicing the above methods. In various embodiments such kits can comprise an antibody that binds to phosphorylated but not unphosphorylated H2AX, a reference smoke product, a detectably labeled second antibody that specifically binds to the antibody that binds to phosphorylated H2AX, and suitable cells, as provided herein elsewhere.

Also provided herein are cells containing DNA having double-stranded breaks produced by exposure to a tobacco smoke product and, in particular, to genetically altered cells comprising cells prepared by a method comprising the steps of: (a) exposing a first cell population to a tobacco smoke product; (b) identifying cells containing a greater degree of phosphorylated H2AX relative to control cells; and (c) selectively collecting the cells identified in step (b) to form the composition of genetically altered cells. In preferred non-limiting embodiments, the cells having a higher degree of phosphorylated H2AX are identified by an immunofluorescence method and selectively collected, for example by fluorescence activated cell sorting. To permit the identification of genes associated with tobacco-induced diseases, also provided herein are libraries prepared by cloning a plurality of nucleic acid molecules prepared from the cells, the cells prepared according to methods provided for forming cells containing DNA having double-stranded breaks produced by exposure to a tobacco smoke product, herein into a plurality of vector molecules. The following section describes several types of modified tobacco that can be used with the methods described herein.

Analysis of Changes in Cell Homeostasis: Changes in Transcriptome or Proteome

High-density microarrays can be used to elucidate how cells of the oral cavity, mouth, tongue, trachea, bronchi, and lung mount a multigenic response to cigarette smoke and the major classes of smoke constituents (e.g., vapor and particulate phases). Using microarray technology and/or Reverse Transcriptase Polymerase Chain Reaction (e.g., qRT-PCR), gene expression patterns and levels of gene expression in short-term cultures of normal human bronchial epithelial (NHBE) cells exposed to cigarette smoke and cigarette smoke condensates were analyzed. It was found that subtle alterations to the 'homeostatic transcriptome' are useful in defining the major signaling pathways activated upon exposure to chronic, but low level, doses of carcinogenic mixtures such as that which occur daily in an individual smoker. This type of analysis is especially relevant for complex bioactive mixtures, such as cigarette smoke (CS), cigarette smoke condensate (CSC), tobacco smoke (TS), tobacco smoke condensate (TSC), and total particulate matter (TPM) since assessing the specific effects of individual components of such mixtures does not reflect the true impact on a cell or the body due to the synergistic or antagonistic interactions that occur with the entirety of the components that are normally present. Moreover, because the contemplated methods described herein analyze human cells of the mouth, oral cavity, trachea, and lungs, either normal or immortalized cell lines (e.g., human bronchial cells (e.g., BEP2D or 16HBE140 cells), human bronchial epithelial cells (e.g., HBEC cells, 1198, or 1170-I cells), normal human bronchial epithelial cells (NHBE cells), BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)), which are contacted with cigarette smoke or smoke condensates (as opposed to exposure to a single agent with a well-defined mechanism of toxicity), one can identify unique genomic responses and cellular damage over time. That is, novel genes and gene expression patterns are identified using the methods described herein because the vapor and particulate components of tobacco smoke contain numerous substances that immediately and directly damage a range of biomolecules, as well as, other substances whose toxicity is activated only after biotransformation by cellular enzymes into reactive nucleophiles that then attack various cellular elements.

Although it is known that cigarette smoke, as well as various smoke components, can cause numerous disruptions to the genome (see Chujo et al., Lung Cancer 38: 23-29, 2002; Wistuba, et al. Semin Oncol 28: 3-13, 2001), transcriptome (see Bhattacharjee, et al. Proc Natl Acad Sci USA 98: 13790-13795, 2001 and Garber et al., Proc Natl Acad Sci USA 98: 13784-13789, 2001), and proteome (see Hanash, et al. Dis Markers 17: 295-300, 2001); relatively little is known about the effects of cigarette smoke condensates (CSC) and cigarette smoke (CS) exposure on the overall impact on steady state mRNA levels, transcriptional regulation, protein production, and protein modification in normal cells of the oral cavity, mouth, tongue, trachea, bronchi, and lung. Accordingly, experiments were conducted to identify a set of biomarkers that could be used to monitor exposure to tobacco toxins, detect pre-malignant disease, improve diagnosis and prognosis of current tobacco-related disease, develop patient-specific treatment options, test risk reduction strategies for current and former smokers, and identify and develop tobacco products that have a lower potential to contribute to a tobacco-related disease (e.g., a tobacco product that has a lower carcinogenic potential than a conventional tobacco product, a reduced risk tobacco product). More particularly, as described herein, several approaches to identify a gene expression pattern or fingerprint from cells of the oral cavity, mouth, tongue, trachea, bronchi, and lung (normal or immortal), which have been exposed to tobacco smoke or a tobacco smoke condensate have been discovered and the information generated by practicing these methods can be used in diagnostics, therapeutic and prophylactic procedures, as well as, approaches to identify and develop less harmful tobacco products. In addition, elucidating the various molecular, genetic, cellular, and systemic effects of cigarette smoke provides a detailed mechanistic understanding of how chronic tobacco exposure ultimately causes disease.

Several studies assessing the clinical usefulness of alterations in global gene and protein expression patterns in malignant and normal human lung tissues have shown that quantitative and/or qualitative changes in a small number of expressed genes and proteins, in combination with standard clinicopathological variables, have prognostic and/or diagnostic potential for patients with tobacco-related diseases. A direct cause and effect relationship between any of these documented molecular events and cell exposure to tobacco smoke is unclear, however. Thus, it was decided to examine the effects of tobacco constituents on the transcriptome of normal lung cells in a controlled in vitro environment.

Several methods described herein analyze the transcriptome of cells of the oral cavity, mouth, tongue, trachea, bronchi, and lung after exposure to a smoke or smoke condensate using high-density microarrays, qRT-PCR, or another conventional nucleic acid or protein detection method such as ELISA or Western blot. The data show that exposure of such cells (e.g., normal human bronchial epithelial cells (NHBE cells) to cigarette smoke or cigarette smoke condensates results in a modulation of a specific set of genes whose expression levels varied over the normal variability of gene expression in these cells. Accordingly, these genes can be used to monitor tobacco-induced changes to the transcriptome. By sorting these genes into biologically functional classes, dominant biochemical pathways known to be relevant to tobacco-related disease were identified. In addition, it was surprising to learn that treatment with an S9 microsomal fraction, a step common in many toxicological studies, has a broad impact on gene expression in normal lung cells that is distinctly different from the impact of tobacco exposure.

Accordingly, some embodiments concern the identification of a gene or a plurality of genes from cells of the oral cavity, mouth, tongue, trachea, bronchi, and lung (e.g., NHBE cells), which are modulated (e.g., up-regulated or down-regulated expression) in response to contact with a cigarette smoke (CS), a cigarette smoke condensate (CSC), tobacco smoke (TS), tobacco smoke condensate (TSC), or total particulate matter (TPM). In some embodiments, a gene expression pattern, fingerprint, or signature is obtained, which is an identification of a specific plurality of genes or set of genes that are modulated (i.e., up-regulated or down-regulated) after contact with CS, CSC, TS, TSC or TPM. The plurality of genes that are affected can be any combination or subset of genes that are identified as being influenced by exposure to CS, CSC, TS, TSC or TPM. In some embodiments, the plurality of affected genes are a subset of suppressor genes. In some embodiments, the plurality of genes that are affected by exposure to CS, CSC, TS, TSC or TPM are a subset of genes affecting cholesterol regulation and production. In some embodiments, the subset of genes that are affected genes are involved in oxidative stress, cell proliferation, apoptosis, protein turn-over, heat shock, ubiquitination, or endoplasmic reticulum stress.

Several approaches to conduct a gene expression analysis that involve the use of NHBE cells are provided herein, whereby said cells are contacted with a CS, CSC, TS, TSC or TPM and a gene, pattern of gene expression or a fingerprint from said CS, CSC, TS, TSC or TPM-treated cells is obtained. The gene expression data generated by the approaches described herein can be recorded onto a recordable media (e.g., a hard drive, memory, cache, floppy, CD-ROM, DVD-ROM) and can be analyzed using various statistical approaches to determine whether said data identifies a genetic modulation event (e.g., an up-regulation or down-regulation of expression) that is statistically relevant. Statistically relevant genetic modulation events that occur in the cells that were contacted with a CS, CSC, TS, TSC or TPM can then be used to identify a molecular pathway that is involved in a tobacco-related disease. Accordingly, the approaches described herein can be used to identify a marker for a tobacco-related disease and to determine whether this marker is modulated (e.g., a marker gene is up-regulated or down-regulated) in response to exposure to a particular CS, CSC, TS, TSC or TPM.

Furthermore, this data can be used to create a genetic profile for a particular tobacco product, which allows one to empirically determine the components of a given tobacco product's smoke (or tobacco per se) that contribute to a gene expression event in a human cell that is associated with a tobacco-related disease. Accordingly, by using the approaches described herein, one can identify specific tobacco products, as well as, growing, harvesting, curing, processing, and blending practices that have a reduced potential to contribute to a genetic modulation that is associated with a tobacco-related disease. That is, the approaches described herein can be used to identify and develop reduced risk cigarettes. Still further, the markers for tobacco-related disease, and the genetic profiles identified by using the approaches described herein can be used to diagnose, provide a prognosis or otherwise identify an individual at risk of acquiring a tobacco-related disease and the effect of tobacco smoke on a subject at a molecular level. The section below describes several methods that can be used to identify genes that are modulated after exposure to CS, CSC, TS, TSC or TPM and to identify and develop tobacco products that have a reduced risk of contributing to a tobacco-related disease.

Tobacco Products that have a Reduced Potential to Contribute to a Tobacco-Related Disease More embodiments concern methods to identify components of a tobacco product that contribute to a tobacco-related disease, the selective removal or inhibition of production of these components, and the determination that the removal of the component(s) modulates expression of a gene that is associated with a tobacco-related disease in a manner that reduces the potential for the tobacco product to contribute to a tobacco related disease. It is contemplated that particular components of tobacco products are the factors that modulate expression of genes in human cells that contribute to tobacco-related disease. It is further contemplated that modification of genes that contribute to the production of these toxic components in tobacco (e.g., genetic engineering or chemical treatment) will, concomitantly, result in a modulation of gene expression in human cells that come in contact with the smoke from said modified tobacco, which is less likely to contribute to a tobacco-related disease than the tobacco prior to modification of the component-producing gene. Accordingly, by selectively removing the components that induce the genetic events that contribute to tobacco-related disease in a human, one can develop tobacco products that are less likely to contribute to a tobacco-related disease.

By one approach, for example, CS is generated using a smoking machine from a first tobacco product that has been genetically modified to have a reduced amount of a compound. A first population of NHBE cells is contacted with said CS obtained from the modified tobacco, as described in Examples 4, 12, and 13. As described in these examples, the RNA is isolated and analyzed by microarray or qRT-PCR or both and a pattern of gene expression and gene product modification events are obtained. Programs such as PathwayAssist™ software (Stratagene, La Jolla, Calif.) and/or Genespring (version 7.2, Agilent Technologies) can be used to determine the identity of the genes that are modulated and their relationship to a tobacco-related disease.

A second population of NHBE cells is then contacted with CS generated from the parental variety of tobacco. That is, the parental variety of tobacco is the unmodified tobacco variety used to generate the modified tobacco variety, wherein the unmodified tobacco retains the component that was removed or inhibited in the modified tobacco. As above, the RNA is isolated and analyzed by microarray or qRT-PCR or both and a pattern of gene expression and gene product modification events are obtained. Programs such as PathwayAssist™ (Stratagene, La Jolla, Calif.) and/or Genespring (version 7.2, Agilent Technologies) can be used to determine the identity of the genes that are modulated and their relationship to a tobacco-related disease.

A comparison of the data obtained from the analysis of the first and second tobacco products will reveal that the modified tobacco modulates fewer genes associated with a tobacco-related disease than the parental, unmodified tobacco. The data will also show that the modified tobacco product induces expression of fewer proto/oncogenes. By this approach, one can effectively identify the contribution of individual components of a tobacco product to a tobacco-related disease. This combinatorial approach can be used to develop tobacco products that are less likely to contribute to a tobacco-related disease and reduced risk tobacco products identified by these methods are aspects of the invention. Further, tobacco products prepared by these approaches can be prepared according to good manufacturing processes (GMP) (e.g., suitable for or accepted by a governmental regulatory body, such as the Federal Drug Administration (FDA), and containers that house said tobacco products can comprise a label or other indicia, with or without structure-function indicia, which reflects approval of said tobacco product from said regulatory body. The example below describes this approach in greater detail.

Example 14

This example provides several approaches that can be used to obtain tobacco and tobacco products that have a reduced potential to contribute to a tobacco-related disease. Generally, these methods involve a two-tiered analysis involving first, an analysis of a parent strain of tobacco that has a component or compound that contributes to a tobacco related disease and second, an analysis of a progeny of the parent strain of tobacco that has been modified to modulate (i.e., up-regulate or down-regulate) expression of a gene that induces a cascade that contributes to a tobacco-related disease.

Accordingly, by one approach, a first tobacco (e.g., Burley 21 LA) that comprises a compound that contributes to a tobacco-related disease (e.g., nicotine) is provided. Next, preferably, smoke is obtained from said first tobacco (e.g., CS), however a smoke condensate from the first tobacco can also be obtained. Once the smoke or smoke condensate has been prepared from the first tobacco, a first isolated population of cells, preferably human cells of the mouth, tongue, trachea, bronchi, or lungs (e.g., NHBE cells) is contacted with said smoke or smoke condensate from said first tobacco. The contact can be made in a smoking chamber, for example, for less than, equal to, or more than, 5 seconds, 20, seconds, 45 seconds, 1 minute, 5 minutes, 10 minutes, 15, minutes, 20 minutes, 30 minutes, 45 minutes, 1 hour, two hours, three hours. Subsequent to the contact with the smoke or smoke condensate, a first gene that is modulated (up-regulated or down-regulated) in said first population of cells in response to said contact with said smoke or smoke condensate from said first tobacco is identified (e.g., an proto/oncogene). The identification of the first gene can be accomplished using an oligonucleotide array, microarray, qRT-PCR, nucleic acid detection (e.g., hybridization), protein detection (e.g., antibody detection, ELISA or Western blot), or detection of a metabolite (e.g., protein fragment or cysteine) or a modified gene product (e.g., oxidized or phosphorylated protein or amino acid). The first gene identified as being modulated (e.g., up-regulated or down-regulated) in response to contact with the smoke or smoke condensate of the first tobacco is then analyzed for its contribution to a tobacco-related disease. The correlation of many of the genes that are identified by the approach above to a tobacco-related disease can be accomplished by simply reviewing available literature or by employing commercially available software that identifies the association of a particular gene with a tobacco-related disease (e.g., PathwayAssist™ available from Stratagene, La Jolla, Calif. and/or Genespring (version 7.2, available from Agilent Technologies).

Next, a second tobacco that is, preferably, the same variety and grown under the same conditions as the first tobacco is provided. The second tobacco has been modified to reduce expression of a second gene, a gene that contributes to the production of a compound or component present in the first tobacco (e.g., a gene involved in nicotine synthesis, such as QPTase or PMTase). The modification of the second gene can be accomplished by genetic engineering or chemical treatment. Several approaches to modify tobacco to reduce the amount of nicotine are known. (See e.g., U.S. patent application Ser. No. 10/729,121, WO0067558A1, WO9428142A1, WO05000352A1, WO05018307A1, WO03086076A1, and WO0218607A2, all of which are hereby expressly incorporated by reference in their entireties).

By one approach, the second tobacco is genetically modified to reduce expression of QPTase, as described above (e.g., Vector 21-41). RNAi constructs that comprise fragments of a gene involved in nicotine synthesis have also been used to reduce the amount of nicotine and TSNA in tobacco, as described above. By one approach, for example, the RNAi construct provided in FIG. 1 was used to generate a reduced nicotine and TSNA tobacco. By another approach, the RNAi construct provided in FIG. 2 was used to generate a reduced nicotine and TSNA tobacco. More details on the preparation of these RNAi constructs and the methods used to create transgenic tobacco having a reduced amount of nicotine and TSNAs is provided in the section that follows and Example 15.

Once the modified second tobacco is obtained, preferably a genetically modified second tobacco (e.g., a second tobacco that has been genetically modified to reduce the amount of nicotine), smoke or a smoke condensate is obtained from said second tobacco. Then, a second isolated population of cells, preferably the same cell type as analyzed above (e.g., NHBE cells) is contacted with the smoke or smoke condensate from the second tobacco, preferably for the same amount of time as the cells that were contacted with the first tobacco. Subsequent to the exposure of the second population of cells to the second tobacco, an approach to identify the modulation of gene expression in said second population of cells is employed, preferably the same approach that was used to analyze the first population of cells after exposure to the smoke or smoke condensate of the first tobacco product (e.g., an oligonucleotide array, microarray, qRT-PCR, nucleic acid detection (e.g., hybridization), protein detection (e.g., antibody detection, ELISA or Western blot), or detection of a metabolite (e.g., protein fragment or cysteine) or a modified gene product (e.g., oxidized or phosphorylated protein or amino acid).

A modulation (up-regulation or down-regulation) in expression of a first gene that contributes to a tobacco-related disease in said second population of cells, as compared to the amount of expression of the same gene induced by the first tobacco, will be observed. This difference in expression of a gene that is related to a tobacco-related disease provides strong evidence that the modification in the second tobacco has resulted in a tobacco that has a reduced potential to contribute to a tobacco-related disease. That is, said (modified) second tobacco has a reduced risk to contribute to a tobacco-related disease, as compared to the first (unmodified) tobacco.

Conventional techniques in cultivation of said second tobacco, harvesting, curing, blending, and processing are then employed so as to generate a tobacco product (e.g., snuff, chew, tobacco leaf, cigarette, pipe tobacco, cigar, or lozenge) and said tobacco product can be identified as a product that has a reduced potential to contribute to a tobacco-related disease as compared to a tobacco product comprising said first tobacco.

It will be appreciated that the promoters used in the above-described vectors can either be constitutive or regulatable. Constitutive promoters are promoters that are always expressed. The constitutive promoters selected for use in the above-described vectors can range from weak promoters to strong promoters depending on the desired amount of interfering RNA to be produced. Regulatable promoters are promoters for which the desired level of expression can be controlled. An example of a regulatable promoter is an inducible promoter. Using an inducible promoter in the above-described vector constructs permits expression of a wide range of concentrations of interfering RNA inside a cell.

It will also be appreciated that there is no requirement that the same or same types of promoters be used in vectors or multiple vector systems that comprise a plurality of promoters. For example, in some vectors or vector systems, a first promoter, which controls the expression of the first interfering RNA strand, can be an inducible promoter, whereas the second promoter, which controls the expression of the second RNA strand, can be a constitutive promoter. This same principal can also be illustrated in a multiple vector system. For example, a multiple vector system may have three vectors each of which includes one or more different types of promoters. Such a system can include, for example, a first vector having repressible promoter that controls the expression of an interfering RNA specific for a first gene product involved in nicotine biosynthesis, a second vector having a constitutive promoter that controls the expression of an interfering RNA specific for a second gene product involved in nicotine biosynthesis and a third vector having an inducible promoter that controls the expression of an interfering RNA specific for a third gene product involved in nicotine biosynthesis.

In other embodiments, interfering RNAs can be produced synthetically and introduced into a cell by methods known in the art. Synthetic interfering RNAs can include a variety of RNA molecules, which include, but are not limited to, nucleic acids having at least one region of duplex RNA. The duplex RNA in such molecules can comprise, for example, two antiparallel RNA strands that form a double-stranded RNA having flush ends, two antiparallel RNA strands that form a double-stranded RNA having at least one end that forms a hairpin structure, or two antiparallel RNA strands that form a double-stranded RNA, wherein both ends form a hairpin structure. In some embodiments, synthetic interfering RNAs comprise a plurality of RNA duplexes.

By way of example, tobacco having reduced amounts of nicotine and TSNAs is generated from a tobacco plant that is created by exposing at least one tobacco cell of a selected tobacco variety, such as LA Burley 21, to a nucleic acid construct comprising a promoter that is operable in a plant cell, wherein the promoter controls the expression of a RNA comprising both strands of a duplex interfering RNA. For example, the RNA that is expressed comprises a first nucleotide sequence that is substantially similar or identical to at least a portion of an mRNA or at least a portion of the coding strand of a gene that is involved in nicotine biosynthesis. This first nucleotide sequence is followed by a non-complementary sequence that is involved in hairpin formation, and then, a second nucleotide sequence that is complementary or substantially complementary to at least a portion of the first nucleotide sequence. The exposed tobacco cell is then transformed with the nucleic acid construct. Cells that are successfully transformed are selected using either negative selection or positive selection techniques and at least one tobacco plant is regenerated from transformed cells. The regenerated tobacco plant or portion thereof is preferably analyzed to determine the amount of nicotine and/or TSNAs present and these values can be compared to the amount of nicotine and/or TSNAs present in a control tobacco plant or portion thereof. Preferably the transformed and control tobacco plants are of the same variety.

In some embodiments, a cDNA sequence encoding a plant quinolate phosphoribosyl transferase (QPTase) is used (See Example 15). As QPTase activity is strictly correlated with nicotine content, construction of transgenic tobacco plants in which QPTase levels are lowered in the plant roots (compared to levels in wild-type plants) result in plants having reduced levels of nicotine in the leaves. Embodiments of the invention provide methods and nucleic acid constructs for producing such transgenic plants, as well as, the transgenic plants themselves. Such methods include the expression of an interfering RNA, which lowers the amount of QPTase in tobacco roots. Other embodiments include the expression of an interfering RNA, which lowers the amount of any QPTase that may be present in tobacco leaves, stems and/or other tobacco tissues.

Some embodiments also concern transgenic plant cells comprising one or more interfering RNAs that are capable of reducing or eliminating the expression of one or more target genes and/or target gene products involved in nicotine biosynthesis. As described above, an appropriate interfering RNA comprises a duplex RNA that comprises a first strand that is substantially similar or identical to at least a portion of a target gene or target mRNA, which encodes a gene product involved in nicotine biosynthesis. The RNA duplex also comprises a second strand that is complementary or substantially complementary to the first strand.

The interfering RNA or nucleic acid construct comprising the interfering RNA can be introduced into the plant cell in any suitable manner. Plant cells possessing stable interfering RNA activity, for example, by having a nucleic acid construct stably integrated into a chromosome, can be used to regenerate whole plants using methods known in the art. As such, some aspects of the present invention relate to plants, such as tobacco plants, transformed with one or more nucleic acid constructs and/or vectors which encode at least one interfering RNA that is capable of reducing or eliminating the expression of a gene product involved in nicotine biosynthesis. Transgenic tobacco cells and the plants described herein are characterized in that they have a reduced amount of nicotine and/or TSNA as compared to unmodified or control tobacco cells and plants.

The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the low nicotine and/or TSNA tobacco described herein can be processed and blended with conventional tobacco so as to create a wide-range of tobacco products with varying amounts of nicotine and/or TSNAs. These blended tobacco products can be used in tobacco product cessation programs so as to slowly move a consumer from a high nicotine and TSNA product to a low nicotine and TSNA product. Some embodiments of the invention comprise a tobacco use cessation kit, comprising two or more tobacco products with different levels of nicotine and/or TSNAs. For example, a smoker can begin the program smoking blended cigarettes having or delivering by FTC methodology 1-2 mg of nicotine and 0.2 µg of TSNA, gradually move to smoking cigarettes having or delivering 0.75 mg of nicotine and 0.1 µg of TSNA, followed by cigarettes having or delivering 0.5 mg nicotine and 0.1 µg TSNA, followed by cigarettes having or delivering 0.1 mg nicotine and 0.05 µg TSNA, followed by cigarettes having or delivering 0.05 mg nicotine and no detectable TSNA until the consumer decides to smoke only the cigarettes having virtually no nicotine and TSNAs or quitting smoking altogether. Accordingly, the blended cigarettes described herein provide the basis for an approach to reduce the carcinogenic potential in a human in a step-wise fashion. The components of the tobacco use cessation kit described herein may include other tobacco products, including but not limited to, smoking materials (e.g., cigarettes, cigars, pipe tobacco), snuff, chewing tobacco, gum, and lozenges.

Gene silencing has been employed in several laboratories to create transgenic plants characterized by lower than normal amounts of specific gene products. As used herein, "exogenous" or "heterologous" nucleic acids, including DNAs and/or RNAs, refer to nucleic acids that have been introduced into a cell (or the cell's ancestor) through the efforts of humans. Such heterologous nucleic acids can be copies of a sequence which is naturally found in the cell being transformed, or fragments thereof. To produce a tobacco plant having decreased QPTase levels, and a reduced amount of nicotine and TSNAs, as compared to an untransformed or control tobacco plant or portion thereof, a tobacco cell can be transformed with an exogenous nucleic acid construct which encodes an interfering RNA having an RNA duplex comprising a first strand that is substantially similar or identical to at least a portion of the coding strand of the full-length QPT cDNA sequence, a partial QPT chromosomal sequence, a full-length QPT chromosomal sequence, or an mRNA produced from the QPT gene. Alternatively, the tobacco cell can be transformed with a synthetic or an in vitro transcribed interfering RNA. In some embodiments of the present invention, the interfering RNA and/or nucleic acid encoding the interfering RNA are stably transformed. In certain embodiments, the nucleic acid encoding the interfering RNA can be integrated in the cell genome. In other embodiments, the interfering RNA and/or nucleic acid encoding the interfering RNA are transiently transformed.

The nucleic acid constructs that are used with the transgenic plants and the methods for producing the transgenic plants described herein encode one or more interfering RNA constructs comprising regulatory sequences, which include, but are not limited to, a transcription initiation sequence ("promoter") operable in the plant being transformed, and a polyadenylation/transcription termination sequence. Typically, the promoter is located upstream of the 5'-end of the nucleotide sequence to be expressed. The transcription termination sequence is generally located just downstream of the 3'-end of the nucleotide sequence to be transcribed.

In some preferred embodiments, the nucleic acid encoding the exogenous interfering RNA, which is transformed into a tobacco cell, comprises a first RNA strand that is identical to the an endogenous coding sequence of a gene encoding a gene product involved in nicotine biosynthesis. However, minor variations between the exogenous and endogenous sequences can be tolerated. It is preferred, but not necessarily required, that the exogenously-produced interfering RNA sequence, which is substantially similar to the endogenous gene coding sequence, be of sufficient similarity to the endogenous gene coding sequence, such that the complementary interfering RNA strand is capable of binding to the endogenous sequence in the cell to be regulated under stringent conditions as described below.

In some embodiments, the heterologous sequence utilized in the methods of the present invention may be selected so as to produce an interfering RNA product comprising a first strand that is substantially similar or identical to the entire QTPase mRNA sequence, or to a portion thereof, and a second strand that is complementary to the entire QPTase mRNA sequence, or to a portion thereof. The interfering RNA may be complementary to any contiguous sequence of the natural messenger RNA. For example, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the C-terminus of the coding region, or complementary to the 3'-untranslated region of the mRNA.

Interfering RNAs employed in carrying out the present invention include those comprising a first strand having sequence similarity to the QPTase gene or a fragment thereof at least or equal to 50, 100, 150, 200, 250, 300, 350, 400, 450, 500, 550, 600, 650, 700, 750, 800 or more consecutive nucleotides of the QTPase. (See U.S. Pat. No. 6,586,661, which provides the sequence of the QPTase gene and protein, herein expressly incorporated by reference in its entirety). This definition is intended to encompass natural allelic variations in QPTase proteins. Thus, nucleic acid sequences that hybridize to nucleic acids of the QPTase gene under the conditions provided supra may also be employed in carrying out aspects of the invention. Multiple forms of the tobacco QPT enzyme may exist. Multiple forms of an enzyme may be due to post-translational modification of a single gene product, or to multiple forms of the NtQPT1 gene.

Conditions that permit other nucleic acid sequences, which code for expression of a protein having QPTase activity, to hybridize to a QPTase gene or to other nucleic acid sequences encoding a QPTase protein can be determined in a routine manner. For example, hybridization of such sequences to nucleic acids encoding the QPTase protein may be carried out under conditions of reduced stringency or even stringent conditions (e.g., conditions represented by a wash stringency of 0.3 M NaCl, 0.03 M sodium citrate, 0.1% SDS at 60° C. or even 70° C.) herein in a standard in situ hybridization assay. See J. Sambrook et al., Molecular Cloning, A Laboratory Manual (2d Ed. 1989) (Cold Spring Harbor Laboratory)). In general, such sequences will be at least 65% similar, 75% similar, 80% similar, 85% similar, 90% similar, or even 95% similar or more, with the tobacco QPTase gene, or nucleic sequences encoding the QPTase protein. Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.

Differential hybridization procedures are available which allow for the isolation of cDNA clones whose mRNA levels are as low as about 0.05% of poly(A)RNA. (See M. Conkling et al., Plant Physiol. 93, 1203-1211 (1990)). In brief, cDNA libraries are screened using single-stranded cDNA probes of reverse transcribed mRNA from plant tissue (e.g., roots and/or leaves). For differential screening, a nitrocellulose or nylon membrane is soaked in 5×SSC and placed in a 96 well suction manifold; 150 μL of stationary overnight culture is transferred from a master plate to each well and vacuum applied until all liquid has passed through the filter. Approximately, 150 μL of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

IV. Use of Tobacco Products

Nicotine Reduction and/or Tobacco-Use Cessation Programs Methods

It is also contemplated that the low nicotine and/or TSNA tobacco described herein can be processed and blended with conventional tobacco so as to create a wide-range of tobacco products with varying amounts of nicotine and/or TSNAs. These blended tobacco products can be used in nicotine reduction and/or tobacco-use cessation programs so as to move a consumer from a high nicotine and TSNA product to a low nicotine and TSNA product.

In some embodiments provided herein, a stepwise nicotine reduction and/or tobacco-use cessation program can be established using the low nicotine, low TSNA products described above. As an example, the program participant initially determines his or her current level of nicotine intake. The program participant then begins the program at step 1, with a tobacco product having a reduced amount of nicotine, as compared to the tobacco product that was used prior to beginning the program. After a period of time, the program participant proceeds to step 2, using a tobacco product with less nicotine than the products used in step 1. The program participant, after another period of time, reaches step 3, wherein the program participant begins using a tobacco product with less nicotine than the products in step 2, and so on. Ultimately, the program participant uses a tobacco product having an amount of nicotine that is less than that which is sufficient to become addictive or to maintain an addiction. Thus, the nicotine reduction and/or tobacco-use cessation program limits the exposure of a program participant to nicotine and, concomitantly, the harmful effect of nicotine yet retains the secondary factors of addiction, including but not limited to, smoke intake, oral fixation, and taste.

For example, a smoker can begin the program smoking blended cigarettes having or delivering 5 mg of nicotine and 1.5 μg of TSNA, gradually move to smoking cigarettes with 3 mg of nicotine and 4 μg of TSNA, followed by cigarettes having or delivering 1 mg nicotine and 0.5 µg TSNA, followed by cigarettes having or delivering 0.5 mg nicotine and 0.25 µg TSNA, followed by cigarettes having or delivering less than 0.1 mg nicotine and less than 0.1 µg TSNA until the consumer decides to smoke only the cigarettes having virtually no nicotine and TSNAs or quitting smoking altogether. Preferably, a three-step program is followed whereby at step 1, cigarettes providing 0.6 mg nicotine and less than 2 µg/g TSNA are used; at step 2, cigarettes providing 0.3 mg nicotine and less than 1 µg/g TSNA are used; and at step 3, cigarettes providing less than 0.1 mg nicotine and less than 0.7 µg/g TSNA are used. More preferably, a three-step program is followed whereby at step 1, cigarettes providing 0.6 mg nicotine and less than 2 µg/g TSNA are used; at step 2, cigarettes providing 0.3 mg nicotine and less than 1 µg/g TSNA are used; and at step 3, cigarettes providing less than 0.05 mg nicotine and less than 0.7 µg/g TSNA are used. Accordingly, the blended cigarettes described herein provide the basis for an approach to reduce the carcinogenic potential in a human in a step-wise fashion.

The methods described herein facilitate tobacco-use cessation by allowing the individual to retain the secondary factors of addiction such as smoke intake, oral fixation, and taste, while gradually reducing the addictive nicotine levels consumed. Eventually, complete cessation is made possible because the presence of addiction for nicotine is gradually decreased while the individual is allowed to maintain dependence on the secondary factors, above.

Embodiments, for example, include stepwise blends of tobacco products, which are prepared with a variety of amounts of nicotine. These stepwise blends are made to have reduced levels of TSNAs and varying amounts of nicotine. As an example, cigarettes may deliver, for example, 5 mg, 4, 3, 2, 1, 0.5, 0.1, or 0 mg of nicotine per cigarette. More preferably, blended cigarettes provide less than 0.01%, 0.02%, 0.03%, 0.04%, 0.05%, 0.06%, 0.07%, 0.08%, 0.09%, 0.1%, 0.2%, 0.3%, 0.4%, 0.5%, and 0.6% nicotine.

In another aspect provided herein, the cigarettes of varying levels of nicotine are packaged to clearly indicate the level of nicotine present, and marketed as a smoking cessation program. A preferred approach to produce a product for nicotine reduction and/or tobacco-use cessation program is provided below. Individuals may wish to step up the program by skipping gradation levels of nicotine per cigarette or staying at certain steps until ready to proceed to the next level. Significantly, embodiments provided herein allow a consumer to individually select the amount of nicotine that is ingested by selection of a particular tobacco product described herein. Furthermore, because the secondary factors of addiction are maintained, dependence on nicotine can be reduced rapidly.

As an example, Virginia flue tobacco was blended with genetically modified Burley (i.e., Burley containing a significantly reduced amount of nicotine and TSNA) to yield a blended tobacco that was incorporated into three levels of reduced nicotine cigarettes: a step 1 cigarette providing 0.6 mg nicotine, a step 2 cigarette providing 0.3 mg nicotine, and a step 3 cigarette providing less than 0.05 mg nicotine. The stepwise packs of cigarettes are clearly marked as to their nicotine content, and the step in the stepwise nicotine reduction program is also clearly marked on the package. Each week, the user purchases packs containing cigarettes having the next lower level of nicotine, but limits himself to no more cigarettes per day than consumed previously. The user may define his/her own rate of nicotine reduction and/or smoking cessation according to individual needs by choosing a) the number of cigarettes smoked per day b) the starting nicotine levels c) the change in nicotine level per cigarette each week, and d) the final level of nicotine consumed per day. To keep better track of the program, the individual keeps a daily record of total nicotine intake, as well as the number of cigarettes consumed per day. Eventually, the individual will be consuming tobacco products with essentially no nicotine. Since the nicotine-free tobacco products of the final step are non-addictive, it should then be much easier to quit the use of the tobacco products altogether.

The nicotine reduction and/or tobacco-use cessation program limits the exposure of a program participant to nicotine while retaining the secondary factors of addiction. These secondary factors include but are not limited to, smoke intake, oral fixation, and taste. Because the secondary factors are still present, the program participant may be more likely to be successful in the nicotine reduction and/or tobacco-use cessation program than in programs that rely on supplying the program participant with nicotine but remove the above-mentioned secondary factors. Ultimately, the program participant uses a tobacco product having an amount of nicotine that is less than that which is sufficient to become addictive.

In another aspect provided herein, individuals would choose to obtain only cigarettes that provide less than 0.05 mg nicotine per cigarette. Some individuals, such as individuals needing to stop nicotine intake immediately (for example, individuals with medical conditions or individuals using drugs that interact with nicotine) may find this method useful. For some individuals, the mere presence of a cigarette in the mouth can be enough to ease withdrawal from nicotine addiction. Gradually, the addictive properties of smoking can decrease since there is no nicotine in the cigarettes. These individuals are then able to quit smoking entirely. More discussion on Smoking Cessation Programs that use reduced nicotine tobacco can be found in PCT/US2004/01695, which designates the United States and was published in English, hereby expressly incorporated by reference in its entirety.

In another aspect provided herein, packs of cigarettes containing the gradations of nicotine levels are provided as a "smoking cessation kit." An individual who wishes to quit smoking can buy the entire kit of cigarettes at the beginning of the program. Thus any temptation that may occur while buying cigarettes at the cigarette counter is avoided. Thus, the success of this method may be more likely for some individuals. A preferred example of such a kit is provided below.

Various nicotine reduction and/or smoking cessation kits are prepared, geared to heavy, medium, or light smokers. The kits provide all of the materials needed to quit smoking in either a two-week period (fast), a one-month period (medium) or in a two-month period (slow), depending on the kit. Each kit contains a set number of packs of cigarettes modified according the present invention, containing either step 1 cigarettes providing 0.6 mg nicotine, step 2 cigarettes providing 0.3 mg nicotine, and step 3 cigarettes providing less than 0.05 mg nicotine. For example, 1 pack a day smokers would receive 7 packs of cigarettes, each pack containing the above amounts of nicotine per each cigarette. Several weeks worth of additional cigarettes provided less than 0.05 mg nicotine/cigarette would also be provided in the kit, to familiarize the consumer with smoking no nicotine cigarettes. The kit would also contain a diary for keeping track of daily nicotine intake, motivational literature to keep the individual interested in continuing the cessation program, health information on the benefits of smoking cessation, and web site addresses to find additional anti-smoking information, such as chat groups, meetings, newsletters, recent publications, and other pertinent links.

Some tobacco-use cessation or nicotine and/or TSNA reduction kits comprise, for example, a conventional tobacco product and a first reduced nicotine and/or TSNA tobacco product, wherein the first reduced nicotine and/or TSNA tobacco product comprises less nicotine and/or TSNAs than the conventional tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product. The first reduced nicotine and/or TSNA tobacco product can comprise treated tobacco, selectively bred low nicotine tobacco, or genetically modified tobacco or combinations thereof. The first tobacco product can also include exogenous nicotine.

Other embodiments include tobacco-use cessation or nicotine and/or TSNA reduction kits that comprise a conventional tobacco product, a first reduced nicotine and/or TSNA tobacco product and a second reduced nicotine and/or TSNA tobacco product, wherein the first reduced nicotine and/or TSNA tobacco product comprises less nicotine and/or TSNAs than the conventional tobacco product and the second reduced nicotine and/or TSNA tobacco product comprises less nicotine and/or TSNAs than the first reduced nicotine and/or TSNA tobacco product. The first reduced nicotine and/or TSNA tobacco product (e.g., a cigarette) or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g and the second reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product and the amount of nicotine and/or TSNAs in or delivered by the second tobacco product is less than the amount of nicotine and/or TSNAs in or delivered by the first tobacco product. The first and/or second reduced nicotine and/or TSNA tobacco products can comprise treated tobacco, selectively bred low nicotine tobacco, or genetically modified tobacco or combinations thereof. These tobacco products can also include exogenous nicotine.

More embodiments include tobacco-use cessation or nicotine and/or TSNA reduction kits that comprise a conventional tobacco product, a first reduced nicotine and/or TSNA tobacco product, a second reduced nicotine and/or TSNA tobacco product, and a third reduced nicotine and/or TSNA tobacco product, wherein the first reduced nicotine and/or TSNA tobacco product comprises less nicotine and/or TSNAs than the conventional tobacco product, the second reduced nicotine and/or TSNA tobacco product comprises less nicotine and/or TSNAs than the first reduced nicotine and/or TSNA tobacco product and the third reduced nicotine and/or TSNA tobacco product comprises less nicotine and/or TSNAs than the second reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the third reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product, the amount of nicotine and/or TSNAs in or delivered by the second tobacco product is less than the amount of nicotine and/or TSNAs in or delivered by the first tobacco product, and the amount of nicotine and/or TSNAs in or delivered by the third tobacco product is less than the amount of nicotine and/or TSNAs in or delivered by the second tobacco product. The first, second, and/or third reduced nicotine and/or TSNA tobacco products can comprise treated tobacco, selectively bred low nicotine tobacco, or genetically modified tobacco or combinations thereof. These tobacco products can also include exogenous nicotine.

Still more embodiments include tobacco-use cessation or nicotine and/or TSNA reduction kits that comprise a conventional tobacco product, a first reduced nicotine and/or TSNA tobacco product, a second reduced nicotine and/or TSNA tobacco product, a third reduced nicotine and/or TSNA tobacco product and a fourth reduced nicotine and/or TSNA tobacco product, wherein the first reduced nicotine and/or TSNA tobacco product comprises less nicotine and/or TSNAs than the conventional tobacco product, the second reduced nicotine and/or TSNA tobacco product comprises less nicotine and/or TSNAs than the first reduced nicotine and/or TSNA tobacco product, the third reduced nicotine and/or TSNA tobacco product comprises less nicotine and/or TSNAs than the second reduced nicotine and/or TSNA tobacco product, and the fourth reduced nicotine and/or TSNA tobacco product comprises less nicotine and/or TSNAs than the third reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the third reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the fourth reduced nicotine and/or TSNA tobacco product can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product, the amount of nicotine and/or TSNAs in or delivered by the second tobacco product is less than the amount of nicotine and/or TSNAs in or delivered by the first tobacco product, the amount of nicotine and/or TSNAs in or delivered by the third tobacco product is less than the amount of nicotine and/or TSNAs in or delivered by the second tobacco product, and the amount of nicotine and/or TSNAs in or delivered by the fourth tobacco product is less than the amount of nicotine and/or TSNAs in or delivered by the third tobacco product. The first, second, third, and/or fourth reduced nicotine and/or TSNA tobacco products can comprise treated tobacco, selectively bred low nicotine tobacco, or genetically modified tobacco or combinations thereof. These tobacco products can also include exogenous nicotine.

Preferred tobacco-use cessation or nicotine and/or TSNA reduction kits comprise, however, a first reduced nicotine and/or TSNA tobacco product, wherein the first reduced nicotine and/or TSNA tobacco product comprises less nicotine and/or TSNAs than a conventional tobacco product. That is, in some embodiments, the tobacco-use cessation or nicotine and/or TSNA reduction kits do not contain a conventional tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g. The first reduced nicotine and/or TSNA tobacco products can comprise treated tobacco, selectively bred low nicotine tobacco, or genetically modified tobacco or combinations thereof. The first tobacco product can also include exogenous nicotine.

Other embodiments include tobacco-use cessation or nicotine and/or TSNA reduction kits that comprise a first reduced nicotine and/or TSNA tobacco product and a second reduced nicotine and/or TSNA tobacco product, wherein the second reduced nicotine and/or TSNA tobacco product comprises less nicotine and/or TSNAs than the first reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g and the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product. The first and/or second reduced nicotine and/or TSNA tobacco products can comprise treated tobacco, selectively bred low nicotine tobacco, or genetically modified tobacco or combinations thereof. These tobacco products can also include exogenous nicotine.

More embodiments include tobacco-use cessation or nicotine and/or TSNA reduction kits that comprise a first reduced nicotine and/or TSNA tobacco product, a second reduced nicotine and/or TSNA tobacco product, and a third reduced nicotine and/or TSNA tobacco product, wherein the second reduced nicotine and/or TSNA tobacco product comprises less nicotine and/or TSNAs than the first reduced nicotine and/or TSNA tobacco product and the third reduced nicotine and/or TSNA tobacco product comprises less nicotine and/or TSNAs than the second reduced nicotine and/or TSNA tobacco product. The first reduced nicotine and/or TSNA tobacco product (e.g., a cigarette) or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product, and the amount of nicotine and/or TSNAs in or delivered by the third tobacco product is less than the amount of nicotine and/or TSNAs in or delivered by the second tobacco product. The first, second, and/or third reduced nicotine and/or TSNA tobacco products can comprise treated tobacco, selectively bred low nicotine tobacco, or genetically modified tobacco or combinations thereof. These tobacco products can also include exogenous nicotine.

Still more embodiments include tobacco-use cessation or nicotine and/or TSNA reduction kits that comprise a first reduced nicotine and/or TSNA tobacco product, a second reduced nicotine and/or TSNA tobacco product, a third reduced nicotine and/or TSNA tobacco product and a fourth reduced nicotine and/or TSNA tobacco product, wherein the second reduced nicotine and/or TSNA tobacco product comprises less nicotine and/or TSNAs than the first reduced nicotine and/or TSNA tobacco product, the third reduced nicotine and/or TSNA tobacco product comprises less nicotine and/or TSNAs than the second reduced nicotine and/or TSNA tobacco product, and the fourth reduced nicotine and/or TSNA tobacco product comprises less nicotine and/or TSNAs than the third reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the fourth reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product, the amount of nicotine and/or TSNAs in or delivered by the third tobacco product is less than the amount of nicotine and/or TSNAs in or delivered by the second tobacco product, and the amount of nicotine and/or TSNAs in or delivered by the fourth tobacco product is less than the amount of nicotine and/or TSNAs in or delivered by the third tobacco product. The first, second, third, and/or fourth reduced nicotine and/or TSNA tobacco products can comprise treated tobacco, selectively bred low nicotine tobacco, or genetically modified tobacco or combinations thereof. These tobacco products can also include exogenous nicotine.

The tobacco-use cessation or nicotine and/or TSNA reduction kits described herein can, optionally, comprise instructions or guidance on use of the kit and/or tobacco-use cessation or nicotine and/or TSNA reduction and said instructions or guidance can refer the user to counseling programs and literature on the benefits of reduced exposure to nicotine and/or TSNAs and/or tobacco products, in general. The instructions or guidance can be provided in said kits in the form of a paper, CD-ROM, DVD, video, cassette, website link, or other tangible medium. Additionally, the tobacco products provided in said tobacco-use cessation or nicotine and/or TSNA reduction kits can also comprise indicia showing that the product is a member of a series of tobacco products to be consumed in a sequential order.

For example, in some embodiments, the tobacco products and/or packaging has been labeled with a number or letter or symbol or other form of visually identifiable marker to indicate whether the product is a conventional tobacco product, a first tobacco product, a second tobacco product, a third tobacco product, or a fourth tobacco product to be used in said kit or otherwise in conformance with a tobacco-use cessation or nicotine and/or TSNA reduction method described herein. Preferred indicia that identifies the tobacco product as a member of a series of tobacco products used in a tobacco-use cessation or nicotine and/or TSNA reduction method include visually identifiable rings or bars that appear on the tobacco product itself and/or the tobacco product packaging (see e.g., International Publication Number WO/05041151, which designates the U.S., and was published in English, herein expressly incorporated by reference in its entirety) and Quest 1®, Quest 2®, and Quest 3®. The tobacco-use cessation or nicotine and/or TSNA reduction kits and tobacco products and packing of such can also comprise indicia from a regulatory agency (e.g., a governmental body such as the Federal Drug Administration) indicating that said kit or the tobacco products contained therein have been approved for use in a tobacco-use cessation program.

Other embodiments concern methods of reducing the nicotine and/or TSNA consumption or exposure of a tobacco user by providing to said tobacco user a tobacco product or tobacco-use cessation or nicotine and/or TSNA reduction kit, as described herein. In some embodiments, a tobacco user is identified as one in need of a reduction in the consumption and/or exposure to nicotine and/or TSNAs. The identified tobacco user is then provided one or more of the aforementioned reduced nicotine and/or TSNA tobacco products and/or tobacco-use cessation kits described herein. In some methods, the reduction in consumption or exposure to nicotine and/or TSNAs in said tobacco user is measured. In some methods, the abstinence from conventional tobacco use is measured.

Accordingly, by some approaches, a tobacco user, who is, optionally, identified as one in need of a reduction in the consumption or exposure to nicotine and/or TSNAs, is provided a conventional tobacco product and then said tobacco user is provided a first reduced nicotine and/or TSNA tobacco product, wherein the first reduced nicotine and/or TSNA tobacco product comprises less nicotine and/or TSNAs than the conventional tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g. The first reduced nicotine and/or TSNA tobacco products can comprise treated tobacco, selectively bred low nicotine tobacco, or genetically modified tobacco or combinations thereof. The first tobacco product can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

Other embodiments include tobacco-use cessation or nicotine and/or TSNA reduction methods, wherein a tobacco user, who is, optionally, identified as one in need of a reduction in the consumption or exposure to nicotine and/or TSNAs, is provided a conventional tobacco product and then said tobacco user is provided a conventional tobacco product, a first reduced nicotine and/or TSNA tobacco product and a second reduced nicotine and/or TSNA tobacco product, wherein the first reduced nicotine and/or TSNA tobacco product comprises less nicotine and/or TSNAs than the conventional tobacco product and the second reduced nicotine and/or TSNA tobacco product comprises less nicotine and/or TSNAs than the first reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g and the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product and the amount of nicotine and/or TSNAs in or delivered by the second tobacco product is less than the amount of nicotine and/or TSNAs in or delivered by the first tobacco product. The first and/or second reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

More embodiments include tobacco-use cessation or nicotine and/or TSNA reduction methods, wherein a tobacco user, who is, optionally, identified as one in need of a reduction in the consumption or exposure to nicotine and/or TSNAs, is provided a conventional tobacco product, a first reduced nicotine and/or TSNA tobacco product, a second reduced nicotine and/or TSNA tobacco product, and a third reduced nicotine and/or TSNA tobacco product, wherein the first reduced nicotine and/or TSNA tobacco product comprises less nicotine and/or TSNAs than the conventional tobacco product, the second reduced nicotine and/or TSNA tobacco product comprises less nicotine and/or TSNAs than the first reduced nicotine and/or TSNA tobacco product and the third reduced nicotine and/or TSNA tobacco product comprises less nicotine and/or TSNAs than the second reduced nicotine and/or TSNA tobacco product. The first reduced nicotine and/or TSNA tobacco product (e.g., a cigarette) or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product, the amount of nicotine and/or TSNAs in or delivered by the second tobacco product is less than the amount of nicotine and/or TSNAs in or delivered by the first tobacco product, and the amount of nicotine and/or TSNAs in or delivered by the third tobacco product is less than the amount of nicotine and/or TSNAs in or delivered by the second tobacco product. The first, second, and/or third reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

Still more embodiments include tobacco-use cessation or nicotine and/or TSNA reduction methods, wherein a tobacco user, who is, optionally, identified as one in need of a reduction in the consumption or exposure to nicotine and/or TSNAs, is provided a conventional tobacco product, a first reduced nicotine and/or TSNA tobacco product, a second reduced nicotine and/or TSNA tobacco product, a third reduced nicotine and/or TSNA tobacco product and a fourth reduced nicotine and/or TSNA tobacco product, wherein the first reduced nicotine and/or TSNA tobacco product comprises less nicotine and/or TSNAs than the conventional tobacco product, the second reduced nicotine and/or TSNA tobacco product comprises less nicotine and/or TSNAs than the first reduced nicotine and/or TSNA tobacco product, the third reduced nicotine and/or TSNA tobacco product comprises less nicotine and/or TSNAs than the second reduced nicotine and/or TSNA tobacco product, and the fourth reduced nicotine and/or TSNA tobacco product comprises less nicotine and/or TSNAs than the third reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the fourth reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the first tobacco product is less than the amount of nicotine and/or TSNAs in or delivered by the conventional tobacco product, the amount of nicotine and/or TSNAs in or delivered by the second tobacco product is less than the amount of nicotine and/or TSNAs in or delivered by the first tobacco product, the amount of nicotine and/or TSNAs in or delivered by the third tobacco product is less than the amount of nicotine and/or TSNAs in or delivered by the second tobacco product, and the amount of nicotine and/or TSNAs in or delivered by the fourth tobacco product is less than the amount of nicotine and/or TSNAs in or delivered by the third tobacco product. The first, second, third and/or fourth reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

Preferred tobacco-use cessation or nicotine and/or TSNA reduction methods, however, include approaches, wherein a tobacco user, who is, optionally, identified as one in need of a reduction in the consumption or exposure to nicotine and/or TSNAs, is provided a first reduced nicotine and/or TSNA tobacco product, wherein the first reduced nicotine and/or TSNA tobacco product comprises less nicotine and/or TSNAs than the conventional tobacco product. That is, said tobacco-use cessation or nicotine and/or TSNA reduction methods do not contain the step whereby a conventional tobacco product is provided. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g. The first reduced nicotine and/or TSNA tobacco products can comprise treated tobacco, selectively bred low nicotine tobacco, or genetically modified tobacco or combinations thereof. The first tobacco product can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

Other embodiments include tobacco-use cessation or nicotine and/or TSNA reduction methods, wherein a tobacco user, who is, optionally, identified as one in need of a reduction in the consumption or exposure to nicotine and/or TSNAs, is provided a first reduced nicotine and/or TSNA tobacco product and a second reduced nicotine and/or TSNA tobacco product, wherein the second reduced nicotine and/or TSNA tobacco product comprises less nicotine and/or TSNAs than the first reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g and the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product. The first and/or second reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

More embodiments include tobacco-use cessation or nicotine and/or TSNA reduction methods, wherein a tobacco user, who is, optionally, identified as one in need of a reduction in the consumption or exposure to nicotine and/or TSNAs, is provided a first reduced nicotine and/or TSNA tobacco product, a second reduced nicotine and/or TSNA tobacco product, and a third reduced nicotine and/or TSNA tobacco product, wherein the second reduced nicotine and/or TSNA tobacco product comprises less nicotine and/or TSNAs than the first reduced nicotine and/or TSNA tobacco product and the third reduced nicotine and/or TSNA tobacco product comprises less nicotine and/or TSNAs than the second reduced nicotine and/or TSNA tobacco product. The first reduced nicotine and/or TSNA tobacco product (e.g., a cigarette) or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product, and the amount of nicotine and/or TSNAs in or delivered by the third tobacco product is less than the amount of nicotine and/or TSNAs in or delivered by the second tobacco product. The first, second, and/or third reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

Still more embodiments include tobacco-use cessation or nicotine and/or TSNA reduction methods, wherein a tobacco user, who is, optionally, identified as one in need of a reduction in the consumption or exposure to nicotine and/or TSNAs, is provided a first reduced nicotine and/or TSNA tobacco product, a second reduced nicotine and/or TSNA tobacco product, a third reduced nicotine and/or TSNA tobacco product and a fourth reduced nicotine and/or TSNA tobacco product, wherein the second reduced nicotine and/or TSNA tobacco product comprises less nicotine and/or TSNAs than the first reduced nicotine and/or TSNA tobacco product, the third reduced nicotine and/or TSNA tobacco product comprises less nicotine and/or TSNAs than the second reduced nicotine and/or TSNA tobacco product, and the fourth reduced nicotine and/or TSNA tobacco product comprises less nicotine and/or TSNAs than the third reduced nicotine and/or TSNA tobacco product. The first reduced nicotine and/or TSNA tobacco product (e.g., a cigarette) or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the second reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; the third reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g; and the fourth reduced nicotine and/or TSNA tobacco product or a tobacco therein can comprise (e.g., on the leaf or tobacco rod) or deliver (e.g., side-stream or main-stream smoke by the FTC and/or ISO methods), for example, less than or equal to 1.0 mg/g, 0.6 mg/g, 0.3 mg/g, or 0.05 mg/g nicotine and/or a collective content of TSNAs (e.g., NNN, NAT, NAB, or NNK) of less than or equal to 5.0 µg/g, 4.0 µg/g, 3.0 µg/g, 2.0 µg/g, 1.0 µg/g, 0.5 µg/g, or 0.2 µg/g so long as the amount of nicotine and/or TSNAs in or delivered by the second tobacco product is less than the amount of nicotine and/or TSNAs in or delivered by the first tobacco product, the amount of nicotine and/or TSNAs in or delivered by the third tobacco product is less than the amount of nicotine and/or TSNAs in or delivered by the second tobacco product, and the amount of nicotine and/or TSNAs in or delivered by the fourth tobacco product is less than the amount of nicotine and/or TSNAs in or delivered by the third tobacco product. The first, second, third, and/or fourth reduced nicotine and/or TSNA tobacco products can comprise treated tobacco, selectively bred low nicotine tobacco, or genetically modified tobacco or combinations thereof. These tobacco products can also include exogenous nicotine. In some methods, the reduction in consumption or exposure to nicotine and/or TSNAs in said tobacco user is measured. In some methods, the abstinence from conventional tobacco use is measured. In some methods, a marker of nicotine addiction is measured (e.g., regional cerebral metabolic rate for glucose and/or cerebral blood flow, which are measurable using positron emission tomography (PET)).

In some embodiments, the tobacco-use cessation or nicotine and/or TSNA reduction kits and tobacco use cessation methods can also comprise a conventional NRT product (e.g., nicotine patches, nicotine gum, capsules, inhalers, nasal sprays, and lozenges). That is, aspects of the invention also include tobacco-use cessation or nicotine and/or TSNA reduction kits that comprise nicotine patches, nicotine gum, capsules, inhalers, nasal sprays, and lozenges that can be used in conjunction with a tobacco product as described herein. It is contemplated that the ability to quit tobacco use can be increased by providing a conventional NRT product in conjunction with one or more of the tobacco products described herein or supplementing one or more of the tobacco-use cessation methods described herein with a conventional NRT product and a conventional NRT nicotine-dependence reduction strategy. For example, a tobacco-use cessation or nicotine and/or TSNA reduction program can include the steps of providing a tobacco user who has, optionally, been identified as one in need of a reduction in conventional tobacco use one or more of the tobacco products described herein and a nicotine patch. Preferably, said tobacco user is provided a plurality of tobacco products described herein and a plurality of nicotine patches, wherein at least two tobacco products and at least two nicotine patches have different amounts of nicotine. That is, in some embodiments, a tobacco user is provided a first tobacco product that comprises a tobacco that has a reduced amount of nicotine (e.g., comprising on the leaf or tobacco rod or delivering in the side-stream or main-stream smoke, as determined by the FTC and/or ISO methods) less than or equal to 1.0 mg/g, 0.6 mg/g, 0.3 mg/g, or 0.05 mg/g) and a nicotine patch comprising an amount of nicotine (e.g., 21 mg, 14 mg, or 7 mg).

In some embodiments, a tobacco user is provided at least two reduced nicotine tobacco products (e.g., a first tobacco product comprising on the leaf or tobacco rod or delivering in the side-stream or main-stream smoke, as determined by the FTC and/or ISO methods) less than or equal to 1.0 mg/g nicotine and a second tobacco product comprising (e.g., on the leaf or tobacco rod) or delivering (e.g., side-stream or main-stream smoke by the FTC and/or ISO methods) less than or equal to 0.6 mg/g nicotine and a nicotine patch (e.g., 21 mg, 14 mg, or 7 mg nicotine); and, in other embodiments, a tobacco user is provided at least three reduced nicotine tobacco products described herein, for example, a first tobacco product comprising (e.g., on the leaf or tobacco rod) or delivering (e.g., side-stream or main-stream smoke by the FTC and/or ISO methods) less than or equal to 1.0 mg/g nicotine, a second tobacco product comprising (e.g., on the leaf or tobacco rod) or delivering (e.g., side-stream or main-stream smoke by the FTC and/or ISO methods) less than or equal to 0.6 mg/g nicotine, and a third reduced nicotine tobacco product comprising (e.g., on the leaf or tobacco rod) or delivering (e.g., side-stream or main-stream smoke by the FTC and/or ISO methods) less than or equal to 0.3 mg/g nicotine) and a nicotine patch (e.g., 21 mg, 14 mg, or 7 mg nicotine); and, in some embodiments, a tobacco user is provided at least four tobacco products described herein, for example, a first tobacco product comprising (e.g., on the leaf or tobacco rod) or delivering (e.g., side-stream or main-stream smoke by the FTC and/or ISO methods) less than or equal to 1.0 mg/g nicotine, a second tobacco product comprising (e.g., on the leaf or tobacco rod) or delivering (e.g., side-stream or main-stream smoke by the FTC and/or ISO methods) less than or equal to 0.6 mg/g nicotine, a third reduced nicotine tobacco product comprising (e.g., on the leaf or tobacco rod) or delivering (e.g., side-stream or main-stream smoke by the FTC and/or ISO methods) less than or equal to 0.3 mg/g nicotine, and a fourth reduced nicotine tobacco product comprising (e.g., on the leaf or tobacco rod) or delivering (e.g., side-stream or main-stream smoke by the FTC and/or ISO methods) less than or equal to 0.05 mg/g nicotine) and a nicotine patch (e.g., 21 mg, 14 mg, or 7 mg nicotine). Preferably, a tobacco user is provided a tobacco product that comprises (e.g., on the leaf or tobacco rod) or delivers (e.g., side-stream or main-stream smoke by the FTC and/or ISO methods) less than or equal to 0.05 mg/g nicotine and a nicotine patch comprising 21 mg, 14 mg, or 7 mg.

By one approach, a step 1 tobacco product is comprised of approximately 25% low nicotine/TSNA tobacco and 75% conventional tobacco; a step 2 tobacco product can be comprised of approximately 50% low nicotine/TSNA tobacco and 50% conventional tobacco; a step 3 tobacco product can be comprised of approximately 75% low nicotine/TSNA tobacco and 25% conventional tobacco; and a step 4 tobacco product can be comprised of approximately 100% low nicotine/TSNA tobacco and 0% conventional tobacco. A tobacco-use cessation or nicotine and/or TSNA reduction kit can comprise an amount of tobacco product from each of the aforementioned blends to satisfy a consumer for a single month program. That is, if the consumer is a one pack per day smoker, for example, a single month kit would provide 7 packs from each step, a total of 28 packs of cigarettes. Each tobacco-use cessation kit would include a set of instructions that specifically guide the consumer through the step-by-step process. Of course, tobacco products having specific amounts of nicotine and/or TSNAs would be made available in conveniently sized amounts (e.g., boxes of cigars, packs of cigarettes, tins of snuff, and pouches or twists of chew) so that consumers could select the amount of nicotine and/or TSNA they individually desire. There are many ways to obtain various low nicotine/low TSNA tobacco blends using the teachings described herein and the following is intended merely to guide one of skill in the art to one possible approach.

Although the invention has been described with reference to embodiments and examples, it should be understood that various modifications can be made without departing from the spirit provided herein. All references cited herein are hereby expressly incorporated by reference.

What is claimed:

1. A method of producing a transgenic tobacco plant comprising inhibiting expression of an endogenous gene comprising SEQ. ID. NO: 5 by RNA interference (RNAi) in a tobacco plant, wherein leaves from said transgenic tobacco plant have a reduced amount of nornicotine or nicotine or both nornicotine and nicotine, as compared to a control tobacco.

2. The method of claim 1, wherein the leaves from said transgenic tobacco plant have a lower amount of nicotine as compared to a control tobacco.

3. The method of claim 2, wherein the amount of nicotine is between 2.17 mg/g and 3.99 mg/g.

4. The method of claim 1, wherein said leaves from said transgenic tobacco plant are a tobacco product.

5. The method of claim 2, wherein said leaves from said transgenic tobacco plant are a tobacco product.

6. The method of claim 3, wherein said leaves from said transgenic tobacco plant are a tobacco product.

7. The method of claim 4, wherein said tobacco product is a cigarette.

8. The method of claim 5, wherein said tobacco product is a cigarette.

9. The method of claim 6, wherein said tobacco product is a cigarette.

10. The method of claim 1, wherein the amount of nornicotine is 0.00 mg/g.

11. The method of claim 1, wherein the amount of nornicotine is 0.06 mg/g.

12. The method of claim 1, wherein the amount of nornicotine is 0.03 mg/g.

13. The method of claim 2, wherein the amount of nicotine is 2.17 mg/g.

14. The method of claim 2, wherein the amount of nicotine is 2.30 mg/g.

15. The method of claim 2, wherein the amount of nicotine is 2.58 mg/g.

16. The method of claim 2, wherein the amount of nicotine is 2.61 mg/g.

17. The method of claim 2, wherein the amount of nicotine is 3.48 mg/g.

18. The method of claim 2, wherein the amount of nicotine is 3.56 mg/g.

19. The method of claim 2, wherein the amount of nicotine is 3.59 mg/g.

20. The method of claim 2, wherein the amount of nicotine is 3.94 mg/g.

21. The method of claim 2, wherein the amount of nicotine is 3.99 mg/g.

* * * * *

SEQUENCE LISTING

```
<160> NUMBER OF SEQ ID NOS: 56

<210> SEQ ID NO 1
<211> LENGTH: 4
<212> TYPE: PRT
<213> ORGANISM: Nicotiana tabacum

<400> SEQUENCE: 1

Asp Glu Val Asp
1
```

<210> SEQ ID NO 2
<211> LENGTH: 1056
<212> TYPE: DNA
<213> ORGANISM: Nicotiana tabacum

<400> SEQUENCE: 2

| | | | | | |
|---|---|---|---|---|---|
| atgtttagag | ctattccttt | cactgctaca | gtgcatcctt | atgcaattac | agctccaagg | 60
| ttggtggtga | aaatgtcagc | aatagccacc | aagaatacaa | gagtggagtc | attagaggtg | 120
| aaaccaccag | cacacccaac | ttatgattta | aggaagtta | tgaaacttgc | actctctgaa | 180
| gatgctggga | atttaggaga | tgtgacttgt | aaggcgacaa | ttcctcttga | tatggaatcc | 240
| gatgctcatt | ttctagcaaa | ggaagacggg | atcatagcag | gaattgcact | tgctgagatg | 300
| atattcgcgg | aagttgatcc | ttcattaaag | gtggagtggt | atgtaaatga | tggcgataaa | 360
| gttcataaag | gcttgaaatt | tggcaaagta | caaggaaacg | cttacaacat | tgttatagct | 420
| gagagggttg | ttctcaattt | tatgcaaaga | atgagtggaa | tagctacact | aactaaggaa | 480
| atggcagatg | ctgcacaccc | tgcttacatg | ttggagacta | ggaaaactgc | tcctggatta | 540
| cgtttggtgg | ataaatgggc | ggtattgatc | ggtgggggga | agaatcacag | aatgggctta | 600
| tttgatatgg | taatgataaa | agacaatcac | atatctgctg | ctggaggtgt | cggcaaagct | 660
| ctaaaatctg | tggatcagta | tttggagcaa | aataaacttc | aaatagggt | tgaggttgaa | 720
| accaggacaa | ttgaagaagt | acgtgaggtt | ctagactatg | catctcaaac | aaagacttcg | 780
| ttgactagga | taatgctgga | caatatggtt | gttccattat | ctaacggaga | tattgatgta | 840
| tccatgctta | aggaggctgt | agaattgatc | aatgggaggt | ttgatacgga | ggcttcagga | 900
| aatgttaccc | ttgaaacagt | acacaagatt | ggacaaactg | tgttaccta | catttctagt | 960
| ggtgccctga | cgcattccgt | gaaagcactt | gacatttccc | tgaagatcga | tacagagctc | 1020
| gcccttgaag | ttggaaggcg | tacaaaacga | gcatga | | | 1056

<210> SEQ ID NO 3
<211> LENGTH: 360
<212> TYPE: DNA
<213> ORGANISM: Nicotiana tabacum

<400> SEQUENCE: 3

| | | | | | |
|---|---|---|---|---|---|
| atgtttagag | ctattccttt | cactgctaca | gtgcatcctt | atgcaattac | agctccaagg | 60
| ttggtggtga | aaatgtcagc | aatagccacc | aagaatacaa | gagtggagtc | attagaggtg | 120
| aaaccaccag | cacacccaac | ttatgattta | aggaagtta | tgaaacttgc | actctctgaa | 180
| gatgctggga | atttaggaga | tgtgacttgt | aaggcgacaa | ttcctcttga | tatggaatcc | 240
| gatgctcatt | ttctagcaaa | ggaagacggg | atcatagcag | gaattgcact | tgctgagatg | 300
| atattcgcgg | aagttgatcc | ttcattaaag | gtggagtggt | atgtaaatga | tggcgataaa | 360

<210> SEQ ID NO 4
<211> LENGTH: 241
<212> TYPE: DNA
<213> ORGANISM: Nicotiana tabacum

<400> SEQUENCE: 4

| | | | | | |
|---|---|---|---|---|---|
| cattttacca | tctttcgcca | gaagtatgat | cgagtcttaa | tcaagtgaat | aatgaacact | 60
| ggtagtacaa | tcattggacc | aagatcgagt | cttaatcaag | tgaataaata | agtgaaatgc | 120
| gacgtattgt | aggagaattc | tgcagtaatt | atcataattt | ccaattcaca | atcattgtaa | 180

```
aattctttct ctgtggtgtt tcgtacttta atataaattt tcctgctgaa gttttgaatc    240
g                                                                    241

<210> SEQ ID NO 5
<211> LENGTH: 628
<212> TYPE: DNA
<213> ORGANISM: Nicotiana tabacum

<400> SEQUENCE: 5
tgatcaagtg aacatcatca agcaattaa agaagctgga atatcaaga gatttcttcc      60 ttcagaattt ggatttgatg tggatcatgc tcgtgcaatt gaaccagctg catcactctt   120
cgctctaaag gtaagaatca ggaggatgat agaggcagaa ggaattccat acacatatgt   180
aatctgcaat tggttttgcag atttcttctt gcccaacttg gggcagttag aggccaaaac   240
ccctcctaga gacaaagttg tcattttggg cgatggaaat cccaaagcaa tatatgtgaa   300
ggaagaagac atagcgacat acactatcga agcagtagat gatccacgga cattgaataa   360
gactcttcac atgagaccac ctgccaatat tctatccttc aacgagatag tgtccttgtg   420
ggaggacaaa attgggaaga ccctcgagaa gttatatcta tcagaggaag atattctcca   480
gattgtacaa gagggacctc tgccattaag gactaatttg gccatatgcc attcagtttt   540
tgttaatgga gattctgcaa actttgaggt tcagcctcct acaggtgtcg aagccactga   600
gctatatcca aaagtgaaat acacaacc                                      628

<210> SEQ ID NO 6
<211> LENGTH: 439
<212> TYPE: DNA
<213> ORGANISM: Nicotiana tabacum

<400> SEQUENCE: 6
ccacattggg gcttctgtta ctcaatgctt cataaggttt ctcgtagctt tgctctcgtc    60
attcaacaac ttcccgtcga gcttcgtgac gccgtgtgca ttttctattt ggttcttcga   120
gcacttgaca ctgttgagga tgataccagc attcccaccg atgttaaagt acctattctg   180
atctcttttc atcagcatgt ttatgatcgt gaatggcatt tttcatgtgg tacaaaagag   240
tacaaggttc tcatggacca gttccatcat gtttcaactg cttttctgga gcttaggaaa   300
cattatcagc aggcaattga ggatattacc atgaggatgg gtgcaggaat ggcaaaattc   360
atatgcaagg aggtggaaac aactgatgat tatgacgaat attgtcacta tgtagctggg   420
cttgttgggc taggattgt                                                439

<210> SEQ ID NO 7
<211> LENGTH: 850
<212> TYPE: DNA
<213> ORGANISM: Nicotiana tabacum

<400> SEQUENCE: 7
gaggctgtaa atgatggcaa agacctccat atttcagtaa ctatgccttc tattgaggtt    60
ggcacagttg gtggtggaac tcaacttgca tcacagtcag cttgcttgaa cttattagga   120
gtgaaaggtg caaacaggga ggcagcaggg tcaaatgcaa ggctcttggc cacaatagta   180
gcaggttctg ttcttgctgg tgagttatct ctcatgtctg ctatctcagc agggcagctg   240
gttaagagtc acatgaaata caatagatct agcaaagatg ttactaagat ttcctcttag   300
taaggaaaaa gacaaattta ttatcccaac atcgtgtaca tcaccatcct ttatggacca   360
tcattattaa agaaatggat tacaataaaa gtaggaataa aattttccaa ttagggagag   420
```

```
caataagtaa agggtagacc aaaaagttga aaaagtgtaa ggcattagtc atgtggagaa      480
agatcaagaa gaaaaagaca agcaaatcaa gggtggacgt ggatctgtat gtagtgttgt      540
attctttcta tgaaggcatg tgaggaggta gggtcgtatt tttttctgag ttcgtgtaaa      600
aaaacctgca aatatttggt gaagatctac gaaaggtgtt aggtgggatg gtgaccagtg      660
gggttaactt gtaattcaac atttggttaa tttcattcat gcgccaagga agataacccc      720
ttttttttta aataatcttt tctgttgtac tgtctttcgt ttgtttgtta attgtgacta      780
gattgtaatt tagagagaaa tggcatctca aactctttat gtttgctcag aaagtttgct      840
tttgtatatg                                                            850

<210> SEQ ID NO 8
<211> LENGTH: 780
<212> TYPE: DNA
<213> ORGANISM: Nicotiana tabacum

<400> SEQUENCE: 8
agaagctacc tgccatgcac cagatccatt gggatgctat aaagagattt accgggtgct       60
gaagcctggt caatgtttcg ctgtgtatga gtggtgcatg accgattctt acaaccccaa      120
taacgaagag cacaacagga tcaaggccga aattgagctc ggaaatggcc tccctgaggt      180
tagattgaca acacagtgcc tcgaagcagc caaacaagct ggttttgaag ttgtatggga      240
caaggatctg gctgatgact cacctgttcc atggtacttg cctttggata cgagtcactt      300
ctcgctcagt agcttccgcc taacagcagt tggcagactt ttcaccagaa atctggtttc      360
ggcgcttgaa tacgtgggac ttgctcctaa aggtagtcaa agggttcaag ctttcttaga      420
gaaagctgca gaaggtcttg tcggtggtgc caagaaaggg attttcacac caatgtactt      480
cttcgtggtt cgcaagccca tttcagactc tcagtaatat ggagtttagt cacttagctt      540
tttgctttag ctagcaaatc tgtaagattc ttcgcacaga actttacaca ttgaatatga      600
ccgccctaat taaggtgact acagttttg gagggcgttg tgggtggagg gttttctttt       660
ctgtgttgct tgtctggcac aatttgattt catgtcttgc tattttttgcc attgatgtcc      720 ttgttctaag atatataccct attgacaagc tcataaaggt gggcatttgc taatatatgg      780

<210> SEQ ID NO 9
<211> LENGTH: 885
<212> TYPE: DNA
<213> ORGANISM: Nicotiana tabacum

<400> SEQUENCE: 9
aagaatatca cgttcttcgt tggcccagaa gtgtcggccc atttctttaa ggccccagaa       60
accgatctca gtcaacaaga ggtttatcag ttcaatgtgc ctacttttgg ccctggtgtg      120 gttttttgacg ttgattatac tatcagacaa gagcaattta ggttctttac tgaatctttg      180
agggtaaata aattgaaggg atatgtggat cagatggtca tggaagctga ggagtacttc      240
tcaaaatggg gtgatagtgg tgaagtggac ttgaagtatg aactggagca tcttatcata      300
ctgacagcta gtagatgtct gttgggagaa gaggttcgca ataaactctt tgaggatgtc      360
tctgctctct tccatgacct ggacaatggg atgcttccta tcagtgtaat ctttccctac      420
cttcccattc cagcccatcg ccgtcgtgac aatgcccgca agaagctcgc ggagatcttt      480
gcaaacatca tagattctag aaaacgtaca ggcaaggcgg agagcgatat gttacaatgc      540
ttcattgact ccaagtacaa agatgggcgg gcaacgacag agtctgagat cacaggtctt      600
```

| | | |
|---|---|---|
| ctgattgctg ctcttttcgc tgggcaacac accagttcca tcacctccac ttgggcaggg | 660 | |
| gcataccttc tctgcaacaa caagtacatg tctgccgtcg tagatgaaca gaagaatctg | 720 | |
| atgaagaaac atgggaataa ggtcgatcat gacatccttt ccgagatgga agtcctctat | 780 | |
| agatgcataa aggaagccct gagactccat cctccactga taatgcttct acgtagttcg | 840 | |
| catagtgatt tcactgttaa aaccagggaa ggaaaagagt atgat | 885 | |

<210> SEQ ID NO 10
<211> LENGTH: 1701
<212> TYPE: DNA
<213> ORGANISM: Arabidopsis thaliana

<400> SEQUENCE: 10

| | | |
|---|---|---|
| atggttgtgt ttgggaatgt ttctgcggcg aatttgcctt atcaaaacgg gttttttggag | 60 | |
| gcactttcat ctggaggttg tgaactaatg ggacatagct ttagggttcc cacttctcaa | 120 | |
| gcgcttaaga caagaacaag gaggaggagt actgctggtc ctttgcaggt agtttgtgtg | 180 | |
| gatattccaa ggccagagct agagaacact gtcaatttct tggaagctgc tagtttatct | 240 | |
| gcatccttcc gtagtgctcc tcgtcctgct aagcctttga agttgtaat tgctggtgct | 300 | |
| ggattggctg gattgtcaac tgcaaagtac ctggctgatg caggccacaa acctctgttg | 360 | |
| cttgaagcaa gagatgttct tggtggaaag atagctgcat ggaaggatga agatggggac | 420 | |
| tggtatgaga ctggttttaca tatttttcttc ggtgcttatc gaatgtgca gaatttattt | 480 | |
| ggagaacttg ggatcaatga tcggttgcag tggaaggaac actccatgat ttttgctatg | 540 | |
| ccaagtaaac ctggagaatt tagtagattt gacttcccag atgtcctacc agcacccttta | 600 | |
| aatggtattt gggctatttt gcggaacaac gagatgctga catggccaga gaaaataaag | 660 | |
| tttgctattg acttttgcc agccatggtc ggcggtcagg cttatgttga ggcccaagat | 720 | |
| ggtttatcag tcaaagaatg gatggaaaag cagggagtac ctgagcgcgt gaccgacgag | 780 | |
| gtgtttattg ccatgtcaaa ggcgctaaac tttataaacc ctgatgaact gtcaatgcaa | 840 | |
| tgcatttga tagctttgaa ccggttcttt caggaaaaac atggttccaa gatggcattc | 900 | |
| ttggatggta atcctccgga aaggctttgt atgccagtag tggatcatat tcgatcacta | 960 | |
| ggtggggaag tgcaacttaa ttctaggata aagaaaattg agctcaatga cgatggcacg | 1020 | |
| gttaagagtt tcttactcac taatggaagc actgtcgaag gagacgctta tgtgtttgcc | 1080 | |
| gctccagtcg atatcctgaa gctccttttta ccagatccct ggaaagaaat accgtacttc | 1140 | |
| aagaaattgg ataaattagt tggagtacca gttattaatg ttcatatatg gttttgatcga | 1200 | |
| aaactgaaga acacatatga tcacctactc tttagcagaa gtaaccttct gagcgtgtat | 1260 | |
| gccgacatgt ccttaacttg taaggaatat tacgatccta accggtcaat gctggagcta | 1320 | |
| gtatttgcac cagcagagga atggatatca cggactgatt ctgacatcat agatgcaaca | 1380 | |
| atgaaagaac ttgagaaact cttccctgat gaaatctcag ctgaccaaag caaagctaaa | 1440 | |
| attctgaagt accatgtcgt taagactcca agatctgggt acaagaccat cccaaactgt | 1500 | |
| gaaccatgtc gtcctctaca aagatcacct attgaaggat tctacttagc tggagattac | 1560 | |
| acaaaacaga agtacttagc ttccatgaaa ggcgctgtcc tctctggcaa attctgctct | 1620 | |
| cagtctattg ttcaggatta cgagctactg gctgcgtctg gaccaagaaa gttgtcggag | 1680 | |
| gcaacagtat catcatcatg a | 1701 | |

<210> SEQ ID NO 11
<211> LENGTH: 1701

```
<212> TYPE: DNA
<213> ORGANISM: Arabidopsis thaliana

<400> SEQUENCE: 11
atggttgtgt ttgggaatgt ttctgcggcg aatttgcctt atcaaaacgg gttttttggag    60
gcactttcat ctggaggttg tgaactaatg ggacatagct ttagggttcc cacttctcaa   120
gcgcttaaga caagaacaag gaggaggagt actgctggtc ctttgcaggt agtttgtgtg   180
gatattccaa ggccagagct agagaacact gtcaatttct tggaagctgc tagtttatct   240
gcatccttcc gtagtgctcc tcgtcctgct aagcctttga agttgtaat tgctggtgct   300
ggattggctg gattgtcaac tgcaaagtac ctggctgatg caggccacaa acctctgttg   360
cttgaagcaa gagatgttct tggtggaaag atagctgcat ggaaggatga agatggggac   420
tggtatgaga ctggtttaca tattttcttc ggtgcttatc cgaatgtgca gaatttattt   480
ggagaacttg ggatcaatga tcggttgcag tggaaggaac actccatgat ttttgctatg   540
ccaagtaaac ctgagaatt tagtagattt gacttcccag atgtcctacc agcacccta   600
aatggtattt gggctatttt gcggaacaac gagatgctga catggccaga gaaaataaag   660
tttgctattg gacttttgcc agccatggtc ggcggtcagg cttatgttga gcccaagat    720
ggtttatcag tcaaagaatg gatggaaaag cagggagtac ctgagcgcgt gaccgacgag   780
gtgtttattg ccatgtcaaa ggcgctaaac tttataaacc ctgatgaact gtcaatgcaa   840
tgcattttga tagctttgaa cccgtttctt caggaaaaac atggttccaa gatggcattc   900
ttggatggta atcctccgga aaggctttgt atgccagtag tggatcatat tcgatcacta   960
ggtggggaag tgcaacttaa ttctaggata aagaaattg agctcaatga cgatggcacg  1020
gttaagagtt tcttactcac taatggaagc actgtcgaag gagacgctta tgtgtttgcc  1080
gctccagtcg atatcctgaa gctcctttta ccagatccct ggaaagaaat accgtacttc  1140
aagaaattgg ataaattagt tggagtacca gttattaatg ttcatatatg gtttgatcga  1200
aaactgaaga acacatatga tcacctactc tttagcagaa gtaaccttct gagcgtgtat  1260
gccgacatgt ccttaacttg taaggaatat tacgatccta accggtcaat gctggagcta  1320
gtatttgcac cagcagagga atggatatca cggactgatt ctgacatcat agatgcaaca  1380
atgaaagaac ttgagaaact cttccctgat gaaatctcag ctgaccaaag caaagctaaa  1440
attctgaagt accatgtcgt taagactcca agatctgtgt acaagaccat cccaaactgt  1500
gaaccatgtc gtcctctaca aagatcacct attgaaggat tctacttagc tggagattac  1560
acaaaacaga gtacttagc ttccatggaa ggcgctgtcc tctctggcaa attctgctct  1620
cagtctattg ttcaggatta cgagctactg gctgcgtctg gaccaagaaa gttgtcggag  1680
gcaacagtat catcatcatg a                                             1701

<210> SEQ ID NO 12
<211> LENGTH: 1701
<212> TYPE: DNA
<213> ORGANISM: Arabidopsis thaliana

<400> SEQUENCE: 12
atggttgtgt ttgggaatgt ttctgcggcg aatttgcctt atcaaaacgg gttttttggag    60
gcactttcat ctggaggttg tgaactaatg ggacatagct ttagggttcc cacttctcaa   120
gcgcttaaga caagaacaag gaggaggagt actgctggtc ctttgcaggt agtttgtgtg   180
gatattccaa ggccagagct agagaacact gtcaatttct tggaagctgc tagtttatct   240
```

```
gcatccttcc gtagtgctcc tcgtcctgct aagcctttga aagttgtaat tgctggtgct     300
ggattggctg gattgtcaac tgcaaagtac ctggctgatg caggcccaca acctctgttg     360
cttgaagcaa gagatgttct tggtggaaag atagctgcat ggaaggatga agatggggac     420
tggtatgaga ctggtttaca tattttcttc ggtgcttatc cgaatgtgca gaatttattt     480
ggagaacttg ggatcaatga tcggttgcag tggaaggaac actccatgat ttttgctatg     540
ccaagtaaac ctggagaatt tagtagattt gacttcccag atgtcctacc agcacccta      600
aatggtattt gggctatttt gcggaacaac gagatgctga catggccaga gaaaataaag     660
tttgctattg acttttgcc agccatggtc ggcggtcagg cttatgttga ggcccaagat      720
ggtttatcag tcaaagaatg gatggaaaag cagggagtac ctgagcgcgt gaccgacgag     780
gtgtttattg ccatgtcaaa ggcgctaaac tttataaacc ctgatgaact gtcaatgcaa     840
tgcattttga tagctttgaa ccggtttctt caggaaaaac atggttccaa gatggcattc     900
ttggatggta atcctccgga aaggctttgt atgccagtag tggatcatat tcgatcacta     960
ggtggggaag tgcaacttaa ttctaggata aagaaaattg agctcaatga cgatggcacg    1020
gttaagagtt tcttactcac taatggaagc actgtcgaag gagacgctta tgtgtttgcc    1080
gctccagtcg atatcctgaa gctcctttta ccagatccct ggaaagaaat accgtacttc    1140
aagaaattgg ataaattagt tggagtacca gttattaatg ttcatatatg gtttgatcga    1200
aaactgaaga acacatatga tcacccactc tttagcagaa gtaaccttct gagcgtgtat    1260
gccgacatgt ccttaacttg taaggaatat tacgatccta accggtcaat gctggagcta    1320
gtatttgcac cagcagagga atggatatca cggactgatt ctgacatcat agatgcaaca    1380
atgaaagaac ttgagaaact cttccctgat gaaatctcag ctgaccaaag caaagctaaa    1440
attctgaagt accatgtcgt taagactcca agatctgtgt acaagaccat cccaaactgt    1500
gaaccatgtc gtcctctaca agatcaccct attgaaggat tctacttagc tggagattac    1560
acaaaacaga gtacttagc ttccatggaa ggcgctgtcc tctctggcaa attctgctct     1620
cagtctattg ttcaggatta cgagctactg gctgcgtctg gaccaagaaa gttgtcggag    1680
gcaacagtat catcatcatg a                                              1701

<210> SEQ ID NO 13
<211> LENGTH: 1061
<212> TYPE: DNA
<213> ORGANISM: Nicotiana tabacum

<400> SEQUENCE: 13
aatatgaaag gaaacatatt caatacattg tagtttgcta ctcataatcg ctagaatact      60
ttgtgccttg ctaataaaga tacttgaaat agcttagttt aaatataaat agcataatag     120
attttaggaa ttagtatttt gagtttaatt acttattgac ttgtaacagt ttttataatt     180
ccaaggccca tgaaaaattt aatgctttat tagttttaaa cttactatat aaattttca      240
tatgtaaaat ttaatcggta tagttcgata ttttttcaat ttatttttat aaaataaaaa     300
acttacccta attatcggta cagttataga tttatataaa aatctacggt tcttcagaag     360
aaacctaaaa atcggttcgg tgcggacggt tcgatcggtt tagtcgattt tcaaatattc     420
attgacactc ctagttgttg ttataggtaa aaagcagtta cagagaggta aaatataact     480
taaaaaatca gttctaagga aaaattgact tttatagtaa atgactgtta tataaggatg     540
ttgttacaga gaggtatgag tgtagttggt aaattatgtt cttgacggtg tatgtcacat     600
attatttatt aaaactagaa aaaacagcgt caaaactagc aaaaatccaa cggacaaaaa     660
```

```
aatcggctga atttgatttg gttccaacat ttaaaaaagt ttcagtgaga agaatcggt      720 gactgttgat gatataaaca aagggcacat tggtcaataa ccataaaaaa ttatatgaca     780
gctacagttg gtagcatgtg ctcagctatt gaacaaatct aaagaaggta catctgtaac    840
cggaacacca cttaaatgac taaattaccc tcatcagaaa gcagatggag tgctacaaat    900
aacacactat tcaacaacca taaataaaac gtgttcagct actaaacaa atataaataa     960 atctatgttt gtaagcactc cagccatgtt aatggagtgc tattgcctgt taactctcac   1020
ttataaaata gtagtagaaa aaatatgaac caaaacacaa c                       1061

<210> SEQ ID NO 14
<211> LENGTH: 711
<212> TYPE: DNA
<213> ORGANISM: Nicotiana tabacum

<400> SEQUENCE: 14
gaattcaatg gagaaggaaa atatttccag tgtaaacaca agtgaatgaa gagaagccaa     60
aataatctct atcattcaag ccttaggtgg agattaaaaa aattatttac tttcttatca    120
aagtaatagg tgatcaacag ctttcgtaaa acgtcattag gagaatatta taatctcttt    180
tatgctgaag aacccacata aggaagatca taaaatacat gactttcaga tgacttcttg    240
gagctttatt tttaaagagt ggctagctgg tcagcaaaga ggtgctcgtc agatatcata    300 aaatttttact attatttgtt ttaagaggga gatggggcac acatgcttgt gacaaaagta   360
agaggaagaa aggagacaga agaggaaata gatttgggggg ggggggggggg ggtttcacaa   420 tcaaagaaaa ttttttaaaat ggagagagaa atgagcacac acatatacta acaaaatttt   480
actaataatt gcaccgagac aaacttatat tttagttcca aaatgtcagt ctaaccctgc    540
acgttgtaat gaattttttaa ctattatatt atatcgagtt gcgccctcca ctcctcggtg    600
tccaaattgt atttaaatgc atagatgttt attgggagtg tacagcaagc tttcggaaaa   660
tacaaaccat aatactttct cttcttcaat ttgtttagtt taattttgaa a            711

<210> SEQ ID NO 15
<211> LENGTH: 1278
<212> TYPE: DNA
<213> ORGANISM: Nicotiana tabacum

<400> SEQUENCE: 15
tgcgtcaaat ggataaacaa aaaatagca taagttagtt ttgttactcg agagttatgt       60
attataaggt atagggaaat gactcaaaca taccactgaa cttaacgaaa cgacgcatat     120
atatactact taacttaacg aaaaggggt gagagtggat gggtgctggt aaataatgaa     180
gggtttatat aacgtcacgt gtcaaaattc gatagtagta gtttcgttag ttgtaatagc    240
atatatggcc caaagttata atatagataa tatgtttatg tccaactatt aacgagtgac    300
atagacagtt cattttgtga agttcaatga catatttggag ccctttcccct tttattatct   360 cctttttattt gttctaataa aagaatggca tttattatgt acatagacaa ataactattt    420
tctttggaat ataattttgt tatatatttt aaaatcatgt ctcaatttag tttgttttgt    480
gcatatttca actattcaat tttgtccata tatttattac cttcccccat ttacaagcat    540
tgaaccgctt tgctcaccaa aacttatgca cattgcaaaa atatcatgta aaggttttat    600
gtatgctgta attaaggtct gaactcatcg tgatttttatt tttaggcttc attgaccact    660
accaaactct ttgatgctac attttctaat tatattggag ttcgattata tccgaattcg    720
```

| | |
|---|---|
| cgttgcgtag ggcccattcg agggaaaaca ctccctatca aggattttt catacccaga | 780 |
| gctcgaactc aagacatctg gttaagggaa gaacagtctc atccactgca ccatatcctt | 840 |
| ttgtggtcaa caagtaaatt ttatgtagaa ccaaaaacta tactcgaatt gataaaataa | 900 |
| atggtgtaaa atattgtttt cttcttaca ttttggacag taaatatgta ggacaataat | 960 |
| aattagcgtg gggtcttaag aaaattagca tagatttcca gaattccaa atcaaccggc | 1020 |
| agttccaggt ttgaaaacta caactcattc cgacggttca aacttcaaac catgcttgct | 1080 |
| gactcggctt cttctttctt tttcaccaag acagagcagt agtcacgtga caccctcac | 1140 |
| gtgcctcccc cctttatatt tcagactgca acctacact tcgctacat tcactaccat | 1200 |
| attcttttca ctaagcaatt ttctctccta cttttctta aaccctttt ttctccccta | 1260 |
| agccatggca tctagatc | 1278 |

<210> SEQ ID NO 16
<211> LENGTH: 1079
<212> TYPE: DNA
<213> ORGANISM: Nicotiana tabacum

<400> SEQUENCE: 16

| | |
|---|---|
| atcttattgt ataaatatcc ataaacacat catgaaagac actttctttc acggtctgaa | 60 |
| ttaattatga tacaattcta atagaaaacg aattaaatta cgttgaattg tatgaaatct | 120 |
| aattgaacaa gccaaccacg acgacgacta acgttgcctg gattgactcg gtttaagtta | 180 |
| accactaaaa aaacggagct gtcatgtaac acgcggatcg agcaggtcac agtcatgaag | 240 |
| ccatcaaagc aaaagaacta atccaagggc tgagatgatt aattagttta aaaattagtt | 300 |
| aacacgaggg aaaaggctgt ctgacagcca ggtcacgtta tctttacctg tggtcgaaat | 360 |
| gattcgtgtc tgtcgatttt aattattttt ttgaaaggcc gaaaataaag ttgtaagaga | 420 |
| taaacccgcc tatataaatt catatatttt ctctccgctt tgaattgtct cgttgtcctc | 480 |
| ctcactttca tcggccgttt ttgaatctcc ggcgacttga cagagaagaa caaggaagaa | 540 |
| gactaagaga gaaagtaaga gataatccag gagattcatt ctccgttttg aatcttcctc | 600 |
| aatctcatct tcttccgctc tttctttcca aggtaatagg aactttctgg atctacttta | 660 |
| tttgctggat ctcgatcttg ttttctcaat ttccttgaga tctggaattc gtttaatttg | 720 |
| gatctgtgaa cctccactaa atcttttggt tttactagaa tcgatctaag ttgaccgatc | 780 |
| agttagctcg attatagcta ccagaatttg gcttgacctt gatggagaga tccatgttca | 840 |
| tgttacctgg gaaatgattt gtatatgtga attgaaatct gaactgttga agttagattg | 900 |
| aatctgaaca ctgtcaatgt tagattgaat ctgaacactg tttaagttag atgaagtttg | 960 |
| tgtatagatt cttcgaaact ttaggatttg tagtgtcgta cgttgaacag aaagctattt | 1020 |
| ctgattcaat cagggtttat ttgactgtat tgaactcttt ttgtgtgttt gcagctcat | 1079 |

<210> SEQ ID NO 17
<211> LENGTH: 1943
<212> TYPE: DNA
<213> ORGANISM: Nicotiana tabacum

<400> SEQUENCE: 17

| | |
|---|---|
| aagcttttta tttagctttt tcctccctat ttcaatatat aatggctcaa tttttgtcag | 60 |
| atagcaataa aaccatacaa gaaaataaaa caaatcacaa aatacaaaaa gaggttatat | 120 |
| ctccatgtat gcaatttcat tatatgcata taagcatctt acgtataaaa aaaagagggg | 180 |
| aatcatggac gtgtctttct aatccaagta gggtcaactt tatagggtcg gtgtatgtgt | 240 |

```
agtttaatcg aaaaagaatt ccatcattag gtaatttaca attagatcct taaattatac    300
aaatatataa gggtataaaa gttgatcaat atttcaggga tattttagtc gttcaacatt    360
tagtataaat tattcgtact tttataataa taaatagata gataaacata gatatagata    420
taaatataga tagataaatg ggggatttgc atctataccc acttttttggg tcacgtttta   480 atttgtgccc gctttgcaaa aaaaattgca agcgtacaca cttttttcgcg taacttcagc   540 atacggggct aaagtagcaa agacagtcac gcaaaacttc agcatacttc agtctttgct    600
acttcagccc cgtatgctga agttatgcga aaagcgggta tgcttgtaat ttttttgcaa    660
agcgagcata agttaaaacg tgacacaaaa agcgggtata gatacaaatg gcccttttt    720 ttctagccaa attttattca tttttttgga atactttttc actttatttt aaaattagtg    780
tttggttata aattttttaaa tacaacttgg agttggactc caaagtcttt acatacttat    840 ttttagttt attaccctat ttttttttaac atgagatatt tactttttaca gatctaaaaa    900 tgatattttc ttagtttttaa cactataaat agccatgaag gcccatttcc tccctttgca   960
aaaagtatac ccaaacgcaa ctccgtcttc acctccaact ccaacttcat aatttcaatt    1020
aaagtgaaaa ttatttaag agaccatttg gacatgataa ttttttcact ttttccgaac     1080
ttttttttac tttttttcaa atcagtgttt ggccataaaa ttttcatttt tcacttgaag    1140
ttgaattttt gaattttcg agaattcgaa aaacccagaa aagctgttt tcaaaatttt       1200 cactcggatc ctcacaaaac ttccaaaata acccaaaatt atattcatgt ccaacacaac    1260 tctaatttc aaataccatt ttcacttgaa aagaaattc accttttttt ttttttgaa        1320 ctttacaatt cttatgtcca aacgccccct tcgaatctac ggccaacgtt tattaagtaa    1380
ggaaagaaaa atggctataa taattatatc cctttttgaag taaatataat tctaccaaat   1440
taattaatat gcttaaaaac aataaaaata atcaaaattg ctagagagga caaccaatta    1500
gccgaagcat tgtcaagatt gagcagggcg cagaatgaag aaagtagttt tttatctttt   1560
gatgccctac gccttttgta ttaaaatact atatacaaga tttgaaaaag acgagttcca    1620
ttcaaaacag ttcccttgtc ccgaaatgtt cattgatgaa gtaatatgca cttttaaaat    1680
tatttttttc cagtttatcc taaaaaaaat attattttta taatcacata gaataatat     1740 atatcaaata acaaagggaa aaagaaagta gggaagaaa ataataattg aagtgggctg     1800
ggctttgaca tggaaggaa tggcttagta ataattgaag ttagcatcgg atctatttga    1860
agtgccactc atccctcaga aaaacagtgt tagtattttc tctcacaaat tgattctgtg    1920
gtccgaattg gagttcctaa atc                                             1943
```

<210> SEQ ID NO 18
<211> LENGTH: 690
<212> TYPE: DNA
<213> ORGANISM: Arabidopsis thaliana

<400> SEQUENCE: 18

```
ttcgttgaaa aatcatcgaa attttcgacg gattccaatg atcaaaaatt cgtcaataat    60
ttccaacgat attctgacta aactaaatct gatgaaatat ttttgacggc tttccaacca   120
aaatatttcg ttgtgacttg tcaaaaatcc gttagaatac taagcaactt tcgacagat   180 tttcagcaaa aatattcggt aatataacgt gttaaaaata tgataaaaaa aaaaacttga   240
tgaatctact aaaactaaat tttcaatcat atatatctat tattcatata tttcattcat   300
tttattattt ttctcttaac aattatttag ttattctggt atcgtgtaat tatattcata   360
```

```
tgatttattc tgatattgat tcggttagca tccggataaa tctgggttgg gcttttaac      420 ttggtttttc taagaaaaat tctaatatga tttggttagc atccggatta gtctagtttg      480
gtaggcctgc ctttgtgatt cttaactcgg tcttttgtat gggtttgaac aattactaca      540
ccatttagat tcttctgacc catatcaaat aaagatccac ttaggcccat tagggttaga      600
acaaacatga ggttgcagaa taaaaagggt tcattttcct cactctcaag ttggatctca      660
aaaccctaat atctgaactt cgccgtcgag                                        690
```

<210> SEQ ID NO 19
<211> LENGTH: 995
<212> TYPE: DNA
<213> ORGANISM: Arabidopsis thaliana

<400> SEQUENCE: 19

```
ttctgttcgt atatttgtaa ctattatgtg tattttatt ttgttagtat tactaattca       60
agtggtttaa gttgttgaga ctctttaaaa tctaagcatt ttataaacaa taatatataa      120
ttattgttta ggctaaattt gtcactaatt aaggtttgga tacatagtgt ctaaactaag      180
ctaataatat cacttaacgt ttacttgtaa cgctaggtga tgatgtcgtc aagtcaattg      240
gtacaaggaa taaacgagtg gtcatatgac attatgacca tatgaattca aactccagta      300
atccaatggt aattggattc aatgatcaag acttgaacca cgtaatccac ccttatcctt      360
agaagctcat aaatatcact aaagggacag gcaacactta accagtagtt gtccaataat      420
ttagttttcc aaaatgaaaa attattgttg tcatctattt taggtgtttt agttcaatgt      480
ggattcctcg tcctaacaaa tacttgacga atatatctag actataaaat tggttatgag      540
ttctactttt ttttgtttgt gaaattatca aaatttgtta tatttattta tttattctca      600
ttaatttgag tactaatttt taaatatttt atactaaaaa caattactaa gatacaaaaa      660
tggataagag catggtgtat agatatttaa tgggatagaa tatttcccat aattgtatgt      720
gtgtgagagg ttttgttttc gtaaggaaag aaacaaaaac catttgacca agaaaagca      780 aagaaggca aggaatcaaa caacaaatgt tgcaaggcag aataatggga cgttatgtta      840
atgtagtgtc gtcacacgtg acttaaaaga gacgagtctg cgtgtcaaac taaaaatgta      900
tgcaactata aaaatgggat ttgattatct ttttagtacc gaagcctacc aaccacatgc      960
acactaattc tactcgccaa ataaagtgaa aagag                                  995
```

<210> SEQ ID NO 20
<211> LENGTH: 1017
<212> TYPE: DNA
<213> ORGANISM: Arabidopsis thaliana

<400> SEQUENCE: 20

```
aagtaacttt tagaattgat tcaatctttt tagaatagat ttttttttt tttttttttg       60 gatttcgctg aggttttacc attttgttac tcagcatatt ttaacgatgt tgcatttgtg      120
tcccatatac gttattgtta gtgaaaaata taatgtaaga ataatttata taactatcct      180
actagcaaag ctaacgcaaa ttttgaactc gaactttagt taccgtgaat gaaaataaca      240
gacttgaact ttataatact cgtagtatac gtaattttg cttttttgcag atatgcttgc      300 cactaataaa gtcataaatt ttatattttc ataactata gttatacact tttgactaaa      360
caaacaaaat cggtttagca aaagaaaaag ttacttttct gatgaactag gataggaat      420 tcggaactga attttgctac gttctctctg gaccacacac actgaacacc cttttaagat      480
tttctccttc tcttttttcaa cgtaatttat cttttgatca gaaacgacaa aaaagaagtc      540
```

```
taacaatatc aaacaatttt tttatagata ttttttagata ttttttcctgc taattttatc    600 tagtgtagac aaacccaaat atacgattat tataaaaaca cgaaatacca agtggacgac    660
tgaggttaat agatctagcc gtagaataaa gatctgcatg aaaggcggtg agaatctaaa    720
cggtgataag accataacac acggaacatc ggtacgctct cgaacgtaca agaatcgacg    780
acacacaaac actccacaat tatttgaaca ctggacaatt attgaaccga cgtacgagaa    840
tcaatgcgct gagggtaaag acgtaaatga agaactagtt ttggagataa gagcggagaa    900
agattgcgac acatgtatgg tcaatattaa tctcatttag cttataaatt tgggagcttc    960
ctctatcatt aattttcatt cataaatttt tcttcaatttt gaattttctc gagaaaa       1017

<210> SEQ ID NO 21
<211> LENGTH: 273
<212> TYPE: DNA
<213> ORGANISM: Arabidopsis thaliana

<400> SEQUENCE: 21
gcaagtgtgt tgcctttgtg tggaaatgaa gaggtacttg cgaggacttt gcgtttatca     60
gtttatgtgt ttgtatatct atttgatcca gttattatgg attatatacg cttgaaactc    120
attttaagcc attgttattg aacgtttatc aaatacttta ttatgccaag caagtcaaac    180
acatgcttgt tgattgaaat caagctatag aaatctcttc ttcacataca gcagtttaga    240
ttcacaatac aacaagcgaa acgataaagt ttc                                 273

<210> SEQ ID NO 22
<211> LENGTH: 1131
<212> TYPE: DNA
<213> ORGANISM: Arabidopsis thaliana

<400> SEQUENCE: 22
gtccgtcgct tctcttccat ttcttctcat tttcgatttt gattcttatt tctttccagt     60
agctcctgct ctgtgaattt ctccgctcac gatagatctg cttatactcc ttacattcaa    120
ccttagatct ggtctcgatt ctctgtttct ctgttttttt cttttggtcg agaatctgat    180
gtttgtttat gttctgtcac cattaataat aatgaactct ctcattcata caatgattag    240
tttctctcgt ctacaaaacg atatgttgca ttttcacttt tcttcttttt ttctaagatg    300
atttgctttg accaatttgt ttagatcttt attttatttt attttctggt gggttggtgg    360
aaattgaaaa aaaaaaaaac agcataaatt gttatttgtt aatgtattca ttttttggct    420
atttgttctg ggtaaaaatc tgcttctact attgaatctt tcctggatttt tttactccta    480 ttgggttttt atagtaaaaa tacataataa aaggaaaaca aaagttttat agattctctt    540
aaacccctta cgataaaagt tggaatcaaa ataattcagg atcagatgct ctttgattga    600
ttcagatgcg attacagttg catggcaaat tttctagatc cgtcgtcaca ttttattttc    660
tgtttaaata tctaaatctg atatatgatg tcgacaaatt ctggtggctt atacatcact    720
tcaactgttt tcttttggct tgtttgtca acttggtttt caatacgatt tgtgatttcg    780
atcgctgaat ttttaataca agcaaactga tgttaaccac aagcaagaga tgtgacctgc    840
cttattaaca tcgtattact tactactagt cgtattctca acgcaatcgt ttttgtattt    900
ctcacattat gccgcttctc tactctttat tccttttggt ccacgcattt tctatttgtg    960
gcaatccctt tcacaacctg atttcccact ttggatcatt tgtctgaaga ctctcttgaa   1020
tcgttaccac ttgtttcttg tgcatgctct gttttttaga attaatgata aaactattcc   1080
```
atagtcttga gttttcagct tgttgattct tttgcttttg gttttctgca g       1131

<210> SEQ ID NO 23
<211> LENGTH: 5688
<212> TYPE: DNA
<213> ORGANISM: Artificial Sequence
<220> FEATURE:
<223> OTHER INFORMATION: Artificially created chimeric nucleic acid
      sequence

<400> SEQUENCE: 23

```
ctcgaggatc taaattgtga gttcaatctc ttccctattg gattgattat cctttctttt     60
cttccaattt gtgtttcttt tgcctaatt tattgtgtta tccccttat cctattttgt    120
ttctttactt atttatttgc ttctatgtct ttgtacaaag atttaaactc tatggcacat    180
atttttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaatttta atgctttatt agttttaaac ttactatata aatttttcat atgtaaaatt   1200
taatcggtat agttcgatat ttttttcaatt tattttttata aaataaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
aaactagaaa aaacagcgtc aaaactagca aaaatccaac ggacaaaaaa atcggctgaa   1620
tttgatttgg ttccaacatt taaaaaagtt tcagtgagaa agaatcggtg actgttgatg   1680
atataaacaa agggcacatt ggtcaataac cataaaaaat tatatgacag ctacagttgg   1740
tagcatgtgc tcagctattg aacaaatcta agaaggtac atctgtaacc ggaacaccac   1800
ttaaatgact aaaattaccct catcagaaag cagatggagt gctacaaata acacactatt   1860
caacaaccat aaataaaacg tgttcagcta ctaaaacaaa tataaataaa tctatgtttg   1920
taagcactcc agccatgtta atggagtgct attgcctgtt aactctcact tataaaatag   1980
```

```
tagtagaaaa aatatgaacc aaaacacaac aacatctcaa aatatttgaa gtaacacaga    2040
attttacata caccaaactt ataaatcaag tattttcatt gtaacaaatt ccatgaaaca    2100
tgaaaacaaa gctataatga aattaccaac tcaagcaata aggttggaaa agagccatct    2160
gagatattcc agcaatttac atcttttttgt ttgattacac agtgaaggat cttttgtttg   2220
acaactagta aaatgattct tatttgcacc tttcagctat tcagctgctt ttactccaac    2280
cctatagcag aagtaatggc gctcatgctc gttttgtacg ccttccaact tcaagggcga    2340
gctctgtatc gatcttcagg gaaatgtcaa gtgctttcac ggaatgcgtc agggcaccac    2400
tagaaatgta ggtaacacca gtttgtccaa tcttgtgtac tgtttcaagg gtaacatttc    2460
ctgaagcctc cgtatcaaac ctcccattga tcaattctac agcctcctta agcatggata    2520
catcaatatc tccgttagat aatggaacaa ccatattgtc cagcattatc ctagtcaacg    2580
aagtctttgt ttgagatgca tagtctagaa cctcacgtac ttcttcaatt gtcctggttt    2640
caacctcaac ccctatttga agtttatttt gctccaaata ctgatccaca gattttagag    2700 cttttgccgac acctccagca gcagatatgt gattgtcttt tatcattacc atatcaaata   2760
agcccattct gtgattcttc cccccaccga tcaataccgc ccatttatcc accaaacgta    2820
atccaggagc agttttccta gtctccaaga tgtaagcagg gtgtgcagca tctgccattt    2880
ccttagttag tgtagctatt ccactcattc tttgcataaa attgagaaca accctctcag    2940
ctataacaat gttgtaagcg tttccttgta ctttgccaaa tttcaagcct ttatgaactt    3000
tatcgccatc atttacatac cactccacct ttaatgaagg atcaacttcc gcgaatatca    3060
tctcagcaag tgcaattcct gctatgatcc cgtcttcctt tgctagaaaa tgagcatcgg    3120
attccatatc aagaggaatt gtcgccttac aagtcacatc tcctaaattc ccagcatctt    3180
cagagagtgc aagtttcata acttccttta aatcataagt tgggtgtgct ggtggtttca    3240
cctctaatga ctccactctt gtattcttgg tggctattgc tgacattttc accaccaacc    3300
ttggagctgt aattgcataa ggatgcactg tagcagtgaa aggaatagct ctaaacatgg    3360
tttttttttg ggggggttgt gaaatgaatt ttgtggaaaa tagttttttgg ggcacatcaa   3420 tcctgcggtg acattcggaa tgtttctaac aagaaagata tcgttggtcc gagccttgct    3480
ctacatcata gctcagtgca taggggccct gtgcgggtgc gccttagtca agacattgca    3540
gcgagatcat tacaaccact atggcggtgg cgctaaccag ctcgttgatg gttatagccg    3600
aggcactggc cttgctgttg agattatggg caccttttatt cttctgtata ctgtcttctc   3660
cgccactgat cccaaacgca atgctagaga ttcccatgtt cctgtcttgg ctccactccc    3720
cattggcttt gctgtcttca ttgttcacct cgccaccatt cccgtcaccg gcactggcat    3780
caacccagcg agcaaaaact attttccaca aaattcattt cacaaccccc ccaaaaaaaa    3840
accatgttta gagctattcc tttcactgct acagtgcatc cttatgcaat tacagctcca    3900
aggttggtgg tgaaaatgtc agcaatagcc accaagaata caagagtgga gtcattagag    3960
gtgaaaccac cagcacaccc aacttatgat ttaaaggaag ttatgaaact tgcactctct    4020
gaagatgctg ggaatttagg agatgtgact tgtaaggcga caattcctct tgatatggaa    4080
tccgatgctc attttctagc aaaggaagac gggatcatag caggaattgc acttgctgag    4140
atgatattcg cggaagttga tccttcatta aggtggagt ggtatgtaaa tgatggcgat     4200
aaagttcata aaggcttgaa atttggcaaa gtacaaggaa acgcttacaa cattgttata    4260
gctgagaggg ttgttctcaa ttttatgcaa agaatgagtg gaatagctac actaactaag    4320
gaaatggcag atgctgcaca ccctgcttac atcttggaga ctaggaaaac tgctcctgga    4380
```

```
ttacgtttgg tggataaatg ggcggtattg atcggtgggg ggaagaatca cagaatgggc   4440
ttatttgata tggtaatgat aaaagacaat cacatatctg ctgctggagg tgtcggcaaa   4500
gctctaaaat ctgtggatca gtatttggag caaaataaac ttcaaatagg ggttgaggtt   4560
gaaaccagga caattgaaga agtacgtgag gttctagact atgcatctca aacaaagact   4620
tcgttgacta ggataatgct ggacaatatg gttgttccat tatctaacgg agatattgat   4680
gtatccatgc ttaaggaggc tgtagaattg atcaatggga ggtttgatac ggaggcttca   4740
ggaaatgtta cccttgaaac agtacacaag attggacaaa ctggtgttac ctacatttct   4800
agtggtgccc tgacgcattc cgtgaaagca cttgacattt ccctgaagat cgatacagag   4860
ctcgcccttg aagttggaag gcgtacaaaa cgagcatgag cgccattact tctgctatag   4920
ggttggagta aaagcagctg aatagctgaa aggtgcaaat aagaatcatt ttactagttg   4980
tcaaacaaaa gatccttcac tgtgtaatca acaaaaaga tgtaaattgc tggaatatct   5040
cagatggctc ttttccaacc ttattgcttg agttggtaat ttcattatag ctttgttttc   5100
atgtttcatg gaatttgtta caatgaaaat acttgattta aagtttggt gtatgtaaaa    5160 ttctgtgtta cttcaaatat tttgagatgt tgagctcgtg aaatggcctc tttagttttt   5220
gattgaatca tagggtatt agttttctat ggccgggagt ggtcttcttg cttaattgta    5280
atggaataac cagagaggaa ctactgtgtt atctttgagg aatgtgggc ttttttcgtt    5340 tgaattatca tgaatgaaat tttactttt cccaatacaa gtttgtttc gtttcttggt     5400 ttttgttatc ccttggttta tgtcttggtt tggcttaaat gattgaagat tacactacct   5460
atgtttctgc tattcctgtt gaagatcaca tttgataata atgcatcgaa tgcattaaag   5520
tttcttattg gctctgtcaa aagtattgaa ggtggatttt tctaattggc aagagaaagt   5580 attaagagg tgatttatta gtacttatat ttttctcagc atctctcttt cagtgttgga    5640
gcttcataaa attagcactt cagagtttca gtcgggagct gaattcga                5688
```

```
<210> SEQ ID NO 24
<211> LENGTH: 4134
<212> TYPE: DNA
<213> ORGANISM: Artificial Sequence
<220> FEATURE:
<223> OTHER INFORMATION: Artificially created chimeric nucleic acid
      sequence

<400> SEQUENCE: 24
```

```
ctcgaggatc taaattgtga gttcaatctc ttccctattg gattgattat cctttctttt     60
cttccaattt gtgtttcttt ttgcctaatt tattgtgtta tcccctttat cctatttgt     120 ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420 aattttatt agtaataaag attctatata gctgttatag agggataatt ttacaaagaa     480
cactataaat atgattgttg ttgttagggt gtcaatggtt cggttcgact ggttatttta    540
taaaatttgt accataccat tttttcgat attctatttt gtataaccaa aattagactt     600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
```

```
cttttatagg acttagcaaa agctctctag acatttttac tgtttaaagg ataatgaatt      780
aaaaaacatg aaagatggct agagtataga tacacaacta ttcgacagca acgtaaaaga      840
aaccaagtaa aagcaaagaa aatataaatc acacgagtgg aaagatatta accaagttgg      900
gattcaagaa taaagtctat attaaatatt caaaaagata aatttaaata atatgaaagg      960
aaacatattc aatacattgt agtttgctac tcataatcgc tagaatactt tgtgccttgc     1020
taataaagat acttgaaata gcttagttta aatataaata gcataataga ttttaggaat     1080
tagtattttg agtttaatta cttattgact tgtaacagtt tttataattc caaggcccat     1140
gaaaaattta atgctttatt agttttaaac ttactatata aattttttcat atgtaaaatt     1200 taatcggtat agttcgatat ttttttcaatt tatttttata aaataaaaaa cttaccctaa     1260
ttatcggtac agttatagat ttatataaaa atctacggtt cttcagaaga aacctaaaaa     1320
tcggttcggt gcggacggtt cgatcggttt agtcgatttt caaatattca ttgacactcc     1380
tagttgttgt tataggtaaa aagcagttac agagaggtaa aatataactt aaaaaatcag     1440
ttctaaggaa aaattgactt ttatagtaaa tgactgttat ataaggatgt tgttacagag     1500
aggtatgagt gtagttggta aattatgttc ttgacggtgt atgtcacata ttatttatta     1560
aaactagaaa aaacagcgtc aaaactagca aaaatccaac ggacaaaaaa atcggctgaa     1620
tttgatttgg ttccaacatt taaaaaagtt tcagtgagaa agaatcggtg actgttgatg     1680
atataaacaa agggcacatt ggtcaataac cataaaaaat tatatgacag ctacagttgg     1740
tagcatgtgc tcagctattg aacaaatcta agaaggtac atctgtaacc ggaacaccac     1800
ttaaatgact aaattaccct catcagaaag cagatggagt gctacaaata acacactatt     1860
caacaaccat aaataaaacg tgttcagcta ctaaaacaaa tataaataaa tctatgtttg     1920
taagcactcc agccatgtta atggagtgct attgcctgtt aactctcact tataaaatag     1980
tagtagaaaa aatatgaacc aaaacacaac tttatcgcca tcatttacat accactccac     2040
ctttaatgaa ggatcaactt ccgcgaatat catctcagca agtgcaattc ctgctatgat     2100
cccgtcttcc tttgctagaa aatgagcatc ggattccata tcaagaggaa ttgtcgcctt     2160
acaagtcaca tctcctaaat tcccagcatc ttcagagagt gcaagtttca taacttcctt     2220
taaatcataa gttgggtgtg ctggtggttt cacctctaat gactccactc ttgtattctt     2280
ggtggctatt gctgacattt tcaccaccaa ccttggagct gtaattgcat aaggatgcac     2340
tgtagcagtg aaaggaatag ctctaaacat gtccgtcgct tctcttccat ttcttctcat     2400
tttcgatttt gattcttatt tctttccagt agctcctgct ctgtgaattt ctccgctcac     2460
gatagatctg cttatactcc ttacattcaa ccttagatct ggtctcgatt ctctgtttct     2520 ctgtttttt cttttggtcg agaatctgat gtttgtttat gttctgtcac cattaataat     2580
aatgaactct ctcattcata caatgattag tttctctcgt ctacaaaacg atatgttgca     2640
ttttcacttt tcttcttttt ttctaagatg atttgctttg accaatttgt ttagatcttt     2700
attttatttt attttctggt gggttggtgg aaattgaaaa aaaaaaaaac agcataaatt     2760
gttatttgtt aatgtattca ttttttggct atttgttctg ggtaaaaatc tgcttctact     2820
attgaatctt tcctggattt tttactccta ttgggttttt atagtaaaaa tacataataa     2880
aaggaaaaca aaagttttat agattctctt aaacccctta cgataaaagt tggaatcaaa     2940
ataattcagg atcagatgct ctttgattga ttcagatgcg attacagttg catggcaaat     3000
tttctagatc cgtcgtcaca ttttattttc tgtttaaata tctaaatctg atatatgatg     3060
```

-continued

| | |
|---|---|
| tcgacaaatt ctggtggctt atacatcact tcaactgttt tcttttggct ttgtttgtca | 3120 |
| acttggtttt caatacgatt tgtgatttcg atcgctgaat ttttaataca agcaaactga | 3180 |
| tgttaaccac aagcaagaga tgtgacctgc cttattaaca tcgtattact tactactagt | 3240 |
| cgtattctca acgcaatcgt ttttgtattt ctcacattat gccgcttctc tactcttat | 3300 |
| tccttttggt ccacgcattt tctatttgtg gcaatccctt tcacaacctg atttcccact | 3360 |
| ttggatcatt tgtctgaaga ctctcttgaa tcgttaccac ttgtttcttg tgcatgctct | 3420 |
| gtttttaga attaatgata aaactattcc atagtcttga gttttcagct tgttgattct | 3480 |
| tttgcttttg gttttctgca gatgtttaga gctattcctt tcactgctac agtgcatcct | 3540 |
| tatgcaatta cagctccaag gttggtggtg aaaatgtcag caatagccac caagaataca | 3600 |
| agagtggagt cattagaggt gaaaccacca gcacacccaa cttatgattt aaaggaagtt | 3660 |
| atgaaacttg cactctctga agatgctggg aatttaggag atgtgacttg taaggcgaca | 3720 |
| attcctcttg atatggaatc cgatgctcat tttctagcaa aggaagacgg gatcatagca | 3780 |
| ggaattgcac ttgctgagat gatattcgcg gaagttgatc cttcattaaa ggtggagtgg | 3840 |
| tatgtaaatg atggcgataa agcaagtgtg ttgccttgt gtggaaatga agaggtactt | 3900 |
| gcgaggactt tgcgtttatc agtttatgtg tttgtatatc tatttgatcc agttattatg | 3960 |
| gattatatac gcttgaaact cattttaagc cattgttatt gaacgtttat caaatacttt | 4020 |
| attatgccaa gcaagtcaaa cacatgcttg ttgattgaaa tcaagctata gaaatctctt | 4080 |
| cttcacatac agcagtttag attcacaata caacaagcga aacgataaag tttc | 4134 |

<210> SEQ ID NO 25
<211> LENGTH: 3896
<212> TYPE: DNA
<213> ORGANISM: Artificial Sequence
<220> FEATURE:
<223> OTHER INFORMATION: Artificially created chimeric nucleic acid sequence

<400> SEQUENCE: 25

| | |
|---|---|
| ctcgaggatc taaattgtga gttcaatctc ttccctattg gattgattat cctttctttt | 60 |
| cttccaattt gtgtttcttt ttgcctaatt tattgtgtta tccccttat cctatttgt | 120 |
| ttctttactt atttatttgc ttctatgtct ttgtacaaag atttaaactc tatgcacat | 180 |
| atttaaagt tgttagaaaa taattcttt caagattgat gaaagaactt tttaattgta | 240 |
| gatatttcgt agatttatt ctcttactac caatataacg cttgaattga cgaaaatttg | 300 |
| tgtccaaata tctagcaaaa aggtatccaa tgaaaatata tcatatgtga tcttcaaatc | 360 |
| ttgtgtctta tgcaagattg atactttgtt caatggaaga gattgtgtgc atatttttaa | 420 |
| aattttatt agtaataaag attctatata gctgttatag agggataatt ttacaaagaa | 480 |
| cactataaat atgattgttg ttgttagggt gtcaatggtt cggttcgact ggttatttta | 540 |
| taaaatttgt accataccat ttttttcgat attctatttt gtataaccaa aattagactt | 600 |
| ttcgaaatcg tcccaatcat gtcggtttca cttcggtatc ggtaccgttc ggttaatttt | 660 |
| catttttttt taaatgtcat taaaattcac tagtaaaaat agaatgcaat aacatacgtt | 720 |
| cttttatagg acttagcaaa agctctctag acattttac tgtttaaagg ataatgaatt | 780 |
| aaaaaacatg aaagatggct agagtataga tacacaacta ttcgacagca acgtaaaaga | 840 |
| aaccaagtaa aagcaaagaa aatataaatc acacgagtgg aaagatatta accaagttgg | 900 |
| gattcaagaa taaagtctat attaaatatt caaaagata aatttaaata atatgaaagg | 960 |

-continued

```
aaacatattc aatacattgt agtttgctac tcataatcgc tagaatactt tgtgccttgc    1020
taataaagat acttgaaata gcttagttta aatataaata gcataataga ttttaggaat    1080
tagtattttg agtttaatta cttattgact tgtaacagtt tttataattc caaggcccat    1140
gaaaaattta atgctttatt agttttaaac ttactatata aattttttcat atgtaaaatt    1200 taatcggtat agttcgatat ttttcaatt tattttata aaataaaaaa cttaccctaa     1260
ttatcggtac agttatagat ttatataaaa atctacggtt cttcagaaga aacctaaaaa    1320
tcggttcggt gcggacggtt cgatcggttt agtcgatttt caaatattca ttgacactcc    1380
tagttgttgt tataggtaaa aagcagttac agagaggtaa aatataactt aaaaaatcag    1440
ttctaaggaa aaattgactt ttatagtaaa tgactgttat ataaggatgt tgttacagag    1500
aggtatgagt gtagttggta aattatgttc ttgacggtgt atgtcacata ttatttatta    1560
aaactagaaa aaacagcgtc aaaactagca aaaatccaac ggacaaaaaa atcggctgaa    1620
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta agaaggtac atctgtaacc ggaacaccac    1800
ttaaatgact aaattaccct catcagaaag cagatggagt gctacaaata acacactatt    1860
caacaaccat aaataaaacg tgttcagcta ctaaaacaaa tataaataaa tctatgtttg    1920
taagcactcc agccatgtta atggagtgct attgcctgtt aactctcact tataaaatag    1980
tagtagaaaa aatatgaacc aaaacacaac cgattcaaaa cttcagcagg aaaatttata    2040
ttaaagtacg aaacaccaca gagaaagaat tttacaatga ttgtgaattg gaaattatga    2100
taattactgc agaattctcc tacaatacgt cgcatttcac ttatttattc acttgattaa    2160
gactcgatct tggtccaatg attgtactac cagtgttcat tattcacttg attaagactc    2220
gatcatactt ctggcgaaag atggtaaaat ggtccgtcgc ttctcttcca tttcttctca    2280
ttttcgattt tgattcttat ttcttttccag tagctcctgc tctgtgaatt tctccgctca    2340
cgatagatct gcttatactc cttacattca accttagatc tggtctcgat tctctgtttc    2400
tctgtttttt tcttttggtc gagaatctga tgtttgttta tgttctgtca ccattaataa    2460
taatgaactc tctcattcat acaatgatta gtttctctcg tctacaaaac gatatgttgc    2520
attttcactt ttcttctttt tttctaagat gatttgcttt gaccaatttg tttagatctt    2580
tattttattt tattttctgg tgggttggtg gaaattgaaa aaaaaaaaaa cagcataaat    2640
tgttatttgt taatgtattc atttttttggc tatttgttct gggtaaaaat ctgcttctac    2700
tattgaatct ttcctggatt ttttactcct attgggtttt tatagtaaaa atacataata    2760
aaaggaaaac aaaagtttta tagattctct taaaccccctt acgataaaag ttggaatcaa    2820
aataattcag gatcagatgc tctttgattg attcagatgc gattacagtt gcatggcaaa    2880
ttttctagat ccgtcgtcac attttatttt ctgtttaaat atctaaatct gatatatgat    2940
gtcgacaaat tctggtggct tatacatcac ttcaactgtt ttcttttggc tttgtttgtc    3000
aacttggttt tcaatacgat ttgtgatttc gatcgctgaa tttttaatac aagcaaactg    3060
atgttaacca caagcaagag atgtgacctg ccttattaac atcgtattac ttactactag    3120
tcgtattctc aacgcaatcg ttttttgtatt tctcacatta tgccgcttct ctactcttta    3180
ttccttttgg tccacgcatt ttctatttgt ggcaatccct ttcacaacct gatttcccac    3240
tttggatcat ttgtctgaag actctcttga atcgttacca cttgtttctt gtgcatgctc    3300
tgttttttag aattaatgat aaaactattc catagtcttg agtttcagc ttgttgattc    3360
```

-continued

| | |
|---|---|
| ttttgctttt ggttttctgc agcattttac catctttcgc cagaagtatg atcgagtctt | 3420 |
| aatcaagtga ataatgaaca ctggtagtac aatcattgga ccaagatcga gtcttaatca | 3480 |
| agtgaataaa taagtgaaat gcgacgtatt gtaggagaat tctgcagtaa ttatcataat | 3540 |
| ttccaattca caatcattgt aaaattcttt ctctgtggtg tttcgtactt taatataaat | 3600 |
| tttcctgctg aagttttgaa tcggcaagtg tgttgccttt gtgtggaaat gaagaggtac | 3660 |
| ttgcgaggac tttgcgttta tcagtttatg tgtttgtata tctatttgat ccagttatta | 3720 |
| tggattatat acgcttgaaa ctcatttaa gccattgtta ttgaacgttt atcaaatact | 3780 |
| ttattatgcc aagcaagtca aacacatgct tgttgattga aatcaagcta tagaaatctc | 3840 |
| ttcttcacat acagcagttt agattcacaa tacaacaagc gaaacgataa agtttc | 3896 |

<210> SEQ ID NO 26
<211> LENGTH: 4670
<212> TYPE: DNA
<213> ORGANISM: Artificial Sequence
<220> FEATURE:
<223> OTHER INFORMATION: Artificially created chimeric nucleic acid
      sequence

<400> SEQUENCE: 26

| | |
|---|---|
| ctcgaggatc taaattgtga gttcaatctc ttccctattg gattgattat cctttctttt | 60 |
| cttccaattt gtgtttcttt ttgcctaatt tattgtgtta tccccttat cctattttgt | 120 |
| ttctttactt atttatttgc ttctatgtct ttgtacaaag atttaaactc tatggcacat | 180 |
| atttaaagt tgttagaaaa taattcttt caagattgat gaaagaactt tttaattgta | 240 |
| gatatttcgt agattttatt ctcttactac caatataacg cttgaattga cgaaaatttg | 300 |
| tgtccaaata tctagcaaaa aggtatccaa tgaaaatata tcatatgtga tcttcaaatc | 360 |
| ttgtgtctta tgcaagattg atactttgtt caatggaaga gattgtgtgc atatttttaa | 420 |
| aattttatt agtaataaag attctatata gctgttatag agggataatt ttacaaagaa | 480 |
| cactataaat atgattgttg ttgttagggt gtcaatggtt cggttcgact ggttatttta | 540 |
| taaaatttgt accataccat tttttcgat attctatttt gtataaccaa aattagactt | 600 |
| ttcgaaatcg tcccaatcat gtcggtttca cttcggtatc ggtaccgttc ggttaatttt | 660 |
| cattttttt taaatgtcat taaaattcac tagtaaaaat agaatgcaat aacatacgtt | 720 |
| cttttatagg acttagcaaa agctctctag acattttac tgtttaaagg ataatgaatt | 780 |
| aaaaaacatg aaagatggct agagtataga tacacaacta ttcgacagca acgtaaaaga | 840 |
| aaccaagtaa aagcaaagaa aatataaatc acacgagtgg aaagatatta accaagttgg | 900 |
| gattcaagaa taaagtctat attaaatatt caaaaagata aatttaaata atatgaaagg | 960 |
| aaacatattc aatacattgt agtttgctac tcataatcgc tagaatactt tgtgccttgc | 1020 |
| taataaagat acttgaaata gcttagttta aatataaata gcataataga ttttaggaat | 1080 |
| tagtattttg agtttaatta cttattgact tgtaacagtt tttataattc caaggcccat | 1140 |
| gaaaaattta atgctttatt agttttaaac ttactatata aattttcat atgtaaaatt | 1200 |
| taatcggtat agttcgatat ttttttcaatt tattttata aataaaaaa cttaccctaa | 1260 |
| ttatcggtac agttatagat ttatataaaa atctacggtt cttcagaaga aacctaaaaa | 1320 |
| tcggttcggt gcggacggtt cgatcggttt agtcgatttt caaatattca ttgacactcc | 1380 |
| tagttgttgt tataggtaaa aagcagttac agagaggtaa aatataactt aaaaaatcag | 1440 |
| ttctaaggaa aaattgactt ttatagtaaa tgactgttat ataaggatgt tgttacagag | 1500 |

```
aggtatgagt gtagttggta aattatgttc ttgacggtgt atgtcacata ttatttatta    1560
aaactagaaa aaacagcgtc aaaactagca aaaatccaac ggacaaaaaa atcggctgaa    1620
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta agaaggtac atctgtaacc ggaacaccac     1800
ttaaatgact aaattaccct catcagaaag cagatggagt gctacaaata acacactatt    1860
caacaaccat aaataaaacg tgttcagcta ctaaaacaaa tataaataaa tctatgtttg    1920
taagcactcc agccatgtta atggagtgct attgcctgtt aactctcact tataaaatag    1980
tagtagaaaa aatatgaacc aaaacacaac ggttgtgtat ttcacttttg gatatagctc    2040
agtggcttcg acacctgtag gaggctgaac ctcaaagttt gcagaatctc cattaacaaa    2100
aactgaatgg catatggcca aattagtcct taatggcaga ggtccctctt gtacaatctg    2160
gagaatatct tcctctgata gataaacttc tcgagggtc ttcccaattt tgtcctccca     2220
caaggacact atctcgttga aggatagaat attggcaggt ggtctcatgt gaagagtctt    2280
attcaatgtc cgtggatcat ctactgcttc gatagtgtat gtcgctatgt cttcttcctt    2340
cacatatatt gctttgggat ttccatcgcc aaaaatgaca actttgtctc taggaggggt    2400
tttggcctct aactgcccca agttgggcaa gaagaaatct gcaaaccaat tgcagattac    2460
atatgtgtat ggaattcctt ctgcctctat catcctcctg attcttacct ttagagcgaa    2520
gagtgatgca gctggttcaa ttgcacgagc atgatccaca tcaaatccaa attctgaagg    2580
aagaaatctc ttgatatttc cagcttcttt aattgctttg atgatgttca cttgatcagt    2640
ccgtcgcttc tcttccattt cttctcattt tcgattttga ttcttatttc tttccagtag    2700
ctcctgctct gtgaatttct ccgctcacga tagatctgct tatactcctt acattcaacc    2760
ttagatctgg tctcgattct ctgtttctct gttttttct tttggtcgag aatctgatgt     2820
ttgtttatgt tctgtcacca ttaataataa tgaactctct cattcataca atgattagtt    2880
tctctcgtct acaaaacgat atgttgcatt ttcactttc ttctttttt ctaagatgat      2940 ttgctttgac caatttgttt agatcttat tttattttat tttctggtgg ttggtggaa      3000 attgaaaaaa aaaaaacag cataaattgt tatttgttaa tgtattcatt ttttggctat     3060
ttgttctggg taaaaatctg cttctactat tgaatctttc ctggattttt tactcctatt    3120
gggtttttat agtaaaaata cataataaaa ggaaaacaaa agttttatag attctcttaa    3180
accccttacg ataaagttg gaatcaaaat aattcaggat cagatgctct ttgattgatt     3240
cagatgcgat tacagttgca tggcaaattt tctagatccg tcgtcacatt ttattttctg    3300
tttaaatatc taaatctgat atatgatgtc gacaaattct ggtggcttat acatcacttc    3360
aactgttttc ttttggcttt gtttgtcaac ttggttttca atacgatttg tgatttcgat    3420
cgctgaattt ttaatacaag caaactgatg ttaaccacaa gcaagagatg tgacctgcct    3480
tattaacatc gtattactta ctactagtcg tattctcaac gcaatcgttt tgtatttct     3540 cacattatgc cgcttctcta ctctttattc cttttggtcc acgcattttc tatttgtggc    3600
aatccctttc acaacctgat ttcccacttt ggatcatttg tctgaagact ctcttgaatc    3660
gttaccactt gtttcttgtg catgctctgt tttttagaat taatgataaa actattccat    3720
agtcttgagt tttcagcttg ttgattcttt tgcttttggt tttctgcagt gatcaagtga    3780
acatcatcaa agcaattaaa gaagctggaa atatcaagag atttcttcct tcagaatttg    3840
```

```
gatttgatgt ggatcatgct cgtgcaattg aaccagctgc atcactcttc gctctaaagg     3900
taagaatcag gaggatgata gaggcagaag gaattccata cacatatgta atctgcaatt     3960
ggtttgcaga tttcttcttg cccaacttgg ggcagttaga ggccaaaacc cctcctagag     4020
acaaagttgt catttttggc gatggaaatc ccaaagcaat atatgtgaag gaagaagaca     4080
tagcgacata cactatcgaa gcagtagatg atccacggac attgaataag actcttcaca     4140
tgagaccacc tgccaatatt ctatccttca acgagatagt gtccttgtgg gaggacaaaa     4200
ttgggaagac cctcgagaag ttatatctat cagaggaaga tattctccag attgtacaag     4260
agggacctct gccattaagg actaatttgg ccatatgcca ttcagttttt gttaatggag     4320
attctgcaaa ctttgaggtt cagcctccta caggtgtcga agccactgag ctatatccaa     4380
aagtgaaata cacaaccgca agtgtgttgc ctttgtgtgg aaatgaagag gtacttgcga     4440
ggactttgcg tttatcagtt tatgtgtttg tatatctatt tgatccagtt attatggatt     4500
atatacgctt gaaactcatt ttaagccatt gttattgaac gtttatcaaa tactttatta     4560
tgccaagcaa gtcaaacaca tgcttgttga ttgaaatcaa gctatagaaa tctcttcttc     4620
acatacagca gtttagattc acaatacaac aagcgaaacg ataaagtttc                4670
```

<210> SEQ ID NO 27
<211> LENGTH: 5390
<212> TYPE: DNA
<213> ORGANISM: Artificial Sequence
<220> FEATURE:
<223> OTHER INFORMATION: Artificially created chimeric nucleic acid
      sequence

<400> SEQUENCE: 27

```
ctcgaggatc taaattgtga gttcaatctc ttccctattg gattgattat cctttctttt       60
cttccaattt gtgtttcttt ttgcctaatt tattgtgtta tcccctttat cctattttgt      120
ttctttactt atttatttgc ttctatgtct ttgtacaaag atttaaactc tatggcacat      180
attttaaagt tgttagaaaa taaattcttt caagattgat gaaagaactt tttaattgta      240
gatatttcgt agattttatt ctcttactac caatataacg cttgaattga cgaaaatttg      300
tgtccaaata tctagcaaaa aggtatccaa tgaaaatata tcatatgtga tcttcaaatc      360
ttgtgtctta tgcaagattg atactttgtt caatggaaga gattgtgtgc atatttttaa      420 aattttatt agtaataaag attctatata gctgttatag agggataatt ttacaaagaa      480
cactataaat atgattgttg ttgttagggt gtcaatggtt cggttcgact ggttatttta      540
taaaatttgt accataccat ttttttcgat attctatttt gtataaccaa aattagactt      600
ttcgaaatcg tcccaatcat gtcggtttca cttcggtatc ggtaccgttc ggttaatttt      660
catttttttt taaatgtcat taaaattcac tagtaaaaat agaatgcaat aacatacgtt      720
cttttatagg acttagcaaa agctctctag acatttttac tgtttaaagg ataatgaatt      780
aaaaaacatg aaagatggct agagtataga tacacaacta ttcgacagca acgtaaaaga      840
aaccaagtaa aagcaaagaa aatataaatc acacgagtgg aaagatatta accaagttgg      900
gattcaagaa taaagtctat attaaatatt caaaaagata aatttaaata atatgaaagg      960
aaacatattc aatacattgt agtttgctac tcataatcgc tagaatactt tgtgccttgc     1020
taataaagat acttgaaata gcttagttta aatataaata gcataataga tttaggaat     1080 tagtattttg agtttaatta cttattgact tgtaacagtt tttataattc caaggcccat     1140
gaaaaattta atgctttatt agtttaaaac ttactatata aatttttcat atgtaaaatt     1200
```

```
taatcggtat agttcgatat tttttcaatt tatttttata aaataaaaaa cttaccctaa    1260
ttatcggtac agttatagat ttatataaaa atctacggtt cttcagaaga aacctaaaaa    1320
tcggttcggt gcggacggtt cgatcggttt agtcgatttt caaatattca ttgacactcc    1380
tagttgttgt tataggtaaa aagcagttac agagaggtaa aatataactt aaaaaatcag    1440
ttctaaggaa aaattgactt ttatagtaaa tgactgttat ataaggatgt tgttacagag    1500
aggtatgagt gtagttggta aattatgttc ttgacggtgt atgtcacata ttatttatta    1560
aaactagaaa aaacagcgtc aaaactagca aaaatccaac ggacaaaaaa atcggctgaa    1620
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta aagaaggtac atctgtaacc ggaacaccac    1800
ttaaatgact aaattaccct catcagaaag cagatggagt gctacaaata acacactatt    1860
caacaaccat aaataaaacg tgttcagcta ctaaaacaaa tataaataaa tctatgtttg    1920
taagcactcc agccatgtta atggagtgct attgcctgtt aactctcact tataaaatag    1980
tagtagaaaa aatatgaacc aaaacacaac tttatcgcca tcatttacat accactccac    2040
ctttaatgaa ggatcaactt ccgcgaatat catctcagca agtgcaattc ctgctatgat    2100
cccgtcttcc tttgctagaa aatgagcatc ggattccata tcaagaggaa ttgtcgcctt    2160
acaagtcaca tctcctaaat tcccagcatc ttcagagagt gcaagtttca taacttcctt    2220
taaatcataa gttgggtgtg ctggtggttt cacctctaat gactccactc ttgtattctt    2280
ggtggctatt gctgacattt tcaccaccaa ccttggagct gtaattgcat aaggatgcac    2340
tgtagcagtg aaaggaatag ctctaaacat ggttgtgtat ttcacttttg gatatagctc    2400
agtggcttcg acacctgtag gaggctgaac ctcaaagttt gcagaatctc cattaacaaa    2460
aactgaatgg catatggcca aattagtcct taatggcaga ggtccctctt gtacaatctg    2520
gagaatatct tcctctgata gatataactt ctcgagggtc ttcccaattt tgtcctccca    2580
caaggacact atctcgttga aggatagaat attggcaggt ggtctcatgt gaagagtctt    2640
attcaatgtc cgtggatcat ctactgcttc gatagtgtat gtcgctatgt cttcttcctt    2700
cacatatatt gctttgggat ttccatcgcc aaaaatgaca actttgtctc taggaggggt    2760
tttggcctct aactgcccca agttgggcaa gaagaaatct gcaaaccaat tgcagattac    2820
atatgtgtat ggaattcctt ctgcctctat catcctcctg attcttacct ttagagcgaa    2880
gagtgatgca gctggttcaa ttgcacgagc atgatccaca tcaaatccaa attctgaagg    2940
aagaaatctc ttgatatttc cagcttcttt aattgctttg atgatgttca cttgatcagt    3000
ccgtcgcttc tcttccattt cttctcattt tcgattttga ttcttatttc tttccagtag    3060
ctcctgctct gtgaatttct ccgctcacga tagatctgct tatactcctt acattcaacc    3120
ttagatctgg tctcgattct ctgtttctct gttttttttct tttggtcgag aatctgatgt    3180
ttgtttatgt tctgtcacca ttaataataa tgaactctct cattcataca atgattagtt    3240
tctctcgtct acaaaacgat atgttgcatt ttcacttttc ttcttttttt ctaagatgat    3300
ttgctttgac caatttgttt agatcttttat tttatttttat tttctggtgg ttggtggaa    3360
attgaaaaaa aaaaaaacag cataaattgt tatttgttaa tgtattcatt ttttggctat    3420
ttgttctggg taaaaatctg cttctactat tgaatctttc ctggattttt tactcctatt    3480
gggttttttat agtaaaaata cataataaaa ggaaaacaaa agtttatag attctcttaa    3540
accccttacg ataaaagttg gaatcaaaat aattcaggat cagatgctct ttgattgatt    3600
```

```
cagatgcgat tacagttgca tggcaaattt tctagatccg tcgtcacatt ttattttctg   3660
tttaaatatc taaatctgat atatgatgtc gacaaattct ggtggcttat acatcacttc   3720
aactgttttc ttttggcttt gtttgtcaac ttggttttca atacgatttg tgatttcgat   3780
cgctgaattt ttaatacaag caaactgatg ttaaccacaa gcaagagatg tgacctgcct   3840
tattaacatc gtattactta ctactagtcg tattctcaac gcaatcgttt ttgtatttct   3900
cacattatgc cgcttctcta ctctttattc cttttggtcc acgcattttc tatttgtggc   3960
aatccctttc acaacctgat ttcccacttt ggatcatttg tctgaagact ctcttgaatc   4020
gttaccactt gtttcttgtg catgctctgt tttttagaat taatgataaa actattccat   4080
agtcttgagt tttcagcttg ttgattcttt tgcttttggt tttctgcagt gatcaagtga   4140
acatcatcaa agcaattaaa gaagctggaa atatcaagag atttcttcct tcagaatttg   4200
gatttgatgt ggatcatgct cgtgcaattg aaccagctgc atcactcttc gctctaaagg   4260
taagaatcag gaggatgata gaggcagaag gaattccata cacatatgta atctgcaatt   4320
ggtttgcaga tttcttcttg cccaacttgg ggcagttaga ggccaaaacc cctcctagag   4380
acaaagttgt catttttggc gatggaaatc ccaaagcaat atatgtgaag gaagaagaca   4440
tagcgacata cactatcgaa gcagtagatg atccacggac attgaataag actcttcaca   4500
tgagaccacc tgccaatatt ctatccttca acgagatagt gtccttgtgg gaggacaaaa   4560
ttgggaagac cctcgagaag ttatatctat cagaggaaga tattctccag attgtacaag   4620
agggacctct gccattaagg actaatttgg ccatatgcca ttcagttttt gttaatggag   4680
attctgcaaa ctttgaggtt cagcctccta caggtgtcga agccactgag ctatatccaa   4740
aagtgaaata cacaaccatg tttagagcta ttcctttcac tgctacagtg catccttatg   4800
caattacagc tccaaggttg gtggtgaaaa tgtcagcaat agccaccaag aatacaagag   4860
tggagtcatt agaggtgaaa ccaccagcac acccaactta tgatttaaag gaagttatga   4920
aacttgcact ctctgaagat gctgggaatt taggagatgt gacttgtaag gcgacaattc   4980
ctcttgatat ggaatccgat gctcattttc tagcaaagga agacgggatc atagcaggaa   5040
ttgcacttgc tgagatgata ttcgcggaag ttgatccttc attaaaggtg gagtggtatg   5100
taaatgatgg cgataaagca agtgtgttgc ctttgtgtgg aaatgaagag gtacttgcga   5160
ggactttgcg tttatcagtt tatgtgtttg tatatctatt tgatccagtt attatggatt   5220
atatacgctt gaaactcatt ttaagccatt gttattgaac gtttatcaaa tactttatta   5280
tgccaagcaa gtcaaacaca tgcttgttga ttgaaatcaa gctatagaaa tctcttcttc   5340
acatacagca gtttagattc acaatacaac aagcgaaacg ataaagtttc               5390
```

<210> SEQ ID NO 28
<211> LENGTH: 3773
<212> TYPE: DNA
<213> ORGANISM: Artificial Sequence
<220> FEATURE:
<223> OTHER INFORMATION: Artificially created chimeric nucleic acid
      sequence

<400> SEQUENCE: 28

```
gacggtccga tgtgagactt tcaacaaag ggtaatatcc ggaaacctcc tcggattcca     60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga cccccaccca cgaggagcat cgtggaaaaa gaagacgttc caaccacgtc    240
```

```
ttcaaagcaa gtggattgat gtgatggtcc gatgtgagac ttttcaacaa agggtaatat      300
ccggaaacct cctcggattc cattgcccag ctatctgtca ctttattgtg aagatagtgg      360
aaaaggaagg tggctcctac aaatgccatc attgcgataa aggaaaggcc atcgttgaag      420
atgcctctgc cgacagtggt cccaaagatg accccaccc cacgaggagc atcgtggaaa       480
aagaagacgt tccaaccacg tcttcaaagc aagtggattg atgtgatatc tccactgacg      540
taagggatga cgcacaatcc cactatcctt cgcaagaccc ttcctctata aaggaagtt       600 catttcattt ggagaggaat catactcttt tccttccctg gttttaacag tgaaatcact      660
atgcgaacta cgtagaagca ttatcagtgg aggatggagt ctcagggctt cctttatgca      720
tctatagagg acttccatct cggaaggat gtcatgatcg accttattcc catgtttctt      780
catcagattc ttctgttcat ctacgacggc agacatgtac ttgttgttgc agagaaggta      840
tgcccctgcc caagtggagg tgatggaact ggtgtgttgc ccagcgaaaa gagcagcaat      900
cagaagacct gtgatctcag actctgtcgt tgcccgccca tctttgtact ggagtcaat       960 gaagcattgt aacatatcgc tctccgcctt gcctgtacgt tttctagaat ctatgatgtt     1020
tgcaaagatc tccgcgagct tcttgcgggc attgtcacga cggcgatggg ctggaatggg     1080
aaggtaggga agattacac tgataggaag catcccattg tccaggtcat ggaagagagc      1140
agagacatcc tcaaagagtt tattgcgaac ctcttctccc aacagacatc tactagctgt     1200
cagtatgata agatgctcca gttcatactt caagtccact tcaccactat cacccccattt    1260 tgagaagtac tcctcagctt ccatgaccat ctgatccaca tatcccttca atttatttac     1320
cctcaaagat tcagtaaaga acctaaattg ctcttgtctg atagtataat caacgtcaaa     1380
aaccacacca gggccaaaag taggcacatt gaactgataa acctcttgtt gactgagatc     1440
ggtttctggg gccttaaaga aatgggccga cacttctggg ccaacgaaga acgtgatatt     1500
cttgtccgtc gcttctcttc catttcttct cattttcgat tttgattctt attctttcc      1560 agtagctcct gctctgtgaa tttctccgct cacgatagat ctgcttatac tccttacatt     1620
caaccttaga tctggtctcg attctctgtt tctctgtttt tttcttttgg tcgagaatct     1680
gatgtttgtt tatgttctgt caccattaat aataatgaac tctctcattc atacaatgat     1740
tagtttctct cgtctacaaa acgatatgtt gcattttcac ttttcttctt tttttctaag     1800
atgatttgct ttgaccaatt tgtttagatc tttatttat tttattttct ggtgggttgg      1860
tggaaattga aaaaaaaaaa aacagcataa attgttattt gttaatgtat tcattttttg     1920
gctatttgtt ctgggtaaaa atctgcttct actattgaat cttccctgga ttttttactc     1980
ctattgggtt tttatagtaa aaatacataa taaaaggaaa acaaaagttt tatagattct     2040
cttaaacccc ttacgataaa agttggaatc aaaataattc aggatcagat gctctttgat     2100
tgattcagat gcgattacag ttgcatggca aatttctag atccgtcgtc acattttatt      2160
ttctgtttaa atatctaaat ctgatatatg atgtcgacaa attctggtgg cttatacatc     2220
acttcaactg ttttctttg gctttgtttg tcaacttggt tttcaatacg atttgtgatt      2280
tcgatcgctg aattttaat acaagcaaac tgatgttaac cacaagcaag agatgtgacc      2340
tgccttatta acatcgtatt acttactact agtcgtattc tcaacgcaat cgttttgta      2400 tttctcacat tatgccgctt ctctactctt tattccttt ggtccacgca ttttctatt       2460 gtggcaatcc ctttcacaac ctgatttccc actttggatc atttgtctga agactctctt    2520
gaatcgttac cacttgtttc ttgtgcatgc tctgtttttt agaattaatg ataaaactat     2580
```

-continued

```
tccatagtct tgagttttca gcttgttgat tcttttgctt ttggttttct gcagaagaat    2640
atcacgttct tcgttggccc agaagtgtcg gcccatttct ttaaggcccc agaaaccgat    2700
ctcagtcaac aagaggttta tcagttcaat gtgcctactt ttggccctgg tgtggttttt    2760
gacgttgatt atactatcag acaagagcaa tttaggttct ttactgaatc tttgagggta    2820
aataaattga agggatatgt ggatcagatg gtcatggaag ctgaggagta cttctcaaaa    2880
tggggtgata gtggtgaagt ggacttgaag tatgaactgg agcatcttat catactgaca    2940
gctagtagat gtctgttggg agaagaggtt cgcaataaac tctttgagga tgtctctgct    3000
ctcttccatg acctggacaa tgggatgctt cctatcagtg taatctttcc ctaccttccc    3060
attccagccc atcgccgtcg tgacaatgcc cgcaagaagc tcgcggagat ctttgcaaac    3120
atcatagatt ctagaaaacg tacaggcaag gcggagagcg atatgttaca atgcttcatt    3180
gactccaagt acaaagatgg gcgggcaacg acagagtctg agatcacagg tcttctgatt    3240
gctgctcttt tcgctgggca acacaccagt tccatcacct ccacttgggc aggggcatac    3300
cttctctgca acaacaagta catgtctgcc gtcgtagatg aacagaagaa tctgatgaag    3360
aaacatggga ataaggtcga tcatgacatc cttccgaga tggaagtcct ctatagatgc    3420
ataaaggaag ccctgagact ccatcctcca ctgataatgc ttctacgtag ttcgcatagt    3480
gatttcactg ttaaaaccag ggaaggaaaa gagtatgatg atcgttcaaa catttggcaa    3540 taaagttttct taagattgaa tcctgttgcc ggtcttgcga tgattatcat ataatttctg    3600
ttgaattacg ttaagcatgt aataattaac atgtaatgca tgacgttatt tatgagatgg    3660
gtttttatga ttagagtccc gcaattatac atttaatacg cgatagaaaa caaaatatag    3720 cgcgcaaaact aggataaatt atcgcgcgcg gtgtcatcta tgttactaga tcg          3773
```

<210> SEQ ID NO 29
<211> LENGTH: 3563
<212> TYPE: DNA
<213> ORGANISM: Artificial Sequence
<220> FEATURE:
<223> OTHER INFORMATION: Artificially created chimeric nucleic acid sequence

<400> SEQUENCE: 29

```
gacggtccga tgtgagactt ttcaacaaag ggtaatatcc ggaaacctcc tcggattcca     60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga ccccacccca cgaggagcat cgtggaaaaa gaagacgttc caaccacgtc    240
ttcaaagcaa gtggattgat gtgatggtcc gatgtgagac ttttcaacaa agggtaatat    300
ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gaccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taggaagtt     600 catttcattt ggagaggacc atatattagc aaatgcccac ctttatgagc ttgtcaatag    660
gtatatatct tagaacaagg acatcaatgg caaaaatagc aagacatgaa atcaaattgt    720
gccagacaag caacacagaa aaagaaaccc tccaccaca cgccctcca aaaactgtag     780 tcaccttaat tagggcggtc atattcaatg tgtaaagttc tgtgcgaaga atcttacaga    840
```

```
tttgctagct aaagcaaaaa gctaagtgac taaactccat attactgaga gtctgaaatg    900
ggcttgcgaa ccacgaagaa gtacattggt gtgaaaatcc ctttcttggc accaccgaca    960
agaccttctg cagctttctc taagaaagct tgaacccttt gactaccttt aggagcaagt   1020
cccacgtatt caagcgccga aaccagattt ctggtgaaaa gtctgccaac tgctgttagg   1080
cggaagctac tgagcgagaa gtgactcgta tccaaaggca agtaccatgg aacaggtgag   1140
tcatcagcca gatccttgtc ccatacaact tcaaaaccag cttgtttggc tgcttcgagg   1200
cactgtgttg tcaatctaac ctcagggagg ccatttccga gctcaatttc ggccttgatc   1260
ctgttgtgct cttcgttatt ggggttgtaa gaatcggtca tgcaccactc atacacagcg   1320
aaacattgac caggcttcag cacccggtaa atctctttat agcatcccaa tggatctggt   1380
gcatggcagg tagcttctgt ccgtcgcttc tcttccattt cttctcattt tcgattttga   1440
ttcttatttc tttccagtag ctcctgctct gtgaatttct ccgctcacga tagatctgct   1500
tatactcctt acattcaacc ttagatctgg tctcgattct ctgtttctct gttttttttct   1560
tttggtcgag aatctgatgt tgttatgt tctgtcacca ttaataataa tgaactctct   1620
cattcataca atgattagtt tctctcgtct acaaaacgat atgttgcatt ttcacttttc   1680
ttcttttttt ctaagatgat ttgctttgac caatttgttt agatcttat tttattttat   1740
tttctggtgg gttggtggaa attgaaaaaa aaaaaaacag cataaattgt tatttgttaa   1800
tgtattcatt ttttggctat ttgttctggg taaaaatctg cttctactat tgaatctttc   1860
ctggattttt tactcctatt gggttttat agtaaaaata cataataaaa ggaaaacaaa   1920
agttttatag attctcttaa accccttacg ataaagttg gaatcaaaat aattcaggat   1980
cagatgctct tgattgatt cagatgcgat tacagttgca tggcaaatt tctagatccg   2040
tcgtcacatt ttatttctg tttaaatatc taaatctgat atatgatgtc gacaaattct   2100
ggtggcttat acatcacttc aactgttttc ttttggcttt gtttgtcaac ttggttttca   2160
atacgatttg tgatttcgat cgctgaattt ttaatacaag caaactgatg ttaaccacaa   2220
gcaagagatg tgacctgcct tattaacatc gtattactta ctactagtcg tattctcaac   2280
gcaatcgttt ttgtatttct cacattatgc cgcttctcta ctctttattc cttttggtcc   2340
acgcattttc tatttgtggc aatccctttc acaacctgat ttcccacttt ggatcatttg   2400
tctgaagact ctcttgaatc gttaccactt gtttcttgtg catgctctgt tttttagaat   2460
taatgataaa actattccat agtcttgagt tttcagcttg ttgattcttt tgcttttggt   2520
tttctgcaga gaagctacct gccatgcacc agatccattg ggatgctata aagagattta   2580
ccgggtgctg aagcctggtc aatgtttcgc tgtgtatgag tggtgcatga ccgattctta   2640
caaccccaat aacgaagagc acaacaggat caaggccgaa attgagctcg aaatggcct   2700
ccctgaggtt agattgacaa cacagtgcct cgaagcagcc aaacaagctg tttttgaagt   2760
tgtatgggac aaggatctgg ctgatgactc acctgttcca tggtacttgc cттттggaтac   2820
gagtcacttc tcgctcagta gcttccgcct aacagcagtt ggcagacttt tcaccagaaa   2880
tctggtttcg gcgcttgaat acgtgggact tgctcctaaa ggtagtcaaa gggttcaagc   2940
tttcttagag aaagctgcag aaggtcttgt cggtggtgcc aagaaaggga тттттcacacc   3000
aatgtacttc ttcgtggttc gcaagcccat ttcagactct cagtaatatg gagtttagtc   3060
acttagcttt tgctttagc tagcaaatct gtaagattct tcgcacagaa ctttacacat   3120
tgaatatgac cgccctaatt aaggtgacta cagtttttgg agggcgttgt gggtggaggg   3180
tttctttttc tgtgttgctt gtctggcaca atttgatttc atgtcttgct atttttgcca   3240
```

```
ttgatgtcct tgttctaaga tatataccta ttgacaagct cataaaggtg ggcatttgct    3300
aatatatggg atcgttcaaa catttggcaa taaagtttct taagattgaa tcctgttgcc    3360
ggtcttgcga tgattatcat ataatttctg ttgaattacg ttaagcatgt aataattaac    3420
atgtaatgca tgacgttatt tatgagatgg gtttttatga ttagagtccc gcaattatac    3480
atttaatacg cgatagaaaa caaaatatag cgcgcaaact aggataaatt atcgcgcgcg    3540
gtgtcatcta tgttactaga tcg                                            3563
```

<210> SEQ ID NO 30
<211> LENGTH: 2881
<212> TYPE: DNA
<213> ORGANISM: Artificial Sequence
<220> FEATURE:
<223> OTHER INFORMATION: Artificially created chimeric nucleic acid
      sequence

<400> SEQUENCE: 30

```
gacggtccga tgtgagactt ttcaacaaag ggtaatatcc ggaaacctcc tcggattcca     60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga ccccccaccca cgaggagcat cgtggaaaaa gaagacgttc caaccacgtc    240
ttcaaagcaa gtggattgat gtgatggtcc gatgtgagac ttttcaacaa agggtaatat    300
ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gaccccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taggaagtt    600 catttcattt ggagaggaac aatcctagcc caacaagccc agctacatag tgacaatatt    660
cgtcataatc atcagttgtt tccacctcct tgcatatgaa ttttgccatt cctgcaccca    720
tcctcatggt aatatcctca attgcctgct gataatgttt cctaagctcc agaaaagcag    780
ttgaaacatg atggaactgg tccatgagaa ccttgtactc ttttgtacca catgaaaaat    840
gccattcacg atcataaaca tgctgatgaa aagagatcag aataggtact ttaacatcgg    900
tgggaatgct ggtatcatcc tcaacagtgt caagtgctcg aagaaccaaa tagaaaatgc    960
acacggcgtc acgaagctcg acgggaagtt gttgaatgac gagagcaaag ctacgagaaa   1020
ccttatgaag cattgagtaa cagaagcccc aatgtgggtc cgtcgcttct cttccatttc   1080
ttctcatttt cgattttgat tcttatttct ttccagtagc tcctgctctg tgaatttctc   1140
cgctcacgat agatctgctt atactcctta cattcaacct tagatctggt ctcgattctc   1200
tgtttctctg ttttttttctt ttggtcgaga atctgatgtt tgtttatgtt ctgtcaccat   1260
taataataat gaactctctc attcatacaa tgattagttt ctctcgtcta caaaacgata   1320
tgttgcattt tcacttttct tcttttttc taagatgatt tgctttgacc aatttgttta   1380
gatctttatt ttattttatt ttctggtggg ttggtggaaa ttgaaaaaaa aaaaacagc    1440 ataaattgtt atttgttaat gtattcattt tttggctatt tgttctgggt aaaaatctgc   1500
ttctactatt gaatctttcc tggatttttt actcctattg ggttttata gtaaaaatac    1560 ataataaaag gaaaacaaaa gttttataga ttctcttaaa cccctaacga taaaagttgg   1620
aatcaaaata attcaggatc agatgctctt tgattgattc agatgcgatt acagttgcat   1680
```

```
ggcaaatttt ctagatccgt cgtcacattt tattttctgt ttaaatatct aaatctgata    1740
tatgatgtcg acaaattctg gtggcttata catcacttca actgttttct tttggctttg    1800
tttgtcaact tggttttcaa tacgatttgt gatttcgatc gctgaatttt taatacaagc    1860
aaactgatgt taaccacaag caagagatgt gacctgcctt attaacatcg tattacttac    1920
tactagtcgt attctcaacg caatcgtttt tgtatttctc acattatgcc gcttctctac    1980
tctttattcc ttttggtcca cgcatttcct atttgtggca atcccttca caacctgatt      2040 tcccactttg gatcatttgt ctgaagactc tcttgaatcg ttaccacttg tttcttgtgc    2100
atgctctgtt tttagaatt aatgataaaa ctattccata gtcttgagtt ttcagcttgt      2160
tgattctttt gcttttggtt ttctgcagcc acattggggc ttctgttact caatgcttca    2220
taaggtttct cgtagctttg ctctcgtcat tcaacaactt cccgtcgagc ttcgtgacgc    2280
cgtgtgcatt ttctatttgg ttcttcgagc acttgacact gttgaggatg ataccagcat    2340
tcccaccgat gttaaagtac ctattctgat ctcttttcat cagcatgttt atgatcgtga    2400
atggcatttt tcatgtggta caaaagagta caaggttctc atggaccagt tccatcatgt    2460
ttcaactgct tttctggagc ttaggaaaca ttatcagcag gcaattgagg atattaccat    2520
gaggatgggt gcaggaatgg caaaattcat atgcaaggag gtggaaacaa ctgatgatta    2580
tgacgaatat tgtcactatg tagctgggct tgttgggcta ggattgtgat cgttcaaaca    2640
tttggcaata aagtttctta agattgaatc ctgttgccgg tcttgcgatg attatcatat     2700
aatttctgtt gaattacgtt aagcatgtaa taattaacat gtaatgcatg acgttattta    2760
tgagatgggt ttttatgatt agagtcccgc aattatacat ttaatacgcg atagaaaaca    2820
aaatatagcg cgcaaactag gataaattat cgcgcgcggt gtcatctatg ttactagatc    2880
g                                                                      2881
```

<210> SEQ ID NO 31
<211> LENGTH: 3703
<212> TYPE: DNA
<213> ORGANISM: Artificial Sequence
<220> FEATURE:
<223> OTHER INFORMATION: Artificially created chimeric nucleic acid
      sequence

<400> SEQUENCE: 31

```
gacggtccga tgtgagactt ttcaacaaag ggtaatatcc ggaaacctcc tcggattcca     60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga ccccacccca cgaggagcat cgtggaaaaa gaagacgttc caaccacgtc    240
ttcaaagcaa gtggattgat gtgatggtcc gatgtgagac ttttcaacaa agggtaatat    300 ccggaaaccct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gaccccaccc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taaggaagtt    600
catttcattt ggagaggaca tatacaaaag caaactttct gagcaaacat aaagagtttg    660
agatgccatt tctctctaaa ttacaatcta gtcacaatta acaacaaac gaaagacagt    720 acaacagaaa agattatttta aaaaaaaagg ggttatcttc cttggcgcat gaatgaaatt    780
```

```
aaccaaatgt tgaattacaa gttaacccca ctggtcacca tcccacctaa cacctttcgt    840
agatcttcac caaatatttg caggttttt tacacgaact cagaaaaaaa tacgacccta     900
cctcctcaca tgccttcata gaaagaatac aacactacat acagatccac gtccacccct     960
gatttgcttg tctttttctt cttgatcttt ctccacatga ctaatgcctt acactttttc    1020 aacttttgg tctacccttt acttattgct ctccctaatt ggaaaattt attcctactt     1080 ttattgtaat ccatttcttt aataatgatg gtccataaag gatggtgatg tacacgatgt    1140
tgggataata aatttgtctt tttccttact aagaggaaat cttagtaaca tctttgctag    1200
atctattgta tttcatgtga ctcttaacca gctgccctgc tgagatagca gacatgagag    1260
ataactcacc agcaagaaca gaacctgcta ctattgtggc caagagcctt gcatttgacc    1320
ctgctgcctc cctgtttgca cctttcactc ctaataagtt caagcaagct gactgtgatg    1380
caagttgagt tccaccacca actgtgccaa cctcaataga aggcatagtt actgaaatat    1440
ggaggtcttt gccatcattt acagcctcgt ccgtcgcttc tcttccattt cttctcattt    1500
tcgattttga ttcttatttc tttccagtag ctcctgctct gtgaatttct ccgctcacga    1560
tagatctgct tatactcctt acattcaacc ttagatctgg tctcgattct ctgtttctct    1620 gttttttct tttggtcgag aatctgatgt tgtttatgt tctgtcacca ttaataataa     1680
tgaactctct cattcataca atgattagtt tctctcgtct acaaaacgat atgttgcatt    1740
ttcacttttc ttctttttt ctaagatgat ttgctttgac caatttgttt agatctttat     1800
tttattttat tttctggtgg gttggtggaa attgaaaaaa aaaaaaacag cataaattgt    1860
tatttgttaa tgtattcatt ttttggctat ttgttctggg taaaaatctg cttctactat    1920
tgaatctttc ctggattttt tactccctatt gggtttttat agtaaaaata cataataaaa   1980
ggaaaacaaa agtttatag attctcttaa accccttacg ataaagttg gaatcaaaat      2040 aattcaggat cagatgctct ttgattgatt cagatgcgat tacagttgca tggcaaattt    2100
tctagatccg tcgtcacatt ttattttctg tttaaatatc taaatctgat atatgatgtc    2160
gacaaattct ggtggcttat acatcacttc aactgttttc ttttggcttt gtttgtcaac    2220
ttggttttca atacgatttg tgatttcgat cgctgaattt ttaatacaag caaactgatg    2280
ttaaccacaa gcaagagatg tgacctgcct tattaacatc gtattactta ctactagtcg    2340
tattctcaac gcaatcgttt ttgtatttct cacattatgc cgcttctcta ctctttattc    2400
cttttggtcc acgcattttc tatttgtggc aatcccttc acaacctgat ttcccacttt     2460
ggatcatttg tctgaagact ctcttgaatc gttaccactt gtttcttgtg catgctctgt    2520
tttttagaat taatgataaa actattccat agtcttgagt tttcagcttg ttgattcttt    2580
tgcttttggt tttctgcagg aggctgtaaa tgatggcaaa gacctccata tttcagtaac    2640
tatgccttct attgaggttg gcacagttgg tggtggaact caacttgcat cacagtcagc    2700
ttgcttgaac ttattaggag tgaaaggtgc aaacagggag gcagcagggt caaatgcaag    2760
gctcttggcc acaatagtag caggttctgt tcttgctggt gagttatctc tcatgtctgc    2820
tatctcagca gggcagctgg ttaagagtca catgaaatac aatagatcta gcaaagatgt    2880
tactaagatt tcctcttagt aaggaaaaag acaaatttat tatcccaaca tcgtgtacat    2940
caccatcctt tatggaccat cattattaaa gaaatggatt acaataaaag taggaataaa    3000
attttccaat tagggagagc aataagtaaa gggtagacca aaaagttgaa aaagtgtaag    3060
gcattagtca tgtggagaaa gatcaagaag aaaaagacaa gcaaatcaag ggtggacgtg    3120
```

| | |
|---|---|
| gatctgtatg tagtgttgta ttctttctat gaaggcatgt gaggaggtag ggtcgtattt | 3180 |
| ttttctgagt tcgtgtaaaa aaacctgcaa atatttggtg aagatctacg aaaggtgtta | 3240 |
| ggtgggatgg tgaccagtgg ggttaacttg taattcaaca tttggttaat ttcattcatg | 3300 |
| cgccaaggaa gataacccct ttttttttaa ataatctttt ctgttgtact gtctttcgtt | 3360 |
| tgtttgttaa ttgtgactag attgtaattt agagagaaat ggcatctcaa actcttatg | 3420 |
| tttgctcaga aagtttgctt ttgtatatgg atcgttcaaa catttggcaa taaagtttct | 3480 |
| taagattgaa tcctgttgcc ggtcttgcga tgattatcat ataatttctg ttgaattacg | 3540 |
| ttaagcatgt aataattaac atgtaatgca tgacgttatt tatgagatgg gttttatga | 3600 |
| ttagagtccc gcaattatac atttaatacg cgatagaaaa caaaatatag cgcgcaaact | 3660 |
| aggataaatt atcgcgcgcg gtgtcatcta tgttactaga tcg | 3703 |

<210> SEQ ID NO 32
<211> LENGTH: 4286
<212> TYPE: DNA
<213> ORGANISM: Artificial Sequence
<220> FEATURE:
<223> OTHER INFORMATION: Artificially created chimeric nucleic acid sequence

<400> SEQUENCE: 32

| | |
|---|---|
| ttctgttcgt atatttgtaa ctattatgtg tatttttatt ttgttagtat tactaattca | 60 |
| agtggtttaa gttgttgaga ctctttaaaa tctaagcatt ttataaacaa taatatataa | 120 |
| ttattgttta ggctaaattt gtcactaatt aaggtttgga tacatagtgt ctaaactaag | 180 |
| ctaataatat cacttaacgt ttacttgtaa cgctaggtga tgatgtcgtc aagtcaattg | 240 |
| gtacaaggaa taaacgagtg gtcatatgac attatgacca tatgaattca aactccagta | 300 |
| atccaatggt aattggattc aatgatcaag acttgaacca cgtaatccac ccttatcctt | 360 |
| agaagctcat aaatatcact aaagggacag gcaacactta accagtagtt gtccaataat | 420 |
| ttagttttcc aaaatgaaaa attattgttg tcatctattt taggtgtttt agttcaatgt | 480 |
| ggattcctcg tcctaacaaa tacttgacga atatatctag actataaaat tggttatgag | 540 |
| ttctactttt ttttgtttgt gaaattatca aaatttgtta tatttattta tttattctca | 600 |
| ttaatttgag tactaatttt taaattattt atactaaaaa caattactaa gatacaaaaa | 660 |
| tggataagag catggtgtat agatatttaa tgggatagaa tatttcccat aattgtatgt | 720 |
| gtgtgagagg ttttgttttc gtaaggaaag aaacaaaaac catttgacca agaaaagca | 780 |
| aaagaaggca aggaatcaaa caacaaatgt tgcaaggcag aaataatgga cgttatgtta | 840 |
| atgtagtgtc gtcacacgtg acttaaaaga gacgagtctg cgtgtcaaac taaaaatgta | 900 |
| tgcaactata aaaatgggat ttgattatct ttttagtacc gaagcctacc aaccacatgc | 960 |
| acactaattc tactcgccaa ataaagtgaa aagagccata tattagcaaa tgcccacctt | 1020 |
| tatgagcttg tcaataggta tatatctag aacaaggaca tcaatggcaa aaatagcaag | 1080 |
| acatgaaatc aaattgtgcc agacaagcaa cacagaaaaa gaaccctcc acccacaacg | 1140 |
| ccctccaaaa actgtagtca ccttaattag ggcggtcata ttcaatgtgt aaagttctgt | 1200 |
| gcgaagaatc ttcagatttt gctagctaaa gcaaaaagct aagtgactaa actccatatt | 1260 |
| actgagagtc tgaaatgggc ttgcgaacca cgaagaagta cattggtgtg aaaatcccttt | 1320 |
| tcttggcacc accgacaaga ccttctgcag ctttctctaa gaaagcttga acccctttgac | 1380 |
| tacctttagg agcaagtccc acgtattcaa gcgccgaaac cagatttctg gtgaaaagtc | 1440 |

```
tgccaactgc tgttaggcgg aagctactga gcgagaagtg actcgtatcc aaaggcaagt    1500
accatggaac aggtgagtca tcagccagat ccttgtccca tacaacttca aaaccagctt    1560
gtttggctgc ttcgaggcac tgtgttgtca atctaacctc agggaggcca tttccgagct    1620
caatttcggc cttgatcctg ttgtgctctt cgttattggg gttgtaagaa tcggtcatgc    1680
accactcata cacagcgaaa cattgaccag gcttcagcac ccggtaaatc tctttatagc    1740
atcccaatgg atctggtgca tggcaggtag cttctgtaag ttcctgtttt cacctgcacc    1800
atgaaaaata tactattact attattttc atttatttgt gtggtccata ttgctatgtg     1860
tgaaatgaaa aaatattttt tttctcaaac tacaatattg tcagaaagaa aggaattaat    1920
attccgaatt tataccaaaa aattaatttc ttttttctct ttggtaagct ggattctgtt    1980
attctttggt aaaacggaga ataattttgt ttatcaactt ctgttgattt tatgaacaat    2040
tctcaattaa ttgaaggggt agtttaaggc tgatgaatct tttggatgag ttacttgagc    2100
agtatggatt gactcacatg actaactgct tcactagctt ccaatatttt ttagttatta    2160
catgttgtgt atgttgatta ttgtgctcta agcaatcgga ttctcttgtt aaataaaaac    2220
tatcatagtt tatttattca ataatcgagt ttgagctaac actcctgtct atctggaata    2280
caaaaggaaa gataataaaa gttttggta ccttgaaaac tagaagtatc aggaagggga     2340
gccttgaaca aggtcaagt tgtctccgtt tgacctacat gtcatgttcg agccattgat     2400
gcttgcatca ggatagactg cctacatcac cccctcttgc ggtacggccc ttccccggac    2460
ctgcgtgaac gcgggatact ttgtgcaccg gaaaactaca agtatcccta acacatatca    2520
ggattttagt gatatccctt cactgccgtg ttcgataaag gttacataaa gttttaaatt    2580
tatgggtgct aaatatcaca gctaaatata cacattaaag atattactgc atccatatat    2640
gttgccatga ccatacatca gtatacatc caccctaat ttttgagtgt ttttgagatg      2700
cagcaaagtt gaaggagatt ataatagttt gatgtggaga gactaatttt ttttttaaca   2760
tcactttcta agggtgctat cttttcacca ccatcactgg tggcttgttg atttgtagct    2820
aatcattatc ttttgatgaa aacaaggaca ttctttagtg cactaagatt gttaaacgtt    2880
cgtgcttcat tgtaaatgta atatactcgc gcttgttggc atgaacactt ggaattgttt    2940
actggaacac tgcagagaag ctacctgcca tgcaccagat ccattgggat gctataaaga    3000
gatttaccgg gtgctgaagc ctggtcaatg tttcgctgtg tatgagtggt gcatgaccga    3060
ttcttacaac cccaataacg aagagcacaa caggatcaag gccgaaattg agctcggaaa    3120
tggcctccct gaggttagat tgacaacaca gtgcctcgaa gcagccaaac aagctggttt    3180
tgaagttgta tgggacaagg atctggctga tgactcacct gttccatggt acttgccttt    3240
ggatacgagt cacttctcgc tcagtagctt ccgcctaaca gcagttggca gacttttcac    3300
cagaaatctg gtttcggcgc ttgaatacgt gggacttgct cctaaaggta gtcaaagggt    3360
tcaagctttc ttagagaaag ctgcagaagg tcttgtcggt ggtgccaaga agggattttt    3420
cacaccaatg tacttcttcg tggttcgcaa gcccatttca gactctcagt aatatggagt    3480
ttagtcactt agctttttgc tttagctagc aaatctgtaa gattcttcgc acagaacttt    3540
acacattgaa tatgaccgcc ctaattaagg tgactacagt ttttggaggg cgttgtgggt    3600
ggagggtttc tttttctgtg ttgcttgtct ggcacaattt gatttcatgt cttgctatt     3660 ttgccattga tgtccttgtt ctaagatata tacctattga caagctcata aaggtgggca    3720
tttgctaata tatggtttcc ctttgctttt gtgtaaacct caaaacttta tccccccatct   3780 ttgattttat ccttgttttt ctgcttttt tcttctttct tgggttttaa tttccggact     3840
```

```
taacgtttgt tttccggttt gcgagacata ttctatcgga ttctcaactg tctgatgaaa    3900
taaatatgta atgttctata agtctttcaa tttgatatgc atatcaacaa aaagaaaata    3960
ggacaatgcg gctacaaata tgaaatttac aagtttaaga accatgagtc gctaaagaaa    4020
tcattaagaa aattagtttc acattcaatt cttgtcacat gattaacgag cttgagaggt    4080
ttagagtaac aatatcttga agcaaaagat gacccacttg aaatctagtg atggatacat    4140
aagtggacgt gccttgttta ggataggatt ctggataaga gtctcgaata ttcatttta    4200 ccaagtatat tcaaggatct tgtggatcat atatttcctc aatcaaggg acttgaccca    4260 aattcacata aagatatttt ggagtc                                         4286
```

<210> SEQ ID NO 33
<211> LENGTH: 8956
<212> TYPE: DNA
<213> ORGANISM: Artificial Sequence
<220> FEATURE:
<223> OTHER INFORMATION: Artificially created chimeric nucleic acid
      sequence

<400> SEQUENCE: 33

```
ctcgaggatc taaattgtga gttcaatctc ttccctattg gattgattat cctttctttt      60
cttccaattt gtgtttcttt ttgcctaatt tattgtgtta tccccttat cctattttgt     120 ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atatttttaa    420
aattttattt agtaataaag attctatata gctgttatag agggataatt ttacaaagaa    480
cactataaat atgattgttg ttgttaggggt gtcaatggtt cggttcgact ggttattta    540 taaaatttgt accataccat ttttttcgat attctatttt gtataaccaa aattagactt    600
ttcgaaatcg tcccaatcat gtcggtttca cttcggtatc ggtaccgttc ggttaatttt    660
catttttttt taaatgtcat taaaattcac tagtaaaaat agaatgcaat aacatacgtt    720
cttttatagg acttagcaaa agctctctag acattttac tgtttaaagg ataatgaatt    780 aaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agtttaaac ttactatata aattttcat atgtaaaatt    1200 taatcggtat agttcgatat tttttcaatt tatttttata aataaaaaaa cttaccctaa   1260
ttatcggtac agttatagat ttatataaaa atctacggtt cttcagaaga aacctaaaaa   1320
tcggttcggt gcggacggtt cgatcggttt agtcgatttt caaatattca ttgacactcc   1380
tagttgttgt tataggtaaa aagcagttac agagaggtaa aatataactt aaaaaatcag   1440
ttctaaggaa aaattgactt ttatagtaaa tgactgttat ataaggatgt tgttacagag   1500
aggtatgagt gtagttggta aattatgttc ttgacggtgt atgtcacata ttatttatta   1560
```

```
aaactagaaa aaacagcgtc aaaactagca aaaatccaac ggacaaaaaa atcggctgaa    1620
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta agaaggtac atctgtaacc ggaacaccac    1800
ttaaatgact aaattaccct catcagaaag cagatggagt gctacaaata acacactatt    1860
caacaaccat aaataaaacg tgttcagcta ctaaaacaaa tataaataaa tctatgtttg    1920
taagcactcc agccatgtta atggagtgct attgcctgtt aactctcact tataaaatag    1980
tagtagaaaa aatatgaacc aaaacacaac ggttgtgtat ttcacttttg gatatagctc    2040
agtggcttcg acacctgtag gaggctgaac ctcaaagttt gcagaatctc cattaacaaa    2100
aactgaatgg catatggcca aattagtcct taatggcaga ggtccctctt gtacaatctg    2160
gagaatatct tcctctgata gatataactt ctcgagggtc ttcccaattt tgtcctccca    2220
caaggacact atctcgttga aggatagaat attggcaggt ggtctcatgt gaagagtctt    2280
attcaatgtc cgtggatcat ctactgcttc gatagtgtat gtcgctatgt cttcttcctt    2340
cacatatatt gctttgggat ttccatcgcc aaaaatgaca actttgtctc taggaggggt    2400
tttggcctct aactgcccca agttgggcaa gaagaaatct gcaaaccaat tgcagattac    2460
atatgtgtat ggaattcctt ctgcctctat catcctcctg attcttacct ttagagcgaa    2520
gagtgatgca gctggttcaa ttgcacgagc atgatccaca tcaaatccaa attctgaagg    2580
aagaaatctc ttgatatttc cagcttcttt aattgctttg atgatgttca cttgatcagt    2640
ccgtcgcttc tcttccattt cttctcattt tcgattttga ttcttatttc tttccagtag    2700
ctcctgctct gtgaatttct ccgctcacga tagatctgct tatactcctt acattcaacc    2760
ttagatctgg tctcgattct ctgttctct gtttttttct tttggtcgag aatctgatgt    2820
ttgtttatgt tctgtcacca ttaataataa tgaactctct cattcataca atgattagtt    2880
tctctcgtct acaaaacgat atgttgcatt ttcactttc ttcttttttt ctaagatgat    2940
ttgctttgac caatttgttt agatcttat tttattttat tttctggtgg gttggtggaa    3000
attgaaaaaa aaaaaaacag cataaattgt tatttgttaa tgtattcatt ttttggctat    3060
ttgttctggg taaaaatctg cttctactat tgaatctttc ctggattttt tactcctatt    3120 gggttttat agtaaaaata cataataaaa ggaaaacaaa agttttatag attctcttaa    3180
accccttacg ataaaagttg gaatcaaaat aattcaggat cagatgctct ttgattgatt    3240
cagatgcgat tacagttgca tgcaaattt tctagatccg tcgtcacatt ttatttctg    3300 tttaaatatc taaatctgat atatgatgtc gacaaattct ggtggcttat acatcacttc    3360
aactgttttc ttttggcttt gtttgtcaac ttggttttca atacgatttg tgatttcgat    3420
cgctgaattt ttaatacaag caaactgatg ttaaccacaa gcaagagatg tgacctgcct    3480
tattaacatc gtattactta ctactagtcg tattctcaac gcaatcgttt ttgtatttct    3540
cacattatgc cgcttctcta ctctttattc cttttggtcc acgcattttc tatttgtggc    3600 aatcccttc acaacctgat ttcccacttt ggatcatttg tctgaagact ctcttgaatc    3660
gttaccactt gtttcttgtg catgctctgt ttttagaat taatgataaa actattccat    3720
agtcttgagt tttcagcttg ttgattcttt tgcttttggt tttctgcagt gatcaagtga    3780
acatcatcaa agcaattaaa gaagctggaa atatcaagag atttcttcct tcagaatttg    3840
gatttgatgt ggatcatgct cgtgcaattg aaccagctgc atcactcttc gctctaaagg    3900
```

```
taagaatcag gaggatgata gaggcagaag gaattccata cacatatgta atctgcaatt    3960
ggtttgcaga tttcttcttg cccaacttgg ggcagttaga ggccaaaacc cctcctagag    4020
acaaagttgt cattttttggc gatggaaatc ccaaagcaat atatgtgaag gaagaagaca  4080
tagcgacata cactatcgaa gcagtagatg atccacggac attgaataag actcttcaca   4140
tgagaccacc tgccaatatt ctatccttca acgagatagt gtccttgtgg gaggacaaaa   4200
ttgggaagac cctcgagaag ttatatctat cagaggaaga tattctccag attgtacaag   4260
agggacctct gccattaagg actaatttgg ccatatgcca ttcagttttt gttaatggag   4320
attctgcaaa ctttgaggtt cagcctccta caggtgtcga agccactgag ctatatccaa   4380
aagtgaaata cacaaccgca agtgtgttgc ctttgtgtgg aaatgaagag gtacttgcga   4440
ggactttgcg tttatcagtt tatgtgtttg tatatctatt tgatccagtt attatggatt   4500
atatacgctt gaaactcatt ttaagccatt gttattgaac gtttatcaaa tactttatta   4560
tgccaagcaa gtcaaacaca tgcttgttga ttgaaatcaa gctatagaaa tctcttcttc   4620
acatacagca gtttagattc acaatacaac aagcgaaacg ataaagtttc ttctgttcgt   4680
atatttgtaa ctattatgtg tattttttatt tgttagtat tactaattca agtggtttaa   4740
gttgttgaga ctctttaaaa tctaagcatt ttataaacaa taatatataa ttattgttta   4800
ggctaaattt gtcactaatt aaggtttgga tacatagtgt ctaaactaag ctaataatat   4860
cacttaacgt ttacttgtaa cgctaggtga tgatgtcgtc aagtcaattg gtacaaggaa   4920
taaacgagtg gtcatatgac attatgacca tatgaattca aactccagta atccaatggt   4980
aattggattc aatgatcaag acttgaacca cgtaatccac ccttatcctt agaagctcat   5040
aaatatcact aaagggacag gcaacactta accagtagtt gtccaataat ttagtttttcc   5100
aaaatgaaaa attattgttg tcatctattt taggtgtttt agttcaatgt ggattcctcg   5160
tcctaacaaa tacttgacga atatatctag actataaaat tggttatgag ttctactttt   5220
ttttgtttgt gaaattatca aaatttgtta tatttattta tttattctca ttaatttgag   5280
tactaatttt taaattattt atactaaaaa caattactaa gatacaaaaa tggataagag   5340
catggtgtat agatatttaa tgggatagaa tatttcccat aattgtatgt gtgtgagagg   5400
ttttgttttc gtaaggaaag aaacaaaaac catttgacca agaaaagca aaagaaggca    5460
aggaatcaaa caacaaatgt tgcaaggcag aaataatgga cgttatgtta atgtagtgtc   5520
gtcacacgtg acttaaaaga gacgagtctg cgtgtcaaac taaaaatgta tgcaactata   5580
aaaatgggat ttgattatct ttttagtacc gaagcctacc aaccacatgc acactaattc   5640
tactcgccaa ataaagtgaa aagagccata tattagcaaa tgcccacctt tatgagcttg   5700
tcaataggta tatatcttag aacaaggaca tcaatggcaa aaatagcaag acatgaaatc   5760
aaattgtgcc agacaagcaa cacagaaaaa gaaaccctcc acccacaacg ccctccaaaa   5820
actgtagtca ccttaattag ggcggtcata ttcaatgtgt aaagttctgt gcgaagaatc   5880
ttacagattt gctagctaaa gcaaaaagct aagtgactaa actccatatt actgagagtc   5940
tgaaatgggc ttgcgaacca cgaagaagta cattggtgtg aaaatcccctt tcttggcacc   6000
accgacaaga ccttctgcag cttttctctaa gaaagcttga acccctttgac taccctttagg   6060
agcaagtccc acgtattcaa gcgccgaaac cagatttctg gtgaaaagtc tgccaactgc   6120
tgttaggcgg aagctactga gcgagaagtg actcgtatcc aaaggcaagt accatggaac   6180
aggtgagtca tcagccagat ccttgtccca tacaacttca aaaccagctt gtttggctgc   6240
ttcgaggcac tgtgttgtca atctaacctc agggaggcca tttccgagct caatttcggc   6300
```

-continued

```
cttgatcctg ttgtgctctt cgttattggg gttgtaagaa tcggtcatgc accactcata      6360
cacagcgaaa cattgaccag gcttcagcac ccggtaaatc tctttatagc atcccaatgg      6420
atctggtgca tggcaggtag cttctgtaag ttcctgtttt cacctgcacc atgaaaaata      6480
tactattact attattttc atttatttgt gtggtccata ttgctatgtg tgaaatgaaa       6540 aaatatttt  tttctcaaac tacaatattg tcagaaagaa aggaattaat attccgaatt     6600
tataccaaaa aattaatttc ttttttctct ttggtaagct ggattctgtt attctttggt     6660
aaaacggaga ataattttgt ttatcaactt ctgttgattt tatgaacaat tctcaattaa     6720
ttgaaggggt agtttaaggc tgatgaatct tttggatgag ttacttgagc agtatggatt     6780
gactcacatg actaactgct tcactagctt ccaatatttt ttagttatta catgttgtgt    6840
atgttgatta ttgtgctcta agcaatcgga ttctcttgtt aaataaaaac tatcatagtt    6900
tatttattca ataatcgagt ttgagctaac actcctgtct atctggaata caaaaggaaa    6960
gataataaaa gttttggta ccttgaaaac tagaagtatc aggaagggga gccttgaaca     7020
aaggtcaagt tgtctccgtt tgacctacat gtcatgttcg agccattgat gcttgcatca    7080
ggatagactg cctacatcac cccctcttgc ggtacggccc ttccccggac tgcgtgaac     7140 gcgggatact ttgtgcaccg gaaaactaca agtatcccta acacatatca ggattttagt    7200
gatatccctt cactgccgtg ttcgataaag gttacataaa gttttaaatt tatgggtgct    7260
aaatatcaca gctaaatata cacattaaag atattactgc atccatatat gttgccatga    7320
ccatacatca agtatacatc caccctaat ttttgagtgt ttttgagatg cagcaaagtt    7380
gaaggagatt ataatagttt gatgtggaga gactaatttt ttttttaaca tcactttcta    7440
agggtgctat cttttcacca ccatcactgg tggcttgttg atttgtagct aatcattatc     7500
ttttgatgaa acaaggaca ttctttagtg cactaagatt gttaaacgtt cgtgcttcat     7560
tgtaaatgta atatactcgc gcttgttggc atgaacactt ggaattgttt actggaacac    7620
tgcagagaag ctacctgcca tgcaccagat ccattgggat gctataaaga gatttaccgg    7680
gtgctgaagc ctggtcaatg tttcgctgtg tatgagtggt gcatgaccga ttcttacaac    7740
cccaataacg aagagcacaa caggatcaag gccgaaattg agctcggaaa tggcctccct    7800
gaggttagat tgacaacaca gtgcctcgaa gcagccaaac aagctggttt tgaagttgta    7860
tgggacaagg atctggctga tgactcacct gttccatggt acttgccttt ggatacgagt    7920
cacttctcgc tcagtagctt ccgcctaaca gcagttggca gacttttcac cagaaatctg    7980
gtttcggcgc ttgaatacgt gggacttgct cctaaaggta gtcaaagggt tcaagctttc    8040
ttagagaaag ctgcagaagg tcttgtcggt ggtgccaaga aagggattt  cacaccaatg    8100 tacttcttcg tggttcgcaa gcccatttca gactctcagt aatatggagt ttagtcactt    8160 agcttttgc  tttagctagc aaatctgtaa gattcttcgc acagaacttt acacattgaa    8220
tatgaccgcc ctaattaagg tgactacagt ttttggaggg cgttgtgggt ggagggtttc    8280
tttttctgtg ttgcttgtct ggcacaattt gatttcatgt cttgctattt ttgccattga   8340
tgtccttgtt ctaagatata taccattga caagctcata aaggtgggca tttgctaata    8400
tatggtttcc ctttgctttt gtgtaaacct caaaactta tcccccatct ttgattttat    8460
cccttgtttt tctgcttttt tcttctttct tgggttttaa tttccggact taacgtttgt    8520
tttccggttt gcgagacata ttctatcgga ttctcaactg tctgatgaaa taatatgta    8580 atgttctata agtctttcaa tttgatatgc atatcaacaa aaagaaaata ggacaatgcg    8640
```

| | |
|---|---|
| gctacaaata tgaaatttac aagtttaaga accatgagtc gctaaagaaa tcattaagaa | 8700 |
| aattagtttc acattcaatt cttgtcacat gattaacgag cttgagaggt ttagagtaac | 8760 |
| aatatcttga agcaaaagat gacccacttg aaatctagtg atggatacat aagtggacgt | 8820 |
| gccttgttta ggataggatt ctggataaga gtctcgaata ttcatttta ccaagtatat | 8880 |
| tcaaggatct tgtggatcat atatttcctc aatcaaggg acttgaccca aattcacata | 8940 |
| aagatatttt ggagtc | 8956 |

<210> SEQ ID NO 34
<211> LENGTH: 3600
<212> TYPE: DNA
<213> ORGANISM: Artificial Sequence
<220> FEATURE:
<223> OTHER INFORMATION: Artificially created chimeric nucleic acid
      sequence

<400> SEQUENCE: 34

| | |
|---|---|
| tctagaatgt tcgtgcgtca aatggataaa caaaaaaata gcataagtta gttttgttac | 60 |
| tcgagagtta tgtattataa ggtataggga atgactcaa acataccact gaacttaacg | 120 |
| aaacgacgca tatatatact acttaactta acgaaaaagg ggtgagagtg gatgggtgct | 180 |
| ggtaaataat gaagggttta taacgtca cgtgtcaaaa ttcgatagta gtagtttcgt | 240 |
| tagttgtaat agcatatatg gcccaaagtt ataatataga taatatgttt atgtccaact | 300 |
| attaacgagt gacatagaca gttcattttg tgaagttcaa tgacatattt gagcccttc | 360 |
| cctttattta tctcctttta tttgttctaa taaagaatg gcatttatta tgtacataga | 420 |
| caaataacta ttttctttgg aatataattt gtttatatat tttaaaatca tgtctcaatt | 480 |
| tagtttgttt tgtgcatatt tcaactattc aattttgtcc atatatttat taccttcccc | 540 |
| catttacaag cattgaaccg ctttgctcac caaaacttat gcacattgca aaaatatcat | 600 |
| gtaaaggttt tatgtatgct gtaattaagg tctgaactca tcgtgatttt atttttaggc | 660 |
| ttcattgacc actaccaaac tctttgatgc tacattttct aattatattg gagttcgatt | 720 |
| atatccgaat tcgcgttgcg tagggcccat tcgaggaaaa acactcccta tcaaggattt | 780 |
| tttcatacc agagctcgaa ctcaagacat ctggttaagg gaagaacagt ctcatccact | 840 |
| gcaccatatc cttttgtggt caacaagtaa atttttatgta gaaccaaaaa ctatactcga | 900 |
| attgataaaa taaatggtgt aaaatattgt tttctttctt acattttgga cagtaaatat | 960 |
| gtaggacaat aataattagc gtggggtctt aagaaaatta gcatagattt ccagaaattc | 1020 |
| caaatcaacc ggcagttcca ggtttgaaaa ctacaactca ttccgacggt tcaaacttca | 1080 |
| aaccatgctt gctgactcgg cttcttcttt ctttttcacc aagacagagc agtagtcacg | 1140 |
| tgacacccct cacgtgcctc cccccttat atttcagact gcaaccctac actttcgcta | 1200 |
| cattcactac catattcttt tcactaagca attttctctc ctactttct ttaaacccct | 1260 |
| tttttctccc ctaagccatg gcatctagat catgttacgt cctgtagaaa ccccaacccg | 1320 |
| tgaaatcaaa aaactcgacg gcctgtgggc attcagtctg gatcgcgaaa actgtggaat | 1380 |
| tgatcagcgt tggtgggaaa gcgcgttaca agaaagccgg gcaattgctg tgccaggcag | 1440 |
| ttttaacgat cagttcgccg atgcagatat tcgtaattat gcgggcaacg tctggtatca | 1500 |
| gcgcgaagtc tttataccga aaggttgggc aggccagcgt atcgtgctgc gtttcgatgc | 1560 |
| ggtcactcat tacggcaaag tgtgggtcaa taatcaggaa gtgatggagc atcagggcgg | 1620 |
| ctatacgcca tttgaagccg atgtcacgcc gtatgttatt gccgggaaaa gtgtacgtat | 1680 |

-continued

```
caccgtttgt gtgaacaacg aactgaactg gcagactatc ccgccgggaa tggtgattac      1740
cgacgaaaac ggcaagaaaa agcagtctta cttccatgat ttctttaact atgccggaat      1800
ccatcgcagc gtaatgctct acaccacgcc gaacacctgg gtggacgata tcaccgtggt      1860
gacgcatgtc gcgcaagact gtaaccacgc gtctgttgac tggcaggtgg tggccaatgg      1920
tgatgtcagc gttgaactgc gtgatgcgga tcaacaggtg gttgcaactg acaaggcac      1980 tagcgggact ttgcaagtgg tgaatccgca cctctggcaa ccgggtgaag gttatctcta      2040
tgaactgtgc gtcacagcca aaagccagac agagtgtgat atctaccgc ttcgcgtcgg      2100 catccggtca gtggcagtga agggcgaaca gttcctgatt aaccacaaac cgttctactt      2160
tactggcttt ggtcgtcatg aagatgcgga cttgcgtggc aaaggattcg ataacgtgct      2220
gatggtgcac gaccacgcat taatggactg gattggggcc aactcctacc gtacctcgca      2280
ttacccttac gctgaagaga tgctcgactg ggcagatgaa catggcatcg tggtgattga      2340
tgaaactgct gctgtcggct ttaacctctc tttaggcatt ggtttcgaag cgggcaacaa      2400
gccgaaagaa ctgtacagcg aagaggcagt caacggggaa actcagcaag cgcacttaca      2460
ggcgattaaa gagctgatag cgcgtgacaa aaaccaccca agcgtggtga tgtggagtat      2520
tgccaacgaa ccggataccc gtccgcaagg tgcacgggaa tatttcgcgc cactggcgga      2580
agcaacgcgt aaactcgacc cgacgcgtcc gatcacctgc gtcaatgtaa tgttctgcga      2640
cgctcacacc gataccatca gcgatctctt tgatgtgctg tgcctgaacc gttattacgg      2700
atggtatgtc caaagcggcg atttggaaaa ggcagagaag gtactggaaa aagaacttct      2760
ggcctggcag gagaaactgc atcagccgat tatcatcacc gaatacggcg tggatacgtt      2820
agccgggctg cactcaatgt acaccgacat gtggagtgaa gagtatcagt gtgcatggct      2880
ggatatgtat caccgcgtct ttgatcgcgt cagcgccgtc gtcggtgaac aggtatggaa      2940
tttcgccgat tttgcgacct cgcaaggcat attgcgcgtt ggcggtaaca agaaagggat      3000
cttcactcgc gaccgcaaac cgaagtcggc ggcttttctg ctgcaaaaac gctggactgg      3060
catgaacttc ggtgaaaaac cgcagcaggg aggcaaacaa tgagagctcg tgaaatggcc      3120
tctttagttt ttgattgaat catagggta ttagttttct atggccggga gtggtcttct      3180
tgcttaattg taatggaata accagagagg aactactgtg ttatctttga ggaatgttgg      3240
gcttttttcg tttgaattat catgaatgaa attttacttt ttcccaatac aagtttgttt      3300
tcgtttcttg gttttttgtta tcccttggtt tatgtcttgg tttggcttaa atgattgaag      3360
attacactac ctatgtttct gctattcctg ttgaagatca catttgataa taatgcatcg      3420
aatgcattaa agtttcttat tggctctgtc aaaagtattg aaggtggatt tttctaattg      3480
gcaagagaaa gtattaaaga ggtgatttat tagtacttat attttctca gcatctctct      3540 ttcagtgttg gagcttcata aaattagcac ttcagagttt cagtcgggag ctgaattcga      3600
```

<210> SEQ ID NO 35
<211> LENGTH: 3387
<212> TYPE: DNA
<213> ORGANISM: Artificial Sequence
<220> FEATURE:
<223> OTHER INFORMATION: Artificially created chimeric nucleic acid sequence

<400> SEQUENCE: 35

```
cgttttgacg agttcggatg tagtagtagc cattatttaa tgtacatact aatcgtgaat        60
agtgaatatg atgaaacatt gtatcttatt gtataaatat ccataaacac atcatgaaag       120
```

```
acactttctt tcacggtctg aattaattat gatacaattc taatagaaaa cgaattaaat    180
tacgttgaat tgtatgaaat ctaattgaac aagccaacca cgacgacgac taacgttgcc    240
tggattgact cggtttaagt taaccactaa aaaaacggag ctgtcatgta acacgcggat    300
cgagcaggtc acagtcatga agccatcaaa gcaaaagaac taatccaagg gctgagatga    360
ttaattagtt taaaaattag ttaacacgag ggaaaaggct gtctgacagc caggtcacgt    420
tatctttacc tgtggtcgaa atgattcgtg tctgtcgatt ttaattattt ttttgaaagg    480
ccgaaaataa agttgtaaga gataaacccg cctatataaa ttcatatatt ttctctccgc    540
tttgaattgt ctcgttgtcc tcctcacttt catcggccgt ttttgaatct ccggcgactt    600
gacagagaag aacaaggaag aagactaaga gagaaagtaa gagataatcc aggagattca    660
ttctccgttt tgaatcttcc tcaatctcat cttcttccgc tctttctttc caaggtaata    720
ggaactttct ggatctactt tatttgctgg atctcgatct tgttttctca atttccttga    780
gatctggaat tcgtttaatt tggatctgtg aacctccact aaatcttttg gttttactag    840
aatcgatcta agttgaccga tcagttagct cgattatagc taccagaatt tggcttgacc    900
ttgatggaga gatccatgtt catgttacct gggaaatgat tgtatatgt gaattgaaat    960 ctgaactgtt gaagttagat tgaatctgaa cactgtcaat gttagattga atctgaacac   1020
tgtttaagtt agatgaagtt tgtgtataga ttcttcgaaa ctttaggatt gtagtgtcg    1080 tacgttgaac agaaagctat ttctgattca atcagggttt atttgactgt attgaactct   1140
ttttgtgtgt ttgcagctca tatggttgtg tttgggaatg tttctgcggc gaatttgcct   1200
tatcaaaacg ggttttttgga ggcactttca tctggaggtt gtgaactaat gggacatagc   1260
tttagggttc ccacttctca agcgcttaag acaagaacaa ggaggaggag tactgctggt   1320
cctttgcagg tagtttgtgt ggatattcca aggccagagc tagagaacac tgtcaatttc   1380
ttggaagctg ctagtttatc tgcatccttc cgtagtgctc ctcgtcctgc taagcctttg   1440
aaagttgtaa ttgctggtgc tggattggct ggattgtcaa ctgcaaagta cctggctgat   1500
gcaggccaca aacctctgtt gcttgaagca agagatgttc ttggtggaaa gatagctgca   1560
tggaaggatg aagatgggga ctggtatgag actggtttac atattttctt cggtgcttat   1620
ccgaatgtgc agaatttatt tggagaactt gggatcaatg atcggttgca gtggaaggaa   1680
cactccatga ttttgctat gccaagtaaa cctggagaat ttagtagatt tgacttccca   1740
gatgtcctac cagcacccct aaatggtatt tgggctattt tgcggaacaa cgagatgctg   1800
acatggccag agaaaataaa gtttgctatt ggacttttgc cagccatggt cggcggtcag   1860
gcttatgttg aggcccaaga tggtttatca gtcaaagaat ggatggaaaa gcagggagta   1920
cctgagcgcg tgaccgacga ggtgtttatt gccatgtcaa aggcgctaaa ctttataaac   1980
cctgatgaac tgtcaatgca atgcattttg atagctttga accggtttct tcaggaaaaa   2040
catggttcca agatggcatt cttggatggt aatcctccgg aaaggctttg tatgccagta   2100
gtggatcata ttcgatcact aggtggggaa gtgcaactta attctaggat aaagaaaatt   2160
gagctcaatg acgatggcac ggttaagagt ttcttactca ctaatggaag cactgtcgaa   2220
ggagacgctt atgtgtttgc cgctccagtc gatatcctga agctccttt accagatccc   2280 tggaaagaaa taccgtactt caagaaattg gataaattag ttggagtacc agttattaat   2340
gttcatatat ggtttgatcg aaaactgaag aacacatatg atcacctact ctttagcaga   2400
agtaaccttc tgagcgtgta tgccgacatg tccttaactt gtaaggaata ttacgatcct   2460
aaccggtcaa tgctggagct agtatttgca ccagcagagg aatggatatc acggactgat   2520
```

| | |
|---|---:|
| tctgacatca tagatgcaac aatgaaagaa cttgagaaac tcttccctga tgaaatctca | 2580 |
| gctgaccaaa gcaaagctaa aattctgaag taccatgtcg ttaagactcc aagatctggg | 2640 |
| tacaagacca tcccaaactg tgaaccatgt cgtcctctac aaagatcacc tattgaagga | 2700 |
| ttctacttag ctggagatta cacaaaacag aagtacttag cttccatgga aggcgctgtc | 2760 |
| ctctctggca aattctgctc tcagtctatt gttcaggatt acgagctact ggctgcgtct | 2820 |
| ggaccaagaa agttgtcgga ggcaacagta tcatcatcat gagaaaaggg cgaattcgtt | 2880 |
| aaccgcagac gagctcgtga aatggcctct ttagttttg attgaatcat aggggtatta | 2940 |
| gttttctatg gccgggagtg gtcttcttgc ttaattgtaa tggaataacc agagaggaac | 3000 |
| tactgtgtta tctttgagga atgttgggct ttttcgttt gaattatcat gaatgaaatt | 3060 |
| ttacttttc ccaatacaag tttgttttcg tttcttggtt tttgttatcc cttggtttat | 3120 |
| gtcttggttt ggcttaaatg attgaagatt acactaccta tgtttctgct attcctgttg | 3180 |
| aagatcacat ttgataataa tgcatcgaat gcattaaagt ttcttattgg ctctgtcaaa | 3240 |
| agtattgaag gtggattttt ctaattggca agagaaagta ttaaagaggt gatttattag | 3300 |
| tacttatatt tttctcagca tctctctttc agtgttggag cttcataaaa ttagcacttc | 3360 |
| agagtttcag tcgggagctg aattcga | 3387 |

<210> SEQ ID NO 36
<211> LENGTH: 1701
<212> TYPE: DNA
<213> ORGANISM: Arabidopsis thaliana

<400> SEQUENCE: 36

| | |
|---|---:|
| atggttgtgt ttgggaatgt ttctgcggcg aatttgcctt atcaaaacgg gttttttggag | 60 |
| gcactttcat ctggaggttg tgaactaatg ggacatagct ttagggttcc cacttctcaa | 120 |
| gcgcttaaga caagaacaag gaggaggagt actgctggtc ctttgcaggt agtttgtgtg | 180 |
| gatattccaa ggccagagct agagaacact gtcaatttct tggaagctgc tagtttatct | 240 |
| gcatccttcc gtagtgctcc tcgtcctgct aagccttga aagttgtaat tgctggtgct | 300 |
| ggattggctg gattgtcaac tgcaaagtac ctggctgatg caggccacaa acctctgttg | 360 |
| cttgaagcaa gagatgttct tggtggaaag atagctgcat ggaaggatga agatggggac | 420 |
| tggtatgaga ctggtttaca tatttttcttc ggtgcttatc cgaatgtgca gaatttattt | 480 |
| ggagaacttg ggatcaatga tcggttgcag tggaaggaac actccatgat ttttgctatg | 540 |
| ccaagtaaac ctggagaatt tagtagattt gacttcccag atgtcctacc agcacccttta | 600 |
| aatggtattt gggctatttt gcggaacaac gagatgctga catggccaga gaaaataaag | 660 |
| tttgctattg gactttttgcc agccatggtc ggcggtcagg cttatgttga gcccaagat | 720 |
| ggtttatcag tcaaagaatg gatggaaaag cagggagtac ctgagcgcgt gaccgacgag | 780 |
| gtgtttattg ccatgtcaaa ggcgctaaac tttataaacc ctgatgaact gtcaatgcaa | 840 |
| tgcatttga tagctttgaa ccggttctt caggaaaaac atggttccaa gatggcattc | 900 |
| ttggatggta tcctccgga aaggctttgt atgccagtag tggatcatat tcgatcacta | 960 |
| ggtgggggaag tgcaacttaa ttctaggata aagaaaattg agctcaatga cgatggcacg | 1020 |
| gttaagagtt tcttactcac taatggaagc actgtcgaag gagacgctta tgtgtttgcc | 1080 |
| gctccagtcg atatcctgaa gctccttta ccagatccct ggaaagaaat accgtacttc | 1140 |
| aagaaattgg ataaattagt tggagtacca gttattaatg ttcatatatg gtttgatcga | 1200 |

```
aaactgaaga acacatatga tcacctactc tttagcagaa gtaaccttct gagcgtgtat   1260
gccgacatgt ccttaacttg taaggaatat tacgatccta accggtcaat gctggagcta   1320
gtatttgcac cagcagagga atggatatca cggactgatt ctgacatcat agatgcaaca   1380
atgaaagaac ttgagaaact cttccctgat gaaatctcag ctgaccaaag caaagctaaa   1440
attctgaagt accatgtcgt taagactcca agatctgtgt acaagaccat cccaaactgt   1500
gaaccatgtc gtcctctaca agatcaccct attgaaggat tctacttagc tggagattac   1560
acaaaacaga agtacttagc ttccatggaa ggcgctgtcc tctctggcaa attctgctct   1620
cagtctattg ttcaggatta cgagctactg gctgcgtctg gaccaagaaa gttgtcggag   1680
gcaacagtat catcatcatg a                                             1701

<210> SEQ ID NO 37
<211> LENGTH: 2010
<212> TYPE: DNA
<213> ORGANISM: Nicotiana tabacum

<400> SEQUENCE: 37
ctcgaggatc taaattgtga gttcaatctc ttccctattg gattgattat cctttctttt     60
cttccaattt gtgtttcttt tgcctaatt tattgtgtta tcccctttat cctatttgt     120
ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atattttaa    420
aatttttatt agtaataaag attctatata gctgttatag agggataatt ttacaaagaa    480
cactataaat atgattgttg ttgttagggt gtcaatggtt cggttcgact ggttatttta    540
taaaatttgt accataccat tttttcgat attctatttt gtataaccaa aattagactt    600
ttcgaaatcg tcccaatcat gtcggtttca cttcggtatc ggtaccgttc ggttaatttt    660
cattttttt taaatgtcat taaaattcac tagtaaaaat agaatgcaat aacatacgtt    720
ctttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaagata aatttaaata atatgaaagg    960
aaacatattc aatacattgt agtttgctac tcataatcgc tagaatactt tgtgccttgc   1020
taataaagat acttgaaata gcttagttta aatataaata gcataataga ttttaggaat   1080
tagtattttg agtttaatta cttattgact tgtaacagtt tttataattc caaggcccat   1140
gaaaaattta atgctttatt agttttaaac ttactatata aatttttcat atgtaaaatt   1200
taatcggtat agttcgatat ttttttcaatt tatttttata aaataaaaaa cttaccctaa   1260
ttatcggtac agttatagat ttatataaa atctacggtt cttcagaaga aacctaaaaa     1320
tcggttcggt gcggacggtt cgatcggttt agtcgatttt caaatattca ttgacactcc    1380
tagttgttgt tataggtaaa aagcagttac agagaggtaa aatataactt aaaaaatcag    1440
ttctaaggaa aaaattgactt ttatagtaaa tgactgttat ataaggatgt tgttacagag   1500
aggtatgagt gtagttggta aattatgttc ttgacggtgt atgtcacata ttatttatta    1560
aaactagaaa aaacagcgtc aaaactagca aaaatccaac ggacaaaaaa atcggctgaa    1620
```

```
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta agaaggtac atctgtaacc ggaacaccac     1800
ttaaatgact aaaattaccct catcagaaag cagatggagt gctacaaata acacactatt  1860
caacaaccat aaataaaacg tgttcagcta ctaaaacaaa tataaataaa tctatgtttg   1920
taagcactcc agccatgtta atggagtgct attgcctgtt aactctcact tataaaatag    1980
tagtagaaaa aatatgaacc aaaacacaac                                     2010

<210> SEQ ID NO 38
<211> LENGTH: 254
<212> TYPE: DNA
<213> ORGANISM: Agrobacterium tumefaciens

<400> SEQUENCE: 38
gatcgttcaa acatttggca ataaagtttc ttaagattga atcctgttgc cggtcttgcg    60
atgattatca tataatttct gttgaattac gttaagcatg taataattaa catgtaatgc    120
atgacgttat ttatgagatg ggtttttatg attagagtcc cgcaattata catttaatac    180
gcgatagaaa acaaaatata gcgcgcaaac taggataaat tatcgcgcgc ggtgtcatct    240
atgttactag atcg                                                       254

<210> SEQ ID NO 39
<211> LENGTH: 202
<212> TYPE: DNA
<213> ORGANISM: Nicotiana tabacum

<400> SEQUENCE: 39
tatgggaagg ttctgacttt ggatggagca attcaacata cagagaatgg tggatttcca    60
tacactgaaa tgattgttca tctaccactt ggttccatcc caaacccaaa aaaggttttg    120
atcatcggcg gaggaattgg ttttacatta ttcgaaatgc ttcgttatcc ttcaatcgaa    180
aaaattgaca ttgttgagat cg                                              202

<210> SEQ ID NO 40
<211> LENGTH: 344
<212> TYPE: DNA
<213> ORGANISM: Nicotiana tabacum

<400> SEQUENCE: 40
ccagcaaaag atttgtttga gaggccattc tttgaggcag tagccaaagc ccttaggcca    60
ggaggagttg tatgcacaca ggctgaaagc atttggcttc atatgcatat tattaagcaa    120
atcattgcta actgtcgtca agtctttaag ggttctgtca actatgcttg gacaaccgtt    180
ccaacatatc ccaccggtgt gatcggttat atgctctgct ctactgaagg gccagaagtt    240
gacttcaaga atccagtaaa tccaattgac aaagagacaa ctcaagtcaa gtccaaatta    300
ggacctctca agttctacaa ctctgatatt cacaaagcag catt                     344

<210> SEQ ID NO 41
<211> LENGTH: 155
<212> TYPE: DNA
<213> ORGANISM: Arabidopsis thaliana

<400> SEQUENCE: 41
gtaataagat cttcaacacc tacaccattt ttttaatcac tactacccat tgcattgaac    60
```
aaacttccaa gttcttctta gcttcagatt aagaaagtac cctttcttgg ctttgttgat    120
gtggtaccat tgtccattgt cttgtgtgtt tccag    155

<210> SEQ ID NO 42
<211> LENGTH: 4115
<212> TYPE: DNA
<213> ORGANISM: Artificial Sequence
<220> FEATURE:
<223> OTHER INFORMATION: Artificially created chimeric nucleic acid
      sequence

<400> SEQUENCE: 42
ctcgaggatc taaattgtga gttcaatctc ttccctattg gattgattat cctttctttt     60
cttccaattt gtgtttcttt ttgcctaatt tattgtgtta tcccctttat cctattttgt    120
ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttatt ctcttactac caatataacg cttgaattga cgaaaatttg    300
tgtccaaata tctagcaaaa aggtatccaa tgaaaatata tcatatgtga tcttcaaatc    360
ttgtgtctta tgcaagattg atactttgtt caatggaaga gattgtgtgc atattttaa     420 aattttatt agtaataaag attctatata gctgttatag agggataatt ttacaaagaa    480
cactataaat atgattgttg ttgttagggt gtcaatggtt cggttcgact ggttatttta    540
taaaatttgt accataccat ttttttcgat attctatttt gtataaccaa aattagactt    600
ttcgaaatcg tcccaatcat gtcggtttca cttcggtatc ggtaccgttc ggttaattt     660 catttttttt taaatgtcat taaaattcac tagtaaaaat agaatgcaat aacatacgtt    720
cttttatagg acttagcaaa agctctctag acatttttac tgtttaaagg ataatgaatt    780
aaaaaacatg aaagatggct agagtataga tacacaacta ttcgacagca acgtaaaaga    840
aaccaagtaa aagcaaagaa aatataaatc acacgagtgg aaagatatta accaagttgg    900
gattcaagaa taaagtctat attaaatatt caaaaagata aatttaaata atatgaaagg    960
aaacatattc aatacattgt agtttgctac tcataatcgc tagaatactt tgtgccttgc    1020
taataaagat acttgaaata gcttagttta aatataaata gcataataga ttttaggaat    1080
tagtattttg agtttaatta cttattgact tgtaacagtt tttataattc caaggcccat    1140
gaaaaattta atgctttatt agtttaaac ttactatata aattttttcat atgtaaaatt    1200 taatcggtat agttcgatat ttttttcaatt tatttttata aaataaaaaa cttaccctaa    1260
ttatcggtac agttatagat ttatataaaa atctacggtt cttcagaaga aacctaaaaa    1320
tcggttcggt gcggacggtt cgatcggttt agtcgatttt caaatattca ttgacactcc    1380
tagttgttgt tataggtaaa aagcagttac agagaggtaa aatataactt aaaaaatcag    1440
ttctaaggaa aaattgactt ttatagtaaa tgactgttat ataaggatgt tgttacagag    1500
aggtatgagt gtagttggta aattatgttc ttgacggtgt atgtcacata ttatttatta    1560
aaactagaaa aaacagcgtc aaaactagca aaaatccaac ggacaaaaaa atcggctgaa    1620
tttgatttgg ttccaacatt taaaaaagtt tcagtgagaa agaatcggtg actgttgatg    1680
atataaacaa agggcacatt ggtcaataac cataaaaaat tatatgacag ctacagttgg    1740
tagcatgtgc tcagctattg aacaaatcta agaaggtac atctgtaacc ggaacaccac    1800
ttaaatgact aaaattaccct catcagaaag cagatggagt gctacaaata acacactatt    1860
caacaaccat aaataaaacg tgttcagcta ctaaaacaaa tataaataaa tctatgtttg    1920

```
taagcactcc agccatgtta atggagtgct attgcctgtt aactctcact tataaaatag    1980
tagtagaaaa aatatgaacc aaaacacaac tttatcgcca tcatttacat accactccac    2040
ctttaatgaa ggatcaactt ccgcgaatat catctcagca agtgcaattc ctgctatgat    2100
cccgtcttcc tttgctagaa aatgagcatc ggattccata tcaagaggaa ttgtcgcctt    2160
acaagtcaca tctcctaaat tcccagcatc ttcagagagt gcaagtttca taacttcctt    2220
taaatcataa gttgggtgtg ctggtggttt cacctctaat gactccactc ttgtattctt    2280
ggtggctatt gctgacattt tcaccaccaa ccttggagct gtaattgcat aaggatgcac    2340
tgtagcagtg aaaggaatag ctctaaacat gtccgtcgct tctcttccat ttcttctcat    2400
tttcgatttt gattcttatt tctttccagt agctcctgct ctgtgaattt ctccgctcac    2460
gatagatctg cttatactcc ttacattcaa ccttagatct ggtctcgatt ctctgtttct    2520
ctgttttttt cttttggtcg agaatctgat gtttgtttat gttctgtcac cattaataat    2580
aatgaactct ctcattcata caatgattag tttctctcgt ctacaaaacg atatgttgca    2640
ttttcacttt tcttctttt ttctaagatg atttgctttg accaatttgt ttagatcttt    2700
attttatttt atttttctggt gggttggtgg aaattgaaaa aaaaaaaaac agcataaatt    2760
gttatttgtt aatgtattca tttttggct atttgttctg ggtaaaaatc tgcttctact    2820
attgaatctt tcctggattt tttactccta ttgggttttt atagtaaaaa tacataataa    2880
aaggaaaaca aaagttttat agattctctt aaacccctta cgataaagt tggaatcaaa     2940 ataattcagg atcagatgct ctttgattga ttcagatgcg attacagttg catggcaaat    3000
tttctagatc cgtcgtcaca tttatttc tgtttaaata tctaaatctg atatatgatg     3060
tcgacaaatt ctggtggctt atacatcact tcaactgttt tcttttggct ttgtttgtca    3120
acttggtttt caatacgatt tgtgatttcg atcgctgaat ttttaataca agcaaactga    3180
tgttaaccac aagcaagaga tgtgacctgc cttattaaca tcgtattact tactactagt    3240
cgtattctca acgcaatcgt ttttgtattt ctcacattat gccgcttctc tactcttat    3300 tccttttggt ccacgcattt tctatttgtg gcaatccctt tcacaacctg atttcccact    3360
ttggatcatt tgtctgaaga ctctcttgaa tcgttaccac ttgtttcttg tgcatgctct    3420
gttttttaga attaatgata aaactattcc atagtcttga gttttcagct tgttgattct    3480
tttgcttttg gttttctgca gatgtttaga gctattcctt tcactgctac agtgcatcct    3540
tatgcaatta cagctccaag gttggtggtg aaaatgtcag caatagccac caagaataca    3600
agagtggagt cattagaggt gaaaccacca gcacacccaa cttatgattt aaaggaagtt    3660
atgaaacttg cactctctga agatgctggg aatttaggag atgtgacttg taaggcgaca    3720
attcctcttg atatggaatc cgatgctcat tttctagcaa aggaagacgg gatcatagca    3780
ggaattgcac ttgctgagat gatattcgcg gaagttgatc cttcattaaa ggtggagtgg    3840
tatgtaaatg atggcgataa agatcgttca acatttggc aataaagttt cttaagattg     3900
aatcctgttg ccggtcttgc gatgattatc atataatttc tgttgaatta cgttaagcat    3960
gtaataatta acatgtaatg catgacgtta tttatgagat gggttttat gattagagtc     4020 ccgcaattat acatttaata cgcgatagaa aacaaaatat agcgcgcaaa ctaggataaa    4080
ttatcgcgcg cggtgtcatc tatgttacta gatcg                                4115

<210> SEQ ID NO 43
<211> LENGTH: 2835
<212> TYPE: DNA
<213> ORGANISM: Artificial Sequence
```

<220> FEATURE:
<223> OTHER INFORMATION: Artificially created chimeric nucleic acid sequence

<400> SEQUENCE: 43

```
gaattcaatg gagaaggaaa atatttccag tgtaaacaca agtgaatgaa gagaagccaa      60
aataatctct atcattcaag ccttaggtgg agattaaaaa aattatttac tttcttatca     120
aagtaatagg tgatcaacag ctttcgtaaa acgtcattag gagaatatta taatctcttt     180
tatgctgaag aacccacata aggaagatca taaaatacat gactttcaga tgacttcttg     240
gagctttatt tttaaagagt ggctagctgg tcagcaaaga ggtgctcgtc agatatcata     300
aaattttact attatttgtt ttaagaggga gatggggcac acatgcttgt gacaaaagta     360
agaggaagaa aggagacaga agaggaaata gatttggggg ggggggggg ggtttcacaa      420
tcaaagaaaa ttttttaaaat ggagagagaa atgagcacac acatatacta acaaaatttt    480
actaataatt gcaccgagac aaacttatat tttagttcca aaatgtcagt ctaaccctgc     540
acgttgtaat gaattttttaa ctattatatt atatcgagtt gcgccctcca ctcctcggtg    600
tccaaattgt atttaaatgc atagatgttt attgggagtg tacagcaagc tttcggaaaa    660
tacaaaccat aatactttct cttcttcaat ttgtttagtt taattttgaa atttatcgcc    720
atcatttaca taccactcca cctttaatga aggatcaact ccgcgaata tcatctcagc     780
aagtgcaatt cctgctatga tcccgtcttc ctttgctaga aaatgagcat cggattccat     840
atcaagagga attgtcgcct tacaagtcac atctcctaaa ttcccagcat cttcagagag    900
tgcaagtttc ataacttcct ttaaatcata agttgggtgt gctggtggtt tcacctctaa    960
tgactccact cttgtattct tggtggctat tgctgacatt ttcaccacca accttggagc   1020
tgtaattgca taaggatgca ctgtagcagt gaaaggaata gctctaaaca tgtccgtcgc   1080
ttctcttcca tttcttctca ttttcgattt tgattcttat ttcttccag tagctcctgc    1140
tctgtgaatt tctccgctca cgatagatct gcttatactc cttacattca accttagatc   1200
tggtctcgat tctctgtttc tctgtttttt tcttttggtc gagaatctga tgtttgttta   1260
tgttctgtca ccattaataa taatgaactc tctcattcat acaatgatta gtttctctcg    1320
tctacaaaac gatatgttgc atttttcactt tcttctttt tttctaagat gatttgcttt    1380
gaccaatttg tttagatctt tattttattt tattttctgg tgggttggtg gaaattgaaa    1440
aaaaaaaaaa cagcataaat tgttatttgt taatgtattc attttttggc tatttgttct    1500
gggtaaaaat ctgcttctac tattgaatct ttcctggatt ttttactcct attgggtttt    1560
tatagtaaaa atacataata aaaggaaaac aaaagtttta tagattctct taaacccctt    1620
acgataaaag ttggaatcaa aataattcag gatcagatgc tctttgattg attcagatgc    1680
gattacagtt gcatggcaaa ttttctagat ccgtcgtcac atttttatttt ctgtttaaat   1740
atctaaatct gatatatgat gtcgacaaat tctggtggct tatacatcac ttcaactgtt   1800
ttcttttggc tttgtttgtc aacttggttt tcaatacgat ttgtgatttc gatcgctgaa   1860
ttttttaatac aagcaaactg atgttaacca caagcaagag atgtgacctg ccttattaac   1920
atcgtattac ttactactag tcgtattctc aacgcaatcg ttttttgtatt tctcacatta   1980
tgccgcttct ctactcttta ttccttttgg tccacgcatt ttctatttgt ggcaatccct   2040
ttcacaacct gatttcccac tttggatcat ttgtctgaag actctcttga atcgttacca   2100
cttgtttctt gtgcatgctc tgttttttag aattaatgat aaaactattc catagtcttg   2160
agttttcagc ttgttgattc ttttgctttt ggttttctgc agatgtttag agctattcct    2220
```

| | |
|---|---|
| ttcactgcta cagtgcatcc ttatgcaatt acagctccaa ggttggtggt gaaaatgtca | 2280 |
| gcaatagcca ccaagaatac aagagtggag tcattagagg tgaaaccacc agcacaccca | 2340 |
| acttatgatt taaaggaagt tatgaaactt gcactctctg aagatgctgg gaatttagga | 2400 |
| gatgtgactt gtaaggcgac aattcctctt gatatggaat ccgatgctca ttttctagca | 2460 |
| aaggaagacg ggatcatagc aggaattgca cttgctgaga tgatattcgc ggaagttgat | 2520 |
| ccttcattaa aggtggagtg gtatgtaaat gatggcgata agcaagtgt gttgcctttg | 2580 |
| tgtggaaatg aagaggtact tgcgaggact ttgcgtttat cagtttatgt gtttgtatat | 2640 |
| ctatttgatc cagttattat ggattatata cgcttgaaac tcattttaag ccattgttat | 2700 |
| tgaacgttta tcaaatactt tattatgcca agcaagtcaa acacatgctt gttgattgaa | 2760 |
| atcaagctat agaaatctct tcttcacata cagcagttta gattcacaat acaacaagcg | 2820 |
| aaacgataaa gtttc | 2835 |

<210> SEQ ID NO 44
<211> LENGTH: 1893
<212> TYPE: DNA
<213> ORGANISM: Artificial Sequence
<220> FEATURE:
<223> OTHER INFORMATION: Artificially created chimeric nucleic acid sequence

<400> SEQUENCE: 44

| | |
|---|---|
| aatatgaaag gaaacatatt caatacattg tagtttgcta ctcataatcg ctagaatact | 60 |
| ttgtgccttg ctaataaaga tacttgaaat agcttagttt aaatataaat agcataatag | 120 |
| attttaggaa ttagtatttt gagtttaatt acttattgac ttgtaacagt ttttataatt | 180 |
| ccaaggccca tgaaaatttt aatgctttat tagtttaaa cttactatat aaattttca | 240 |
| tatgtaaaat ttaatcggta tagttcgata ttttttcaat ttattttat aaaataaaaa | 300 |
| acttacccta attatcggta cagttataga tttatataaa aatctacggt tcttcagaag | 360 |
| aaacctaaaa atcggttcgg tgcggacggt tcgatcggtt tagtcgattt tcaaatattc | 420 |
| attgacactc ctagttgttg ttataggtaa aaagcagtta cagagaggta aaatataact | 480 |
| taaaaaatca gttctaagga aaaattgact tttatagtaa atgactgtta tataaggatg | 540 |
| ttgttacaga gaggtatgag tgtagttggt aaattatgtt cttgacggtg tatgtcacat | 600 |
| attatttatt aaaactagaa aaaacagcgt caaaactagc aaaaatccaa cggacaaaaa | 660 |
| aatcggctga atttgatttg gttccaacat ttaaaaaagt ttcagtgaga agaatcggt | 720 |
| gactgttgat gatataaaca aagggcacat tggtcaataa ccataaaaaa ttatatgaca | 780 |
| gctacagttg gtagcatgtg ctcagctatt gaacaaatct aaagaaggta catctgtaac | 840 |
| cggaacacca cttaaatgac taaattaccc tcatcagaaa gcagatggag tgctacaaat | 900 |
| aacacactat tcaacaacca taaataaaac gtgttcagct actaaaacaa atataaataa | 960 |
| atctatgttt gtaagcactc cagccatgtt aatggagtgc tattgcctgt taactctcac | 1020 |
| ttataaaata gtagtagaaa aaatatgaac caaaacacaa ccgatctcaa caatgtcaat | 1080 |
| tttttcgatt gaaggataac gaagcatttc gaataatgta aaaccaattc ctccgccgat | 1140 |
| gatcaaaacc tttttgggt ttgggatgga accaagtggt agatgaacaa tcatttcagt | 1200 |
| gtatggaaat ccaccattct ctgtatgttg aattgctcca tccaaagtca gaaccttccc | 1260 |
| atagtaataa gatcttcaac acctacacca ttttttaat cactactacc cattgcattg | 1320 |
| aacaaacttc caagttcttc ttagcttcag attaagaaag tacccttcct ggctttgtt | 1380 |

```
gatgtggtac cattgtccat tgtcttgtgt gtttccagta tgggaaggtt ctgactttgg    1440
atggagcaat tcaacataca gagaatggtg gatttccata cactgaaatg attgttcatc    1500
taccacttgg ttccatccca aacccaaaaa aggttttgat catcggcgga ggaattggtt    1560
ttacattatt cgaaatgctt cgttatcctt caatcgaaaa aattgacatt gttgagatcg    1620
gcaagtgtgt tgcctttgtg tggaaatgaa gaggtacttg cgaggacttt gcgtttatca    1680
gtttatgtgt ttgtatatct atttgatcca gttattatgg attatatacg cttgaaactc    1740
attttaagcc attgttattg aacgtttatc aaatacttta ttatgccaag caagtcaaac    1800
acatgcttgt tgattgaaat caagctatag aaatctcttc ttcacataca gcagtttaga    1860
ttcacaatac aacaagcgaa acgataaagt ttc                                 1893

<210> SEQ ID NO 45
<211> LENGTH: 4098
<212> TYPE: DNA
<213> ORGANISM: Artificial Sequence
<220> FEATURE:
<223> OTHER INFORMATION: Artificially created chimeric nucleic acid
      sequence

<400> SEQUENCE: 45
gatctaaatt gtgagttcaa tctcttccct attggattga ttatcctttc ttttcttcca      60
atttgtgttt cttttgcct aatttattgt gttatcccct ttatcctatc ttgtttcttt     120
acttatttat ttgcttctat gtctttgtac aaagatttaa actctatggc acatatttta    180
aagttgttag aaaataaatt cttcaagat tgatgaaaga acttttttaat tgtagatatt    240 tcgtagattt tattctctta ctaccaatat aacgcttgaa ttgacgaaaa tttgtgtcca    300
aatatttagc aaaaaggtat ccaatgaaaa tatatcat gtgatcttca aatcttgtgt      360
cttatgcaag attgatactt tgttcaatgg aagagattgt gtgcatattt tcaaaatttt    420
tattagtaat aaagattcta tatagctgtt atagagggaa aattttacaa agaacactat    480
aaatatgatt gttgttgtta ggggtgtcaa tggttcggtt cgactggtta ttttataaaa    540
tttgtaccat accattttt cggatattct atttttgtata accaaaatta gacttttcga    600
aatcgtccca atcatgtcgg tttcacttcg gtatcggtac cgttcggtta attttcatttt   660 ttttttaaat gtcattaaaa ttcactagta aaaatagaat gcaataacat acgttctttt    720
ataggactta gcaaaactct ctagacattt ttactgttta aaggataatg aattaaaaaa    780
catgaaagat ggctagagta tagatacaca actattcgac agcaacgtaa aagaaaccaa    840
gtaaaagcaa agaaaatata aatcacacga gtggaaagat attaaccaag ttgggattca    900
agaataaagt ctatattaaa tattcaaaaa gataaattta ataatatga aaggaaacat     960 attcaataca ttgtagtttg ctactcataa tcgctagaat actttgtgcc ttgctaataa   1020
agatactaga aatagcttag tttaaatata aatagcataa tagattttag gaattagtat   1080 tttgagtttta attacttatt gacttgtaac agttttttata attccaaggc ccaatgaaaa  1140
atttaatgct ttattagttt taaacttact atataaattt ttcatatgta aaatttaatc   1200
ggtatagttc gatatttttt caattttattt ttataaaata aaaaacttac cctaattatc   1260
ggtacagtta tagatttata taaaaatcta cggttcttca gaagaaacct aaaaatcggt   1320
tcggtgcggg acggtcgat cggtttagtc gattttcaaa tattcattga cactcctagt    1380
tgttggtata ggtaaaaagc agttacagag aggtaaaata taacttaaaa aatcagttct   1440
aaggaaaaat tgactttat agtaaatgac tgttatataa ggatgttgtt acagagaggt   1500
```

```
atgagtgtag ttggtaaatt atgttcttga cggtgtatgt cgcatattat ttattaaaac    1560
tagaaaaaac agcgtcaaaa ctagcaaaaa tccaaaggac aaaaaaatcg gctgaatttg    1620
atttggttcc aacatttaaa aaagtttcag tgagaaagaa tacggtgact gttgatgata    1680
taaacaaagg gcacattggt caataaccat aaaaaattat atgacagcta cagttggtag    1740
catgtgctca gctattgaac aaatctaaag aaggtacatc tgtaaccgga acagcactta    1800
aatgactaaa ttaccctcat cagaaagcag atggagtgct acaaataaca cactattcaa    1860
caaccataaa taaaacgtgt tcagctacta aaacaaatat aaataaatct atgtatgtaa    1920
gcactccagc catgttaatg gagtgctatt gcctgttaac tctcactata aaatagtagt    1980
agaaaaaata tgaaccaaaa cacaacaatg ctgctttgtg aatatcagag ttgtagaact    2040
tgagaggtcc taatttggac ttgacttgag ttgtctcttt gtcaattgga tttactggat    2100
tcttgaagtc aacttctggc ccttcagtag agcagagcat ataaccgatc acaccggtgg    2160
gatatgttgg aacggttgtc caagcatagt tgacagaacc cttaaagact tgacgacagt    2220
tagcaatgat ttgcttaata atatgcatat gaagccaaat gctttcagcc tgtgtgcata    2280
caactcctcc tggcctaagg gctttggcta ctgcctcaaa gaatggcctc tcaaacaaat    2340
cttttgctgg gtccgtcgct tctcttccat ttcttctcat tttcgatttt gattcttatt    2400
tctttccagt agctcctgct ctgtgaattt ctccgctcac gatagatctg cttatactcc    2460
ttacattcaa ccttagatct ggtctcgatt ctctgtttct ctgttttttt cttttggtcg    2520
agaatctgat gtttgtttat gttctgtcac cattaataat aatgaactct ctcattcata    2580
caatgattag tttctctcgt ctacaaaacg atatgttgca ttttcacttt tcttcttttt    2640
ttctaagatg atttgctttg accaatttgt ttagatcttt attttatttt attttctggt    2700
gggttggtgg aaattgaaaa aaaaaaaaac agcataaatt gttatttgtt aatgtattca    2760 tttttttggct atttgttctg ggtaaaaatc tgcttctact attgaatctt tcctggattt    2820
tttactccta ttgggttttt atagtaaaaa tacataataa aaggaaaaca aaagttttat    2880
agattctctt aaacccctta cgataaaagt tggaatcaaa ataattcagg atcagatgct    2940 cttttgattga ttcagatgcg attacagttg catggcaaat tttctagatc cgtcgtcaca    3000
ttttattttc tgtttaaata tctaaatctg atatatgatg tcgacaaatt ctggtggctt    3060
atacatcact tcaactgttt tcttttggct ttgtttgtca acttggtttt caatacgatt    3120
tgtgatttcg atcgctgaat ttttaataca agcaaactga tgttaaccac aagcaagaga    3180
tgtgacctgc cttattaaca tcgtattact tactactagt cgtattctca acgcaatcgt    3240
ttttgtattt ctcacattat gccgcttctc tactctttat tccttttggt ccacgcattt    3300
tctatttgtg gcaatccctt tcacaacctg atttcccact ttggatcatt tgtctgaaga    3360
ctctcttgaa tcgttaccac ttgtttcttg tgcatgctct gttttttaga attaatgata    3420
aaactattcc atagtcttga gttttcagct tgttgattct tttgcttttg gttttctgca    3480
gccagcaaaa gatttgtttg agaggccatt ctttgaggca gtagccaaag cccttaggcc    3540
aggaggagtt gtatgcacac aggctgaaag catttggctt catatgcata ttattaagca    3600
aatcattgct aactgtcgtc aagtcttta gggttctgtc aactatgctt ggacaaccgt    3660
tccaacatat cccaccggtg tgatcggtta tatgctctgc tctactgaag ggccagaagt    3720
tgacttcaag aatccagtaa atccaattga caaagagaca actcaagtca agtccaaatt    3780
aggacctctc aagttctaca actctgatat tcacaaagca gcattgcaag tgtgttgcct    3840
```

```
ttgtgtggaa atgaagaggt acttgcgagg actttgcgtt tatcagttta tgtgtttgta    3900
tatctatttg atccagttat tatggattat atacgcttga aactcatttt aagccattgt    3960
tattgaacgt ttatcaaata ctttattatg ccaagcaagt caaacacatg cttgttgatt    4020
gaaatcaagc tatagaaatc tcttcttcac atacagcagt ttagattcac aatacaacaa    4080
gcgaaacgat aaagtttc                                                  4098

<210> SEQ ID NO 46
<211> LENGTH: 307
<212> TYPE: DNA
<213> ORGANISM: Agrobacterium tumefaciens

<400> SEQUENCE: 46
gatcatgagc ggagaattaa gggagtcacg ttatgacccc cgccgatgac gcgggacaag    60
ccgttttacg tttggaactg acagaaccgc aacgttgaag gagccactca gccgcgggtt   120
tctggagttt aatgagctaa gcacatacgt cagaaaccat tattgcgcgt tcaaaagtcg   180
cctaaggtca ctatcagcta gcaaatattt cttgtcaaaa atgctccact gacgttccat   240
aaattcccct cggtatccaa ttagagtctc atattcactc tcaatccaaa taatctgcac   300
cggatct                                                              307

<210> SEQ ID NO 47
<211> LENGTH: 795
<212> TYPE: DNA
<213> ORGANISM: Escherichia coli

<400> SEQUENCE: 47
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat gggcgaagt gccggggcag   300 gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgatgatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795

<210> SEQ ID NO 48
<211> LENGTH: 1757
<212> TYPE: DNA
<213> ORGANISM: Artificial Sequence
<220> FEATURE:
<223> OTHER INFORMATION: Artificially created chimeric nucleic acid
      sequence

<400> SEQUENCE: 48
gatcatgagc ggagaattaa gggagtcacg ttatgacccc cgccgatgac gcgggacaag    60
```

```
ccgttttacg tttggaactg acagaaccgc aacgttgaag gagccactca gccgcgggtt        120
tctggagttt aatgagctaa gcacatacgt cagaaaccat tattgcgcgt tcaaaagtcg        180
cctaaggtca ctatcagcta gcaaatattt cttgtcaaaa atgctccact gacgttccat        240
aaattcccct cggtatccaa ttagagtctc atattcactc tcaatccaaa taatctgcac        300
cggatctgga tcgtttcgca tgattgaaca agatggattg cacgcaggtt ctccggccgc        360
ttgggtggag aggctattcg gctatgactg ggcacaacag acaatcggct gctctgatgc        420
cgccgtgttc cggctgtcag cgcaggggcg cccggttctt tttgtcaaga ccgacctgtc        480
cggtgccctg aatgaactgc aggacgaggc agccgcggcta tcgtggctgg ccacgacggg        540
cgttccttgc gcagctgtgc tcgacgttgt cactgaagcg ggaagggact ggctgctatt        600
gggcgaagtg ccggggcagg atctcctgtc atctcacctt gctcctgccg agaaagtatc        660
catcatggct gatgcaatgc ggcggctgca tacgcttgat ccggctacct gcccattcga        720
ccaccaagcg aaacatcgca tcgagcgagc acgtactcgg atggaagccg gtcttgtcga        780
tcaggatgat ctggacgaag agcatcaggg gctcgcgcca gccgaactgt tcgccaggct        840
caaggcgcgc atgcccgacg gcgatgatct cgtcgtgacc catggcgatg cctgcttgcc        900
gaatatcatg gtggaaaatg gccgcttttc tggattcatc gactgtggcc ggctgggtgt        960
ggcggaccgc tatcaggaca tagcgttggc tacccgtgat attgctgaag agcttggcgg       1020
cgaatgggct gaccgcttcc tcgtgcttta cggtatcgcc gctcccgatt cgcagcgcat       1080
cgccttctat cgccttcttg acgagttctt ctgagcggga ctctggggtt cgaaatgacc       1140
gaccaagcga cgcccaacct gccatcacga gatttcgatt ccaccgccgc cttctatgaa       1200
aggttgggct tcggaatcgt tttccgggac gccggctgga tgatcctcca gcgcggggat       1260
ctcatgctgg agttcttcgc ccacgggatc tctgcggaac aggcggtcga aggtgccgat       1320
atcattacga cagcaacggc cgacaagcac aacgccacga tcctgagcga caatatgatc       1380
gggcccggcg tccacatcaa cggcgtcggc ggcgactgcc caggcaagac cgagatgcac       1440
cgcgatatct tgctgcgttc ggatatttte gtggagttcc cgccacagac ccggatgatc       1500
cccgatcgtt caaacatttg gcaataaagt ttcttaagat tgaatcctgt tgccggtctt       1560
gcgatgatta tcatataatt tctgttgaat tacgttaagc atgtaataat taacatgtaa       1620
tgcatgacgt tatttatgag atgggttttt atgattagag tcccgcaatt atacatttaa       1680
tacgcgatag aaaacaaaat atagcgcgca aactaggata aattatcgcg cgcggtgtca       1740
tctatgttac tagatcg                                                      1757

<210> SEQ ID NO 49
<211> LENGTH: 5872
<212> TYPE: DNA
<213> ORGANISM: Artificial Sequence
<220> FEATURE:
<223> OTHER INFORMATION: Artificially created chimeric nucleic acid
      sequence

<400> SEQUENCE: 49
gatcatgagc ggagaattaa gggagtcacg ttatgacccc cgccgatgac gcgggacaag         60
ccgttttacg tttggaactg acagaaccgc aacgttgaag gagccactca gccgcgggtt        120
tctggagttt aatgagctaa gcacatacgt cagaaaccat tattgcgcgt tcaaaagtcg        180
cctaaggtca ctatcagcta gcaaatattt cttgtcaaaa atgctccact gacgttccat        240
aaattcccct cggtatccaa ttagagtctc atattcactc tcaatccaaa taatctgcac        300
```

| | |
|---|---|
| cggatctgga tcgtttcgca tgattgaaca agatggattg cacgcaggtt ctccggccgc | 360 |
| ttgggtggag aggctattcg gctatgactg ggcacaacag acaatcggct gctctgatgc | 420 |
| cgccgtgttc cggctgtcag cgcaggggcg cccggttctt tttgtcaaga ccgacctgtc | 480 |
| cggtgccctg aatgaactgc aggacgaggc agcgcggcta tcgtggctgg ccacgacggg | 540 |
| cgttccttgc gcagctgtgc tcgacgttgt cactgaagcg ggaagggact ggctgctatt | 600 |
| gggcgaagtg ccggggcagg atctcctgtc atctcacctt gctcctgccg agaaagtatc | 660 |
| catcatggct gatgcaatgc ggcggctgca tacgcttgat ccggctacct gcccattcga | 720 |
| ccaccaagcg aaacatcgca tcgagcgagc acgtactcgg atggaagccg gtcttgtcga | 780 |
| tcaggatgat ctggacgaag agcatcaggg gctcgcgcca gccgaactgt tcgccaggct | 840 |
| caaggcgcgc atgcccgacg cgatgatct cgtcgtgacc catggcgatg cctgcttgcc | 900 |
| gaatatcatg gtggaaaatg gccgcttttc tggattcatc gactgtggcc ggctgggtgt | 960 |
| ggcggaccgc tatcaggaca tagcgttggc tacccgtgat attgctgaag agcttggcgg | 1020 |
| cgaatgggct gaccgcttcc tcgtgcttta cggtatcgcc gctcccgatt cgcagcgcat | 1080 |
| cgccttctat cgccttcttg acgagttctt ctgagcggga ctctgggtt cgaaatgacc | 1140 |
| gaccaagcga cgcccaacct gccatcacga gatttcgatt ccaccgccgc cttctatgaa | 1200 |
| aggttgggct tcggaatcgt tttccgggac gccggctgga tgatcctcca gcgcgggat | 1260 |
| ctcatgctgg agttcttcgc ccacgggatc tctgcggaac aggcggtcga aggtgccgat | 1320 |
| atcattacga cagcaacggc cgacaagcac aacgccacga tcctgagcga caatatgatc | 1380 |
| gggcccggcg tccacatcaa cggcgtcggc ggcgactgcc caggcaagac cgagatgcac | 1440 |
| cgcgatatct tgctgcgttc ggatattttc gtggagttcc cgccacagac ccggatgatc | 1500 |
| cccgatcgtt caaacatttg gcaataaagt ttcttaagat tgaatcctgt tgccggtctt | 1560 |
| gcgatgatta tcatataatt tctgttgaat tacgttaagc atgtaataat taacatgtaa | 1620 |
| tgcatgacgt tatttatgag atgggttttt atgattagag tcccgcaatt atacatttaa | 1680 |
| tacgcgatag aaaacaaaat atagcgcgca aactaggata aattatcgcg cgcggtgtca | 1740 |
| tctatgttac tagatcgctc gaggatctaa attgtgagtt caatctcttc cctattggat | 1800 |
| tgattatcct ttcttttctt ccaatttgtg tttcttttg cctaatttat tgtgttatcc | 1860 |
| cctttatcct attttgtttc tttacttatt tatttgcttc tatgtctttg tacaaagatt | 1920 |
| taaactctat ggcacatatt ttaaagttgt tagaaaataa attctttcaa gattgatgaa | 1980 |
| agaactttt aattgtagat atttcgtaga ttttattctc ttactaccaa tataacgctt | 2040 |
| gaattgacga aaatttgtgt ccaaatatct agcaaaaagg tatccaatga aaatatatca | 2100 |
| tatgtgatct tcaaatcttg tgtcttatgc aagattgata ctttgttcaa tggaagagat | 2160 |
| tgtgtgcata ttttaaaat ttttattagt aataaagatt ctatatagct gttatagagg | 2220 |
| gataattta caaagaacac tataaatatg attgttgttg ttagggtgtc aatggttcgg | 2280 |
| ttcgactggt tattttataa aatttgtacc ataccatttt tttcgatatt ctattttgta | 2340 |
| taaccaaaat tagacttttc gaaatcgtcc caatcatgtc ggtttcactt cggtatcggt | 2400 |
| accgttcggt taattttcat ttttttttaa atgtcattaa aattcactag taaaaataga | 2460 |
| atgcaataac atacgttctt ttataggact tagcaaaagc tctctagaca ttttactgt | 2520 |
| ttaaaggata atgaattaaa aaacatgaaa gatggctaga gtatagatac acaactattc | 2580 |
| gacagcaacg taaagaaac caagtaaaag caaagaaaat ataaatcaca cgagtggaaa | 2640 |
| gatattaacc aagttgggat tcaagaataa agtctatatt aaatattcaa aaagataaat | 2700 |

```
ttaaataata tgaaaggaaa catattcaat acattgtagt ttgctactca taatcgctag    2760
aatactttgt gccttgctaa taaagatact tgaaatagct tagtttaaat ataaatagca    2820
taatagattt taggaattag tattttgagt ttaattactt attgacttgt aacagttttt    2880
ataattccaa ggcccatgaa aaatttaatg ctttattagt tttaaactta ctatataaat    2940
ttttcatatg taaaatttaa tcggtatagt tcgatatttt ttcaatttat tttttataaaa   3000 taaaaaactt accctaatta tcggtacagt tatagattta tataaaaatc tacgttctt    3060 cagaagaaac ctaaaaatcg gttcggtgcg gacggttcga tcggtttagt cgattttcaa    3120
atattcattg acactcctag ttgttgttat aggtaaaaag cagttacaga gaggtaaaat    3180
ataacttaaa aaatcagttc taaggaaaaa ttgactttta tagtaaatga ctgttatata    3240
aggatgttgt tacagagagg tatgagtgta gttggtaaat tatgttcttg acggtgtatg    3300
tcacatatta tttattaaaa ctagaaaaaa cagcgtcaaa actagcaaaa atccaacgga    3360
caaaaaaatc ggctgaattt gatttggttc caacatttaa aaaagtttca gtgagaaaga    3420
atcggtgact gttgatgata taaacaaagg gcacattggt caataaccat aaaaaattat    3480 atgcagcta  cagttggtag catgtgctca gctattgaac aaatctaaag aaggtacatc    3540
tgtaaccgga acaccactta aatgactaaa ttaccctcat cagaaagcag atggagtgct    3600
acaaataaca cactattcaa caaccataaa taaaacgtgt tcagctacta aaacaaatat    3660
aaataaatct atgtttgtaa gcactccagc catgttaatg gagtgctatt gcctgttaac    3720
tctcacttat aaaatagtag tagaaaaaat atgaaccaaa acacaacttt atcgccatca    3780
tttacatacc actccacctt taatgaagga tcaacttccg cgaatatcat ctcagcaagt    3840
gcaattcctg ctatgatccc gtcttccttt gctagaaaat gagcatcgga ttccatatca    3900
agaggaattg tcgccttaca agtcacatct cctaaattcc cagcatcttc agagagtgca    3960
agtttcataa cttcctttaa atcataagtt gggtgtgctg gtggtttcac ctctaatgac    4020
tccactcttg tattcttggt ggctattgct gacattttca ccaccaacct tggagctgta    4080
attgcataag gatgcactgt agcagtgaaa ggaatagctc taaacatgtc cgtcgcttct    4140
cttccatttc ttctcatttt cgattttgat tcttatttct ttccagtagc tcctgctctg    4200
tgaatttctc cgctcacgat agatctgctt atactcctta cattcaacct tagatctggt    4260
ctcgattctc tgtttctctg ttttttttctt ttggtcgaga atctgatgtt tgtttatgtt    4320
ctgtcaccat aataataat gaactctctc attcatacaa tgattagttt ctctcgtcta    4380
caaaacgata tgttgcattt tcacttttct tcttttttttc taagatgatt tgctttgacc    4440
aatttgttta gatctttatt ttatttttatt ttctggtggg ttggtggaaa ttgaaaaaaa    4500
aaaaaacagc ataaattgtt atttgttaat gtattcattt tttggctatt tgttctgggt    4560
aaaaatctgc ttctactatt gaatctttcc tggattttttt actcctattg ggttttttata   4620 gtaaaaatac ataataaaag gaaaacaaaa gttttataga ttctcttaaa ccccttacga    4680
taaaagttgg aatcaaaata attcaggatc agatgctctt tgattgattc agatgcgatt    4740
acagttgcat ggcaaatttt ctagatccgt cgtcacattt tattttctgt ttaaatatct    4800
aaatctgata tatgatgtcg acaaattctg gtggcttata catcacttca actgttttct    4860
tttggctttg tttgtcaact tggttttcaa tacgatttgt gatttcgatc gctgaatttt    4920
taatacaagc aaactgatgt taaccacaag caagagatgt gacctgcctt attaacatcg    4980
tattacttac tactagtcgt attctcaacg caatcgtttt tgtatttctc acattatgcc    5040
```

```
gcttctctac tctttattcc ttttggtcca cgcatttttct atttgtggca atcccttttca    5100
caacctgatt tcccactttg gatcatttgt ctgaagactc tcttgaatcg ttaccacttg    5160
tttcttgtgc atgctctgtt ttttagaatt aatgataaaa ctattccata gtcttgagtt    5220
ttcagcttgt tgattctttt gcttttggtt ttctgcagat gtttagagct attccttttca   5280
ctgctacagt gcatccttat gcaattacag ctccaaggtt ggtggtgaaa atgtcagcaa    5340
tagccaccaa gaatacaaga gtggagtcat taggggtgaa accaccagca cacccaactt    5400
atgatttaaa ggaagttatg aaacttgcac tctctgaaga tgctgggaat ttaggagatg    5460
tgacttgtaa ggcgacaatt cctcttgata tggaatccga tgctcatttt ctagcaaagg    5520
aagacgggat catagcagga attgcacttg ctgagatgat attcgcggaa gttgatcctt    5580
cattaaaggt gggagtggta tgtaaatgatg gcgataaaga tcgttcaaac atttggcaat    5640
aaagtttctt aagattgaat cctgttgccg gtcttgcgat gattatcata taatttctgt    5700
tgaattacgt taagcatgta ataattaaca tgtaatgcat gacgttattt atgagatggg    5760
tttttatgat tagagtcccg caattataca tttaatacgc gatagaaaac aaaatatagc    5820
gcgcaaacta ggataaatta tcgcgcgcgg tgtcatctat gttactagat cg          5872

<210> SEQ ID NO 50
<211> LENGTH: 2006
<212> TYPE: DNA
<213> ORGANISM: Nicotiana tabacum

<400> SEQUENCE: 50
gatctaaatt gtgagttcaa tctcttccct attggattga ttatcctttc ttttcttcca      60
atttgtgttt cttttttgcct aatttattgt gttatcccct ttatcctatc ttgtttcttt    120
acttatttat ttgcttctat gtctttgtac aaagatttaa actctatggc acatatttta    180
aagttgttag aaaataaatt ctttcaagat tgatgaaaga acttttttaat tgtagatatt    240
tcgtagattt tattctctta ctaccaatat aacgcttgaa ttgacgaaaa tttgtgtcca    300
aatatttagc aaaaaggtat ccaatgaaaa tatatcatat gtgatcttca aatcttgtgt    360
cttatgcaag attgatactt tgttcaatgg aagagattgt gtgcatattt tcaaaatttt    420
tattagtaat aaagattcta tatagctgtt atagagggat aattttacaa agaacactat    480
aaatatgatt gttgttgtta ggggtgtcaa tggttcggtt cgactggtta ttttataaaa    540
tttgtaccat accatttttt cggatattct attttgtata accaaaatta gacttttcga    600
aatcgtccca atcatgtcgg tttcacttcg gtatcggtac cgttcggtta attttcattt    660
tttttttaaat gtcattaaaa ttcactagta aaaatagaat gcaataacat acgttctttt   720
ataggactta gcaaaactct ctagacattt ttactgttta aaggataatg aattaaaaaa    780
catgaaagat ggctagagta tagatacaca actattcgac agcaacgtaa aagaaaccaa    840
gtaaaagcaa agaaaatata atcacacga gtggaaagat attaaccaag ttgggattca    900
agaataaagt ctatattaaa tattcaaaaa gataaattta ataatatga aaggaaacat    960
attcaataca ttgtagtttg ctactcataa tcgctagaat actttgtgcc ttgctaataa   1020
agatactaga aatagcttag tttaaatata aatagcataa tagattttag gaattagtat   1080
tttgagttta attacttatt gacttgtaac agttttttata attccaaggc ccaatgaaaa   1140
atttaatgct ttattagttt taaacttact atataaattt ttcatatgta aaatttaatc   1200
ggtatagttc gatattttttt caatttattt ttataaaata aaaaacttac cctaattatc   1260
ggtacagtta tagatttata taaaaatcta cggttcttca gaagaaacct aaaaatcggt   1320
```

```
tcggtgcggg acggttcgat cggtttagtc gattttcaaa tattcattga cactcctagt    1380
tgttgttata ggtaaaaagc agttacagag aggtaaaata taacttaaaa aatcagttct    1440
aaggaaaaat tgacttttat agtaaatgac tgttatataa ggatgttgtt acagagaggt    1500
atgagtgtag ttggtaaatt atgttcttga cggtgtatgt cgcatattat ttattaaaac    1560
tagaaaaaac agcgtcaaaa ctagcaaaaa tccaaaggac aaaaaaatcg gctgaatttg    1620
atttggttcc aacatttaaa aaagtttcag tgagaaagaa tacggtgact gttgatgata    1680
taaacaaagg gcacattggt caataaccat aaaaaattat atgacagcta cagttggtag    1740
catgtgctca gctattgaac aaatctaaag aaggtacatc tgtaaccgga acagcactta    1800
aatgactaaa ttaccctcat cagaaagcag atggagtgct acaaataaca cactattcaa    1860
caaccataaa taaaacgtgt tcagctacta aaacaaatat aaataaatct atgtatgtaa    1920
gcactccagc catgttaatg gagtgctatt gcctgttaac tctcactata aaatagtagt    1980
agaaaaaata tgaaccaaaa cacaac                                         2006

<210> SEQ ID NO 51
<211> LENGTH: 75
<212> TYPE: DNA
<213> ORGANISM: Artificial Sequence
<220> FEATURE:
<223> OTHER INFORMATION: Synthetically prepared primer sequence

<400> SEQUENCE: 51
ccttgcgctt ctcagccacg caaactcaag aggatcgcat caccatcacc atcacagtga    60
ccttgaccgg tgcac                                                     75

<210> SEQ ID NO 52
<211> LENGTH: 70
<212> TYPE: DNA
<213> ORGANISM: Artificial Sequence
<220> FEATURE:
<223> OTHER INFORMATION: Synthetically prepared primer sequence

<400> SEQUENCE: 52
ataatctaga tgatcatggc ttcctccaag ttactctccc tagccctctt ccttgcgctt    60
ctcagccacg                                                           70

<210> SEQ ID NO 53
<211> LENGTH: 47
<212> TYPE: DNA
<213> ORGANISM: Artificial Sequence
<220> FEATURE:
<223> OTHER INFORMATION: Synthetically prepared primer sequence

<400> SEQUENCE: 53
attcgagctc ttaaagttca tcatgagcca tagaaacagg cattact                  47

<210> SEQ ID NO 54
<211> LENGTH: 23
<212> TYPE: PRT
<213> ORGANISM: Artificial Sequence
<220> FEATURE:
<223> OTHER INFORMATION: Synthetic amino acid sequence

<400> SEQUENCE: 54

Met Ile Met Ala Ser Ser Lys Leu Leu Ser Leu Ala Leu Phe Leu Ala
1               5                   10                  15

Leu Leu Ser His Ala Asn Ser
```

```
<210> SEQ ID NO 55
<211> LENGTH: 9
<212> TYPE: PRT
<213> ORGANISM: Artificial Sequence
<220> FEATURE:
<223> OTHER INFORMATION: Synthetic amino acid sequence

<400> SEQUENCE: 55

Arg Gly Ser His His His His His His
1               5

<210> SEQ ID NO 56
<211> LENGTH: 4
<212> TYPE: PRT
<213> ORGANISM: Artificial Sequence
<220> FEATURE:
<223> OTHER INFORMATION: Plant specific endoplasmic reticulum retention
      signal sequence

<400> SEQUENCE: 56

His Asp Glu Leu
```